US012110491B2

(12) United States Patent
Bennett et al.

(10) Patent No.: US 12,110,491 B2
(45) **Date of Patent: *Oct. 8, 2024**

(54) SELECTIVE REDUCTION OF ALLELIC VARIANTS

(71) Applicant: Ionis Pharmaceuticals, Inc., Carlsbad, CA (US)

(72) Inventors: C. Frank Bennett, Carlsbad, CA (US); Susan M. Freier, San Diego, CA (US); Sarah Greenlee, San Diego, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/577,832

(22) Filed: Jan. 18, 2022

(65) Prior Publication Data

US 2022/0403386 A1 Dec. 22, 2022

Related U.S. Application Data

(63) Continuation of application No. 15/961,567, filed on Apr. 24, 2018, now abandoned, which is a continuation of application No. 14/581,235, filed on Dec. 23, 2014, now abandoned, which is a continuation of application No. 13/577,616, filed as application No. PCT/US2011/024103 on Feb. 8, 2011, now Pat. No. 8,957,040.

(60) Provisional application No. 61/371,635, filed on Aug. 6, 2010, provisional application No. 61/302,469, filed on Feb. 8, 2010.

(51) Int. Cl.
*C12N 15/11* (2006.01)
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/341* (2013.01); *C12N 2310/346* (2013.01); *C12N 2320/34* (2013.01); *C12N 2320/35* (2013.01)

(58) Field of Classification Search
None
See application file for complete search history.

(56) References Cited

U.S. PATENT DOCUMENTS

| | | | |
|---|---|---|---|
| 5,801,154 | A | 9/1998 | Baracchini et al. |
| 6,268,490 | B1 | 7/2001 | Imanishi et al. |
| 6,331,617 | B1 | 12/2001 | Weeks et al. |
| 6,525,191 | B1 | 2/2003 | Ramasamy |
| 6,582,908 | B2 | 6/2003 | Fodor et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,399,845 | B2 | 7/2008 | Seth et al. |
| 8,084,437 | B2 | 12/2011 | Freier et al. |
| 8,093,222 | B2 | 1/2012 | Freier et al. |
| 8,957,040 | B2 | 2/2015 | Bennett et al. |
| 9,006,198 | B2 | 4/2015 | Bennett et al. |
| 9,688,985 | B2 | 6/2017 | Bhat et al. |
| 9,695,418 | B2 | 7/2017 | Seth et al. |
| 9,752,142 | B2 | 9/2017 | Oestergaard et al. |
| 9,914,922 | B2 | 3/2018 | Freier et al. |
| 10,017,764 | B2 | 7/2018 | Freier et al. |
| 10,202,599 | B2 | 2/2019 | Seth et al. |
| 10,260,069 | B2 | 4/2019 | Oestergaard et al. |
| 10,337,007 | B2 | 7/2019 | Freier et al. |
| 11,149,264 | B2 | 10/2021 | Seth et al. |
| 11,236,335 | B2 | 2/2022 | Oestergaard et al. |
| 11,332,733 | B2 | 5/2022 | Seth et al. |
| 11,732,261 | B2 | 8/2023 | Seth et al. |
| 2001/0053519 | A1 | 12/2001 | Fodor et al. |
| 2002/0081611 | A1 | 6/2002 | O'Brien et al. |
| 2002/0165189 | A1 | 11/2002 | Crooke |
| 2002/0187931 | A1 | 12/2002 | Hayden et al. |
| 2003/0073123 | A1 | 4/2003 | Shen et al. |
| 2003/0109476 | A1 | 6/2003 | Kmiec et al. |
| 2003/0228597 | A1 | 12/2003 | Cowsert et al. |
| 2004/0171570 | A1 | 9/2004 | Allerson et al. |

(Continued)

FOREIGN PATENT DOCUMENTS

| | | |
|---|---|---|
| JP | 2008-513507 | 5/2008 |
| WO | WO 99/14226 | 3/1999 |

(Continued)

OTHER PUBLICATIONS

Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71:7731-7740.

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16:917-926.

(Continued)

*Primary Examiner* — Ekaterina Poliakova-Georgantas

(74) *Attorney, Agent, or Firm* — McNeill PLLC

(57) ABSTRACT

Disclosed herein are antisense compounds and methods for selectively reducing expression of an allelic variant of a gene containing a single nucleotide polymorphism (SNP). Such methods, compounds, and composition are useful to treat, prevent, or ameliorate diseases, including neurodegenerative diseases, such as Huntington's Disease (HD).

50 Claims, 161 Drawing Sheets

Specification includes a Sequence Listing.

(56) References Cited

U.S. PATENT DOCUMENTS

| | | | | |
|---|---|---|---|---|
| 2005/0096284 | A1* | 5/2005 | McSwiggen | A61K 47/551 536/23.1 |
| 2005/0176045 | A1 | 8/2005 | Fedorov et al. | |
| 2006/0063730 | A1 | 3/2006 | Monia et al. | |
| 2007/0031844 | A1 | 2/2007 | Khvorova et al. | |
| 2007/0123484 | A1 | 5/2007 | Bhat et al. | |
| 2007/0161590 | A1 | 7/2007 | Van Bilsen et al. | |
| 2007/0287831 | A1 | 12/2007 | Seth et al. | |
| 2008/0015162 | A1 | 1/2008 | Bhanot et al. | |
| 2008/0039418 | A1 | 2/2008 | Freier | |
| 2008/0039618 | A1 | 2/2008 | Allerson et al. | |
| 2009/0012281 | A1 | 1/2009 | Swayze et al. | |
| 2009/0318536 | A1 | 12/2009 | Freier et al. | |
| 2010/0144834 | A1 | 6/2010 | Freier et al. | |
| 2010/0299768 | A1 | 11/2010 | Perrin et al. | |
| 2015/0051389 | A1 | 2/2015 | Seth et al. | |
| 2020/0056187 | A1 | 2/2020 | Oestergaard et al. | |
| 2020/0377946 | A1 | 12/2020 | Bennett et al. | |
| 2021/0238591 | A1 | 8/2021 | Seth et al. | |
| 2023/0113863 | A1 | 4/2023 | Seth et al. | |

FOREIGN PATENT DOCUMENTS

| | | | |
|---|---|---|---|
| WO | WO 2003/004602 | 1/2003 | |
| WO | WO 2004/106356 | 12/2004 | |
| WO | WO 2007/002904 | 1/2007 | |
| WO | WO-2007089584 A2 * | 8/2007 | A61P 25/00 |
| WO | WO 2007/134181 | 11/2007 | |
| WO | WO 2008/005562 | 1/2008 | |
| WO | WO 2008/049085 | 4/2008 | |
| WO | WO 2008/147887 | 12/2008 | |
| WO | WO 2008/147930 | 12/2008 | |
| WO | WO 2008/150729 | 12/2008 | |
| WO | WO 2008/154401 | 12/2008 | |
| WO | WO 2009/006478 | 1/2009 | |
| WO | WO 2009/135322 | 11/2009 | |
| WO | WO 2011/139702 | 11/2011 | |
| WO | WO 2013/022967 | 2/2013 | |

OTHER PUBLICATIONS

Altmann et al., "Second Generation of Antisense Oligonucleotides: From Nuclease Resistance to Biological Efficacy in Animals" Chimia (1996) 50:168-176.

Altmann et al., "Second-generation antisense oligonucleotides: structure-activity relationships and the design of improved signal-transduction inhibitors" Biochem. Soc. Trans. (1996) 24:630-637.

Alves et al., "Allele-Specific RNA Silencing of Mutan Ataxin-3 Mediates Neuroprotection in a Rat Model of Machado-Joseph Disease" PLOS ONE (2008) 3(10): e3341.

Bonini et al., "Silencing Polyglutamine Degeneration with RNAi" Neuron (2005) 48:715-718.

Braasch et al., "Locked nucleic acid (LNA): fine-tuning the recognition of DNA and RNA" Chem. Biol. (2001) 8:1-7.

Branch et al., "A good antisense molecule is hard to find, " TIBS (1998) 23:45-50.

Brookes, "The essence of SNPs" Gene (1999) 234(2):177-186.

Bruge et al., "A novel Real Time PCR strategy to detect SOD3 SNP using LNA probes" Mutation Res (2009) 669(1): 80-84.

Carroll et al., "Potent and Selective Antisense Oligonucleotides Targeting Single-Nucleotide Polymorphisms in the Huntington Disease Gene / Allele-Specific Silencing of Mutant Huntingtin" Molecular Therapy (2011) 19(12):2178-2185.

Chan et al., "Antisense Oligonucleotides: From Design To Therapeutic Application" Clin. Exp. Pharmacol. Physiol. (2006) 33:533-540.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1: 1-50.

Denovan-Wright et al., "RNAi: a potential therapy for dominantly inherited nucleotide repeat diseases" Gene Therapy (2006) 13(6):525-531.

Dragatsis et al., "Inactivation of Hdh in the brain and testis results in progressive neurodegeneration and sterility in mice" Nat. Genet. (2000) 26:300-306.

Elayadi et al., "Application of PNA and LNA oligomers to chemotherapy" Curr. Opinions Invens. Drugs (2001) 2:558-561.

Ellis, "Spot-On SNP Genotyping" Genome Res. (2000) 10:895-897.

Freier et al., "The ups and downs of nucleic acid duplex stability: structure-stability studies on chemically-modified DNA:RNA duplexes" Nucleic Acids Res. (1997) 25:4429-4443.

Frieden et al., "Expanding the design horizon of antisense oligonucleotides with alpha-L-LNA" Nucleic Acids Research (2003) 21:6365-6372.

Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.

Gossen et al., "Tight control of gene expression in mammalian cells by tetracycline-responsive promoters." PNAS (1992) 89:5547-5551.

Gray et al., "Full-Length Human Mutant Huntingtin with a Stable Polyglutamine Repeat Can Elicit Progressive and Selective Neuropathogenesis in BACHD Mice" J. Neurosc. (2008) 28(24):6182-6195.

Fluiter et al., "Killing cancer by targeting genes that cancer cells have lost: allele-specific inhibition, a novel approach to the treatment of genetic disorders." Cell Mol Life Sci (2003) 60: 834-43.

Gagnon et al. "Allele-selective inhibition of mutatn huntington expression with antisense oligonucleotides targeting the expanded CAG repeat" Biochemistry (2010) 49:10166-78.

Gow et al., "The unfolded protein response in protein aggregating diseases" NeuroMol. Med. (2003) 4(1-2):73-94.

Hizawa et al., "Functional single nucleotide polymorphisms of the CCL5 gene and nonemphysematous phenotype in COPD patients" Eur. Respir. J. (2008) 32(2):372-378.

Griffin et al., "Single-nucleotide polymorphism analysis by MALDI-TOF mass spectrometry" Trends Biotechnol. (2000) 18(2):77-84.

Gutekunst et al., "Identification and localization of huntingtin in brain and human lymphoblastoid cell lines with anti-fusion protein antibodies " PNAS (1995) 92(19):8710-8714.

Handley et al., "Pharmaceutical, cellular and genetic therapies for Huntington's disease" Clin. Sci. (2006) 110:73-88.

Hu et al., "Allele-specific silencing of mutant huntingtin and ataxin-3 genes by targeting expanded CAG repeats in mRNAs" Nature Biotechnology (2009) 27(5):478-484.

Kordasiewicz et al., "Sustained Therapeutic Reversal of Huntington's Disease by Transient Repression of Huntingtin Synthesis" Neuron (2012) 74:1031-1044.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Leumann, "DNA Analogues: From Supramolecular Principles to Biological Properties" Bioorganic & Medicinal Chemistry (2002) 10:841-854.

Lombardi et al., "A majority of Huntington's disease patients may be treatable by individualized allele-specific RNA interference" Experimental Neurology (2009) 217(2): 312-319.

Hu et al., "Allele-selective Inhibition of Mutant Huntingtin by Peptide Nucleic Acid-Peptide Conjugates, Locked Nucleic Acid, and Small Interfering RNA" Oligonucleotide Therapeutics Ann NY Acad Sci (2009) 1175: 24-31.

Kurreck et al., "Antisense Technologies Improvement Through Novel Chemical Modifications" European Journal of Biochemistry (2003) 270: 1628-1644.

(56) References Cited

OTHER PUBLICATIONS

Liu et al., "Linking SNP identity to CAG repeat length in Huntington's Disease patients," Nature Methods (2008) 5(11): 951-953.
Macdonald et al., "A novel gene containing a trinucleotide repeat that is expanded and unstable on Huntington's disease chromosomes" Huntington's Disease Collaborative Research Group, Cell (1993) 72(6):971-983.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
Nasir et al., "Targeted disruption of the Huntington's disease gene results in embryonic lethality and behavioral and morphological changes in heterozygotes" Cell (1995) 81(5):811-823.
New England Biolabs 1998/99 Catalog (cover page and pp. 121 and 284).
Orum et al., "Locked nucleic acids: A promising molecular family for gene-function analysis and antisense drug development" Curr. Opinion Mol. Ther. (2001) 3:239-243.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Schwarz et al., "Designing siRNA that distinguish between genes that differ by a single nucleotide" PLOS Genetics (2006) 2(9): p. e140.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Pfister et al., "Five siRNAs targeting three SNPs may provide therapyfor three-quarters of Huntington's Disease patients," Current Biology (2009) 19:774-778.
Ostergaard et al. "Rational design of antisense oligonucleotides targeting single nucleotide polymorphisms for potent and allele selective suppression of mutant Huntingtin in the CNS." Nucleic Acids Res. (2013) 41:9634-50.
McWhinney et al., "Intronic single nucleotide polymorphisms in the RET protooncogene are associated with a subset of apparently sporadic pheochromocytoma and may modulate age of onset" J. Clin. Endocrinol. Metab. (2003) 88(10):4911-4916.
Southwell et al. "Antisense oligonuceltide therapeutics for inherited neurodegenerative diseases" Trends Mol Med (2012) 18:634-43.
Vickers et al., "Efficient Reduction of Target RNAs by Small Interfering RNA and Rnase H-dependent Antisense Agents. A comparative analysis." J Biol. Chem. (2003) 278:7108-7118.
Takagi-Sato et al., "Fine-tuning of ENA gapmers as antisense oligonucleotides for sequence-specific inhibition" Oligonucleotides (2007) 17(3): 291-301.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Van Bilsen et al., "Identification and allele-specific silencing of the mutant huntingtin allele in Huntington's disease patient-derived fibroblasts" Human Gene Therapy (2008) 19:710-718.
Wahlestedt et al., "Potent and nontoxic antisense oligonucleotides containing locked nucleic acids" PNAS (2000) 97:5633-5638.
Warby et al., "CAG expansion in the Huntington disease gene is associated with a specific and targetable predisposing haplogroup" The American Journal of Human Genetics (2009) 84(3):351-366.
Woolf et al., "Specificity of antisense oligonucleotide in vivo" PNAS (1992) 89:7305-7309.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
European Search report for application EP 09741640.8 dated Dec. 11, 2012.
European Search report for application EP 11740542.3 dated Aug. 14, 2014.
European Search report for application EP 11740543 dated Sep. 18, 2013.
International Search Report for application PCT/CA2009/000645 dated Aug. 25, 2009.
International Search Report for application PCT/US11/24103 dated Jul. 15, 2011.
International Search Report for application PCT/US11/24104 dated Jul. 20, 2011.
International Search Report for application PCT/US14/14722 dated Aug. 25, 2014.
Extended European Search report for application EP 17206749.8 dated Feb. 13, 2018.
Extended European Search report for EP 19161655.6 dated Aug. 29, 2019.
Extended European Search report for EP 19164928.4 dated Sep. 17, 2019.
Extended European Search report for EP 19191293.0 dated Feb. 24, 2020.
Extended European Search report for EP 21161967.1 dated Nov. 12, 2021.
Extended European Search report for EP 22166711.6 dated Dec. 13, 2022, 9 pages.
Banait et al., "DNA and RNA analogues—oligonucleotide phosphoramidates with bridging nitrogen" Expert Opinion on Therapeutic Patents (2002) 12: 543-559.
Bertrand et al., "Comparison of antisense oligonucleotides and siRNAs in cell culture and in vivo", Biochem Biophys Res Commun, (2002) 296: 1000-1004.
Database European Nucleotide Archive [Online] Stein Nils: "HDP08C05T HDP Hordeum vulgare subsp. Vulgare cDNA clone HDP08C05, mRNA sequence" (2007) accession No. EX591233, 2 pages.
Extended European Search report for EP 23181830.3 dated Feb. 26, 2024, 12 pages.
Lennox et al., "Characterization of modified antisense oligonucleotides in Xenopus laevis embryos" Oligonucleotides (2006) 16: 26-42.
Miroshnichenko et al., "Mesyl phosphoramidate antisense oligonucleotides as an alternative to phosphorothioates with improved biochemical and biological properties" PNAS (2019) 116: 1229-1234.

* cited by examiner

FIG. 1 A

```
CLUSTAL 2.0.12 multiple sequence alignment

genome          GCCCAGCAGGTGTCAGCCTCATTTTACCCCGCCCCTATTCAAGATGAAGTTGTTCTGGTT 60
mRNA            ------------------------------------------------------------

genome          CCAACGCCTCTGACATATTAGCTGCATCATTTTACATTTCTTTTTTTTTTTTCCTTTTAA 120
mRNA            ------------------------------------------------------------

genome          ATGGGGTCTTGCTCTGTCACCCAGGCTGGAGTGCTGTGGTATGATCTCGGCTCACTGCAA 180
mRNA            ------------------------------------------------------------

genome          TCTCCACCTCCGAGGTTCCAGCGATTCTCTTGCCTCAGCCTCCCGAGTAGCTGGGACTAC 240
mRNA            ------------------------------------------------------------

genome          AGGCACCCACCATCATACTGGGCTAATTTTTGTGTTTTTAGTAGAGATGGGGTTTCCCCA 300
mRNA            ------------------------------------------------------------

genome          TGTTGCCCAGGCTGATCTCAAACTCCTGGGCTTAAGCAATACAGCCGCGTTGGCCTCCCA 360
mRNA            ------------------------------------------------------------

genome          AAGTGTTGGGATTACAAGCATGAGCTACCCCACCCAGCTCATTTTACATTTCCACTTGTT 420
mRNA            ------------------------------------------------------------

genome          AAACTGAAAACTGGCCCGAGAAAGCTTCTGTACTGCCATCCTTGCGTCCTTGCAGATGAA 480
mRNA            ------------------------------------------------------------

genome          TCGTAACCTAGCATAGTAGGTAGGCAGACTGAAAACCTAACTTAGCAGTAGGCTTCTGTA 540
mRNA            ------------------------------------------------------------

genome          ACAACAGCTGTGTCTCAGCCAGTTCCTGCAGCCAGACTTCAACCACTCACAGGCCGCAAA 600
mRNA            ------------------------------------------------------------

genome          CTGTTCAAACTGTGTTCGGAGAAGGCGAATTCATCTGGCTGTTAACGTGCCTCACTTCTG 660
mRNA            ------------------------------------------------------------

genome          CTTTCTGTGGCCACTTTCCCTTTTCTGTCCATAAATTTGCTTTGACCACACAGCATCCCT 720
mRNA            ------------------------------------------------------------

genome          AGAGTCTCCCTGAATCTGCTGTGATTCTGGGACCTGCACCATTTGTGAATTGTTTTTTTT 780
mRNA            ------------------------------------------------------------

genome          TTCCTTGATCAGCTAAACTCTGTTCAATTCAATTTGTTGGAAGTTTTTAACATACCAATG 840
mRNA            ------------------------------------------------------------

genome          GTGCACCAAGGTTCCAATTTCTCCACTTCCTCATAAATAAGTCATTTTAAATGGCTTTTC 900
mRNA            ------------------------------------------------------------

genome          AGTATTCCAATATTTGGAAGTATTAATGTTTCTACCAATTTTCTATTTTTGGACATTGAG 960
mRNA            ------------------------------------------------------------

genome          GTTGTTTCATTTTTTTTTTCTTTTTTTGAGACAGAGTCTCGCTCCGTCACCCAGGCTGGA 1020
mRNA            ------------------------------------------------------------

genome          GTGCAGTGGCCTGATCCCGGCCCACTGCAACCTCCACCTCCCTCCTCAGCCTCCTGAGTA 1080
mRNA            ------------------------------------------------------------

genome          GCTGGGATTACAGGTGCATGCACCACCACACCCAGCTAATTTTTGTATTTTTAGTAGAGA 1140
mRNA            ------------------------------------------------------------

genome          TGGGGTTTCACCATGTTGGTCAGGCTGGTCTCAAACTCCTGACCTCAGGTGGTCCACCTG 1200
mRNA            ------------------------------------------------------------

genome          CCTTGGCCTCCCAAAATGCTGGGATTACAGGCCTGAGCCACTGCGCCTGGCCTCATCTTC 1260
```

FIG. 1 B

```
mRNA      ------------------------------------------------------------

genome    TTGATATTAATGTTGCTTTAACATCTTTGTCCCTGTGTTTTTTGTTTTTTTTTTTGAGAC 1320
mRNA      ------------------------------------------------------------

genome    GGAGTCTCATTCATTCTGTCACCCAGGCTGGAGTTCAGTGGCGTGATCTCAGCTCACTGC 1380
mRNA      ------------------------------------------------------------

genome    AACCTCTGTCTCCTGGGTTCCAGTGATTCTCCTGCGTCGGTCTCCTGAGTAGCTGTGTTC 1440
mRNA      ------------------------------------------------------------

genome    CTGGGTCTTTCGATGGTTATTTAATACTTCCCTACAGTAATGCCCTGTGCGTACATGCTA 1500
mRNA      ------------------------------------------------------------

genome    AGTGTGATGAAATGGTTGGCACAGTTAAATCTTTTGAAAGACATTGCCAAGTCACTCTTC 1560
mRNA      ------------------------------------------------------------

genome    AGAAAAGTGATAGGAGGTCATAGCAATTTTAAGAAGTCCTCATTTCTACATTTCCTTACT 1620
mRNA      ------------------------------------------------------------

genome    AATCTCGGTTGGTGTCTCTTCAATCTTTCCTCACACTTTTCTTGGGTTTTTCCTGAATCA 1680
mRNA      ------------------------------------------------------------

genome    TGAGTCTACTACATTTACACATTTTAAAGCATCTTTAGAAACAGGATCTCATTTTGTTGC 1740
mRNA      ------------------------------------------------------------

genome    CCAGGCTAGAGTTTGGTGGCATGATTATAGCTCCTCATACTCCTGGGCTCAAGTGATCCT 1800
mRNA      ------------------------------------------------------------

genome    TCCACCTCTGAAACCCCAAAATTTGAGAAAGGTCTCATTTAATTTAGAAAGTTTATTTTG 1860
mRNA      ------------------------------------------------------------

genome    CCAAGGTTGAGGGTGCACACCTGTGATGATATACGAGTTAAAAAGAAATTATTTAGGCAG 1920
mRNA      ------------------------------------------------------------
                                                 rs2857936
genome    ATACTGAGGGTAAGAAAGTCCTCGGTAAGGTTTTCTTTTCAATGAAAAGCAGCCCCCAAG 1980
mRNA      ------------------------------------------------------------

genome    CATTTTCTTTTCTAACAAAGAGCAGCCTGTAAAATCGAGCTGCAGACATACACAAGCAAG 2040
mRNA      ------------------------------------------------------------

genome    CTGGAAGCTTGCACAGGTGAATGCTGGCAGCTGTGCCAATAAGAAAAGGCTACCTGGGGC 2100
mRNA      ------------------------------------------------------------

genome    CAGGCAGATCCAACATGGCGGCTCCATCTTCCCTTTCCTTGTCAACCATGTGCACAGTAA 2160
mRNA      ------------------------------------------------------------

genome    GGAGCAGGCAACATAGTGTCCCCCGAGTAGAGACCAATTTGCATAATAAAAGGTGAGGGT 2220
mRNA      ------------------------------------------------------------

genome    AGGGTGGGCAGCTTCTTTGCATGCTATGTAAACATTATGCCTGGTCCAACCAATCTTTGG 2280
mRNA      ------------------------------------------------------------

genome    GCCCTGTGTAAATTAGACACCACCTCCTCAAGCCTGTCTATAAAACCCTGTCCATTCTGC 2340
mRNA      ------------------------------------------------------------

genome    CGCAGGCTGGAAGACCCACTGGGGCACCCCTCTCTCTCTATAGGAGACAGCTATTCATTT 2400
mRNA      ------------------------------------------------------------

genome    TTCTCTTTCTTTCACCTATTAAAGCTCCACTCTTAACCCCACTCCGTGTGTATCTATGTT 2460
mRNA      ------------------------------------------------------------

genome    CTTGATTTCCTTGGCATGAGGCAATGAACCTTGGGTATTACCCCAGAACCTTGGGTATTA 2520
```

FIG. 1 C mRNA ------------------------------------------------------------ genome TGCCACTTCAGTGACACAGCCTCAGGAAATCCTGATGACATGTTCCCAAGATGGTCGGGG 2580
mRNA ------------------------------------------------------------ genome CACAGCTTGGTTTTATACATTTTAGGGAGACATGAGACGTCAATTCATATATGTAAGAAG 2640
mRNA ------------------------------------------------------------ genome TACATTGGTTCCGTCCAGAAAGGCGGGGACAACTTGAGGCAGGGAGAGAGCTTCTAGGTC 2700
mRNA ------------------------------------------------------------ genome ACAGGTAGACAAATGGTTGCATTCTTTTGAATCTCCGATAAGCCTTTCCAAAGGAGGCAA 2760
mRNA ------------------------------------------------------------ genome TCAGAATATGCGTCTATTGACTGGGCGCAGTGGCTCATGCCTGTAATGCCAGCACTTTGG 2820
mRNA ------------------------------------------------------------ genome GAGGCGGAGGTGGGTGGATCACCTGAGGTCAGGAGTTTGAGAGCAGCCCGGCCAACATGG 2880
mRNA ------------------------------------------------------------ genome TGAAACCCTGTCTCTACTAAAAATACAAAAAATTAGCTGGGCGTGGTGGCGGGCGCCTGT 2940
mRNA ------------------------------------------------------------ genome AATCCCAGCTACTCGGGAGGCTGAGGCAGGAGAATAGCTTGAACCCAGAAGGAAGAGGTT 3000
mRNA ------------------------------------------------------------ genome GCAGTGAGCTGAGATGGTGCCATTGCACTCCAGCCTGGGCAACAAGAGTGAAACTCCATC 3060
mRNA ------------------------------------------------------------ genome TCAGAAAAAAAAAAAAAAGGCCTGGGCAAAGTGGCTCACGCCTGTAATCCCAGCACTTTG 3120
mRNA ------------------------------------------------------------ genome GGAAGCCGAGGCGGGCAGGTCACAAAGTCAGGAGATTGAGACCATCCTGGCTAACATGAT 3180
mRNA ------------------------------------------------------------ genome GAAACCCCATCTCTACTAAAAAATACAAAAAACTAGCTGGGTGTGGTGGCGAGCACCTGT 3240
mRNA ------------------------------------------------------------ genome AGTCCCAGCTACTCGGCAGGCTGAGGCAGGAGAATGGCGTGAACCGGGGAGGCGGAGCTT 3300
mRNA ------------------------------------------------------------ genome GCAGTGAGCCGAGATCACACCACTGCACTCCAGCCCGGACGACAGGGCAAGACTCTATCT 3360
mRNA ------------------------------------------------------------ genome CAAATTAAAAAAAAAAAAAAAAAAAAAAAAAAAGAGAGAGAGAATATGCATCTATCTCAG 3420
mRNA ------------------------------------------------------------ genome TGAGCAGAAGGATGACTTTGAATGGAATGGGAGCAGTTCCTAGCTTGAACTTCCCCTTTA 3480
mRNA ------------------------------------------------------------ genome GCTTCAGTGATTTGGGGGCTCAAGGTATGTTCCTTTCACATACCTCAGCCTCCCAAGTAG 3540
mRNA ------------------------------------------------------------ genome CTGGGACCACAAGTGCATGCCACCACACGTGGCTAATGTTTTATTTTTTTTGTAGGAATA 3600
mRNA ------------------------------------------------------------ genome GGGTCTCACTATGTGTCCAGGCTGGTCTAAAACCCCTGAGCTCAAATGGTCCTCCCGCCT 3660
mRNA ------------------------------------------------------------ rs12506200 genome CAGCCTCCCGAAATGCTGGGATTACAGGCATGAGCCAGCATGCCCGGCCTAGTCTACATT 3720
mRNA ------------------------------------------------------------

FIG. 1 D

```
genome          TTTATAAATTGCTAATTCAAAGTTCCCTCTCCAAAACCTCATGGTTTTCCCTGTTCTCAT 3780
mRNA            ------------------------------------------------------------

genome          CCCCTGCACCCTCCCTTCCCCTGGAGTACTCACCTGGCCTTGGAGGTCTGGTGTGAGCCC 3840
mRNA            ------------------------------------------------------------

genome          GGACTTCGATTCTAGGCACAGCATGTGATGAGCGCCCCCAGGTCAAACACCTCCCCTCTG 3900
mRNA            ------------------------------------------------------------

genome          CGGCCTGTGCTTCACCGCCTTGACAGTGAGAAAGGTCTCCCTTCGGCTCATTCTCGAAGT 3960
mRNA            ------------------------------------------------------------

genome          CTCAAACTTCACTTCTCCTGTGCGCTGATTCTGAATTCAGCCCCCGTCCAAGGTCCTGGC 4020
mRNA            ------------------------------------------------------------

genome          CCCTTTCTCTTCTGCTTGGCGTGTTGTTCATCACCACTGTGCACTGCTGAGGGTAAGTGC 4080
mRNA            ------------------------------------------------------------

genome          GGTTCTCTGGACCTCTGCTTTATCATTAGAACAGACTCTTGCGGTTTCCCACGACATTCC 4140
mRNA            ------------------------------------------------------------

genome          TTTCACTTCTCACTTGGAAGATGAGCCGTGAGGAAATCCTGTGTTGTGTGGTATGTGGGC 4200
mRNA            ------------------------------------------------------------

genome          TGTGCTTCTGCTTGACTTGAGGGCCAAGCAGCATTGCAAGCCATGGTTTTAAATAAGAAA 4260
mRNA            ------------------------------------------------------------

genome          GAACATTTCTAACCTTCATCTTCTAGTAAGGAAACAAGTGGGCTTTAGAGTTCTTGCTCA 4320
mRNA            ------------------------------------------------------------

genome          GGAAAGACCTATGTCCCAGTCCAACCGGACCTTTTACTAAAGAGATCTTCCTGATCCTCC 4380
mRNA            ------------------------------------------------------------

genome          TCCCCAGGCCAGGGGAGGGGTCCTCCCTGGGGTTGGAGCCTTTAGTAGGGGGTCGGAGAC 4440
mRNA            ------------------------------------------------------------

genome          ACGACGTAGCCTTCATGACATTCATAGTCTAGTTACACGATCCCTGTAAGGGTCAGTTGA 4500
mRNA            ------------------------------------------------------------

genome          AGTAAGTGCTACAAAGGAAGGGAGGTGCTCAGTGGAGAGGGCTCTCTTTTATGTATTATA 4560
mRNA            ------------------------------------------------------------

genome          TTTCTTTCATGGGGAGGGATATGGATCAGGGATCAGCAGAGGTGTTTCAGTCCCGAGGGA 4620
mRNA            ------------------------------------------------------------

genome          AAGAAAGTCAGCGTGGCTTGGGAGTTGGGAGCAGCAAGACAGTGGCTCAAGATATCTTAA 4680
mRNA            ------------------------------------------------------------

genome          GACTAGTGGAGTACACCTTGCATGTTAAAAGCCTTGCTCAGGGCTGCCTGGTTCTTGTAG 4740
mRNA            ------------------------------------------------------------

genome          GACGACAGAGATGGCCTAGCTCTGCATACTGCACCCCCAGGGGCTCAGAACAGTGCAAAT 4800
mRNA            ------------------------------------------------------------

genome          GTCAGTCTATCTGTCAGTGGCAGAGCCAGCCTTGGAGCAGGGGTGCAAGGAGGTCTCTGC 4860
mRNA            ------------------------------------------------------------

genome          ACTGGCCAGGCATGCAGAACATTCTGTTCAGTAGCACTGGACAGAAGGCCCCATCTAGAT 4920
mRNA            ------------------------------------------------------------

genome          GAGACAGAGCTGGTGGGGCAGGACAAAGACTCCTGGCAGCTCAAACGGCCTGGCAGATGC 4980
mRNA            ------------------------------------------------------------
```

FIG. 1 E

```
genome    TTGGAGAGAGGGGGCTTCTTGAGACAGCACCATTTCTGGGAAGAGAGTCACCTGGGAGGG 5040
mRNA      ------------------------------------------------------------

genome    ATGAGGCCACGCTCCGGCTTGGAGGTGAAGAGAGGGGCTGCTGCAAGAAAGAATTAGAGA 5100
mRNA      ------------------------------------------------------------

genome    CATGCCAGCCTTTGCTGTGTTGCCCAGGCTGGTCATGAACTCTTGGCCTCAAGCAATCTT 5160
mRNA      ------------------------------------------------------------

genome    CCCACCTCAGCCTCCCCAAGCGCTGGGATTATAGACATGAGCCCCCATGCTGGCCAATAA 5220
mRNA      ------------------------------------------------------------

genome    AAGATGATTTTATGGAGGGGATGGTGGTGAAGGTTGTGGGTGGTATGAAATAGTAAGAAA 5280
mRNA      ------------------------------------------------------------

genome    TATATATTGGTCTGCACCCAGTTCCTGCCACAGAGCTCCTAAAATCCTGAGAACTTCCTG 5340
mRNA      ------------------------------------------------------------

genome    GGTGAGCATCTTTTGTTCTAATGAGGTGACTCTTGGTGGCTCCTGGATAGGAGTGAATCA 5400
mRNA      ------------------------------------------------------------

genome    CCAGAAAGATCAAGCCAGAGTTAGAAGCAGAAAGTGCTGGCTATAACACAGGAAAGCTGT 5460
mRNA      ------------------------------------------------------------

genome    AACACAAATAATAAAGTTTTTTTTTTTTTTTTTGAGATGGAGCCTCACTCTGTTGCCCAG 5520
mRNA      ------------------------------------------------------------

genome    GCTGGAGTGCAATGGTGCAATCTCAGCTCACTACAAGCTCTGCCTCCCAGGTTCAAGTGA 5580
mRNA      ------------------------------------------------------------

genome    TTCTCCTGCCTCAGCCTCCTGAGCAGTTGGGACTACAGGTGTGTGCCACCACATCTGGCT 5640
mRNA      ------------------------------------------------------------

genome    AATTTTTGTATTTTTAGCAGAGACGGGGTTTCACCATATTAACCAGGCTGGCCTCAAACT 5700
mRNA      ------------------------------------------------------------

genome    CCTTACCTTGTGATCCGCCTGCCTCAGCCTCCCAAAGTGCTGGGATTACAGGCATGAGCC 5760
mRNA      ------------------------------------------------------------

genome    ACCGTGCCTGGCCAAAAGACATTGTTCTTAAAAGAATCAACTAACTAACCAAATAAATAA 5820
mRNA      ------------------------------------------------------------

genome    AAATCTAACCTAATTAAGAAACTAAAAATACACAAAAATTAATTTCAAGGGGAGAAAAAT 5880
mRNA      ------------------------------------------------------------

genome    CATGTAAAGAGAGAAAGATAATGAATACTTTGCAGAAATTTATGAACATAAACATAAAAC 5940
mRNA      ------------------------------------------------------------

genome    TTGGATGAAATGCATTTCTAGGAAAACATAATTTATCAAAACTAACCACAAGTAAAATAG 6000
mRNA      ------------------------------------------------------------

genome    AAGCCTAAATAGGATATTTTCAAGAGAAGAAGTAAAGTTGTCAAAGTGCTACCCTTCAAA 6060
mRNA      ------------------------------------------------------------

genome    AAAACACCAGGCTCAAACAATCTGACATGGGAATGTTAGCACACCTTAGAGAGCAAATAA 6120
mRNA      ------------------------------------------------------------

genome    AACTTTGAATGGGCTTGAAATATTCCAGACTCTAGAAAAACAAAACTTCCCAATTCTTTT 6180
mRNA      ------------------------------------------------------------

genome    TATAAAGCAAGTATAAATTGATACCAAAATCTTATAAAGACCTTATACAAAACTTCATAC 6240
mRNA      ------------------------------------------------------------
```

FIG. 1 F

```
genome    CAATCTCTTTTATGAATACAAAACCCTTAATAAAGTATTACCAGACAGAACCCAACAATA 6300
mRNA      ------------------------------------------------------------

genome    CATAAAAATGTCACATCATAACATAGTGGGGTTTATTTCAATAATGCATGGATGGTTCAA 6360
mRNA      ------------------------------------------------------------

genome    TACAAGGAAATTCAGTAACACAATATAATAGATCATGTGAATATACCCAAAGAAAAAATA 6420
mRNA      ------------------------------------------------------------

genome    GATTATTTTCATAGATGCTGTAAAGGCATTTGACCAAATTCAACACCTACTTTTTAGGTG 6480
mRNA      ------------------------------------------------------------

genome    GTCAATAAAATAAATTAGTTACTCCTTCTTTAGCATGATAAAATATATTTATCAGCCCAG 6540
mRNA      ------------------------------------------------------------

genome    AAGGCATCATTTTACCCGATAAGGGCACACGCTGGAGGGAATAATGTTAAAATTAGGAAT 6600
mRNA      ------------------------------------------------------------

genome    AAGAGGATAGCTAGTTTCTTTCTTCTTTTTTTTTTTTGAGACGGAGTCTTGCTCTGTTGC 6660
mRNA      ------------------------------------------------------------

genome    CAGGCTGGAGTGCAGTGGTGCAATGTTGGCTCACTGCACGCCCCCCGCCTCCCAGGTTCA 6720
mRNA      ------------------------------------------------------------

genome    AGCGATTCTCCTGCCTCAGCCTCCCGAGTAGCTGGGACTACAGGCGCGCACCACCATGCC 6780
mRNA      ------------------------------------------------------------

genome    CGGCTAATTTTTTTTTGTATTTTAGTAGAGATGGGGTTTCACCATGTTGGTCAGGCTGGT 6840
mRNA      ------------------------------------------------------------

genome    CTTGAACTCCCAACCTCACGTACTGGGATTACCGGTGTGAGCCACCACGCCAGCCCAACT 6900
mRNA      ------------------------------------------------------------

genome    ACTTTCAACATTATCCTTAATACTGATGCTTATTGACTTACTATGGGGTTACCTCTAGAT 6960
mRNA      ------------------------------------------------------------

genome    AAATCCATAATAAGTTGAAAATATAAGTAAAAAATGCCCTTAATACACCTAACCTACCAA 7020
mRNA      ------------------------------------------------------------

genome    ACATCATAGCTGAGCCCAGCCTGCCTTAGCTATGCTCAGACACTGACGTCAGCCTACAAT 7080
mRNA      ------------------------------------------------------------

genome    TGGCAAAATCACACAGCAGCACAGTCTACTGCAGAGCATCTGCTGTTTGCCCTTGTGACT 7140
mRNA      ------------------------------------------------------------

genome    GCGTGGCTGCCTGGGAGCTTCCCAGCTTCACAAGACAGTATTACGTAGCACATCACTAGC 7200
mRNA      ------------------------------------------------------------

genome    CTGGGGAAAGATCAAAGTTGAAAATTTGAAGTGTGGTTTCCATTGAATGTGTACTGCTTT 7260
mRNA      ------------------------------------------------------------

genome    TGCACCATCATCAAGTCAAAAAATTTTAGTTGAACCAGCCTAAGTTTGGGACCATCTTTA 7320
mRNA      ------------------------------------------------------------

genome    TTTTCAGGAGGAACTTCCATGTACATTGATGACGGACGATAGAATCCGTTTCTATCATCC 7380
mRNA      ------------------------------------------------------------

genome    TAATGAACATAATGAATAAATCCAGACAAACATAAACATTAACAGAGTAAGCAGCTTTCG 7440
mRNA      ------------------------------------------------------------

genome    GGGCTGGAAGCCAGAAGAGGGTGGGAGCGCAGAGAGAGAGGCCAAACACCAGGGCTGCTT 7500
mRNA      ------------------------------------------------------------
```

FIG. 1 G

```
genome     CTGCTTTGCGGGTATTTGCTGATCTGGACAAGGTATCTGGAAGGCTGAGCTAAGCCTCCT 7560
mRNA       ------------------------------------------------------------

genome     TTTTTTTTGAGGTGGCGTCTCACTCTGTTGCCAGGCTGGAGTGCAATGGTGCGATCTCAG 7620
mRNA       ------------------------------------------------------------

genome     CTCACTGCAACCTCCACCTCCCTGGTTCAAGCGATTCTCCTGCCTCAGCCTCCCGAGTAG 7680
mRNA       ------------------------------------------------------------

genome     CTGGGATTACAGGCTCCCGCCACTACACCCAGCTGATTTTTGTAATTTTAGTAGAGACGG 7740
mRNA       ------------------------------------------------------------

genome     GGTTTCACCATGTTGGCCAGGATGGTCTCGATCTCTTGACGTCATGATCTGTCCACCTCG 7800
mRNA       ------------------------------------------------------------

genome     GCCTCCCAAAGTGCTGGGATTATAGGCGTGACCCACCGTGCCCCGTCTGAGCTAAGCCTC 7860
mRNA       ------------------------------------------------------------

genome     TTGAGCATAGGGGACTAAAAATGAAATCTAGCGCATGCCAAGTTTAGGGTCCCAGGCAAT 7920
mRNA       ------------------------------------------------------------

genome     TCCTTTCCACTTTGGGGTCCACTTTGGGGTCCACCCCACCCAAGAAGAAGGATGACTTGG 7980
mRNA       ------------------------------------------------------------

genome     AAGTAAACCAGCTCTGAAATATGGATGGTCCTCTGGGACCATACCAATCCCTTCATATCA 8040
mRNA       ------------------------------------------------------------

genome     ACCACATCCAGTTCCTCAAAACTGGAACTTGGATTAAGATGGCCTAGGACTTCTAGTGTC 8100
mRNA       ------------------------------------------------------------

genome     CCAGGAGCCTGGCATTGCAAACAAAAATCCTCTCCGGAAGAAGATAATACCTTAAGCTTC 8160
mRNA       ------------------------------------------------------------

genome     AAATGACTCTCTAATAAATTTCAAATACAATGTCCAGCACACAAACACAAATTACCAGGA 8220
mRNA       ------------------------------------------------------------

genome     ACGTGATATGAGGCCTGATGGATGGGAATTAGCAGAAACTTCAGGCATGAGAAACATACC 8280
mRNA       ------------------------------------------------------------

genome     CTCAGAGGCCTAGAATCTATCTAGTGTCTAGATAATGGAGATATGAAATACAGACACTTA 8340
mRNA       ------------------------------------------------------------

genome     AACAACTATGTTTCCCATGTTCAAAGAGGAAATTTGCAAAACTTGAAAGTGTTGGCAGGA 8400
mRNA       ------------------------------------------------------------

genome     AATCAGAAACTATAAAATGTGACAACAGCATACTTTAGAGTCAGTATAAATTACGGTCCC 8460
mRNA       ------------------------------------------------------------

genome     GAAAACTGCAGAATTCCAGAACTTAATGGTAAAGCAAGGGTTTAACAGCAGAATAGAAAT 8520
mRNA       ------------------------------------------------------------

genome     AGCCAGAGAGAACTAGGAAGTAAGTCAGATGACACTACCCAGAATAAGGCACTGAGAGGC 8580
mRNA       ------------------------------------------------------------

genome     CAAGGAATGGAAAATGCAGAAGAAAGGATATGGTGAGAGGATCTAATATACATTTATTTG 8640
mRNA       ------------------------------------------------------------

genome     GAGTACCAGGGAGAGAGAGAAGGAGAAGAACAGAAGCCGTGTTTCAAGGACGGTGACTGA 8700
mRNA       ------------------------------------------------------------

genome     GAGGCTTCGAAACTGATGAAAGCCATCAGTTCACAAATTCAAAGCCCAGTGAATTCCAAG 8760
mRNA       ------------------------------------------------------------
```

FIG. 1 H

```
genome   GAGAAAAAAAGAAATCCATACTGTGAAAGCAAGTCCAGACAATGACAAACACCATCAACA 8820
mRNA     ------------------------------------------------------------

genome   ATACACAGGACAGGCATAAGATGCATTTAATGGGGACACTCAGAGGCAGAGGGTTATCAG 8880
mRNA     ------------------------------------------------------------

genome   AAGGAGGCACTTCTCTCCCAAGTTCTCATCATCCCAGGGCCAGGGACAGCTGGTCACACC 8940
mRNA     ------------------------------------------------------------

genome   TTAGGGAGTTCACTAGGAGAGGGATCTGGCTTCTTGTCATTCTGGGTATTTGTAGGGAAA 9000
mRNA     ------------------------------------------------------------

genome   TTGGAAGGGAACCGAGAGCACCTAGCCAATCGCATAGCAATGGGAGATTTCAGGCTGTGG 9060
mRNA     ------------------------------------------------------------

genome   GGAATGTCTTTGCTGGTGAAAAGAACATCCTGACCTTAGAAATCTTTCACCGAGGGGGAT 9120
mRNA     ------------------------------------------------------------

genome   CTGCGTTCCAGAACTTCTGGAGCTGGTATAGGTAAGGCTTTGAGCTTTCCTACTGAGCCA 9180
mRNA     ------------------------------------------------------------

genome   GCCTGTTGCTAGGTTACCAAAGGGGACCTCGAGGGCCATCTGGCCAACAAGCAGACTTGT 9240
mRNA     ------------------------------------------------------------

genome   CTCTCCTTACACCCCCAGACGTATCACTGCAAAACTACAGAAAACCAAAGACAGAGAAAA 9300
mRNA     ------------------------------------------------------------

genome   TCTTAAAAGCAGCCAGATTTAAAAAATGGCATATTAGTTTCAAAGCAGCAGCCATGAAAT 9360
mRNA     ------------------------------------------------------------

genome   TGACAGCTGATGTCTCAACAGCAAGAATGAAAAGTGGAAGACAGGCCAGGTGTGGTGGCT 9420
mRNA     ------------------------------------------------------------
genome   CAGGCCTGTAATCCCAGCACTTTGGGAGGCCGAGGCGGGTGGATCACGAGGTCAGGAGAC 9480
mRNA     ------------------------------------------------------------

genome   CAAGACCATCCTGGCTAACATGGTGAAACCCCGTCTCTACTAAAAATACAAAAAATTAG 9540
mRNA     ------------------------------------------------------------

genome   TCGGGCATGGTGGTGGGTGCCTGTAGTCCCAGCTACTCGGGAGGCTGAGGCAGGAGAATG 9600
mRNA     ------------------------------------------------------------

genome   GCGTGAACCCGGGAGGCGGAGCTTGCAGTGAGCCGAGATTGTGCCACTGCACTCCAGCCT 9660
mRNA     ------------------------------------------------------------

genome   GGGTGACAGAGCAAGACTCTGTCTCAAAAAAAAAAAAAAAAAAAAAAAAAAAAGGGTGAC 9720
mRNA     ------------------------------------------------------------

genome   GAAGCTTCAATCTCCTGAAAGGAAGCAACTGCCGCCTTTGATTCGATACCCACCAAAATC 9780
mRNA     ------------------------------------------------------------

genome   CGTGAAGAAGGAAGGCAAAATAAAAACACTTCCTGATTGAACTGGAAAGATTTCCGCAAT 9840
mRNA     ------------------------------------------------------------

genome   AGAAGACCCACTGTCCAAGGAATTCTAAAGGATGCTTTCCAGGCAGAAGAAAATGACCCC 9900
mRNA     ------------------------------------------------------------

genome   AGAGGAAGATCAGAGATTCAGGAAAGAAATGGAGAGTGATAAAAATGGAAAATTCGGGGG 9960
mRNA     ------------------------------------------------------------

genome   CCAATTTAAACAAAAGCTGACTGCTCTACAACTGTTGTGTCTCTATCTTTTGTAACATAT 10020
mRNA     ------------------------------------------------------------

genome   ATGTGTGTGTAGCTTTTTTTTTTTTTTTTGTCAAGATGGATTCTCACTCTGTCGCCCAGG 10080
```

FIG. 1I

```
mRNA       ------------------------------------------------------------

genome     CTACAGTGAAATGGCACGGTCTCGGCTCACTGCAACCTCTGCCCCTTGGGCTCAAATGAT 10140
mRNA       ------------------------------------------------------------

genome     TCTCTTGCCTCAGCCTCCTGAGTAGCTGAGATTACAGGTGCCTGGCACAATGCCTGGCTA 10200
mRNA       ------------------------------------------------------------

genome     ATTTTTGTATTTTTACTAGAGATGGGATTTCTCCATGTTGGCCAGGCTGGTCTTGAACAC 10260
mRNA       ------------------------------------------------------------

genome     CTGACCTCAGGTGATCCACCTGCCTGGGCCTCCCAAAGTGCTAGGATTACAGGCGCGAGC 10320
mRNA       ------------------------------------------------------------

genome     CACTGCATCTGGCCTATGTGTGTGTTTATATGGAATTAAAACACATGGCAATAATACCCT 10380
mRNA       ------------------------------------------------------------

genome     CCAAATTGGGAGAAACCAAAAATAGCATTTAAATGTTGTAAGCTCCCTGCATAATCAAGA 10440
mRNA       ------------------------------------------------------------

genome     AGAGAATAGATTTACGTTAGATTTTGATACCTGGAGGATGAATGTTGTAATTTCTAGGGT 10500
mRNA       ------------------------------------------------------------

genome     GACCATGAAAAGAGGAGACAACGGTGTATGTTTTTTTTTTTTTGAGATGGAGTCTCACTT 10560
mRNA       ------------------------------------------------------------

genome     TGTCACCCAGGCTGGAGTGTTGTGGTGTGATCTTGGCTCACTGCAACCTCCTCCTCTTGG 10620
mRNA       ------------------------------------------------------------

genome     GTTCAGGCCATCCTCCCACCTAGGCCTCCAGAGTAGGTGGGATCACAGGCACCTGCCACC 10680
mRNA       ------------------------------------------------------------

genome     ACACCTGGCTAATTTTTTTTTTTTTTTAAATATTTAGTAGAGATGGGGTTTCACCATGTT 10740
mRNA       ------------------------------------------------------------

genome     GGCCAGGCTGGTCTTGAACTCCTGACCTCAGGCGATCTGCCTACCTCTGCCTCTCAAAGT 10800
mRNA       ------------------------------------------------------------

genome     GCTGGGATTACAGGTGTGAGCCATCGCGCCCGGCCAACAGTGATCACTTTCAAACTAACA 10860
mRNA       ------------------------------------------------------------

genome     GAGGTTCAAAAATAAAATCAGACTTAACCAAAAACCAGGTAACAGAGCTGGTAGGATATA 10920
mRNA       ------------------------------------------------------------

genome     CAGAAAGACTGACCTCACGTATATCAACGATTACAGTTAATATTAATGAAGGAAATGCTC 10980
mRNA       ------------------------------------------------------------

genome     TAGTTTAAAAACGAGGGTTGTCAAAGACCCCACATAAGAAGCTCCTTACCAGCGGTGCAC 11040
mRNA       ------------------------------------------------------------

genome     CTAGAACCTAAGGAAACAGGACAGATGAAGGAGGACGCGCCCCCGCCGCTGTCCTGCGCC 11100
mRNA       ------------------------------------------------------------

genome     TCAGCCATCCTATGAGACGGGAAAGGTTTCTGTCTGCAGCTGGGCCCGTGCTCTTTACCA 11160
mRNA       ------------------------------------------------------------

genome     GCTCCTGGCTTTCTTCTCTGGAAGGTTCCTGCCTGTTTTGCCCTCACACCTGCTCCTCTC 11220
mRNA       ------------------------------------------------------------

genome     TCAGCCCTCTCAGGGGTGGGGCTGGAGGCCACCAAAGAGCCTCCTCTGCTCTCCAGTTGC 11280
mRNA       ------------------------------------------------------------

genome     TCGACTGCTCCTCATTTCCCCCTGGGGTCTGCGTCAGGGTTTCCTTCTTTTCCAGCCCCA 11340
```

FIG. 1 J

```
mRNA            ------------------------------------------------------------

genome          CCCCGCGTGCATCCCACCTGGTCTCGGGTCGGGGCTGCTCCCGCTTACTGCCCCCTGCCC 11400
mRNA            ------------------------------------------------------------

genome          AGGCTGGTGTGCACCCCCTCTGGCTGCTTTCAAGGCCTCTTCTCTCTTCTCGGCAGGACA 11460
mRNA            ------------------------------------------------------------

genome          GGCACAGGCAGGTGGCCAGGTGTCATGCTTAGCTCCCCGCCCAGTGAGATTCTTTCATTT 11520
mRNA            ------------------------------------------------------------

genome          AACAATCTTCCCCTGAATAGTTCATGTTCATTGCTGAAAATTTGAAAAATATGGAAAAGC 11580
mRNA            ------------------------------------------------------------

genome          ACAAAGATTAAGATATAAACCGCCCTCAATTCCCCTGCCCAGAGAGAGTCACTGCTATGA 11640
mRNA            ------------------------------------------------------------

genome          CTTGGTGACTAGGAACCTTATTTCTCTCTCGCTCTTTTTTTTTTTTTTGAGACAGAGTCT 11700
mRNA            ------------------------------------------------------------

genome          TGCTCTGTCACCCAGGCTGGAGTGCAGTGGCTCGATCTCAGCTCACTGCAACCTCCGCCT 11760
mRNA            ------------------------------------------------------------

genome          CCTGGGTTCAAGCGATTCTCCTGCCTCAGCCTCTTGAGTAGCTGGGATTACAGGCACCTG 11820
mRNA            ------------------------------------------------------------

genome          CCACCATGCCCGGCTAATTTTTGTATTTTTAGTTGAGAGAGGGTTTCATCTTGTTGGTCA 11880
mRNA            ------------------------------------------------------------

genome          GGCGGACTTGAACTCCTGACCTCAGGTGATCAGCCCACCTCGGCCTCCCAAAGTGCTGGG 11940
mRNA            ------------------------------------------------------------

genome          ATTACAGGTGTGAGCCACTGCGCCTTCATCTCTCTTCTGTGTATGTGTACGCTGTTTTTT 12000
mRNA            ------------------------------------------------------------

genome          CTTTAGAATGGGGGACGTTATCAGGCTCTACATGGTGTGTAGTCGGCTAGCATGTTGTAA 12060
mRNA            ------------------------------------------------------------

genome          GCCTTTCCCTGTGTCACAAGTGCTCATCTGGAACAGGATTCTAATGACTGCCTGTGGCTA 12120
mRNA            ------------------------------------------------------------

genome          TGTTGGGATTCCTTTAACTCAGCTCCTTCTGCCCAGCATCTATCTTTTTTCCATCTTTTG 12180
mRNA            ------------------------------------------------------------

genome          TCCTAAGTGTTGCTATAATAAATCATTGATCACACATGCCTGACTGTTTGCATAGGATAA 12240
mRNA            ------------------------------------------------------------

genome          ATTACGGGAAATGTTTTTGCTGTTCAGGGACTGTGCCCATTTTTAGGCCTCAGAGACACC 12300
mRNA            ------------------------------------------------------------

genome          ATGCCAGACTGCCCAGTATTGATCTTTACTCTTTTTAGATGATGCCAAACTTTTCTGTGA 12360
mRNA            ------------------------------------------------------------

genome          ACTTTAAAAACCTGTGTCTTGACAGTCCATTTCTGTAAGTCTTTCACATTAGATTTCCTG 12420
mRNA            ------------------------------------------------------------

genome          TCAGGATGATAGTCAATTCTAGGCAGATGATGTTTTCTCAGCCATGGCTGAAGCAGTTGT 12480
mRNA            ------------------------------------------------------------

genome          GATTTGTTGTGGCCATGTAAAGTCCCGATGATCCATTGCCTCCCTGGATGGGTTGGAATA 12540
mRNA            ------------------------------------------------------------

genome          ATTTGGTTTGGGAGCATATAACAGAATGACCTGGAGTCACAGCAGCTCAGACGGAAGTGT 12600
```

FIG. 1 K

```
mRNA     ------------------------------------------------------------

genome   ATTTCTCCCTTACAGATGAAAGAATTCCAGGCCAGGCTGGAATGACAACTGCACACAGTC 12660
mRNA     ------------------------------------------------------------

genome   ATCTGGGCCCCCTCCTTCCAGCTCCCATCACCCCAGGATGTGGCTTTTATGCAGATGATC 12720
mRNA     ------------------------------------------------------------

genome   CAAAATGGCTGCTCAAGTCCCAGCCAACACATCCCATTCCAGGGAGCAGGAAAAAGGTGT 12780
mRNA     ------------------------------------------------------------

genome   GTCTTTCCCTTCATTTTATGTGATTCCTTTCTAGAAGTACTACTCATTACTTCTGCTTGC 12840
mRNA     ------------------------------------------------------------

genome   ATCTCCCTGGCTAGCACTTACTTAGTTATATGGCCATAGCTAGCTGAAGGAAGGACAGGG 12900
mRNA     ------------------------------------------------------------

genome   ACTGTCATACACTAGCTAAGAGGCAAACTGCTTAGATAAAAAGGTCTCTAAAGAAGGTCA 12960
mRNA     ------------------------------------------------------------

genome   GAGCGGCTGCTAGGGTGCAACTCTATTACTTATTGTTATGGGACGAACTGTGTCCCTCAT 13020
mRNA     ------------------------------------------------------------

genome   TCAGGTTGATGTCCTAAGCCCCAGAACCTCAGAATGGGATTGTATTTGGAGACAGGTTCT 13080
mRNA     ------------------------------------------------------------

genome   TTAAGGAGGTAAGGAGGCTAAAATGAGATCATTAGGGTGGGCCATAATCCGACTGATGTC 13140
mRNA     ------------------------------------------------------------

genome   TTACAAGAAGAGATTAGGACACGGACATGCTCAGAGGGACGGCCACGTGAGGACACCAAG 13200
mRNA     ------------------------------------------------------------

genome   AAAGGCAGCTGTCTGCAAGTCAAGGACAGGGCTCAGGGGAAACCAACCTTGCCAACACCT 13260
mRNA     ------------------------------------------------------------

genome   TCATCTCGGACTTCTAGCCTCTAGGACCATGAGAAGATACATTTCTGTTGTTTAAGCTGC 13320
mRNA     ------------------------------------------------------------

genome   CCGGTCTGTGGTACTTTGTTATGGCAGCCCAAGTAAACAAATACAGTCATCTGCTGCTGG 13380
mRNA     ------------------------------------------------------------

genome   AACAAATCACCCCAGCACTGTGGCTTGGCAGCACACATGTCTAGTCATAGAGTTATATGT 13440
mRNA     ------------------------------------------------------------

genome   AGTTACGTGTAGAGCCATATGTATCGTCACACGTTCTGTGGGTCAGGAATTTGGACCCAG 13500
mRNA     ------------------------------------------------------------

genome   CTTAACCAGCTCCACTTCTCGCCAGGGTTCAGTCAAATACCAGCTGCCTCCCACCTGAGA 13560
mRNA     ------------------------------------------------------------

genome   GCTCAGCCGGGGAAGGGTCCCTTTCCAATCTCACGTGGTGTTGGCAGGATCCAGTTCCTC 13620
mRNA     ------------------------------------------------------------

genome   ATGGCCTGCTGGACTGAGAACCTCAGTTCTCACTGCCTGTTGGCCAGAGGCCGCCTTTAT 13680
mRNA     ------------------------------------------------------------

genome   GTCCTCGCCATGTGGGCCTCTCCAACATGGCAGCTGACTTCATCAGAGCATCCATGCCAA 13740
mRNA     ------------------------------------------------------------

genome   GAAGGCAACAGAGAGGGCCAGGGAGACTGAAGTCATACCCTTTTGCGACCTAGTCATGGG 13800
mRNA     ------------------------------------------------------------

genome   GTGACATTCCATCACCTTTGCCCATTGGTTAGAAGCAGGCCACCAGGTACAGCCCAAGCT 13860
```

FIG. 1 L

```
mRNA      ------------------------------------------------------------

genome    CACGGGGAGGGGTCATACAAGGGTGTCAATACCAGGAGGTGAGGGGTGCTGGGGCCATCT 13920
mRNA      ------------------------------------------------------------

genome    TATGAGTCTGCCCACTGAGGTAACTAACAACCTTGAGGCCTGACACAGTGGACAAAGGCC 13980
mRNA      ------------------------------------------------------------

genome    CTTATTAACAGCAGAGAACTGGGAACTTTATTTATTTATTTATTTTTGAGACAGAGTCTC 14040
mRNA      ------------------------------------------------------------

genome    ACTCTTGTCACCCAGGCTGGAGTGCAATGGCATGATCTTGGCTCACTGCAACCTCCACCT 14100
mRNA      ------------------------------------------------------------

genome    CCCAGGTTCAAGCAATTCTGCCTCAGCCTCCGGAATAGCTGGGACTACAGGCATGCACCA 14160
mRNA      ------------------------------------------------------------

genome    CTACACCCGGCTAATTTTTGTATTTTTAGTAGAGACAGGGTTTCGCCATGTTGGCCAGGC 14220
mRNA      ------------------------------------------------------------

genome    TGGTCTCGAACTCCTGACCTCTGGTGATCTGCCTGCCTTGGCCTCCCAAAGTGCTGGGAT 14280
mRNA      ------------------------------------------------------------

genome    TACAGGCGTGAGCCACCGCACCTCGCTGGAACTTAATTTTTTTAGAGACAGTGTCGCTCT 14340
mRNA      ------------------------------------------------------------

genome    ATCACCCAAGCTGGAGTGCAGTGGTGCAATCCTAGCTCACTTGCAGCCTCAAATTCCTGG 14400
mRNA      ------------------------------------------------------------
                                                      rs762855
genome    GTTCAGGTGATCCTCCCACATCAGCCTCCCAAGAACTGGGAACTAACAGCTGTTTCTCTG 14460
mRNA      ------------------------------------------------------------

genome    CTGTCCTTCTCAAGAAAAGGGAGGCTACTGCTACCCCACTGGGGACAATGCTGGGTTTCC 14520
mRNA      ------------------------------------------------------------

genome    CTTTAGGACAGGCTCTGAGACAAGGCGGAGGTGCTGTTTGTGGCCACAGAGCAGGGGACT 14580
mRNA      ------------------------------------------------------------

genome    CTGGGTTGCAGGTGTGGCCTGGCTAAAGTAGGCTTTACTGGGCTCCTCTCTGCCTGCATC 14640
mRNA      ------------------------------------------------------------

genome    ACCCCCCGGCTGGGCGGTTGTCTCTGAGGCCAACCTTACTCCCTGCTGGGCAGGCTGGAC 14700
mRNA      ------------------------------------------------------------

genome    AGCTGCCCTCTCCGTTTGCCCCTCTACCACCCAAAAGGCAGGAGGCTCTGGAGACCAGGA 14760
mRNA      ------------------------------------------------------------

genome    CCCTGCCCGCCACGGCCTGTGTCCCAGGCGTGAGGGGGTGCCCCACAGACCTCTGCTGAG 14820
mRNA      ------------------------------------------------------------

genome    CTGCTGCTGAATGACGCCCCTTGGGGGTCCTGCCGGAAGGTCAGAGCAGGGGTGCACTCC 14880
mRNA      ------------------------------------------------------------

genome    CATAAAGAAACGCCCCCAGGTCGGGACTCATTCCTGTGGGCGGCATCTTGTGGCCATAGC 14940
mRNA      ------------------------------------------------------------

genome    TGCTTCTCGCTGCACTAATCACAGTGCCTCTGTGGGCAGCAGGCGCTGACCACCCAGGCC 15000
mRNA      ------------------------------------------------------------

genome    TGCCCCAGACCCTCTCCTCCCTTCCGGGGCGCTGCGCTGGGACCGATGGGGGGCGCCAGG 15060
mRNA      ------------------------------------------------------------

genome    CCTGTGGACACCGCCCTGCAGGGGCCTCTCCAGCTCACTGGGGGTGGGGTGGGGGTCACA 15120
```

FIG. 1 M

```
mRNA      ------------------------------------------------------------

genome    CTTGGGGTCCTCAGGTCGTGCCGACCACGCGCATTCTCTGCGCTCTGCGCAGGAGCTCGC 15180
mRNA      ------------------------------------------------------------

genome    CCACCCTCTCCCCGTGCAGAGAGCCCCGCAGCTGGCTCCCCGCAGGGCTGTCCGGGTGAG 15240
mRNA      ------------------------------------------------------------

genome    TATGGCTCTGGCCACGGGCCAGTGTGGCGGGAGGGCAAACCCCAAGGCCACCTCGGCTCA 15300
mRNA      ------------------------------------------------------------

genome    GAGTCCACGGCCGGCTGTCGCCCCGCTCCAGGCGTCGGCGGGGGATCCTTTCCGCATGGG 15360
mRNA      ------------------------------------------------------------

genome    CCTGCGCCCGCGCTCGGCGCCCCCTCCACGGCCCCGCCCCGTCCATGGCCCCGTCCTTCA 15420
mRNA      ------------------------------------------------------------

genome    TGGGCGAGCCCCTCCATGGCCCTGCCCCTCCGCGCCCCACCCCTCCCTCGCCCCACCTCT 15480
mRNA      ------------------------------------------------------------

genome    CACCTTCCTGCCCCGCCCCCAGCCTCCCCACCCCTCACCGGCCAGTCCCCTCCCCTATCC 15540
mRNA      ------------------------------------------------------------

genome    CGCTCCGCCCCTCAGCCGCCCCGCCCCTCAGCCGGCCTGCCTAATGTCCCCGTCCCCAGC 15600
mRNA      ------------------------------------------------------------

genome    ATCGCCCCGCCCCGCCCCCGTCTCGCCCCGCCCCTCAGGCGGCCTCCCTGCTGTGCCCCG 15660
mRNA      ------------------------------------------------------------

genome    CCCCGGCCTCGCCACGCCCCTACCTCACCACGCCCCCCGCATCGCCACGCCCCCCGCATC 15720
mRNA      ------------------------------------------------------------

genome    GCCACGCCTCCCTTACCATGCAGTCCCGCCCCGTCCCTTCCTCGTCCCGCCTCGCCGCGA 15780
mRNA      ------------------------------------------------------------

genome    CACTTCACACACAGCTTCGCCTCACCCCATTACAGTCTCACCACGCCCCGTCCCCTCTCC 15840
mRNA      ------------------------------------------------------------

genome    GTTGAGCCCCGCGCCTTCGCCCGGGTGGGGCGCTGCGCTGTCAGCGGCCTTGCTGTGTGA 15900
mRNA      ------------------------------------------------------------

genome    GGCAGAACCTGCGGGGGCAGGGGCGGGCTGGTTCCCTGGCCAGCCATTGGCAGAGTCCGC 15960
mRNA      ------------------------------------------------------------

genome    AGGCTAGGGCTGTCAATCATGCTGGCCGGCGTGGCCCCGCCTCCGCCGGCGCGGCCCCGC 16020
mRNA      ------------------------------------------------------------

genome    CTCCGCCGGCGCAGCGTCTGGGACGCAAGGCGCCGTGGGGGCTGCCGGGACGGGTCCAAG 16080
mRNA      ------------------------------------------------------------

genome    ATGGACGGCCGCTCAGGTTCTGCTTTTACCTGCGGCCCAGAGCCCCATTCATTGCCCCGG 16140
mRNA      ------------------------------------------------------------

genome    TGCTGAGCGGCGCCGCGAGTCGGCCCGAGGCCTCCGGGGACTGCCGTGCCGGGCGGGAGA 16200
mRNA      ------------------------------------------------------------

genome    CCGCCATGGCGACCCTGGAAAAGCTGATGAAGGCCTTCGAGTCCCTCAAGTCCTTCCAGC 16260
mRNA      ------------------------------------------------------------

genome    AGCAGCAGCAGCAGCAGCAGCAGCAGCAGCAGCAGCAGCAGCAGCAGCAGCAGCAACAGC 16320
mRNA      ------------------------------------------------------------

genome    CGCCACCGCCGCCGCCGCCGCCGCCGCCTCCTCAGCTTCCTCAGCCGCCGCCGCAGGCAC 16380
```

FIG. 1 N

```
mRNA      ------------------------------------------------------------

genome    AGCCGCTGCTGCCTCAGCCGCAGCCGCCCCCGCCGCCGCCCCCGCCGCCACCCGGCCCGG 16440
mRNA      ------------------------------------------------------------

genome    CTGTGGCTGAGGAGCCGCTGCACCGACCGTGAGTTTGGGCCCGCTGCAGCTCCCTGTCCC 16500
mRNA      ------------------------------------------------------------

genome    GGCGGGTCCCAGGCTACGGCGGGGATGGCGGTAACCCTGCAGCCTGCGGGCCGGCGACAC 16560
mRNA      ------------------------------------------------------------

genome    GAACCCCCGGCCCCGCAGAGACAGAGTGACCCAGCAACCCAGAGCCCATGAGGGACACCC 16620
mRNA      ------------------------------------------------------------

genome    GCCCCCTCCTGGGGCGAGGCCTTCCCCCACTTCAGCCCCGCTCCCTCACTTGGGTCTTCC 16680
mRNA      ------------------------------------------------------------

genome    CTTGTCCTCTCGCGAGGGGAGGCAGAGCCTTGTTGGGGCCTGTCCTGAATTCACCGAGGG 16740
mRNA      ------------------------------------------------------------

genome    GAGTCACGGCCTCAGCCCTCTCGCCCTTCGCAGGATGCGAAGAGTTGGGGCGAGAACTTG 16800
mRNA      ------------------------------------------------------------

genome    TTTCTTTTTATTTGCGAGAAACCAGGGCGGGGGTTCTTTTAACTGCGTTGTGAAGAGAAC 16860
mRNA      ------------------------------------------------------------

genome    TTGGAGGAGCCGAGATTTGCTCAGTGCCACTTCCCTCTTCTAGTCTGAGAGGGAAGAGGG 16920
mRNA      ------------------------------------------------------------

genome    CTGGGGGCGCGGGACACTTCGAGAGGAGGCGGGGTTTGGAGCTGGAGAGATGTGGGGGCA 16980
mRNA      ------------------------------------------------------------

genome    GTGGATGACATAATGCTTTTAGGACGCCTCGGCGGGAGTGGCGGGGCAGGGGGGGGGCGG 17040
mRNA      ------------------------------------------------------------

genome    GGAGTGAGGGCGCGTCCAATGGGAGATTTCTTTTCCTAGTGGCACTTAAAACAGCCTGAG 17100
mRNA      ------------------------------------------------------------

genome    ATTTGAGGCTCTTCCTACATTGTCAGGACATTTCATTTAGTTCATGATCACGGTGGTAGT 17160
mRNA      ------------------------------------------------------------

genome    AACACGATTTTAAGCACCACCTAAGAGATCTGCTCATCTAAGCCTAAGTTGGTCTGCAGG 17220
mRNA      ------------------------------------------------------------

genome    CGTTTGAATGAGTTGTGGTTGCCAAGTAAAGTGGTGAACTTACGTGGTGATTAATGAAAT 17280
mRNA      ------------------------------------------------------------

genome    TATCTTAAATATTAGGAAGAGTTGATTGAAGTTTTTTGCCTATGTGTGTTGGGAATAAAA 17340
mRNA      ------------------------------------------------------------

genome    CCAACACGTTGCTGATGGGGAGGTTAATTGCCGAGGGATGAATGAGGTGTACATTTTACC 17400
mRNA      ------------------------------------------------------------

genome    AGTATTCCAGTCAGGCTTGCCAGAATACGGGGGGTCCGCAGACTCCGTGGGCATCTCAGA 17460
mRNA      ------------------------------------------------------------

genome    TGTGCCAGTGAAAGGGTTTCTGTTTGCTTCATTGCTGACAGCTTGTTACTTTTTGGAAGC 17520
mRNA      ------------------------------------------------------------

genome    TAGGGGTTTCTGTTGCTTGTTCTTGGGGAGAATTTTTGAAACAGGAAAAGAGAGACCATT 17580
mRNA      ------------------------------------------------------------

genome    AAAACATCTAGCGGAACCCCAGGACTTTCCCTGGAAGTCTGTGTGTCGAGTGTACAGTAG 17640
```

FIG. 1O

```
mRNA      ------------------------------------------------------------

genome    GAGTTAGGAAGTACTCTGGTGCAGTTCAGGCCTTTCTCTTACCTCTCAGTATTCTATTTC 17700
mRNA      ------------------------------------------------------------

genome    CGATCTGGATGTGTCCCAGATGGCATTTGGTAAGAATATCTCTGTTAAGACTGATTAATT 17760
mRNA      ------------------------------------------------------------

genome    TTTAGTAATATTTCTTGTTCTTTGTTTCTGTTATGATCCTTGTCTCGTCTTCAAAGTTTA 17820
mRNA      ------------------------------------------------------------

genome    ATTAGAAAATGATTCGGAGAGCAGTGTTAGCTTATTTGTTGGAATAAAATTTAGGAATAA 17880
mRNA      ------------------------------------------------------------

genome    ATTATTCTAAAGGATGGAAAAACTTTTTGGATATTTGGAGAAATTTTAAAACAATTTGGC 17940
mRNA      ------------------------------------------------------------

genome    TTATCTCTTCAGTAAGTAATTTCTCATCCAGAAATTTACTGTAGTGCTTTTCTAGGAGGT 18000
mRNA      ------------------------------------------------------------

genome    AGGTGTCATAAAAGTTCACACATTGCATGTATCTTGTGTAAACACTAAACAGGGCTCCTG 18060
mRNA      ------------------------------------------------------------

genome    ATGGGAAGGAAGACCTTTCTGCTGGGCTGCTTCAGACACTTGATCATTCTAAAAATATGC 18120
mRNA      ------------------------------------------------------------

genome    CTTCTCTTTCTTATGCTGATTTGACAGAACCTGCATTTGCTTATCTTCAAAATATGGGTA 18180
mRNA      ------------------------------------------------------------

genome    TCAAGAAATTTCCTTTGCTGCCTTGACAAAGGAGATAGATTTTGTTTCATTACTTTAAGG 18240
mRNA      ------------------------------------------------------------

genome    TAATATATGATTACCTTATTTAAAAAATTTAATCAGGACTGGCAAGGTGGCTTACACCTT 18300
mRNA      ------------------------------------------------------------

genome    TAATCCGAGCACTTTGGGAGGCCTAGGTGGACGAATCACCTGAGGTCAGGAGTTTGAGAC 18360
mRNA      ------------------------------------------------------------

genome    CAGCCTGGCTAACATGGTGAAACCCTGTCTCTACTAAAAATACAAAAATTAGCTGGTCAT 18420
mRNA      ------------------------------------------------------------

genome    GGTGGCACGTGCCTGTAATCCAAGCTACCTGGGAGGCTGAGGCAGGAAAATCGCTTGAAC 18480
mRNA      ------------------------------------------------------------

genome    CCGGGAGGCAGAGTCTGCAGTGAGTTGAGATCACGCCACTGCACTCCAGCCTGGGTGACA 18540
mRNA      ------------------------------------------------------------

genome    GAGCGAGACTCTATCTCAAAAAAAATTTTTTTTAATGTATTATTTTTGCATAAGTAATAC 18600
mRNA      ------------------------------------------------------------

genome    ATTGACATGATACAAATTCTGTAATTACAAAAGGGCAATAATTAAAATATCTTCCTTCCA 18660
mRNA      ------------------------------------------------------------

genome    CCCCTTTCCTCTGAGTACCTAACTTTGTCCCCAAGAACAAGCACTATTTCAGTTCCTCAT 18720
mRNA      ------------------------------------------------------------

genome    GTATCCTGCCAGATATAACCTGTTCATATTGTAAGATAGATTTAAAATGCTCTAAAAACA 18780
mRNA      ------------------------------------------------------------

genome    AAAGTAGTTTAGAATAATATATATCTATATATTTTTTGAGATGTAGTCTCACATTGTCAC 18840
mRNA      ------------------------------------------------------------

genome    CCAGGCTGGAGTGCAGTGATACAATCTCGGCTCACTGCAGTCTCTGCCTCCCAGGTTCAA 18900
```

FIG. 1 P

```
mRNA        ------------------------------------------------------------

genome      ATGCTTCTCCTGCCTCAGCCTTCTGAGTAGCTGGGATTACAGGCGCCCACCACCATGTCC 18960
mRNA        ------------------------------------------------------------

genome      AGCTAATTTTTGTATTTTTAGTAGAGATGGGGTTTCACCATGTTGGCCAGGCTGGTCTTG 19020
mRNA        ------------------------------------------------------------

genome      AACTCCTGACCTTGTGATCTGTCCACCTCGGCCTCCCAAAGTGCTGGGATTACAGGTGTG 19080
mRNA        ------------------------------------------------------------

genome      AGCCACCATGCCTGGCTAGAATAATAACTTTTAAAGGTTCTTAGCATGCTCTGAAATCAA 19140
mRNA        ------------------------------------------------------------

genome      CTGCATTAGGTTTATTTATAGTTTTATAGTTATTTTAAATAAAATGCATATTTGTCATAT 19200
mRNA        ------------------------------------------------------------

genome      TTCTCTGTATTTTGCTGTTGAGAAAGGAGGTATTCACTAATTTTGAGTAACAAACACTGC 19260
mRNA        ------------------------------------------------------------

genome      TCACAAAGTTTGGATTTTGGCAGTTCTGTTCACGTGCTTCAGCCAAAAAATCCTCTTCTC 19320
mRNA        ------------------------------------------------------------

genome      AAAGTAAGATTGATGAAAGCAATTTAGAAAGTATCTGTTCTGTTTTTATGGCTCTTGCTC 19380
mRNA        ------------------------------------------------------------

genome      TTTGGTGTGGAACTGTGGTGTCACGCCATGCATGGGCCTCAGTTTATGAGTGTTTGTGCT 19440
mRNA        ------------------------------------------------------------

genome      CTGCTCAGCATACAGGATGCAGGAGTTCCTTATGGGGCTGGCTGCAGGCTCAGCAAATCT 19500
mRNA        ------------------------------------------------------------

genome      AGCATGCTTGGGAGGGTCCTCACAGTAATTAGGAGGCAATTAATACTTGCTTCTGGCAGT 19560
mRNA        ------------------------------------------------------------

genome      TTCTTATTCTCCTTCAGATTCCTATCTGGTGTTTCCCTGACTTTATTCATTCATCAGTAA 19620
mRNA        ------------------------------------------------------------

genome      ATATTTACTAAACATGTACTATGTGCCTGGCACTGTTATAGGTGCAGGGCTCAGCAGTGA 19680
mRNA        ------------------------------------------------------------

genome      GCAGACAAAGCTCTGCCCTCGTGAAGCTTTCATTCTAATGAAGGACATAGACAGTAAGCA 19740
mRNA        ------------------------------------------------------------

genome      AGATAGATAAGTAAAATATACAGTACGTTAATACGTGGAGGAACTTCAAAGCAGGGAAGG 19800
mRNA        ------------------------------------------------------------
                                       rs3856973
genome      GGATAGGGAAATGTCAGGGTTAATCGAGTGTTAACTTATTTTTATTTTTAAAAAAATTGT 19860
mRNA        ------------------------------------------------------------

genome      TAAGGGCTTTCCAGCAAAACCCAGAAAGCCTGCTAGACAAATTCCAAAAGAGCTGTAGCA 19920
mRNA        ------------------------------------------------------------

genome      CTAAGTGTTGACATTTTTATTTTATTTTGTTTTGTTTTGTTTTTTTTGAGACAGTTCTTG 19980
mRNA        ------------------------------------------------------------

genome      CTCTATCAGCCAGGCTGGAGTGCACTAGTGTGATCTTGGCTCACTGCAACCTCTGCCTCT 20040
mRNA        ------------------------------------------------------------

genome      TGGGTTCAAGTGATTCTCATGCCTCAGCCTCCTGTTTAGCTGGGATTATAGACATGCACT 20100
mRNA        ------------------------------------------------------------

genome      GCCATGCCTGGGTAATTTTTTTTTTTTCCCCCGAGACGGAGTCTTGCTCTGTCGCCCAGG 20160
```

FIG. 1 Q

```
mRNA      ------------------------------------------------------------

genome    CTGGAGTGCAGTGGCGCGATCTCAGCTCACTGCAAGCTCCGCTTCCCGAGTTCACGCCAT 20220
mRNA      ------------------------------------------------------------

genome    TCTCCTGCCTCAGTCTCCCAAGTAGCTGGGACTACAGGCGCCTGCCACCACGTCCAGCTA 20280
mRNA      ------------------------------------------------------------

genome    ATTTTTTTGTATTTTTAATAGAGACGGGGTTTCACCGTGTTAGCCAGGATGATCTTGATC 20340
mRNA      ------------------------------------------------------------

genome    TCCTGACCTCGTCATCCGCCGACCTTGTGATCCGCCCACCTCGGCCTCCCAAAGTGCTGG 20400
mRNA      ------------------------------------------------------------

genome    GATTACAGGCATGAGCCACTGTGCCCGGCCACGCCTGGGTAATTTTTGTATTTTTAGTAG 20460
mRNA      ------------------------------------------------------------

genome    AGATGGGGTTTTGCCATGATGAGCAGGCTGGTCTCGAACTCCCGGCCTCATGTGATCTGC 20520
mRNA      ------------------------------------------------------------

genome    CTGCCTTGGCCTCCCAAAGTGCTAGGATTACAGGCATGAGCCACCATACCTGGCCAGTGT 20580
mRNA      ------------------------------------------------------------

genome    TGATATTTTAAATACGGTGTTCAGGGAAGGTCCACTGAGAAGACAGCTTTTTTTTTTTTT 20640
mRNA      ------------------------------------------------------------

genome    TTTTTTGGGGTTGGGGGGCAAGGTCTTGCTCTTTAACCCAGGCTGGAATGCAGTATCACT 20700
mRNA      ------------------------------------------------------------

genome    ATCGTAGCTCACTTCAGCCTTGAACTCCTGGGCTCAAGTGATCCTCCCACCTCAACCTCA 20760
mRNA      ------------------------------------------------------------

genome    CAATGTGTTGGGACTATAGGTGTGAGCCATCACACCTGGCCAGATGATGGCTTTTGAGTA 20820
mRNA      ------------------------------------------------------------

genome    AAGACCTCAAGCGAGTTAAGAGTCTAGTGTAAGGGTGTATGAAGTAGTGGTATTCCAGAT 20880
mRNA      ------------------------------------------------------------

genome    GGGGGGAACAGGTCCAAAATCTTCCTGTTTCAGGAATAGCAAGGATGTCATTTTAGTTGG 20940
mRNA      ------------------------------------------------------------

genome    GTGAATTGAGTGAGGGGGACATTTGTAGTAAGAAGTAAGGTCCAAGAGGTCAAGGGAGTG 21000
mRNA      ------------------------------------------------------------

genome    CCATATCAGACCAATACTACTTGCCTTGTAGATGGAATAAAGATATTGGCATTTATGTGA 21060
mRNA      ------------------------------------------------------------

genome    GTGAGATGGGATGTCACTGGAGGATTAGAGCAGAGGAGTAGCATGATCTGAATTTCAATC 21120
mRNA      ------------------------------------------------------------

genome    TTAAGTGAACTCTGGCTGACAACAGAGTGAAGGGGAACACCGGCAAAAGCAGAAACCAGT 21180
mRNA      ------------------------------------------------------------

genome    TAGGAAGCCACTGCAGTGCTCAGATAAGCATGGTGGGTTCTGTCAGGGTACCGGCTGTCG 21240
mRNA      ------------------------------------------------------------

genome    GCTGTGGGCAGTGTGAGGAATGACTGACTGGATTTTGAATGCGGAACCAACTGCACTTGT 21300
mRNA      ------------------------------------------------------------

genome    TGAACTCTGCTAAGTATAACAATTTAGCAGTAGCTTGCGTTATCAGGTTTGTATTCAGCT 21360
mRNA      ------------------------------------------------------------

genome    GCAAGTAACAGAAAATCCTGCTGCAATAGCTTAAACTGGTAACAAGCAAGAGCTTATCAG 21420
```

FIG. 1 R

```
mRNA            ------------------------------------------------------------

genome          AAGACAAAAATAAGTCTGGGGAAATTCAACAATAAGTTAAGGAACCCAGGCTCTTTCTTT 21480
mRNA            ------------------------------------------------------------

genome          TTTTTTTTTTTGAAACGGAGTTTCGCTCTTGTCACCCGGGCTGGAGTGCAATGATGTGAT 21540
mRNA            ------------------------------------------------------------

genome          CTCAGCTCACTAAAACCTCTACCTCCTGGGTTCAAGTGATTCTTCTGCCTCAGCCTCCCA 21600
mRNA            ------------------------------------------------------------

genome          AGTAACTGGGATTACAGGCGTATACCACCATGCCCAGCTAATTTTTGTGTTTTTAGTAGA 21660
mRNA            ------------------------------------------------------------

genome          GATGGGGTTTCACCATGTTGGCCAGGCTGGTCTCGAACTTCTGACCTCAGGTGATCCACT 21720
mRNA            ------------------------------------------------------------

genome          CGCCTCAGCCTGCCAAAGTGCTGGGATTACAGGTTTGGGCCACTGCACCCGGTCAGAACC 21780
mRNA            ------------------------------------------------------------

genome          CAGGCTCTTTCTTATACTTACCTTGCAAACCCTTGTTCTCATTTTTTCCCTTTGTATTTT 21840
mRNA            ------------------------------------------------------------

genome          TATTGTTGAATTGTAATAGTTCTTTATATATTCTGGATACTGGATTCTTATCAGATAGAT 21900
mRNA            ------------------------------------------------------------

genome          GATTTGTAAAAACTCTCCCTTCCTTTGGATTGTCTTTTTACTTTCTTGATAGTGTCTTTT 21960
mRNA            ------------------------------------------------------------

genome          GAAGTGTAAAAGTTTTTAATTTTGATGAAGTCGAGTTTATCTATTTTGTCTTTGGTTGCT 22020
mRNA            ------------------------------------------------------------

genome          GTGCTTCAAGTGTCATATCTAAGAAATCATTGTCTAATCCAAAGTCAAAAAGGTTTACTC 22080
mRNA            ------------------------------------------------------------

genome          CTATGTTTTCTTCTAAGAATTTTAGAGTTTTACATTTAAGTCTGATCCATTTTGAGTTAA 22140
mRNA            ------------------------------------------------------------

genome          TTTTTATATATGGTTCAGGTAGAAGTCCAACTTTATTCTTTTCCATGTGGTTATTCAGTT 22200
mRNA            ------------------------------------------------------------

genome          GTCCCAGCACTGTTTGTTGAAGAGACTATTCTTTCCCCATGGAATTATCTTAGTACCCTT 22260
mRNA            ------------------------------------------------------------

genome          GTTGAAAATTAATCGTCCTTAATTGTATAAATTTATTTCTAGACTGTCAGTTCTACCTGT 22320
mRNA            ------------------------------------------------------------

genome          TGGTCTTTATGTCGATCCTGTGCCAGTACCATACAGTCTTGATTACTGAAGTTTGTGTCA 22380
mRNA            ------------------------------------------------------------

genome          CAGTTTAAATTCATGAAATGTGAGTTCTCCAACTTTGTTCCTTTTCAAGATTGATTTGGC 22440
mRNA            ------------------------------------------------------------

genome          CATGCTGGGTCCCTTGCATTTCCGTACGAATTGTAGGATCAGCTTGTCAGTTTCAACAAA 22500
mRNA            ------------------------------------------------------------

genome          GAAGCCAAGTAGGATTCTGAGAGGGATTGTGTTGAATCTGTAGATCAACTTGGGGAGTAT 22560
mRNA            ------------------------------------------------------------

genome          TCGCATCTTAACAATATTGTCTTCCACCTATGAACATGGGCAAACTTTGTGTAAATGGTC 22620
mRNA            ------------------------------------------------------------

genome          AGATTGTAAGTATTTCGGGCTGTGTGGGCACAGTGTCTCTGTCACAGCTACGCGGCTCTG 22680
```

FIG. 1 S

```
mRNA            ------------------------------------------------------------

genome          CCATTGTAGCATGAAAGTAGCCATAAGCAATATGTATGAGTGTCTGTGTTCCAATAGAAT 22740
mRNA            ------------------------------------------------------------

genome          TTTATTAATGACAAGGAAGTTTGAATTTCATATAATTTTCACCTGTCATGAGATAGTATT 22800
mRNA            ------------------------------------------------------------

genome          TGATTATTTTGGTCAACCATTTAAAAATGTAAAAACATTTCTTAGCTTGTGAACTAGCCA 22860
mRNA            ------------------------------------------------------------

genome          AAAATATGCAGGTTATAGTTTTCCCACTCCTAGGTTAAAATATGATAGGACCACATTTGG 22920
mRNA            ------------------------------------------------------------

genome          AAAGCATTTCTTTTTTTTTTTTTTTTTTTTTTTTTTGAGACGGAGTTTCACTCTTGTTGCC 22980
mRNA            ------------------------------------------------------------

genome          CAGGCTGGAGTGCAGTGGCGCGATCTCGGCTCACTGCAACCTCTGCCTCCCAGGTTCAAG 23040
mRNA            ------------------------------------------------------------

genome          ACATTCTCCTGCACGGCCTCCCTAGTAGCTGGGATTACAGGCATGCGCCACCACACCCAG 23100
mRNA            ------------------------------------------------------------

genome          CTAATTTTGTATTTTTAGTAGAGACGGGGTTTCTCCATGTTGGTCAGGCTGGTCTTGAAC 23160
mRNA            ------------------------------------------------------------

genome          TCCTGACCTCAGGTGATCCACCCGCCTCAGCCTCCCAAAGTGCTGGGATTACAGGGTGTG 23220
mRNA            ------------------------------------------------------------

genome          AGCCACCACACCCTGCTGGAAAGCATTTCTTTTTTGGCTGTTTTTGTTTTTTTTTTAAAC 23280
mRNA            ------------------------------------------------------------

genome          TAGTTTTGAAAATTATAAAAGTTACACATATACATTATAAAAATATCTTCAAGCAGCACA 23340
mRNA            ------------------------------------------------------------

genome          GATGAAAAACAAAGCCCTTCTTGCAAGTCTGTCATCTTTGTCTAACTTCCTAAGAACAAA 23400
mRNA            ------------------------------------------------------------

genome          AGTGTTTCTTGTGTCTTCTTCCCAGATTTTAATATGCATATACAAGCATTTAAATGTGTC 23460
mRNA            ------------------------------------------------------------

genome          ATTTTTTGTTTGCTTGACTGAGATCACATTACATATGTATTTTTTTACTTAACAATGTGT 23520
mRNA            ------------------------------------------------------------

genome          CATAGATATTGTTCCATAGCAGTACCTGTAATTCTTATTAATTGCTATGTAATATTTTAG 23580
mRNA            ------------------------------------------------------------

genome          AATTTCTTTTTAAAAGAGGACTTTTGGAGATGTAAAGGCAAAGGTCTCACATTTTTGTGG 23640
mRNA            ------------------------------------------------------------

genome          CTGTAGAATGTGCTGGTGACATATTCTCTCTACCTTGAGAAGTCCCCATCCCCATCACCT 23700
mRNA            ------------------------------------------------------------

genome          CCATTTCCTGTAAATAAGTCAACCACTTGATAAACTACCTTTGAATGGATCCACACTCAA 23760
mRNA            ------------------------------------------------------------

genome          AACATTTAGTCTTATTCAGACAACAAGGAGGAAAAATAAAATACCTTATAAAGCACTGTT 23820
mRNA            ------------------------------------------------------------

genome          TAATATTGTATTAAATTGGATCAATTTGGGGGCTAGAATGTATGTTAGAGACATGATATG 23880
mRNA            ------------------------------------------------------------

genome          TCCATAGGTCCTTGCTATCACAGTGAGGTCTCAGGGACAGTCGTTTGGTATCATTTGGGA 23940
```

FIG. 1 T

```
mRNA        ------------------------------------------------------------

genome      TCTCATAAGCAGACTCTCTCTGCTTGACCTGACAAATCAGAGTCTGTGTTTTAACAGGTT 24000
mRNA        ------------------------------------------------------------

genome      CAGTGAGTGACTTACATGCACATTGGAGTTTGGGAAGCTCCACTGTAGGTGCTTAGACCT 24060
mRNA        ------------------------------------------------------------

genome      TACCTTTGTTGTTGCTAATAACAATGCAAGCATTTGGGAGGAAGACCTGTGTTGCTCATA 24120
mRNA        ------------------------------------------------------------

genome      TGTGTCCAGGTGTAGCTGAGGTGGCCTTGCTTATCTGCTGTAGGGCCGTTGAGCATTTCT 24180
mRNA        ------------------------------------------------------------

genome      GTAGCTGTGATGAGTGAGCTGAGGTGAGCCTGCGGAGAGCTCCCAGCCATTGGTAGTGGG 24240
mRNA        ------------------------------------------------------------

genome      ACTCGCTTAGATGAACTGGAAGGACCCTTTCATCTGAGCAGCCACTATGGAGAAAAACAA 24300
mRNA        ------------------------------------------------------------

genome      CCGAATGAGGGGAGAGACAATGTGCAATTTTATTTAGGGCACAAAGGAGAGCTGTGGTTA 24360
mRNA        ------------------------------------------------------------

genome      GAAGGTGACATTTGAGTGGAAAGGGGGCAAGCCATGTGTATAGCGGGAGAAGAGAGGTCC 24420
mRNA        ------------------------------------------------------------

genome      AGGCAGAGTTAACAGAAGGCAGAAATGCTTTCCATGTTTGAGAACCAGTAAGGAGGCCAG 24480
mRNA        ------------------------------------------------------------

genome      TGGCTGAAGTAAGGTGAAGGGCAGAAATAAGGATGAGGCTGCGAGAGATGAGAGGTTAGA 24540
mRNA        ------------------------------------------------------------

genome      GACGAGCGTCTTGTGCACCAAGATAAGCTTGTGTGGTCAAAACAAGTAGTTTAATTTATG 24600
mRNA        ------------------------------------------------------------

genome      TTTTTAAAAGATCATTTTGGCTGGGCACAATGGTTCATGCCTGTAATACCAGTAGTTTGA 24660
mRNA        ------------------------------------------------------------

genome      GACGGTGTGGTGGGAGGATTGCCTGAGGCCAGACGACCAGCATAGCCAACATAGCAGCAC 24720
mRNA        ------------------------------------------------------------

genome      CTATAAGGTCTCTACAAAAAACTTTAAAAAATTAGCTGGGCATAGTGGTGTGTGCCTGTA 24780
mRNA        ------------------------------------------------------------

genome      GTCCCAGCTACTCAGGAGGCTGAGGAGGCTGGAGGATTGCTTGAGTCCAGGAGTTTGAGG 24840
mRNA        ------------------------------------------------------------

genome      CTGCAGTGAGCTATGATTATGCCACTACACTACAACCTGGGCAAGAGAGTGAGACCCTGT 24900
mRNA        ------------------------------------------------------------

genome      CTCTAAATATACACACACACACACACACACACACACACACACACACACACACACACACAC 24960
mRNA        ------------------------------------------------------------

genome      ACACACATATATATGTATATATATGCATTTAGATGAAAAGATCACTTTGACAATACCACA 25020
mRNA        ------------------------------------------------------------

genome      TGCTGGTGAGGATTTAGAAAAACTAGGTCACTTATTGCTGGTGGGAATATAATATAGTAC 25080
mRNA        ------------------------------------------------------------

genome      GGCCACTCTGGAAAACAGTTTGGCAGTTTGTCATAAAACTGAACATACCGTTAGTATACA 25140
mRNA        ------------------------------------------------------------

genome      GCCCAGCAGCAACTACAATCCTGGGCATTAATCCTAGAGAAATGAAACCTTAATGTTCAC 25200
```

FIG. 1 U

```
mRNA     ------------------------------------------------------------

genome   ATAAAAACCTATACTCAAGTATGCATAGCAGCTTTACCCATAATATCTAAGAACTGGAAT 25260
mRNA     ------------------------------------------------------------

genome   CAGCTCAGATGTCCTTCAACAGGTGAATGGTTAAACTACTCAGTAATAAAAAGGAATGAG 25320
mRNA     ------------------------------------------------------------

genome   CTACTGATAGCATGCAACAGTTTAGGTGAAGTTATGCTAATGAAAAAAGCCAATCCCAAA 25380
mRNA     ------------------------------------------------------------

genome   AGGTTATACATACTGTATGATTCTATGTTTTTTTGCAATGGCACAGTTTTAGGGATGGAG 25440
mRNA     ------------------------------------------------------------

genome   AATAGATTAGTGGTTGCCTGGGGTTAGAGATGGGGTAGTAGAGTAGGTTAGTGGTGGCAG 25500
mRNA     ------------------------------------------------------------

genome   AGGAGAGAAAAGAGAGGGAGGTGAATGTGGTTATAAAAGGACAACACAGGGGAATACTTG 25560
mRNA     ------------------------------------------------------------

genome   TAATGGAAATGCTTTGTCTTTTTTTTTTTTTTTTTTTTTTTGGCGACAGAGTCTTGCTCT 25620
mRNA     ------------------------------------------------------------

genome   GTTGCCCAGGCTGGAGTGCAGTGGCATGATCTTTTCTCACTGCAACCTCTGCCTCCTGGG 25680
mRNA     ------------------------------------------------------------

genome   TTCAAGTGATACTTGTGTCTCAGTCTCCCATGTTCAGAGTGAAACAAACCAGAGGTAATG 25740
mRNA     ------------------------------------------------------------

genome   TTCATCCAAATAATCCAACACACATGACATTAAAACATCAAGATCAGGTCGGACGTGGTG 25800
mRNA     ------------------------------------------------------------

genome   GCTCATGCCTGTAATCCCAGCACTTTTGGGAGGCCAAGGTGGGCAGATCACTTGAGGTCA 25860
mRNA     ------------------------------------------------------------

genome   GGAGTTCGAGACCAGCCGGGCCAACATGATGAAACCCCATCTTGACTAAAAATACAAAAA 25920
mRNA     ------------------------------------------------------------

genome   TTAGCCGGGCATGGTGGTGTGCACCTGTAGTCCCAGCTACTTGGGAGGCTGAGGCAAGAG 25980
mRNA     ------------------------------------------------------------

genome   AACTGCTTGAACCCGAGGGGCAGAGGTTGCAGTGAGCTGAGAGTGCGCCATTGCACTTCA 26040
mRNA     ------------------------------------------------------------

genome   GCCTGTGTGACAGAGTAAGACTCCATCTCCAAAAAAAAAAAAACCAAGATCAATTAAAATA 26100
mRNA     ------------------------------------------------------------

genome   CAGCATTACTGGGCCGGGTGTGGTGGCTCACACCTGTAATCCCAGCACTTTGGGAGGCCG 26160
mRNA     ------------------------------------------------------------

genome   AGATGGGCAGATCACGAGGTCAGGAGATCCAGACCATCCCGGCTAACACGGTGAAACCCC 26220
mRNA     ------------------------------------------------------------

genome   GTCTCTACTAAAAAATACAAAAAATTAGCCGGGTATAGTGGTGGGTGCCTGTAGTCCCAG 26280
mRNA     ------------------------------------------------------------

genome   CTACTTGGGAGGCTGAAGCAGGAGAATGGTGTGAACCCGGGAGGCAGAGCTGGCAGTGAG 26340
mRNA     ------------------------------------------------------------

genome   CTGAGATCGCGCCACTGCACTCCAGCCTGGGCGACAGAGCAAGACTCCGTCTCGGGGGAA 26400
mRNA     ------------------------------------------------------------

genome   AAAAAAAAATAAATAAATAGAATGCTGTAGTGTCCTTGAGTTTACATGCCCCTCCTTACG 26460
```

FIG. 1 V

```
mRNA      ------------------------------------------------------------

genome    CTTGTGTGCCCGTGCAGATTGCTTGATTACACAATTAGAGGAGGCTGGCGGAGGATTGTT 26520
mRNA      ------------------------------------------------------------

genome    TTAATTTTTTTTTTTTTGAGACAGTCTGGCTCTGTTCCCCAGGCTAGAGTGCAATGGCGC 26580
mRNA      ------------------------------------------------------------

genome    AATCTTGGTGCACTGCAACCTCTGCCTCCTGGGTTCAAGCAGTTCTTCTGCCGCAGCCTC 26640
mRNA      ------------------------------------------------------------

genome    CCGAGTAGCTGGGATTATAGGCGCCCGCCACCACGCCCAACTATTTTTTGTATTTTTAGT 26700
mRNA      ------------------------------------------------------------

genome    AGAGCAGCGTTTCACCATGCTGGCCAGGCTGGTCTCGAACTCCTGACCTCAGATGATCTG 26760
mRNA      ------------------------------------------------------------

genome    CTGCCCCAGCCTCCCAAAGTGCTGGGATTACAGGCGTGAGCCACACCTGGCCGTTTGTTT 26820
mRNA      ------------------------------------------------------------

genome    TAATTTTGAAGGTGAAGTGAAAGTGACTACATTTACCAAAAGTGATTGAAAAGCCAGGAC 26880
mRNA      ------------------------------------------------------------

genome    TGTTCTTACCCTGTTTTTCCAGTTCTTGCTCAGAGCAAGGTGGTTTCTTTTTCACTTAAT 26940
mRNA      ------------------------------------------------------------

genome    CACCATACTTACTTTTCATGTAGAACAAGTCAGTTTGAGTTATCAGTTCATCATCTTAAC 27000
mRNA      ------------------------------------------------------------

genome    TAAATTCCATGGGGGAAGGAATTAGTTTTAGTTTCTTAAACTTCCAGGTTTGCTTATTGG 27060
mRNA      ------------------------------------------------------------

genome    ACAAAATGAGATAGCAAGGCAGTGTTTTTAAGTTAGATTTTTTATTTCTTTGGTAATACA 27120
mRNA      ------------------------------------------------------------

genome    ATTTTCTCAGAAACTTAGTAGTCTTTTAGTTTAGTTGTTTTTAGTTGGTCCTATGTTTTG 27180
mRNA      ------------------------------------------------------------

genome    GATCACCCCTCTCTACTTTATTTTGATAGTGCCAACTGTGAAGACATCTGAAGCCATAGG 27240
mRNA      ------------------------------------------------------------

genome    TTTGGATGGGAAGGAGGCATCTTTAGCCTGATCATCTTCGCCAGGCTGTTTATCTCCTTT 27300
mRNA      ------------------------------------------------------------

genome    TGCTTGGCTGAGAAGTCTTAATAGGAGGCTTATTCCCAGCTATTTGGGGACATAGAAGCA 27360
mRNA      ------------------------------------------------------------

genome    GTTAGCCATTGCTTATATTTTACTGAGGTCTGTGTGGTATGTTGATTGTAGTCAGTTAAC 27420
mRNA      ------------------------------------------------------------

genome    GATTTTGAGAACTGAAGGCAGCCTGGTATATATAGAGTAGGTATTAGACTGTGTTTCTTC 27480
mRNA      ------------------------------------------------------------

genome    TAATTGAATTTCCCATCTCTTGTAATCTATGCCATCATCTTCTGTACTGCTGAGAAAGAA 27540
mRNA      ------------------------------------------------------------

genome    AGAAAGTTTCTAATCAAACTATACCACTGGTTGTAAGATGCAGTTTGGCTTTAGTGATGT 27600
mRNA      ------------------------------------------------------------

genome    TAACACATGATTCAAACGTGAAATTGATTGAGTATTGGTGAAATACAGAGGAGATTTAAA 27660
mRNA      ------------------------------------------------------------

genome    GCCAGAAGACCTGGGTTTAAATGCTGGCTGTATGACTTCATATCTGTGTGATCTTGGGCA 27720
```

FIG. 1 W

```
mRNA     ------------------------------------------------------------

genome   TGTCATGGTTGGCACTTCAATTTCTTCTCTCTATAATGGGGGAAGTGAGGCCAGTCATGG 27780
mRNA     ------------------------------------------------------------

genome   TGGCTCATACCTATAATCCCAGTGCTTTGGGAGGCCAAGATGGGAAGATCGCTTGAGGCC 27840
mRNA     ------------------------------------------------------------

genome   AGGAGTTTGAGCAATTGGGCAACATCGTGAGGCCCCGTCTCTACAAAATATTTTGAAAAA 27900
mRNA     ------------------------------------------------------------

genome   ATTAGCCAGGCCCAGTGGTGCGTGCCTGTGGTCCGCGCCACTCAGGAGGCTGAGACGGGA 27960
mRNA     ------------------------------------------------------------

genome   GGATCCTTTCAGCCTAGGAGTTTAAGGCTAAAGTGAGCCATGATTGTGCTATCGTACTCC 28020
mRNA     ------------------------------------------------------------

genome   AGCCTGGGCAGCAGAGCAAGATCCTGACTCTAAAAAAAAGTAAAATAAAGTAAAATGGGG 28080
mRNA     ------------------------------------------------------------

genome   GAAATGAACTGCTTTAGTAACATCATCTGTTTTTTCTGTGAGCAGCGTAGCTTGACAGCC 28140
mRNA     ------------------------------------------------------------

genome   ATTGGTGAACTCGTGCCCTGTGCTTCCCTGTCCAGATCCCCATTCTGCCCGCAACATGGA 28200
mRNA     ------------------------------------------------------------

genome   GTATAACGGTTTATTCATAGTAGTCGAGAAACACTCACTGAATGAATGAATGAGGTGTAG 28260
mRNA     ------------------------------------------------------------

genome   AACTAAGTGGAGTGGGTAATTCAACACATATTAATTTCCTTCTTTTTTTTATTTTTAGAA 28320
mRNA     ------------------------------------------------------------

genome   AGAAAGAACTTTCAGCTACCAAGAAAGACCGTGTGAATCATTGTCTGACAATATGTGAAA 28380
mRNA     ------------------------------------------------------------

genome   ACATAGTGGCACAGTCTGTCAGGTAATTGCACTTTGAACTGTCTAGAGAAAATAAGAACT 28440
mRNA     ------------------------------------------------------------

genome   TTGTATATTTTCAGTCTTAATGGGCTAGAATATTCTTTGTGTCCCAGCTATTTTAAATGG 28500
mRNA     ------------------------------------------------------------

genome   ATTCAGAAATCCATTTAAGATGAAGAAGGACCCTTTTCCCATATTTCTGGCTATATACAA 28560
mRNA     ------------------------------------------------------------

genome   GGATATCCAGACACTGAAATGAATAATGTTCCCTTTTTGTAATCTTTTATGCAAAAATTA 28620
mRNA     ------------------------------------------------------------

genome   AAACCATTATGGTAATTGAACAACATGTTTATGTTTAGTTAACACCCTTAGCAACTATAG 28680
mRNA     ------------------------------------------------------------

genome   TTATTTTAAAACCATCTATGGTTTGATATTTTTGCATTTGTTGCAATAGTAGGAACAGCA 28740
mRNA     ------------------------------------------------------------

genome   CAAGACAGTTCAGTTTGTCTCTCTTATTTGCTTTTTCTTGGCAGTTTGCTGTCCTATTGT 28800
mRNA     ------------------------------------------------------------

genome   ACCTCTGCTCCTAGCAGTGGCTGGAGCCCACTCCTCTGTGCTTCGGGATTAGTGGGGATC 28860
mRNA     ------------------------------------------------------------
                                                          rs2285086
genome   GTGGGGCATTGACTGTAGGTCAGCTTTCCTTGCTTGATCTTTCTCACTGGGATGAACTAG 28920
mRNA     ------------------------------------------------------------

genome   CAGCACCTTCTTTTGTAGCTGCTTTGCTTTTGACTATCTTTCTGACCGTTGTTCCTAGTA 28980
```

FIG. 1 X

```
mRNA      ------------------------------------------------------------

genome    GCTGTAGATGGTAAATATATTTAGGCCTGTTTCCAATGGCTCAGTAGGAGACATATTCAC 29040
mRNA      ------------------------------------------------------------

genome    CTATGATATCTGAATTCTGTTACCCACATGGGCATGCGTGAAATAGTTGCCTTGCCTTAC 29100
mRNA      ------------------------------------------------------------

genome    TTTCCCTTGGAATAAATAATTCATGTTATTCTCCTGGTAGAAGCTAGAAAAAGCCTTTAT 29160
mRNA      ------------------------------------------------------------

genome    AGTCAGTCAGAAAAAAATTTTTAGACAAATAATCTTGATTTTAGTACTGACAAAAACGTG 29220
mRNA      ------------------------------------------------------------

genome    TGGTGATTCTTTTTTTAATTTTTTTTTGAGACGGAGTTTCACTCTTGTTGCCCAGGCTGG 29280
mRNA      ------------------------------------------------------------

genome    AGTGCAATGGCGTGATCTCGGCTCACTGCAACCTCTGCCTCCTGGGTTCAAGTGATTCTC 29340
mRNA      ------------------------------------------------------------

genome    CTGCCTCAGCCTCCCAAGTAGCTGGAGTTACAGGCATGTGCTACTGTGCCCAGCTAATTT 29400
mRNA      ------------------------------------------------------------

genome    TGTATTTTTAGTAGAGATGTTGGTCAGGCTGATCTCGAACTCCCAACCTTAGGTGATCTG 29460
mRNA      ------------------------------------------------------------

genome    CCCGCCTCAGCCTCCCAAAGTGCTGGGATTACAGGCGTGAGCCAGGGCGCCCGGTGATTC 29520
mRNA      ------------------------------------------------------------

genome    ATTTGTTTTTTCAAAAAATTTCCTCTTGGCCATTGCTTTTCACTTTTGTTTTTTTTTTTT 29580
mRNA      ------------------------------------------------------------

genome    TTTTGAGACGGAGTCACGATCTGTCACCCAGGCTGGAGTGCAGTGGCATGATCTTGGCTT 29640
mRNA      ------------------------------------------------------------

genome    ACTGCAAGCTCTGCCTCCCAGGTTCACGCCATTCTCCTGCTTCAGCCTGGCGAGTAGCTG 29700
mRNA      ------------------------------------------------------------

genome    GGACTACAGGTGCTCGCCACCACACCCGGCTAATTTTTTGTATTTTTAGTAGAGATGGGG 29760
mRNA      ------------------------------------------------------------

genome    TTTCACCGTGGTCTTGATCTCCTGACCTCATGACCCGCTCAACTCAGCCTCCCAAAGTGC 29820
mRNA      ------------------------------------------------------------

genome    TGGGATTACAGGCGTGAGCCACCGCGCCCGGCCCTCTCTTGTCTTTTTATTGTGGTAAAA 29880
mRNA      ------------------------------------------------------------

genome    TGCACATAAAATTGACTGTCTTAACCATTTTTAGGGGTACAGTTCAGTATATATATTCGT 29940
mRNA      ------------------------------------------------------------

genome    AATGTTGTACAGCCATCACTGCCATCTACTTCATAAGTTTTTCTTCTGTCAAAACTGAAC 30000
mRNA      ------------------------------------------------------------

genome    ATCTGTCTTCATTAAACTCCCTATCATCCATTCTTTCCTGTAGTCCCTTTCTACTTTCTG 30060
mRNA      ------------------------------------------------------------

genome    TCTGTATGAGTGTAACTGCTCTGGAGACCTCATGTAAGTGGATTCCTACAGGATTTGTGT 30120
mRNA      ------------------------------------------------------------

genome    TTTTTTTTTGGTGATCTGCTTATTTTTAATGCCTCTGTGCATTTGTATTATATACTTTCA 30180
mRNA      ------------------------------------------------------------

genome    AAGTGATTTCACAAAACCGTTTCATTTTAGGTTAACTCATTTCTGTTGTTTGTGAAATAC 30240
```

FIG. 1 Y

```
mRNA      ------------------------------------------------------------

genome    TGTGTATGATTCTGTTCTGTTTCTGTCTAATTTGTGGAAATGTTGTGGGAAGAAAATGAA 30300
mRNA      ------------------------------------------------------------

genome    ATAACAAATGAGCATATGTCCTGAAAATAAAAATATAAAAATTCTAAGTTAGCATGCTAT 30360
mRNA      ------------------------------------------------------------

genome    TGTAGAATACAACGCTATGATAAAAGTAGGAAAAAAAAAGGTTTGAATTCTATCTCTGCT 30420
mRNA      ------------------------------------------------------------

genome    ACCTGTGTAAGCTGGGTGACTTTAGATAAGCTGTAACGTGTTTGAGCCTTACTGGCTCAT 30480
mRNA      ------------------------------------------------------------

genome    TTTTGAAATGTAATCCCTAGTTACACAGTTCTTGTGGGATCAGATGGTACATGTGAAACA 30540
mRNA      ------------------------------------------------------------

genome    CTGTGAAAAAGCAACTGCATAGATATGTTCATTAGCCACCTGAGCGGGAAGCGTATCCCA 30600
mRNA      ------------------------------------------------------------

genome    TTGCGATGCCCATCATCCAAAGCTATATGTTATCTTTACTTTTTTTTTTTGAGACAGAG 30660
mRNA      ------------------------------------------------------------

genome    TCTTGCTCTGTTGCCCAGGCTAGAGTGCAGTGGTGCAATCTCAGCTCACTGCAAGCTCCA 30720
mRNA      ------------------------------------------------------------

genome    CCTCCCGGGTTCACGCTATTCTCCTGCCCCAGCCTCCCAAGTAGCTGGGACTACAGGCAC 30780
mRNA      ------------------------------------------------------------

genome    CCGCCACCATGCCTGGCTAAATTTTTGTATTTTTAGTAGAGATGGGGTTTCACCGTGTTA 30840
mRNA      ------------------------------------------------------------

genome    GCCAGGATGGTCTTGATCTCCTGACCTCGTGATCCGCCCGCCTCGGCCTCCCAAAGTGCT 30900
mRNA      ------------------------------------------------------------

genome    GGGATTACAGGCGTGAGCCACTGCCCCTGGCCATCTTTACTTTTTTTGTGAAATGACTTT 30960
mRNA      ------------------------------------------------------------

genome    AAATACTTGGCAAACATTTGGTCATTGTTCATCTGATCTCCACCATCCAGGTCTCAGAGA 31020
mRNA      ------------------------------------------------------------

genome    ACATAATTTCTCTCTGAAAGCTTATTGACCCAGGAAATAAGATCTCTTTCAATCTGAGTG 31080
mRNA      ------------------------------------------------------------

genome    CGTCAGGCTTTATTCTTGTCATTTTGTCTTTTGATAATTTTCAAATGGAATTCATGGAAT 31140
mRNA      ------------------------------------------------------------

genome    GTTGGCTTATATTCATATATTAGTAAAGTATGTTGAGACATCTTAAGATTGATTTGTGGT 31200
mRNA      ------------------------------------------------------------

genome    TCTATATGCCATATTAAATCAAAATAATAGCTGTTAATGGTTTTCACATTAGTCTGTCTC 31260
mRNA      ------------------------------------------------------------

genome    TTGTTTTTATGGAGTAATGCTGAGAGTTCATTATGCTTGTTCTACAGAAGAGCATGTTAA 31320
mRNA      ------------------------------------------------------------

genome    AAGGAGTTTTTGGAGTCAGAGAGGTTATTCTTGGTTTCATAGGATACACTCTATACTTTT 31380
mRNA      ------------------------------------------------------------

genome    TAGGGATTTCAGAGTATATAGCTGAAGGTGATATTTTATGTAAATATGTTTTATGGAAAC 31440
mRNA      ------------------------------------------------------------

genome    TTATTGCTCATCGCTGTTTCCTGTTAACTCTCCTAAAATATAATTAAACTTTTGGAACTT 31500
```

FIG. 1 Z

```
mRNA            ------------------------------------------------------------

genome          TTTTATAGCTTTTGTGCTAGACTAATTTTTGTCTCTAATGAGGTTATATAAATGGCAGCT 31560
mRNA            ------------------------------------------------------------

genome          TCTGACGTTTTCAATGTAGGAAGTCATTTAAAACTTCATGTATATTGTGAAAATGTAGTC 31620
mRNA            ------------------------------------------------------------

genome          TGCTTTAAGCTCTCTAAAGTGGTCTAAGTTACTGGTTCCTAAGTATGGATGAGCATCAAA 31680
mRNA            ------------------------------------------------------------

genome          ATCATCTGGAAAATTTGTTAAAAATACAGTAATGAAGGCACCTCACTGTCCTTTTTCCCA 31740
mRNA            ------------------------------------------------------------

genome          AACATACTTCTGCATTCTGTTTGAGTAGGTAGGGACTACACATTTTTCACAAGTATCCTC 31800
mRNA            ------------------------------------------------------------

genome          TTGGGAATACCCAGGAATGCTTACTTGAGCAACCTCTTACTAATATGTACCTTGATAAGG 31860
mRNA            ------------------------------------------------------------

genome          TGGCTAGGTAAACATAAATATACAAAAATCCATAGATCTCCCATATATTAGCATAAATCA 31920
mRNA            ------------------------------------------------------------

genome          GCTAGAAAATATAACGTTTAAAGATCTAGTTCACAGTAGCACCAATATATCGAACTCTAA 31980
mRNA            ------------------------------------------------------------

genome          GGAATCGATAAATATGCAAAAACTTTATAAAAACTTCTGTTAATGTTTCTGAAAGATATA 32040
mRNA            ------------------------------------------------------------

genome          GGTGACCACTTTCTAGATAGGAAGATTTTATATTACTAAGTTGAATTTTCTCTAAATTAA 32100
mRNA            ------------------------------------------------------------

genome          CACAGAAATTTAAAATAATCTTGATCAAAATTCTAGTAGAGGTATTTTTGAACTTGTTCA 32160
mRNA            ------------------------------------------------------------

genome          CTGCAAGAATAAATACATAATTGCAAAGAATATCTCAAAATCATCACCAGGCCTGGTGTG 32220
mRNA            ------------------------------------------------------------

genome          GTGGCCCATGCCTGTAATCCCAGCACTTTGGGAGGCTGAGGCAGGCAGATCACCTGAGGT 32280
mRNA            ------------------------------------------------------------

genome          CAAGAGTTTGAGACCAGCTGGACCAGTGCGGTGAAACACTGCCTCTACTAAAAATACAAA 32340
mRNA            ------------------------------------------------------------

genome          AATTAGCTGGGTGTGGTGGTGCATGCCTGTAGTCCCAGCTACTTGGGAGGCTGAGGCAGG 32400
mRNA            ------------------------------------------------------------

genome          AGAATTGCTTGAACCCAGGAGGTACAGGTTGCGGTGAGCCTAGATCGCACCACTGCATTC 32460
mRNA            ------------------------------------------------------------

genome          CAGCCTGGGCGACAAGAGCAAAATTCTGTCTCAAGAAAAAAGAGAAAAAAGAAAAAGAAA 32520
mRNA            ------------------------------------------------------------

genome          TCAACACTAATATGGTGAGACTTAATGTATGTGACATTAAAATAGTGATTGGATGTTAAA 32580
mRNA            ------------------------------------------------------------

genome          ACAGGTATAGAACAGAAAGAAGAGTGTATGTGTGTATCTGTATGAATTTATGATGGGTGT 32640
mRNA            ------------------------------------------------------------

genome          AACATATATGTATTAGGGAAATGAGGGAAATGATACATTTCTCTGACTTTGGGAGAACAT 32700
mRNA            ------------------------------------------------------------

genome          TATATCTCTACCTCATATTGCAAACAAACATAAAGTTCAGATTAATTACCTAAATGTGAA 32760
```

FIG. 1 AA

```
mRNA            ------------------------------------------------------------

genome          AAAATGAAATAATTTCTTTAAAAAATGTAATCTTAGTTTGAGGAAGGTTAACATTATAAA 32820
mRNA            ------------------------------------------------------------

genome          GGAAAAAACTGTTTTGAGTGGAATATAGTTCAATATGTCAAAATCCACCTTCAACAAAAT 32880
mRNA            ------------------------------------------------------------

genome          TGAAAGTAAATTGAACTTGGGGAAAGTATTGACAGCATATAGATCAAAGGTTACTAGCCT 32940
mRNA            ------------------------------------------------------------

genome          GTGTAAAGAGCAGTTATAAATATCGTTAAGAAAAACACTGTCGACCTGTCGGCACCTTGT 33000
mRNA            ------------------------------------------------------------

genome          TCTCCGACTCCCAGCCTCCAGAACTGTGACGAGTAAGTGCTTATTGTTTAAACCACCCAG 33060
mRNA            ------------------------------------------------------------

genome          TCTGTATGTGGTATTTTGTTATAGAAACTCAAGCTGATTAGGACACTAGTAATCAGTAGA 33120
mRNA            ------------------------------------------------------------

genome          CTGAAACTGAAACAAAAATAAGAACCTTTTTTACCTGTCAAATTGGCAAACATTAAGAAT 33180
mRNA            ------------------------------------------------------------

genome          ATTCAGATTTTTGTCAGAGGTGATACAACCTTCTAAGAAGGCAATTTGGGAAAATATAAA 33240
mRNA            ------------------------------------------------------------

genome          GCTTTAGATTATTATATGTCTGACCTAGCAGTTTTACCTCTAGGGTGCTTACCCCTAGGA 33300
mRNA            ------------------------------------------------------------

genome          AAGTGTGTAATGATATTGGTGCAGTGCCCTTCATCCCATTAGAAAATTAAAAATAACCTT 33360
mRNA            ------------------------------------------------------------

genome          AATGGCCTACCACTAAAAGGGGATTGAAAATTTAAGATATATTTATTTATGTGTTTATTG 33420
mRNA            ------------------------------------------------------------

genome          AGATGGAGTCTTGCACTGTCCGCCTGGGCCAGAGTGCAATGGTGCGATCTCGGCTCACTG 33480
mRNA            ------------------------------------------------------------

genome          CAACCTCTGCTTCCCGGGTTCATGTGATTCTCCTGCCTCAGCCTCCTGAGTAGCTGGGAT 33540
mRNA            ------------------------------------------------------------

genome          TACAGGCTCACACCACCGCACCCGGCTAATTTTTTGTATTTTTAGTAGAGATGGGGTTTC 33600
mRNA            ------------------------------------------------------------

genome          ACTGTGTTGGCCAGACTGGTCTCGAACTCCTGACCTCATGATCCGCGCCCCTCGGCCTCC 33660
mRNA            ------------------------------------------------------------

genome          CAGTGTTGGGATTACAGGTGTGAGCCACTGCGCCTGGCCAGATACATTTATACAAGAGAA 33720
mRNA            ------------------------------------------------------------

genome          TGTTAGTTAACATTCATAGATATTTATATTTTGTTTACTTTTTATTAAAAAAATTTTTTT 33780
mRNA            ------------------------------------------------------------

genome          TAGAGACAGGATCTTACTCTGTCACCCAGGCAGGATGCAGTTGCACAATCATAGCCCACT 33840
mRNA            ------------------------------------------------------------

genome          GCAGCCTGAACTCCTGGGCTTAAGTGATCCTTCTGCCTCAGCCTTTTGAGTACCTGGGGG 33900
mRNA            ------------------------------------------------------------

genome          ACTTTAGGCAGTGCTACTATACCTGGCTAATTTTTAAATGTTTTATAGATGAGATCTTGC 33960
mRNA            ------------------------------------------------------------

genome          TGTATTGCCCAGGCTGGTCTAGAATTCCTGGGCCCAAGTGATCCTCCCACCTTGGCCTCC 34020
```

FIG. 1 BB

```
mRNA      ------------------------------------------------------------

genome    CAAAGCGCTGAGATTACAGGCATGAGCCACCACTTCTGACCAATAGATATTTATATTTGT 34080
mRNA      ------------------------------------------------------------

genome    GACTGGAAAATATATTAACAATGTGTTAAAAAATTCAGTTAAAAAATAATGAAAGATTTT 34140
mRNA      ------------------------------------------------------------

genome    TGCTTCTGGCTAAGATAGAATAACAAGGACAGCATTTATCTTCTTGCCTTGAAATAGTTG 34200
mRNA      ------------------------------------------------------------

genome    AAAACGGAAGAAATATATGTAACAGTGGTTTTCAAGTTATTGGGCATCAGGCAAAGAAGA 34260
mRNA      ------------------------------------------------------------

genome    ATAGTTATCCCAGGAAAATGAATGTGGAGAGCCCTACAATTTCCTTACATTACTGCCTGG 34320
mRNA      ------------------------------------------------------------

genome    TCATGGCAAGAGGAAAAACTGAGAGGAGACTGAGGCTGAGCCAGTGGTTTGCTGGGTTGA 34380
mRNA      ------------------------------------------------------------

genome    GGAGGCAGAGCTGGGAGTGCAGAGATGCAAGGTGGTGAGAGCCCATATGGAAGAATACCA 34440
mRNA      ------------------------------------------------------------

genome    GGGAAGAGAGCTGCAGAGGGAGCTCCGGAGACCTGCACCCTGCCCTCTCAGTACCCTGTC 34500
mRNA      ------------------------------------------------------------

genome    ATGTGTGTAGCTGAGTACTGACGAGCACTTGCTTGTGCGGAAATGACCCAGGGCTGGAGG 34560
mRNA      ------------------------------------------------------------

genome    TAGAGCCACCTGAAAGGATTAGAAGGAACAGTTGCTGAAAGTCACACAGGGCCAGGAAGA 34620
mRNA      ------------------------------------------------------------

genome    ATTTCTAATCACACCAGTTGGAGTGGAAAACCTCAGCTCTCATAGAGCAGGTAGGGTACT 34680
mRNA      ------------------------------------------------------------

genome    CAGAAGGGTTTGCCCACCTAGCCCCAGACTAAGTTTCGTTACTCTGACCCTACCTAATAT 34740
mRNA      ------------------------------------------------------------

genome    TAAAAAGAGATTAATTAAATTGTTCGCAACAAAAATAATATATTTCAGTGTTTGTAACAC 34800
mRNA      ------------------------------------------------------------

genome    GTAGAAGTGAATTGTATGACAATAGCATAAAGGCTGGAAGAGCAGAAATTGACATGTATT 34860
mRNA      ------------------------------------------------------------

genome    TGCGCTGGGCAGAATAATGCTCCCCTCTTTCCCCAAAAGATATCAAGTCCTAATCCCTGG 34920
mRNA      ------------------------------------------------------------

genome    AGCCTGTAAATATTACTTTATATGGAAAATTGTTTTATGATGTGATTAAATTCAGGATCT 34980
mRNA      ------------------------------------------------------------

genome    TGAGATGAGGGGGCTATCTTGGATGATCTGGGTAGGCACTAAATGCAATCACATATATAT 35040
mRNA      ------------------------------------------------------------

genome    AAAAAGGAGGCAGAGGGAGATTTTACACACAGAGAGAAGGCCCTGTGAAGATGGAACAGA 35100
mRNA      ------------------------------------------------------------

genome    AAGATTTGAAGGTGCTGGCCTTGAAAATTGGAGTGATGAAGCTATAAGCCAAGGAATGCA 35160
mRNA      ------------------------------------------------------------

genome    GCAGCCACCAAAGCTGGAAGAGGCACGGAGCAGTTCTCATTTAGAGCCTACTCCAGAGGG 35220
mRNA      ------------------------------------------------------------

genome    AATGTGGTGCTGCCAATTCCTTTTTTTTTTTTTTTTTTAAGATATCATTTACCCCTTTAA 35280
```

FIG. 1 CC

```
mRNA      ------------------------------------------------------------

genome    GTTGGTTTTTTTTTTTTTTTTTTTTTTTTTAGTATTTATTGATCATTCTTGGGTGTTTCTT 35340
mRNA      ------------------------------------------------------------

genome    GGAGAGGGGGATTTGGCAGGGTCATAGGACAATAGTGGAGGGAAGGTCAGCAGATAAACA 35400
mRNA      ------------------------------------------------------------

genome    TGTAAACAAAGGTCTCTGGTTTTCCTAGGCAGAGGGCCCTGCCACGTTCTGCAGTGTTTG 35460
mRNA      ------------------------------------------------------------

genome    TGTCCCTGGGTACTTGAGATTAGGGAGTGGTGATGACTCTTAACGAGTATGCTGCCTTCA 35520
mRNA      ------------------------------------------------------------

genome    AGCATCTGTTTAACAAAGCACATCTTGCACCGCCCTTAATCCATTTAACCCTTAGTGGAC 35580
mRNA      ------------------------------------------------------------

genome    ACAGCACATGTTTCAGAGAGCACGGGGTTGGGGGTAAGGTTATAGATTAACAGCATCCCA 35640
mRNA      ------------------------------------------------------------

genome    AGGCAGAAGAATTTTTCTTAGTACAGAACAAAATGGAGTGTCCTATGTCTACTTCTTTCT 35700
mRNA      ------------------------------------------------------------

genome    ACGCAGACACAGTAACAATCTGATCTCTCTTTCTTTTCCCACATTTCCTCCTTTTCTATT 35760
mRNA      ------------------------------------------------------------

genome    CGACAAAACTGCCACCGTCATCATGGACTGTTCTCAATGAGCTATTGGGTACACCTCCCA 35820
mRNA      ------------------------------------------------------------

genome    GATGGGGTGGCGGCCGGGCAGAGGGGCTCCTCACTTCCCAGATGGGGCGGCCGGGCAGAG 35880
mRNA      ------------------------------------------------------------

genome    GCGCCCCCCAACCTCCCAGACGGGGCGGCGGCTGGGCGGGGGCTGCCCCCCACCTCCCGG 35940
mRNA      ------------------------------------------------------------

genome    ACGGGGCGGGTGGCCGGGCGGGGGCTGCCCACCACCTCCCGGACGGGGCGGCTGGCCGGG 36000
mRNA      ------------------------------------------------------------

genome    CGGGGGCTGCCCCCCACCTCCCGGACGGGGCGGGTGGCCGGGCGGGGGCTGCCCCCCACC 36060
mRNA      ------------------------------------------------------------

genome    TCCCGGACGGGGCGGCTGGCCGGGCGGGGGCTGCCCCCCACCTCCCGGACGGAGCGGCTG 36120
mRNA      ------------------------------------------------------------

genome    CCGGGCGGAGGGGCTCCTCACTTCCCGGACGGGGCGGCTGCTGGGCGGAGGGGCTCCTCA 36180
mRNA      ------------------------------------------------------------

genome    CTTCTCAGACGGGGCGGCTGGTCAGAGACGCTCCTCACCTCCCAGACGGGGTGGCAGTGG 36240
mRNA      ------------------------------------------------------------

genome    GGCAGAGACATTCTTAAGTTCCCAGACGGAGTCACGGCCGGGCAGAGGTGCTCTTCACAT 36300
mRNA      ------------------------------------------------------------

genome    CTCAGACGGGGCGGCGGGGCAGAGGTGCTCCCCACTTCCCAGACGATGGGCGGCCGGGCA 36360
mRNA      ------------------------------------------------------------

genome    GAGATGCTCCTCACTTCCTAGATGGGATGACAGCCGGGAAGAGGCGCTCCTCACTTCCCA 36420
mRNA      ------------------------------------------------------------

genome    GACTGGGCAGCCAGGCAGAGGGGCTCCTCACATCCCAGACGATGGGCGGCCAGGCAGAAA 36480
mRNA      ------------------------------------------------------------

genome    CGCTCCTCACTTCCTAGACGGGGTGGCGGCTGGGCAGAGGCCGCAATCTTGGCACTTTGG 36540
```

FIG. 1 DD

```
mRNA      ------------------------------------------------------------

genome    GAGGCCAAGGCAGGCGGCTGGGAGGTGAAGGTTGTAGTGACCCGAGATCACGCCACTGCA 36600
mRNA      ------------------------------------------------------------

genome    CTCCAGCCTGGGCAACACTGAGCACTGAGTGAGCGAGACTCCGTCTGCAATCCCGGCACC 36660
mRNA      ------------------------------------------------------------

genome    TCGGGAGGCCGAGGCTGGCAGATCACTTGCAGTCAGGAGCTGGAGACCAGCCCGGCCAAC 36720
mRNA      ------------------------------------------------------------

genome    ACGGCGAAACCCCGTCTCCACCAAAAAACACGAAAACCAGTCAGACATGGCGGTGCGTGC 36780
mRNA      ------------------------------------------------------------

genome    CTGCAATCCCAGGCACTTGGCAGGCTGAGGCAGGAGAATCAGGTAGGGAGGTTGCAGTGA 36840
mRNA      ------------------------------------------------------------

genome    GTAGAGATGGTGGCAGTACAGTCCAGCCTTGGCTCGGCATCAGAGGGAGACTGTGCGAGG 36900
mRNA      ------------------------------------------------------------

genome    GCGAGGGCGAGGGCGAGGGAATTCCTTAATTTCAGTTTAGTGATACTAATTTTGGACTCT 36960
mRNA      ------------------------------------------------------------

genome    GGCCTCTAAAACTGTGAAAGAAAAAATTTTTTGTTTGTTTGTTTCTTTTAAGCCACATAG 37020
mRNA      ------------------------------------------------------------

genome    TTTGTGGTAATTTGTTACAGCAGCTGCAGGAAACTAATTTATGCTGCATGTGAAATGGTG 37080
mRNA      ------------------------------------------------------------

genome    TAATAAGGTAGATTGTGATGAAGATACATAGTATAAACAATTAAGCAACAACTAAAAGCA 37140
mRNA      ------------------------------------------------------------

genome    CAACAAGGAATTATAGCTAATGAACCAAAAAAGGAGATTAGAATAATAAAAATGGTGAAT 37200
mRNA      ------------------------------------------------------------

genome    CCCAAAGAAGCCAGAAATAGGGGAAGAGGCAAATAAAGGAAAGAAAGAGCTTGATGGTAG 37260
mRNA      ------------------------------------------------------------

genome    ATTTCAACCTAACTATGTCAAAAAGGACATTACATGTAAAAGGCAGCGATTTTTCAGATT 37320
mRNA      ------------------------------------------------------------

genome    GAATGGAAAAGTAAGACTCGGTATATGCTGCTGCCTGCAAGAAACACATTCTAAATATAA 37380
mRNA      ------------------------------------------------------------

genome    AGGCAAAAATAACCTACAGGTAACAGAACGGAAAGAAGTTCACTGTGCTTACAAGAATTA 37440
mRNA      ------------------------------------------------------------

genome    GATGCAAGCTAGACTGGTTCTGTTAATATCAGACAAAGTGGATTTCAAAGCAAAGGCTCT 37500
mRNA      ------------------------------------------------------------

genome    TGCCCAGGATGAGATGGTCATTTCATAATGATGAAGGGGATTCGTTCATCAGCCTGGCAT 37560
mRNA      ------------------------------------------------------------

genome    AGCAAGCTGAAATGTTTATGCACCGGACTACAGAGCTAAAATACATGAAGCAAAGCCTGA 37620
mRNA      ------------------------------------------------------------

genome    CAGAACTACAAGTAGAAACAGACAAATCCACAGTGATAGAGATTTCAGTAGCCGCTCTCA 37680
mRNA      ------------------------------------------------------------

genome    ATGATTTGTAGAACACGTAGCCATAATATCTGGATCTAGAACACTTGACCAACACTGTCC 37740
mRNA      ------------------------------------------------------------

genome    CCTGTGCAACCTCATTGGCATTTACAGGACACTCCACCCAGCACCAGCAGAAGAGACACT 37800
```

FIG. 1 EE

```
mRNA      ------------------------------------------------------------

genome    CTCTCAAGTGCTCACAGAATGTTTGCCAAGATAGAGCAGATGCTGGGCCATAAAACAAGT 37860
mRNA      ------------------------------------------------------------

genome    CTCTAAATTAAAAGCATTCAAATTATTCAGAGTATGTTTTCTGACCTCAGTATCATTAAG 37920
mRNA      ------------------------------------------------------------
                                                          rs7659144
genome    TTGGAATATATTATAGGAAGATAACCTGGAAAAGCCTCAGATATGTGGAAAAACCCATTT 37980
mRNA      ------------------------------------------------------------

genome    CCACATGGCCCATGGGTCAGAAGTGAAGTCAAAAGGGAAATTTGAAAGTCTTTTGGATTG 38040
mRNA      ------------------------------------------------------------

genome    ACTGATATAAAAACAATAGATTTCTAAACTTGTGGGGTGCTGTTACAGCATAGTAAATGG 38100
mRNA      ------------------------------------------------------------

genome    AAATTTCTAGCATTAAATGCCTGTTTTAGGAAAGAAAGATTTCAAATCAATGACCTCAGC 38160
mRNA      ------------------------------------------------------------

genome    TTCTACCTTTGGAAACTTGAAAATGACAAGCAAATGGAATCCAGAGTTACCAGAAGGGCC 38220
mRNA      ------------------------------------------------------------

genome    AGGTACGGTGGCTTATGCCTGCAGTTCTGCCACTTTGGGAGGCCGAGGCAGGTGGATTGT 38280
mRNA      ------------------------------------------------------------

genome    TTGAGACTGGCAGTTGAAGACCAGCCTGGGCAGCCTAGGGAGACCCCATATCTACAAAAA 38340
mRNA      ------------------------------------------------------------

genome    ACAAAAAAATTAGCCAGGTGTGGTGGCATGTGCCTGTAGTCCCAGCTAACCAGGAGTCTA 38400
mRNA      ------------------------------------------------------------

genome    AGGTGGGAGGATTGCTTGAGTCTGGGAGGTTGAGGCTGCAGTGAACTGTGATTGTGCCAC 38460
mRNA      ------------------------------------------------------------

genome    TGTGTTCCATCCTGGGCAACAGAATGAGACCCTGTCTCAAAAACAAAAACAGTTACTAGA 38520
mRNA      ------------------------------------------------------------

genome    AGAATGGACATCATAAAGATAGGAGCAGAAGTCAGTAAAATAGAAAACAAAAATACATAG 38580
mRNA      ------------------------------------------------------------

genome    GAAATCAATAAAACCAAAAGCTGGTTCATCAAGAACATCAATAAATTGGTAAAGCTGATA 38640
mRNA      ------------------------------------------------------------

genome    GGAAAAACAGTGAAGTCACAAATTAGCAATATCAGGAATGAGGGAGATGACAGTAGTATA 38700
mRNA      ------------------------------------------------------------

genome    GATTATATAGATATTAAAAGGACTGTATGAGGCAGGTGTGGTGGTTCACGCCTGTAATCC 38760
mRNA      ------------------------------------------------------------

genome    CAGCACCTTGGGAGGCCGAGGTGGACAGATCACCTGAGGTCAGGAGTTTGGGACCAGCCT 38820
mRNA      ------------------------------------------------------------

genome    GGCCAACATGGTGAAACTCTGTCTCTACTAAAAATACAAAAATTAGTTGGTCGTGGTGCT 38880
mRNA      ------------------------------------------------------------

genome    GTGTGCCTGTAATCCCAGCTACTTGGGAGGCTGAGGCAGGAGAATTGCTTGAACCTGGGA 38940
mRNA      ------------------------------------------------------------

genome    GGCGGAGGTTGCAGTGAGCTGAGATTGTGCCGTTGCACTCCAGCCTGGGTGACAGAGCAA 39000
mRNA      ------------------------------------------------------------

genome    GACTCCATCTCAAAACAAATAAATAAATAAAAAGGACTATATGGTAATATTATGAACAAC 39060
```

FIG. 1 FF

```
mRNA            ------------------------------------------------------------

genome          TTTATGCCAATAAATTTGACAACTTATAGATGAAATGGATGAGTTCCTTGAAAGACACAG 39120
mRNA            ------------------------------------------------------------

genome          AAACTATTAAAGCTCTCTCAAGAAGATATAGATAAGCTGATTAGCCCTATATCTATTTTA 39180
mRNA            ------------------------------------------------------------

genome          TTGAATTTAAATGTAAAAATCAATATTTAGTTACTGGAAAACTTTTAAGTGTGGTTGGAA 39240
mRNA            ------------------------------------------------------------

genome          ATGGTATACGAACTTTTTCAACTGAATTTTATGAAGTCTAATCACAGGTAAAGGTTTTCT 39300
mRNA            ------------------------------------------------------------

genome          GATGAAAATTTAGTGTCTGAATTGAGATATACTGTAAAAAATGTTATATATCTTAATTAT 39360
mRNA            ------------------------------------------------------------

genome          TTCTTCACATTAATTACATGTTGAAATAATACTTTGGGTGTATTGGGTTAAATTAAATAT 39420
mRNA            ------------------------------------------------------------

genome          TATGAAAATCTTGCCTGTTTTCTTTTTACTTTTGATGCGTCAGCTAGGAAATATAAAAGT 39480
mRNA            ------------------------------------------------------------

genome          GTAGCTCACATTCTGTTTCTGTTGACAGTACTGCTTTGGAGCACAGTGTTTGAATGATCT 39540
mRNA            ------------------------------------------------------------

genome          ATCATTTCAAAGACCTTTCCTCAGTTCGTTATTCATGGCTGTCTGTATTCCACATAGATA 39600
mRNA            ------------------------------------------------------------

genome          AGGTCTGAAATACTGCTAAGTGGCATGTTTTGTTTTATGCTTTTATAAGTTTGTTGATCA 39660
mRNA            ------------------------------------------------------------

genome          TTACTGATGTGGACTTTTGGTGCCTCTTAGGCTCATTGCTATCTTCCAACCATTGTTTGC 39720
mRNA            ------------------------------------------------------------

genome          AATTTTTACCTAGAGATAAAGAGAAAGAGACATTTGGTTTCAGAGTAGTTAGATTGGGAT 39780
mRNA            ------------------------------------------------------------

genome          CATGAAAGAGCAACCTCATTTTGATGCTTCAAAAATAGCACATCCCCCGTATTACTGGGA 39840
mRNA            ------------------------------------------------------------

genome          TTTGCTATTCTTGGGATTACTTCAAGAACATCCTTGTGTTACTGGTTTGGATGCTTCTGA 39900
mRNA            ------------------------------------------------------------

genome          ATGCTGTGAAGTCAGTTTCATGTACATGGCTCATCAGTTTAGCTCTCTCTTGGCTTTGTT 39960
mRNA            ------------------------------------------------------------

genome          TAGACAGTTGGAGCATGATGGCCTAAACAGCTTCTTTCAATTAAACATTTTAAAATAGTT 40020
mRNA            ------------------------------------------------------------

genome          TACAAATAGTAAACAAACTCCAGTTTTTGTGACTCTTTGTCTCGCACAACAAAAACACAA 40080
mRNA            ------------------------------------------------------------

genome          TCTGACCATGATCATCTGGCATCTTAGGGTGAAATATGGTTATACTTTGGCCCATACCGA 40140
mRNA            ------------------------------------------------------------

genome          AAGCAAGATTAAAAAGGGGCAGGAGAGATAGACTGCTGAACTGATTTTCAAGGTTCCAAG 40200
mRNA            ------------------------------------------------------------

genome          AATATTGTAGGTTAAGAGTAAAAGTAAACTTTTGGTAGAAAGCAGTGGGTTGTCTAGGAT 40260
mRNA            ------------------------------------------------------------

genome          TGAAGTATCTGAAGTTTTTAAACGAAAATTTAAAAAGAAAAATGAGAATTGCCTTACAAG 40320
```

FIG. 1 GG

```
mRNA      ------------------------------------------------------------

genome    TACAATCTCTTCTTTTTTAAAAAATAAACTTTATTTTGAAATAGTTTTAGATTTATAGAA 40380
mRNA      ------------------------------------------------------------

genome    AAAAATTAGATAGGGTAGGAAGTTTTCATATACCCTACATCCAGTTACCCCAGTTATTAT 40440
mRNA      ------------------------------------------------------------

genome    CATCCTAATTTAGTGTGAGACATTTTCATGTTTAATGAATCAATATTGATATGCTATTAA 40500
mRNA      ------------------------------------------------------------

genome    CTTAAGTCCAGACTTTATTCAGATTTTCTTAATTTCTATGTAATGTCCTTTTTCTGTTCC 40560
mRNA      ------------------------------------------------------------

genome    AGAATTCCATGCAGGACACCGGATACCTCATTACATTTCATTGTCATGTCACCTTAGGCT 40620
mRNA      ------------------------------------------------------------

genome    CCTCTTGACAGTTTCTCTTCTTTTTTTGCTTAGAAATTCTCCAGAATTTCAGAAACTTCT 40680
mRNA      ------------------------------------------------------------

genome    GGGCATCGCTATGGAACTTTTTCTGCTGTGCAGTGATGACGCAGAGTCAGATGTCAGGAT 40740
mRNA      ------------------------------------------------------------

genome    GGTGGCTGACGAATGCCTCAACAAAGTTATCAAAGTAAGAACCGTGTGGATGATGTTCTC 40800
mRNA      ------------------------------------------------------------

genome    CTCAGAGCTATCATTGTTGTAGGCTGAGAGAAGAAGCGATCATTGAGTGTTCTTCTGTTT 40860
mRNA      ------------------------------------------------------------

genome    TGAGTCCCTGAGGATGTCTGCACTTTTTTCCTTTCTGATGTATGGTTTGGAGGTGCTCTG 40920
mRNA      ------------------------------------------------------------

genome    TTGTATGGTTTGGAGGTGCTCTGTTGTATGGTTTGGAGGTGCTCTATTGTATGGTTTGGA 40980
mRNA      ------------------------------------------------------------

genome    GGTGCTCTGTTGTATGGTTTGGAGGTGCTCTTGTATGGTTTGGAGGTGCTCTTGTATGGT 41040
mRNA      ------------------------------------------------------------

genome    TTGGAGGTGCTCTGTTGTATGGTTTGGAGGTGGTCTTGTATGGTTTGCAGGTGCTCTATT 41100
mRNA      ------------------------------------------------------------

genome    GCATGGTTTGCAGGTGCTCTATTGTATGGTTTGGAAGTGCTCTTGTATGGTTTGGAGGTG 41160
mRNA      ------------------------------------------------------------

genome    CTCTTGTATGGTTTGGAGATGCTCTATTGTATGGTTTGCAGGTGCTCTATTGTATGGTTT 41220
mRNA      ------------------------------------------------------------

genome    GGAAGTGCTCTTGTATGGTTTGGAGGTGCTCTTGTATGGTTTGGAGGTGCTCTGTTGTAT 41280
mRNA      ------------------------------------------------------------

genome    GGTTTGGAGGTGCTCTGTTGTATGGTTTGGAGGTGCTCTTGTATGGTTTGGAGGTGCTCT 41340
mRNA      ------------------------------------------------------------

genome    ATTGTATGGTTTGGAGATGCTCTGGTATCTGCCTGCATTGCTTGCCACACCTGCCCGGTC 41400
mRNA      ------------------------------------------------------------

genome    AGAAGGCGCTATGTTGACAATTGTGCCTGCACGGTGCCTAGGTCAATGAAGGGAACCGAT 41460
mRNA      ------------------------------------------------------------

genome    GGTAGCCACTGGATGCTCCTGGGAAAATGTCACTACAGGCACCAGAGAAGCCAGAGCTAT 41520
mRNA      ------------------------------------------------------------

genome    GCCCAAATTTCTATGAGTCTCAGTTTTCTTAACCATAAAATGGGATCAATGTTTTTGTGG 41580
```

FIG. 1 HH

```
mRNA      ------------------------------------------------------------

genome    CATGTGTATGAGTGTGTGTCTGTGTATGTGTGAGGATTAAATTGTGTATGTGTGAGGACT 41640
mRNA      ------------------------------------------------------------

genome    AATTGCCACTACTGGATCCTCAAAGTGGTAAGAAGTGTTCTTATTAATAATGACATCCTT 41700
mRNA      ------------------------------------------------------------

genome    ACACTCTTACCCAGCAAGATTGATGGGTGTGGCACTGCTTCTCTTTTTCCATCACATGGT 41760
mRNA      ------------------------------------------------------------

genome    TTCCATGGTATCCTTTTGCCCAGGGAATCTTTGCTTTGTGGCTAGCACTTTGTTGTTTGG 41820
mRNA      ------------------------------------------------------------

genome    CTAATCACGCTTTCTGTGGTCAGGACGCTGGCTTCTCTGGAGCCATGGGATTCTAGCTCC 41880
mRNA      ------------------------------------------------------------

genome    CTGTCTTGTCCCTAGAGTGGTCACTGTCTTCTCTCTCCGCTTGCAATTCCTGCTTTGCTC 41940
mRNA      ------------------------------------------------------------

genome    GCATCTCACTTATGCAGTGACGTATATCAGTTTCACCTTGTTCTCCGTGCCTGCTGATCA 42000
mRNA      ------------------------------------------------------------

genome    TTGGCACCACTTGCATGGTGCCATTTAGGGCCTGCTTCCAGTTAAGCTTGCTTCTCCACA 42060
mRNA      ------------------------------------------------------------

genome    GGCCTAAATATCCTTGCTTGCTTCTTTTATTCTCACTGGCAGGACCAGGGCGGTCTGTCT 42120
mRNA      ------------------------------------------------------------

genome    TTGCATGAGACAGGGTCTCGCTCAGTCACCCAGGCTGGAGTGCAGTGGCTGATCACGGCT 42180
mRNA      ------------------------------------------------------------

genome    CATTGCAGCCTTGAGCTACCGGGCTCAAGCTATCCTCCTGGCTTGGCCCCTTGAGTAGCT 42240
mRNA      ------------------------------------------------------------

genome    GGGACTACAGGCGTGCACCACCATGCCCAGCTAATTTTTAAAATTATTTGTAGAGATGGG 42300
mRNA      ------------------------------------------------------------

genome    ATCTCGCCAGGTTGCCCAGGCTGGTCTTGAACGCCTGGGCTCAAGTGATCCTCCCTCCTT 42360
mRNA      ------------------------------------------------------------

genome    GGTTTCCCAAAGTGCTGGGATCACAGGTGTGAGCCACTGTGCCTGGCCCTTGATGTTTCA 42420
mRNA      ------------------------------------------------------------

genome    GTTCTTGATATTTGATCCTCAGAGTCAGAAAATCTAAAAAGAGGGCTATCCCAGGTTGCC 42480
mRNA      ------------------------------------------------------------

genome    TTGGTTCATGGCAAATGGGACGTTAAGAGGGCAGAGAGAATATGAACAGAAACTGTTCTA 42540
mRNA      ------------------------------------------------------------

genome    ATATTGGTCATTTAATGTGTAAGTATTGTTCTTTTTTAAACCTCCTTCATTTTTTTTCCA 42600
mRNA      ------------------------------------------------------------

genome    GGAATTGCTGGACACAGTGGCTTGGTGTGTGTCTGAGGACTGTAGGCCATGGCCCTAGGT 42660
mRNA      ------------------------------------------------------------

genome    TGTGGTTTTAGGTCTCAGGTGCTCTTCCTGGCTGTCTCCTTGCTTCTTTCCCATGTCCTC 42720
mRNA      ------------------------------------------------------------

genome    TTCTTTGTTTCCAGCCATTTCTCCCTTATGCTTAAGTTTGGTGCAGCAGGGTTTGGCTGC 42780
mRNA      ------------------------------------------------------------

genome    TCTCAGATTCCTGCTTCCTCAGATGCTGTAGTTGTCAGGCCCAGCGGGCTGGCAGCGGGA 42840
```

FIG. 1 II

```
mRNA        ------------------------------------------------------------

genome      TCAGGATCTGGCTAGGTTTGCTCTCACTGTGGCAGAGTAGGGGGAGGCGTGGGAGAGCAC 42900
mRNA        ------------------------------------------------------------

genome      GTGTGACCCCAGGCCAGCTGTAGGGAGCATAGGCATGGTCACGTAGCCTTCAGGTCCTAG 42960
mRNA        ------------------------------------------------------------

genome      ACTTTGTCTTCTCATGAGTATGGCTGTGTGTGTATGGTGAAAACTAGGTTCTACTTAGCC 43020
mRNA        ------------------------------------------------------------

genome      CAAGAAAATGGGCACATTTTGCATGTGGTTTCTGTAGAGAAATGCACTGGGTATCTGACA 43080
mRNA        ------------------------------------------------------------

genome      TAGCCTGGCAGCATGCCTCCCTCAGGTAGGTTAGTCTCAGGCGGTGAAGCACGTGTGTCC 43140
mRNA        ------------------------------------------------------------

genome      AGCAAGAACTTCATATGTGGCATAAAGTCTCCGTTCTGTGAGGTGCTGGCAAATCACCAC 43200
mRNA        ------------------------------------------------------------

genome      CACCGTCAAGAGGCTGAAGTGATTTTTGTCTAGGGAGGCAGGAAAGGCTTCCTGGAGTCA 43260
mRNA        ------------------------------------------------------------

genome      GCAGCCAGTAGGTGAAAGAGTAGATTGGAGACCTTCTTAATCATCACCGCCTCTTGTCTC 43320
mRNA        ------------------------------------------------------------

genome      AAGGGGTGCCAGGAAGCTGTGGAGGCTGAACCCATCTTATGCTGCCAGAGAGTGGGACAC 43380
mRNA        ------------------------------------------------------------

genome      CATGAGGGTCAGGTCAAGGGGTTGTACCTTGTTTGGTAGAGAATTAGGGGCTCTTGAAGA 43440
mRNA        ------------------------------------------------------------

genome      CTTTGGATGTGGTCAGGGGAGTGTATCATTTAGGAAGAGTGACCCGGTGAGGACGTGGGG 43500
mRNA        ------------------------------------------------------------

genome      TAGAGGAGGACAGGTGGGAGGGAGTCCAGGTGGGAGTGAGTAGACCCAGCAGGAGTGCAG 43560
mRNA        ------------------------------------------------------------

genome      GGCCTCGAGCCAGGATGGTGGCAGGGCTGTGAGGAGAGGCAGCCACCTGTGTGTCTGCGG 43620
mRNA        ------------------------------------------------------------

genome      AAGCAGGGGCAAGAGGGAAGAGGCCAGCAGCGTGCTGCCATCACCCAGCGACTGGCGTAG 43680
mRNA        ------------------------------------------------------------

genome      ATTGTGAGAGACCATTCCCTGCTCTTAGGAGGGGCTGAGTTTTAGTTTTCTCTTGTTATA 43740
mRNA        ------------------------------------------------------------

genome      CAATAAGCTTGGTATTTGTTTACAAAACATTTGTAAAGCTAAATCAAGGTTTGATAAGGC 43800
mRNA        ------------------------------------------------------------

genome      TTCTAGTTTTATTTAAGAAGTAATGTTGAAATAAATGTTTGTCCAATTCGCTTTGCTCAT 43860
mRNA        ------------------------------------------------------------

genome      TTAAGGACTTTCAGTACAAACTGCAACAACAGGATTAGGATTTAAACGTTTCTGAGATGT 43920
mRNA        ------------------------------------------------------------

genome      TTTTACTCCTCAGAATTTCCCAGAATGTGATCTGGTTTTGATTTTCAAGCTTGCTGACCC 43980
mRNA        ------------------------------------------------------------

genome      AATAGGTTAACCCACAAGTTTTACGAAGACCATCTCAGTCCACTTACATCAACTGCCCAT 44040
mRNA        ------------------------------------------------------------
          rs16843804
genome      GCCACGGTTAAAGAGATCATCGACTGATGTTTGGCACAGCTTCCTCCCTCTTGGGTGGGC 44100
```

FIG. 1 JJ

```
mRNA      ------------------------------------------------------------

genome    AAGCATTTGGAAGAGAAGGCTCCTATGGGTGAGAGTGGGGCACCAAAGTCTTCCCTGTCC 44160
mRNA      ------------------------------------------------------------

genome    CATCCCCTAGCTTGAGAAGCCCTTCTCTAATGTGGACTTTGTGCCGTTAGCATCGTTACT 44220
mRNA      ------------------------------------------------------------
       rs2024115
genome    AGCTTGAAGTTGACCATCTGGACGTACTTTCTGGTTTAGCCTCACAAGTGAGCAAGGAGG 44280
mRNA      ------------------------------------------------------------

genome    GTTGAGAGATGTGCTGTGAGGAATGTGGGGCCCCAGCTGGCAGCAGGCTCTGGGTCAGGG 44340
mRNA      ------------------------------------------------------------

genome    GGGCAGGGACCACGGGCATACCTGACAGTGAGGAGGGGCCACACCTGCAGAAAAGGATGC 44400
mRNA      ------------------------------------------------------------

genome    AGGACTCCGCCTTGGGAAGTGTTCTAGGCCAGAGCGAGGGTCTGTGGTTTATAAGTACAC 44460
mRNA      ------------------------------------------------------------

genome    CCACAGTGCTCGGGACCCTGCAGATGTCCAGGGTGCCGTCTGAGCCCGTATCATCCAACA 44520
mRNA      ------------------------------------------------------------

genome    GAATGTTCTGCTAGTGAAGATTAAAGATTTACTCCAGGGGCTTTAGGATTTATTATATAT 44580
mRNA      ------------------------------------------------------------

genome    ATATAAATCCTATATATATAATTTTTTTTTTTTTTTTTTGAGATGGAGTTTCGCTCTT 44640
mRNA      ------------------------------------------------------------

genome    GTTGCCCAGGCTGGAGTGCAATGGCGTGATCTTGGCTCACTGCAACCTCCGCCTCCCGGG 44700
mRNA      ------------------------------------------------------------

genome    TTCAAACTATTCTCCTGCCTCAGCCTCTCGAGTAGCTGGGATTACAGGCGCCCACCACCA 44760
mRNA      ------------------------------------------------------------

genome    CACCCGGCTAATTTTTGTATTTTTTAGTAGAGACGGAGTTTCTCCATGTTGGTCAGGCTG 44820
mRNA      ------------------------------------------------------------

genome    GTCTTGAACTCCTGACCTCAGGTGATCTGCCCGCCTTGGCCTCCCAAAGTGCTGGGATTA 44880
mRNA      ------------------------------------------------------------

genome    CAGGCATGAGCCACCCCACCTGGCCAGGATTTATTGTATTTGAACCATCTACCATTTTAA 44940
mRNA      ------------------------------------------------------------

genome    TTTTGATGTTATGTAGTATTTGATGATAATGAAAGTTAAATTGTTTTTCTTTCCATTTTT 45000
mRNA      ------------------------------------------------------------

genome    CTGTTTAAGTGAATGACCTGTATCTAGTTTATTCAGTAACTTCCTGCATATATTTGTTTC 45060
mRNA      ------------------------------------------------------------

genome    TTTCATTCTTAATGAATATATTCTTAATTTAGTTGCTATTATGTTTTGCTTTGCCCCAAA 45120
mRNA      ------------------------------------------------------------

genome    ATTGAAATCTTAGTTTCCTTTTAGCTCGTTTTAGAACTAGTGATGGGATGTGTCTTCCAT 45180
mRNA      ------------------------------------------------------------

genome    AAATCTCTTGTGATTTGTTGTAGGCTTTGATGGATTCTAATCTTCCAAGGTTACAGCTCG 45240
mRNA      ------------------------------------------------------------

genome    AGCTCTATAAGGAAATTAAAAAGGTGGGCCTTGCTTTTCTTTTTTAAAAATGTTTTAAAT 45300
mRNA      ------------------------------------------------------------

genome    TTTAAATTTTTATAGGTACACGTATTTTGTAGGTACATGTAAATGTATATATTTATGGGG 45360
```

FIG. 1 KK

```
mRNA      ------------------------------------------------------------

genome    TACATGAGATATTTTGATACAGGTATACAATACATAATAATCACACCATGGAAAGTTGGA 45420
mRNA      ------------------------------------------------------------

genome    TATCCATGCCCTCAAGCATTTATCCTTTGTGTTACAAACAATCCAGTTACATGCTTTACT 45480
mRNA      ------------------------------------------------------------

genome    TATTTTATTTTATTTTTGAGACAGAGTCTTGCTTTCACCCATGCTAGAGTACAGTGGCAT 45540
mRNA      ------------------------------------------------------------

genome    GACCTTGGCTCACTGCAACCTCCGCCTCCCGGGTTCAACCGAACTTTGGGCTGGTCTCAA 45600
mRNA      ------------------------------------------------------------

genome    ACTCCTGACCTCAGGTGATCCGCCCGCCTCGGCCTCCCAAAGTGTTGGGATTACAGGCGT 45660
mRNA      ------------------------------------------------------------

genome    GAGCCACTGTGCCGGGCCTGATTGTACATTTTAAAATAACTAAAACAGTCAGGGCACAGT 45720
mRNA      ------------------------------------------------------------

genome    GGCTCATGCCTGTAATCCCAGCATTTTGGGAGGCTGAGGCAGGTGATCACCTGAGATCAG 45780
mRNA      ------------------------------------------------------------

genome    GAGTTCGAGACCAGCCTGGCCAACATGGAGAAACCCTGTCTCTACTAAAAATACAAAAAT 45840
mRNA      ------------------------------------------------------------

genome    TAGCCAAGTGTGGTGGCGGGCGCCTGTAATCCTGGCTACTCGGGAGGCTGAGGTAGGGGA 45900
mRNA      ------------------------------------------------------------

genome    ATCGCTTGAACCTGGGGGTGGAGGTTGCAGTGAGCCGAGATCACGCCACTGCATTCCAGC 45960
mRNA      ------------------------------------------------------------

genome    CTGAGCGACAGAGTGAGACTTTGTCTCAAAAAAATAAAAATGAAATAAAATTGGGCCGGGT 46020
mRNA      ------------------------------------------------------------

genome    GTGGTGGCTCACACCTTAGTCCCAGCACTTTGGGAACCTGAGGCAGGTGGATGCTTGAGA 46080
mRNA      ------------------------------------------------------------

genome    CCAGGAGTTTGAGACCAGCATGGGCAACATGGCAAAACGCTGTCTGTACAGAAATTAGCT 46140
mRNA      ------------------------------------------------------------

genome    GGGTGTGGTGGTGCACAACTATAGTCTCAGCTACTTGGGAGATTGAGGTGGGAGGATTAA 46200
mRNA      ------------------------------------------------------------

genome    TTGAGCCTGGAAGGTTGAATCTATAGGTAGCTGAGATTGTGCCACTGCCCTTCAGCCTGG 46260
mRNA      ------------------------------------------------------------

genome    GCGACCAAGTGAGACCCTGTCTCAAAAGAAAAACAAAAAAACAAAAAACAAACCACTATT 46320
mRNA      ------------------------------------------------------------

genome    ATCGACTATATATTATTGTCTATGATCCCTCTGCTGTGCTGTCGAATACCAGGTCTTGGG 46380
mRNA      ------------------------------------------------------------

genome    CCCTTATTTCCATCACTGAGCAAACTTCACTCTGTTAAGCAGCAGGTGTGGGATTTCATC 46440
mRNA      ------------------------------------------------------------

genome    GTTATTCAGTAATTCACAATGTTAGAAGGAAATGCTGTTTGGTAGACGATTGCTTTACTT 46500
mRNA      ------------------------------------------------------------

genome    TTCTTCAAAAGGTTACTCTTTATTAGATGAGATGAGAATTAAAAATGGTAACTTACTTTA 46560
mRNA      ------------------------------------------------------------

genome    TATCTTTATAATTGAAGCCCACTAGACCTTAAAGTAGTTACCAGATGTTTTATGCATTTA 46620
```

FIG. 1 LL

```
mRNA            ------------------------------------------------------------

genome          AATGGCCTTTTCTCTAAAATTAGAAAGTAACAAGGAAAGAAAATGCTTCGTTTCTATGCA 46680
mRNA            ------------------------------------------------------------

genome          ACCCTCTTGGTGACTAGTATGTGACTCTTAATGCAACCCTCATTGCACCCCCTCAGAATG 46740
mRNA            ------------------------------------------------------------

genome          GTGCCCCTCGGAGTTTGCGTGCTGCCCTGTGGAGGTTTGCTGAGCTGGCTCACCTGGTTC 46800
mRNA            ------------------------------------------------------------

genome          GGCCTCAGAAATGCAGGTAAGTTGTACACTCTGGATGTTGGTTTTTGTCGGGGGCCAGCT 46860
mRNA            ------------------------------------------------------------

genome          GCTACTGATCCTTTATGTCTCAGCTCAGATGTCATTTCAAAAGTCTGCTCTGCCCTCTCC 46920
mRNA            ------------------------------------------------------------

genome          AAATTGCAGTCGACCTTGCCCTGTTTATGTTTCCCTCATAGCACTAATCCATGTCAGAAA 46980
mRNA            ------------------------------------------------------------

genome          TTGTCACGTACAGTCTATCTGTGTGCTTGTTTATTTTCTATCCCACCCTTCCGCAAGAGA 47040
mRNA            ------------------------------------------------------------

genome          CTTATGGGATGTGTGCCCCAGGACAGCAGGGGTCTTACTGTCTTATGCTCTGTTGCAGCC 47100
mRNA            ------------------------------------------------------------

genome          CAGCAGCGATAACAGTGTCTGCACATAGTACTTGCTTAAAAGATACTTGCCAAATTGTTG 47160
mRNA            ------------------------------------------------------------

genome          AAGGTTGAGGTACCAATTTCATTATTGCTGACTATAGGAGTTATAGCAAAATATCCATTT 47220
mRNA            ------------------------------------------------------------

genome          GTCTGTTACATGAGTTAAAAATATGGTTGTTGCACTGTGAATAGTTTGGTTTAGTCAAAA 47280
mRNA            ------------------------------------------------------------

genome          CAGTTGTATCTTAACGGATTGAGAAACAAAAGCAGGACCACTTTTCATCAGCTCCCTCCT 47340
mRNA            ------------------------------------------------------------

genome          TCTCCTTAACCAGCAATACATGCTGATGCTGATATCCCATAGACCCTCAGCTCCATCCTG 47400
mRNA            ------------------------------------------------------------

genome          AGTCACTGGGAATGTGGTCTAAACCCTCACTATTAATATGAACTGAGTTTCAATAAGAAT 47460
mRNA            ------------------------------------------------------------

genome          CTTATATGGGTCGGGCATAGTGGCTCATACCTTTGATCCCAGCACTTCAGGAGGCCAAGG 47520
mRNA            ------------------------------------------------------------

genome          CAGGTGGATTGCTTGACCCAGACTAGGCAACATGGTGAAACGCCGCCTCTACAAAAAATA 47580
mRNA            ------------------------------------------------------------

genome          CAAAACTTAGCCAGGCATGGTGGTGCGTGCCTGTGGTCACAGCCACTCGAGAGGCTGAGG 47640
mRNA            ------------------------------------------------------------

genome          TGGGAGGATCACTTGAGCCTGGGAGGTGGAGGTCGTGTTGAGCCAAGATCGCACCACTGC 47700
mRNA            ------------------------------------------------------------

genome          ACTCCAGCCTGGGCAACAGAGTGAGACCTGTCTCAAAAAAACCAAAATCCAGAAAAGAAC 47760
mRNA            ------------------------------------------------------------

genome          TTATATGGCTGCAGAGGTATAATCACTAAGGAAATTTCCTTTTGTATAATCTTTTTTCTT 47820
mRNA            ------------------------------------------------------------

genome          TTACTATCATTTAAAAAAATGTGTTATATTTCTGAAGCAACACATCCAGGTTCTGCACAT 47880
```

FIG. 1 MM

```
mRNA            ------------------------------------------------------------

genome          AGCAGCCAAAGTGACCTTAAAGAATATAACTGGGTCTTGTCATTCCCTTATTTAAACTCT 47940
mRNA            ------------------------------------------------------------

genome          TGTACCCATTTCCCAGTGCCGTTTAGATAGAGATTCCAGACTCGTCAATGGCTCTGTCAC 48000
mRNA            ------------------------------------------------------------

genome          CTCAGACACCCTGCATTGACTCATTAGTCTGATTAGAGTCAGGTTTTTCTTCCTCCTGAT 48060
mRNA            ------------------------------------------------------------

genome          GGTTTTTTTTTCCCCCTTAGTTCTCAGCGGAACAGTCACTTCCTTAGGGAGGTTTCCCCA 48120
mRNA            ------------------------------------------------------------

genome          GCCACCCTCTGAGGCCGTGCTTGTTGCCAGACTCTGCCACTAGAGGGCAGGGCTGCACCA 48180
mRNA            ------------------------------------------------------------

genome          CTCCTGGCACCTCGCACCCGGCCTGCCCTGTCACTCTGTGTGTTGGGTGAATTCCTGTGA 48240
mRNA            ------------------------------------------------------------

genome          TCTGTGACTCACTGCTCTGTGTCCTACACATTCGGCTTTTCTTCTCTCCCCACAACCCCA 48300
mRNA            ------------------------------------------------------------

genome          TTTTATAATTCTCCTTTTTCAGGAAAGCTTTATTCCCATTTAAAAATTTTTGTTTTTAAA 48360
mRNA            ------------------------------------------------------------

genome          ATGGTATTTTCTTACACTTATTTTCTAATTAAAAATGAGTGTTTTAAGAAGTATTATGAT 48420
mRNA            ------------------------------------------------------------

genome          TTACTGCAAATAATTTTTAAACCCAGCCTTTTAGATCCTCTGTGATCATAAGAGAAATGA 48480
mRNA            ------------------------------------------------------------

genome          AGGATGTCTCCCAACACTTGAGCTTCATCCACATTTCATCCTCCTGTTCTTTCAGCTGAG 48540
mRNA            ------------------------------------------------------------

genome          TTTTCCCCATCCCATTAGGGACTGTTGGAATATAAAACTGGCTTTTCCCTAACAGGGAAT 48600
mRNA            ------------------------------------------------------------

genome          GAATTGCTTCTGTTTCTCCTGAAGGAGAGCTGGAAGAATGACTTGCGTTCTTTTGCATAC 48660
mRNA            ------------------------------------------------------------

genome          ACAGGCCTTACCTGGTGAACCTTCTGCCGTGCCTGACTCGAACAAGCAAGAGACCCGAAG 48720
mRNA            ------------------------------------------------------------

genome          AATCAGTCCAGGAGACCTTGGCTGCAGCTGTTCCCAAAATTATGGCTTCTTTTGGCAATT 48780
mRNA            ------------------------------------------------------------

genome          TTGCAAATGACAATGAAATTAAGGTATGATTGTTGCCTCAGGTCACAAACATGCGAGTGA 48840
mRNA            ------------------------------------------------------------

genome          TGCTGTGAGTGAGTCTGTGGAGGGTGAGGGCTTCTGAACAGGGAGTCCTGTGGGAGTGCT 48900
mRNA            ------------------------------------------------------------

genome          TCTTGGGGTATGTTGTATGTCGTAATTTAGACTACCATCATTTGTGTTATTTTTGAGGCA 48960
mRNA            ------------------------------------------------------------

genome          CCTAAGGACTTCTTTCCACTTCTCATTTCTTACTGTGGGGTGAAGAGTTGAATTGGGAGA 49020
mRNA            ------------------------------------------------------------

genome          TGGTTTCTAGATGCAAATTGAAAAGGCATTTTTCCAGAGCAGATTTGTTTTCGGCGTACT 49080
mRNA            ------------------------------------------------------------
                           rs10015979
genome          AGAGTGACTCTTTAACCTAGCTGCGGGAAGATGACTGTGCCAAGACTGCAGGTAGGAGAA 49140
```

FIG. 1 NN

```
mRNA        ------------------------------------------------------------

genome      AGCTCACTGACGAGGCCTTGTGGGTCTGAACGTCCTGCAGCTATCAGAGCCTGTTGGCTT 49200
mRNA        ------------------------------------------------------------

genome      CCTGTTGTGCATTCCAACAAATCATCTTCAAACCCACTTTAGTGTTTTGTTTATAATGTC 49260
mRNA        ------------------------------------------------------------

genome      CAGAAATAGTGACCCTGTCACATGCTCTACAGATTACAGGATTCTTAGCCTCTTCCTTTT 49320
mRNA        ------------------------------------------------------------

genome      TGGTAGGTCAGTCCTGGGTTTGAGCCCAAGTGACCCTCCTGGGAGGTGATGATACACACT 49380
mRNA        ------------------------------------------------------------

genome      GGGTAGAGTGGAATCAGATGGACTTGGATTAGAATTCTGTCCTCTTTACTAGTTATTTTC 49440
mRNA        ------------------------------------------------------------

genome      CTCTAGGCAAACTGCCCAACAGCTCTAAGCTATTTCCTTCGTATTCTGAAAAATAAGCCT 49500
mRNA        ------------------------------------------------------------

genome      TAATGGGACCCATATAGGGCAACTCTGAGAGTAAAATAAAGGAATATGTGTTAGAGTGTA 49560
mRNA        ------------------------------------------------------------

genome      GCATAGTCACCCACGGGAAGGGCTTAGATGTTAGCTGCTACTGCTCTTATTAGCTGAATG 49620
mRNA        ------------------------------------------------------------

genome      ATTTGGAATAAACTGTTAGCCTCTCTCATGTTTTTTCTCTTGAGCTTCGAAGTTTTCTTG 49680
mRNA        ------------------------------------------------------------

genome      TTAATACTAAGGAGATATTCAAACTAGTCATGGGGTTTTGGAATGACGAAGGGAGATGAT 49740
mRNA        ------------------------------------------------------------

genome      GAATCTAAAGAATTTAGTGTAATATTTCTTCATGCTCAGTAAATGGTAGTTTCTGCTGCT 49800
mRNA        ------------------------------------------------------------

genome      GTTATTTTTATTACCATCTCTTTGGAATGGGAGTAGGTGCTCCTTTGTGGTCAGAGGCTG 49860
mRNA        ------------------------------------------------------------

genome      TGAGAGCTCCACAGCGCCAGTTTGCCCATCTGTACACTGGGGTCTGTTGAAGGCAGTCCC 49920
mRNA        ------------------------------------------------------------

genome      CTCTGTGATATCTCTGGCTGTCAGAGCTCAGATGATAGATGGTATTTTTGTACTCTTAGT 49980
mRNA        ------------------------------------------------------------

genome      TCTCATCATTTTCATGATTTCGATCACCATTTGAGTATGATGATGCTAACACTTTGTTGA 50040
mRNA        ------------------------------------------------------------

genome      ACGTAGAATCCGTTAATTACTTCCTTCCTGAACCTTTGGCATTAAAAAAAATCTATTCTG 50100
mRNA        ------------------------------------------------------------

genome      CTACCTCTCTGCTCATTTATGGTTATTCAAATTTATTATCAAGAGCCTGGTACAGTGGCT 50160
mRNA        ------------------------------------------------------------

genome      TGTGCCTATAATTGTAGCTACTTGGGAGGCTGAGGTAGGAGGATTGCTTGAGGCCAGGAG 50220
mRNA        ------------------------------------------------------------

genome      TTTGAGACCAGCCTGGGCAAGATAGTGAGACCCTATCTCTAAAAAAACTGAAAAAAAATT 50280
mRNA        ------------------------------------------------------------

genome      AGCTGGACATGATGGCATGTGCCTGTGGTCCTAGCTACTCAGGAGGCTGAGACAGGAGGC 50340
mRNA        ------------------------------------------------------------

genome      TCGGTTGAGCCCAGGAGTTGGAGTTCGAGGCTACACTGAGCTGTGATTGTGCCACCACAC 50400
```

FIG. 1 OO

```
mRNA      ------------------------------------------------------------

genome    TCCAGCATGGGTGGTAAAACAAGATGCCATTTCTTAAAAAAAAAAAATATATATATATAT 50460
mRNA      ------------------------------------------------------------

genome    ATTATCAATGAAATTCAGTAGTACCAACAGGATTATAAACAAAGATAGTAGTTCCCTTCC 50520
mRNA      ------------------------------------------------------------

genome    TACTTTTTCTCTTAATCCTTGTGTCTCACAGGCAAACATAACTCTTAGTATTTCTTCCAA 50580
mRNA      ------------------------------------------------------------

genome    TATTTACTTTCATGTTTCTTTCTTTCTTTCTTTTTTTTTCTTTGAGATGGAGTTTTGCTC 50640
mRNA      ------------------------------------------------------------

genome    TTGTTGCCAAGGCTGGAGTGCAATGACGCAATCTTGGCTCACCACAACCTCTGTCTCCCG 50700
mRNA      ------------------------------------------------------------

genome    GGTTCAAGCGATTCTCCTGCCTCAGCCTCCTAGTAGCTGGGATTACAGGCATGCATCACC 50760
mRNA      ------------------------------------------------------------

genome    ACGCTCGGCTAATTTTGTACTTTTAGTAGAGATGGGGTTTCTCCGGGTTGGTCAGGCTGG 50820
mRNA      ------------------------------------------------------------

genome    TCTCGAACTCCTGACCTCAGGTGATCCTCCCACCTCAGCCTCCCAAAGTGCTGGGATTAC 50880
mRNA      ------------------------------------------------------------

genome    AGGCGTGAGCCACTGCGCCCAGCAACTTCCACATTTCTAAATAACATGCTTCTACTGCTA 50940
mRNA      ------------------------------------------------------------

genome    TTTTTTTTTTCAATTTTAGACATTTTTTTACTTTCACTATAGTTCTATCAGAATTCAGTG 51000
mRNA      ------------------------------------------------------------

genome    TGTACGTTATTATGCCTAAGTAAATAGTCATGGTTGCTTACGTATTATATTTCTTTGATT 51060
mRNA      ------------------------------------------------------------
          rs7691627
genome    GTGTTTCTTATTTGATGAGAAAGCTGTGTTTTTTGCTCTGGGTTGAAACTGGAGAGAGGA 51120
mRNA      ------------------------------------------------------------

genome    CCTGGGGAGGAGGAGGAGGACAGATGAAGTTGGTGACTGTACCTTCATGGCCATAGCTGG 51180
mRNA      ------------------------------------------------------------

genome    GTTCTCAGCACCCGGGGATCTGCTGATCACCTACTCATAGGCCAGGCCCCTATCGAAGTT 51240
mRNA      ------------------------------------------------------------

genome    CTAGGTGACCCAGTGCTGGGGACGGGGGGGCCACCTGCAAGGTCTAATCATGGAGGTGGG 51300
mRNA      ------------------------------------------------------------

genome    GGCTACAGTGTTGGCTTGTGCTGGGGCCAGCATCCTTAGGAAGGCATCTTGGAGGTGGAG 51360
mRNA      ------------------------------------------------------------

genome    GAGACAGCCGCCCACTTCTTGATTGGGGCCTTCAGCAGCACCAGCTTCTTGGGCAGGCTG 51420
mRNA      ------------------------------------------------------------

genome    GTGCTGGCTTTCATCACCATGTCGTGTTCAATCTTCTTCCAGATCCTGACTTCTAGGTTC 51480
mRNA      ------------------------------------------------------------

genome    AGCTTTCCTCAGACCCTGGTTCCTTTCAGAGGCCATTGCTGCTGCCTTGCTCTTTGCTGG 51540
mRNA      ------------------------------------------------------------

genome    CTTGTGCCTTGATTATATGTCTTTGTACAACTTTTTGTTTTCCTGGAGTTAATCTTCACA 51600
mRNA      ------------------------------------------------------------

genome    TCTGTTTTCTTGGAGTTAATCGTTACCTCTATATCGCTTGCTTATTATTCTTTGGCCTTT 51660
```

FIG. 1 PP

```
mRNA      ------------------------------------------------------------

genome    TTGTCTTCTCACACCTTCCAACTTCTTTGTAATATGTGTTTAGTACAATTTTTCATGACA 51720
mRNA      ------------------------------------------------------------

genome    GGTAGTTTACTGAATCAGTTTTTCCCCAGTGTGGTCATCCAACTTGAGTTATCCAGCTCT 51780
mRNA      ------------------------------------------------------------

genome    CTGCCCCAGTCTGGGCAGGTTGATCTTCAGGTCTGTAGTACACTTGTATCCTAGGACTTC 51840
mRNA      ------------------------------------------------------------

genome    TCTTTGCCATTAGCCTGGAATTTCCTTTGCAGTTCTCCCGTTGGATGCCCAGTTCCTAGA 51900
mRNA      ------------------------------------------------------------

genome    TGCCATATGTTTTTCTATCGTCTAGTAGCTTCCTGAGAGAAGATGAATGGGAGGGAAATT 51960
mRNA      ------------------------------------------------------------

genome    GTATGAGGTTTTGCATTCATAAAAATGCCATTTTTTTTTCCTGTACACTTGGCTGGGTATG 52020
mRNA      ------------------------------------------------------------

genome    GTGTTCTGGGGTAGAAATCATTTTCCCTCAGAAATGCAAAGTCTTTGCCCTGTTGTCTTA 52080
mRNA      ------------------------------------------------------------

genome    AAATCTCCAACGTGACCCGATTCCTTAACCTATGAATGTACTTTTCTTTGGAAGCTTTCC 52140
mRNA      ------------------------------------------------------------

genome    ATTTTTGGGGAGGTGAAGTGCTAGGTACTTAGTAGGCCTTTTAATTTGGAAACTTACATC 52200
mRNA      ------------------------------------------------------------

genome    CCTTCAGTTCTGGGAAAATTTTCTTAACATTTCTCTGAGAAGTTCTTGCCTTTTATTTTC 52260
mRNA      ------------------------------------------------------------

genome    TGTGTTCTCTCCTGAAATTGGTTAGTTGGATGTTGGTCCTCCTAGATTGACTCACATCTT 52320
mRNA      ------------------------------------------------------------

genome    ACCTTTTTCTTTTCTTTTTCTGGTACTTTTTAGATATCCATCTCAAACTCTTCTATTCAT 52380
mRNA      ------------------------------------------------------------

genome    TGTTATGTTTTTAACTTCTTTCTTTTCTTTGTCTCTTGATGGGGTCTTGCCCTGTTGCCC 52440
mRNA      ------------------------------------------------------------

genome    AGGTTGTGGTGCAGTGGTGCGATCATAGCTCACTGCAGCCTCAAATTCCTGGGCTCAAGC 52500
mRNA      ------------------------------------------------------------

genome    AGCTGTTCTGCCTCACCCTCCCAAGTAGTTGGGACTACAGGTATGCACCACCACGTCCAG 52560
mRNA      ------------------------------------------------------------

genome    CTATTTTCTTTACTTTTTTTTTTTTTTTTTTGAGATGGAGTCCTACTCTGTCGCCCAGGC 52620
mRNA      ------------------------------------------------------------

genome    TAGAGTGCGGTGGTGGGATTTTGGCTCACTTAAGCCTCTGCCTCCCAGGTTCAAGCAGTT 52680
mRNA      ------------------------------------------------------------

genome    CTCCTGCCTCAGCCTCTCAAGTAGCTGGGATTACAGGTGTGCACCACCATGCCCGGCTAA 52740
mRNA      ------------------------------------------------------------

genome    TTTTTGTATTTTTAGTAGAGCCAGAGTTTCACCATGTTGGCCAGGCTGGTCTCGAACGCC 52800
mRNA      ------------------------------------------------------------

genome    TGACCTCAGGTGATCCGCCTGCCTTGGCCTCCGAAAGTGCCGGGATTACAGGCGTGAGCC 52860
mRNA      ------------------------------------------------------------

genome    CATCATTAGATCTTTAAATACCAGTATCTATAAGTCTTTTCCTCTTGAGTCAGCTAGTAT 52920
```

FIG. 1 QQ

```
mRNA       ------------------------------------------------------------

genome     CCCTGGAAGGAAATTACTCATTTTCCTGCTTGGAGGCTATAAGCTTGGCTATGTTTATCC 52980
mRNA       ------------------------------------------------------------

genome     TGCAACCGGGGACTGGAAGGGAGGGGACTGACAGTGTTGCTGGTCAGGGTGCCCTCTTAC 53040
mRNA       ------------------------------------------------------------

genome     TTTTTGTTTTCTGTGTGCATCTCACGTCTGTCCTCAGCCTATGTAAACACCTCTTGAGAT 53100
mRNA       ------------------------------------------------------------

genome     TATCCCTCTCAATCTTTGCCGGAGGTGGGGGAGGGGCTGCTTCCTGGGCTGCCTTGGATT 53160
mRNA       ------------------------------------------------------------

genome     GGAGGGAAGACCTCAGGTGAGTGGGTGGGAATTTGCCCAAGGAGCCATGAGACCAGCCAC 53220
mRNA       ------------------------------------------------------------

genome     TATTTCACCCTCTCCATCCCTCCACTTTCAGATGTATGTGGCGCCTCCAAAGCCCGAGCT 53280
mRNA       ------------------------------------------------------------

genome     CTTCTTGGCGTCTGTGGCTTCAATAAGCTTGCTTTTTGCTGGTATCCCTCCTACCCTCCC 53340
mRNA       ------------------------------------------------------------

genome     CTGTCCCCAGCAAAGCTTGCATTTGAACTTCTTCCTACGGGCTAACAAATCAGTCAGTTA 53400
mRNA       ------------------------------------------------------------

genome     TGTAGCTCTTGTTACTTTTTAGCTTCCGAAGTTTTGTTGACACCCGTAGTCTGCTAATGT 53460
mRNA       ------------------------------------------------------------

genome     CCCTGTTCTGTTCTTTCTGTTCGTGTAAATATATGCTTTATACAACTTCTTTACATGATT 53520
mRNA       ------------------------------------------------------------

genome     TTTGTGGGGTTTCTGGGTAGCAGAGCTTCACAAGTTCAATCCAGCGTGTTGGATTAGAAA 53580
mRNA       ------------------------------------------------------------

genome     TCTCCCACCCTCTGGTTTATTCTTATTCTCAAAATTACCTGCCAAACACTGATACTCCCT 53640
mRNA       ------------------------------------------------------------

genome     TGTTTTTCCTTTTCCTGACAGGAAATGTACATACCATACAGGACAGAAATCATTAGTGTA 53700
mRNA       ------------------------------------------------------------

genome     TCCCTTGGTGAATAACCACAAAGTGAACTTAACCCTTGTAACCGCCACCCAGGTCAAGAC 53760
mRNA       ------------------------------------------------------------

genome     AGAATATTACCAAGCACTCAGAAGCCTCTCCCCTATTCCCCCGTCACTGCTCCTGCCTTC 53820
mRNA       ------------------------------------------------------------

genome     CTCCCCAAGGTCATGACTGCTGGCTTCTAATTCCAGAGTCTGTTTTTAAATTCTGTGTAC 53880
mRNA       ------------------------------------------------------------

genome     ATAGACCATGGATTAAGTGTTCTTTTTGTCTGGTTTATTTTGGTCGACATTAAGTTCATG 53940
mRNA       ------------------------------------------------------------

genome     AGAGTCTTCTATATTATCGTGTGTATTAGTATTCCTGTAGTTTTAGGAGCTTCATAGCAT 54000
mRNA       ------------------------------------------------------------

genome     TCCATTGTAGGGATATACCACAGTTTATTCATTGTATTATCACTGGGTTGTTTCTAGTTC 54060
mRNA       ------------------------------------------------------------

genome     TTGGCTATTGCGAGCAGTGCTACTGTGACCACTCTTAGGTGTGTCTTTTGGAGTACATGT 54120
mRNA       ------------------------------------------------------------

genome     GCAGGTTTCCATCTTGCACAGCTAGAGGTGGAGTTGTTGGGTGATAGGGTGTGTGCATCT 54180
```

FIG. 1 RR

```
mRNA      ------------------------------------------------------------

genome    CAGCTGCAGTAGAAACTGCCAAATAGCTTTCCTTGAGTGCTTGTACCAGCTCACCCTTTT 54240
mRNA      ------------------------------------------------------------

genome    GCCACTGTGTATGGGGATTCCAGGAGCTCTGGTCCTCGCTAGCACTTGGAATTGCTGATG 54300
mRNA      ------------------------------------------------------------

genome    CTTTTACTCTTAGCCTTCCTGATGGGTGTTTTCTGGAATCACATTATGATTTTAATTTCC 54360
mRNA      ------------------------------------------------------------

genome    ATTCCTTAAAGTACCCTTGGCTCTGAAGTTTAATGATTCATGCATCTCTTCCCTTTTGAA 54420
mRNA      ------------------------------------------------------------

genome    GTACTCTTACAGGTATGTTGTGCATGTGTTGAAAAGTGGCACTATCTATTCTAAAATACA 54480
mRNA      ------------------------------------------------------------
           rs2798235
genome    GTATGCCTCCTCTGTGTTTGAACAGTTGTAGCGTGGCCTTGGGGCCTCCTGTTAGCTGGC 54540
mRNA      ------------------------------------------------------------

genome    TTGGAGAAGGGATTCTTGGGATTGTAGAGATTAGACCTGAGGAGGCCCCTTGGAGCTCTC 54600
mRNA      ------------------------------------------------------------

genome    TGACTAAATTTTATTCTTTATTATTCCAAACTATTTAAGCTCACCGTGTGCTGACTCATC 54660
mRNA      ------------------------------------------------------------

genome    ATAATAATGAGTAGCTCTCATTGTGCTTGTCTATTTGGACTCATACAATGATTTTTTTTT 54720
mRNA      ------------------------------------------------------------

genome    TTTCTTTGAGACAGAGTCTTGCTCTGTTGCCTAGGCTGGAGTGCAGTGGCACAATCTCGG 54780
mRNA      ------------------------------------------------------------

genome    CTCACTGCAGCCTCCACCTCCCAGGTTCAAGTGATTCTTGTGCCTCAGCTTCTCAAGTAG 54840
mRNA      ------------------------------------------------------------

genome    CTGAGACTGCAGGTGCGTACCACCATGCCTGGCTAATGTTTGTATTTTTAGTAGAGACGG 54900
mRNA      ------------------------------------------------------------

genome    GGTTTCACCATGTTGGCCAGGTTGGTCTCAAACTCCTGACCTCAAGTGATCTGCCTTCTT 54960
mRNA      ------------------------------------------------------------

genome    CAGCCTCCCAAAGTGCTGGGATTACAGGTGTGAGCCACTGAGCTTGGCCAAAGTAGTTTT 55020
mRNA      ------------------------------------------------------------

genome    TTAAGATGTTAGTATCTTTTCTTGCAGCTAAAAAAGTTTGTCAGAGATGATTCTACTTTG 55080
mRNA      ------------------------------------------------------------

genome    TTCTCCAGGTGTTTTCTCAGGGAGAAATTGGAGGCAGTAAGCCACTGGGGGAGTCCTGTG 55140
mRNA      ------------------------------------------------------------

genome    GCTGGGGGGTGGGGTAGTCCTGTGGCTCCTTGTCAGGGAGTCCTGTGGCTGGCAAGGAGA 55200
mRNA      ------------------------------------------------------------

genome    GAAGTCCTGTGGCTGGGTTGGGAGGGAGTCCTGTGGCTGGGGTCTCATCCTGTGCCTAAC 55260
mRNA      ------------------------------------------------------------

genome    AGTGTCCAGAGGTGCCGAGACCAGCTCAGTCGGGGAGACCCTAACCCAGCAGCGCTAGAG 55320
mRNA      ------------------------------------------------------------

genome    GAATTAAAGACACACACACAGAAATATAGAGGTGTGAAGTGGGAAATCAGGGGTCTCACA 55380
mRNA      ------------------------------------------------------------

genome    GCCTTTAGAGCTGAGAGCCCTGAACAGAGATTTACCCACATATTTATTAATAGCAAACCA 55440
```

FIG. 1 SS

```
mRNA            ------------------------------------------------------------

genome          GTCATTAGCATTGTTTCTATAGATGTTAAATTAACTAAAAGTATCCCTTATGGGAAACGA 55500
mRNA            ------------------------------------------------------------

genome          GGGGATGGGCCGAATTAAAAGAAGAGGTTGGGCTAGTTAACCGCAGCAGGAGCATGTCCT 55560
mRNA            ------------------------------------------------------------

genome          TAAGGCACAGATCGCTCATGCTATTGTTTGTGGCTTAAGAATGCCTTTAAGCGGTTTTCC 55620
mRNA            ------------------------------------------------------------

genome          ACCCTGGGTGGGCCAGGTGTTCCTTGCCCCTCATTCCTGTCAACCCACAACCTTCCAGTGT 55680
mRNA            ------------------------------------------------------------

genome          GGGCATTAGGGCCATTATGAACATGTTACAGTGCTTCAGAGATTTTGTTTATGGCCAGTT 55740
mRNA            ------------------------------------------------------------

genome          TTGGGGCCAGTTTATGGCCAGATTTTGGGGGGCCTGCTCCCAATACAGAGGTCTCGTGTA 55800
mRNA            ------------------------------------------------------------

genome          AATTCCCTGGGAGGCGATAAGCCTCTGAGAAACAGACTATGCTAACCACGCCATGAAAGA 55860
mRNA            ------------------------------------------------------------

genome          GAAACTTATTTATAAATCAGATGCCAGTTACTAGTTTACTGCTTATTTGCCCAGGCGTAG 55920
mRNA            ------------------------------------------------------------

genome          CTCTGACAGAGTCCCCGACTCATAGTGCTTGCTCAGTGCATGCTGAACAATGATTGGAAT 55980
mRNA            ------------------------------------------------------------

genome          CAAGTCATGGCTCAGAGCATAGTTTTGAATAATGGGAAATGGATGTTCTTAAGTAACATA 56040
mRNA            ------------------------------------------------------------

genome          GTCACCAAGATAATGCGACTAGCTGGGTCACCCCTTTTCAATTTTAGGATATTTTTATCA 56100
mRNA            ------------------------------------------------------------

genome          AGATTTAAATGGCCATCATTAGAGTTATAGCACTTTCTCCTTTGGATTGTCCTAGAGGCC 56160
mRNA            ------------------------------------------------------------

genome          CATGAGAAAGTATTCCCTAATTTCTTAGGAGAACAGTTTGTGGGTAGTATGCGGTCATGT 56220
mRNA            ------------------------------------------------------------

genome          CCAGTTAAATTGCAGATATTTCCGATCGAAGATGTTCCAGTCCTGAGAACTTCGTGACAT 56280
mRNA            ------------------------------------------------------------

genome          TAGCAGGACTTCTACAAGCCATCTCTTAGGGTGGGGCATTTACTGCAGTTGGCTAGTACT 56340
mRNA            ------------------------------------------------------------

genome          CTTTTCTCCTTAACTTTGTCATTTGTTGATTTTTTTTTAACTGTCCCCAAATACTGTGGG 56400
mRNA            ------------------------------------------------------------

genome          CAGAGTGTATCTAGAATTGAGGCCTCCACCATTGCGGAGAGGACATGGATGCTGAGCAGT 56460
mRNA            ------------------------------------------------------------

genome          CCCCTGAGTGAAGGTTATAAAGAAGCAAATAGACTACACATGTCTGTAAACTGCTCTTGA 56520
mRNA            ------------------------------------------------------------

genome          GTGTCCCAAATTTGGGGTACTTCAGTTCAGCTGTAGGAAAAGCCTCAAACTGTTTATACT 56580
mRNA            ------------------------------------------------------------

genome          TTGCAAGAATTGGAAACTTCTAATTCACGTTAAGTTTTATGTAATACATGATAAGCTTCA 56640
mRNA            ------------------------------------------------------------

genome          TAGGAGCTTCATCTTTTATCTACTTGGACTTTTGCTTCCGTAGGTTTTGTTAAAGGCCTT 56700
```

FIG. 1 TT

```
mRNA          ------------------------------------------------------------

genome        CATAGCGAACCTGAAGTCAAGCTCCCCCACCATTCGGCGGACAGCGGCTGGATCAGCAGT 56760
mRNA          ------------------------------------------------------------

genome        GAGCATCTGCCAGCACTCAAGAAGGACACAATATTTCTATAGTTGGCTACTAAATGTGCT 56820
mRNA          ------------------------------------------------------------

genome        CTTAGGTAAGGTGGAGGCATATGAGTGGAAGAGTCTCCAGCATGTACTCAAGATAGACCT 56880
mRNA          ------------------------------------------------------------

genome        TTGAAATAAATAAAACCAGATGATCCCTCAGCTTCTAGACCAGGCTATTTGGCACTGGTT 56940
mRNA          ------------------------------------------------------------

genome        GATTGAATGTGAACTGCACTGGGGCTGCTGTGAGCCCGCATGGGTCTCTGTGACCCTGCA 57000
mRNA          ------------------------------------------------------------

genome        GATGCAGCCGTGCCCAGGGACTGGGCAGTGGGTGTGGGCTGGTGTGAGCCCTGTCTGCCA 57060
mRNA          ------------------------------------------------------------

genome        CCCAGGGCCTGGCCCTCTGTCTGTGTCGGCCATGACTATGGTGAGTCTTGTAGGCTTGAG 57120
mRNA          ------------------------------------------------------------

genome        ACTGTGCCTCGGGTTCCTGCGGGTTCTCTGTAGGTCAGTTGACAGTTTCTCCTGTTGTTT 57180
mRNA          ------------------------------------------------------------

genome        GGGTAACTGTGGAAACGAACACTGGCAAGTGCTGAAGCGAGCATGTGGACGTGCGATATG 57240
mRNA          ------------------------------------------------------------

genome        AAATAACGACCTGGCTTTCAAAGGCAGTGAGGCTCTCTGGAAAGGACCTTGCTGAGCTAG 57300
mRNA          ------------------------------------------------------------

genome        GGATGTGGGTGTGTAGCCATTCCCAGTGGGCCTCATGGCGTACTCGTTCATGATCATGTT 57360
mRNA          ------------------------------------------------------------

genome        TGTGCCATCTTGATCTCTCAGGATCTCTTCTTTTTTAACAGATTAAGCCGGGAATCTCCA 57420
mRNA          ------------------------------------------------------------

genome        AACAGTGAGTCAGATGTTAAGATGTCTTGCTTCCACCCCCACAGGCTTACTCGTTCCTGT 57480
mRNA          ------------------------------------------------------------

genome        CGAGGATGAACACTCCACTCTGCTGATTCTTGGCGTGCTGCTCACCCTGAGGTATTTGGT 57540
mRNA          ------------------------------------------------------------

genome        GCCCTTGCTGCAGCAGCAGGTCAAGGACACAAGCCTGAAAGGCAGCTTCGGAGTGACAAG 57600
mRNA          ------------------------------------------------------------

genome        GAAAGAAATGGAAGTCTCTCCTTCTGCAGAGCAGCTTGTCCAGGTAGGAGCACAGGGTTT 57660
mRNA          ------------------------------------------------------------

genome        ACTCTAGGCCCTGCATGTGAATGACTGACATTCAAAGAACCGATTAATTTGGAAGAGAAG 57720
mRNA          ------------------------------------------------------------

genome        CGGCAGAACCGAGAGTTAGAGGTGTGGACTCTGGAGCTGCGCTGCTCGTTTCCAACCCTA 57780
mRNA          ------------------------------------------------------------

genome        GGTGCTGACCTCTAGCTGTCTTCCCTCTGTATGTCCCTGTCACCGTGAGTCAAATGCGGG 57840
mRNA          ------------------------------------------------------------

genome        TGATGCCTCCTCAGGTGCCGTGTTACCTAAGCCTCTCAGAGACCACTGCTACCCTGTTTC 57900
mRNA          ------------------------------------------------------------

genome        TAAAACCAGAGGTCACGATATGTGTTCATCCACCCAGTAAATACTGATTGAGCACCCACT 57960
```

FIG. 1 UU

```
mRNA            ------------------------------------------------------------

genome          GTGTGCTAGGCTCTGGGATAGGGGCTGGGTATACAATGGTGAGTATTTCAGCTGCAGCTT  58020
mRNA            ------------------------------------------------------------

genome          CTGCCCCGTGGAGGCTGTGGCCTAGCACACTGGTCTAGGCACGGTGGTATATGCTCACTC  58080
mRNA            ------------------------------------------------------------

genome          AAGGAGATAGGGACGTGGTCGTTTGGGGTGTCGGAACAAAATGTCGGAACTTCTCTTTCC  58140
mRNA            ------------------------------------------------------------

genome          AATGCAGAGAAACCTTGCAGTAATTCTAATGTACTGTGATTGGCAGTTGACTTCAGTTCT  58200
mRNA            ------------------------------------------------------------

genome          TTGTAGCACGCTTACTCAGGTTATTTCACTAACTATGTAACCATGCAGCCTCATTTTAAG  58260
mRNA            ------------------------------------------------------------

genome          CAATTGGATTTTTTGAACTTTACTTAAAATGTTATGTCAGGGTTTTTATTGTGCTTAATG  58320
mRNA            ------------------------------------------------------------

genome          TGTGCCATTTAGCTAAGTTTTGTAGGATACGAAATTGTAAGTGGCTTAAAATGATTCTTA  58380
mRNA            ------------------------------------------------------------

genome          ATAGAATCATGAATTGAAGATAATGCTAATAATTTAAGCACTGAGTTAGGTAGTGTTTGT  58440
mRNA            ------------------------------------------------------------

genome          AAAATGCTTAGAATGCTTCCTGGCACATGTTAAGGCCATGTAAGTGCTGCGTGTTGATAA  58500
mRNA            ------------------------------------------------------------

genome          ACAGCTGAGCAAAAGTGGACTCTTAAGAAAGTATTGGGGCTGAGAGTTCTGTTCCAACCA  58560
mRNA            ------------------------------------------------------------

genome          GCTGCCCTTTGGTTATTTTTCAGAATAAAAGCAGAGTCTCATGGGATATGACATTTATAT  58620
mRNA            ------------------------------------------------------------

genome          TTCCTTCACAAAAAACACTGCTGAGTGTTTTGTTGAGTAAAAAGGGTGTAGCCATGGTAA  58680
mRNA            ------------------------------------------------------------

genome          TAATACATTTAAAATATAGTTTATTTCATCTTTACCTTGCCTTGTTTTTTTTTAAGCTA  58740
mRNA            ------------------------------------------------------------

genome          GCTTTTTATTGAGAATTCCACACATACAAAAGTATCAACTCATGACCAGTTATATTTCAT  58800
mRNA            ------------------------------------------------------------

genome          TTATAATCCTACTTCTCCCTTTTTTTATTATTTGAAAGCAAACCCCAATTATCCTCTTAT  58860
mRNA            ------------------------------------------------------------

genome          TTCATCTATAAGTATTTCAGTATCTCTATAGATGAGGACTCTTCTTTATTTTTAAAACTT  58920
mRNA            ------------------------------------------------------------

genome          TATTTTTAAAATGATGGTCAGATGCAGTGTTCATGCCTGTAATCCCAGAACTTTGGGAGG  58980
mRNA            ------------------------------------------------------------

genome          CCAAGCTGGGCGGATCACTTGAACCTGGGAGTTTGAGACCAGCCCGGGAAACATGGCGAA  59040
mRNA            ------------------------------------------------------------

genome          ACCCCATGTCTTAAAGAAAAAAATCAGCCAAGTGTGGTGATGCATGCCTGTAGTCCCAGC  59100
mRNA            ------------------------------------------------------------

genome          TACTTGGGAGGCTGAGATGGGAGGGTCACATGAGCCTGGAAGATCAAGGCTGCAGTGATC  59160
mRNA            ------------------------------------------------------------
```

FIG. 1 VV

```
genome   CATGATTGTACCACTGCACTCCATCCTGGGTGATGGAGCAAGATTCTGTCTCAAAAAAAC 59220
mRNA     ------------------------------------------------------------

genome   AAAACTGCAAAACAACGTCACAAAACAGTGCCATTGTTAGACCTGAAAATATTAAACATT 59280
mRNA     ------------------------------------------------------------

genome   TCCTACATCAAATACCCACCAACTCATTATCAATTTTTCTCTCTACTCTTTTGGAATCAG 59340
mRNA     ------------------------------------------------------------

genome   CATCTAAATAAAATTGGTCGATAAGGATTGTAAATCTCTTTGATGAACTGGTTCCCCTCC 59400
mRNA     ------------------------------------------------------------

genome   ATCCCAGTTTTTTTCCCTTAGAGTTCATTTATTGAGAAACCAGATTGTTTGTCTTCTAAG 59460
mRNA     ------------------------------------------------------------

genome   TTTTCCTGTGGTCTGATATACTGCTTCCATCTCCACTGTGTAAATTAACACCTTTTTCTC 59520
mRNA     ------------------------------------------------------------

genome   TTCTCTGTATTTCCTGTAAATCAATAATTGGAGGAAAAGCCTTGTCAGATTTAGTGTATA 59580
mRNA     ------------------------------------------------------------

genome   TTTTATATCTGAGTCCAGTATTTCTTATATAATATTTTAAGATAAGTGTACTCTTTTAAA 59640
mRNA     ------------------------------------------------------------

genome   AAGTATTGAAACTATATGCTCAATTTTTTTTAACTGATGCTTTTAAGAAGGCTGCTTGAT 59700
mRNA     ------------------------------------------------------------

genome   CATAAAAGTTTAGAGATCATTGGTCTGATGGGAAAAGCAAATAATTACTAAACCGTTTAG 59760
mRNA     ------------------------------------------------------------

genome   CAAGGTTGAGGTGCACATGGTGGGGCCTGGAGAAGTTCAGTCATGAGCCGTCACTTATGG 59820
mRNA     ------------------------------------------------------------

genome   GCACGTGGAATCTGACCCGGCACAGAGTTGGGAGAAGACAGGAGCTTTATAGACAGAAAA 59880
mRNA     ------------------------------------------------------------

genome   TGTGGTCTTTGCTAAGTCCCAGGAGTGAAAGGGTGAGACAGTGCTCACAGCACACGAGTG 59940
mRNA     ------------------------------------------------------------

genome   TGGGTGCGTAGACAGAGCAAGGGTGGGTCCTGAAAAGGCCTGCAGGCTTTCTCATAGATT 60000
mRNA     ------------------------------------------------------------

genome   AGCAAGAGTGCTGGTTACGGAGGTTTCTAACATTTGTGAACAGATCGAAACTGTGTTAAA 60060
mRNA     ------------------------------------------------------------

genome   TTGGGATTGCAGTAATCCTGGAAGGACAGGGATAGAGGGTGAAGGGGAAAAAAGGGTATG 60120
mRNA     ------------------------------------------------------------

genome   GATGTGAGACTTAATTGCTGATTTTCTTAAGACCTTTCTCCAAAGTAAATAAATGATGTG 60180
mRNA     ------------------------------------------------------------

genome   GCACATTTTTGAACTGGCAAATTCTAAACTCTAGATATGATTATCTCTATAACATATCTT 60240
mRNA     ------------------------------------------------------------

genome   ACTCCATCTTCTTTTGACTAAAAACTGTTCTTAATTAAATTACCATGAGACGTTCAATTC 60300
mRNA     ------------------------------------------------------------

genome   AGCAAATGTAGTTTGGCTAACCATATTTAATTAGAATTTAATATAATCCTAGGCCTGGCC 60360
mRNA     ------------------------------------------------------------

genome   AAACTATTAAGCAAGTGTGGGCAAAATATTGATAATTTTAGATATGCAGGAACTTAGTTT 60420
mRNA     ------------------------------------------------------------
```

FIG. 1 WW

```
genome    GCTTTCCATGTGTGCTTTTCGAAAAAGGAATAAATTGAAAAATAGAGGAAGCCCTGAAAT 60480
mRNA      ------------------------------------------------------------

genome    CCAAGAAGCAAACTCTCTCACCTAGGCATGCAGTAAAAGCAATTCTAGGATGATTGCTGT 60540
mRNA      ------------------------------------------------------------

genome    TTGGCGCGTAGTTCGTATTAGAAACCATTCTTCTTGAATAAATAGTATGTTTAAGAAGCT 60600
mRNA      ------------------------------------------------------------

genome    GGGCAGAGGGAAGGCATATGCATATATTATCAACAAGGAGGGAGAAAAAGGCAATTAGTA 60660
mRNA      ------------------------------------------------------------

genome    ACCATCCATAGGAGGGTCAGCAAGATTTATAAAGGAAATTTGTGATCCAAGTATGAAGCA 60720
mRNA      ------------------------------------------------------------

genome    AAATAAGGTGCAGAATAAATTTTAAGCAAGTAATAGATTAGAGTAAGAGAACCCATTTGA 60780
mRNA      ------------------------------------------------------------

genome    CCATTAACCTTGGGACATTCTCTTTCAAATGACATGGAGTAGTACTGAAATCTTTCTTTC 60840
mRNA      ------------------------------------------------------------

genome    TTTCTGAGTCTAGGTTATTGTGACTGGACTCAGAAAGAAATATTTCATTATTGCAGTGAA 60900
mRNA      ------------------------------------------------------------

genome    TAACATTTGTGAACATTATTGTTCATAAATTATGCAGTGAATAACATTTATGAACACGTG 60960
mRNA      ------------------------------------------------------------

genome    ATGTGTAAGATACATACTGTTTATTTTTAGTTAAGTTTTTTGGCTCAACTTCTAGGCAGA 61020
mRNA      ------------------------------------------------------------

genome    GAACATTAAATGTAAATAGTGTTACCTAGGAGCATGTAAATGGAAATCTCCATAGTATGA 61080
mRNA      ------------------------------------------------------------

genome    AAGCAGTGCTGTTGCTAACAGAATTTAGGAGGGGGCAGATGAGGTGAAGGAAATGTGGGT 61140
mRNA      ------------------------------------------------------------

genome    GCTGATTTCCTTATTACATTGAGAGGAGCCAGGAGATTCTTTGTTCAAAATGGATGGCTT 61200
mRNA      ------------------------------------------------------------

genome    AAGAAGTCAAAGTATAAGCTGATTACGTAGAGCAGGTACCCAAAAATGTTTTGTGTAAGG 61260
mRNA      ------------------------------------------------------------

genome    GGCCAGATAGTAAATATTTTCAGTCTTGCAGGCCATCCCAAGTCTGTGGCAGCTACTCAA 61320
mRNA      ------------------------------------------------------------

genome    CACTACCTTTGTAGCATGAAAGCAGCCACAGGCAGCCCATAAATGTGGCTCTGTTCCGGT 61380
mRNA      ------------------------------------------------------------

genome    GAAACTTTAGGTACAAAAGCAGGTGCAGGCCAGACCTGACCTGTGCACTGTGGTTTGCTG 61440
mRNA      ------------------------------------------------------------

genome    ACCTGGGATTCAGGGGTATAGAAGTTACCATCAGAAGAGCTAAAAGTGAGACTTTTTACT 61500
mRNA      ------------------------------------------------------------

genome    TTATACTCTTCTACACTGTCTGATTTTGAAAAAAAGAAACATGTATTTTATAATATTAAA 61560
mRNA      ------------------------------------------------------------

genome    GATAGGGTTGGCAAATAGCAAATAAAAATACAGAATACCAGTGAAATTTGAACTTCAGAT 61620
mRNA      ------------------------------------------------------------

genome    ACATTATGAGTAATTTTATGGTGTAAGTATATTCCAAATCATGTGGGACATACTTACACT 61680
mRNA      ------------------------------------------------------------
```

FIG. 1 XX

```
genome          ACAAAATTATTTGTTGTTTGTTTACAGTTTAAATTTGAGTGCCTTGTATTTTATCTGGCA 61740
mRNA            ------------------------------------------------------------

genome          ACTGTAATTAAAGGGAAAAAGAATAAATTCATTATGTTCATATAATGTGATATAGCAGGG 61800
mRNA            ------------------------------------------------------------

genome          GTCCCCAACCCCCAGGCTGCAGAGTGGTACTGGTCCATGGGTCCCCAACCCCCAGGCTGC 61860
mRNA            ------------------------------------------------------------

genome          AGAGCGGTATTGGTCCATGGCCTGTTAGGAACCAGGCTGCCCAGCAGGAAGTGAGCAGCA 61920
mRNA            ------------------------------------------------------------

genome          GGTGAGCTGGCATTCCCACCTGAGCACCGCCTCCTGTCAGATCAGTGGCAGCATTAGATT 61980
mRNA            ------------------------------------------------------------

genome          CCCATAGGAGTGCAAACCCTATTGTGAACTGCACATGTGAGGGGTCTAGGTTGTGCGCTC 62040
mRNA            ------------------------------------------------------------

genome          CTTATGAGAATCTAATGCCTGATGATCTGAGGTGGAACAGTCTCGTCTTGAAACCATCCC 62100
mRNA            ------------------------------------------------------------

                                                                  rs4690072
genome          CTGGCCCTGTGGAAAAATTGTCTCCCATGAAACCAGTCTCTGGTGCCAGAAAGGTTGGGT 62160
mRNA            ------------------------------------------------------------

genome          AGCACTGTGATATAGTATTAAAAGTGCTAATAAATATGGCATACTGCCTTTAAAATGTCT 62220
mRNA            ------------------------------------------------------------

genome          GGTAGCTCTTTCTCAGTGGCACTCATAATAGTGTTTTTTGATTTTTAAATGTGTGTCAAG 62280
mRNA            ------------------------------------------------------------

genome          CTGACTCTCCCCTCCGTGTATGCTGGGCTTTATTTTCCCTTTCCTAGTCACCAGTTTTGG 62340
mRNA            ------------------------------------------------------------

genome          GAAATAGAGATCTTCATTCTCATGCTGCTCCTCTAGTGCAAGTGCTCCATTTATTTTTAA 62400
mRNA            ------------------------------------------------------------

genome          GGAATTAATATAACAAAAAATCATGGGAATTTAGAAAACAACATGGAAGCTAATGATCAC 62460
mRNA            ------------------------------------------------------------

genome          ATTGGTGGAAGTGATAGGGAAATATTTAGGGGGAGAAGTTAAGGTATAAACTTTGTCAAT 62520
mRNA            ------------------------------------------------------------

genome          GAAGTCCTATTAAAAACAACAAAAAAGTGAAGCTTAGGATGCATTTTATAAACTCTGACC 62580
mRNA            ------------------------------------------------------------

genome          AGAACACCTGTGTTTCTCTGTTTCTAGGTTTATGAACTGACGTTACATCATACACAGCAC 62640
mRNA            ------------------------------------------------------------

genome          CAAGACCACAATGTTGTGACCGGAGCCCTGGAGCTGTTGCAGCAGCTCTTCAGAACGCCT 62700
mRNA            ------------------------------------------------------------

genome          CCACCCGAGCTTCTGCAAACCCTGACCGCAGTCGGGGGCATTGGGCAGCTCACCGCTGCT 62760
mRNA            ------------------------------------------------------------

genome          AAGGAGGAGTCTGGTGGCCGAAGCCGTAGTGGGAGTATTGTGGAACTTATAGGCAAGTTA 62820
mRNA            ------------------------------------------------------------

genome          TTAGCAAGGTCTACTCTTACAATTAACTTTGCAGTAATACTAGTTACACTCTATTGATTA 62880
mRNA            ------------------------------------------------------------

genome          TGGGCCTGCCCTGTGCTAAGCAGTCTGCATTCCATCTTCCTTGCCAAAACTTATAATACA 62940
mRNA            ------------------------------------------------------------
```

FIG. 1 YY

```
genome    AATTTCATCTTTATTTTATAAATAGGGGAGTTGGGCTGGGTGTGGTGGCTCACGCCTGTA 63000
mRNA      ------------------------------------------------------------

genome    ATTTCAGCACTTTGGAAGGATCGCTTCAGCCCAGGAGTTTGAGACAACCTGGCCAAGTGA 63060
mRNA      ------------------------------------------------------------

genome    GACCCTGTCTCTACAAAAAAAAAAAAAAAAAAAAAATTAGCTGGGCATGGTGGCACATGC 63120
mRNA      ------------------------------------------------------------

genome    CTGTAGTCCCAGCTGCTTTGGAGGCTGAGGTGGTAGGATTGCTTAAGCCCAAGAGGTTGA 63180
mRNA      ------------------------------------------------------------

genome    GGCTGCAGTGAATCTTGATGGCAGCTGCACTGAGCCTGGTGACAGAGCAAGATGCTGTCT 63240
mRNA      ------------------------------------------------------------

genome    CAAAATAAATTTAAAAATAAAATAAGAGAATTAAAGTTTAGCAGGTTGGGTGGCAAAATG 63300
mRNA      ------------------------------------------------------------

genome    AGGCCACACATTTAAAGCCCCTCCTCCTGATTCTTTTCTCTGCCTTGGCTGCCTCCTGTG 63360
mRNA      ------------------------------------------------------------

genome    GCATTTTAGGTGCTGAGAAATGAAAACAGTAGGGAAAATAGTTCCAGGATCCTCATGTTA 63420
mRNA      ------------------------------------------------------------

genome    ATTTGCCAGAAATGGCATCTTCAAGTCGTCAGAGGGATCTGAGAGTTCCTTCCTGGCCTG 63480
mRNA      ------------------------------------------------------------

genome    ACTTGAGAAAATCCGTCTGTCCCCAGCTCTGCGTCTGCCTCCACTGCCCAGTCACCTCCT 63540
mRNA      ------------------------------------------------------------

genome    CTCCATGCTCTTGGGGCTGGGCCCTACCCCACCATGCAGTGCTGCCCTGGAGCAGTGAGC 63600
mRNA      ------------------------------------------------------------

genome    TTGGTGGGTCCTGTCTGGCATGAGAGCTGCCTTTGGGAGCTGGATCCCAGCCTCTACCAC 63660
mRNA      ------------------------------------------------------------

genome    TGGGTCTGGTGCCTAGCAGGCTATGGATAAACTTCTGCTGACTCCGGCCTCTCCTAAGCC 63720
mRNA      ------------------------------------------------------------

genome    ACTGCAACGTGGTCGGTGTAGTGCACAGTGTGTGTGCAGCGTGGCCTTACTCACAGCCTC 63780
mRNA      ------------------------------------------------------------

genome    CACATTAGAGAGAATCTGACTGAAGTCTTACTGCTGCCTCGTGTGAACATAAATGTTTGC 63840
mRNA      ------------------------------------------------------------

genome    CAGAACCATGAGCAGGAAATGTTAATCTGCCTTGTTTCCTGTCCTTTACACGGAAGAATT 63900
mRNA      ------------------------------------------------------------

genome    TTTTTCTGTATGGAATGCGTGCCTTACAAATAATGAGTGGAAATACCCATCGCTAATGAA 63960
mRNA      ------------------------------------------------------------

genome    AAGTTATACTTGACTGTTAGTCAGCTAAATAATCTGAGATTTCTAATACTTTTAATTTGG 64020
mRNA      ------------------------------------------------------------

genome    CTTTTACAATGCAATTTATCTTAGCTTTTTTGATTTCTTAGGTCATATCTTTAGAACTAT 64080
mRNA      ------------------------------------------------------------

genome    ATATTTGAATGTTAATGTAATTTTCATATTGAAATTAAAATGTTGAACTGCGATGTTAAG 64140
mRNA      ------------------------------------------------------------

genome    TGTTTCCTGTGGAAAAACGTTCACATTTTCTCTAGTTTTAAAGTTGAATCAAGCTGTTTG 64200
mRNA      ------------------------------------------------------------
```

FIG. 1 ZZ

```
genome    AAGATTTTCACATTTCTTCTAGATTTTATCAGCTTGTTACTTTATCTGTCACTTTCTGTG 64260
mRNA      ------------------------------------------------------------

genome    ATTTGCAGCTGGAGGGGGTTCCTCATGCAGCCCTGTCCTTTCAAGAAAACAAAAAGGTGA 64320
mRNA      ------------------------------------------------------------

genome    TTATTTCAGAAATCAGAGTCTTGTGTTGAATCTTACTGATTTTCTTGTATTTCTGTAATG 64380
mRNA      ------------------------------------------------------------

genome    TAATGTATCTTGTATTTCTTGTAATACTGTATTGGACTCTGTGTATATCTCTTCTCAGAT 64440
mRNA      ------------------------------------------------------------

genome    GAGTGATTATATGTGTGAATGTTGCTGGAATCTGATAACCAGGCCTGAATAGTTTTGTAG 64500
mRNA      ------------------------------------------------------------

genome    GGTGGCTTTTAAAAATTACTTTCATATCAGAATTGCTTTGTCATAAATTTTGAACGCATC 64560
mRNA      ------------------------------------------------------------

genome    ATAAATTTCTAATGTTCGGGGTCAGCAGACTTTTTTTGTAAAGGGACAGAGTGTAAACAT 64620
mRNA      ------------------------------------------------------------

genome    CTTAGCTTTATGGGCCATATGGTCTCTTTTGCAACATTCAGCTCTGCCCTGTGACAGGAA 64680
mRNA      ------------------------------------------------------------

genome    TGCAGTTGTAAAGACATGAGCTACTGGCCAGCTATGTTCCAGTAGAACTTTACTTACAGA 64740
mRNA      ------------------------------------------------------------

genome    AACAGACAGGCTGTAGTTTGCCAATACCTGCCTTAGGGAATGTGTTGTTATATTTTGTGA 64800
mRNA      ------------------------------------------------------------

genome    GTTACCTTCTCAGTAAATTTTATTTAGTATTAGTCAGGAATATTATTAAGTAGCTTCTTT 64860
mRNA      ------------------------------------------------------------

genome    TCCAGCCTGGTCAACATAGTGAGACCCGGTCTCTACCAAAACAAAACAAAACAAAAAAAC 64920
mRNA      ------------------------------------------------------------

genome    AGCCACGCATGTGGCATGTGCCTGTAGCCTCAGCTGCTGCTCAGGGGGCTGAGGCAAGAG 64980
mRNA      ------------------------------------------------------------

genome    GATTGTTTGAGCCCAGGAGTTTGAGGTCACAGTGAGCTGTAGTCATGCCACTGCACTCCA 65040
mRNA      ------------------------------------------------------------

genome    GCCTAGGCAACAGAATGAGACCTTGTGTCTTAAAAAAAAAAAGTTTCCTTTGTTGGGTTA 65100
mRNA      ------------------------------------------------------------

genome    TTTTAATTTGGACCTGGTTATCATTTTTCAGCCATATTTAACTTTGTACATATCAGAATG 65160
mRNA      ------------------------------------------------------------

genome    TTCTGATAAAACTTAACTTTTATTAAAGTGTTTGTGATATAATCTGCTAGTTTTGGTACA 65220
mRNA      ------------------------------------------------------------

genome    CATTATCTTTTGCAATGCCAGTTATTTTCTTTTCCAGTGTGGGTTTGCATAGGAAAAGAA 65280
mRNA      ------------------------------------------------------------

genome    TTGCTGTCACTTTCTATTTTGAAATCTTAAAAGACTGATCCTTTTTTGTGTCATGATTTG 65340
mRNA      ------------------------------------------------------------

genome    AGTATTTAATTGAGAGCCTAATGCCTAATATTATTTGCAGTATTAAATGGGATCTTAACA 65400
mRNA      ------------------------------------------------------------

genome    GGAATAGCATTCTAGCCTTCATTGAATTAAGTAAACATTTCTTAAGAGAACTTGGAATCT 65460
mRNA      ------------------------------------------------------------
```

FIG. 1 AAA

```
genome    ATAATATTTGCGTCATCATAGTATGAGATACTTAATCAAGTTTGAGATTTTAGTGAAACA 65520
mRNA      ------------------------------------------------------------

genome    TTGTTTAGAAGCCAAAAGGATTCTAGGAAAAATTAATGTCTATATTCTTGAATTAGGAGA 65580
mRNA      ------------------------------------------------------------

genome    GATTTTGGGACGTGTGACTAAGTTACGCTGACACTTGTTTGTTTCTTAGTCGCTTTTTCC 65640
mRNA      ------------------------------------------------------------

genome    AGTGGCGGTGAGAACGAAGATGACTGATTCACATTGCTCAGATGAGTTTATCCTCTTCTG 65700
mRNA      ------------------------------------------------------------

genome    GCTGGGACATGGGATATATCCTGTCTCTTTTAAGCCTTTTTGGTATTTTTCCCCCATTGA 65760
mRNA      ------------------------------------------------------------

genome    GAGCTGTGTCTTCAAACTCTTCTGTTATAGCTGGAAAATCCTTTTTAAGTGAAATCTGCC 65820
mRNA      ------------------------------------------------------------

genome    CAAATTATAAGACAGATGAAGGTAGAGTTGTGTTGGATATAGGATTAGGGTGAAAGTAGT 65880
mRNA      ------------------------------------------------------------

genome    GGGGGTGTCCTGGAGCCTCTCTTCTGGTGGCAGCCTAGCTCTTGTGCCTTTGAGGAAATT 65940
mRNA      ------------------------------------------------------------

genome    ACCCTGGGGACGGCTCTGTGGAACATATTTGCAAACCACTGATTTGGAAGATAGAGATGG 66000
mRNA      ------------------------------------------------------------

genome    CTTTTGTTAAGATCTGAATTCACCTTTTTGGCATTTTATTTGATTTCTCAAGGTAAAGAA 66060
mRNA      ------------------------------------------------------------

genome    CTTATTTTGTAATAAAGTTTCCTATTATTTAGTAGATAGGCCAAGTTGCTGTGTTAATTC 66120
mRNA      ------------------------------------------------------------

genome    CATGTAGATTTTGGGTTTCCTTTGCTCATTTTTTTCACTCTTAATCTCACATCATTGTAAG 66180
mRNA      ------------------------------------------------------------

genome    TTTATGGAAGTTATCATACTTCTGACTTTTTCTTTGAAGAGCAGAAATTAGAAATTCCCA 66240
mRNA      ------------------------------------------------------------

genome    ATAATTATTTTGATAGTGTCATTTAATGACACTCACATGTGATGTAGCCACAAAGATTTA 66300
mRNA      ------------------------------------------------------------

genome    ATGAGTTCAGTTTTAAATCATATTAAGACTGTTGGTTTCATTTGTTCTCATTAATGTAAT 66360
mRNA      ------------------------------------------------------------

genome    TCTGAAGATGAACAATAAAATGTATTTTTAGAACTTTCAAATGAAATATTATTTCATCCT 66420
mRNA      ------------------------------------------------------------
                                                      rs6446723
genome    TCCAGATCATATAATGCTTAAGTTCTGATTGTTAATCATAAAGTCTAGAAAATTAAAAGA 66480
mRNA      ------------------------------------------------------------

genome    TAATAAAATGAAAGTGACTTTTAGGTATTAGAGTTTTATTATAAATTCTGGTGTGTCATT 66540
mRNA      ------------------------------------------------------------

genome    GGAGCTATGACATGAATATTTCAAAGGCCAATAGCATTGGATCTTTACAGTTATAACTTA 66600
mRNA      ------------------------------------------------------------

genome    CCATTTTTAAGTTTAAGTAGTAATATAGATTATTTAATAATCAAAATCAATAAATATTAA 66660
mRNA      ------------------------------------------------------------

genome    TTATTAAAATGTTTTGTGGTATAGTTTGAGAATCATTGCTTTTAACTTTTTCCATATAGG 66720
mRNA      ------------------------------------------------------------
```

FIG. 1 BBB

```
genome    TTTATTGACTTTAATAGCATTCTAAACATAACATCTCTACATTCTTTGTGTTTAATACTG 66780
mRNA      ------------------------------------------------------------

genome    TGGAGGTATAAAAATACTTATATATGATGATAAACTATATTAGAGTAAATTAAATATTCT 66840
mRNA      ------------------------------------------------------------

genome    TATGAGTTTCATTTTAGAGTGCATTTACTTAATTTTGAAGTCCTTATTTTTAGCAAACTA 66900
mRNA      ------------------------------------------------------------

genome    AAAGGAATGTTGGTACATTATTTACTAGGCAAAGTGCTCTTAGGAGAAGAAGAAGCCTTG 66960
mRNA      ------------------------------------------------------------

genome    GAGGATGACTCTGAATCGAGATCGGATGTCAGCAGCTCTGCCTTAACAGGTAGTTCTCAC 67020
mRNA      ------------------------------------------------------------

genome    TAGTTAGCCGCTGGTGTGGACCTTCACTGTCTGCCTTCCACCCCTTGCCCTTCCTGCTCG 67080
mRNA      ------------------------------------------------------------

genome    TCCCCCTGCACCTGGTGGACAGCACGACTGGGGGCAGCAGTGGAGCCAGGTTGCTTAAAT 67140
mRNA      ------------------------------------------------------------

genome    GGGGCATATTCGGGCTTCTTTTATAATACTTACTCTGAAGCTTGTGTGTCTGTGGTGTTT 67200
mRNA      ------------------------------------------------------------

genome    GCATCATATATTTGTTGTTTTCCATGGTTTAGGCTGTTTTAAAATTAGGTTTATGGCTTG 67260
mRNA      ------------------------------------------------------------

genome    AGCATAGGGCTTTGTGAGTAGGGGATGGCAGGTCGAAACATCTCATGAGTTGGATGGGTT 67320
mRNA      ------------------------------------------------------------

genome    ATGCTGGGGGTTGGGAAATGGGATGAAAAATTATGGGATGAAAAATTGCCTATGGATAGT 67380
mRNA      ------------------------------------------------------------

genome    TTAACTTGAAAGAATCTGCCTTTGTTTACAGATAGTTATCTTTTTTCTTTTTTGAGATAG 67440
mRNA      ------------------------------------------------------------

genome    AGTCTCACACTGTCACCCAGTGCAGATACCCAGTGTCACTGGAGTGCAGTGGTGTGCTCT 67500
mRNA      ------------------------------------------------------------

genome    TGGTGCACTGCAGCCTCCGCCTTCTGGGTTCCAGCGATTCTCCTGCCTCAGCCTCCCAAG 67560
mRNA      ------------------------------------------------------------

genome    TAGCTGGGACTACAGGTGCCCGCCACCACGCTTGGCTAATTTTTGTATTTTTTTGTGGAG 67620
mRNA      ------------------------------------------------------------

genome    ACGGGTTTTTGCCATGTTGGTCAGGCTGGTCTTGAACTCCTGACCTCAAGTGATCTGCCT 67680
mRNA      ------------------------------------------------------------

genome    GCCTCAGCCTCCCACAGTGCCGGGATTACAGGAGTGAGCCACTGTGCCCGGCCAGTTACA 67740
mRNA      ------------------------------------------------------------

genome    GATACTTATCTAATGAAATTCTCTGTGTACTTTATAAAAGATGAGGATTAACTGAAGGTA 67800
mRNA      ------------------------------------------------------------

genome    CTAATAACTGGATTATATGAGGGTGGTTTTGGTTGTATAATCCTATCTAAAAGAATATTT 67860
mRNA      ------------------------------------------------------------

genome    TAGCTATAACTGAAAGTAAGACTTAAATATTTAGAGAGGAAAATCTGAATAATTCTAGTA 67920
mRNA      ------------------------------------------------------------

genome    GTAATTATTTATTTACAAAATAAAAATAGATTTTTTTTTGATTACACAAATTAAACAACA 67980
mRNA      ------------------------------------------------------------
```

FIG. 1 CCC

```
genome    ATAAAACATCACAGCAATCCGGATACTATAAAGCTCACATGCTTACCGACCCAACTGCCC  68040
mRNA      ------------------------------------------------------------

genome    CAGGAGTGACCACTGCCAACAGCTTCATGTCGACCTTTTTGCCATAATTTTTATATAGCC  68100
mRNA      ------------------------------------------------------------

genome    TTTTTTGTTTTTAAATGGTAATTTAGAAAGTCAACTAGGAAAATGTGTTACAGGTTTATC  68160
mRNA      ------------------------------------------------------------

genome    TTCCAGGAGAATAGGACTGGAGTCGAGATCTTGAATGTGGCTTGGAAGAAGGCAAGCCCA  68220
mRNA      ------------------------------------------------------------

genome    CCCCAGAGAGATGAGTTGACAGTTGTTTCTGACCACTGCTTGCTTAGAGGGCCTGCGTGT  68280
mRNA      ------------------------------------------------------------

genome    CTGTGACCGCCTAGCTTTGCGCCCCTGACTAGGCTGCCCCTTAATTACAAATGTCTTTAT  68340
mRNA      ------------------------------------------------------------

genome    ATATTGCTCCAGCTAAGGCTTGGAGTAGTCGGTTAAGAACTTGAACTTCGGTTTTTGCAG  68400
mRNA      ------------------------------------------------------------

genome    TGAAACAGCATTTGAGAATATCACCTTCTGATAAGCCTTATTTTATAAGGTGGGTACTGT  68460
mRNA      ------------------------------------------------------------

genome    AGTGGGAGGCAGTGTGAGAGATGCTTGAAGGATGCACTGCTGTCCTGCATTTCAGCATCT  68520
mRNA      ------------------------------------------------------------

genome    TCAGGATGCTGTGCAGCTGAAACATTTGATAACGGTGGAACTGTTCGTTATTTTGCAAGC  68580
mRNA      ------------------------------------------------------------

genome    CTGTGATTCCCTATTGAATGTTTTCTCTCGCCATTTGACAAATGAGTGTTTCTCTGTCTT  68640
mRNA      ------------------------------------------------------------

genome    CAGCCTCAGTGAAGGATGAGATCAGTGGAGAGCTGGCTGCTTCTTCAGGGGTTTCCACTC  68700
mRNA      ------------------------------------------------------------

genome    CAGGGTCAGCAGGTCATGACATCATCACAGAACAGCCACGGTCACAGCACACACTGCAGG  68760
mRNA      ------------------------------------------------------------

genome    CGGACTCAGTGGATCTGGCCAGCTGTGACTTGACAAGCTCTGCCACTGATGGGGATGAGG  68820
mRNA      ------------------------------------------------------------

genome    AGGATATCTTGAGCCACAGCTCCAGCCAGGTCAGCGCCGTCCCATCTGACCCTGCCATGG  68880
mRNA      ------------------------------------------------------------

genome    ACCTGAATGATGGGACCCAGGCCTCGTCGCCCATCAGCGACAGCTCCCAGACCACCACCG  68940
mRNA      ------------------------------------------------------------

genome    AAGGGCCTGATTCAGCTGTTACCCCTTCAGACAGTTCTGAAATTGTAAGTGGGCAGAGGG  69000
mRNA      ------------------------------------------------------------

genome    GCCTGACATCTTTTTTTTTATTTTTTATTTGAGACAGAGTCTCACTCCATAGTGCAGTGG  69060
mRNA      ------------------------------------------------------------

genome    AGGCCGGGCACAGGGGCTCATGCCTGTAATCCCAGCACTTTGGGAGACTGAGGCAGGCGG  69120
mRNA      ------------------------------------------------------------

genome    ATCACTTGAGGTCAGGAGTTCGAGACCAGCCTGGCCAACATGGTGAAACCCTGTCTCTAC  69180
mRNA      ------------------------------------------------------------

genome    TAAAAATACAAAAATTAGTTGGGCGTGGTGGCACATGTCTGTAGTCCCAGCTGTTAGGGA  69240
mRNA      ------------------------------------------------------------
```

FIG. 1 DDD

```
genome    GGCTGAGGCAGGAGAATTGCTTGAGCCTGGGAGGCAGAGGTTGCAATGAGCCGAGATCGT 69300
mRNA      ------------------------------------------------------------

genome    GACACTGCACTCCAGCCCGGGCAACAGAGCAAGACTCCATTTCAAAAAAAATAAAAAAAT 69360
mRNA      ------------------------------------------------------------

genome    AAAGTGCAGTGGCTCGTTCTCAGCCCACTGCAACTTCTGCCTCCCAGGCTCGAGCGATTC 69420
mRNA      ------------------------------------------------------------

genome    TCCCGCCTCAGCCTCCTGAGTAGGTGGGATTACAGGTGGGCACCACCACACTCAGCTAAT 69480
mRNA      ------------------------------------------------------------

genome    GTTTGTATTTTCAGTAGAGACAGGGTTTCACCATGTTGGCCAGGCTGGTCTCAAACTCCT 69540
mRNA      ------------------------------------------------------------

genome    GACCTTAGATGATCCACCCACCTTGGCCTCCTAAAGTATTGGGATTATAGTTGTGAGCCA 69600
mRNA      ------------------------------------------------------------

genome    CCATGCCCGGCCCTGCCACCTGCCATCTTTTGAGTTCTTCCCTGGAGACCTAGACCTGAA 69660
mRNA      ------------------------------------------------------------

genome    CCCTCCTGCTTGTTCTCTTGTTATCTAATACCCCTATTGACAGCGCAGCTTAGATCATTA 69720
mRNA      ------------------------------------------------------------

genome    ATGGAGAGCTTGACCTCATCTGATACCTTCACTGAAGGAAACAACTTAGTGTCTTTTGTG 69780
mRNA      ------------------------------------------------------------

genome    TTGAACACTGAGGTAAAAAATTGGAATAGTTGATTATATGAACTCTGCTAAAATTGAGTG 69840
mRNA      ------------------------------------------------------------

genome    CATTTTACATTTTTTAAGGCCTTGTTGGGCCCTGGTTAAATAATTATTTTTAAAAATCCT 69900
mRNA      ------------------------------------------------------------

genome    TAAGGAGCCTATTATAAACAGATCTGTGGTCTTAATGAAATGTGATTAATACTGTGCATT 69960
mRNA      ------------------------------------------------------------

genome    ATTTTAAGAACTTTTGACTTTTCAAAAAACTTTTACAACATTTCCCATTTGATAGCGGCA 70020
mRNA      ------------------------------------------------------------

genome    TAGGTTTAAGCACTTCTCATCTCTAAGTTAGTGGACAAAAAACCCTCATGGATAGTCTAA 70080
mRNA      ------------------------------------------------------------

genome    TAATGTTTGCTACAAGTCCATGTTGAGTTTTATACTCCATTTTATTTTCAGTTTTAAAAA 70140
mRNA      ------------------------------------------------------------

genome    CTGTGGTTAAATATGTGTAACATAAAATTTATGTTCTTAACCATTTTTTGCGTATACAGT 70200
mRNA      ------------------------------------------------------------

genome    TCGCTGGTATTAAATACATTTAAATAATGTCATGGAATCATTGCTACCACCCATCTCTGT 70260
mRNA      ------------------------------------------------------------

genome    AACCTTTTGATCATGTAACACTGAAGCTCTGTTCCCATTGAACTCTATTCCTCCTTTCCC 70320
mRNA      ------------------------------------------------------------

genome    GCCAAGTCCCTGGCAACCACGATTCTTCTTTCTGTCTTCTGAATTTGACTACTTTGGGTT 70380
mRNA      ------------------------------------------------------------

genome    CTCATATACTTTAGGAGTCACACAGTATTTGTTTTACTTAGCATAATGTCCCCAAAGCTC 70440
mRNA      ------------------------------------------------------------

genome    ATGCATGTTGTAGCCTATGTTAGAACTTCCTAATGTTTCAGGCCAAATACTATTCCATTG 70500
mRNA      ------------------------------------------------------------
```

FIG. 1 EEE

```
genome    TATGGATAGGCCACATTTTGCTTTTCCATTCCTCTGTCCATGGACACTTGTATTGCTTCA 70560
mRNA      ------------------------------------------------------------

genome    TGTTTTAGCCATTGTGAATCATGCTGTTATGAACGTGGGTGTACAGATAGCTCCTGGAGA 70620
mRNA      ------------------------------------------------------------

genome    CTCTGCTTTCCATTTTTTTGGCTAAATACCCAGAAATGGAGTTGCTTTTACATTCCAATT 70680
mRNA      ------------------------------------------------------------

genome    TTAATTTAAAACATTCATATCATTGAGTGTTTTACTTAATAGTATAGTAGTTAACAAACT 70740
mRNA      ------------------------------------------------------------

genome    TAATAAAATAGTATTTTGGTAATAATTTGCTGGTAGTCCATTGTTCAGTTTTTTTAGGTA 70800
mRNA      ------------------------------------------------------------

genome    AATTACACAGGACATTTCAAGTGGACATGAAACATCTTGTGATGTGGAATCATGCCCCAA 70860
mRNA      ------------------------------------------------------------

genome    GCTGATGGCTAAACATATGAAATACCATACCCTAAATTTAGTAGATTTAGTCTTTGCAAT 70920
mRNA      ------------------------------------------------------------

genome    TTAGGAGATAACCTGTTATATTGTTAGGTTTTTGTCGAAAAGCTTTGTCCTCATATTTCC 70980
mRNA      ------------------------------------------------------------

genome    AACTTGCTGTAAAATTTGTTTGTGAAGACAAATATTTTTGTATGGGTTTTTTCTTTTTCA 71040
mRNA      ------------------------------------------------------------

genome    TATTAAAAAGAAATGTCCACATTGGAATTTTTTTGGAGTTTTTAGAGCTAATAGAGCTTT 71100
mRNA      ------------------------------------------------------------

genome    TCATAATGTAGTGGGAATGAGTGATCAGTAAGCTCTTAGCAGTTTCCATGCGTGCATTTC 71160
mRNA      ------------------------------------------------------------

genome    TGTGCCTTGAAATAAATGACAGATGAGTACATTTGTGTTCTGTGTGTAAAATGTGCTCTT 71220
mRNA      ------------------------------------------------------------

genome    TCCTCATTGCACTTCCATGTTGGAGGGCTTGTCTCTTGGTGATCACACTTCAAAATTCTC 71280
mRNA      ------------------------------------------------------------

genome    ACAGCCCCCCTTGAACCGTTTAGGTGTTAGACGGTACCGACAACCAGTATTTGGGCCTGC 71340
mRNA      ------------------------------------------------------------

genome    AGATTGGACAGCCCCAGGATGAAGATGAGGAAGCCACAGGTATTCTTCCTGATGAAGCCT 71400
mRNA      ------------------------------------------------------------

genome    CGGAGGCCTTCAGGAACTCTTCCATGGGTATGTGGACTACAGGTGATGCGCTACAAAGTG 71460
mRNA      ------------------------------------------------------------

genome    GTTTGTATTCAGACCTGGACATCTTAATTATATCTTTGCTTCCAAGAAGAAGTCCTTTGA 71520
mRNA      ------------------------------------------------------------

genome    TACTGTTTTCTGAGTTCTGAATAGCTGATGAAAATGACCAATTGAGGAATAATCATACTT 71580
mRNA      ------------------------------------------------------------

genome    TTTCTTGATCTAAATCTTATACTTTTGAGTTATCTTAGCATAAATGTATAATTGTATTTT 71640
mRNA      ------------------------------------------------------------

genome    AAGTGGAAATTTGTCACTTAATCTTGATTTCTCTGTTTTTAAAGCCCTTCAACAGGCACA 71700
mRNA      ------------------------------------------------------------

genome    TTTATTGAAAAACATGAGTCACTGCAGGCAGCCTTCTGACAGCAGTGTTGATAAATTTGT 71760
mRNA      ------------------------------------------------------------
```

FIG. 1 FFF

```
genome    GTTGAGAGATGAAGCTACTGAACCGGGTGATCAAGAAAACAAGGTGAGGGACATAGGCTT 71820
mRNA      ------------------------------------------------------------

genome    GAGACGACTTGGTGTTTCTGAGCTTGTGTGAGGATTTAAAATCGCCCTGGCTACTGTCTA 71880
mRNA      ------------------------------------------------------------

genome    CTTTATTGCTTTCCCATCCCTGGGCCTTTAAATTTCCCCTTTAAATACCAGCTCTTCCCA 71940
mRNA      ------------------------------------------------------------

genome    GGCCTGTTGTTTTCTGCCTTTCCAGGTACTACCCACAGCCTTGAGAATTGCCTGAGTTCT 72000
mRNA      ------------------------------------------------------------

genome    GCCTCCTTTGAGAGTGTGCCCCAGACAAATCTATTCTGTACTGAATGTTTCCTTGTCTGA 72060
mRNA      ------------------------------------------------------------

genome    TTTCTTGGATCATTCATTTGATGGTTGCGTATGGCCTGCAACGTTTCTTGTTTTGGTTCT 72120
mRNA      ------------------------------------------------------------

genome    ACTGAACTGTTCTAAAAGTCTCTCTTCATATTATCTTTTTACATGTAAATGTAACTGTCT 72180
mRNA      ------------------------------------------------------------

genome    TCACTTTTAATTCCTCAAGGACAAGGAATAGCGTTTCACAGTTCGTCCCATCAATCAGAA 72240
mRNA      ------------------------------------------------------------

genome    TTATAGCCTTTGGCATCTCCCTATCTACCAGGCCCACTTCCTCTTAGATTTGGGCTTCCC 72300
mRNA      ------------------------------------------------------------

genome    CAGGCTGTTGCCTTTCCCCAAGTAGCTTCTGCTTGTCCTGTAGAAGACCTTTCATGCTTT 72360
mRNA      ------------------------------------------------------------

genome    GCTTCTGCAGCAGCCGTTCCTGAATGCCTAGTGTCAACTGCCTTCTTACCACGCCCACCC 72420
mRNA      ------------------------------------------------------------

genome    TCCCTGCATGCTGCATTTATCCCCTGCCACAGCCCTGTGACCCTGTGTCCTGCTGCCTCT 72480
mRNA      ------------------------------------------------------------

genome    GACTTGTCTGTTTCTGCTTGGCCATGGTCTCTGTGAGGTCAGGTGTGCATATGGGCACAA 72540
mRNA      ------------------------------------------------------------

genome    ACCAGGGCATCTCTTTATCCCCAGCACCTGGCTTAAGTGCTGCTCTGGAACTATCTGTTG 72600
mRNA      ------------------------------------------------------------

genome    AATGAACTAATGCATGAATGTATTGTTGAGTATGAGACAAACAAGTGTCATTGTCTCCTT 72660
mRNA      ------------------------------------------------------------

genome    TCTAGCCTTGCCGCATCAAAGGTGACATTGGACAGTCCACTGATGATGACTCTGCACCTC 72720
mRNA      ------------------------------------------------------------

genome    TTGTCCATTGTGTCCGCCTTTTATCTGCTTCGTTTTTGCTAACAGGGGGAAAAAATGGTG 72780
mRNA      ------------------------------------------------------------

genome    AGTACAAAAGGGGATGTGCACAGTTGAAGGAAATAACTAGGTTTCAGAGGTCAGCTTGGT 72840
mRNA      ------------------------------------------------------------

genome    GGCCTGTTTTTGCCTTGCGTGCAGCAGAGGAAGTAGAATCTGAGGATGAGTTTGGTTTTC 72900
mRNA      ------------------------------------------------------------

genome    ACTAGCCGAGGGGAGGGAGGAAATGATGGGAGCAGGTAGGTTATTGGGTCTGGTTTTGTT 72960
mRNA      ------------------------------------------------------------

genome    CATTTGAAAACAATCTGTTGTTTGAGGCTGAAGGTGGCTTGGGTGATTTCTTGGCAGTGC 73020
mRNA      ------------------------------------------------------------
```

FIG. 1 GGG genome TGGTTCCGGACAGGGATGTGAGGGTCAGCGTGAAGGCCCTGGCCCTCAGCTGTGTGGGAG 73080
mRNA ------------------------------------------------------------ genome CAGCTGTGGCCCTCCACCCGGAATCTTTCTTCAGCAAACTCTATAAAGTTCCTCTTGACA 73140
mRNA ------------------------------------------------------------ genome CCACGGAATACCCTGGTATGTTAAAAGTTCACATCTTATTTTCTCAGATTTAATCATTAT 73200
mRNA ------------------------------------------------------------ genome TGTAAAAACTATTTCAGTATTGACTATTTTAGTTTTAGAGCAGTAAGTGTTTTGAGTTCA 73260
mRNA ------------------------------------------------------------ rs363081
genome TTTGGGATATTTGACCTGCGTTGTAGCTCTTCAGAAAACACATGAATAGTGAAGTTCTTT 73320
mRNA ------------------------------------------------------------ genome GTTTCATGGGTTCCCTTTAGATGAAACCCATAGAGGAGAAAAGTAGAAACCTCAGCACGT 73380
mRNA ------------------------------------------------------------ genome AAGAGCCAACATATATACACATCGGATTTAAACCTAAAGCACAAATTGTGCCTGGTCGCA 73440
mRNA ------------------------------------------------------------ genome GTGGCGCTGAGTCGCACTCAGCCAGGCCAGGCATTCACACTCAGGGTGAGTGGGAACCAG 73500
mRNA ------------------------------------------------------------ genome GACTGGCTGAGGCAGCAGTGGACCCAAGTCTCCATCGCGCCCATGCTTACTATGGAGCCT 73560
mRNA ------------------------------------------------------------ rs363080
genome TCTCGTTCTCTCTTTTTCTTTGGGTGAGAGGGTACACTTGTGTTTTTGAATTTATATGAG 73620
mRNA ------------------------------------------------------------ genome GTAAGTGTGTAATAGGGTTTTTTCTAATCTTTTTTAAGTGGAATCTGGAATTTTAATCAG 73680
mRNA ------------------------------------------------------------ genome ATTTATTATCTGACAACCTAGAATTATAATCCAGAAAGTCTGTGGTATTGAGGACATATT 73740
mRNA ------------------------------------------------------------ genome GGCAATATGATGAATCTCTAATTCTTAAATCCTGAAACTTTTTTTTTTTTAATCACTTAG 73800
mRNA ------------------------------------------------------------ genome GGTTATTATAGTGAAGTCATTTCTGAATTTGGATCTTCTCTTCACACCTCTTTTTCTCTT 73860
mRNA ------------------------------------------------------------ genome TCCTGAGAATTAAGCTTTTGTTTCGAGTTAGAAAGTTGATAGTAGGGAATTGTTCCATGG 73920
mRNA ------------------------------------------------------------ genome CTGAGCAATTTATCTCCACAGAGGAACAGTATGTCTCAGACATCTTGAACTACATCGATC 73980
mRNA ------------------------------------------------------------ genome ATGGAGACCCACAGGTTCGAGGAGCCACTGCCATTCTCTGTGGGACCCTCATCTGCTCCA 74040
mRNA ------------------------------------------------------------ genome TCCTCAGCAGGTCCCGCTTCCACGTGGGAGATTGGATGGGCACCATTAGAACCCTCACAG 74100
mRNA ------------------------------------------------------------ genome GTAACGGCCAGTTTTTCAGCTGTGTTTTTTCTAGTTATGCTTACTAAGGTTTAAGTTTAG 74160
mRNA ------------------------------------------------------------ genome ATGATGATGTTTGTTGCTTGTTCTTCTGGTTAGGAAATACATTTTCTTTGGCGGATTGCA 74220
mRNA ------------------------------------------------------------ genome TTCCTTTGCTGCGGAAAACACTGAAGGATGAGTCTTCTGTTACTTGCAAGTTAGCTTGTA 74280
mRNA ------------------------------------------------------------

FIG. 1 HHH

```
genome    CAGCTGTGAGGGTGAGCATAATCTTCTGTGGAACCATTTCTTCACTTAGTGGACATTTTA 74340
mRNA      ------------------------------------------------------------

genome    TCATTGCTACAATTAAAATTGGAGCTTAATAGGAAATATTTCCATGCACTCTAAAGCTGT 74400
mRNA      ------------------------------------------------------------

genome    AACCAGTAATACCCACCATGTATCCATCTCTCAGCTTTAGAAAGAAAACGTTGCCAGTAA 74460
mRNA      ------------------------------------------------------------

genome    AGTTAATGCTTCATAAACTTCAGTTTAAGTTCTAATTCTCAGAATATTTGTTTGAAATAG 74520
mRNA      ------------------------------------------------------------

genome    ACCTCTTCCTAAAGGATATATTTAGAAATAACCTATCATTAAGTGTAAAGTCTGTTGAAT 74580
mRNA      ------------------------------------------------------------

genome    ATGCTGGGCACGGTGACTCACACCTGTAATCTGACCACTTTGGGAGGCCAAGGTGGAAGG 74640
mRNA      ------------------------------------------------------------

genome    ATTGCTTGAGCCCAGGAGTTCAAGACTATGGGCAACATAGTTGACCCTGTCCCTACAGAA 74700
mRNA      ------------------------------------------------------------

genome    AATTAAAAAAAAAAAAAAAAAAAGTAGCTGGGTATGGTGGTGCATACCTGTAGTCTCAGC 74760
mRNA      ------------------------------------------------------------

genome    TACTCGGGAAGCTGAGGTGGAGGGGGGATTGCTTGAGCCCCAGAGATCAAGGCTGCAGTA 74820
mRNA      ------------------------------------------------------------

genome    AGGCGTGGTTACACCACTGCCCTCTAGCCTGGGCAACAGAGTGAGACTGTCTCAAAAATA 74880
mRNA      ------------------------------------------------------------

genome    ATAGTAATAATAATCAGTTGAATTAAAAAAAAAAAAAAAAAAAACCACTGTGCTAGGCCCA 74940
mRNA      ------------------------------------------------------------

genome    TAGTATGGTAAGAGTTAAAGTGAGCCTTAGGGATTATTTACTCAACCTCTGTTTCTGTAT 75000
mRNA      ------------------------------------------------------------

genome    AAAGTGGAATAGGCTCAATTCTTTAAGTGATAGCATGTTGAACCTTTCCATACCAACTGG 75060
mRNA      ------------------------------------------------------------

genome    CTCATAAGTCACAACTGGCCAGTCAACAAGAGTAAAAATTAACTGGTAAAAATCAAAGCA 75120
mRNA      ------------------------------------------------------------

genome    AAAAACCTACAATTGTCAAATTTGTGGGATAACTCCCCCTTTTAAAATGTCATGCCTGAC 75180
mRNA      ------------------------------------------------------------

genome    AGTAATTTCTCTCTAGTTTCCAGGTTTTCAGTCAGTTGTGTCTTTTTTGAGCAGAAGGAA 75240
mRNA      ------------------------------------------------------------

genome    GCATGCTAAGAGCTCAATCTTGTGGCTAGCTGGGGGTCTTTGTGTCAGCCATGCATGTGA 75300
mRNA      ------------------------------------------------------------

genome    TGGTGCCCCTGGGTGCTTGGGGCTGCAGGGGAGGGGTACAGCAGTAGGGGCCTGTTCTGT 75360
mRNA      ------------------------------------------------------------

genome    TCTCTCGTGCTGTGGAGTACATAGTGACATAGTGGGGTGGTCCTTGGTGTAGGTCCCTTG 75420
mRNA      ------------------------------------------------------------

genome    TTCCTACCCCTGGGTCTGAGATTTATTTAGAAGTGGTGTTGGGGCTGTGCGGCAGGCCCC 75480
mRNA      ------------------------------------------------------------

genome    TCTGTAACTGATCAATGTTTGTGAAGTTGCTGTTTGAGAGTTGAAACCATGACATAAGCA 75540
mRNA      ------------------------------------------------------------
```

FIG. 1 III

```
genome    GAAATGGAAGGAAGAAAGAACCAGTTATGTGAAAGGGACACATTTACTTTTAAGCTTGTA 75600
mRNA      ------------------------------------------------------------

genome    TTTACTGAGATAAAGTATTCTTAATCAATGTTCTTGAGAGGTGTGGGAAAAATGCAACAT 75660
mRNA      ------------------------------------------------------------

genome    CCTGGTTGCAGTTAAACCCAGAACATTGTGTGTTGAAGAGTGACGGTTCTCAAACCGTCA 75720
mRNA      ------------------------------------------------------------

genome    AGACGCGGGTACTGAGTGGGACTAACCTGCTGTCCTCTTGCCTTGGACCTTGTGTTCCAG 75780
mRNA      ------------------------------------------------------------

genome    AACTGTGTCATGAGTCTCTGCAGCAGCAGCTACAGTGAGTTAGGACTGCAGCTGATCATC 75840
mRNA      ------------------------------------------------------------

genome    GATGTGCTGACTCTGAGGAACAGTTCCTATTGGCTGGTGAGGACAGAGCTTCTGGAAACC 75900
mRNA      ------------------------------------------------------------

genome    CTTGCAGAGATTGACTTCAGGTAAGTGAGTCACATCCATTAGATTTCATGAACTAAGCTC 75960
mRNA      ------------------------------------------------------------

genome    AATTGAAAGTTCTGGGATCACTTGATGCAAGGAATGATGTTATCAAGTACCCTGTCCATC 76020
mRNA      ------------------------------------------------------------

genome    AGAAATCCGAGTGGTTTAGGTAGATGACAGTGATTTTCTCCTCCCAGTGGCTTTTTGCTG 76080
mRNA      ------------------------------------------------------------

genome    AACTTTGCCCTATGCTTGGAATTTTATTTTATTTTATTATTTATTTAGAGACAAGATCTT 76140
mRNA      ------------------------------------------------------------

genome    GCTCTGTCGCCCAGGCTTGAATGCAGTAGCACAATCATAGCTCACTGAAGCTTTGAACTC 76200
mRNA      ------------------------------------------------------------

genome    TAGGACTCAAGTGGTCCTCCTGCCTCAGCCTCCCGATTAGCTAGGAGAATAGGTGTGTGC 76260
mRNA      ------------------------------------------------------------

genome    CGTCACACTGGCTAATATTTTTTGTAGAAATGGGGTCTTGCTATGTTGCCCAGGCTGGTC 76320
mRNA      ------------------------------------------------------------

genome    TCAAACTCCTGGGCTTGATTGATCCTCCATCTTGGCCTCCCAAAGTGCTGGGATTACAGG 76380
mRNA      ------------------------------------------------------------

genome    CATGAGCCACTGTGCCTGGCCTAGAATTTTAAAATATAAGTAGAAGAGTAGATTTTTTTT 76440
mRNA      ------------------------------------------------------------

genome    TTTGGTAGTCCTCGTCATTTAAGTATTCTGGATAGTGGGAATAAAAGAGCTTAGAATTTT 76500
mRNA      ------------------------------------------------------------

genome    TCATCTTTGTCTTAAACTTTTAAAAAAATGTAGCTTATATTAATTCTGCTTGTTTAAAAA 76560
mRNA      ------------------------------------------------------------

genome    GAATATACTCTTCATTATACTGAACCTAGGTAAGACAGCTGGTTTATATTTTGTTGCAAT 76620
mRNA      ------------------------------------------------------------

genome    TAAAAAACGTGAGCTGTGGTTGCAGTGAGCCAAGATTGTGGCCATTGCACTTCAGCCTGG 76680
mRNA      ------------------------------------------------------------

genome    CAACAGAGTGAGACTTGGCCTCAAAAAAAAAAAAATAACATGAGCTGTGTTGGCACTTTC 76740
mRNA      ------------------------------------------------------------

genome    ATTTTCTAAGAGTAGTTTTGGCTGGAGAAGTTTTCTTTCAGTACTTTCTTTTAGAAGGGA 76800
mRNA      ------------------------------------------------------------
```

FIG. 1 JJJ

```
genome  AATTTTCCTTTATAATTTAGGGTTTGTTTTTTTTTTTTCCAAGCCACCTTTTATAGAGCC 76860
mRNA    ------------------------------------------------------------

genome  CTTGTGGGTTATTTCATTTAATCCTTAGAATGTTTATAAATCTGGGCTTGTTCTCGGCTC 76920
mRNA    ------------------------------------------------------------

genome  CACCCACAGATAGGGACGCTGAGCGTGCATGAGTGGGCAGCAAGATAGCAGGTTATGGAG 76980
mRNA    ------------------------------------------------------------

genome  GGCCCAGCTCACCCCTTCTGTGGCTTGAGCCAATTTTATAGGGCACTTACAGAGTCTTTT 77040
mRNA    ------------------------------------------------------------

genome  GAAATAGTATTTATTTTGAAGAAAAAGAAAAACAGTTTACTGAGTACTGTCTTATTGAGT 77100
mRNA    ------------------------------------------------------------

genome  CTGGAATTGTGAGAGGAATGCCACCTCTATTTATTTAAAGCCATTGGCCTTTTTTGTTGT 77160
mRNA    ------------------------------------------------------------

genome  TTTGAGTAAGTGCTGCCCAAGGTCCTTCCAGGGCACCTGGATGAGCCTGCTCTGGAGCAA 77220
mRNA    ------------------------------------------------------------

genome  GCTGGCGGTAAGTGTTTACTGAGTAACTAAATGATTTCATTGTTAAATGTGCTCTTTTGT 77280
mRNA    ------------------------------------------------------------
                                                     rs363075
genome  TAGGCTGGTGAGCTTTTTGGAGGCAAAAGCAGAAAACTTACACAGAGGGGCTCATCATTA 77340
mRNA    ------------------------------------------------------------

genome  TACAGGGGTAAGCGGTTTATTTTTGTGAGATGCTGTTTTACCTTCAAGAAGGTGAAAGTG 77400
mRNA    ------------------------------------------------------------

genome  AGGCTTTCCTTGTGGAATTTCTCTAAATGCATTCGTCATGTTTTAGATGTTTATTTCACA 77460
mRNA    ------------------------------------------------------------

genome  GTTTATATCATGAAAGTTATAATCTTGTCATATGGATTTAAGTCTAGTAATGTTGAGTTC 77520
mRNA    ------------------------------------------------------------

genome  TTTCTCACTAGCTTTCCAAAATATCTTACCTAAAATTTAGTCAAATACAAGATTATGTTT 77580
mRNA    ------------------------------------------------------------

genome  ATTTTTATTATCCTTCTCTCTAAAGCTTTTAAAACTGCAAGAACGAGTGCTCAATAATGT 77640
mRNA    ------------------------------------------------------------

genome  TGTCATCCATTTGCTTGGAGATGAAGACCCCAGGGTGCGACATGTTGCCGCAGCATCACT 77700
mRNA    ------------------------------------------------------------

genome  AATTAGGTATTTACCAATATTTTATCTCTTTTCCTTTTTTGGTTGAAGTACTAAAAGATA 77760
mRNA    ------------------------------------------------------------

genome  CGAGAATGGAAAGAGAGGGAAGAATTCAAAGGATGTAGAGCAGTATTCCTGAATCTGAGC 77820
mRNA    ------------------------------------------------------------

genome  TCATTTCAGCCATTCTATTCTTAAACTATAATGAAAAAAAAATCCAAAAAAGTCTAAAAT 77880
mRNA    ------------------------------------------------------------

genome  TATAATTAAAAAAACAACAAAATACTAACTGTCCATTGTAAAAAGTAATGCACTTTCATT 77940
mRNA    ------------------------------------------------------------

genome  GTAAAAATTTTGGACTATAGAGAATAGTACTAAGAAGAAAAAAAAAATCACCTTCAATTC 78000
mRNA    ------------------------------------------------------------

genome  TGCTGCCACCTGGAGGTAATCACTGTTAATATTTTGCTATATACTCTATGAGTTTCTTGT 78060
mRNA    ------------------------------------------------------------
```

FIG. 1 KKK

```
genome   TCAAAATCAGGTCAAAATTACATGCAATTTTGTAATCTGACAATTTCCACTTAATATTTT 78120
mRNA     ------------------------------------------------------------

genome   ATTAGCATTTTCCTGTTATGAAACAGTAATTTTAGTTATGGGTCGTTGTTTTGCTATGCG 78180
mRNA     ------------------------------------------------------------

genome   GTTGGGATAAAATTTTATATACTTTTTTTGGCAATTACTTATTATACATAAATGTTTGTG 78240
mRNA     ------------------------------------------------------------

genome   TATAGTTTTCTTTTTCTGAGAATTCCTGGAAGTTGAGTTACCAGGCCCGGCTTTGAATTT 78300
mRNA     ------------------------------------------------------------

genome   TTTTTTTTATTTTTTTTTTGAGACAGAGTCCTGCTCTATTGTCCAGGTGCTATCTCGGCT 78360
mRNA     ------------------------------------------------------------

genome   CACTGCAACCTCTGTCTCCCTGGTTCAAGCGATTCTCCTGCCTCAGCCTCCCGAGTAGCT 78420
mRNA     ------------------------------------------------------------

genome   GGGATTACAGGGGCACACCACCACGCCCAATTAATTTTTGTATTTTTAGTAGAGACAGGG 78480
mRNA     ------------------------------------------------------------

genome   TTTCACGATATTGGCCAGGCTGGTCTCGAACTTCTGACCCCGTGATCCACCTGCATTGGC 78540
mRNA     ------------------------------------------------------------

genome   CTCCCAAAGTGCTGGGATTACAGGCGTGAGCCATGGCGCCTGGCCAGGCTTTAAATTTAA 78600
mRNA     ------------------------------------------------------------

genome   AACAAATCTTCTAATAGCTTTATGGAGGTTATAATTTACATTTCTTGAAATGTACTCACT 78660
mRNA     ------------------------------------------------------------

genome   TTGAGTGTATAGTAAACTCCAATTTTATCACATTTCTGTCACCCCAAATGTATCCTTGTG 78720
mRNA     ------------------------------------------------------------

genome   CCCATTTGCTGTAACCTCCGGTTCCTGCCCCAACTCCTAGGCAGCCACTCATCTATTTTC 78780
mRNA     ------------------------------------------------------------

genome   TGTCCCTTAAGATTTGTGTTTTCGCCAGGCGCTCATGCCTGTAATCCCAGCACTTTGGGA 78840
mRNA     ------------------------------------------------------------

genome   GGCCGAGGTTGGTGGATCACTTGAGGTCAGGAGTTCGAGACCAGCCTGGCCAACATGGTG 78900
mRNA     ------------------------------------------------------------

genome   AAACCTTGTCTCTACTAAAAATACAAAAATTAGTCGGATGTGGTGGCACACGCCTGTAAT 78960
mRNA     ------------------------------------------------------------

genome   CCCAGCTACTCGGGAGGCTGAGGCAGGAGAATCACTTGAACCTGGGAGGCGGAGGTTGCA 79020
mRNA     ------------------------------------------------------------

genome   GTGAGCAGAGATCGCGCCACTGCCTTCCAACCTGGGCAACAGAGAGAGACTGTCTCAAAA 79080
mRNA     ------------------------------------------------------------

genome   CAAACAAAGATTTGTATTTTCTGGACATTTTATAGTACTGGGGTCATAGTATAGATGGAC 79140
mRNA     ------------------------------------------------------------

genome   TTTTGCATTTGGCTTCTTTTACTTAATTGTGAGATTGGTTCTTGTTGTAGCATGTATCAG 79200
mRNA     ------------------------------------------------------------

genome   TAGTTTGTTCATTTTTATTGGCGAAAGTATTCTATTATATGAATAATACCATATTTTATC 79260
mRNA     ------------------------------------------------------------

genome   TATCCATCAGATGGATATTATAGAGTTCATGTTTTGGCTAATTTATGAATTATGGTACTG 79320
mRNA     ------------------------------------------------------------
```

FIG. 1 LLL

```
genome   TGAACATTTGCCTGCAAGATTTTGTGTAGACATGTCTTCATTTCTCTTGAGTAGATCACC 79380
mRNA     ------------------------------------------------------------

genome   TAGAAGTGGATTTTTAAATAATTTTGGTACTTACTGTGAAACTGCTCTTCAAAAACATAC 79440
mRNA     ------------------------------------------------------------

genome   CATTGTTCCTTCCTTCCTTCCTTCCTTCCTTCCTTCCTTCTTTCCTTCCTCCCTTCCTCC 79500
mRNA     ------------------------------------------------------------

genome   CTCCCTTCCCTACTTCCCTCTCCCTTTCCCTTTCCCTTCCCCTTTTCCCTTCCCCTTCCC 79560
mRNA     ------------------------------------------------------------

genome   GCCTGCCTGCCTGCCTGCCTTCCTTCCTTCCTTCCTTCGTTTCTTTCTACATATACACAT 79620
mRNA     ------------------------------------------------------------

genome   TTTTTTAAATTTCAATGGTTTTTGGGGTACAAGTGGTTTTTGGTTACATGGCTGAATTTT 79680
mRNA     ------------------------------------------------------------

genome   GGTTACATGGTGAAGTCTGAGATTTTAGTACACCTGTCACCCGAGTAGTGTACCTTGTAC 79740
mRNA     ------------------------------------------------------------

genome   CCAATATGTAGTTTTTTGTCCCTCACCTTCCAGCCTTCCGCCTTGTGAGTCTCCAATGTC 79800
mRNA     ------------------------------------------------------------

genome   CATTATACCACACTGTATGCCCTTGCGTACCCACAGCTCAGCTCCCACTTCTGAGAACAT 79860
mRNA     ------------------------------------------------------------

genome   ATAGCAGAAACATGCCAAAGTATACTCCCACTACCAGAATGTGATTGTGCCTGATTCTTC 79920
mRNA     ------------------------------------------------------------

genome   TCACCAGTACAAATATTTCAAAAAAAGTTAAATATGTATCAGTTTTTTGGGCAGAAGTTG 79980
mRNA     ------------------------------------------------------------

genome   ATACTTCTCTTTATTTATTTATTTTTTTTGAGATAGGGTCTCATTCTATGATGCCCAGGC 80040
mRNA     ------------------------------------------------------------

genome   TGGAGTGTGGTGGTGCGATCTCGGCTCACTGCAGTCTCTGCCTCCCAGGTTCAAGTGATT 80100
mRNA     ------------------------------------------------------------

genome   CCCACGTCAGCCTCCCAGGAAGCTGGAATTACAGGCGAGGGCCACCACTGCCAGCTAATT 80160
mRNA     ------------------------------------------------------------

genome   TTTGTATTTTTTGGTAGAGATGGGGTTTCACCATGTTGGCCAGACTGGTCTCAAGCTCCT 80220
mRNA     ------------------------------------------------------------

genome   GACCTCAAGTGATCCACCTGCCTTGGCCTTCCAAAGTGCTGGGATTACAGGCGTGAGCTA 80280
mRNA     ------------------------------------------------------------

genome   CCACACCCGGCTGATATTTCTTTTTAAAATAACTTACCTTCTTTTGAAAGTAATACATGT 80340
mRNA     ------------------------------------------------------------

genome   TTAATGAACAGAATTTAAGGAAAATATAAAAAAACGAAATAATCTTTGTAATCAAACTAC 80400
mRNA     ------------------------------------------------------------

genome   TGAAAAGAAAACCAAAGTTACATTTTGGTGCATATTCTTTTTCATTTTCATCATTGTAAT 80460
mRNA     ------------------------------------------------------------

genome   TTGCATTTCTTTGATTACTTGTGAGACACTCCTTTCATTTACTTAATAGGTTTATATGAC 80520
mRNA     ------------------------------------------------------------

genome   TTGCCTATTCAGAGATTTTGCAGCTTTACCATTTTCTGCAAATGATAGCAACTTCTTTTT 80580
mRNA     ------------------------------------------------------------
```

FIG. 1 MMM

```
genome    GTTTGTTTGTTTGTGGAGACAGAGTCTCGCTCTGTCACTCAGGCAGGAATGCAGTGGTGG 80640
mRNA      ------------------------------------------------------------

genome    AATCTTGGCTCATTGCAACTATTGCCTCCTGGGTTCAAGCGATTTTCCTGCCTCAGCCTC 80700
mRNA      ------------------------------------------------------------

genome    CCAAGTAGCTGGGATTACAGGAGTGTGCCACCATGCCCGGCTAATTTTTGTATCTTTAGT 80760
mRNA      ------------------------------------------------------------

genome    AGAGATGGGGTTTTGCCATGTTGGCCGGGCTGATCTTGAACTCCTGGCCTCAAGCGGTCC 80820
mRNA      ------------------------------------------------------------

genome    CCCTGTCTCGGCCTCCCAAAGTGCTGGGATTACAGGCGTGAGCCACCGTACCCAGCCAGT 80880
mRNA      ------------------------------------------------------------

genome    AGTTACTTCTTATATTCTAGAAAAAATTCTACTCATGATCAAGTCTCCATGAGGAAAGAG 80940
mRNA      ------------------------------------------------------------

genome    ACTTTAATTGAAGATCATGGGGCTTGCAGACCAATATGATAAAATAGTTCATTGTTTCTA 81000
mRNA      ------------------------------------------------------------

genome    AAAGTATTACTGAGTGTTGATGGCAGATATGAACCCTTTTGTTTTTGTAGGAAAATGTTA 81060
mRNA      ------------------------------------------------------------
          rs363064
genome    CCCGTATTCTCCATTTGAATTCAGTTTAGATTTGTTAGGAATCGCAGCTTAAGCTTTGCC 81120
mRNA      ------------------------------------------------------------

genome    ATCTGGGAGTGTTTGGGACAGTTTTGCAGACAAAATTGCAAAAGTGCCTAAGGAATGCAG 81180
mRNA      ------------------------------------------------------------

genome    CTGGCATTCAGACCTGCTCTGTGCTCAGTACTCTGTGGACAGACACTGTTCAGCACTTGT 81240
mRNA      ------------------------------------------------------------

genome    TGATCAGAAGGTTTAGAAAGAGAACTTTCAAAGTTGGTTTTTAATTAAAGCATTTAATAG 81300
mRNA      ------------------------------------------------------------

genome    TGTAAATAGAAAGGGATTAAATTTTATGACAGACAAAAGAAAGTACAGCACCCAGCTGGG 81360
mRNA      ------------------------------------------------------------

genome    CGTGGGGGCTCACGCCTGTAATCCAGCACTATGGGGGGCTGAGGTGGGTGGATCACGAGG 81420
mRNA      ------------------------------------------------------------

genome    TCAGGAGTTCAAGAGTTCAAGAACAGCCTGGCCAAGGTGATGAAACCCTGTCTCTACTAA 81480
mRNA      ------------------------------------------------------------

genome    AACTACAAAAATTAGCCGGGCGCGGTGGCAGGCGCCTGTAATCCCAGCTACTCAGGAGGC 81540
mRNA      ------------------------------------------------------------

genome    TGAGGCAGGAGAATCACTTGAACCTGGACGGCAGAGGTTGCAGTGAGCCAAGATTGCACC 81600
mRNA      ------------------------------------------------------------

genome    ATTGTACTCCGGCCTGGGCCACAGAGTGACATTCTGTCTCAAAAAAAAAAAAAAAAGAAA 81660
mRNA      ------------------------------------------------------------

genome    AAAAGAAAGTACAGCACCCAGTTATGTCCGAGTGGGTGCATGAGAGTGACCCTGAGATTG 81720
mRNA      ------------------------------------------------------------

genome    GAGACAACGCTGTCACGTGCTTGAAGAACGCCACCTGAGAAAGGGGGCGAGAAGTGGTGT 81780
mRNA      ------------------------------------------------------------

genome    CCGCTGGTAACCAGAGGTGTTGGCTTAGCCATCTGCAGGGAGGAGGGTGGTCTATCACAG 81840
mRNA      ------------------------------------------------------------
```

FIG. 1 NNN

```
genome    GTGAGTTTCATCTACTTTCTTAAGCAAATTAACCTTACTTTTGTGTTAGGCTTGTCCCAA 81900
mRNA      ------------------------------------------------------------

genome    AGCTGTTTTATAAATGTGACCAAGGACAAGCTGATCCAGTAGTGGCCGTGGCAAGAGATC 81960
mRNA      ------------------------------------------------------------

genome    AAAGCAGTGTTTACCTGAAACTTCTCATGCATGAGACGCAGCCTCCATCTCATTTCTCCG 82020
mRNA      ------------------------------------------------------------

genome    TCAGCACAATAACCAGGTATGCTGACCCAGTGGCATCTTCACATTGTCGGGAAAATGCCC 82080
mRNA      ------------------------------------------------------------

genome    TTTCCTGATGCCTTTCTTTAGGCTTTAATTGAAAACATTTTATTTTCTAGAAAAAAGCTT 82140
mRNA      ------------------------------------------------------------

genome    CAGCTCAGGATGTTTGAGTGTAGGTCAGTCCTTTGATAGGATATTATCATTTTGAGGATT 82200
mRNA      ------------------------------------------------------------

genome    GACCACACCACCTCTGTATTTAAGCTCTGCCACAATCACTCAGCTGTGACACTGTAAATC 82260
mRNA      ------------------------------------------------------------

genome    TCTTAATAGTTTATTACATTCCATGTGCTGACAGTTGTATTTTTGTTTGTGACACTTACG 82320
mRNA      ------------------------------------------------------------

genome    TATTATCTGTTAAAACATTTTCACTTTAGTTGTGTTACCTTTAAAGAGGATTGTATTCTA 82380
mRNA      ------------------------------------------------------------

genome    TCATGCCTGTTGATTTTTTGGTGAGCGGGCTATTAAAGTCAGTGTTATTTAGGGTTATCC 82440
mRNA      ------------------------------------------------------------

genome    ACTAGTTCAGTGATTTGCGAGATTATCATTCACATTTATTGTGGAGCTTTTGAATATCGT 82500
mRNA      ------------------------------------------------------------

genome    GTCAAATGGCCACATATATCCCATTCTTATCTGCTTCTTAGGTGAGTGGGACACAGTGCT 82560
mRNA      ------------------------------------------------------------

genome    TTAATGAAGCTATAATCTTCAGAATTCTAGCTTGCAGAGAAGATTGCAGAAGTGATAAGA 82620
mRNA      ------------------------------------------------------------

genome    CTTGTGCTTTTTAATTTTGTCTTTTAAATGTTATTTTAAAAATTGGCTTTATATGATACT 82680
mRNA      ------------------------------------------------------------

genome    CTTTTTTTCTGCTGAGTAACAGTGTTTTACAAAACTTGGACTAAATGACTTCTAAGCTTA 82740
mRNA      ------------------------------------------------------------

genome    AATGATCACTTGATGCTTTTTTTCTGAATTAGGAACTCAGCTTATCAAATATCAAAGTCA 82800
mRNA      ------------------------------------------------------------

genome    TAATTCCTGAATAAATAACGTCTTTTTTCATGTAAAGACTGCTTTAAAAAACACATGGAA 82860
mRNA      ------------------------------------------------------------

genome    GGCTGGGTGCGGTGGCTCACGCCTGTAATCCTAACACTTTGGGAGGCCCAGGTGGGCAGG 82920
mRNA      ------------------------------------------------------------

genome    TCGCTTGAGCTCAGGGGTTCAAGACCACCCAGGGCAACATGGCAAAACCCACCTCTACTC 82980
mRNA      ------------------------------------------------------------

genome    AAATACAAAAAATTAGCCAGGCGTGGTGGCGGGCCCCTGTAATCCCAGCTACTCGGGAGG 83040
mRNA      ------------------------------------------------------------

genome    CTGAGGGATGAGAATCACTTGAGCCCCGGAGGCAGAGGTTGCAGTGAGCCAAGATTGTGC 83100
mRNA      ------------------------------------------------------------
```

FIG. 1 OOO

```
genome    CATTGCACTCCCAGCTTGGGCTACAGAGTGAGACTCTGTCTCAAAAAAAGACACACACAC 83160
mRNA      ------------------------------------------------------------

genome    AAACAAAAAAAAACATGGAGACATTTTTTTGGCCACCTTAATATTTCCCCTCAGATAATTT 83220
mRNA      ------------------------------------------------------------

genome    CCTTTGTTTAAACTCAGAACTGGCATTTTCTCTCTTGGAGAAGATTCAGGACAAATACTC 83280
mRNA      ------------------------------------------------------------

genome    CTTTAAGATAAGTAGAAGCAGTGAAAGAGGATTTGATTATCAGGAATTTGATAAGCTTAG 83340
mRNA      ------------------------------------------------------------

genome    AATAAATTGTTGCTTCTTAATGTCATTTCAGAAGATGAATATTTATTAATAGATGCCAAC 83400
mRNA      ------------------------------------------------------------

                                 rs3025849
genome    TGAGATATCATTAAAATTGATTACTAACTACTACTTGGAAAAGTCTCCCAGTTCCAAACT 83460
mRNA      ------------------------------------------------------------

genome    TCAGCAGGCCTCTTGACAATTCAGCTGTGGTCAATTGGGTCTTGCGTGATAGATACAATG 83520
mRNA      ------------------------------------------------------------

genome    ACCAATTGTGCAGCAGAGTGTGCTGCTTAGCTGCCTATTCTGTTAGCATTCATGTGTTAA 83580
mRNA      ------------------------------------------------------------

genome    CTTAAAATCATAATCTCCTTAGTTTTGTTGAGTGTCTCCGTGGACAAGACACTGTGAGGG 83640
mRNA      ------------------------------------------------------------

genome    ATACAAAATCAGATTGGCTTTATTCAAACCACTGGGGTATTATAATTCATTTATAATTTA 83700
mRNA      ------------------------------------------------------------

genome    TTTTATTTTTTGCCTTTTTTCCATGTGTTCTAAAGGAATTAGAGTTTGTATATAACTATA 83760
mRNA      ------------------------------------------------------------

genome    ATGGGGGATAGAAATTGACATGTGCCATGAAGGGAATGCAAAAAAGTGCCGTGGGAGATG 83820
mRNA      ------------------------------------------------------------

genome    AGAAGTGGAGAAAGGAATTTCTTTTTTCTTGGAAGCAGGAATAACTTCATGAAGCATGTA 83880
mRNA      ------------------------------------------------------------

genome    TTTCAACTTAAACAGATAGTAGGCAACGCTGTAAGGGGAGTATGGCTGCAGCAAAAGTGT 83940
mRNA      ------------------------------------------------------------

genome    TCGGGGCAGACTGGGAGGAAGGGAGGGAATAAATTCAGCCATTGTTATGGAATAATGATC 84000
mRNA      ------------------------------------------------------------

genome    AAAATTTATTTTCAGCCCGTTTCACTTAAAAGTTGAGACTGCTTAACTTTTTTTAATCTT 84060
mRNA      ------------------------------------------------------------

genome    TAATCTTAAACTTTTAAATGCCATTTGATCTTTAAAAATATATGTTTTAATAGTGTATTT 84120
mRNA      ------------------------------------------------------------

genome    TAAGTCTCTATATTTTTGTTATTAGAATATATAGAGGCTATAACCTACTACCAAGCATAA 84180
mRNA      ------------------------------------------------------------

genome    CAGACGTCACTATGGAAAATAACCTTTCAAGAGTTATTGCAGCAGTTTCTCATGAACTAA 84240
mRNA      ------------------------------------------------------------

genome    TCACATCAACCACCAGAGCACTCACAGTAAGTCTCTTTCTTGATCGGTCTTACTGACATT 84300
mRNA      ------------------------------------------------------------

genome    GTAATAGTTTTTGGTAGCTTGTATGGCCAGTTAGTTGTATGGTCATCTTACGGTGAGGTG 84360
mRNA      ------------------------------------------------------------
```

FIG. 1 PPP

```
genome    CTTGTCTTACAGCTCTTACTTATCCATGAGGCTTGCTAAGAAATTGTGCTTCTGTGAAAA 84420
mRNA      ------------------------------------------------------------

genome    GAATCTCAGCTTACTCCAGGAATGTAAATGACTATGTTTTTTCTGATTATTAAAGTAATA 84480
mRNA      ------------------------------------------------------------

genome    CACGCCCAAAATAAAAAAATTCAGCCAATTTAGGAAGACACAACAATTAAAATAAGCCAG 84540
mRNA      ------------------------------------------------------------

genome    GCATGGTGGCTCATGCCTGTAATCCCAGCACTTTGGGAGGCCAAGGTTGGGGGCTCACTT 84600
mRNA      ------------------------------------------------------------

genome    GAGGTCAGGAGTCGGATACCAGCCTGGCCAACGTGGTGAAACCCCATCTCTACTAAAAAT 84660
mRNA      ------------------------------------------------------------

genome    ACAAAAATTAGCTGGGCGTGGTGGCGGGCGCCTGTAATCCCAGCTACTCAGGAGGCTGAG 84720
mRNA      ------------------------------------------------------------

genome    GCAGGAGAATCGCTTGAACCTGGGAGGTAGAGGTTGCAGTGAGCTGAGGTCAAGCCACTG 84780
mRNA      ------------------------------------------------------------

genome    CACTCCAGCCTGTGCAATAGAGCGAGACTCTGTCTCAAAAAAAAAAAAAAAAAAAGAAAA 84840
mRNA      ------------------------------------------------------------

genome    GAAAAAAGTAAACTACTGTCACCTGCATTGGTAATGTATCAGAAGTTTAAAATGTCTAGA 84900
mRNA      ------------------------------------------------------------

genome    TTATAATTAACTCAGTGACCTGGTAATATATACTAAGGGAAAAATATTTATAATTTACAT 84960
mRNA      ------------------------------------------------------------

genome    TTTTACATTTTTATTTTTTTAATTTTATTATTTTTTTTTTGAGACAGAGTTTTGCTCTTG 85020
mRNA      ------------------------------------------------------------

genome    TTGCCCAGGCTGGAGTGCAATGGCATGATCTCAGCTCACCACAACCTCCACCTCCCGGGT 85080
mRNA      ------------------------------------------------------------

genome    TCAAGCAATTCTCCTGCCTCAGCCTCCTGAGTAGCTGGGATTACAGGCATGCACCACCAT 85140
mRNA      ------------------------------------------------------------

genome    GCCCGGCTAATTTTGTATTTTTAGTAGAGACAGGGTTTCTCCATGTTGGTCAGGCTGGTC 85200
mRNA      ------------------------------------------------------------

genome    TCAAACTCCCAACCTCAGGTGATCCGCCCTCCTCGACCCCCCAAAGTGCTGGGATTACAG 85260
mRNA      ------------------------------------------------------------

genome    GTGTGAGCCACCATGCCTGGCCTTACATTTTTATAATAAGAATTTATGTTGCTGACATTA 85320
mRNA      ------------------------------------------------------------

genome    GAAAAGAACCATAATATCCAAGAATCCAAGAATAATTAAATTATGTACATATGCTAGTAT 85380
mRNA      ------------------------------------------------------------

genome    ATAGTGTGATGCTTTGGAGAATTTTTAACAATATGGAGATGTATAATCTGGATTGTAATA 85440
mRNA      ------------------------------------------------------------

genome    TTGAGTGAAAAAAGGCAGAATACAAACCTGGTGGGGGTATAGTCGGATTTCAGTTAAGAA 85500
mRNA      ------------------------------------------------------------

genome    AAATAATATTTACATATATACATTTCTCACACTGGCAGATAATCACCAAGATAAATTTTG 85560
mRNA      ------------------------------------------------------------

genome    GGATTGTGGATGATTTTTTTCTTCTTTATATTTTTCAGATATTCTCAAATTTTCTAAAAT 85620
mRNA      ------------------------------------------------------------
```

FIG. 1 QQQ

```
genome    GAGCAAGTATAACTTTTGTTATCAGAAAAAAATAATATACAAAAGTAATGTTAATTTGCT 85680
mRNA      ------------------------------------------------------------

genome    GGTGACCAGGTTAAACCTTTTTATTTTTATTTTTTGAGATGGAATCTCACTCTGTTGCCC 85740
mRNA      ------------------------------------------------------------

genome    AGGCTAGAGCACAGTGGCATGATCTTGGCTCACTGCAGCCTCCGCTTCCTGGGTTCAAAT 85800
mRNA      ------------------------------------------------------------

genome    GATTCTCTGGCCCCAGCCTCCTGAGTGGCTGGAATTACAGGCGTGTGGCACCACACCTGG 85860
mRNA      ------------------------------------------------------------

genome    CTAATTTTTGTATTTTTAGTAGAGGTAGGGTTTCACCAGGTTGGTCAGGCTGGTCTCGAA 85920
mRNA      ------------------------------------------------------------

genome    CTCCTGACCTCGTGATCCACCCACCTCGGCCTCCCAAAGTGCTGGGATTACAGGCGTGAG 85980
mRNA      ------------------------------------------------------------

genome    CTACTGCGCCCAGCCAGACCTTTTTATTTTATTTGACAAAAGAAATACTTCCATGTTATA 86040
mRNA      ------------------------------------------------------------

genome    GAAGACTAAATATTGTTTGGGCTGTCTGCAGTATGGTCTTCCCTTGATTTGTTCAAAATA 86100
mRNA      ------------------------------------------------------------

genome    TCGTAAACTTTGCTTATTTATTTTTATTGTGGCCGACTGTGTCGGGCACTGTTGTAGGCT 86160
mRNA      ------------------------------------------------------------

genome    TGGGATGGAAAAACAGGATTCCTGCCCTTAGGGTTTCTGCAGGCTGGTCAGGGAGACGAT 86220
mRNA      ------------------------------------------------------------

genome    GTGGTAAGCTGGAGCTCAGCTCCTAAGGATGTGCAGGGGCAGTTGAGAGGCGGAAGGGTG 86280
mRNA      ------------------------------------------------------------

genome    GGAGATCATTCCAGGGTGTGGGCAGCACAGGAACCTCTCTTCATTGGGATATAATTGCCA 86340
mRNA      ------------------------------------------------------------

genome    TTCTGATAACACGTGTTTGAGGTGTCTAAAGTAGGAAGTTGTACCATGGTGGGACAGATA 86400
mRNA      ------------------------------------------------------------

genome    TCCTGTGGTTATCATACACAGATCTCAGTTTTCTTCTCATTGTTTGTACTTTTTATAAAG 86460
mRNA      ------------------------------------------------------------

genome    GGTAACAGGAGATATAATTCAATAAACCTTTGTGGTGTTTGGGTGTGATTTTATTGTTTC 86520
mRNA      ------------------------------------------------------------

genome    TTTCTTCTCAGTTTGGATGCTGTGAAGCTTTGTGTCTTCTTTCCACTGCCTTCCCAGTTT 86580
mRNA      ------------------------------------------------------------

genome    GCATTTGGAGTTTAGGTTGGCACTGTGGGTATGTATTTTCCTCAGTATATATTAATAGTT 86640
mRNA      ------------------------------------------------------------

genome    GTCTACAACAGTATGACATAAACATAGTTATTAGGATGCCCTTTTTCTTTCTTTTTAAGT 86700
mRNA      ------------------------------------------------------------

genome    CTTTTATCAATTTGGCTTTTTGGAAAAATATCTGATGGAATACTTGTTTCTGCTATATTA 86760
mRNA      ------------------------------------------------------------

genome    GCTGTGTGAGACTAGTGACAGGAGCTGTGGGAAATGAATGCCAAATGTTCTTAGGCATTG 86820
mRNA      ------------------------------------------------------------

genome    ATGGGAATTTCAGGGTGTGGTCTTCAAGTTCATTTAAGGGAATTTTCATATGCTGGCAAA 86880
mRNA      ------------------------------------------------------------
```

FIG. 1 RRR

```
genome    AGGCTTTTCTCATTAGCTTGACTCTTTCCAAAATTATTTGCTGTGAATTAGAAGTTTAGG 86940
mRNA      ------------------------------------------------------------

genome    AACCTTTTTTCACTTAATTGTGACCTAGCATACGAAATGGTGATGATTTAGGAACTACTG 87000
mRNA      ------------------------------------------------------------

genome    TTCTTGTATTAACAGCTTTTATTTAAAAATGATTTTCCTCCAGTAGATGGCCCTACTAGC 87060
mRNA      ------------------------------------------------------------

genome    ATCTGGGAAATAATTTCAAGTCTTCTCCAGCATTCAGGAATAGGCTTTCATTTTGTGTAT 87120
mRNA      ------------------------------------------------------------

genome    CAATTACTGAGAATGATTTTGGTGACTCACATCACATTTGAGAAGTAAACCTGCAGATTT 87180
mRNA      ------------------------------------------------------------

genome    CTTGTGTGTGTCAGCAAATGACCAACTGATATTTGCTTGAAGTGGATTACATTATCTGCT 87240
mRNA      ------------------------------------------------------------

genome    CTAGAATGATTGCTTTCCCACCTTCCTCACATACAGACTGAGCAGCTACGGTTTCTAATC 87300
mRNA      ------------------------------------------------------------

genome    ATAGGTCTGGCACTAGACTTCACTTCTGGGCAACTTTGGCATTGGAGTAAAATGTATTAA 87360
mRNA      ------------------------------------------------------------

genome    TTTAAAGAAAGTTAAAAATCCGTTCAAGTAAACATACAGTTCTAATACTTTTTACAATTT 87420
mRNA      ------------------------------------------------------------

genome    AAAATATAGATTTAAATGATAAAATAAAAAAGAAAATATGGGTAGACACCATAATCCTCG 87480
mRNA      ------------------------------------------------------------

genome    TTTCTGCATCTGTTCACAAGGGGTTGATATTTATGAGTTCTATTCTCCATATCCATTCTA 87540
mRNA      ------------------------------------------------------------

genome    TGTTCTCTTAATGCTCAGTCAGCACCTCAGGTGGTTGGAGTTCAATGCTTGGTAGTTTGA 87600
mRNA      ------------------------------------------------------------

genome    CTTACACTGTCTTTTCTAGGGGATTGAGCCCTGGGTAGTCCTGCTTATTTGAGGTTGCAA 87660
mRNA      ------------------------------------------------------------

genome    TTTGTCTTTCAATAACTTTTACTACAAGATATGGCGTGTTAAAGGATACCATTGGGGAAC 87720
mRNA      ------------------------------------------------------------

genome    CAACATAATAATATCAGGAAAACTAACCACGTCAGACCTGCCCCATTGTGTATCAAGTAC 87780
mRNA      ------------------------------------------------------------

genome    ACTATTTTTCCATAGTAATAAAGAGTTCACCCCAGCCAATTCTCTTTTATTTTGTGCCTG 87840
mRNA      ------------------------------------------------------------

genome    TTTACTCAATGGCATTAACATGCCCAAATGTCTGGGTAGCTGTCTCATCTCCAGTTCAGC 87900
mRNA      ------------------------------------------------------------

                                      rs6855981
genome    AGAACCATTGTCATATGCCCTAGTAAAAGCATTCCTTCATTGGACACTTAGGCCCCAATA 87960
mRNA      ------------------------------------------------------------

genome    CTTTCATTCAGATCTACTACCTGATTTCATTTCTCAAATGATTTTTATGGAGCTCTGATT 88020
mRNA      ------------------------------------------------------------

genome    TATAGGAAAGATGTTAGTTGATTAAAAATAAAACAATTTCTGAGCTGGTATAAAATGTAT 88080
mRNA      ------------------------------------------------------------

genome    TGTGACATGCCTTCCTCTTGGAATTGCAAGAGAAAGGAAGACTGTTGTTTGCTTAAAAAT 88140
mRNA      ------------------------------------------------------------
```

FIG. 1 SSS

```
genome  TGTCTATAATTTGACTTTGCAAATGTCTGCTTCCAGAGTGCCTCCACTGAGTGCCTCAGA 88200
mRNA    ------------------------------------------------------------

genome  TGAGTCTAGGAAGAGCTGTACCGTTGGGATGGCCACAATGATTCTGACCCTGCTCTCGTC 88260
mRNA    ------------------------------------------------------------

genome  AGCTTGGTTCCCATTGGATCTCTCAGCCCATCAAGATGCTTTGATTTTGGCCGGAAACTT 88320
mRNA    ------------------------------------------------------------

genome  GCTTGCAGGTACTGGTACTGAGTTGAAACAGGGACTCCAGGACTTGGATTTTGATTTCCT 88380
mRNA    ------------------------------------------------------------

genome  TAGGGGGAATGGGGGTGGTGAGCATATGAGGGGAAAATACTATAAGGTCATTGCCAGTGA 88440
mRNA    ------------------------------------------------------------

genome  TGGCTTGTCCCTTTAGTCAAATTTCAGATGTTACCTATATGCATAAACACATGCAGTTGG 88500
mRNA    ------------------------------------------------------------

genome  CAGCTGTTCTGTGCTGAGTATTTTAAAGTAGCCTCTTCCCAATATAGCCCCTCAGTTAAC 88560
mRNA    ------------------------------------------------------------

genome  TACAAGTAAACTCATTTTGAATTTCATTTTAATGGGCACCATATGCCAGTACTCCCTCGG 88620
mRNA    ------------------------------------------------------------

                                                       rs363102
genome  GCACTGGGATGTTAAGAAAGTATAATGTATGGACTTCATTCTCAAGTTAGTTTTAGATTA 88680
mRNA    ------------------------------------------------------------

genome  GAGGGGGATACACGTAAACAAAAGTGCAGTGGTCACACAGAGTGGCCCTAATCACTCTCC 88740
mRNA    ------------------------------------------------------------

genome  TTGGGCAGATTTATGGGCTGGTAGGAAAGAGCACAACACGGAGAGGGTGTAGCACCTTGG 88800
mRNA    ------------------------------------------------------------

genome  CGATGATAATGGAGGATGTGGCCAGCAAGGAAGACGGAGTCCATTGAAATTGATTTTGGG 88860
mRNA    ------------------------------------------------------------

genome  AGAAGTTGCCAATCTCCATGAAAGAATTGGGGCCTGTGCTATTTGCTTCAGGGGGCTATA 88920
mRNA    ------------------------------------------------------------

genome  GGAGAGTTTCGTGAAAGGGACTAAAAGATGAGTATTTTAATAAGATCATTCATCCAACTT 88980
mRNA    ------------------------------------------------------------

genome  GAACATGGGCTGGAGGAGAAGGTAGGGAGACTCAGGAGATTAATGTTGATGCTAAGGCAA 89040
mRNA    ------------------------------------------------------------

genome  GATAATGGCTTTGGGACTGTAGGGAAGACACTGATTGTAAGAGAATGAAGGAGGCAGAAT 89100
mRNA    ------------------------------------------------------------

genome  TGCCAGGCCTGGTTCACCAACTGAACTTCGGTTGTGAAGACAAAGAAACCTGGGATGACT 89160
mRNA    ------------------------------------------------------------

genome  TCACATCCTGGGCAGGTGTGTGGTGGTGACAGTCATGGAAATTGGGAACACAGATTTGTG 89220
mRNA    ------------------------------------------------------------

genome  CGGGAAACATCAGTTTCAGTTTGAGTTTGGCTTATCAGTTGAATATCAGGCACAGATGTC 89280
mRNA    ------------------------------------------------------------

genome  TGGCCAACTCTCAACATAGGGTCTTAAATGACTTCAGTTCCCCAAGCAATTTGTCCTTCC 89340
mRNA    ------------------------------------------------------------

genome  CATGCTATTGGGGTGGAGAGGTAATGTCTGTGCCCATATCACAGCCAGTGCTCCCAAATC 89400
mRNA    ------------------------------------------------------------
```

FIG. 1 TTT

```
genome  TCTGAGAAGTTCATGGGCCTCTGAAGAAGAAGCCAACCCAGCAGCCACCAAGCAAGAGGA 89460
mRNA    ------------------------------------------------------------

genome  GGTCTGGCCAGCCCTGGGGGACCGGGCCCTGGTGCCCATGGTGGAGCAGCTCTTCTCTCA 89520
mRNA    ------------------------------------------------------------

genome  CCTGCTGAAGGTGATTAACATTTGTGCCCACGTCCTGGATGACGTGGCTCCTGGACCCGC 89580
mRNA    ------------------------------------------------------------

genome  AATAAAGGTAATGTCCCACTTGGGTGCTGGATTCATACAGCCTTAATGACTATGGGTTTC 89640
mRNA    ------------------------------------------------------------

genome  CAGACTACCTTTGTTTAGTAATCTGTCCCTTCTTTATTCTCTTTTTGCTTTAAATGAACA 89700
mRNA    ------------------------------------------------------------

genome  AAATTGCTCAGATTGTGACACTAAATTTAACATCAAAATGTGACCATGTGGATGGGTGCA 89760
mRNA    ------------------------------------------------------------

genome  GTGGCTCGTGCCTGTTATTCCAGCACTTTGGGAGACTGAGGCAAGTGGATCACTTGAGGC 89820
mRNA    ------------------------------------------------------------

genome  CAAGAGTTCGAGACCAGCCTGGGCAACATCACGAAACCCCCTCTCTACTAAAAATACAAA 89880
mRNA    ------------------------------------------------------------

genome  AAATTAGATGGGTTGGGCCGGGCGTGGTGGCTCAAGCCTGTAATCCCAGCACTTTGGGAG 89940
mRNA    ------------------------------------------------------------

genome  GCCGAGGTGGGCGGATCACGAGGTCAAGAGATCAAGACCATCCTGGCTAACACAGTGAAA 90000
mRNA    ------------------------------------------------------------

genome  CCCCGTCTCTACTAAAAATACAAAAAAATTATCTGAGCATGGTGGCGGGCGCCTGTAGTC 90060
mRNA    ------------------------------------------------------------

genome  CCAGCTGCTCGGGAGGCTGAGGCAGGAGAATGGCGTGAATCCGGGAGGCGGAGCTTGCAG 90120
mRNA    ------------------------------------------------------------

genome  TGAGCCGAGATCGTGCCACTGCACTCCAGCCTGGGTGACAGAGCGAGACTCCGTCTCAAA 90180
mRNA    ------------------------------------------------------------

genome  AAAAAAATTAGATGGGCATGGTGGTGCGTGCCTGTAATCCCAGCTACTTGGGAGGCTGAG 90240
mRNA    ------------------------------------------------------------

genome  GCAAGAGAGTTGCTTGAACCTGGGAGGCGGAGTTTGCAGTAAGCCTTGATTGTGCCGCTG 90300
mRNA    ------------------------------------------------------------

genome  CACTCCAGCCTGGGTGACAGAGTCAGACTCTTTCCAAAAGAAGAAAAAAATGTGACCATG 90360
mRNA    ------------------------------------------------------------

genome  TGTTTTATAGCTCTTTTAGTATCATCAGTCACTGTTATCCCTAAGAGGGAAATACCTAGC 90420
mRNA    ------------------------------------------------------------

genome  TTTAGTTTTAGGTTTCCAGCATTAGCCAAGAAAGCTCAGAATTGATGTTCCTGGCCAAGT 90480
mRNA    ------------------------------------------------------------

genome  ACCTCATTGCTGTCTCCTTAAATCTTGGTTAATGGCTACTGTCCTGGCTAGCATAGTTAT 90540
mRNA    ------------------------------------------------------------

genome  GGAGCATTTCCATGGTTGTAGAATGTTCTGCCAATCTCAGGGACAGTTTTGCTTTTCTGT 90600
mRNA    ------------------------------------------------------------

genome  GAAGCAATAAAATCAACTTCAAAACAAATGTTAACTATTTGTACAATGGATTTAAGATAG 90660
mRNA    ------------------------------------------------------------
```

FIG. 1 UUU

```
genome          ACCAGTTCACATACTTTTTTTTTTTTTTTTTTTTGAGATGGAGTTTCATTCTTGTTGCCT 90720
mRNA            ------------------------------------------------------------

genome          GGGCTGGAGTGCAATGGTGTGATCTCAGCTCACTGCAACTTCTGCCTCCTGGGTTCAAAC 90780
mRNA            ------------------------------------------------------------

genome          GATTCTTCTGCCTCAGCCTCTCGAGGCAGATTACAGCTGGGATTACAGGCATGCACCACC 90840
mRNA            ------------------------------------------------------------

genome          ACACCCAGCTAATTTTTTTGTAGTTTTAGTAGAGACGGGGTTTCACCATGTTGGTCAGGT 90900
mRNA            ------------------------------------------------------------

genome          TGGTCTCAAACTCCTGACCTGAAGTGATCTATCCGCTTCGGCCTCCCAAAGTGTTGGGAT 90960
mRNA            ------------------------------------------------------------

genome          TACGGGCATGAGCCACCACGCCCAGCCTAAGATAGACCAGTTCACTTACTGTTTATATCT 91020
mRNA            ------------------------------------------------------------

genome          GATTACTCTCTCTTTGCCTTGTCTTCTACCTTTAAAAATCTCCCTACTAACTTCCCATTC 91080
mRNA            ------------------------------------------------------------

genome          TCCTTTAGCTGCCATCAGTCTTCTCCCTTCTCTGCAAACATCTCTGGAGAGTCCCAGCCT 91140
mRNA            ------------------------------------------------------------

genome          CAGCCCACAGAGCTTCCCACTGCTCTGAGGTGGACCTTGTTTGCAAGGCTTCTTTGGCTC 91200
mRNA            ------------------------------------------------------------

genome          TCTTGGCCTGGACCCTGTCTACTACTTCAGCCATCCTTCCTTAACCCCTGCTGGTGGTTT 91260
mRNA            ------------------------------------------------------------

genome          CTGTTGCCACACTCCATAGCAGCGTTTCCCGCCCAGATCATGTCTTTACATCTCTGGGCA 91320
mRNA            ------------------------------------------------------------

genome          CTGCTCTGGTCCTGCCTGCCTTTCCCTCTTTGTATCCTGCAGGCTGCTACCCCCATCTTG 91380
mRNA            ------------------------------------------------------------

genome          AGTGTCCTCTTCAGTTGGCTTTCAGAGGGCCTCCTGGGTGTTCCCTTACCCACTTGCCAC 91440
mRNA            ------------------------------------------------------------
                                          rs11731237
genome          TCCCCAGTCACTGGGTTCAGTCCTTCCTGCCCACCAGCACATGCTTTCTAGGCTCTGTCC 91500
mRNA            ------------------------------------------------------------

genome          TAGGCCGTCTTCTCTCTTTGTAGTCTCTGGGCCAGTGCTGTTCTAGAGAGTGGCAGAATT 91560
mRNA            ------------------------------------------------------------

genome          TTCTATAACCATGGCAGTGCTCCATAGCTATGCCAGGCAAGACAGTAGCCACTAAACACA 91620
mRNA            ------------------------------------------------------------

genome          TATAGCTGTTGAGCCCTTGAAATGCAGCTAGTGTGACTGAAGAACTGAACCCCGATTCGG 91680
mRNA            ------------------------------------------------------------

genome          TTTAATTTTCATTAAATTTAAATTTAAATAACCTTATGTGGGTAGTGGCTCCAGTATTGG 91740
mRNA            ------------------------------------------------------------

genome          GCAGGGCAGCCTGAGAGTCGGGGCTGTTCTCCTGTCTTCAGTGTCTAGATGAGGGACCTC 91800
mRNA            ------------------------------------------------------------

genome          AGAGGACCTGTCTCTGGAGCTGCAGTTCAATGTAGCCAGCTGCCCCGTGACACTTACATA 91860
mRNA            ------------------------------------------------------------

genome          TAGCTGATTTGTGGATATGTCAGACACGGTGTGATGAGCTCAGCTTTCTGTCCTCCTCCC 91920
mRNA            ------------------------------------------------------------
```

FIG. 1 VVV

```
genome    CACATCTGCCCCTGCCCCATTTACCCCACTTTGTGTCTTATCAAGCTAGAAACAGGTCAC 91980
mRNA      ------------------------------------------------------------

genome    CACAAGTCTTCATTTCCACTCACCAAGTCTTTTGTTTCCCCTACTAAATATTTTGCGAGA 92040
mRNA      ------------------------------------------------------------

genome    AGAAAGTGTGTACCTTTGTATTCACATACATGTACATGCACATATACATGCACATATGCA 92100
mRNA      ------------------------------------------------------------

genome    GGGGTCCCCAACCTCTGTTAAAAACCGGACTGCAGGCCGTGCGTGGTGGCTCACGCCTGT 92160
mRNA      ------------------------------------------------------------

genome    AATTCCAGAACTTTGGGAGGCCGAGACCAGTGCATCACAAGGTCAGGAGATCGAGACCAT 92220
mRNA      ------------------------------------------------------------

genome    TCCGGCTCACACGGTGAAACCCCGTCTCTACTAAAAATACAAAAAAAAATTAGCCGGGTG 92280
mRNA      ------------------------------------------------------------

genome    TGGTGGCGGGCGCCCATAGTCCCAGCTACCTGGGAGGCTGATGCAGGAGAACGGCGTGAA 92340
mRNA      ------------------------------------------------------------

genome    CCTGGGAGGCGGAGCTTGCAGTGAGCCGAGATTGTGCCATTGCACTCCAGCCTGGGCGAC 92400
mRNA      ------------------------------------------------------------

genome    AGAGCGAGACTCTGTCTCAAAAACAAAACAAAACAAAAAAAAAAAAAACCAGGCTGCACA 92460
mRNA      ------------------------------------------------------------

genome    GGAAGAAGTGAGCAAGCATTACCATCTGAGCTCTATCTCCTCTCAGGCCAGTGGTGGCAT 92520
mRNA      ------------------------------------------------------------

genome    TAGATTCTCATAGGAGCGTGTATGAGTTCGTTCTCACACTTCTGTAAAGACATACCTGAG 92580
mRNA      ------------------------------------------------------------

genome    ACATATAAAGAAAAGAGGTTTAATTGGCTCACAGTTCTGCAGGCTGTACAGGCTTCTGTT 92640
mRNA      ------------------------------------------------------------

genome    TCTGGGAAGGCCTCAGGAAACTTGCAGTCATGGCAGAAGGTGAAGGGGAAGTAGGCACAT 92700
mRNA      ------------------------------------------------------------

genome    CTTCACATGGCCCACAGGAAAAAGAGAGAAGGAGAGAGAGAGAGAGACAGAGAGAGAGAG 92760
mRNA      ------------------------------------------------------------

genome    AGAAAAAGAAAGATTGAGAGGGAGAGAGGAGGGAGAAAGGAGAGTGCCTGTAGGGGGAGT 92820
mRNA      ------------------------------------------------------------

genome    TGCTACACAAAGGAGCACCAGGGGGATGGTGCTCAACCATTAGAAACTACCCCCATGATC 92880
mRNA      ------------------------------------------------------------

genome    CAATCACCTCCCACCAGGCCCCACCTCCGACACTGGAGATTACAATTCAGCATGAGATTT 92940
mRNA      ------------------------------------------------------------

genome    GGGTGGGGACACAGAGCCAAACCATATCAGAGCATGAACCCTATTGTGAACTGCACATTT 93000
mRNA      ------------------------------------------------------------

genome    GAGGGATCTAGGTTGCATGCTCCTTATGAGAATCTAATGCCTGATGATGATTTGAGGTGG 93060
mRNA      ------------------------------------------------------------

genome    AACAGTTTCATCCCGAAACCATCCCCCGCCAACCCTGGTTTGTGGAAAAATTGTCTTCCA 93120
mRNA      ------------------------------------------------------------

genome    CAGAACCGGTCCCTGGTGCCAAAAAGTTTGGGGACCTCTGCACATATGCATGCACCTGTA 93180
mRNA      ------------------------------------------------------------
```

FIG. 1 WWW genome CATGGACACATAATACATGTACATATGCATACTTTATATTCTCTGCCACTTCTGGTCCAG 93240
mRNA ------------------------------------------------------------ genome ACTGATATACTATCTCATTTGGATTACTGCACTAGCCTTTTGTTTTGGAAACAGCATTTT 93300
mRNA ------------------------------------------------------------ genome TTAAAAAATTTAATTTAATTTTTTTGAGATAGGGTGTCATTCTGTTGCCCAGCTTGGAGT 93360
mRNA ------------------------------------------------------------ genome GCAGTGTCATGATCATAGCTCACTGCGGCCTCGATCTCCCAGGCTCAAGTGATCCTTCTG 93420
mRNA ------------------------------------------------------------ genome CCTCAGCCTTCTCAGTAGTTGGGACTACAGGCATACCCACCATGCCCAGCTAATTTTTTG 93480
mRNA ------------------------------------------------------------ genome ATTTTTTTTTTTTTTTGAGACAGAGTCTCAGCCTGTCGCCCAGGCTGGAGTGGGTTGGCG 93540
mRNA ------------------------------------------------------------ genome CGATCTCAGCTCACTGCAACTTCTGCCTCCCAGGTTCAAGTGATTCTCCTGCCTCAGCCT 93600
mRNA ------------------------------------------------------------ genome CCCGAGTAGTTGGGATTACAGGCGCCTGCCACCACACCCAGCTAACTTTTTGTATTTTTA 93660
mRNA ------------------------------------------------------------ genome GTAGAGACGGGGTTTCACCATGTTGGCCAGGCTGGTCTCGAACTTGTGACCTCGTGATTA 93720
mRNA ------------------------------------------------------------ genome GCCCGCCTCGGCCTCCCAAAGTGCTGGGATTACAGGCGTGAGCTACCGCTCCCAGCCAGG 93780
mRNA ------------------------------------------------------------ genome AAACAGCATTCTTGAGATAATTCATATAATTCACCCATTTAAAGTATATAATTCATTCTC 93840
mRNA ------------------------------------------------------------ genome TTTAGTATGCCCACAGAGTTGTACAGCCATCACCAGAATCAGTTTTAGAACCCATAAAGG 93900
mRNA ------------------------------------------------------------ genome AACTCTGTACTCTTTACCCAAAACCTCCATGCCTCCAGCTGCAGGCAGCCACTAACCTGC 93960
mRNA ------------------------------------------------------------ genome CTTCTGTCTCTGTGACTCTACGTCTTCTGGACATTACTGTGGATGGGCTCATACAGTCAG 94020
mRNA ------------------------------------------------------------ genome TGAGCTTGTGACTGGTGCCTTCTACCAAGCAGGGTTTTCAGTGTAGCAGCCTCTCTGTTT 94080
mRNA ------------------------------------------------------------ genome TTCTTTTTTTTTTAAATTGTGACGGAACTTCTGCCTCCCGGGTTCAAGCGATTCTCCTGC 94140
mRNA ------------------------------------------------------------ genome CTCAGCCTCCCGAGTGGCTGGGACTACAGGCCCATGTCACCATGCCTGGCTAATTTTTTT 94200
mRNA ------------------------------------------------------------ genome TTTTTTTTTTTTTAGTAGAGATGGGTTTCAACATGTTAGCCAGGGTGGTCTCGATCTCCT 94260
mRNA ------------------------------------------------------------ genome GACTTCATGATCCGCCTGCCTCGGCCTCCCAAAGTGCTGGGATTACAGGCGTGAGCCACC 94320
mRNA ------------------------------------------------------------ genome ATGCCCGGCTAACCTTTCATTTACTGTCTGCATTTCTTCCCTGATGCCTTCCAGTCCATG 94380
mRNA ------------------------------------------------------------ genome CACCCGATTGTAGCCATTCATCCTATTATGGTTTAAGGTGACTGTCTTAGTCAGCATGGG 94440
mRNA ------------------------------------------------------------

FIG. 1 XXX

```
genome    TTGCCATAACAAAATACCATAGCCTGGGTGGCTTCAACAACAGAATTTACTTCTCACACT 94500
mRNA      ------------------------------------------------------------

genome    TCTGGAGGTTGGGAAGTCCAAGATCCAGGACTTTCGCCTTGCCCTCATGTGGTGAGGGGG 94560
mRNA      ------------------------------------------------------------

genome    TGAGGAAGCTCTGTGGGGCCTCTTATATATGGATGCTAATCTCATTCATGAGGGGTCTGC 94620
mRNA      ------------------------------------------------------------

genome    CCTCATGACCCAGTCACCTCCCAAAGGCCCCACCTCCTAATACCATCACCCTGGTAATTA 94680
mRNA      ------------------------------------------------------------

genome    AGTTTCAGTGTATAAATTTGGGGGACTATAGACATTGAAACCATAACAAGCACTTTTCTA 94740
mRNA      ------------------------------------------------------------

genome    AGATCAGGGAGTGAGTAAGTAGCAGAGCTAGGACCTCAATTCCACATGTCAGTCATCTTG 94800
mRNA      ------------------------------------------------------------

genome    CCTTCACTCTGCTCCATGATGGCTGCCTCCTAGAGCATTGGGAGTCTCGATGTTCTATAT 94860
mRNA      ------------------------------------------------------------

genome    GCTCTCATGTGTTGTGTATTGGAGATAGTTGAGGCTTTATGAATACATCTGGATTTGTTG 94920
mRNA      ------------------------------------------------------------

genome    ACTTCTAGCTTTGCTGGTAACCAGCTGTGACCTTGAATAAGTTACTTCATCTCTGAGCCT 94980
mRNA      ------------------------------------------------------------

genome    GTTTCCTCTTTTAGAAACAGGAGTTTAAAATGCTGCTTTGGGTTGGGCACGGTGGCTCAT 95040
mRNA      ------------------------------------------------------------

genome    GCCTGTAATTCCAGCACTTTGGGAGGCTGAGATGGGAGGATCACTGGAGCTTGGAGTTCG 95100
mRNA      ------------------------------------------------------------

genome    AGACCAGCCTGGGCATCATAGTGTGAGATCCTGTCTCCTCAAGAAATTAAAAAATTAGCT 95160
mRNA      ------------------------------------------------------------

genome    GGGTGATGTGGCGTGTGCCTGTGGTCCCATCTACTCTGGAGGCTGAGGTGGGAGGATTGC 95220
mRNA      ------------------------------------------------------------

genome    TTGAGCCCAGGAGGTTGAGGCTACAATGAAATATGATTGCACCCCATCCTGGGTGACGAG 95280
mRNA      ------------------------------------------------------------

genome    TGAGACCCTGTCTCAAAAAAGAAAAAAAAAAATGCTGCTTTGTACCCCTTTCATGTCATGG 95340
mRNA      ------------------------------------------------------------

genome    CGTCATGGCCAACATAGAATGCCCTGGTTGTTTGCTGTTGGAGGGCATGGGCCTGGGGGC 95400
mRNA      ------------------------------------------------------------

genome    TCCCTGAGGGCTCCTTCCATCTTCAACTCATTCTCTGTGCACCTGTTAGGAAGTTGTGGG 95460
mRNA      ------------------------------------------------------------

genome    CCAGTCCCTACCATGTATCATTGTGTGGGTAAAAGTAAATAAAATGTGTACAGTGTCTGA 95520
mRNA      ------------------------------------------------------------

genome    ACTGTACATATCAGGGTCCAAGAACAAAATGAGTGACATGGGTTAGCTCTTTTTAATAAA 95580
mRNA      ------------------------------------------------------------

genome    TGGTAAAACCAAATATTCTAATTTTCAGTTTTGTTATACTTCCATCACATGTTTTTGTTT 95640
mRNA      ------------------------------------------------------------

genome    TTTTGTTTTTTGTTTTTGTTTTTCTATTTTAGGCAGCCTTGCCTTCTCTAACAAACCCCC 95700
mRNA      ------------------------------------------------------------
```

FIG. 1 YYY

```
genome  CTTCTCTAAGTCCCATCCGACGAAAGGGGAAGGAGAAAGAACCAGGAGAACAAGCATCTG  95760
mRNA    ------------------------------------------------------------

genome  TACCGTTGAGTCCCAAGAAAGGCAGTGAGGCCAGTGCAGGTAGGAAACAGCGTGGGGAAG  95820
mRNA    ------------------------------------------------------------

genome  GGAGGGACATGAGTGCAGCATCTGTCATGTAGAAACATAGGATTTAAGTAACTTGGTGTT  95880
mRNA    ------------------------------------------------------------

genome  TTAGAGAAATAAATATAATACACATCAGTAAAGTGAGAGAAAGTTTCTCCAGGTGCGGTT  95940
mRNA    ------------------------------------------------------------

genome  CAAGATATTAGAAACTAATGACTGATGTACACAGACCACCTTTTGGTCTGAAGCATTTCT  96000
mRNA    ------------------------------------------------------------

genome  AAGTGCCACTGGCTGACATGCAGCCCCTACAGCCTCCAGGCTTCCAGCCCTAGCATGGAG  96060
mRNA    ------------------------------------------------------------

genome  CATCACTCTCCTATGCTTCCCTGGTTGCAGGTGATGGCTGGAGAGGCCTCCTGATTTTCA  96120
mRNA    ------------------------------------------------------------

genome  GTAAGGGAAGTGGTGTAGATGCTTAGGAATAGATGTAGTGAGTGAAAAAACTGATTCTGA  96180
mRNA    ------------------------------------------------------------

genome  TATGTCAAAAATTCTGATTGGAAATGGAATATTTACATTTGGAAGAGCTAAAGGCGAGAG  96240
mRNA    ------------------------------------------------------------

genome  AAAGTGGGGATAAAGTCATCTGAGTTGGAGGAGCTTAAACCATTCACAAGTTTGGAGGAC  96300
mRNA    ------------------------------------------------------------

genome  CTTTTTTTACCCATGAAAAGGTCAGAACAGAAGGGGCTAGGATTTAGGTGTGACTGCAGT  96360
mRNA    ------------------------------------------------------------

genome  TTATTGAATTCCCATCCATACTGCTCTCGGTGGGCAGTGGCAGGGGCAGGAGAGGAGCCT  96420
mRNA    ------------------------------------------------------------

genome  GGCAAAGCATGAAGTGACTGCTGCTGCCTCTGCTATCTGGGACGCCTGGCCACCTGTCTG  96480
mRNA    ------------------------------------------------------------

genome  TACAGTCTCCCTCCAGACCCATTCTCACGCTGTCTCTTGGCACCCAGGGGCCAGTGATGG  96540
mRNA    ------------------------------------------------------------

genome  TTCTCCCATTTGTTTTGTGTATATAGCATTTATATCAAGGCTATTTATTTATTTATTTAT  96600
mRNA    ------------------------------------------------------------

genome  TTTATTTATTTATTTTTTTGAGACAGAGTCTCACTCTGTCACCCAGGCTGGAGTGCAGTG  96660
mRNA    ------------------------------------------------------------

genome  GTGCAATCTCGGCTCAGTGCAAGCTCTGCCTCCTGGGTTCAAGCAATTCTCCTGCCTCAG  96720
mRNA    ------------------------------------------------------------

genome  CCTCCTGAGTAGCTGGGACTACAGGTGTGCACCACCACACCTGGCTAATTTTTTGTATTT  96780
mRNA    ------------------------------------------------------------

genome  TTTATTAGTGGAGACGGGGTTTCACCTTGTTGGCCAGGATGGTCTTGATCTCCTGACCTC  96840
mRNA    ------------------------------------------------------------

genome  GTGATCCGTCCACCTCAGCCTCTCAAAGTGCTGGGATTACAGGCATGAGTCACTGTACCC  96900
mRNA    ------------------------------------------------------------

genome  GGCCTATTTATTTATTTTTAATTGACAAAATTGTATATATCTGTAATATACAACATGATG  96960
mRNA    ------------------------------------------------------------
```

FIG. 1 ZZZ

```
genome   TTTGAAATATGTGTACATTGGCCAGGCGTGGTGGCTCACACCTGTAATCCCAGCACTTTG 97020
mRNA     ------------------------------------------------------------

genome   GGAGGCTGAGGTGGGCGGATCACGAGGTCGGGAGTTCAAGACCAAACTGGCCAGCATGGT 97080
mRNA     ------------------------------------------------------------

genome   GAAATCCTGTCTCTACTAAAAATACCACAAAAAAAAAAAAAAAAAAAAAAAGCCGGGCAT 97140
mRNA     ------------------------------------------------------------

genome   GGTGGCTCGCGCCAGTCGTCCCAGCTACTTGGGAGGCTGAGGCAGGAGAATTGCTTGAAT 97200
mRNA     ------------------------------------------------------------

genome   CTGGCAGGTGGAGGTTGCAGTGAGCTGAGTTCATGCCACTGCACTCTAGCCTGGGCGATA 97260
mRNA     ------------------------------------------------------------

genome   GAGCGAGACTCCGTCTCAAAAAAAAAAAAAAAAGAAGAAATACATATGCATTGTGGAATG 97320
mRNA     ------------------------------------------------------------

genome   GCTAATTAACCTGTGCATCACCTCACGTATCATTGTTTTGTGGTGAGAACACTTAAAATC 97380
mRNA     ------------------------------------------------------------

genome   TACTCTTTCAGTGATTTTCTTGCATATGGTACATTGCTATTAACTGCAGTCACCATGCTA 97440
mRNA     ------------------------------------------------------------

genome   TACAGTAGATCTCTTGAACTCATTCCTCCTGTCTATAAATGAAATTTTGTATCCTTGACC 97500
mRNA     ------------------------------------------------------------

genome   AACACATTCAAGGTTTTTTTTGAGATGGAGTCTTCTTCACCCAGGCTGGAGTACCATGGC 97560
mRNA     ------------------------------------------------------------

genome   ACGATCTCATCTCACTGCAACCTCCGCCTCCCAGGTTCAAGCAATTCTCCTGCCTCAGCC 97620
mRNA     ------------------------------------------------------------

genome   TCCTGAGTAGCTGGGATTACAGGCACATGCTACTGCACCTGGCTAATTTTTGTATTTTTA 97680
mRNA     ------------------------------------------------------------

genome   GTAGAAGTGGAGTTTCACCATGTTGGCCAGGCTGGTCTCGAACTCCTGACCTCAAGTGAT 97740
mRNA     ------------------------------------------------------------

genome   CCGCCTGCCTTGGCCTGCCAAAGTGCTGGGATTACAGGTGTGAGCCACTGCACCCGGCCT 97800
mRNA     ------------------------------------------------------------

genome   CAAGCGTTTTAAAAGATGCTCTTTTCTAAGGATTGACTGTAGTACAGGAGGAAGATTGAC 97860
mRNA     ------------------------------------------------------------

genome   CTGTTGAAAAGCCTCAGCCTTTACAAGTGTAAAATTATCAGTATATTACTATCATCTTTC 97920
mRNA     ------------------------------------------------------------

genome   TGATGAATTAAATAAACTAAGGACTCCAAGTCAAAAGTCTTCAAACTGAAGTAGAATAGT 97980
mRNA     ------------------------------------------------------------

genome   TGTATATAGTGCTTGGCACTTTAATATTTAGTATCGGTTTAATGATAATGTTTGTGCCTT 98040
mRNA     ------------------------------------------------------------

genome   TGCCGTCTTTAAAACATTTTTACATCATCCCTGTTTGATTACTTGGTGTGCTCATGAAGT 98100
mRNA     ------------------------------------------------------------

genome   TGTTGGCCACTAAGGAATCTTAGGCTCAGAGAGGTTCTGGAATTGGCCAGTGGTCCTTGA 98160
mRNA     ------------------------------------------------------------

genome   ATCAGCTGCTCCTATGATTCTCTAACTGATTTCTCACAAAGCAAACAAGCAATCATAACA 98220
mRNA     ------------------------------------------------------------
```

FIG. 1 AAAA

```
genome     AAACAACTGTGCACACTGCTCTTCTTATTTTGTTATTTAAAAAGTACTTAGGCTCTACTT 98280
mRNA       ------------------------------------------------------------

genome     ATGTTTGTTAGTCAATTTCTCATTACTTCTAGTTAATCAAAAGGTCAGAGGAAATACTTG 98340
mRNA       ------------------------------------------------------------

genome     AATATTTTCATACTAGAATACTTTAAAAAATCATGATTTCCAGTAATCTCTTTAAAACTT 98400
mRNA       ------------------------------------------------------------

genome     GGCAAGTTATTTTGATCTAAAAGTTTATCTTTTGTGTGCATATTTTTAAAGCTTCTAGAC 98460
mRNA       ------------------------------------------------------------

genome     AATCTGATACCTCAGGTCCTGTTACAACAAGTAAATCCTCATCACTGGGGAGTTTCTATC 98520
mRNA       ------------------------------------------------------------

genome     ATCTTCCTTCATACCTCAAACTGCATGATGTCCTGAAAGCTACACACGCTAACTACAAGG 98580
mRNA       ------------------------------------------------------------

genome     TATGGGCCTCTGCATCTTTTAAAAATATATATGCACACATACTTACGTCTAATGGATAGT 98640
mRNA       ------------------------------------------------------------

genome     TGATGTTTTTCTTATGATTTGTAGGATGTATAAGCCCTTTGAGATATGAGTTACATTTAG 98700
mRNA       ------------------------------------------------------------

genome     TTTTTTCAAGTTTGTTTGTCTTTCAGCTTTGTTTATGATAGCTTCTATCATACAGGTGTT 98760
mRNA       ------------------------------------------------------------

genome     TTGGATTTTCATATTGTTTGTACTCACAGCTAAGATTGATTACAGTGACAGAGCTAGGAT 98820
mRNA       ------------------------------------------------------------

genome     GTGCAGCCAGGTTATAGGGGGAAGTGGCCCTGGTGGAGTCTGGAGGGATCCGTGTACAGG 98880
mRNA       ------------------------------------------------------------

genome     CTTCCTTCCCTCCCGTGAGGCTCACACAAAAATACAGCAACATGCTGGTCCTGCAGGTAC 98940
mRNA       ------------------------------------------------------------

genome     CCTCTGCCTAACATGAGCCACAATTCCAGACTCACAGAAGAAAAGCAGGTGTTCGGCATA 99000
mRNA       ------------------------------------------------------------

genome     AACCATGTGTTTCAAATAGTCTGGGCATGGTGAGCCACTTGTTATCAGCTAGGGAAAGTT 99060
mRNA       ------------------------------------------------------------

genome     TATGTCAGCGTAAGAAACTGTTCACCAGATACCCCCAAGAGCCAGCCTTTCTGTCTAGGG 99120
mRNA       ------------------------------------------------------------

genome     ATGTTTTAGTTTTTTAGTTCATTTTTTTTTTTAACTTTAAAATTTTCTGTTCATCTGCAA 99180
mRNA       ------------------------------------------------------------

genome     TTTGTTAGATATGAAGTATGTGTCTAATTTAATTTTTGTTTTTGGTTGTCCCCAATAATG 99240
mRNA       ------------------------------------------------------------

genome     TTTACAGAAGAATTTTTCTGCACTAATTGGCTTGAGTTACTTACATTCTCATAGTTCTCT 99300
mRNA       ------------------------------------------------------------

genome     AGTTTCAGTAGTTTCATTTATTATTTTGTTATATCAATCTATCTGTCTGCTCATCTATTA 99360
mRNA       ------------------------------------------------------------

genome     GAAGCATCCTTGTTTTTTTTTTTTCTTTTTTAGACAGAGTCTTGCTCTGTCCCCAGGTTG 99420
mRNA       ------------------------------------------------------------

genome     GAGTGCAGTGGTGCAACCATGCCTCCCTGCAGTCTCAGGGCTCAAGTGATCCTCCCACCT 99480
mRNA       ------------------------------------------------------------
```

FIG. 1 BBBB

```
genome          CAGCTCCTGAGTACCTGGGACTACCGGCATGTGCCACCACACCCAGCTAATTTTTACATT 99540
mRNA            ------------------------------------------------------------

genome          TTTTGTAGAGACAGGGTCTCCCTAAGTTGCCTGGGCTGGTCTCAAGCTCCTGGCTTAAGT 99600
mRNA            ------------------------------------------------------------

genome          AATCCTCCCTCCTTGGCCTCCCAAAGTGCTGGGATTACAGGTGTGAGCAACTGCACCCGG 99660
mRNA            ------------------------------------------------------------

genome          CTACAAGTATACTTCTTAATTATTGTAGCTTAATGGTATTTATGAGGGGATCAGTTCCCC 99720
mRNA            ------------------------------------------------------------

genome          TGTTGTTCTTTAGAATTTTCTGGATATTCTTCTTTATTGATTTTGGGATGTGAACAATAG 99780
mRNA            ------------------------------------------------------------

                                    rs4690073
genome          AATCAACTTCTACTTGTAGATTGATTTAGGGAGAACTTATACCTCAGATGTTAAGTCACC 99840
mRNA            ------------------------------------------------------------

genome          CTGTCCAGAATGTGGGATGCTTTCCTATTTGTTCAGAACTTTTTAAATTACCTCAGAAGC 99900
mRNA            ------------------------------------------------------------

genome          ACATGAAATTTAAAGGATTTTAAAAAAAACTTAAAGATTATTTCACATAGCTCTTGCACA 99960
mRNA            ------------------------------------------------------------

genome          TTTCTTGATAAATGAATCCTCAGGTATTCCTCTGTTTTTGTTACTAATAGTTACTTCTTA 100020
mRNA            ------------------------------------------------------------

genome          TGGGTTTTTTTTCCCCTGAAAATCATTTATCAAACGTATGTGGCTTATTTTCTGAAGGAT 100080
mRNA            ------------------------------------------------------------

genome          GTTTGATAATTTTGGAAGATATGAAAGTCTTCATATTTTACAAGGTTTGAGGTCTCTTTA 100140
mRNA            ------------------------------------------------------------

genome          AGCTGCATGGTTCTCATGTCAGCTCCCAAAGCAGAAGACGGCATGTTGAAAAATGCCGTA 100200
mRNA            ------------------------------------------------------------

genome          GAGAAGATACTTCTTTTCCACCTGTTTTCAACTCATATCATCTTGAATTTCAGGGCACCT 100260
mRNA            ------------------------------------------------------------

genome          TTCCATGCTCCTAGTGCTTGCTATCTGTTTATTATTTTCCTTCCTGAATACCCTGAACTC 100320
mRNA            ------------------------------------------------------------

genome          CAGCATGTTCTGCTGTAATTCTGGCCTCCCTGGCATCTTGGACTCCTGTTTCCTTTGCTC 100380
mRNA            ------------------------------------------------------------

genome          TGTCATCCCCGCGGTCAGCTCCTGCTGCGCAGCTTCTCAGCTGAAGTGCGTTTGGAGTGC 100440
mRNA            ------------------------------------------------------------

genome          CTGGCGTGTCTTGCTGGATCTTTGAGTATTGCCTCTGGTTTCCTTGGTTCCTTCTGCTGA 100500
mRNA            ------------------------------------------------------------

genome          GTTGCTCAGCGTCTCCACTCCCCATTTCTTGTGTGGCCCTTCCTGCACTCCTCTGATTCC 100560
mRNA            ------------------------------------------------------------

genome          TTTTGTCTTCCCTGGTTTCTTGCTTTGGTTTCGAGTCTCCACAGAACTTTTGCAGCTCTT 100620
mRNA            ------------------------------------------------------------

genome          CTGAAGACCTGGAAGCTTTTTCATCTTAATTCTCATCTCATGACCTCTTTTCCCTTCTTT 100680
mRNA            ------------------------------------------------------------

genome          GAGAGCTAGAACTTCCCATGGTGAACTTCTCTTTCCAGAATTCCATGCCTTCTTTTCCCT 100740
mRNA            ------------------------------------------------------------
```

FIG. 1 CCCC

```
genome    CCCACTTACCTGTTGTCCAGGAGAGGTCAGATTGCTGTGCATATTGGAGGAGAACCCTTT 100800
mRNA      ------------------------------------------------------------

genome    CTTCCCTGGGCTCTTCATCTCACATGACATCACCACATCACCTCGTTCCTTGGACCCTCA 100860
mRNA      ------------------------------------------------------------

genome    GTGGTGTCACTGCTGGATTTTTCTTTCCTTTGGCTGGCCTTAGGGCACACCCAGGTTGAC 100920
mRNA      ------------------------------------------------------------
                                     rs363144
genome    TAGCGTAGTCATGGTATTTAGATCCACTCACATTTTCAGTTTCTGTGTCTGTCTCTTGCC 100980
mRNA      ------------------------------------------------------------

genome    TGCTTCTGACTTCGCCCAGAGAAAGCTTCTCTTTCACAAGGGTTCTTAGATTTATGTTCA 101040
mRNA      ------------------------------------------------------------
                                                            rs3025838
genome    CTGAGCACCTTCTTTTCTGAGGCAGTGTTTTACCAATATTTATTTTCCTAGTCAGTCTCG 101100
mRNA      ------------------------------------------------------------

genome    CCTTACCTTTCTTGTTATGCATGTCTTTGGTCCTGACCCATTCTCTGAGTCTGTAAAATA 101160
mRNA      ------------------------------------------------------------

genome    GAATTGCTGTATAATTTAATTACATGAAATCCTTTAGAATCTTAACACATCTTACACCTG 101220
mRNA      ------------------------------------------------------------

genome    ATTTAATATTTTATTGTATCCAAATTGAACCAACCCTATGTGAATTTGACAGTGATTTCT 101280
mRNA      ------------------------------------------------------------

genome    CCCAGGGATCCTAGTGTATAAGGAATAGGACTTAGTATTTTCTATTTTTTGATATACCAC 101340
mRNA      ------------------------------------------------------------

genome    ATACCAGATACTGATTATGATGGACATTTAACCCTTTTTTCTCATTATGAAAGAAAGTTA 101400
mRNA      ------------------------------------------------------------

genome    GGAATTATTTCTTCCAGTAGCGCCAGTGTAACCTGAAAGCCTTTGAAAGAGTAGTTTTTG 101460
mRNA      ------------------------------------------------------------

genome    TATAGCTATCTGAAAGGAATTTCTTTCCAAAATATTTTTCCAGTGCTGACAACAAACACG 101520
mRNA      ------------------------------------------------------------

genome    CAGACACACCCTGCAAGGTGAGTGTACGGCGCCGCACAGTGGAGGCATCTGCTGCAGCCG 101580
mRNA      ------------------------------------------------------------

genome    TCGATGTTTGTGTCTTTGGTTGTACATTATGAGATCGTGACAGGGCCAGTAACCGTGTGT 101640
mRNA      ------------------------------------------------------------
                                                    rs34315806
genome    TCTCTCCTTCACCTTCCCAAGGTCACGCTGGATCTTCAGAACAGCACGGAAAAGTTTGGA 101700
mRNA      ------------------------------------------------------------
              rs363099
genome    GGGTTTCTCCGCTCAGCCTTGGATGTTCTTTCTCAGATACTAGAGCTGGCCACACTGCAG 101760
mRNA      ------------------------------------------------------------

genome    GACATTGGGAAGGTTTGTGTCTTGTTTTTTCTCCTTGGGTTGTGGCTGGCACACTTGATG 101820
mRNA      ------------------------------------------------------------

genome    TGCGTCTTCTGGGCTGAGTTCATCTAGGATGGAGCCTGGTTCTCCAGGGTGCCTCCGGGA 101880
mRNA      ------------------------------------------------------------

genome    GACTCCTCCCTGCCCCACGTGCTTGCGTCACAGGACCCAAGTCTGACTCTGCCTTAGCCA 101940
mRNA      ------------------------------------------------------------
```

FIG. 1 DDDD

```
genome     TGAAGTTTAGGGGGAAGTTTCTATTTGTATTCTATTTTTGTCTGTTATCATGTATTAGCT 102000
mRNA       ------------------------------------------------------------

genome     TAGACCCAGTTTAGTTTGGAAAATCAGTGGGTTTCAAAATGTGTTTGTAGAGTCCTTTAT 102060
mRNA       ------------------------------------------------------------

genome     TTCTTAACTTGACCTTTTCAAGTGGAAAGGGGCAAAACAGACGGGTAAGGGGGCGGGGCG 102120
mRNA       ------------------------------------------------------------

genome     GGAGGTGTGACTTGCTCTTTTGTGCCTGAGGAAGTAACAGAGCTGGGGTTGACAGTCATA 102180
mRNA       ------------------------------------------------------------

genome     TTCTCTGACACAGATAGTCTCTGACTTATCTCACAGAAAGTCAGCGGCAGAGCCTGAGTT 102240
mRNA       ------------------------------------------------------------

genome     AAAAGTCTCGTAGATTTTCTTTTTCTTTTTTTTGGTGGCTAATTTCAGTTTTATTTATAT 102300
mRNA       ------------------------------------------------------------

genome     TTGTTTATTTATTTATTATACTTTAAGTTCTGGGTTACATGTGCAGAATGTGCAGTTTTG 102360
mRNA       ------------------------------------------------------------

genome     TTACATAGGTATACACGTGCCATGATGGTTTGCTGCACCCATCAACCCATCACCTACATT 102420
mRNA       ------------------------------------------------------------

genome     AGGTATTTCTCCTAATGTTATCCCTCCCCCAGTCCCCTCACTCCCCATGGGCCCCGGTGT 102480
mRNA       ------------------------------------------------------------

genome     GTGATGTTCTCCTCCCTGTGCCCATGTGTTCTCATTGTTCAATTTCCACTTGTGAGTGAG 102540
mRNA       ------------------------------------------------------------

genome     AACATGCGGTGTTTGGTTTTCTGATCTTGTGATAGTTTGCTGAGAATGATGGTTTCCAGC 102600
mRNA       ------------------------------------------------------------

genome     ATCATCCATGTGCCTGCAAAGGACATGAACTCATCCTTTTTTATGGCTGTATAGTATTCC 102660
mRNA       ------------------------------------------------------------

genome     ATGGTGTATATGTGCCACATTTTCTTAATCCAGTCTATCATTGATGGACATTCGGGTTGG 102720
mRNA       ------------------------------------------------------------

genome     TTCCAAGTCTTTGCTATTGTGACTAGTGCCACAATAAACATACATGTGCATGTGTCTTTA 102780
mRNA       ------------------------------------------------------------

genome     TCGTAGAATGATTTATAATCCTTTGGGTATATGCCCAGTAATGGGATTGCTGGGTCAAAT 102840
mRNA       ------------------------------------------------------------

genome     GGTATTTCTAGTTCTAGACCTTTGAGGAATCGCCAGACTGTCTTCCACAATAGTTGAACT 102900
mRNA       ------------------------------------------------------------

genome     AATTTACACTCCCACCAACAGTGTAAAAGTGTTCCTATTTTTCCACAACCTCTCCAGCAT 102960
mRNA       ------------------------------------------------------------

genome     CTGTTGTTTCGTGACTTTTTAACGATCGCCATCCTAACTGGCGTGAGATGGTATCTCATT 103020
mRNA       ------------------------------------------------------------

genome     GTGATTTTGATCTGCATTTCTCTAATGACCAGTGGTGATGAGCATTTTTTCGTATGTCTG 103080
mRNA       ------------------------------------------------------------

genome     TTGGCTGCATAAATGTCTTCTTTTGCGAAGTGTCTGTTCATATCCTTTGTCCATTTTTTG 103140
mRNA       ------------------------------------------------------------

genome     ATGGGGTTGTTTGCTTTTTTTTTCGTAAATTTGTTTAAGTTCTTTGTAGATTCTGGATGTT 103200
mRNA       ------------------------------------------------------------
```

FIG. 1 EEEE

```
genome    AATCTTTTGTCAGATGGGTAGATTGCAAAAATTTTATCCCATTCTGTAGGTTGCCTGTTC 103260
mRNA      ------------------------------------------------------------

genome    ACTCTGATGATAGTTTCTTTTGCTATGCAGAAGCTCTTTAGTTTAATTAGATCCCGTTTG 103320
mRNA      ------------------------------------------------------------

genome    TCAATTTTGGCTTTTGTTGCCATTGCTTTTGGTGTTTTAGACATGAAGTCTTTGCCTATG 103380
mRNA      ------------------------------------------------------------

genome    CCTATGTCCTGAATGTTATGGCCCAGGTTTTCTTCTAGGATTTTTATGGTCCTAGGTCTT 103440
mRNA      ------------------------------------------------------------

genome    ATGTTTAAGTCTTTGATCCATCTTGAGTTGATTTTTGTGTAAGGTATAAGGAAGGGGTCC 103500
mRNA      ------------------------------------------------------------

genome    AGTTTCAGTTTTCTGCATGTGGCTAGCCAGTTTTCCCAACACCATTTATTAAATAGGGAA 103560
mRNA      ------------------------------------------------------------

genome    TCTTTTCCCCATTGCTTATGTGTGTCAGGTTTGTCAAAGATCAGATGATTGTAGATGTGT 103620
mRNA      ------------------------------------------------------------

genome    GGTGGTATTTCTGAGGCCTCTGTTCTGTTCCATTGGTCTATATATCTGTTTTGGTACCAG 103680
mRNA      ------------------------------------------------------------

genome    TACCATGCAGTTTTGGTTACTGTAGTGTTGTAGTATAGTTTGAAGTCAGGTAGTGTGATG 103740
mRNA      ------------------------------------------------------------

genome    CCTCCAGCTTTGTTCTTCTAGCCCAGGATTGTCTTGGCTATGCAGGCTCTTTTTTGGTTC 103800
mRNA      ------------------------------------------------------------

genome    CATATGAAGTTTAAAATAGTTTTTTCCAATTCTGTGAAGAAAGTCAGTGATAGCTTGATG 103860
mRNA      ------------------------------------------------------------

genome    GGGGGATAGCATTGAATCTATAAATTACTTTGGGCAGCAAGGCCATTTTCACGATATTGA 103920
mRNA      ------------------------------------------------------------

genome    TTCGTCCTATCCATGAACATGGAATGTTTTTCTATTTGTTTGTGTCCTCTCTTATTTCCT 103980
mRNA      ------------------------------------------------------------

genome    TGAGCAGTGGTTTGTAGTTCTCCTTGAAGAGGTCCTTCACATCCCTTGTAAGTTGTCTTC 104040
mRNA      ------------------------------------------------------------

genome    CTAGGTGTTTCATTCCCTTAGTAGCATTTGTGAATGGGAGTTCACTCATGATTTGGCTCT 104100
mRNA      ------------------------------------------------------------

genome    CTGTTTGTCTGTTATTGGTGTATAGGAATGCTTGTGATTTTTGCACATTGATTTTGTATC 104160
mRNA      ------------------------------------------------------------

genome    CTGAGACTTTGCTGAAGTTGCTAATCAGCTTAAGGAGATTTTGAGCTGAACCAATAGGGT 104220
mRNA      ------------------------------------------------------------

genome    TTTCTAAATATACAATCATGTCATCTGCAAACAGGGACAGTTTTACTTCCTCTCTTCCTA 104280
mRNA      ------------------------------------------------------------

genome    TTTGAATACCCTTTATTGCTTTCTCTTGCCTGATTGCGCTGGCCAGAACTTCCAATACTA 104340
mRNA      ------------------------------------------------------------

genome    TGTTGAATAGGAGTGGTGAGAGAGGGCATCCTTGTCTTGTGCCGGTTTTCGAAGGGAATG 104400
mRNA      ------------------------------------------------------------

genome    CTTCCAGTTTTTGCCCATTCAGTATGATATTAGCTGTGGGTTTGTCATAAATAGCTCTTA 104460
mRNA      ------------------------------------------------------------
```

FIG. 1 FFFF

```
genome    CTATGTTGAGATACGTTCCATCGATACCTAGTTTATTGAGAGTTTTTAGCATGAAAGGCT 104520
mRNA      ------------------------------------------------------------

genome    GTTGAATTTTGTCAAAGGCCTTTTCTGCATCTGTTGAGATAATCATATGGTTTTTGTTGT 104580
mRNA      ------------------------------------------------------------

genome    TGGTTCTGTTTATGTGATGGATTACGTTTATTGATTTGCGTATGTTGAACCAGCCTTGCA 104640
mRNA      ------------------------------------------------------------

genome    TTCCAGGGATGAAGCTGACTTGATTGTGGTGGATAAGCTTTTTGATGTGCTGCTGGATTC 104700
mRNA      ------------------------------------------------------------

genome    AGTTTGCCAGTATTTTATTGAGGATTTTCACATCGATGTTCATCAGGGATATTGGCCTAA 104760
mRNA      ------------------------------------------------------------

genome    AATTCTCTTTTTTTGTTGTGTCTCTGCCAGGCTTTGGTATCAGGATGATGCTGGCCTCAT 104820
mRNA      ------------------------------------------------------------

genome    AAAATGAGTTAGGGAGGATTCTCTCTTTTTCTATTGATTGGAATAGTTTCAGAAGGAATG 104880
mRNA      ------------------------------------------------------------

genome    GTACCATCTCCTCTTTGTACCTCTGGTAGAATTCGGCTGTGAATCCATCCTGGACTTTTT 104940
mRNA      ------------------------------------------------------------

genome    TTGGTTAGTAGGCTATTAACTATTGCCTCAAGTTTAGAACCTGTTATCAGTCTATTCAGA 105000
mRNA      ------------------------------------------------------------

genome    GATTCAGCTTTTTTCTGGTTTAGTCTTGGGAGGGTGTATGTGTCCAGGAATTTATCCATT 105060
mRNA      ------------------------------------------------------------

genome    TCTTCTAGATTTTCTAGTTTATTTGGGTAGAGATGTTTATAGTATTCTCTGATGGTAGTT 105120
mRNA      ------------------------------------------------------------

genome    TGTATTTCTGTGGGATCGGTGGTGATATCCCCTTTATCGTTTTTATTGAGTCTATTTGAT 105180
mRNA      ------------------------------------------------------------

genome    TCTTCTCTCTTTTCTTCTTTATTAGTCTTGCTAGCGGTCTACCTATTTTATTGATCTTTT 105240
mRNA      ------------------------------------------------------------

genome    CAAAAAACCAGCACCTGGATTCATTGATTTTTTTTGGAGGGTTTTTTTTCGTGTCTCTAT 105300
mRNA      ------------------------------------------------------------

genome    CTCCTTCAGTTCTGCTCTGATCTTAGTTATTTTTTGTCTTCTGCTAGCTTTTGAATTTGT 105360
mRNA      ------------------------------------------------------------

genome    TTGCTCTTGCTTTTCTAGTTCTTTTAATTGTGATGTTAGGGTGTTAATTTTAGATCTTTT 105420
mRNA      ------------------------------------------------------------

genome    CTGCTTTCTCTTGTGGGCATTTAGTGCTATAAATTTCCCTCTACACACTGCTTTAAATGT 105480
mRNA      ------------------------------------------------------------

genome    GTCCCAGAGATTCTGGTATGTTGTGTCTTCGTTCTCATTGGTTTCCAAGAAAATTTTTAT 105540
mRNA      ------------------------------------------------------------

genome    TTCTGCCTTCATTTCGTTATTTACCCAGTAGTCATTCAAGAGCAGGTTGTTCAGTTTCCA 105600
mRNA      ------------------------------------------------------------

genome    TGTAGTTGTGTGGTTTTGAGTGAGATTCTCAATCCTGAGTTCTAATTTGATTGCACTGTG 105660
mRNA      ------------------------------------------------------------

genome    GTCTGACAGACAGTTTGTTGTGATTTCTGTTCTTTTACATTTGCTGAGGAGTGTTTTACT 105720
mRNA      ------------------------------------------------------------
```

FIG. 1 GGGG

```
genome    TCCAACTATGTGGTCAGTTTTAGAATAAGTGCAATGTGGTGCTGAGAAGAATGTATGTTC 105780
mRNA      ------------------------------------------------------------

genome    TGTTGATTTGGGGTGCAGAGTTCTGTAGATGTCTATTAGGTCCGCTTGGTCCAGTGCTGA 105840
mRNA      ------------------------------------------------------------

genome    GTTCAAGTCCTGGATATCCTTGTTAATTTTCTGGCTCATTGATCTGCCTAATATTGACAG 105900
mRNA      ------------------------------------------------------------

genome    TGGGGTGTTAAAGTCTCCCACTATTACCGGGTGGGAGTCTCTTTGTAGGTCTCTAAGAAC 105960
mRNA      ------------------------------------------------------------

genome    TTGCTTCATGAATCTGGGTGCTCCTGTATTGGGGGCGTGTATATTTAGGATAGTTAGCTC 106020
mRNA      ------------------------------------------------------------

genome    TTCTTGTTGAATTGATCCCTTTACCATTATGTAATGGCCTTCTTTGTCTCCTTTGAACTT 106080
mRNA      ------------------------------------------------------------

genome    TGTTGATTTAAAGTCTGTTTTATCAGAGACTAGGATTGCAATCCCTGCTTTTTTTTTGCT 106140
mRNA      ------------------------------------------------------------

genome    TTCCATTTGCTTGTTAGATCTTCCTCCATCCCTTTATTTTGAGCCAATGAGTGTCTTTGC 106200
mRNA      ------------------------------------------------------------

genome    ATGTGAGATGGGTCTCCTGAATACAGCACACCAATGGGTCTTGACTCTTTATCCAATTTG 106260
mRNA      ------------------------------------------------------------

genome    CCAGTCTGTGTCTTTTAATTGGGGCATTTAGCCCATTTACATTTAAGGTTAATATTGCTA 106320
mRNA      ------------------------------------------------------------

genome    TGTGTGAATTTGATCCTGTCATTATGATCCTAGTTGGTTATTTTGCCCGTTAACTGATGC 106380
mRNA      ------------------------------------------------------------

genome    AGTTTCTTCATAGCGTCAGTAGTCTTTACAATTTGGCATGTTTTTGCAGTGGCTGGTACT 106440
mRNA      ------------------------------------------------------------

genome    GGTTGTTCCTTTCCATGTTTAGTGCTTCCTTCAGGAGCTCTTGTAAGGCAGGCCTGGTGG 106500
mRNA      ------------------------------------------------------------

genome    TGACAAAATCTCTGCATTTGCTTGTCTGTAAAGGATTTTATTTCTCGTTCACTTATGAAG 106560
mRNA      ------------------------------------------------------------

genome    CTTAGTTTGGCTGGATATGAAATTCTGGGTTGAAAATACTTTTTTTAAAGAATGTTGAAT 106620
mRNA      ------------------------------------------------------------

genome    ATTGGCTCCCACTCTTTTCTGGCTTGTAGGATTTCTGCAGAGAGATCTGCTGTTAGTCTG 106680
mRNA      ------------------------------------------------------------

genome    ATGGGCTTCCCTTTGTGGGTAACCCGACCTTTCTCTCTGGCTGCCCTTTCCTTCATTTCA 106740
mRNA      ------------------------------------------------------------

genome    ATCTTGGTGGATCTGATGATTATGTGTCTTGGGGTTGCTCTTCTCGAGGAGTATCTTTGT 106800
mRNA      ------------------------------------------------------------

genome    GGTGTTCTCTGTATTTCCTGAATTTGAATGTTGGTCTGCCTTGCTAGGTTGGGGAAGTTC 106860
mRNA      ------------------------------------------------------------

genome    TCCTGGATAATATCCTGAAGAGTGTTTTCTAACTTGGTTCTATTCTCCCCATCACTTTCA 106920
mRNA      ------------------------------------------------------------

genome    GGTACACCAATCAAACGTAGATTTGGTCTTTTCACATAGTCCCATATTTCTTGGAGGCTT 106980
mRNA      ------------------------------------------------------------
```

FIG. 1 HHHH

```
genome    GGTTCATTTCTTTTCACTCTTTTTTCTCTAATCTTGTCTTCTCGCTTTATTTCATTAATT 107040
mRNA      ------------------------------------------------------------

genome    TGATCTTCAATCACTGATATCCTTTCTTCTGCTTGATTGAATCGGCTGTCGAAGCTTGTG 107100
mRNA      ------------------------------------------------------------

genome    TATACTTCACAAAATTCTCGTTCTGTGGTTTTTAGCTCCATCAGGTCATTTAAGCTCTTC 107160
mRNA      ------------------------------------------------------------

genome    TCTACACTGGTTATTCTAGCCATTAGTCTAACATTTTTTTCAAGGTTTTTAGCTTCCTTG 107220
mRNA      ------------------------------------------------------------

genome    TGATGGGTTAGAACATGCTCCTTTAGCTCGGAGAAGTTTGTTATTACCGACCTTCTGAAG 107280
mRNA      ------------------------------------------------------------

genome    CCTACTTCTGTCAATTCATCAAACTCATTCTCCATCCAGTTTTGTTCCCTTGCTGGTGAG 107340
mRNA      ------------------------------------------------------------

genome    GAGTTGTGATCCTTTGGAGGAGAAGAGGTGTTCTGGTTTTTGGAATTTTCAGCCTTTCTG 107400
mRNA      ------------------------------------------------------------

genome    CTATGGTTTCTCCCCATCATTGTGGTTTTATCTACCTTTGGTCTTTGATGTTGGTGACCT 107460
mRNA      ------------------------------------------------------------

genome    ACGGATGGGGTTTTGGTGTGGGTGTCCTTTTTGTTGATGTTGATGCTATTCCTTTCTGTT 107520
mRNA      ------------------------------------------------------------

genome    TGTTAGTTTTCCTTCTAACAGACAGGCCCCTCAGCTGCAGGTCTGTTGGAGTTTGCTGGA 107580
mRNA      ------------------------------------------------------------

genome    GGTCCACTCCAGGCCCTGTTTGCCTGGGCATCACCAGCAGAGGCTGCAGAACAGCAAATA 107640
mRNA      ------------------------------------------------------------

genome    TTGCTGCCTGATCCTTCCTCTGGAAACATCGTCCCAGAGCACGAAGGTGTCTGCCTGTAT 107700
mRNA      ------------------------------------------------------------

genome    GAGGTGTTTGTTGGCCCCTACTGGGAGGTGTCTCCCAGTCAGGCTACATGGGGGTCAGGG 107760
mRNA      ------------------------------------------------------------

genome    ACCCACTTGAGGCAGTCTGTTCATTATCGGAGCTTGAATGCCGTACCGGGAGAACCACTG 107820
mRNA      ------------------------------------------------------------

genome    CTCTCTTCAGAGCTGTCAGGCACGTATGTTTAAATCTGGAGAAGCTGTCTGCTGCCTTTT 107880
mRNA      ------------------------------------------------------------

genome    GTTCAGATGTGCCCTTCCCCCAGAGGTGGAATCTAGAGAGGCAGTAGGCCTTGCTGAGCT 107940
mRNA      ------------------------------------------------------------

genome    GCAGTGGGCTCTGCCCAGTTCGAGCTTCCCTGCTGCTTTGTTTACACTGTGAGCATAGAA 108000
mRNA      ------------------------------------------------------------

genome    CCACCTACTCTAGCCTCAGCAGTGGTGGACACCCCTCCCCCAGCCAAGCTCCTGCATCCC 108060
mRNA      ------------------------------------------------------------

genome    AGGTCGATTTCAGAGTGCTGCGCTAGCAGTGAGCAAGGCCCCATGGGCGTGGGACCCGCT 108120
mRNA      ------------------------------------------------------------

genome    GAGCCAGGCACAGGAGAGAATCTCCTGGTCTGCTGGTTGTGAAGACTGTGGGAAAAGTGC 108180
mRNA      ------------------------------------------------------------

genome    AGTATTTGGGCAGGAGTGTACTGCTCCTTCAGGTACAGTCACTCATGGCTTCCTTTGGCT 108240
mRNA      ------------------------------------------------------------
```

FIG. 1 IIII

```
genome    TGGAAAGGGAAGTCCCCCGACCCCTTGTGCTTCCCAGGTGAGGCAACACCCCGCCCTGCT 108300
mRNA      ------------------------------------------------------------

genome    TCGGCTTGCCCTCCGTGGGCTGCACCCACTGTCCAGCAAGTCCCAGTGAGATGAACTAGG 108360
mRNA      ------------------------------------------------------------

genome    TACCTCAGTTGGAAATGCAGAAATCACCTGTCTTCTGTGTCGATCTCACTGGGAGCTGTA 108420
mRNA      ------------------------------------------------------------

genome    GACTGGAGCTGTTCCTATTCGGCCATTTTGGAAGCATCCCTTGTTTTTTGAGGTGGAGTC 108480
mRNA      ------------------------------------------------------------

genome    TTGCTCTGTCGCCCAGGCTGACGTGCATCGGCACAATCTCGGCCCACTGCAACCTTTGCC 108540
mRNA      ------------------------------------------------------------

genome    TCCTGGTTTCAAGCGATTCTCCTACCTCAGCCTCCGGAGTAGCTGGGATTACAGGCACCT 108600
mRNA      ------------------------------------------------------------

genome    GCCACCATGCCTGGCTAATTTTTTGTATTTTTAGTGGAGATGGGGTTTCACCACATTGGC 108660
mRNA      ------------------------------------------------------------

genome    CAGGCTAGTCTCGAACTCCTGACCTTGTGATCCACCCACCTCAGCCTCCTAGAGTGCTGG 108720
mRNA      ------------------------------------------------------------

genome    GATCACAGGTGTCAGCCACCACGCCCAGCCATATTTTCAGATCTCCCTCTCTTTGCCCTA 108780
mRNA      ------------------------------------------------------------

genome    AACCACTGTGCTTAATAAGTAGTTTTTAGTGGCCAGCAGTCTCCATGTATAACACATTTT 108840
mRNA      ------------------------------------------------------------

genome    AGCAAAATGGAAAATACTATATGTTTTAAATTTGAACGTGAGATTATACTGAAATAAAAA 108900
mRNA      ------------------------------------------------------------

genome    TCATCTAACTGGGATTCTTTAAATAGTAAGATTTTCTTTTTTGTATGTGGGTTTTTTTTT 108960
mRNA      ------------------------------------------------------------

genome    AACCTTATTATTATGACTGTCATATATAGAAATGGCTGTTTTTCAGTTACAGTCAGTGAA 109020
mRNA      ------------------------------------------------------------

genome    TGTATCAAATGCTGCCTTATCCAAATAATAAAAGTAAATTATTAATAAGTCACAATTTAA 109080
mRNA      ------------------------------------------------------------

genome    TGAAGATTGATGTTAGTTGATCTTTATATTCTTGAAATCAGCCATATGGTTGTGTGTGTA 109140
mRNA      ------------------------------------------------------------

genome    TGTATATATTTTTAAAGGTACATAAAGATAATAAGCTCATCTCTGAAAATTTTTACATTT 109200
mRNA      ------------------------------------------------------------

genome    GGCATAAGAATAACTGGATAATTAAGCATCTTATTCTCTGGCCTGTGTCTTTACAGTTAA 109260
mRNA      ------------------------------------------------------------

genome    AGGTAGATTTACTCACCTCTCCTTTTTTGTTTTTCTAAGTTCATCTTTTTTGCTGTTTCA 109320
mRNA      ------------------------------------------------------------

genome    AGACAGAGGCCCATTTTAGCTTTCTCGCATATCCTTTTGTTTGTACTTTGGAAGCCTCAC 109380
mRNA      ------------------------------------------------------------

genome    CTGCTTAATTGTTGAGTTTTTATCCGTGGTCTTTTAGAGGGGGATATGTAGGGTAGAAGC 109440
mRNA      ------------------------------------------------------------

genome    TTTCACAGGTTCTTGTTTGCACTTGGCCCCTGACTGTTTTGAGGAATCTCCCTCACTGAC 109500
mRNA      ------------------------------------------------------------
```

FIG. 1 JJJJ

```
genome    TCACAGCATGGCAAGGTTTCAGATCTCTTTCTGCCACACAGCAGTTCTGAGGCAGCTGGA 109560
mRNA      ------------------------------------------------------------

genome    AAGATATCCAGATGCTTAGATTGTCAGGCCAGGCTTGAGATATACAAACTATTGAGCCTT 109620
mRNA      ------------------------------------------------------------

genome    ATCTGTGACCTTGCTTAGGTGAAGGCATCAGAGCCCCTGCACCAACATGCATAGGCCTCT 109680
mRNA      ------------------------------------------------------------

genome    GCATGTGTGCGGGGCTGGGTGTTGAGGTCTGAGCACAAGTGTAGCTGGAGAGGTGAGCTT 109740
mRNA      ------------------------------------------------------------

genome    GATGTGGCGACGGGTATGAGCAGGTTTTCTTCAGACTTCTGTGAGTTTACCTAGTTCCAG 109800
mRNA      ------------------------------------------------------------

genome    GATTTAAAGGCACAGAGACTTTAGAATTAAAATAGAATCATTTTCTTTTTCTAAATAGCA 109860
mRNA      ------------------------------------------------------------

genome    ACACTAGGAATAAAAAATAATAATTCCACATTCTTGACAGGTAATGTTTTTTCTTGTCTT 109920
mRNA      ------------------------------------------------------------

genome    CTAATCCTTATTTATTCCATACTCATTTTTATACATAATTGAAATGTATTATGCATTGGA 109980
mRNA      ------------------------------------------------------------

genome    TTTTTCTTTTGCATTATATTATAGACGATTTTTCATGTAACTCCTTACTGTTCCATTTTA 110040
mRNA      ------------------------------------------------------------

genome    TATGTTTTGTCTGGTTTAAGACTTTATCTGCAAACCGGGAAACTGTCTCTACAAAAAGAA 110100
mRNA      ------------------------------------------------------------

genome    AAACAAAAATAGTTGGCCGCAGTGGCATGCGTCTGTGGTCCCAGCTACTCGGGGCTGAGG 110160
mRNA      ------------------------------------------------------------

genome    TGGGAGGATTGCTTGAGCCTTGGGAGGTTGAGGCTGCAAAGAGCCATGATCATGCCATTG 110220
mRNA      ------------------------------------------------------------

genome    CACTCCAGCATGGGTGACAGACTTTATACTGTCTGTTTTGGGTGATTTGATAATGATATG 110280
mRNA      ------------------------------------------------------------

genome    CCCTGATGTAGTTTTTTTATATCTTGTGTTTCTTGTGCCTGGGTTTATTGAGGTTGGGTC 110340
mRNA      ------------------------------------------------------------

genome    TGTGGCTTCATAGTATTTTTAAAGTTTGGAAAATTTTAGGCCATTCTTTCTTTCTTTCTT 110400
mRNA      ------------------------------------------------------------

genome    TCTTTTTTTTTTTTTTTGAGACAGTGTCTCGCTCTGTCGCCTGCGTTGGAGTGCAGTGACA 110460
mRNA      ------------------------------------------------------------

genome    CTATCTTGGCTCACTGCAAGCTCTGCCTCCTGGGTTCACGCCATTCTCCTGCCTCAGCCT 110520
mRNA      ------------------------------------------------------------

genome    CCTGAGTAGCTGGGACTACAGGCGCCTGCCACCACGCCTGGCTAATTTTTTGTATTTTTA 110580
mRNA      ------------------------------------------------------------

genome    GTAGAGACGAGGTTTCACTGTGTTAGCCAGGATGGTCTCAATCTCCTGACCTCGTGATCT 110640
mRNA      ------------------------------------------------------------

genome    GCCCGCCTGGGCCTCCCAAAGTGCTGGGATTACAGGCGTGAGCCACTGCACCCAGCTAGG 110700
mRNA      ------------------------------------------------------------

genome    CCATTATTTCTTCAAAGATTTTTTTTCTGCCCTGCCTCCCTCCTTTTTTCCCTCTCTTAA 110760
mRNA      ------------------------------------------------------------
```

FIG. 1 KKKK

```
genome    AGGGGCTGTGATTTCCTGAATGATTGCTTAGTGTTGTCCCATAGCTTACTGATGCTCTTT 110820
mRNA      ------------------------------------------------------------

genome    TCAGTGTTTGATTGTTTTATGTGTTTTCTGTTTTGTATAGTTTCTATTATTGTGTTTTCA 110880
mRNA      ------------------------------------------------------------

genome    AGTTCTCTGATCTTTTCTTCTACAGTGTCTACTCTGTTGTTAATCTGTTAATCTGTTGTT 110940
mRNA      ------------------------------------------------------------

genome    AATCCTGTCCAGCGTATTTTTTTTTTTTGTTTTTGAAACAGTCTCACTCTGTTGCCCAGGC 111000
mRNA      ------------------------------------------------------------

genome    TGGAGTTTAGTGGTGCGATATCAGCTCACTGCAACCTCCACCTCCCAGGCTCAAGCAATT 111060
mRNA      ------------------------------------------------------------

genome    CTTCTGCCTCAGCCTCCCGAGTAGCTGGGACTATAGGCACGTGCCACCACACCTGGCTAA 111120
mRNA      ------------------------------------------------------------

genome    TTTGTGTATTTTTATTAGAGATGGGGTTTCACCATGTTGGCCAAACTGGCCTTGAACTCC 111180
mRNA      ------------------------------------------------------------

genome    TGACCTCAGGTGATTCATCCGCCTCGGTCTCCCAAAGTGTTGGGATTATAGGCATGAGCC 111240
mRNA      ------------------------------------------------------------

genome    ACCGTGTCTGGCCCCTGTTCAGTGTATATCACTAATTTTGTTTTTATCTCTAGAAGTTTG 111300
mRNA      ------------------------------------------------------------

genome    ATTTAGGTCTTTTAAAAATGTCTCCCTGTGTTTCTGTTTAGCTTTGTGAACACAATTGTA 111360
mRNA      ------------------------------------------------------------

genome    ATAACTGTTTTAATATCCTTCTCTGCTAGTTCTAAGATCTTCTAATAACTTCCCAGTTCT 111420
mRNA      ------------------------------------------------------------

genome    TGGTGTTTCTCATTGGTTGATTGATACTCCTCGTTTTGGGTTGTATTTTCCTGCCTCTTT 111480
mRNA      ------------------------------------------------------------

genome    GTATGGCTGCCAATTTTTTATTGGATGCCCAACCTTGTGAATTTTACTTTGTTGGATGCT 111540
mRNA      ------------------------------------------------------------

genome    ATATATTTTTGTGTTCCCATAGATCTTCTTGAGCTTTGTTCTGAGGTTAGTTGAGTTACA 111600
mRNA      ------------------------------------------------------------

genome    TATAGATGGTTTACTCTTTTGGGTCTTGCTTTATAATTTGTCAGATGGGTTGGAGCAGTG 111660
mRNA      ------------------------------------------------------------

genome    CTTAGTTTAGGACTAATTTTTTTTTTTGGACTAATTATTCCTCTTTAGGAATAATTAGGTA 111720
mRNA      ------------------------------------------------------------

genome    CCATGCTTAGGAGGCAAGACCATCCTGAGTACTCTACCTAATGAACCAGAAAGTTTGGGT 111780
mRNA      ------------------------------------------------------------

genome    TTTCCAGTCCGCCTGCTGAGAACAGTGACTTTCTAGCCCTGTGTGAGCGCTGAGCTCTGC 111840
mRNA      ------------------------------------------------------------

genome    TCCTTCTAATCCTTTCCAATGCTTCTTTCCCTGGCCTCAGGGAGTTTTCTCACACACATA 111900
mRNA      ------------------------------------------------------------

genome    TCTCTGCTGAGTACTCGAGAGGGACCTTCCCCAGATCTCCAGAGCTCTCTCTGTCTTGTT 111960
mRNA      ------------------------------------------------------------

genome    TTCTCTTCTCTGGTGCTCTGTCTTATGAACTGTGGCTGTCTTGGTCTCCTTAGATTCTCA 112020
mRNA      ------------------------------------------------------------
```

FIG. 1 LLLL

```
genome   GCACCTCTTCAATTCAGAGGGTTGCCTGTCCCTCCTCCTTGTGCCACAGCCTAGGAACTC 112080
mRNA     ------------------------------------------------------------

genome   TCTCAAAGCAGCGAGTTGGGGCAGCCATAGGGCTGACTTAGTCTCTCGTCTCCCAGGGAT 112140
mRNA     ------------------------------------------------------------

genome   CACTGTCCTTCATTGCTCATGTCCAGTGTCTTGAGGACTCTGGGTTTTGTCTGTTTTGTT 112200
mRNA     ------------------------------------------------------------

genome   TTTTGGTTTGCTTTGGTTGTCTCAGGCAGGAGGGTAAACCCAGTCCCTCACCCTCATTGT 112260
mRNA     ------------------------------------------------------------

genome   GCTCAGTAGTGGAAGTCTCACTCTATTACATTAGATATTAGTATTTGTAGCAGAGCCCTG 112320
mRNA     ------------------------------------------------------------

genome   GTTCCCTGGTACTTGGGGAGCTCTTGAAAGGCCAGAAACAGCATGCTTTCTCACCTTTTC 112380
mRNA     ------------------------------------------------------------

genome   CAGGGCTTCAGTTTCTGGTGCACATCAAGCATTCCATACACATTTGTTAAAGTCCTTTGT 112440
mRNA     ------------------------------------------------------------

genome   TAGACAAGTAGTGATTCACAGGTTCTATTTGTAATTTTTTCAGTTAACATGTATTGGGTA 112500
mRNA     ------------------------------------------------------------

genome   TCTGCTGGGAGCTAGTAAAAACAAAAAGTGGTGTGTGACAAATTCAATTCTGACAAGAAC 112560
mRNA     ------------------------------------------------------------

genome   AACCTTAAACACTTAGAATATACTTTGAGCATATCAGAATTTTAAAAATGTGTGGCCCTT 112620
mRNA     ------------------------------------------------------------

genome   GAGTATTTGAAACCAACAAGAATCTATTGCTTATTAGTAGAGGATATTTTGTTAAACAAG 112680
mRNA     ------------------------------------------------------------

genome   TGGAGAGAGAGGCATTTTCAGTCTAATTGGTGTTGGCTTTTAGCAGCTGATGGAAACCAG 112740
mRNA     ------------------------------------------------------------

genome   TTCGTGATTAGCCAGGCAGTGGTGAAACAGGCTGTGCATTCTGAATGCCTAGGTATCTAG 112800
mRNA     ------------------------------------------------------------

genome   GCATTCAGAATGGTGGCGCTCTTTGAGTTAGCATCTTCTTCTTTCTTGATTCTTTTTTTT 112860
mRNA     ------------------------------------------------------------

genome   TTTTTTTTGAGATGGACTTTCGCTCTTGTTGCCCAGGTAACAACTCCAGTGCAATGGCGC 112920
mRNA     ------------------------------------------------------------

genome   CATCTCGGCTCACTGTAACCTCTGCCTCCCTGGTTCAAGCGATTCTCCTGCCTCAGCCTC 112980
mRNA     ------------------------------------------------------------

genome   TCAAGTAGCTGGGATTACAGGTGTGCGCCACCACGCCTGGCTAATTTTGTATTTTTGGTA 113040
mRNA     ------------------------------------------------------------

genome   GAGATGGGGTTTCACTATATTGGTCAGGCTGGTCTTGAACTCCTGACCTCAAGTGATGCA 113100
mRNA     ------------------------------------------------------------

genome   CCTGCCTCGATCTCCCAAAATGCTGGGATTACAGGCGTGAGCCACCACTCCCAGCCCCTT 113160
mRNA     ------------------------------------------------------------

genome   CTTGATTCTTGAAAAGGACATTGGGTGCTGTACATCTCGTTATAGATGTTGATAAAAATG 113220
mRNA     ------------------------------------------------------------

genome   CTTGTGAGAAGAGTAACATTAAGGTAGTTATTTGGTCATTTTTGCAGATTATTTTAAGAC 113280
mRNA     ------------------------------------------------------------
```

FIG. 1 MMMM

```
genome    AATTCTAGGACTGATTTGTGGTAAATCACACATTGCTGTATCATAGTTGTGTTCACTGAA 113340
mRNA      ------------------------------------------------------------

genome    CATATTCAGGGGCTCTACAGATGCAGGGCTCTTAGCTGCTTTGCACACTTCTGAATTCCT 113400
mRNA      ------------------------------------------------------------

genome    GCCCTGCGAACAGGACTGGATACCTAATAGACAACAGGTACTTGATAACAGTTTATTGAA 113460
mRNA      ------------------------------------------------------------

genome    TTAATGAGTGAATGAACAGATACATAAATGCATGAAAGAATGGTTGTAATGTATATAACT 113520
mRNA      ------------------------------------------------------------

genome    TGGATTTCAAGACTTTTTACTGACTGTTCAAAATAAGAAATTGAAAACTTTCCTCTGATT 113580
mRNA      ------------------------------------------------------------

genome    TTCCTCTACTATTTACACAATTTAAATGGAAGTTATCTTGTACCTTCAATTTCTGTCTAG 113640
mRNA      ------------------------------------------------------------

genome    GATTCGTACAATAACGGGTCATCTCTGAGTCGCTTAATGTCTCACTTGTCTTTCTACAGT 113700
mRNA      ------------------------------------------------------------

genome    GTGTTGAAGAGATCCTAGGATACCTGAAATCCTGCTTTAGTCGAGAACCAATGATGGCAA 113760
mRNA      ------------------------------------------------------------

genome    CTGTTTGTGTTCAACAAGTAAGAGCTTCATTCTTTTCCTCTTCTGTTAAGACGTTCGGGT 113820
mRNA      ------------------------------------------------------------

genome    ATGACAGCAAAACGCTGCTACTCCTTAAGAGGCAGGCGCTGTTGGCATAATCAGCTGGGA 113880
mRNA      ------------------------------------------------------------

genome    GGATTGTGGGGTCCAGCGCAGCACTTTTTGGCTCAGTCCATGATTGAGCCAAGAGGCCAT 113940
mRNA      ------------------------------------------------------------

genome    CCTTCCCTTCACTCCCCAGGAGGACGAGGTCTGTCACTGTGGAGGGCAGAGGACACCAGA 114000
mRNA      ------------------------------------------------------------

genome    AGCTCCTCTGCAACCTCGCTAGTTAACTTCCAGTCCCTCGGAGTTTCTGTTTAGAATGCT 114060
mRNA      ------------------------------------------------------------

genome    CAATCTCATTTAGAATTGCAAGGAAACCCAAAACGCCTATTTAAGGTACAAACAGCACTT 114120
mRNA      ------------------------------------------------------------

genome    CATACAATATCTCATGAGGTATTAATAGTGATTCACAGGAAGAATTTCACGCTGTGAGTC 114180
mRNA      ------------------------------------------------------------

genome    TTTGCTAACATATCCAGTTATTTACAGATGGATTTGATATTTGTGTGGGAGATTCTTAAA 114240
mRNA      ------------------------------------------------------------

genome    AGTGTTGTTCACGCCACATTGTTGATGCCTCATTTTTTTCACTGTAGTTGTTGAAGACTC 114300
mRNA      ------------------------------------------------------------

genome    TCTTTGGCACAAACTTGGCCTCCCAGTTTGATGGCTTATCTTCCAACCCCAGCAAGTCAC 114360
mRNA      ------------------------------------------------------------

genome    AAGGCCGAGCACAGCGCCTTGGCTCCTCCAGTGTGAGGCCAGGCTTGTACCACTACTGCT 114420
mRNA      ------------------------------------------------------------

genome    TCATGGCCCCGTACACCCACTTCACCCAGGCCCTCGCTGACGCCAGCCTGAGGAACATGG 114480
mRNA      ------------------------------------------------------------

genome    TGCAGGCGGAGCAGGAGAACGACACCTCGGGGTAACAGTTGTGGCAAGAATGCTGTCGTT 114540
mRNA      ------------------------------------------------------------
```

FIG. 1 NNNN

```
genome    GGTGGAAGCACGAAAGAGCAAGCAGGAAATACTTTGTAAAAGAATAAAAACGAAAAATGT 114600
mRNA      ------------------------------------------------------------

genome    TAGCGAACATCTTCTAATAGTCTGCTGTATTCAGAGAACTCTAGGAGATATATATGGTTG 114660
mRNA      ------------------------------------------------------------

genome    ATGCAAAGATGATTTAAGGCATAGCCCGGCCTTCCAAGAAGTGTGTGGCCAGTGAGTGAG 114720
mRNA      ------------------------------------------------------------

genome    ATGGGCTTGGGACTTACACATCTCAGAGGTGGGGGTAGAGGAGGAGGAACACTGAGTGGG 114780
mRNA      ------------------------------------------------------------

genome    CTGAGAAGCAGCCAGCTCTCATTGCCAAAGTGTGTCAGCAAACCAGAATGCAGTTCATAA 114840
mRNA      ------------------------------------------------------------

genome    TGTCCCCACCCATTCAAAGCACAGGACCTGTAGAGTGGTGTGGCATGTGTTGGTGGCACT 114900
mRNA      ------------------------------------------------------------

genome    TTTCAGGCCTGTAACAAGGATGAAAGAACAGCTTCATAGCAGCACAGTAGTGCTGGTGTT 114960
mRNA      ------------------------------------------------------------

genome    CAGAGGTGTGTGAAGGCCATAGAAGCATCTTGGATATATTACCTTGTGTTTTGTCAGCTT 115020
mRNA      ------------------------------------------------------------

genome    TATGACTAGAAGTCTCTTTTCACTTAAATTTGTTTTTTTTTTTTTGAGACGGAGTCTTG 115080
mRNA      ------------------------------------------------------------

genome    CTCTGTCGCCCAGGCTGGAGTGCAGTGGTGCAATCTCAGCTCACTGCAAGCTCTGCATCC 115140
mRNA      ------------------------------------------------------------

genome    TGGGTTCATGCCATTCTCCTGCCTCAGCCTCCCGAGTAGCTGGGACTACAGGCGCCTGCC 115200
mRNA      ------------------------------------------------------------

genome    ATCACGCCTGGCTAACTTTTTTTTGTATTTTTAGTAGAGACGGGGTTTCACCATGTTAGC 115260
mRNA      ------------------------------------------------------------

genome    CAGGATGGTCTCGATCTCCTGACCTCGTGATCTGCCCGTCCCGGCCTCCCAAAGTGCTGG 115320
mRNA      ------------------------------------------------------------

genome    GATTACAGGCGTGAGCCACCGCGCCCGGCCTCTTTTCACTTAAATTTATGTTTGTGTTTT 115380
mRNA      ------------------------------------------------------------

genome    TAATGCCTAGTATACAGGACTTCTTAAATTGCCTTAAGTATGAACAGGTATTTGAGTTGC 115440
mRNA      ------------------------------------------------------------

genome    TAATCTGTATAGTAGCAATAATAGAATCCCTTGTTTTTCCTTTTATAAATTTAGCGATTA 115500
mRNA      ------------------------------------------------------------

genome    AATAGCTACAATTAAAACACTAGAGTCAGGAGTCAAGGAAAATACCCATGTTCCAGGCTG 115560
mRNA      ------------------------------------------------------------

genome    TATGTTAGTGATGTACTTACTATATATTGGAGTTTCAGGAGTAAGTCTGTTTCAATGCTT 115620
mRNA      ------------------------------------------------------------

genome    TCTGTAACCATTTGGGGTATTAATAAGCATGTGAGTGTGTGCATGTTTGGGTTAATTTCA 115680
mRNA      ------------------------------------------------------------

genome    TATATGTTTCTTAGAAGGGATATCATTGATGTAAATATTTTAAAGGCTTGTCCTCCAAAA 115740
mRNA      ------------------------------------------------------------

genome    AAATCATGTAATTTCTTCTAAATTACTGATCTTTTAAATGACCTTCACCTTTCTCTCAAA 115800
mRNA      ------------------------------------------------------------
```

FIG. 1 OOOO

```
genome    TCTCACTTAAGACTGGGCTGAGTAGTCAGTTTCCTGTAGCAGAAAAAAGCTCAGACTTGA 115860
mRNA      ------------------------------------------------------------

genome    GTAGCCTTCTGCGAGTGAGGAGACTTGATGGCTGTCAGGCAGCTGTAAACTCTAAATAGA 115920
mRNA      ------------------------------------------------------------

genome    GTGTCATTATCTGAAGAGGGCGATGCTGCCACACTGAGTGGCCTTTCAAGTTGTTTCTCA 115980
mRNA      ------------------------------------------------------------

genome    ATCTGACACGTTCTGATCGTGTGAATGTGAAATTGGTTTGAGCAGGAGTATATCTGAGTG 116040
mRNA      ------------------------------------------------------------

genome    CAGAGGAGATTATTTAAAGATATTCTCATTCTCTGCTTCCCTTTTATTCCCATTTGGCAG 116100
mRNA      ------------------------------------------------------------

genome    ATGGTTTGATGTCCTCCAGAAAGTGTCTACCCAGTTGAAGACAAACCTCACGAGTGTCAC 116160
mRNA      ------------------------------------------------------------

genome    AAAGAACCGTGCAGATAAGGTAAATGGTGCCGTTTGTGGCATGTGAACTCAGGCGTGTCA 116220
mRNA      ------------------------------------------------------------

genome    GTGCTAGAGAGGAAACTGGAGCTGAGACTTTCCAGGTATTTTGCTTGAAGCTTTTAGTTG 116280
mRNA      ------------------------------------------------------------

genome    AAGGCTTACTTATGGATTCTTTCTTTCTTTTTTTCTTTTTTATAGAATGCTATTCATAAT 116340
mRNA      ------------------------------------------------------------

genome    CACATTCGTTTGTTTGAACCTCTTGTTATAAAAGCTTTAAAACAGTACACGACTACAACA 116400
mRNA      ------------------------------------------------------------

genome    TGTGTGCAGTTACAGAAGCAGGTTTTAGATTTGCTGGCGCAGCTGGTTCAGTTACGGGTT 116460
mRNA      ------------------------------------------------------------

genome    AATTACTGTCTTCTGGATTCAGATCAGGTTTGTCACTTTTATCTTTCATCCATCATACCT 116520
mRNA      ------------------------------------------------------------

genome    GTTCCTAATTTAGTACAAATTACCCTAAAAGACACTGAAATCTACTTTAAAGAAATGTGG 116580
mRNA      ------------------------------------------------------------

genome    TCTGCATGTTTCCCTCATCAGTTGCTGCTGCTTATCTTTTTCATGCACCTAGCTGGTGCA 116640
mRNA      ------------------------------------------------------------

genome    GAAGGCCTGGGGCATAGCCAGCCTCAGCAAGTCAGCATCCTTGCCCCAGCTCCCTGGACT 116700
mRNA      ------------------------------------------------------------

genome    CAAGGCTAACCTGGGGTTGGCTGTTAGGGATTTCCAAAGGTTTGTCCCATCCACTTGCCT 116760
mRNA      ------------------------------------------------------------

genome    CCCCTCCAAAATAAGTTTGAATTTAAATTGTGAGATACAATTAAGATTTATTGTTTGGGG 116820
mRNA      ------------------------------------------------------------

genome    AACATTTTTGCAAAATCTAGAGTTAGTTTAAACAGATTATCAATTATTACCATAATTGAT 116880
mRNA      ------------------------------------------------------------

genome    CATCTGCAGTTTCAAGCTATCTAACAGGTTCACTTACCTCTTTAAAAAGGAATGGAATTT 116940
mRNA      ------------------------------------------------------------

genome    AGCAGGACAGTAACTGAGACCCGTGCTCCTGGAGTCCATGTGGGAGCTGTGTGGCTCTGC 117000
mRNA      ------------------------------------------------------------

genome    ACAAGCATTTGCACGCTTCCCCTCTTGACTGCATTACCTTCCTCCTATAGTTGCTGTGGG 117060
mRNA      ------------------------------------------------------------
```

FIG. 1 PPPP

```
genome    CACCAGATTCTGGCTAGTCCTGTCCCTTCATGATGCACATTTTCCTCAAGATTCGTCCCA 117120
mRNA      ------------------------------------------------------------

genome    GTTAAATCACTGCAGATGAAACTGCCTTTTCATCGTCAAAATTTAACTGTCATTTTTGAG 117180
mRNA      ------------------------------------------------------------

genome    CCGTGATCTTGGGCTACTTTCTTATGTGGGGTAGGAATATTTGTGAGTTAGAAATATTAC 117240
mRNA      ------------------------------------------------------------

genome    ACTTCTCTATTTCCTTCTAGACGTAAATCTGTTAATCCTGTCAGCACTGTTACTCACCTG 117300
mRNA      ------------------------------------------------------------

genome    AAAGGGTCTGTTTCCCTAGGAGAACTGAGGGCACTCGGTCAACACTGATTTTCCACAGTG 117360
mRNA      ------------------------------------------------------------

genome    GGTATTGGGGTGGTATCTGCTTGTTTTTTTTGTTGTTGTTGTTTGTTTTTTTTTGTTTTT 117420
mRNA      ------------------------------------------------------------

genome    TTTTTGAGATGGAGTCTCGCTCTGTCACCCAGGCTGGAGTGCAGGGGTGCGATCTCGGCT 117480
mRNA      ------------------------------------------------------------

genome    CACTGCCAGCTCCGCCTCAGAGGTTCACGCCATTCTCCTGCCTCAGCCTCCCGAGTAGCT 117540
mRNA      ------------------------------------------------------------

genome    GGGACTACAGGCACCCACCACTACGCCAGGCTAATTTTTTGTATTTTTAGTAGAGACGAG 117600
mRNA      ------------------------------------------------------------

genome    GTTTCACTGTGTTAGCCAGGATGGTCTCCATCTCCTGACCTCGTGATCTGCCCGCCTCGG 117660
mRNA      ------------------------------------------------------------

genome    CCTCCCAAAGTGCTGGGATGACAGGCGTGAGCCACCGCGCCCGGCCTGGGGTCTGCTTTT 117720
mRNA      ------------------------------------------------------------

genome    AATGAAGGAGGCATCAAGGGGTGGGCTTTGCGTTGGCCTGATGCTTTCATCTTTCTTTCA 117780
mRNA      ------------------------------------------------------------

genome    CAAAACCTGTCCGAAGAAAATCCGTCTAAATGGGCCATTGCTCTCCTCAGGAAATAGTCA 117840
mRNA      ------------------------------------------------------------

genome    TTGGGAACTTCTTTTCCTTTCCTTTGACACTAGGAGGCTGACTGGGGAGAAGCCCTGGTC 117900
mRNA      ------------------------------------------------------------

genome    TATGGCTGTGGGCAGCAGGGGCTGAGAGGAGCAGGCTCTCAGGGGGGCACGGGTACCCCA 117960
mRNA      ------------------------------------------------------------

genome    AGGGAAGCCAGAGCCCTGATTTGTTCCATTCTAGTAAGAACAAAGACTGCTCTGGTTTCA 118020
mRNA      ------------------------------------------------------------

genome    TGTTTGTTCTGATTGCCTTTCATCAACCGGTCCCCTTTCTCCCAGTTCTTAAGATTCAGT 118080
mRNA      ------------------------------------------------------------

genome    ACAGTGACAGTTTTATGAACAAGAATAGAACACTAGAACAGACAAACCATTGAACTCTAT 118140
mRNA      ------------------------------------------------------------

genome    GCTGATAAAGATTTATTGAGCTCCTGCTGTATGTTTGCATTCTGCCCAGAGGCTCTGAGA 118200
mRNA      ------------------------------------------------------------

genome    AAACCAGGCCATATGCTCCATGCTTTATCCATGGAAGCTCCCCGTCAGGTTGGGAAAGCT 118260
mRNA      ------------------------------------------------------------

genome    GACAGCTGCAGGGAATACAGTGTGACACAAAACTGGCTCCCATGCAGCCCTTACGTGTCG 118320
mRNA      ------------------------------------------------------------
```

FIG. 1 QQQQ

```
genome   CCTCTCAGATGGTTGGGGGACGAAGGTCGACTCCTTTGGGTATCTTATTACTAAACCAGT 118380
mRNA     ------------------------------------------------------------

genome   TTCAGGGAATCTGTGCCACCCTATCTGCCATTAACGTGAACAGATGAGTCCCCAAGGTGT 118440
mRNA     ------------------------------------------------------------

genome   AATTTTGGGTATTGTCTGATGTCTCTTGGAATTTATTATTTGTTTTTCCAATGAGATTTC 118500
mRNA     ------------------------------------------------------------

genome   ACCTCAGGGTATAGTAAAGTTGTTGAGGGGATTCCTGGATGTGTTCTGCAATTATCTAGG 118560
mRNA     ------------------------------------------------------------

genome   CTGATTTCAGAATAGAGTTATGCTTATAGTCAAATTTATCAGCTGTCAAGAATTTTATTT 118620
mRNA     ------------------------------------------------------------

genome   AAAATTTATGCAGATAAGCAGGAGGAAAAGAAGCCTGGTTTTTACATTTTAATCCTATTA 118680
mRNA     ------------------------------------------------------------

genome   TTGATGTGAAATTTTATTTTCCTTCCTGTAGGTGTTTATTGGCTTTGTATTGAAACAGTT 118740
mRNA     ------------------------------------------------------------

genome   TGAATACATTGAAGTGGGCCAGTTCAGGTAATAGCATTTTATTATTTTAGATTTTTTTCT 118800
mRNA     ------------------------------------------------------------

genome   TCTTCTTGTGTACTTACATGTAATTTAGGTTATTAAGTGAATGTTTAAACTACTGTTAGG 118860
mRNA     ------------------------------------------------------------

genome   CATTTTTGCTGTTTTCTTTAAATGGAAATCTGACTAACATACTGTGCATTTTTGCTTCTC 118920
mRNA     ------------------------------------------------------------

genome   TTAAAAATTAATGTATATCTCAAGACTTGTTTGGAAGTAGTTATGTATCTGAAAATTCCA 118980
mRNA     ------------------------------------------------------------

genome   TATGTTGTCAGTATTCATTGCACATTTCAAAGCATTTAATTGTGTTGACAGATGGTGGAA 119040
mRNA     ------------------------------------------------------------

genome   TGAAATCTTGTGGTGGAGCACTAGTTTTTAAATCTTCTTAGAGAAAGCAGTTTTATATAA 119100
mRNA     ------------------------------------------------------------

genome   TGTTGTCTTTAGTAATTATTATGCATTTGTATTCTCTGCAGCTTTTTCTTGCTAGATGTT 119160
mRNA     ------------------------------------------------------------

genome   GAGGTTTTAATACTTCTTGCTAGTCCATTACAGGTTTATAATTATTAAAAGTTAAAATTC 119220
mRNA     ------------------------------------------------------------

genome   TTTTAGTACCTAAAATGCTTAATAAACATTGTAATTAGGAAAATTTAGTGCAGAAGGAAA 119280
mRNA     ------------------------------------------------------------

genome   GTGTTCCCAGATTCCCTGGGGTCTGGAAACATAGTGTTTATTCTAATTACATGACACCTC 119340
mRNA     ------------------------------------------------------------

genome   CACTGTGTTTTGGGGCAAGTTACTGTTTCTCTTTTGAGTTTCAATTTCTTCAAGAGCAAA 119400
mRNA     ------------------------------------------------------------

genome   GAGGCAGAGGAGAGCTAGGAAGATCGTAGCTGCTGTGCCCCTGTGCCGTCGGGTGCCTTC 119460
mRNA     ------------------------------------------------------------

genome   TACCTGCTGCCTCCGAACCTTTACACATGTCCCTGCTCTGCGCGAGGGCACAGATGGGAT 119520
mRNA     ------------------------------------------------------------

genome   GCACTGTGGCAGGGGTGGGGTTAGAGTAGATCACGGACACCTGTTAGCTTGATGTGTGCT 119580
mRNA     ------------------------------------------------------------
```

FIG. 1 RRRR

```
genome    TGCTGTCAAGGTTGAATCATGAATTATTTTATGTTGCTTATATTGATATGTATCTTAATT 119640
mRNA      ------------------------------------------------------------

                                               rs363096
genome    TTAAAAGAAAGGTCTAAATGGATGTTTTTGTTTTTAGGGAATCAGAGGCAATCATTCCAA 119700
mRNA      ------------------------------------------------------------

genome    ACATCTTTTTCTTCTTGGTATTACTATCTTATGAACGCTATCATTCAAAACAGATCATTG 119760
mRNA      ------------------------------------------------------------

genome    GAATTCCTAAAATCATTCAGCTCTGTGATGGCATCATGGCCAGTGGAAGGAAGGCTGTGA 119820
mRNA      ------------------------------------------------------------

genome    CACATGGTAACGGGACACACCTTTCACTGTCGTCTTCGGTGTCGTGATGTGCTTGGCAGT 119880
mRNA      ------------------------------------------------------------

genome    GTTCGTTTTCATATACCCACTTTGAACGTTGTCAGTGGCAGCCATGTGCTTCTCAGGCTC 119940
mRNA      ------------------------------------------------------------

genome    TGCATGTGTGTCTGTGTATGTGAAGGTACTGGTTAGAGACGTTTCAAAAGAGAAGAGAGC 120000
mRNA      ------------------------------------------------------------

genome    ATATTCTTTACTCTCAGCAATTTGTAATCTTCTCAGGGAAAAAAATTCAAGAAACAGTAA 120060
mRNA      ------------------------------------------------------------

genome    GATAACCTAAGGTACAGATAGATTCTGAATATAAAGTTCCTGTTCATTCACATGAAACGC 120120
mRNA      ------------------------------------------------------------

genome    TAAAAGTTCTTCACTTGATCTTAGCCAAAAGGCCAAGAAGCGATGCAACACTAAAAATTC 120180
mRNA      ------------------------------------------------------------

genome    TTAAATCGAACTTGCCGTGAATTAAATTTTGATCTCTCATCCAGTGGTATTGGAGATATA 120240
mRNA      ------------------------------------------------------------

genome    GTTTGACTTGGGTTCAGGGCTTTCTGTTTTGCCTGATGATTTTGCTGGAGCTTAAATAAG 120300
mRNA      ------------------------------------------------------------

genome    GAACCCAGGAGATGGCCAGCTGTGCAAGCCCCCAGCCTGTGGAAGGAGCTAGTGTGGTTT 120360
mRNA      ------------------------------------------------------------

genome    TATGAATGAGTTGCAAATCTTTCTTTGAGCTTTTTGAACTGATCTTCCAGCATTGCCCTA 120420
mRNA      ------------------------------------------------------------

genome    TTGACCCCTCCCTGACTCCTTTGCTGGAATCTGTAGGCTTTTGAACTTTGACAGGGACAC 120480
mRNA      ------------------------------------------------------------

genome    ATCCTAAGACCCTTGCAAACTCCCAGATGTGAGAATGGCACTACTACTTAGAGTCTTTTC 120540
mRNA      ------------------------------------------------------------

genome    GACTCAGCGTGTGTGCAGAAGAGCATCAACCGGGCTGTGTTGCGAGGCAGGGCCTTGGCT 120600
mRNA      ------------------------------------------------------------

genome    GACCTCTCAGTGTTTACATAGCTAAGCCAGTTAGTGTTTGCCACGGCCTCACAAGGGCTT 120660
mRNA      ------------------------------------------------------------

genome    CAGATTCACACAGCCAAAGTATAGATTATTAAAGGCATAGGTGTTTGGTTTCCTGGACTT 120720
mRNA      ------------------------------------------------------------

genome    GGAGGGTCTTTGGACAGAAAATCAGTAGGCAACCACACCCAGTACTTTGTGCTGGGAAGC 120780
mRNA      ------------------------------------------------------------

genome    TTGGTCATCTGTGAGAGGGTCAGAGAGTATACCCATGCGTGCATGCCACCGAAGGGTCAG 120840
mRNA      ------------------------------------------------------------
```

FIG. 1 SSSS

```
genome          TGAGTATTCCTGTGTGTGCATGTCTCAGGGCCGGAGAGAGTATGTGTCACTGAGAGGTCA 120900
mRNA            ------------------------------------------------------------

genome          GAGTGTTTGTGTGTGTGTCAAAGAGGGTTGCATTGTGCCCTTCACTGAGGGGTCAGAGGG 120960
mRNA            ------------------------------------------------------------

genome          TGCCTCGCGTGTGTGTGTGTGTACGTGTGTGTGTGTCACTGAGGGGTCAGAGTGTGCCTG 121020
mRNA            ------------------------------------------------------------

genome          TGTGTGTGCTTGTGTGTGCGTACATGTCACTGAGGGGTCAGAGTGTGCCTCTGTGTGTGT 121080
mRNA            ------------------------------------------------------------

genome          GCTCATGTGTGTGCATACGTGTCACTGAGGGGTCAGAGTGTGCCTCTGTGTGTGCTCATT 121140
mRNA            ------------------------------------------------------------

genome          TGTGAGCGTATGTGTCACTGAGGGGGTCAGAGTGTGCCTCTGTGTGTGTGCTCATGTGTG 121200
mRNA            ------------------------------------------------------------

genome          AGCGTATGTGTCACTGAGGGGGTCAGAGTGTGCCTCTGTGTGTGTGCTCATGTGTGAGCG 121260
mRNA            ------------------------------------------------------------

genome          TATGTGTCACTGAGGGGTCAGTGTTCCTATGTGCTCATGACATTGAGGGTCAGAGTGTGC 121320
mRNA            ------------------------------------------------------------

genome          CTGTGTGCCAATGAAAGGCATTTCTTATATTTTTTATATGTGGTCATAGTAGACCAGTT 121380
mRNA            ------------------------------------------------------------

genome          AATTTATTTTGACTCCTGTGTTAGACCAAAATAAGACTTGGGGGAAAGTCCCTTATCTAT 121440
mRNA            ------------------------------------------------------------

genome          CTAATGACAGAGTGAGTTTACTTAAAAAAGCATAATAATCCAGTGGCTTTGACTAAATGT 121500
mRNA            ------------------------------------------------------------

genome          ATTATGTGGAAGTCTTTATTGTCTTTTCAGATGAATCAAGTAGATTATTCTTGAGACCAG 121560
mRNA            ------------------------------------------------------------

genome          GAATGTTGCTGTTTTGGTTATTTGGAAAGTTTTATCATTTTCAAATTGACTTTTGAATTT 121620
mRNA            ------------------------------------------------------------

genome          GAGTCACCTTTTTTCAGAAGTGGTGTTAAATTATAGGAGCCCTAGGTTTTTTTTCTTTTT 121680
mRNA            ------------------------------------------------------------

genome          TTAGAAGTCATCACAAAATGATCAGTGTTCAGAGGAAGAGCTTTGACCTTCCACATGGTA 121740
mRNA            ------------------------------------------------------------

genome          TAATGATTGATAACCTTAATTCATCTCTTACCATAAACCAAGTATGTGTAAGGGTTTTCT 121800
mRNA            ------------------------------------------------------------

genome          TTATTTCTTGAAAGCATTTTGTAGATGTTGAGAGCAGTTTTCCAAATGTAATTTCCATGA 121860
mRNA            ------------------------------------------------------------

genome          AATGCCTGATAAGGGTACCCTTTTGTCCCCACAGCCATACCGGCTCTGCAGCCCATAGTC 121920
mRNA            ------------------------------------------------------------

genome          CACGACCTCTTTGTATTAAGAGGAACAAATAAAGCTGATGCAGGAAAAGAGCTTGAAACC 121980
mRNA            ------------------------------------------------------------

genome          CAAAAAGAGGTGGTGGTGTCAATGTTACTGAGACTCATCCAGTACCATCAGGTAAGAGGA 122040
mRNA            ------------------------------------------------------------

genome          ATGTATGTTGGAACTGTCGTGGATACTTTATTGACCCGTGCAGATGGAAGGAAGTGCCAT 122100
mRNA            ------------------------------------------------------------
```

FIG. 1 TTTT

```
genome    GTGGTAACGCTCACTGTTAACTGTGTTACTTTGAACCAGGTTTGGGCTTTCTGGGGCCTG 122160
mRNA      ------------------------------------------------------------

genome    GGTAGATGCCGGTGCAGGGGGATGGGGAGGGAGGCGGGGGGTGGGGGGGTGTGGTGGAGT 122220
mRNA      ------------------------------------------------------------

genome    TGGGGAGGTGCAGTGGCAGGAGGTGTTGTTGGTGTGTATCCTTTTTTTTTTTTTGAGATG 122280
mRNA      ------------------------------------------------------------

genome    GAGTCTCTCTCCGTCGCCCAGGCTGGAGTGTGGTGGCACGATCTTGGCTCATTGCAAGCT 122340
mRNA      ------------------------------------------------------------

genome    CCACCTCCCGGGTTTAAGCAATTCTCCTGCCTCCACCTCCCGAGTAGCTGGGATTACAGG 122400
mRNA      ------------------------------------------------------------

genome    CATGCACCACCATGCCCAGCAAATTTTTTTTTTTGTATTTTTAGTAGAGATGGGGTTTCA 122460
mRNA      ------------------------------------------------------------

genome    CCATGATGGCCAAGCTGTTTCGAACTCCTGACCTCAAGTGATCCTCCTGCCTTGGCCTCC 122520
mRNA      ------------------------------------------------------------

genome    CAAAGTGCTAGGATTACAGGCGTGAGCCACCATGCCCAGCCTGGTGTTTATCTTTAAAGT 122580
mRNA      ------------------------------------------------------------

genome    GGGCACAGCCACAGGAGTTCACCTGACTCCTGGTCTGAGAGTCACGAGATCGTTCAAGAT 122640
mRNA      ------------------------------------------------------------

genome    AGTGAGGCCCTCTTTTCCAAAACGAGGACCAAAAATCAATTGACAGTGTTGGTCAAGATG 122700
mRNA      ------------------------------------------------------------

genome    GTAGAAACCTTAAAATGATAGAAATCTCAACTCTGAAATAAAAACTTTATTTGTATATTT 122760
mRNA      ------------------------------------------------------------

genome    ATTTACCACTATTTTGACATAGGGCTAAGGTCTTTTTCTTTGAGCTGATTTCTGGTTTTG 122820
mRNA      ------------------------------------------------------------

genome    TTTTCTTAAAGTGGCATAAGAATTCAAAGACATTTTGAGGAAGGCTGAGTGCAGAAATCT 122880
mRNA      ------------------------------------------------------------

genome    CTCTTTTTAAATGACTTCTCCTTTCTTTTAACTTGCACTGTTGTCTAGCCCTCACTTATT 122940
mRNA      ------------------------------------------------------------

genome    TTGTCAATTCTTTTTAGCTGTTTGTCTTTGAATCTTCATAAAGCCATAGCTTTTCTCATA 123000
mRNA      ------------------------------------------------------------

genome    AGAAGCAGCACTTTCTTTGTTCATTCATATTTTAATGAACCCCTGTAGTATTTAATTAAA 123060
mRNA      ------------------------------------------------------------

genome    TACTTAATGCCTAATTAAATCACATAATTGCAATGCAAAAGTACATGTATCATAAAGAGG 123120
mRNA      ------------------------------------------------------------

genome    TCTGAAAATGAGCAACTGGCAAGCAGGTGGTGGCAGGCAGAGCTGCTTGGGTGGGTGGGT 123180
mRNA      ------------------------------------------------------------

genome    GTCATGGAGAGGAGTTCATCAGCCACATGTTCAGTGAGCTCTGGATATGTCTGTTTAGAA 123240
mRNA      ------------------------------------------------------------

genome    ATGATCACTAATAAACTTGTGCTCAACCATGTATACCTCTGGGAAGCAGGTGCTCTTCAG 123300
mRNA      ------------------------------------------------------------

genome    TAGATTGCCTCTGCAGAGAACACAGAATTGAAGTGAATGTCCACAAAGGCAATGAGCCAC 123360
mRNA      ------------------------------------------------------------
```

FIG. 1 UUUU

```
genome    CTGCAGAATAGTTTAGTCAAGGCTGTGTTTGAAGTTTGCCAAAGATTAATATACATTTGA 123420
mRNA      ------------------------------------------------------------

genome    TTTTCATGTTGTGCCTTTTCTCTGATTGTGAAATATTACAAATTCTATACAAATAACAAT 123480
mRNA      ------------------------------------------------------------

genome    GATGGCAAATCCTCCTGAGCAAAGTGTGCACCTTGTATGTGCCCTAGAGGAACTTGTGTT 123540
mRNA      ------------------------------------------------------------

genome    TCGTTCTGATTCCCCTACATTTCTCATGTCATAGAGTGGGGGTTGCATTAGTGTCCCCCT 123600
mRNA      ------------------------------------------------------------

genome    GTCCTCGCTGGGATCACATCTGTTTGGATCCTAGAGTCTTCCAGCTGAACTGGGACAAGT 123660
mRNA      ------------------------------------------------------------

genome    ATAACAGACGGACACGTAGGGGTGGAAAGGCGTCTCTTGGCAGCAGACTTTCTAATTGTG 123720
mRNA      ------------------------------------------------------------

genome    CACGCTCTTATAGGTGTTGGAGATGTTCATTCTTGTCCTGCAGCAGTGCCACAAGGAGAA 123780
mRNA      ------------------------------------------------------------

genome    TGAAGACAAGTGGAAGCGACTGTCTCGACAGATAGCTGACATCATCCTCCCAATGTTAGC 123840
mRNA      ------------------------------------------------------------

genome    CAAACAGCAGGTTTGTCCCCGCAGCCTTGGCTTGTTGTTGCATAGTGATGGTAGCTTAAG 123900
mRNA      ------------------------------------------------------------

genome    GTCCTTGTGAAAGGTGGGTGGCTGGAATCAGCTCTTCCTTCAGTCCTAATCTGTGCCTTG 123960
mRNA      ------------------------------------------------------------

genome    ATAGCAGTTCTCCGTGCTAGTCATGGGACAGCTGACTTCATTTCTTCTCACAATGCCATC 124020
mRNA      ------------------------------------------------------------

genome    TCAGGTTGGTATTGCCCACCTACTTTACAGGGGGGGATCCCACAGCTCCGAGAGGTTATGG 124080
mRNA      ------------------------------------------------------------

genome    AGGTGATCAGGCAGCACACAGCTTTAGAGTGCTGGGGTGAGGGCGGGCCAAGGCTAACTC 124140
mRNA      ------------------------------------------------------------

genome    TAAAGCCCGAACCCTTACCTCCTACACTGCCTCCTGCATTCTGGTCAACCCAGTGTTTTA 124200
mRNA      ------------------------------------------------------------

genome    TTTGGTGGTTAGATTTTTGTTTTTGTTACCTTACTGCTTGTAATTTAGCAGTTTTCCTTT 124260
mRNA      ------------------------------------------------------------

genome    CCTTTCCCTTCCTTTCCTTTCCGACAGGGTCTCACTCTGTCACCCAGGCTAGAGTGCAGT 124320
mRNA      ------------------------------------------------------------

genome    CGTGTAATCTCACTGCAACAACCTCTGCCTCCCAGGTTCAACCAATTCTCCCACCTCAGC 124380
mRNA      ------------------------------------------------------------

genome    CTCCTGAGTAGCAAGGACCACAGGTGTGCACCACTACGCCTGGCTAGTTTTTTGTATTTT 124440
mRNA      ------------------------------------------------------------

genome    TAGTAGAGATGAGGTCTCGCTGTGTTGCCCAGGCTGGTTTTAAACTCCTGGGCGCAAGTG 124500
mRNA      ------------------------------------------------------------

genome    ATCCACCAACCTTGGCCTGCCAAAGTGCTGGCATTACAGGTGTGAGCCACCTCGCCTGGC 124560
mRNA      ------------------------------------------------------------

genome    CTATTCATCACTAATCAGAATTTCTATGATCAAATGACATGAATCATTGTTTCCACAACT 124620
mRNA      ------------------------------------------------------------
```

FIG. 1 VVVV

```
genome    GCAGTGGAAGGAAATGGCCTGGCAGTGCCAGTTTCAGAAGCAGCCTGCCCCCAGTCAGGC 124680
mRNA      ------------------------------------------------------------

genome    ACAGGCCACTGTGCCCCCAGTGTAGCAGCACCTCTGTAGCTCACAGAGAAGGGTGGTGGG 124740
mRNA      ------------------------------------------------------------

genome    GACCTCCTTGAGGCAGCTCTGCCAGAAAATCTCATGAGCTGCCTGGCACAGCTTGAGGTT 124800
mRNA      ------------------------------------------------------------

genome    GCCTTTTAAGTGGACTCAGCAAATACATGTTTGTTCATCTTGATTATACACAATAAACAA 124860
mRNA      ------------------------------------------------------------

genome    CTACTCTGTATAGTACGAGTAGTCCGTGGTTTTTGGCATTTGATTTAAACTTAGAGGCAT 124920
mRNA      ------------------------------------------------------------

genome    GTGATATTGATGTTACTGCCTTCATGACTGCACCCCCATTCTGATTTCATAATGGAATGT 124980
mRNA      ------------------------------------------------------------

genome    TATCTTGAGACCAGTTAGACAACAGGACAGGGATCTTGGCTTCTGGTGAGATTGACAGCA 125040
mRNA      ------------------------------------------------------------

genome    GTTTTAGTGTGGTCAGGGTCTCCCTGCCTACAGATGGTTTTAGAATGGTGCCCTGGAAGC 125100
mRNA      ------------------------------------------------------------

genome    TTTATCCCATTCTTTTCTGTGCGTAATCTGAGTAGAGTGGAGATCGAAGGCCTGAATACA 125160
mRNA      ------------------------------------------------------------

genome    TAGTAAATACCTGACTTAATATCTGCCGCAATGGAAATTGTGTGATACAACATTTATGAA 125220
mRNA      ------------------------------------------------------------

genome    ACGCTTAGTGCAGCACCTGCCAGGTAGCTCACCACAGGTGCATGTTGCATTCAGAAGTAG 125280
mRNA      ------------------------------------------------------------

genome    TGCTAGATACTATCCTGTTACTGGCAGTGCATACATCAGTGATCAAAGCAGATTAAAGAA 125340
mRNA      ------------------------------------------------------------
                                                                rs2298967
genome    AGACCCCCTGCCTTCTTGGAGTGAAGATTTTGTTGGGATGCGGGTAAGGGGACAGACAAT 125400
mRNA      ------------------------------------------------------------

genome    AGAAAAGCAAGTGAGTGAAGTCTATACCATGGCGGCTGATCAGGAACACCGTACAGAAGA 125460
mRNA      ------------------------------------------------------------

genome    ATCCAGGAGGGAAGAGAGTTAGGTGGTGTCTGCGGTGGGAGTGGCATTGTTCAGCTGGTG 125520
mRNA      ------------------------------------------------------------

genome    ATGAGAAGAAGCTTTGGTGATCTGGTGACATTTGAGTGAATTTGCAGAAAGGAAAGATAC 125580
mRNA      ------------------------------------------------------------

genome    AAGCCTAGGAGATACCTGGGGAAGGAACATTCCAGGCAGAGCAAATAGCAGTGCAAAGGC 125640
mRNA      ------------------------------------------------------------

genome    CCTGGCGGGGGGCGGACATGCTGTTAGGGTACAAGCAATGAGGGTGGAGGAGTGGGGCAG 125700
mRNA      ------------------------------------------------------------

genome    CCATGGGGAGGGAAGGGAGTGAGGCCTGGTGGGGTGAGGCCAGTGTGGAGGAGCCTTGAG 125760
mRNA      ------------------------------------------------------------

genome    AGGGTTTGCGCTGATGTGGTGTAGGTTTTAGCAGGATCATTCTTATTCCTGAGTTGAGAA 125820
mRNA      ------------------------------------------------------------

genome    TAGCCTTGAGGGGGAGGTGAGGGCAGAGCAGGGCCACCCATGTGAGACCCGGCACTGGAG 125880
mRNA      ------------------------------------------------------------
```

FIG. 1 WWWW

```
                         rs2298969
genome   TGGAATGGCCCAAGTCAGCATCCCTTGGCAGCATGAAAGCAAAACCAGCAAGGTTTGCTG 125940
mRNA     ------------------------------------------------------------

genome   GTGGCTTAGATGTGGCATGTGAGAGAGAGCAGGGCTTTGGGGGTGATTTCAGGGTGAGGA 126000
mRNA     ------------------------------------------------------------

genome   CAGGGTGGCTGTGGACAAGGTAGGGCAGACATTGGGGGCAGCAGGAGGTCAGAGCCTGTC 126060
mRNA     ------------------------------------------------------------

genome   TGGATGTAGCAGTTGAGACCCCATAGGTGCCTAATGAGGTGAGGCCAGCATCAGGTGTAT 126120
mRNA     ------------------------------------------------------------

genome   GAGCCTGGAGTTGTCGAGAGACTGTGGGGCAGGGGGTCAGCATCTGAGATGTCCACTCAC 126180
mRNA     ------------------------------------------------------------

genome   AGTGGACCCAGACTGGCTGGAGAGGAGGAGGAGCTTGAATACCGAGCCTGCTGAGTCCCA 126240
mRNA     ------------------------------------------------------------

genome   GCTCCAAGGTCAGGTAGGTGAGGGGAGCCAGTGCTGGGGCAGGGGGAGTAGGCAGGTGTG 126300
mRNA     ------------------------------------------------------------

genome   GGGTTCCTAAAGCCAAGATTTTTTTAAGGCATTTTGTGCAGGAGGGCGACATCTGCTGT 126360
mRNA     ------------------------------------------------------------

genome   CAGCACCTTGGGAACTTGGCCCAGGTTTGGCAGCACCGAGGGCACTGATGAGTGCTTTTG 126420
mRNA     ------------------------------------------------------------

genome   GAGGAGCAAAGGGAGCCAAACCCTAATGGGAATGTGTTCCTGAAAGGACAGGAGAGAGAC 126480
mRNA     ------------------------------------------------------------

genome   TTGGGAAAAGGTTTTACTTGAAGAGGGAACGGAGAAATAGGGCAGTAGCCAGAGGAGGAG 126540
mRNA     ------------------------------------------------------------

genome   AGGAGTCGGCAATGGGTTAAGTTGGCAGAAATGAAGGCCTGTTTACGCACTGAGGGCAGA 126600
mRNA     ------------------------------------------------------------

genome   AGCAACAGGGAGGATCAGTTCATGACACAGGAGACACAAATCGCCGTTGTGGTGTTCACA 126660
mRNA     ------------------------------------------------------------

genome   GACATGGGTTAGGATTGGCTGCATGGATGACAGAGCACTGTGGGTTCTCCCAGAGTTGCT 126720
mRNA     ------------------------------------------------------------

genome   GGGGAGGAGGCAGAGTTGGTGAGCACAGGCGAGGGTCCAGGATGCAGGAATCCTGGAGCT 126780
mRNA     ------------------------------------------------------------

genome   CAAGTCAGTTGTTCCCTTGTTGTAAGATGTGGCCAGTGTTGTGAGCTTCACATCTGTGCC 126840
mRNA     ------------------------------------------------------------

genome   TTGAAAAACACCACATCTGTTTGCAGAGTTGTTTACTATGTATACACACTCAGTAGAAAC 126900
mRNA     ------------------------------------------------------------

genome   AAAAATTGGAAACAGTCAGTGCCCACCATCAATAAGTAATGGTTGAACACACTGTGGTAT 126960
mRNA     ------------------------------------------------------------

genome   AAGCTTAGACTATTTTAGCTTGGGCTATTTTGCATGATTAAAAATGTTCTGGCCAGGTGT 127020
mRNA     ------------------------------------------------------------

genome   GGTGGCTCATGCCTGTAATCCCAGCACTTTGGGAGGCCAAGGCAGGCAGATTGCTTGAGC 127080
mRNA     ------------------------------------------------------------

genome   TCAGGAGTTTGAGACCAGCCTGGGCAACATGGTGAAACCCTGTCTCTACTAGAAATACAA 127140
mRNA     ------------------------------------------------------------
```

FIG. 1 XXXX

```
genome    AAAGTAGCTGGGTGTGGTGGTGTGCGCCTGTAGTCCTGGCTAACTCAGGAGGCTGAGGTG 127200
mRNA      ------------------------------------------------------------

genome    GGAGGATCACTTGAGCCCATTCGTGCGCCACTGCACTCCTGGGGCACAGAGTGAGACTCT 127260
mRNA      ------------------------------------------------------------

genome    GTTAGAAAGAGAGAGAGAGAGAAAGAAGAGAGAGGGAGGGAGGAAGGAAGGAAGGAAATAAA 127320
mRNA      ------------------------------------------------------------

genome    TGGAAGAAATGGAAGGGAGGAAGGGGAGGGAGGAAGGAAGAAAGGAAGTTCAGCCAGTTG 127380
mRNA      ------------------------------------------------------------

genome    CCTTGGGAGTTCTCCATTGCACTGGGTTAAGTGAGAAGAGCAGAGACGTTTATGATTTTT 127440
mRNA      ------------------------------------------------------------

genome    CAAAACAACTAAAACAAAACCTCTGTGGGTGAGGGGGCAAGGATATGGCTATAGGAACAT 127500
mRNA      ------------------------------------------------------------

genome    GGGGCAGATTAAGAAAGGGATATACACACACCACTTAGCATTTGTTACAACTGTTGTGGG 127560
mRNA      ------------------------------------------------------------

genome    AGGGATGGAGTGCAGAAAAAGAAAAAAAAAAGTGCACACCATCCCATGTATGTGTATACA 127620
mRNA      ------------------------------------------------------------

genome    AAGGGACGCTTGGAAGACTGGTCCCCAAAATGTTGGTAATGATTGTGTCAGGGTGCTGCA 127680
mRNA      ------------------------------------------------------------

genome    GTGCTAGTTGATTTTTTTTCACACTTTTGTATATTTGAGTCTTTTACAGAAAGCATTTAT 127740
mRNA      ------------------------------------------------------------

genome    TATTTATGTAATAAAAATCTAAATGACAAGATTTCTGTTATGGGAAAAATGTAGCTATAC 127800
mRNA      ------------------------------------------------------------

genome    AGTGTTGTTGTAAAAATGTTTGCTTGGTTCACCACTGAACTTAAAATGCTTTTAAATGAG 127860
mRNA      ------------------------------------------------------------

genome    GGAAGGTGACGATGAGATGATTATGATGATTTGCCCTTGAGTTACATAGCTGGTGTACAG 127920
mRNA      ------------------------------------------------------------

genome    GAAGCTGTCGTTTCTTTTGGCTTACGTAGAAATGTTTGTGGTGTCTAATTCCACAGATGC 127980
mRNA      ------------------------------------------------------------

genome    ACATTGACTCTCATGAAGCCCCTTGGAGTGTTAAATACATTATTTGAGATTTTGGCCCCTT 128040
mRNA      ------------------------------------------------------------

genome    CCTCCCTCCGTCCGGTAGACATGCTTTTACGGAGTATGTTCGTCACTCCAAACACAATGG 128100
mRNA      ------------------------------------------------------------

genome    TGAGTCTCTCGCCTGGCTCAGCAGATGAATCTGGACGGCTTGTTCAGGCTCTGATTACTG 128160
mRNA      ------------------------------------------------------------

genome    GGACCACCCCCAGAATGTCTGAGTCAGTCAGTTTGGGTAGGGCTTCTTGAGAGTTTGCTT 128220
mRNA      ------------------------------------------------------------

genome    TTTTTTTTTTTTTTTTTTTTGGTGTGGGGGTGGTGCGGAACAGAGTCTCACTCTGTCGCC 128280
mRNA      ------------------------------------------------------------

genome    CAGGCTGGAGTACAGTGTCATGATCTCGGCTCACTGCAAGCTCTGCCTTCCAGCTTCACA 128340
mRNA      ------------------------------------------------------------

genome    CCATTCTCCTGCCTCAGCCTCCCGAGTTGCTGGGACTACAAGCGCCCACCACCACGCCCG 128400
mRNA      ------------------------------------------------------------
```

FIG. 1 YYYY

```
genome GCTAATTTTTTTGTATTTTTAGTAGAGATGGGGTTTCACCGTGTTAGCCAGGATGGTCTT 128460
mRNA   ------------------------------------------------------------

genome GATCTCCTGACCTCGTGACCCGCCCATCTCAGCCTCCCAAAGTGCTGGGATTACAGGCGT 128520
mRNA   ------------------------------------------------------------

genome GAGCCACCGCACCCGGCCTTTTTATTTTTTTTGGAGATGGAGCCTTGCTCTGTCACCCAG 128580
mRNA   ------------------------------------------------------------

genome GCTGGAGTACAGTGGCGCTACCTCGACTCACTGCAACCTCCGCCTCCCGGGTTCAAGCAA 128640
mRNA   ------------------------------------------------------------

genome TTTTCCTGCCTCAGCCTCCCGAGTAGCTGGGACTACAGGTGCGTGCCACTGTGCCCGGCT 128700
mRNA   ------------------------------------------------------------

genome AATTTTTTGTATTTTTAGTAGAGACGGGGTTTCACTGTGTTAGCCAGGATGGTCGCGATC 128760
mRNA   ------------------------------------------------------------

genome TCCTGACCTTGTGATCCGCCCGCCTCGGCCTCCCAAAGTGTTGGGATTACAGGTGGCTCT 128820
mRNA   ------------------------------------------------------------

genome CGCACCAAGCCAAGAGTTTGCATTTTTAGCAAATTCCCAGGTGAAACTAATGCCTGCTTT 128880
mRNA   ------------------------------------------------------------

genome TCTGGGAGCACACTTTGGGACTCAGTGATAGAGAGGTTTATTGGTAGGATAGTAAAATAG 128940
mRNA   ------------------------------------------------------------

genome GAGTTATTTTCTTTCACAAAATTGGCAATTGGGGGAAATTTAATCTTCCTTTTTTCTTCA 129000
mRNA   ------------------------------------------------------------

genome GCTGTGACTTATGTATTATGTTTATTTTAGGCGTCCGTGAGCACTGTTCAACTGTGGATA 129060
mRNA   ------------------------------------------------------------

genome TCGGGAATTCTGGCCATTTTGAGGGTTCTGATTTCCCAGTCAACTGAAGATATTGTTCTT 129120
mRNA   ------------------------------------------------------------

genome TCTCGTATTCAGGAGCTCTCCTTCTCTCCGTATTTAATCTCCTGTACAGTAATTAATAGG 129180
mRNA   ------------------------------------------------------------

genome TTAAGAGATGGGGACAGTACTTCAACGCTAGAAGAACACAGTGAAGGGAAACAAATAAAG 129240
mRNA   ------------------------------------------------------------

genome AATTTGCCAGAAGAAACATTTTCAAGGTATGCTTTCTATCTGAGCCTATAACTAACCCAT 129300
mRNA   ------------------------------------------------------------

genome GCCTTTTGGGAAGTCACGTGATGTTTCACAGTCAGTAAGTCTGGAATAATACCTGGTCTT 129360
mRNA   ------------------------------------------------------------

genome GCTTCACTTCTGAGTTGGGTAAAGAAGTCTGTATCAGTGTAATTTTCTAATCCGTCCTGC 129420
mRNA   ------------------------------------------------------------

genome ATTATCTATGGCTCTTGGTTCATACCTGTCTTGAAGTTCTGTCATGTTCTGTCTCTTGTC 129480
mRNA   ------------------------------------------------------------

genome CTCAGTAGAGATGCTACAGCAGTGGCTCGCCTCAGGCAGGGCAGGGCAGTGGGGTGGCTG 129540
mRNA   ------------------------------------------------------------

genome TCCTGGGGGCAGGCAGTAGGGGCACGCTGACGTCAGGGAAGTTGAAACCCAAGAGAAGCC 129600
mRNA   ------------------------------------------------------------

genome AGTAAAAGTGAGTCTCAGATTGTCACCATGTGCTGGCAGTTTTACACGCTGTCAGTAATA 129660
mRNA   ------------------------------------------------------------
```

FIG. 1 ZZZZ

```
genome          AAAGTCTTCTCCCTGCAGGGCAGCCTGCCTCCAATAAATACGTGTAGTATCAAATCCTGT 129720
mRNA            ------------------------------------------------------------

genome          CTTCCCTCATAAATTGTTTGGAAGCTCCCCAAGGACAGTGATGAGGCACTCGTAAGTGCT 129780
mRNA            ------------------------------------------------------------

genome          TGCTGCCTAGATGGGTCCCTCTCCACCTTTGCTAGATTCTGAGCATTCACTGAGTTAGAG 129840
mRNA            ------------------------------------------------------------

genome          CTGCTTCTGCAAATGTGCTGCTTCTGCTAAGTGGCTGTGACTTCATGCAGCCTTCACTTG 129900
mRNA            ------------------------------------------------------------

genome          GTTTGTCATCAGTGGAGATGCCCTGTGTTGTCGAAGGAGATAAGCCCAGTAAGCCTGCTG 129960
mRNA            ------------------------------------------------------------

genome          GGCACCTTTTGGTTTGCAGGTTCAGCAGGCAGCCCATGGCTTTCCCTGTGTCGCATTGAA 130020
mRNA            ------------------------------------------------------------

genome          GCAGCTGGCTAAAATTGATGATACATTAAATTCCTGTGACAGATGATCAGCTTGTATTTG 130080
mRNA            ------------------------------------------------------------
                                                                   rs6844859
genome          TGTAATGGTGTACAGTTCACAAAGCTTAAAAAAATGCTACCTGCCATTTCATCCTCAGTG 130140
mRNA            ------------------------------------------------------------

genome          AGGAAGGTGATACACAGAGAGACCAAGTGACTGTGTCCACGGCGACGGCGCTCTGCATTT 130200
mRNA            ------------------------------------------------------------

genome          CACTTTAGCGGTTAATGTACTCTACCTATATTTTTACTTTATATTTACCATATATCTTTT 130260
mRNA            ------------------------------------------------------------

genome          CATGTATACTTGGCGTAAGTGCTTTATAGTAGTCACCTAATTCACTGTCATCTTTTTTGT 130320
mRNA            ------------------------------------------------------------

genome          TTCTTGGAAGGTTTCTATTACAACTGGTTGGTATTCTTTTAGAAGACATTGTTACAAAAC 130380
mRNA            ------------------------------------------------------------

genome          AGCTGAAGGTGGAAATGAGTGAGCAGCAACATACTTTCTATTGCCAGGAACTAGGCACAC 130440
mRNA            ------------------------------------------------------------

genome          TGCTAATGTGTCTGATCCACATCTTCAAGTCTGGTAGGTGAATCACATTAGTCTTCCTGG 130500
mRNA            ------------------------------------------------------------

genome          AGTGTCTCGTTCCCCATTCTGCACTATACACTCTCAGAGTGTAGGAGCTGTGCTGCCCGG 130560
mRNA            ------------------------------------------------------------

genome          TAGAAACTCTGCCTTGCCCAGTGTGCCAGTTGAAAATATTTGTTGCTGTAAGAGTACACC 130620
mRNA            ------------------------------------------------------------

genome          TGATACCATGTGACCCAGCAGTTCCACTCTTGGGTATATACCCAAAAGAATGGAAAGCAG 130680
mRNA            ------------------------------------------------------------

genome          GGTGGTGAAAAGATATTTGCATGCCAGCATTCATAGCAGCATTATTCACGATAGCTAAAA 130740
mRNA            ------------------------------------------------------------

genome          TGTGGAACCAACTGAAGTGTCCCTCGATGGATGAATGGATAAGCAAAATCTGGTGTATAT 130800
mRNA            ------------------------------------------------------------

genome          TTACAGTGGAATATTATTCAGCCTTAAAAAAAGGACATTCTGACACATGCTACAACATGG 130860
mRNA            ------------------------------------------------------------

genome          GTGACCCTTAAGGACATTATGCTAAATGAAATAAGCCAGTCACAAAAGGACAAATACTAT 130920
mRNA            ------------------------------------------------------------
```

FIG. 1 AAAAA

```
genome   GTGATTCCACTTACATGAGGGACCTGGAGTAGTTAATTCATAGATATAGAAAGTAGAATG 130980
mRNA     ------------------------------------------------------------

genome   GTGGTTGCCAGGGGCTGCAGGGGAGGGGAGTTATTTTTACAAGATGAAGAGAGTTATTCT 131040
mRNA     ------------------------------------------------------------

genome   AGAAATGAATGGTGGTGATGGTTGTATAACATTATGAATGTACTTAATGCTACTGAACTG 131100
mRNA     ------------------------------------------------------------

genome   TACAGTTAAAAATAGTTAAGAGGACCAGGTGTCATGGCTCATGCCTGAAATCCAAGCACT 131160
mRNA     ------------------------------------------------------------

genome   TTGAGAGGCCAAGGCAGGAGGATTGCTTGAGCCAAGGAGTTTGAGACCAGCCTCAGCAAC 131220
mRNA     ------------------------------------------------------------

genome   ATGGTAGGACCCCATCTGTACAAACAAACTAGCCGGGGATAGTGGTGTGCATGTGGTCCC 131280
mRNA     ------------------------------------------------------------

genome   AGCTACTCAGGAGACTGAGGCTGGAGGATCGCTTGAGCCCAGGAGGTTAAGTCTCTAGTG 131340
mRNA     ------------------------------------------------------------

genome   AGATGTGTTCATGCCACTGCACTCCAGCCTCGGCTATAGAGTAAGACCCTGCCTCAAAAA 131400
mRNA     ------------------------------------------------------------

genome   AACAAAACAAAACAAGACAAGAGCCAAAAATGGTTAAGATGGGCCAATCACAGTGGCTTA 131460
mRNA     ------------------------------------------------------------

genome   TGCCTGTAATCCCAACACTTTGGGAGGTCAAGGTAAAAGGATCACTTGAAGCCAGGAGCT 131520
mRNA     ------------------------------------------------------------

genome   TGGGACCAGCCTGAGCAACATATCGAGACCCCTATCTCTACAAAGAAAATCAAAAACTAG 131580
mRNA     ------------------------------------------------------------

genome   CTAGATATGGTGGGCACATGCCTGTAGTCCCAGCTACTTGGGAGGCTGAGGTGGGAGGAT 131640
mRNA     ------------------------------------------------------------

genome   CTCTTGAGCTCAGGAGTTCGAGGCTGCAGGGAGCTATTATTGCACTCCAGCCTGGGCTAC 131700
mRNA     ------------------------------------------------------------

genome   AGAATGATACCCTGCCTCTTATTAAAAAAAAATCCAAAAAAAAAAAAAAGTAAACCTGAG 131760
mRNA     ------------------------------------------------------------

genome   AGCTTCCTCCTCCTGTGTTAAATTTGGAGGCCAAGATGTTTTTGTTACTTTTACAAATGA 131820
mRNA     ------------------------------------------------------------

genome   TCAAGGACGGTGAAGGTTGGGCATGGTAGCTCACACCTGAAATCCCAGCACTTTGGGAGG 131880
mRNA     ------------------------------------------------------------

genome   CTGAGGCGGGGTGATCGCTTGAGCTTGAGACCAGCCTGGACAACATAGCAAGAGACCCCA 131940
mRNA     ------------------------------------------------------------

genome   TCTCCACAAAAATAAAAAAATAAAAAAAAATAGCCAGGAGTAGTGGCATGAGCCTGAGCC 132000
mRNA     ------------------------------------------------------------

genome   CAGGAGGTCAAGCTGTAGTGAGCCATGATCATGCCACTGCACTCCAGCCTGGGCGAGATC 132060
mRNA     ------------------------------------------------------------

genome   GAGACCATGTCTCTAGAGAAAGAAAATGACAAGGACAGTGAACCCAAGAAAGTCATAAGA 132120
mRNA     ------------------------------------------------------------

genome   TGCCAGCTGTGCAGCAAGCATGGAAAGCAGCCAGTCCAAATTAGGACAGTGTGTTTTCCA 132180
mRNA     ------------------------------------------------------------
```

FIG. 1 BBBBB

```
genome   AGAAGAACGATCGTTTGTAATGAGAATGCTTTGCTTTAAATAAATGACTAAATAGCTAGA 132240
mRNA     ------------------------------------------------------------

genome   AGCCTAGTTCTAGGGGATAGGCACGTCTTTCTTCTCTCAAGAAAATAGAAAGGCAATTCT 132300
mRNA     ------------------------------------------------------------

genome   AATTTCTAGTAACAGCAAACAGCATTAAGTCATGGTCCAAATATGAGGCAAACCAAAATG 132360
mRNA     ------------------------------------------------------------

genome   TGGCTTGATTGTTCAGCAGTTGATCTGTTGGAAGCCCTTGATATTAAAAAGGTTCTCCTT 132420
mRNA     ------------------------------------------------------------

genome   TAAGCGGCTTAGGAGTCACGATCAAAGACCTATAGAAAGAGATGCCATCCTTCTAGGATC 132480
mRNA     ------------------------------------------------------------

genome   CTTGGCTCTCTTGGGAACTAGATTCAGATAGTCATAATGTAAATACTGCTTGAGCTTTCT 132540
mRNA     ------------------------------------------------------------

genome   TTCTTTCTTTCTTTCTTTCTTTTTTTTTTTGAGACAGAGTTTCACTCTTGTTGCCCATCC 132600
mRNA     ------------------------------------------------------------

genome   TGGAGTGCAATGGTGCCATCTCGGCTCACCGCAACCTCTGCCTCCCAGGTTCAAGCAATT 132660
mRNA     ------------------------------------------------------------

genome   CTCCTGCCTCAGCCTCCCGAGTAGCTGGGATTACGGGCATGCACCACCACGCCTGGCTAA 132720
mRNA     ------------------------------------------------------------

genome   TTTTTGTATTTTTAGTAGAGACAGGGTTTCTCCATGTTGAGGCTGGTCTCGAACTCCTG 132780
mRNA     ------------------------------------------------------------

genome   ACCTCAGGTGATCCACCCGCCTCGGCCTCCCAAAGTGCTGGGATTACAGGTGTGAGCCAC 132840
mRNA     ------------------------------------------------------------

genome   CGCACCCGGCCCGAGCTTTCATTTTTGAAATCAATGTATGACTGAAACACTGAAGACTTA 132900
mRNA     ------------------------------------------------------------

genome   CTGACTTAATTATGGTTTCAGAACAGAATGAAAATGTCTTCGGTTCTGATGAATATAAAA 132960
mRNA     ------------------------------------------------------------

genome   GGAAAACTAACCAAGTTAATTTGGCAAGTAGATGGTAGAGATAGAGGTGGGGAGTGGAAG 133020
mRNA     ------------------------------------------------------------

genome   GGGAACTAAAATCTTCACCTAGCATTGTTGGGATTATATGGTTACATCATCTGAAGTTGA 133080
mRNA     ------------------------------------------------------------

genome   CAGACCAAAATATAGAGGCTTCAGAGGTCTCCAAATAGAACTAAACATGTAATTCAGATT 133140
mRNA     ------------------------------------------------------------

genome   GTTAGGAGGTAGTATAAATGAGCTAAATCTCATCTTTATTACGGTAGAGTTAATGGGTGA 133200
mRNA     ------------------------------------------------------------

genome   TGTCTAAAGTTGTCTGAAGTCTATAAATCATGACAAATTATGATGTGGTGATTGTATTCA 133260
mRNA     ------------------------------------------------------------

genome   ACAGTCTTTCAGTTGCAGGGATAAAACCCCAGTTTAAACTAGAGTAAGAGAAAGAATGTG 133320
mRNA     ------------------------------------------------------------

genome   TTGGTTTAAGCTCCTGGAAAGTGCAGGCAAGGGTAGTTGGTAGGACTGCATCTAGTGTTG 133380
mRNA     ------------------------------------------------------------

genome   TAATTCTGTGGTCTGCATTGTATATTTATGCATCTCAGCTCTGCTTTCTTCTTTTCATTT 133440
mRNA     ------------------------------------------------------------
```

FIG. 1 CCCCC

```
genome    ATATAATTTTTAAATTTTATTTTAAAGATAGGGTCTCACTTTGTCGCCTAGGCTGAAGTG 133500
mRNA      ------------------------------------------------------------

genome    CAGTGGCATGAAGTGCAGTGCGAGGCTCACTCTAGCCTCGAACTCCTGGGCTCTAGAGTT 133560
mRNA      ------------------------------------------------------------

genome    CTTCCTGCCTCAGCCTTCTAAGTAGCTGAGACAATAGGCATGTACCAACATGCCTGGATA 133620
mRNA      ------------------------------------------------------------

genome    GGTTTTAAAATTTTTTTGTAGAAATGGAAGTCTTGCTGTGTTGCCCAGGCGGGTCTTTAA 133680
mRNA      ------------------------------------------------------------

genome    CTCTTAGCTTCAGGCGATCCTCCTGCCTCTGCCTCCCAAAATGCTGAGGTTATAGGTGTC 133740
mRNA      ------------------------------------------------------------

genome    ACCCACCACGCCCAGTCTCATCTCTGCTTCCTGTGTTAGTTTTGTTCTCTGGTGGGCTGT 133800
mRNA      ------------------------------------------------------------

genome    TTTCACATGACCGAAGATGACCTCTAGCAGGCTGTGTTCTCAGCCCCTCAAGTAGGCCTA 133860
mRNA      ------------------------------------------------------------

genome    TGTGATTGGCCTTGCATGAGTAATATGGGTGACCATAAACCCCTGAATGCTCTGGTCCAC 133920
mRNA      ------------------------------------------------------------

genome    ATGGGCCAAATGGGAGACTGGACAGCATTCCATTGATGAGGAGGTGGGGCTGGTCTCCGG 133980
mRNA      ------------------------------------------------------------

genome    GAGTAAGGGAGAGGAGCACATGCAGTAACTGATGGTCTGCTGCAAGGGATAGCAGCACAG 134040
mRNA      ------------------------------------------------------------

genome    CAGTTAGAATTTTGGAGGTAACTACCAGAACTGAAAACAGAAATGATAACAAGTAGTTGC 134100
mRNA      ------------------------------------------------------------

genome    CTTAAAAAGGGATGGGAGCAGGGTGCTTTTGTGATCAAAGCTCCTTTCTCTTACTGGATT 134160
mRNA      ------------------------------------------------------------

genome    TTTGTACACATTTTGCATACATATCTTAGAGTAAAAGATAGCATTTTCAGCCTTGGTCCA 134220
mRNA      ------------------------------------------------------------

genome    TTTGAGGATACTCTTGGCGTGGCCCGCCTCCATGCTAGCAGGCTCTGGTTGTGCCAAGTT 134280
mRNA      ------------------------------------------------------------

genome    CAGTTGAGCATCCTGGCTCTTGCCTGCACGGAACTTCCAGTCAGTGCGTCAGTATCACAA 134340
mRNA      ------------------------------------------------------------

genome    GTCTTGATATTTCCTATGAAGAAGAACAGTAGTGCAGTGACAGACGAAATGGGTGGGCAG 134400
mRNA      ------------------------------------------------------------

genome    GCAGAGGCAGGATTTCTGAGGGAGAGAAGTAGCTAGCTTTTTGCAGAGAAGAGTTCCGGC 134460
mRNA      ------------------------------------------------------------

genome    ACCCAAGAGAGCAGCTGAGAGTACAGGCAGGCAGGCAGGATGCCGGTAGGGCCCGGCCGC 134520
mRNA      ------------------------------------------------------------

genome    ACGGCGCCACAGAATCCTGGAGAAAGGGGCCTCTTCATGGCCTCTGCATTCAGCTGCTGT 134580
mRNA      ------------------------------------------------------------

genome    CACCCTCCGCACAGGCCATGGCCAAAATTTAATTTTCATAGTGGACTCTAGTTTTTGAGC 134640
mRNA      ------------------------------------------------------------

genome    CTTACTTGCTATTATTGAAATAATTTTCTTGTTTCTTTTTAAAGATCTTCGGATTATGCT 134700
mRNA      ------------------------------------------------------------
```

FIG. 1 DDDDD

```
genome    TCACTGACCACTGTAATAAGTTTAAAGTTGAGAAAATATGGCTTGTTAATGAATGATAGG 134760
mRNA      ------------------------------------------------------------

genome    TCAATTTTAGTATGTTGGTCATTTTAATATTTTGCCACCAGTTGGTTTGGATTTGATGCC 134820
mRNA      ------------------------------------------------------------

genome    AGGAGGAGACAGCCTCATTTCTAAGGACTAGTCTTGCCTTTGTGGGATAAGGGTGGTGTG 134880
mRNA      ------------------------------------------------------------

genome    TTCTGTGTCCTTCTACATGTCCGAGCGATCTCTGTGCAGCTCAAATGTGGTCACTGTCTT 134940
mRNA      ------------------------------------------------------------

genome    ATTGCGCTGATTTCCTCTCCTTCCATCTCACAATTGAGGCAAAATATTGTTACTGTTGAA 135000
mRNA      ------------------------------------------------------------

genome    GTGTTGTCCAATAGGACTTCCAGCAGAGACAGGATGTCTGCACTGTCTAATTTAGTTGCC 135060
mRNA      ------------------------------------------------------------

genome    TTTAGCCACATGTGGTGTTCTGTACCTGAAATGTGGCTGGTCTGATTGGATAGCTTAATT 135120
mRNA      ------------------------------------------------------------

genome    TATAATTTTATTTAATTTTAATTAACTTAAATTTAAACAGCTCTGTGTGGATAGTGGCTC 135180
mRNA      ------------------------------------------------------------

genome    CTGTATGAGACAGTGCAGGTCTGTTGAGAAGCAGCTTTACTGGTGGGAGTGGAGGGCTTG 135240
mRNA      ------------------------------------------------------------

genome    GAGAGGGCACGTGGGTTTCCTGCTGGTATCTTTTGACCTTATTTAATCTGCCCAACATTT 135300
mRNA      ------------------------------------------------------------

genome    GCAAGTAAGTTGTGTGTGTGTGTGTATATATAAATGTGTGTTTCTGTCTTCTTGTTTCCTTT 135360
mRNA      ------------------------------------------------------------

genome    GACTGCATTTATTTGAAAGACACTAGGTGGCAGAATTACTGTATTTGATTGGTTTCAAGA 135420
mRNA      ------------------------------------------------------------

genome    TAAGAGTTGAAATAATTCATCTCGTGTTTTTATATAAGTAAGGTGTGTTTAGCATGTAAA 135480
mRNA      ------------------------------------------------------------

genome    ATTGGTAATATGTATTCACGTACTGCTTAAACAAAGGCTATGAATTCCACCCATAAACCG 135540
mRNA      ------------------------------------------------------------

genome    AAAATGAAGACCTTTAAATTTGTCCATTTCAGGCGTGGGTACTTCTTAAATAATACCTGG 135600
mRNA      ------------------------------------------------------------

genome    TTCAGGAACTAGTCAGAATGGCACCCTTGACTTTTTGTTTCCTGCTTTTCCTCTTGTTGG 135660
mRNA      ------------------------------------------------------------
                                 rs363092
genome    GAGAGGAGGGTATTCATCCCAAAGTGGTTTGCCTATTTCACATTCCATCTAGGATAAGCA 135720
mRNA      ------------------------------------------------------------

genome    GAATAGCCAAGAAAGATAGCTGTCCTCCTGTTTACAACATTTGGGGTAACCAGCATCCCT 135780
mRNA      ------------------------------------------------------------

genome    CTCTTTTGGTCCAAGATAGACTGGTTTAGAAACAGATGATGGCACCAGAGGCCCAGGAGG 135840
mRNA      ------------------------------------------------------------

genome    TGGAAACATCAGCTTTGTTTGTTGTCCATGTGGCTGAATTAGAGCTGTCTGGCCTTGTAG 135900
mRNA      ------------------------------------------------------------

genome    CCTCAACACGGCCTTCCAGCTTTGCTCACCGTGATTTTCAAGGACACATCTTGTGCTCTT 135960
mRNA      ------------------------------------------------------------
```

FIG. 1 EEEEE

```
genome    CCCTGCCTGCCATCCAGACTATACCCAGTCAGGGTGGCAGGAGCTGCTGCCCCTTCCTCC 136020
mRNA      ------------------------------------------------------------

genome    CTGAGTCCTGGTCGTGGGTGGTGGAGATGTGCCATGACGCTCACGGAGGCATGCTCACCC 136080
mRNA      ------------------------------------------------------------

genome    CTTCCTCTGTGGCAGAGGGGATGGCTGCACGACAGCTCTTCCCTGTCCTTTCCAAAGCGT 136140
mRNA      ------------------------------------------------------------

genome    CTGTGGTTCCACTTTTTGGGGCAAAGCAGGAATACTGGAAGAGAGAGAAAGTGGTCCTTT 136200
mRNA      ------------------------------------------------------------

genome    CTATAGTAATAAAGTTGACATTGATTCAAGTTCATGCTTGGGGAAAGGACAGGGCTACTA 136260
mRNA      ------------------------------------------------------------

genome    ACAATTATAATGCTGGGAGCAATGGAATTTTCTCATGGGTATGTGGTAGGTTTAATTTTA 136320
mRNA      ------------------------------------------------------------

genome    ATTATCCCAGTTAATTCTTAGAACTGCTCTGTGAAGTATTTCCCGCTTTGTGCTTAAGTT 136380
mRNA      ------------------------------------------------------------

genome    CTAAAAGATCCTGTGCCAAAACCAAGAATGAAAACCCAAGCATTCTTTCTTGCCCATCGA 136440
mRNA      ------------------------------------------------------------

genome    TCTTTCTCTCATCAGGCCACTTCTTGGGTTGATAGTGGTGAGTGTAGCCGCTGCCACTTT 136500
mRNA      ------------------------------------------------------------

genome    CAGAATACCCACCATGGGCCCCAGTCACTGTGTGGCGTGGAGAAGAGATGGTTCTCTCTG 136560
mRNA      ------------------------------------------------------------

genome    TGTCATAGCTGAACAAGCCCAGCCCAGAGAGGTTTCTGCCCTAGGAGCTCTCGATGGTGG 136620
mRNA      ------------------------------------------------------------

genome    AATTGGGATGCGATCCCACATCCTGCCTGTTTTGAAAACAGCATTCTTTATTTCCAATTC 136680
mRNA      ------------------------------------------------------------

genome    CTGCTTCCATTGTTCCTTTTAATATTTCTTTGTTTAGCTCACAAAAACACGGCTTGCGGA 136740
mRNA      ------------------------------------------------------------

genome    GCTGCTGCGTGCAGCTGTAGCTGTTTCTCTGGGTGCAGCCTGCATCCGCCTTCCTGCCCG 136800
mRNA      ------------------------------------------------------------

genome    CCTCCTTTCCTGCACTGCCATCGTGGTCTCCGGGCACTTGGTCCCTTTCTCTTCCCCTGA 136860
mRNA      ------------------------------------------------------------

genome    GTCCCTTTGGCTCCCCTGTGCCACCCTTGTGATCCACAGGCTCTGCCTTCTTTCTGTCTC 136920
mRNA      ------------------------------------------------------------

genome    AGACTGCTGCTCATCACTACTCGGGACCCTAGGAAGGGAGGTTCCACCGAGAAGCATCTT 136980
mRNA      ------------------------------------------------------------

genome    CTCATCTCAGCCACGTTCTCAGTGCCACTGTTGTCTTTGTTAGGTAATGGTAGCTACTGT 137040
mRNA      ------------------------------------------------------------

genome    AACAAATAAACCAACATTTCCATGGCTTCACACCAGAGAAGGTTGTTTCTTGGTTTTATG 137100
mRNA      ------------------------------------------------------------

genome    ACAATGTATTGAGGGTGTTCTTGGTTCACGGATGGTTTTCCTCCATGTGGGAATTCGGGG 137160
mRNA      ------------------------------------------------------------

genome    ACCCAGGCTCCTTTCCTTCTTTTGGTTCTGTTCTCCAGGCCTTCACATCCTCTGTGTCTG 137220
mRNA      ------------------------------------------------------------
```

FIG. 1 FFFFF

```
genome    GTTGGGGACAAGGAGAGGGAAGGTAAAGAAGGCTTTGTGGCCTTGGATAAGTGACAGGCA 137280
mRNA      ------------------------------------------------------------

genome    TGCCTTTGCTGGTGTTCTCTCGTGGTGACAGGTCACAGCCCCACCCTGTAAAAGGGGACT 137340
mRNA      ------------------------------------------------------------

genome    GAGAGACGTCGTCCTGCTGCTTCCCAGCAGCAGCACTGTGGTCTCTGATGTGTTTTCTGT 137400
mRNA      ------------------------------------------------------------

genome    GAGGATAAAAACAGGTGATTCCAGGATGAGGAAAGTCAGGGAAACCCTTGGAAGGAGGGG 137460
mRNA      ------------------------------------------------------------

genome    ACCAGGCGGGTGTCACCATGGGATTAGTGGTGGCTTCAGAATGAGCTGCAGCGAGTGCCA 137520
mRNA      ------------------------------------------------------------

genome    TGCCTTCTAAAGCTTTTGCTATTCTGATATGCCCACACCATGCCCAGCAGGTGTCTGCCT 137580
mRNA      ------------------------------------------------------------

genome    TGCTCTCCGCAGAGAGAGTGATGAATCCTTCTCATGAGCCTCTGTCCAGTTGTTCCTCCC 137640
mRNA      ------------------------------------------------------------

genome    TCCACCTGGAAGGGACCCTGGGTTCCTCATAACATCCCAGCGGAACAGGGGACCTTCTAT 137700
mRNA      ------------------------------------------------------------

genome    CCTGTCCCCAAGTTCATCCTCATCCTCCTGCCGGCTTCCTGGCCCCTCTTATGTCTGCTT 137760
mRNA      ------------------------------------------------------------

genome    CCTGACGCCACATCCTTCTGGATTCTCTGGAATTGAATTTTGCCTTTGATGCTTATTTAA 137820
mRNA      ------------------------------------------------------------

genome    AAATATCCATTGCAGGCCAGGTGTGGTGGCTCACACCTGTAATCCTGTGCACTTTGGGAA 137880
mRNA      ------------------------------------------------------------

genome    GCCAAGGTGGGCAGATTGCTTGAGCCCAGGAGTTTGAGATTAGCCTGAGCAACATGTTGA 137940
mRNA      ------------------------------------------------------------

genome    AATCCTGTTTCTATAGAAAATACAAAAATTAGCTGGGCATGGTGGCGCACACCTATACTC 138000
mRNA      ------------------------------------------------------------

genome    CCAGCTACTCAGGAACCTGAGACAGGAGGATCAATTGAGCCCCGGAGGCCAAAGCTACAG 138060
mRNA      ------------------------------------------------------------

genome    TGGGCTGTGATCGTGCCACTGTACTCCAGTCTGGTCAAACAGAGTGAGACCCTGTCTGAA 138120
mRNA      ------------------------------------------------------------

genome    AAAAAAAAAAAAATCCATTGCATACTTCACCGTAGCGAAACATGTATGTCTTACCTTTCC 138180
mRNA      ------------------------------------------------------------

genome    TTTCCTGCCTGTAGCTGCTCTTTTACACTTAACAGCCACACTAAGCCAGCCTTAAATGAA 138240
mRNA      ------------------------------------------------------------

genome    AAACAAACCAGCACTTCCTGTGCCCTCCTGCTTCCTTCATGAGGGGTCCCTCCCTCTGTG 138300
mRNA      ------------------------------------------------------------

genome    TACACTCCATTCTCATTGCCCATGGTGGTTTGTTTCCCTCTTGTTTCTCAAGCCATGGCA 138360
mRNA      ------------------------------------------------------------

genome    GCCTGCCTCTTGCCCTCTTTACTAAAAAGGCCTTTGCAGAGGCTGCCTGTGTTCTTTCTT 138420
mRNA      ------------------------------------------------------------

genome    TCTAGGTCTCTCTCATCCTAGGCCCTCCAGCTTGATTCTGTGGAGCTGCCCTCTTGTCAC 138480
mRNA      ------------------------------------------------------------
```

FIG. 1 GGGGG

```
genome    TCAGTAGCTTGTGGGGTCTTCTCTGTCTAGCCACTTAATTGATTGTGTTCCTCGAGTTGC 138540
mRNA      ------------------------------------------------------------

genome    TGTCCATGGTCTCTCGTTACTGTTTTCTCTGTGTTTCTGCCTCTCTCCTTGGCCTTGGTA 138600
mRNA      ------------------------------------------------------------

genome    GGTCCATCCCCTTTGTGACCTTGGCTGTTGCTCTCATGGACAACTTTCTCTTGCTGGTCC 138660
mRNA      ------------------------------------------------------------

genome    TTGTAGTCCTGGCATCCAGCTTCTCGACACGGGACTTGTCCTGCCAGTACCTCAGACTTG 138720
mRNA      ------------------------------------------------------------

genome    CACTTAAAATTGAACTAGCACCACTGTCACTCTCCAGGGCCTCTTCTTGTTAATTAGATC 138780
mRNA      ------------------------------------------------------------

genome    ATTAGGGATGTTCAGAATCCCAGCATCATAGTATGTTCCTCCTCCCGCTACCCCAGGAAC 138840
mRNA      ------------------------------------------------------------

genome    CCTAACCTTACCTCCTCCTCTCTATCTACTAGGAGGTGGCCCTCAGAGTCCGTCTCATCT 138900
mRNA      ------------------------------------------------------------

genome    TCCACCTGAACTTCCCTAATAGGCTCCAGCAGCTGCCACCCCGGGGGCTGAGTACTTCCT 138960
mRNA      ------------------------------------------------------------

genome    CCATGCCTTGTGCAGTGCTGAGCCCTTTACCTGGGTTCTCCTGTTTGCTCCTTATTACAG 139020
mRNA      ------------------------------------------------------------

genome    CCCTGCGAACAGATACTGCTCTTAATTCCATCTTACACCTAAGGAAGCTGAGGCCCCAGG 139080
mRNA      ------------------------------------------------------------

genome    TAAGGTGCATCCAAGGTCACCCAGGTAGTAGACAGTAGAGCCACGATCTGAACCAGGCAG 139140
mRNA      ------------------------------------------------------------

genome    TCTGATTCAGAGCCTGTGTTGACACTCAGCCACCTAGAACACAGCTTGGATTGTGGGTTT 139200
mRNA      ------------------------------------------------------------

genome    CTATTACCTGTTCAAAACCCCTACATCCCGGGTCTGTCCCTGCACGTGCTCTGTGGCCTG 139260
mRNA      ------------------------------------------------------------

genome    GCTGCATCTTCCTTGAAGGCAGTGCATGCCTCTTCACTCAGGGGGCCCATGCAGGAACAG 139320
mRNA      ------------------------------------------------------------

genome    AGGGCCCCACAGAAGGATGAGGCCAGTGCAGAATGGGCTGGAGGGGACAATGCTGACCAG 139380
mRNA      ------------------------------------------------------------

genome    GAAGCAAGTGTAGAGAAATCCCAGGAAACCTGGAGGAGCCAGAGACAAGGCATTAGAACT 139440
mRNA      ------------------------------------------------------------

genome    CCTCGTCGTGACCTGGTCTGCATTCTCTGAGTGTGCTGCTTCTGTTAGCTCGCTTCCTTG 139500
mRNA      ------------------------------------------------------------

genome    GTCTCAGGTTATAGTTTAAGGCATTGTGGAGCCCTAAAAAGCCTGTACTCTGTTTTTACC 139560
mRNA      ------------------------------------------------------------

genome    TGTTTTAGGACCCTTTCACTTTGGGGATGTGTTGATTTTTTTTTTTTTTTTTTTTTTTTT 139620
mRNA      ------------------------------------------------------------

genome    TTTGAGATAGAGTCTCGCTCCATTGCCCAGGCTAGAGTGCAGTGGCACGATCTTGGCCAC 139680
mRNA      ------------------------------------------------------------

genome    TGCTGCCCCTGCCTCCTGGGTTCAAGCAATTCTTGTGCTCCCGCCTCCCAAATACCTGGG 139740
mRNA      ------------------------------------------------------------
```

FIG. 1 HHHHH

```
genome    ATTACAGGCACCCGCCACCACACTCGGCCAATTTTTGTATTTTTAGTGGAGACAGGGTTT 139800
mRNA      ------------------------------------------------------------

genome    TACCATGTTGGTCAGGCTGGTCTCGAACTCCTGACCTCAAGTGATCTGCCCACCTTGGCC 139860
mRNA      ------------------------------------------------------------

genome    TCCCAAAGTGCTGTGATTATAGGCGTGAGCCACCACACCCGGCCTGAAATTTAAATCAGA 139920
mRNA      ------------------------------------------------------------

genome    AATAAAATTTTGATCCCAACAGTGATGCCAGGCAGCCCAGATCTGGGGGAGAGGGTGGCC 139980
mRNA      ------------------------------------------------------------

genome    TTGGCCAGCTGGGCCTTTCTCTGTTTCCCAAGTCTTGCTGCCTCTCCCTGCTGGGCTTTG 140040
mRNA      ------------------------------------------------------------

genome    CAGCCTGTGCATGTCTCTGTGCCTTTGACCTTGTTTATCCAAAGGAGAGGATAGAATGAA 140100
mRNA      ------------------------------------------------------------

genome    GTCATGATTCCTGGAGCCCTGAGAAGGATGCTGTGGAGAAATTTGCCGGTAGAATCTAGC 140160
mRNA      ------------------------------------------------------------

genome    TGAGTGTGTTGCTGAGGTGCCAGCATTGTGTGTGGGGAGGCTGACCGCTTGGCCTGCCTA 140220
mRNA      ------------------------------------------------------------

genome    GGCCCAGGATGCTCCATGGCCGGGCACAGAGGCCACTTGGCTGTCAGGTGTCAGGAGCCT 140280
mRNA      ------------------------------------------------------------

genome    GCAGAGGGCACACAGAGCCTGGACCGCAGGGGGGTCCTGCTTTCTCACCTGGCCTCCTTC 140340
mRNA      ------------------------------------------------------------

genome    AGCATTTCTGTCCCTCAGTCCTTAGCAAGCCCAGGAGCTGTTGAGTTTGGCAGGTGCCGA 140400
mRNA      ------------------------------------------------------------

genome    GTGCTGTTCCTGCCTGTGTAGCTGTGGCTCAGTCCTGTGGGGGCCCCGCTGTGGCCCGAG 140460
mRNA      ------------------------------------------------------------

genome    TGCAGTGATTCGAGGCGCTGAGTGTTCCCTGACTCCTTCTCCAGGAGCTGTGTTCAGACT 140520
mRNA      ------------------------------------------------------------

genome    TTCGCAGCTCTTGGCTTGGAGCTCCTGGAGGGCTTGGCATTGCCGACCAATGTGGAGGTC 140580
mRNA      ------------------------------------------------------------

genome    GACAGTGAGAGAGGAGGAATGCTAGCTTTCTTGACCAGTCCATTAAATAAGTGGGATATT 140640
mRNA      ------------------------------------------------------------

genome    GGCCAGGCACGGCGGCTCACGCCTTAATCCCAGCACTTTGGGAGGCTGAGGCGGGTGGAT 140700
mRNA      ------------------------------------------------------------

genome    CACGAGCTCAGGAGTTCAAGACCAGCCTGGCCAACATGGTGAAACCCCCTCTATACTAAA 140760
mRNA      ------------------------------------------------------------

genome    AATACAAATATTAGCTGGGCGTGGTGGCAGGCGCCTGTAATCCTAGCTACTTGGGAGGCT 140820
mRNA      ------------------------------------------------------------

genome    GAGGCAGGAGAACAGCTTGAAACCGGAAGGTGGAGTTTGCAGTGAGCCAAGATTGCGCCA 140880
mRNA      ------------------------------------------------------------

genome    CTGCACTCCAACCTGGGCAACAAGAGCAAAACTCTATCTCAAAAAAAAAAAAAAAAGTAG 140940
mRNA      ------------------------------------------------------------

genome    GATATCTGTTTCTGCTTAGAAAAATCAGAATTTTCTAAATGCCAGGTGTTCTGAATACGT 141000
mRNA      ------------------------------------------------------------
```

FIG. 1 IIIII

```
genome    AAGTATGGGAGACGACTCAGCCTGTTTCATTTTTATGTAAAATCTTCGCGTAGCCATGTG 141060
mRNA      ------------------------------------------------------------

genome    GCACTGGACCGAGATGAAAGCAAAGACATTTCTCCTTAACTTTGTTTCTAGGAATGTTCC 141120
mRNA      ------------------------------------------------------------

genome    GGAGAATCACAGCAGCTGCCACTAGGCTGTTCCGCAGTGATGGCTGTGGCGGCAGTTTCT 141180
mRNA      ------------------------------------------------------------

genome    ACACCCTGGACAGCTTGAACTTGCGGGCTCGTTCCATGATCACCACCCACCCGGCCCTGG 141240
mRNA      ------------------------------------------------------------

genome    TGCTGCTCTGGTGTCAGATACTGCTGCTTGTCAACCACACCGACTACCGCTGGTGGGCAG 141300
mRNA      ------------------------------------------------------------

genome    AAGTGCAGCAGACCCCGAAGTAGGTTCATAATGCCCCACAGCCCAGGGCGCCAGCCCAGC 141360
mRNA      ------------------------------------------------------------

genome    ACCCTGTCCTGAGACTCCCAGTAACCTGAGCTTTGGCCACCGTTAAAGCATTTTCATTTT 141420
mRNA      ------------------------------------------------------------

genome    CCATTTTTTGTGAGGGCTTGTGAAATTTCTGCTGCATATTAATATTCCTTTCATGGACAG 141480
mRNA      ------------------------------------------------------------

genome    CATATTATTGGGACAAACATGCGGTCCAGCTAAAGGCATTCAAAATAGCAGTTGCTTTCT 141540
mRNA      ------------------------------------------------------------

genome    AAATGCGATTTTCTTTGGCAGGTTCTTTGACACCATTGCATCTTGTGGGATATGCTTGTC 141600
mRNA      ------------------------------------------------------------

genome    ATGCTCTGTGGCTCCTACTAAGTTCTAGTCCTTAAATTGGTTCCATAGCCAGACATGTTG 141660
mRNA      ------------------------------------------------------------

genome    CAATGTCTTAACCTCATTATAAAGTAAATGTGGTTCTGGTTATCCTTAGATAATGAAGTA 141720
mRNA      ------------------------------------------------------------

genome    ACAGTGTAGCAAATTTCAAAACCTCTTGGAAATGTTATTTTACCATTCAAAAAGGCTTAC 141780
mRNA      ------------------------------------------------------------

genome    TAAGGTTCTCGTTATGGGTGGCCCTCTTTTTGCAAAAGGTTTTCAGGCTTAAGCTCCATT 141840
mRNA      ------------------------------------------------------------

genome    TCTAGGTGCTCCAACACTCCATTATTTGTATATGTATGGAAATAAAAGCTGTGACCACCC 141900
mRNA      ------------------------------------------------------------

genome    CCAACCCTGGCCCCCGCCCAGCTGAATCCTCAGCACAGTATTTCTGGAAGGCTCAAGATC 141960
mRNA      ------------------------------------------------------------

genome    CCACGCTGGGGAAAAGAAGTTCTGGAGACAAAAGAGGGCAGGTGCTGCCGTGCCTCTCTG 142020
mRNA      ------------------------------------------------------------

genome    CTCAGTATGGATACTGGACCTTGTGCTGCCAGGGCTCCCAGTAGGGCCAGTTCATGGCAC 142080
mRNA      ------------------------------------------------------------

genome    TCAGCTGGAAAGTCCACTGTTGGGAGGCATTCTTAACCATCCACTCTGTGCCGTATGTAG 142140
mRNA      ------------------------------------------------------------

genome    TGGGGTCTGGTCATTCTGTTGGAGGAGACAGACCAGTGACGACATTTGAAATGCTTGGTG 142200
mRNA      ------------------------------------------------------------

genome    GATGTCTTAGGCCTGTTACGATGACTGAGCACTGTGGGGGCAGGAGACAGAAAGTCAGTG 142260
mRNA      ------------------------------------------------------------
```

FIG. 1 JJJJJ

```
genome    TCTCCTAGTTCTGTGCTGCTTTAACGTGCATAGAAATCAGCTGCGGATTCAGCAGATCAC 142320
mRNA      ------------------------------------------------------------

genome    TCCTTTTCTGACAGATGGGCCTGCTTACTCTGATGTTATATCAGAAAGCTCTGAATCTGG 142380
mRNA      ------------------------------------------------------------

genome    GAATTGTGTCCCCTGAATTGGAGTAACAGAAATGCTTAGATGATGAGTGTTTAAAAGAAA 142440
mRNA      ------------------------------------------------------------

genome    TAAACCAAAGGTAAATTTAGTTTGGAATTCAGCAAGCGTCTTCATTCAGCCCTCTGAGGG 142500
mRNA      ------------------------------------------------------------

genome    CAAACTACAGCTTTTTGTAAATGTAGGTAAATTCTGTGACTGTTTCGTGACCCCCTCTGA 142560
mRNA      ------------------------------------------------------------

genome    TCCAGTTTTCCTTTATAACCTTCTGTATTGTTCCTTCTATTATCCTGAAATAACATTAAT 142620
mRNA      ------------------------------------------------------------

genome    AGATTAGGCTGGGCGTGGTGGCTCATGCCTATAATCCCAGCACCTTGGGAAGCCAAGGCG 142680
mRNA      ------------------------------------------------------------

genome    GGCAGATCACCTGAGGCCAGGACTTCGAGACCAGCCTGGCCAACATGATGAAATGCTGTC 142740
mRNA      ------------------------------------------------------------

genome    TCTACTGAAAATAACAAAAATTAGCCGAGCATGGTGACAGGTGCCTGTAGTCCCTGCTAC 142800
mRNA      ------------------------------------------------------------

genome    TCAGAAGGCTGAGGCGGGAGAATCGCTTGAACCTAGGAGGAAAAGGTTGCAGTGAGCTGA 142860
mRNA      ------------------------------------------------------------

genome    GATCGCGCCACTGCACTCTAGCCTGGGTGACAGAGTGAGACTCCATCTCAAAAAAAAAAA 142920
mRNA      ------------------------------------------------------------

genome    AAAAAAAAAAAAATTAATGGATCAATGGATTTTTAACCTAATAATTAAATTTCAAAAAAT 142980
mRNA      ------------------------------------------------------------

genome    ATCGTTCTTTAATGGTAATGTAAAGGTAAAATTAAGATAATATGTAACAAGCATGTGAGT 143040
mRNA      ------------------------------------------------------------

genome    GTCTAAGGTGTCCCCGTGGTGGAAGGAAAAAATAAATCCCCATAAGTGTCCAAGATGCCC 143100
mRNA      ------------------------------------------------------------

genome    ATAGAGAGCAGAGCTGTTCTGGTTTAAACCCCTGCTCTTAGCACTGTGTTTTTCCAGCTG 143160
mRNA      ------------------------------------------------------------

genome    TGGGTGGTGGGGGATGAGTATCTTTTTATTTCCATGAGATGAGAAAAATGAATTACTAGA 143220
mRNA      ------------------------------------------------------------

genome    AGTGTGAAATACAAAACACAGCTGCTCTTTTTTTAGCCATAGACTCAGCAGCCATAAAAT 143280
mRNA      ------------------------------------------------------------

genome    TGCTGTATCCAGTTGCAGAAATTCCTGCTGCTTACTCTTGACCCTCTCTCGGTTTGTGTG 143340
mRNA      ------------------------------------------------------------

genome    CATCTCCTCTCAGGCTGGCTCCCAGATGGGAGCTGGCTCCAGGCGACACTGGGTGCTCTG 143400
mRNA      ------------------------------------------------------------

genome    CTCCAGGAGGTCCTTATGTGGGTCCTGCCCTAGCCTAGCCCCTCTCTTATGGACTCTGTC 143460
mRNA      ------------------------------------------------------------

genome    ACTGTGGGTTTATGATTCACTCTCAATCTGTCTTACCTCTTGGTGAACTGTTAGAGTCCT 143520
mRNA      ------------------------------------------------------------
```

FIG. 1 KKKKK

```
genome    GCCTATACTTTGGCGCTTGTGGGTGTGTTGTGGTACACATGATGTGTTGGTCACTTCCCA 143580
mRNA      ------------------------------------------------------------

genome    GCTCATCTTGTTCTGAGTCACCCTAGATTTGGGACATTCATTCGCCACCAGTACCGGGCG 143640
mRNA      ------------------------------------------------------------

genome    GTGTATGGCCTGAGATTTGGGGGGGCTTGTGCTGCTACAAATTGGGGCTGAATTTGAGTT 143700
mRNA      ------------------------------------------------------------

genome    GACAGTGGACCTTCTTTATGTCTACTGCTCATATTTGAATTGCAAATACTGCCTCTTCTC 143760
mRNA      ------------------------------------------------------------

genome    TTTCAGAGGCTCATTACCCTATAGCTGTATTATTGCAAAGTGCACAATTACAGCTTGAGT 143820
mRNA      ------------------------------------------------------------

genome    GTAAGTCACACTGCGCTGGCAGGACGGCCCACTGAGAAAGGGCACGTTTCCTGTTCGTTA 143880
mRNA      ------------------------------------------------------------

genome    GTTTTCACATTGACACATAATTTACAATACAGTAAAATGTACTTTTCTATCAACTGTAGT 143940
mRNA      ------------------------------------------------------------

genome    CAGTAACAGCCCCCCTCCCCCAACCACATCAAGATATAGAGGAGTGCTGTCACTTCAAAC 144000
mRNA      ------------------------------------------------------------

genome    AGTTCCCTCTTCCTCTGCCACATCCTGCCCCTCCCCAGGTCTAACCACCAATCCGTGCTC 144060
mRNA      ------------------------------------------------------------

genome    TGTCCCTCTGTTCAGCCCATTGCAGAAGGCCATAGAAATAGAATCTATAGGCTAGGTGTG 144120
mRNA      ------------------------------------------------------------

genome    GTGGCTCATGCCTGTAATCCCAGTATTTTGAGAGGCTGAAGTGGGAGGATGACTTGAGGC 144180
mRNA      ------------------------------------------------------------

genome    TGGGAGTTCAAGACTAGCCTGGGCTGCCTAGCAAGACCCCATCTCCAGAAAAAAAAAATT 144240
mRNA      ------------------------------------------------------------

genome    TAAAAATTACAATCACGTCCCTGTAGTTCAGCTGCTTGGGAGGCTGAGGCAGGAGGATCA 144300
mRNA      ------------------------------------------------------------

genome    CTTGAGCTCAGGAGTTAGAGGTTACAGTGAGCTATGATCGTGCCACTGTGCTCCAGCCTA 144360
mRNA      ------------------------------------------------------------

genome    GGTGACACAGCAAGACGTTGTCTCTGGGGAAAAAAGAAAGAAACGGAACCACGCGGTGTG 144420
mRNA      ------------------------------------------------------------

genome    CAGCCTTCTGAGTCTGGCCCCTTTCGGTGAGCAGTGTCTAAAGTTCTGTCGCGTGTTGCC 144480
mRNA      ------------------------------------------------------------

genome    CACGCGTCGGTGGCTCGCTCCTTGCAACTGCTGAGCATTGTATGGCTAGGCTGTAGTTTG 144540
mRNA      ------------------------------------------------------------

genome    TTTTCACTTCACCAGTTGGGAAACAGAGAAAAGGCACTTTTTAAAAAGTTTAAATCTGTA 144600
mRNA      ------------------------------------------------------------

genome    GAATTTTGGTTTTTACCAGTTCTCTTCTAAATCCTGAGGGATTACAGGAAAAGTTGTTGT 144660
mRNA      ------------------------------------------------------------

genome    ATTTCAGAATATTCTTAGCTTGATGTGACCTCTGTCCCCGTTAAGGCCCTTTGCCGCAAT 144720
mRNA      ------------------------------------------------------------

genome    GGGAAGGACGTCGCTCGGTCAGACCCTGAAGGTCAGAGGGGCAGTTTGGGAGTGTGTCAA 144780
mRNA      ------------------------------------------------------------
```

FIG. 1 LLLLL

```
genome    CATTTTAACTGTATGGACTAGAGCCAAGAGTCTCAAGGTTTATAATTCCCACGTATTCAA 144840
mRNA      ------------------------------------------------------------

genome    AAAGAAAAAAACAATAAAGTGAGAAGTCAGTGTAGAGTGAAATAACCTGTGTTAGTGGGG 144900
mRNA      ------------------------------------------------------------

genome    AAGAAGTGTTTTTAAACAGGATTTCCATAACGTATAACATCAACATGTTTAGAGTGGTGA 144960
mRNA      ------------------------------------------------------------

genome    TGTTTCATTGGGAAACGAACAGTAAAACATGAAAGCAGGGAGGTTTTCATTCTGGCAGTT 145020
mRNA      ------------------------------------------------------------

genome    GGCAACTTTCACGGCAGATGGAGAATTTCAAAAGCAATTGCTCAATTATCAAACATAGCC 145080
mRNA      ------------------------------------------------------------

genome    AGTGTGAGTTCTGAAATAAAGGTGCTGATTGAATGTGCAGCTTTATGGTGGATTTTGCTA 145140
mRNA      ------------------------------------------------------------

genome    TTCAGGCAAGCATTTTAATTTTCTGCCTGTTAAATTCTGTTTTCTTTAGTTTTTCATATG 145200
mRNA      ------------------------------------------------------------

genome    TGGTTTATTGTAGCTTAGGAATAGATAACTGAGAGTATATATTACACATACAACATTCTG 145260
mRNA      ------------------------------------------------------------

genome    ATATGGCAATATTTAAAACAACTTGTCTGTTTTAGAACTAGAATTAAACATAATCATCTT 145320
mRNA      ------------------------------------------------------------

genome    CAGTATTTTGCAAATAAGCTCACTGCCATCCAGAAACATTGTCAATGCATCTGTTGCTCC 145380
mRNA      ------------------------------------------------------------

genome    TTCTAGAAGACACAGTCTGTCCAGCACAAAGTTACTTAGTCCCCAGATGTCTGGAGAAGA 145440
mRNA      ------------------------------------------------------------

genome    GGAGGATTCTGACTTGGCAGCCAAACTTGGAATGTGCAATAGAGAAATAGTACGAAGAGG 145500
mRNA      ------------------------------------------------------------

genome    GGCTCTCATTCTCTTCTGTGATTATGTCGTAAGTTTGAAATGCCTGTAAACGGGGTTGAG 145560
mRNA      ------------------------------------------------------------

genome    GGAGGTGGGGACCAGGAGAACATCCTGTGTAGATGACACTTGCATGGACCCTCTGGAACC 145620
mRNA      ------------------------------------------------------------

genome    CAGACCGCCCGGTGTCCTGCCAAGCTCCATCGAAACTAAATCTAGAATGAATGTTTACTT 145680
mRNA      ------------------------------------------------------------

genome    CTGCTGTGACATATAATTGGAGACCAGGCCTGGCCTTCCAGTCACTGGATTCTAAGTTGG 145740
mRNA      ------------------------------------------------------------

genome    ACTGTGAGAGTTTTTGCAGCTGACTCATTTATCAAATGCCCGGCTATTGGCTCACGCCTA 145800
mRNA      ------------------------------------------------------------

genome    CATGATGCTGGGTATGTTTGTTAATTTGAGGGAAGCAATGGAATAATAATAACTAATGAT 145860
mRNA      ------------------------------------------------------------

genome    TTAAAAAACAAAGTAAGTGCATTGACTGTAGTGGGGTTCTGATTTTAAATTTTTTTAAAA 145920
mRNA      ------------------------------------------------------------

genome    ATTAATACCAGGAGCAGTGGCTTATGCCTAAATTCCAGCAACTCGAGAGGCTGAGGTAGG 145980
mRNA      ------------------------------------------------------------

genome    AAGATCACTTGAGCCCAGGAGTTTGAGACAAGCCTGGGCTATGGTGTGAGACACCCATCT 146040
mRNA      ------------------------------------------------------------
```

FIG. 1 MMMMM

```
genome    CTAAAAAAATAAAAAATAAAAAATTATCCAAGTGTGGTGGCTCGTGCCTGTAATCACAGC 146100
mRNA      ------------------------------------------------------------

genome    TCTTTGAGAAGCTGAGGGCGGAGGATGGCTTGAGCCTGGGAGTTCGAGACCAGCCTGGCA 146160
mRNA      ------------------------------------------------------------

genome    ACACAGAGAAACCCTGCCTCTACCAAAAAAAGAAAGAGAGGAAGAAAGAAAAATTAGCCT 146220
mRNA      ------------------------------------------------------------

genome    GGCGTGGTGGTGCATGCCTGTGGTCCCAGCCACCTGAGAGACTGAGAAGGGAGGATTGCT 146280
mRNA      ------------------------------------------------------------

genome    TGAGCCCAGAAGTTTGAGGCTGCAGTGAGCTGTGACTGTGTCACTGCACTCCGGCCTGGG 146340
mRNA      ------------------------------------------------------------

genome    TGACAAGGCGAGACCCCTGCTCTAAAATAATTTTTTTAAGTTAATTTGTAGAAAAGGTGT 146400
mRNA      ------------------------------------------------------------

genome    TAGATGTTCTTTGTCACATTTTATGATGGATTCCTGTTTAAATGCCGTTCTCTTTAAAGA 146460
mRNA      ------------------------------------------------------------

genome    AAAAAAAATAACTTGTGGGAGTTTTTAACCATAAAACTAGCATCACATATTTACCATGGA 146520
mRNA      ------------------------------------------------------------

genome    GAATTTACAAAAAAACAAATAAACGGAGGAAAATAAAACCTCCTGTAATCATACTACTCA 146580
mRNA      ------------------------------------------------------------

genome    GAGATAACTTGCTGTTAGATTTTGGTCTAGATTTAATACTTTTTCTATATTTATATTAAA 146640
mRNA      ------------------------------------------------------------

genome    AATATTTAAAACATATGCATTTCTTTGTCACAAACATGGTATCTTATAGATACTACTGTC 146700
mRNA      ------------------------------------------------------------

genome    ACATAGCAAAACAGTGTTAAATATTCTGAATCAGAAAAGGAAGCCGACTCTCCAACTGAA 146760
mRNA      ------------------------------------------------------------
                                              rs7685686
genome    AGAGGTGTTATCCTAGAGACTTTTTCTGGTGATGACAATTTATTAATAGTCACTTTTTGC 146820
mRNA      ------------------------------------------------------------

genome    TTTACTTTCTCTATTGAAGTAGTTTTTCTATTTTGTTCTACTTTTAAGGATAATATAATT 146880
mRNA      ------------------------------------------------------------

genome    TATAATGCTGTTTTTCACAGAAATATAAGAAAAAAGATACTAATTTTATAAGTTAATAAA 146940
mRNA      ------------------------------------------------------------

genome    GTTTGATCATCCCAAATCCAAAAATCTGAAATCCAAAATGCTCCAAATTCTGAAGCTTTT 147000
mRNA      ------------------------------------------------------------

genome    TGAGTGCTGACATTATGTTCAAAGGAAATGTTCATTGGAAGGTTTCAGATTTTCGGATTT 147060
mRNA      ------------------------------------------------------------

genome    AGGGAGCTCAACAAATAAGTATAATGCACATATTTCAAAACCTGAAAAAAATCCTAAATT 147120
mRNA      ------------------------------------------------------------

genome    CAGAATACTTCTGATCCCAAACATTTCAGATAAGGGTTATTCAACCTGTACTGTCAGATG 147180
mRNA      ------------------------------------------------------------

genome    ATCCCAAATGAAAAATATTAATCGTTAACCAAATATCAAGGAATTGATCACATTTTACAG 147240
mRNA      ------------------------------------------------------------

genome    TTTCTGCCTAGGATTATGAATCAAGATGAAAAGGCTCTGCATGTTTAAAAATATATATTT 147300
mRNA      ------------------------------------------------------------
```

FIG. 1 NNNNN

```
genome  TTATTTTCTTATAAATCTTAAATATCTACACTTAAGATTTATTTGATATGTGGGATCCAT 147360
mRNA    ------------------------------------------------------------

genome  TCATATTTTGGATTCAACAGTTCTGTCAAAACTGTGGCAGTGATAGGGGATTCTTTTTTT 147420
mRNA    ------------------------------------------------------------

genome  CCCACTGAACTATCACAAAATTGGAAAAAGAGTAATTGGAGAACCCCACTGGCTTAGCCG 147480
mRNA    ------------------------------------------------------------

genome  GCCCGAAGCCCGGGAGAGGGCAGGCAGTGCTGTGGATGGGGTCATCCCAGCGCAACGCTG 147540
mRNA    ------------------------------------------------------------

genome  CCCCTGCTACCTGCGGATCTCGCTGAGGCCTGCCTTTGTCCTTTGACCCTTGGCCATTTG 147600
mRNA    ------------------------------------------------------------

genome  TTAGTGTCTCTGAGAGCTGGACTGCTGTACCCTACTTCCCCAGGGGGCCTAACTTCACAC 147660
mRNA    ------------------------------------------------------------

genome  AGCCTCTGCCGCAGTGCGTGGTTGGAGGTGACGGCCTTGGTAAATCGAGTTTCCTACCTC 147720
mRNA    ------------------------------------------------------------

genome  CTCAATTATTTGTGCTCATACACTGTATATTTTTAGTGAGGTTTATATTTGGGATGTGTT 147780
mRNA    ------------------------------------------------------------

genome  TTCTCCTTCTTACCCTTTCTGGCCTTTCTATGGCATTAATACCTGGTCTCTTCTTGTGTA 147840
mRNA    ------------------------------------------------------------

genome  CTTGAAAATGAATCTCTCATCATATTTTTCCTTAGTGTCAGAACCTCCATGACTCCGAGC 147900
mRNA    ------------------------------------------------------------

genome  ACTTAACGTGGCTCATTGTAAATCACATTCAAGATCTGATCAGCCTTTCCCACGAGCCTC 147960
mRNA    ------------------------------------------------------------

genome  CAGTACAGGACTTCATCAGTGCCGTTCATCGGAACTCTGCTGCCAGCGGCCTGTTCATCC 148020
mRNA    ------------------------------------------------------------

genome  AGGCAATTCAGTCTCGTTGTGAAAACCTTTCAACTGTACGTCTTCATCCTGCCGACTATT 148080
mRNA    ------------------------------------------------------------

genome  GCCAGTTGCAGTTTTCCCTGCCTTAAAAATGGAGTATTGAAATTTTTAACTTTAATTTCT 148140
mRNA    ------------------------------------------------------------

genome  GATTTGCAAAATAGTCATCTTTTGTTCTTTTCCTTCTTGCTGTTAGCCAACCATGCTGAA 148200
mRNA    ------------------------------------------------------------

genome  GAAAACTCTTCAGTGCTTGGAGGGGATCCATCTCAGCCAGTCGGGAGCTGTGCTCACGCT 148260
mRNA    ------------------------------------------------------------

genome  GTATGTGGACAGGCTTCTGTGCACCCCTTTCCGTGTGCTGGCTCGCATGGTCGACATCCT 148320
mRNA    ------------------------------------------------------------

genome  TGCTTGTCGCCGGGTAGAAATGCTTCTGGCTGCAAATTTACAGGTATTGGGAAGAGAAAC 148380
mRNA    ------------------------------------------------------------

genome  CCTGATATTGATTTATATTGAAAATTTAGCAGGCCAAGCAAAACAGGTGGCTGGCTTTTT 148440
mRNA    ------------------------------------------------------------

genome  CCTCCGTAAGTATGGTCTTGACATGGTCACCGATAGAAACATGGAAACATCTGCAAACTT 148500
mRNA    ------------------------------------------------------------

genome  GCCGTTACTCGTGTGTCCGATCTGACTGTTTCTTGTATTTTTTTCTAGTCTGCCCTTACT 148560
mRNA    ------------------------------------------------------------
```

FIG. 1 OOOOO

```
genome   AGGATGAACTGTACACATCAGTTCATCCTTTTTAAATGAGCATGAGGTTATTTTGGGTTG 148620
mRNA     ------------------------------------------------------------

genome   TTAGGTGTTACAAACACACTAATGTGTTTTTGTCTATTAGAGCAGCATGGCCCAGTTGCC 148680
mRNA     ------------------------------------------------------------

genome   AATGGAAGAACTCAACAGAATCCAGGAATACCTTCAGAGCAGCGGGCTCGCTCAGAGGTA 148740
mRNA     ------------------------------------------------------------

genome   ATGCTGGAAACACAGGTCGTCCTTGTGTTAGGACAACCCAGGATATAAAGGATATAGATT 148800
mRNA     ------------------------------------------------------------

genome   TGTACGGGAATAAATTCACAGGACAAGAAATCGATGTGCCTTATAGGTGGGTTTACTGCA 148860
mRNA     ------------------------------------------------------------

genome   GAAGTGCCATAATAGAACCTTCCTACTTTTAAAACAACCAGATCTCACTTTCTAAAGAGT 148920
mRNA     ------------------------------------------------------------

genome   AAAGGATGACCGGCAGGATCACGTCTGTGACGTGAGTGGAGGCAGTTTGCACTCCTGGTG 148980
mRNA     ------------------------------------------------------------

genome   GCTGTTTGAGAGGTAGCATTTAGAATGCCTGTATTCACTGTCCTGTGATGAGTGGGAAAA 149040
mRNA     ------------------------------------------------------------

genome   TAGGTTATCAGGTTTATCTTAGCAAAATCAAAGCATGTCATCTAATTGCTAAACAAGAGT 149100
mRNA     ------------------------------------------------------------

genome   TGGCAAATCTGAGAGACATTACTCAATCCTTGGCATGCAGGACTTACATCTGCATCCTGT 149160
mRNA     ------------------------------------------------------------

genome   TGCCATTTTATGTCTTCAAAGCATTTAATCATTTAGTTGTGTTTGCAAAGTCTTTGAGAA 149220
mRNA     ------------------------------------------------------------

genome   GCCTTTGTCAGAAATCCCTACATCTCCTATGTGAGTGTATTTCCATGACTGCAGAATAAG 149280
mRNA     ------------------------------------------------------------

genome   TTAAACTTTTACCTTTTTCCTTCCCTTGCGGGGCGGGGTGGGGGGCAGGGATTGTGTGTG 149340
mRNA     ------------------------------------------------------------

genome   TGAGAGGGAGAGAGAGACAGCAGAGAAGGAGAATATAATTATCATGCTGTGTACTTTGAG 149400
mRNA     ------------------------------------------------------------

genome   CTGAAACTGCAAAAAAGGAAAAACACACAAAAATTATTATGCTTTTCAGTCTTTAGAGTA 149460
mRNA     ------------------------------------------------------------

genome   CCTTGTCTATTATGCTTTTCAGTCTTTAGAGTACCTTGTTGATGGTGTTTTTAAATGGGA 149520
mRNA     ------------------------------------------------------------

genome   TTGGGCACAATTAGGTGGACAGTTTGGGATGATTTTTCAGTCTGTAGGGCCAAGCTCTTT 149580
mRNA     ------------------------------------------------------------

genome   TGTAATTTGCATTATGAAGTTGTCACTCTCATAGCAGATGGCGGGAGATAAACTATTATT 149640
mRNA     ------------------------------------------------------------

genome   ACTTTTTGACCCTAGACTTAGTCTTCAGTCCAGATGAGGGAGATTAAAAGATTATAAATA 149700
mRNA     ------------------------------------------------------------

genome   TCTTGTGCCAGATGAGGTGATTTTATTTTGAAATGACCATGAATTCCTATCAGTTGTCTT 149760
mRNA     ------------------------------------------------------------

genome   ACTGGGATATTTGATAGTGGAATTTGTGCATTTGAGTCTTAGATGATCTGTTTTACATTT 149820
mRNA     ------------------------------------------------------------
```

FIG. 1 PPPPP

```
genome   ATTAAGAAAGCCTTTATTAGCTTTTATACTGTGTATTGCCTGTTGCAGTGTTTGAGTATA 149880
mRNA     ------------------------------------------------------------

genome   AATGAAATTTCTGGAAAATATTAATGGAGTACAAACTGTGATACTTAAAAGTAAACTAGG 149940
mRNA     ------------------------------------------------------------

                                                     rs363088
genome   GCCTGCATTTGTATCATGACCTGTTTGAGTATTGATGAGAAGATAGCTGTGAAGAAAAAG 150000
mRNA     ------------------------------------------------------------

genome   GTTTAAACAAGTGTATTTTCCTTTAAGAAGCCACTAATAGTGCATCTCCTTAGAGTGTAT 150060
mRNA     ------------------------------------------------------------

genome   ATTTCTAGAATCCTAGTGTGCAGAGTTTAGACTAAGACTAAAAAAAAAAAAAAACAAATT 150120
mRNA     ------------------------------------------------------------

genome   ATACTGTAATTTCATTTTTATTTGTATTTTAGACACCAAAGGCTCTATTCCCTGCTGGAC 150180
mRNA     ------------------------------------------------------------

genome   AGGTTTCGTCTCTCCACCATGCAAGACTCACTTAGTCCCTCTCCTCCAGTCTCTTCCCAC 150240
mRNA     ------------------------------------------------------------

genome   CCGCTGGACGGGGATGGGCACGTGTCACTGGAAACAGTGAGTCCGGACAAAGTAAGTGTC 150300
mRNA     ------------------------------------------------------------

genome   CAGCGTGTCTGCATGGGAGGCACAGGGCGCTGAGTGCCTCTGTCACCTGTGGCAGATACA 150360
mRNA     ------------------------------------------------------------

genome   GAGAGTGCAGAGGAGGTGCCGTGGACCCAAGGAGTTCTGGCGCTCGGCTCGGCTCAGTGA 150420
mRNA     ------------------------------------------------------------

genome   AGCTGTGGTTAGAGACGTGGGGGGCCATCAAGGTCTGAGGGAGCCAAGCAGTGCTGATGT 150480
mRNA     ------------------------------------------------------------

genome   GGGACCCTTTTGGTAGGAGTGTGGGGTGAGTAGTTAGTGGGTGAATCAAGGAATAGTCGG 150540
mRNA     ------------------------------------------------------------

genome   CCGTGGCCTGCAGGCCCCTGACTGCACAGGCCTTCAAGCACATGTCAATGCCGTTAGCCT 150600
mRNA     ------------------------------------------------------------

genome   CCCTCCATCTCCTCATACCTTCTGGCCACCTGTGAGTTGCACTGCCACTGCCAGCCATTC 150660
mRNA     ------------------------------------------------------------

genome   TGGTATGTTGTCAGCACCTCCACTGCTCATACCTCATGGTTAGGGACCACCTGGAGCCTT 150720
mRNA     ------------------------------------------------------------

genome   GGTAGAGCCTTGGTAGAGCCTTGGTACTCTACTTTCCTGGACAAAGTTCAGCTTATGAAT 150780
mRNA     ------------------------------------------------------------

genome   ATGAATTTAGATTTCAAAAACCAGCAGCCCAAGTATAAGAAAGCGAAGGTTCAGTCCTGC 150840
mRNA     ------------------------------------------------------------

genome   CTTCTTAGGCTCTATTCGCTAAGCACCTGCCCTGCCCTGGTTGCTGGGGAGAGATGAGTA 150900
mRNA     ------------------------------------------------------------

genome   AAGCAGACAACCCAGGAGAGGATGGCAAAGGGGCCGCTAACCCTTAGTGGTTTAGCTATA 150960
mRNA     ------------------------------------------------------------

genome   TTTGGAAGGCCTATTGGAAGTTCACCAGGTGAAGGGGGAGGCTGTGAGGGTGCCCAGGCA 151020
mRNA     ------------------------------------------------------------

genome   GGTAACAGAAGTCCAAAGGGGAAAACCTGTGGTGTGGTGAGCCGTATAGCCACAGCCTGC 151080
mRNA     ------------------------------------------------------------
```

FIG. 1 QQQQQ

```
genome    CGGCCGGCAGCCCTCTCAGCCTAGTGCGGTGTTCCCAAGCACTGGCCTAGGCCTGTAGCT 151140
mRNA      ------------------------------------------------------------

genome    CCAGGGATGTGAAGTCCCCTTGAACGCCGCCCATCATGTTCCCCTTATCCATTTTTTTCT 151200
mRNA      ------------------------------------------------------------

genome    TCCCAGGACTGGTACGTTCATCTTGTCAAATCCCAGTGTTGGACCAGGTCAGATTCTGCA 151260
mRNA      ------------------------------------------------------------

genome    CTGCTGGAAGGTGCAGAGCTGGTGAATCGGATTCCTGCTGAAGATATGAATGCCTTCATG 151320
mRNA      ------------------------------------------------------------

genome    ATGAACTCGGTACGGGGGGAGCAGTGGAGGCAAGGAATCCTCAGCTTTTCTTGTGACTTC 151380
mRNA      ------------------------------------------------------------

genome    CAAGTGGGATTTGTCTCATCATCATGTGACCCACTTGTTGACAACACATGTTGGGGACTC 151440
mRNA      ------------------------------------------------------------

genome    CAGTCTGGGCAGGGACGGGATGTCGGAGAGACTCCACTCTGAATGGGGCCGGGAAGTGGG 151500
mRNA      ------------------------------------------------------------

genome    GAGGACTCCATTTCAGATGGGGTCGGGACATGGGGGTTATGCTGATCGAGACAGAAAAGC 151560
mRNA      ------------------------------------------------------------

genome    ACATTGTTTCAGCCACATTAGAATCCACGGAGGTGTTGTTTTGAAATCCAGCTGGCCCCA 151620
mRNA      ------------------------------------------------------------

genome    AGGCTGGGTGTATGGTTTGGGATGAGAACTATCTGGCCTCCACTGGAGGAACAAACACAG 151680
mRNA      ------------------------------------------------------------

genome    GATGTTATCATCTAAGCTCCATGGCCAAGACAGAATGGAAGTCAAGGTTGCGTATTTGCC 151740
mRNA      ------------------------------------------------------------

genome    GTAGACTTCAACACAGTGTCGTAATGCGTGACGTCAATAACTTGTTTCTAGTGTCTTGGA 151800
mRNA      ------------------------------------------------------------

genome    AGTTGATCTTTAGTCGTAAAAGAGACCCTTGGATGCAGCGAGATTTCCTCTACTCACACC 151860
mRNA      ------------------------------------------------------------

genome    TCTGTTAGATGTAGTGAGGTTCTTCACCCCCCAACCCCAGATGTCAGAGGGCACCCTGCG 151920
mRNA      ------------------------------------------------------------

genome    CAGAGCTAGGAGGCCATGCAAAGCCTTGGTGTCCCTGTCCCTCACCCGTGGGCAGGTCCT 151980
mRNA      ------------------------------------------------------------

genome    GTGAGCAGTGGGGGGGCCACCTCTTGGGTATGGTGCAGCCATGGCCCAAGCAGGGCTTCT 152040
mRNA      ------------------------------------------------------------

genome    TCTCAGACCTACTAGGACGGGAGAAACCTCCTGGTGCTTTAGCCCTGCGTTGATATGCAG 152100
mRNA      ------------------------------------------------------------

genome    CAAATGGGAGGGAAGTGGGCACCTGGGAGGACAAATGCCTGTAGAGGCCGGGAGTGACGG 152160
mRNA      ------------------------------------------------------------

genome    CAGGTGTTCATGAAAAGAGACCTTGTGGGGAGGGCAACACAACAGTGTGTTCTGATGTAC 152220
mRNA      ------------------------------------------------------------

genome    TGAAGAGCTCAACTGAAAACAACAGGAGAATTAGCCCAAAATCCATTTACTAAAATTGTT 152280
mRNA      ------------------------------------------------------------

genome    TATCTTTTTTTTTTTTTTTGAGACAAAGTCTCGCTGTTGTCCCCCAGGCTGGAGTGCAAT 152340
mRNA      ------------------------------------------------------------
```

FIG. 1 RRRRR

```
genome    GGCGCTATCTTGGCTCACTGCAACCTCCGCCTCCTGGGTTCATACGATTCTCCTGCCTCA 152400
mRNA      ------------------------------------------------------------

genome    GCCTCCCAAATAGCTGGTATTAACAGGCATGCACCACCACGCCCGGCTAATTTTTGTATT 152460
mRNA      ------------------------------------------------------------

genome    TTTAGTAGAGACGGGATTTCACCATGTTGGCCAGGCTGGTCTCAAACTCCTGACCTCAGG 152520
mRNA      ------------------------------------------------------------

genome    TGATCCGCCCACCTCGGCCTCCCAAAGTGCTGGGATTATAGGCCTGAGCCACCACGCCCG 152580
mRNA      ------------------------------------------------------------

genome    GCCTAAAATTGTTTATCTTAAGATTCATGCAGTGAAAGCTAACTTACTGAGTGATAAATT 152640
mRNA      ------------------------------------------------------------

genome    TGCTTAGTGATCTGTTTATTAGGTTTTCCAAATTTGCTAATTGGGCTTTGAACAGCTGTA 152700
mRNA      ------------------------------------------------------------

genome    AAAGTTCTGACTGTAAAAGAAAGCTTCAACTTTTGGCATTCATGATGCTTTTCTGAGTAT 152760
mRNA      ------------------------------------------------------------

genome    TAAACTAAGATAGATGTTTTACCTGAAGGATCGGCCACCAATCTTTAAATGGCTAAACAA 152820
mRNA      ------------------------------------------------------------

genome    AAGGGTTGCTAAAACATAATCCAAATTGACATAAGAAATACCATTTTTCCAACCAAAATT 152880
mRNA      ------------------------------------------------------------

genome    TTGGCATTCATATGGCTACTTTTACGTATTTCAGCTGCATTTGAACATCTTTTTCAAACT 152940
mRNA      ------------------------------------------------------------

genome    TTAGGGTGGTTGGTGTATCACTGAGGTCTTGGATGACACTTTAGCTTTGATTTTGTTTTT 153000
mRNA      ------------------------------------------------------------

genome    ATGAATTAAAATTGTCATACCAAAATTTTTATTTCAAGCAAATCCAAGAGCATAAAAAAT 153060
mRNA      ------------------------------------------------------------

genome    TAAAATATTACTTAAAATACTAAGAGAGAACAGATATATATTTTACTAAGCATATGTTGA 153120
mRNA      ------------------------------------------------------------

genome    ATGAAATTGTTCAAATATTTATAACAGGCATAGAGTAGAATTTTCTTAAAAATATTTTTG 153180
mRNA      ------------------------------------------------------------

genome    ATGGTATACCAATTTGTATTTTCTCAGAAACATTTGCCTTATTCTTTTTTCTGTTGTGTT 153240
mRNA      ------------------------------------------------------------

genome    TTTCTTACCTGATTGAAAGCTCATAATCTGTTGTTATTGTTTGTTAACCTTTAATGCTCT 153300
mRNA      ------------------------------------------------------------

genome    GATTTCAGGAGTTCAACCTAAGCCTGCTAGCTCCATGCTTAAGCCTAGGGATGAGTGAAA 153360
mRNA      ------------------------------------------------------------

genome    TTTCTGGTGGCCAGAAGAGTGCCCCTTTTTGAAGCAGCCCGTGAGGTGACTCTGGCCCGTG 153420
mRNA      ------------------------------------------------------------

genome    TGAGCGGCACCGTGCAGCAGCTCCCTGCTGTCCATCATGTCTTCCAGCCCGAGCTGCCTG 153480
mRNA      ------------------------------------------------------------

genome    CAGAGCCGGCGGCCTACTGGAGCAAGTTGAATGATCTGTTTGGTAATTAAAATTAAAATT 153540
mRNA      ------------------------------------------------------------

genome    TATCTTATTTTTAAAAAGCATTCCAGGGCCAGTATAGTACTTTGCACCAAGTAAATGTAC 153600
mRNA      ------------------------------------------------------------
```

FIG. 1 SSSSS

```
genome    AATAAAGGCAGTGGATCTAATACATTGAAAGCGTTTACAGAGGTAGCTAAAGAGCAGCAC 153660
mRNA      ------------------------------------------------------------

genome    GGGTGTCCTCGGCTCAGAATTTCTTCCTGTGTGTTTGCCACTTTGCCATTCATTGACATG 153720
mRNA      ------------------------------------------------------------

genome    GTCATGGACATAGGGCTCTAAGCCCTTGAGGAAGGCTGGGCCAGACCTCAGGGGAGATGC 153780
mRNA      ------------------------------------------------------------

genome    AGCCCCAAACCACGTGCAGTCCTGTGGACGGATGTGTAGATGTGCCACTGAGGAACAATG 153840
mRNA      ------------------------------------------------------------

genome    TCTTGAGCTTTCATCAGATTCTCAGAGAATTGCTTGACTGCCTTTCGAAGTTGATGCATC 153900
mRNA      ------------------------------------------------------------

genome    TGTGCTCACGTTTGCACCCACCCACGAGGTCCTTCTGTTTCAGGGGATGCTGCACTGTAT 153960
mRNA      ------------------------------------------------------------

genome    CAGTCCCTGCCCACTCTGGCCCGGGCCCTGGCACAGTACCTGGTGGTGGTCTCCAAACTG 154020
mRNA      ------------------------------------------------------------

genome    CCCAGTCATTTGCACCTTCCTCCTGAGAAAGAGAAGGACATTGTGAAATTCGTGGTGGCA 154080
mRNA      ------------------------------------------------------------

genome    ACCCTTGAGGTAAGAGGCAGCTCGGGAGCTCAGTGTTGCTGTGGGGAGGGGGCATGGGGC 154140
mRNA      ------------------------------------------------------------

genome    TGACACTGAAGAGGGTAAAGCAGTTTTATTTGAAAAGCAAGATCTCTGACCAGTCCAGTC 154200
mRNA      ------------------------------------------------------------

genome    ACTTTTCCATCTCAGCCTGGCAGTAAGTCTTGTCACCGTCAAGTTATTGTAGCCATCCTT 154260
mRNA      ------------------------------------------------------------

genome    CACCCTCACCTCGCCACTCCTCATGGTGGCCTGTGAGGTCAGCCAGGTCCCCTTCTCATC 154320
mRNA      ------------------------------------------------------------

genome    TGCACCTACCATGTTAGGTGGATCCTAATTTTAGAGACATGAAAAATAATCATCTGGAAG 154380
mRNA      ------------------------------------------------------------

genome    TACTTTATGTCTTAAGTTGGCCTGGACATGTCAGCCAAGGAATACTTACTTGGTTTGTGT 154440
mRNA      ------------------------------------------------------------

genome    TAGTGCTTGTAATTCGCCCCCAGAATGTGTACACGTTCTGGATGCATTAAAGTCTGGCCT 154500
mRNA      ------------------------------------------------------------

genome    GTATCCTTAAAGGGCCATCGCTGTGCTGCCTGCCCTCAGCAAGGACACACTTTGCAGACC 154560
mRNA      ------------------------------------------------------------

genome    CACAGAGGCTCCGCCTCCACCTCACACCAAAGAAAGGGAGGAGTCCAAAGGGCATCAGTG 154620
mRNA      ------------------------------------------------------------

genome    CCATTACTCACAAAATGATAAATACACCCTTATTCTGAACCACGTGGAGTCATATGGTTT 154680
mRNA      ------------------------------------------------------------

genome    GTGATCCCTGTCCTTCAGGTTTCAGCTTAGTGGGGAAGTGGGAAAGTCAGCGTGTGATCA 154740
mRNA      ------------------------------------------------------------

genome    CAGCACAGGGTGATTGCTGCTGATTATATTATGTGCCTGCTGTATGCAGGATGAAATACT 154800
mRNA      ------------------------------------------------------------

genome    TTATATGCGTCATCTTATTTGACTCTCACAACCCCCTGTGAGATAGGCTCTGTTACTCCC 154860
mRNA      ------------------------------------------------------------
```

FIG. 1 TTTTT

```
genome          ATTTGACAGGTGAGGAAAGCAAGGCTTAGAGAATTTCAGTGACTTGCCCAGGTCCTCTGA 154920
mRNA            ------------------------------------------------------------

genome          GCTAGGAAGTAGCCATTCTGGCATTTGAACCCAAGGCCTGCTATCCCTAGAACCCACGCT 154980
mRNA            ------------------------------------------------------------

genome          CTCAAATTCAACCTATGACAGAGGCAAGCCCTGGTGCTGTGGGAGCCCCAAGGAAGAGCC 155040
mRNA            ------------------------------------------------------------

genome          TCTGGCCTGGTGGCCACGTAGCCCAGGAGAGATTTCTACAGGAGCCCACAGCGCTGAAGG 155100
mRNA            ------------------------------------------------------------

genome          AGAGAGAGGCAGCAGAGTAAGGGGGCTTTGTGGCAGAGAGGGGACTGGCACTTTGGGGAA 155160
mRNA            ------------------------------------------------------------

genome          TAGGTGGGTCAGGACTGAATGTAATGGAGCCATGTCAGAGCTGTCCTTCTGGAAGGGCAA 155220
mRNA            ------------------------------------------------------------

genome          GGGCACCTGGACGCGCTGCCCCTCAGTGCTTTGGACGGTTCCACAACTGTGATTCACACG 155280
mRNA            ------------------------------------------------------------

genome          GCTTCCCCAAACGAAGGTACACGAGTGGGCATTCTGTGACTCGGTACTTCCCTTTAGGCC 155340
mRNA            ------------------------------------------------------------

genome          CTGTCCTGGCATTTGATCCATGAGCAGATCCCGCTGAGTCTGGATCTCCAGGCAGGGCTG 155400
mRNA            ------------------------------------------------------------

genome          GACTGCTGCTGCCTGGCCCTGCAGCTGCCTGGCCTCTGGAGCGTGGTCTCCTCCACAGAG 155460
mRNA            ------------------------------------------------------------
                                            rs362331
genome          TTTGTGACCCACGCCTGCTCCCTCATCTACTGTGTGCACTTCATCCTGGAGGCCGGTGAG 155520
mRNA            ------------------------------------------------------------

genome          TCCCCGTCCATGAACGGTGGGTTCCTATCATAGTTCCTGTCTGCTTCACCATGTTTTTAT 155580
mRNA            ------------------------------------------------------------

genome          TTTGTGCTGCCTGTTTGCCAGGTACTAAGCTAGGAATTGGGGATGGAGAGGTAGATAAAA 155640
mRNA            ------------------------------------------------------------

genome          TATGCATCAGGAAGGGCTGGGCCCCATCTCTTACTCTCCAATATATTGGAGTCTACACTG 155700
mRNA            ------------------------------------------------------------

genome          GAATTTAACTGGAATTTGCTTTTTTAGTCATTTTATTTAGATTTTGAAGTTTCAGCTTTC 155760
mRNA            ------------------------------------------------------------

genome          ATCAAAAATACCTCTAAACTTTATGTCTCTGTGATCTTTGGTCTTAGCTGTTTTATGTAT 155820
mRNA            ------------------------------------------------------------

genome          TTAGTCTTATATGATCATAAGATTAATAACATTACATTCAGAAGATTATTTGTTTTCTGT 155880
mRNA            ------------------------------------------------------------

genome          CAGAGTTAAAATGTTTGTTTTTATACTGCATTGTAATATTAACGTACTGTAAAATAAAAG 155940
mRNA            ------------------------------------------------------------

genome          TGGCTTGTTCTTTTCAAGGAACAGTATCCTCAACAAGGGTCATTAGCCACAATTTTTAAA 156000
mRNA            ------------------------------------------------------------

genome          AAATTGGACGTCATAGTTTACATGTTAGAGGGCGTTTTGAAGCTTTGTATTTTTAAATTA 156060
mRNA            ------------------------------------------------------------

genome          AATGTTATAGAGTGATGTTTTCATGTTTCATAATTGTTTTCATCTGTGCATTTGTAGCCA 156120
mRNA            ------------------------------------------------------------
```

FIG. 1 UUUUU

```
genome          ACTTGAAAACAAAGATCCAGGGATTACTACTTAAAAGCCAGACTTCTTGGAGGTTATAGT 156180
mRNA            ------------------------------------------------------------

genome          GATGATTTTGATAGTATCTTGAGCCGTCTCATAATAACCTCAGGGTGAGAGATGGCCAAC 156240
mRNA            ------------------------------------------------------------

genome          AGGAGACAGTCGAGGGACTTAGAAATCTGAATGAAATCTGAAGTTCAAATCTTCAGACAT 156300
mRNA            ------------------------------------------------------------

genome          ATACCACTAACCAAGAGATTGGTACCTCAGTCTAGTATTGTCTGTTTGTCTAAAATTGGT 156360
mRNA            ------------------------------------------------------------

genome          TCTAAGGAATCTAGGCTAGTCTGTCTATCCCTTTCAACTTTTGTGAGGCTGCACAAATGT 156420
mRNA            ------------------------------------------------------------
                                                             rs916171
genome          AAAATGTTGAATAAAAAGCACTGATGGAAGTGTGTAGAAATTCTTCTCTTTGTTCTGTTG 156480
mRNA            ------------------------------------------------------------

genome          TAATTTTAGTTGCAGTGCAGCCTGGAGAGCAGCTTCTTAGTCCAGAAAGAAGGACAAATA 156540
mRNA            ------------------------------------------------------------

genome          CCCCAAAAGCCATCAGCGAGGAGGAGGAGGAAGTAGATCCAAACACACAGAGTAAGTCTC 156600
mRNA            ------------------------------------------------------------

genome          AGGACCCATTTTTTTCTTACATGTTGTTCCTCCAGGACTTAAAAATCATTCACAGAGACG 156660
mRNA            ------------------------------------------------------------

genome          TGCACCGCGGTGAGTGTGGACTCCTGGAAGCGCACCGTAGCTCCGCTGTGTCCTGCTGCT 156720
mRNA            ------------------------------------------------------------

genome          CCTCCCTAGCTGTCAGGGAGGCTGTAGTCCATTGCTTTGCCAGCTCTTTTGTTTCCGAGT 156780
mRNA            ------------------------------------------------------------

genome          GAACACCTTATCCGTACACATGCGGCTGTCTCTGACCCTACAGACCAGCTGGGATGCCAC 156840
mRNA            ------------------------------------------------------------

genome          TGGGGGAGCGCTCCCTTCCCCCCGCACTTCCCACACTCTGCAGTTATTCTGAGATCCTTG 156900
mRNA            ------------------------------------------------------------

genome          AGGGCAGGGAACAGGTTTGTCTTCTTTGTGTTCTCAGAAATTAATGCTCGGCCTCTGGTC 156960
mRNA            ------------------------------------------------------------

genome          AGCAAGCAACAACCTTTTGTTGAGTGATAATGAATAAATAAATGTTTCCCACATGAGTAT 157020
mRNA            ------------------------------------------------------------

genome          TCAGTAACCTCAGTGTCAGGTTCAGCCATCTGTTTTGGTGGATATTTAAAAGAAAATTCC 157080
mRNA            ------------------------------------------------------------

genome          GCTTTTCCTACAGAAAAAAAAAAAAATCCAAATCCCAGTGATTTAAGCCAGTTATAGACT 157140
mRNA            ------------------------------------------------------------

genome          TAGACATATACTACGGCTTTTCATGCACTTTCCTCCCAATTCTAGAGTAGGTATTTTACT 157200
mRNA            ------------------------------------------------------------

genome          AGGAAAATGGTGGCAGTGCCTGTTGGGAGGAAGATTCTTTGGCCAAGTGTCTTTTGTTCT 157260
mRNA            ------------------------------------------------------------

genome          TGCCAGGGCCCCTAGGCTGCTGGGGTGCTTCAGCTTCTTTAGCCCAGTGTCTGGTGGGGA 157320
mRNA            ------------------------------------------------------------

genome          ATGGCCCCTGTTGCCTGTCCCACAGAGGTGGGGGTGCCTCACCTGGAGCCTGTCCACACA 157380
mRNA            ------------------------------------------------------------
```

FIG. 1 VVVVV

```
genome    TTTTACACAGCACGCTTACCTGGAGCATCAGGCATCTTTTCCATGCTCTGTGGCTCAGGA 157440
mRNA      ------------------------------------------------------------

genome    AACACGCCTTTTCAATCATGAGTGCACCAGTGCTTTTGGGCTTTTTCTCCCCGCTTTTGT 157500
mRNA      ------------------------------------------------------------

genome    GCAATCCTGGTTGTGGATGGAGTTTTCCTGTCTTTAGTCTTCTGCATAGTACTTTTCTCT 157560
mRNA      ------------------------------------------------------------

genome    TCTGGTTCCCGGTTCAAGGTTTTGTAATTAGAGAATGACCCAGAAGCAATGGCATTTTAA 157620
mRNA      ------------------------------------------------------------

genome    TGCACAGCCAAGGACTTCTCTGAATTTGTATCTCAAACCTCTGTGGGTCCTTCAGGCTTC 157680
mRNA      ------------------------------------------------------------

genome    AGTTTGTGATTTCATGATTTCTTGTTGCTACCTAAGGAATATGAAAACACCCACCTCCCT 157740
mRNA      ------------------------------------------------------------

genome    ACTCTGCATCTTCCAGCCGAGTGGCACCTCAGGCTGTGGATCCTGTGCTTCTGTGGTGAG 157800
mRNA      ------------------------------------------------------------

genome    GATAAGAATAGTGCCAACCGTGTGGATTGAAATCAATCAGTTAATCCCTCCATGTAAAGC 157860
mRNA      ------------------------------------------------------------

genome    ACCTGGAACGGATGACAGTCTTGTTATGAATACTCAACAAATGCTATCATGATTTTTAGT 157920
mRNA      ------------------------------------------------------------

genome    TAGATTTCCATTGCTTTAAAACAGTTGAGACATCTTGGCGGTTTGAGTTAGAGCAACGGG 157980
mRNA      ------------------------------------------------------------

genome    CCCTGAAGTGGGTTCTGTTTGGGTGAAGATGATTATGCTTATTCCCCATGGCCCTCTTTA 158040
mRNA      ------------------------------------------------------------

genome    GGCAAGAGTGGGAAGCTTTCTTTGTTTTTTTAATCACCTCGATAGGACGTTACTTCTTAA 158100
mRNA      ------------------------------------------------------------

genome    AGGTCATCCAATAAATATTAATAGGCCGGGCGCGGTGGCTCACGCCTGTAATCCCAGCAC 158160
mRNA      ------------------------------------------------------------

genome    TTTGGGAGGCCGAGGCGGGCGGATCACGAGGTCAGGAGATCGAGACCATCCCAGCTAAAA 158220
mRNA      ------------------------------------------------------------

genome    CGGTGAAACCCCGTCTCTACTAAAAATACAAAAAATTAGCCGGGCGTAGTGGCGGGCGCC 158280
mRNA      ------------------------------------------------------------

genome    TGTAGTCCCAGCTACTTGGGAGGCTGAGGCAGGAGAATGGCGTGAACCCGGGAGGCGGAG 158340
mRNA      ------------------------------------------------------------

genome    CTTGCAGTGAGCCGAGATCCCGCCACTGCACTCCAGCCTGGGCGACAGAGCAAGACTCCG 158400
mRNA      ------------------------------------------------------------

genome    TCTCAAAAAAAAAAAAAAATATTAATAAAGCCAACTCGTTAGCGTGGGGCTTAATTGCTT 158460
mRNA      ------------------------------------------------------------

genome    AAGTCCAATGAGAAGTCCTTCTCTATCCTAGGAAGTTGCCCAAACTGTAGAATCTCGTGG 158520
mRNA      ------------------------------------------------------------

genome    CCTGTGGGTAATAGCCACGTAATACACACTCACTGCCTCAACAAATCATATTTTAGTAGG 158580
mRNA      ------------------------------------------------------------

genome    TATGATATTCTAGACTCAAGACACCATTCTGTGGATCTTCCCAAGGGTGTGAAGTGTCCA 158640
mRNA      ------------------------------------------------------------
```

FIG. 1 WWWWW

```
genome   CAGCGTCTGCCTTGGGAGTTTCCATGCCCACCAGAACCATGCCCCAAGCCCCTCAAGCAC 158700
mRNA     ------------------------------------------------------------

genome   TCTGACCTAGGAAAGCCAGTGAAGCAAGGATGACAACATGGCCCTTTGATACTAGCTGAG 158760
mRNA     ------------------------------------------------------------

genome   GGACAGACACAGGTCCTGGGAGACCAGAGAAAGACGAGGGGCAGAGGAGGTGTCCTAAAG 158820
mRNA     ------------------------------------------------------------

genome   GAAGTCTGAGGCTGAGGAGCCACAGGATGGCTTCCAGCTGTCACAGGCTGCTGCTGGCCT 158880
mRNA     ------------------------------------------------------------

genome   TATCACAGAGAGTGGGCCAGAGGGCTGGGAACCAAGGCCAGAGCTCAGGTTCAGGACCAT 158940
mRNA     ------------------------------------------------------------

genome   TCCAGCAATCCCAGCAGAAAATGGGGAGAATTGTATGGTATAGGCGGATATGAAGGTAGA 159000
mRNA     ------------------------------------------------------------

genome   ATCTGCAGGCCTTCAGTGGCCAACTCAGAGTCTAAGTGGATTCCACAGTTACAGCTTGAG 159060
mRNA     ------------------------------------------------------------

genome   CAGCTGGTTGTAGGTCATGCTTTCTACACTGGGCATATAGGATGTGTTTTTTAAAAAGTC 159120
mRNA     ------------------------------------------------------------

genome   CTCTCTTAACCGTTGCTTGTTTAGATCCTAAGTATATCACTGCAGCCTGTGAGATGGTGG 159180
mRNA     ------------------------------------------------------------

genome   CAGAAATGGTGGAGTCTCTGCAGTCGGTGTTGGCCTTGGGTCATAAAAGGAATAGCGGCG 159240
mRNA     ------------------------------------------------------------

genome   TGCCGGCGTTTCTCACGCCATTGCTAAGGAACATCATCATCAGCCTGGCCCGCCTGCCCC 159300
mRNA     ------------------------------------------------------------

genome   TTGTCAACAGCTACACACGTGTGCCCCCACTGGTGAGTCTGCTCGTTCCTTGCAGAAGAC 159360
mRNA     ------------------------------------------------------------

genome   CAAGTACGGTGAAAGGCACCGGTAGGCCCTGGGCTGGGCACACGTGAGAGGGCGGGACAG 159420
mRNA     ------------------------------------------------------------

genome   AATCCCCGCAGCCCAGAGGCTGCCTGCTGTGGTTCTGGTGCCCACTGTGGTTCTGGTGCC 159480
mRNA     ------------------------------------------------------------

genome   AGGCTGCTTTCCTCAGGCACCACGTGTGGAGGTCGCTAGTAGAAATACTGGGTTTTCTAA 159540
mRNA     ------------------------------------------------------------

genome   AATGAACTGAGGCCCTACATCCCTAAGAGATTAGTGTTAGACCTGATTCTAGAGCAACTA 159600
mRNA     ------------------------------------------------------------

genome   GACCACTTTGCTTAATAGCAGACCAGAAACCACACCCCCTCGAGTGAGTGAGATTTTCCT 159660
mRNA     ------------------------------------------------------------

genome   TTGGAGATAATTCATGTTTTTCTACACAGTTTTGCAGTTGTCTTCAGAATTGGTTTAAAG 159720
mRNA     ------------------------------------------------------------

genome   TAGGTGTTATTGCCAGGCGCAGTAGCTCATGCCTGTAATCCCAGCACTTTGGGAAGCCAA 159780
mRNA     ------------------------------------------------------------

genome   GGTGGGCGGATCACTTGAGGTCAGGATTTCGAGACCAGCCTGGCCAACATGGTGAAACCC 159840
mRNA     ------------------------------------------------------------

genome   CATCTCTACTAAAAATATAAAAATTAGCCAGGTGTGGTGGTGTACGCCTGTAATCCCAGC 159900
mRNA     ------------------------------------------------------------
```

FIG. 1 XXXXX

```
genome   TACTCAGGAGACTGAGACAGGAGAATCGCTTGAACCCAGGAGGCGAAGGTTGCAGTAAGC 159960
mRNA     ------------------------------------------------------------

genome   CGAGATCGCGCCACTGCACTCTAGCCTGGGCAACAGAGCAAGACTCCGTCTCAAAAAAAA 160020
mRNA     ------------------------------------------------------------

genome   AAAAGGTAGGTGTTATTGATCAGAACCCTTGTTTCAGATAACATGAGGAGCTTAGCTTGA 160080
mRNA     ------------------------------------------------------------

genome   GGAGAGTGAGGGTTGATGGAGGGGGACTGACTTCTGCCCAGTGAAATGGCATCATCTCCC 160140
mRNA     ------------------------------------------------------------

genome   ACCAGCCCGCTGAAATAAGATGATGGGGCCTGTTCCTTAGGGCCTGCAGCATCCTCAGGC 160200
mRNA     ------------------------------------------------------------

genome   AGGAAAGAAAGGCCGACCTGGCAGGGTGTGAGCCAGCAGGTGTAGGTCAGGGAGAATGGA 160260
mRNA     ------------------------------------------------------------

genome   GCCAGGTCCCAGGGAAGAGGCTTGTGGCTGCCTGAGAAGGGTGCGTGCCTGCCTGTGTGT 160320
mRNA     ------------------------------------------------------------

genome   GTGTGTGCACGTGTGTGTATGTATGCTGGAGAGTCTAGGGAGGCTTGCTCCAAGGACGCA 160380
mRNA     ------------------------------------------------------------

genome   GTATTGTTTGATCCTGAGAGATAAGGATTCTGCCGCAGGGAATGAAGGTATTCCAGATGG 160440
mRNA     ------------------------------------------------------------

genome   CGGGCTTATTCCGAAGAAGAGGCCAGTGCCTGGCGGTGCTGGAAGCAGTTGCAGAACAGG 160500
mRNA     ------------------------------------------------------------

genome   GAGTTGTAGGCTTTCCTGGGAAGAGAGCAGCAGGGGTGCTGGAGAAGCAGGCCACACTTG 160560
mRNA     ------------------------------------------------------------

genome   CTGCATGGGGTTGCTCTCGGCCCCACTCTTGGTGCACAGCGAGTCACTGTGGGTTCATTA 160620
mRNA     ------------------------------------------------------------

genome   GCATCTGGTTATGAGACAGTAACTGCTCCTTTGGAGGGGCTCGTGGAGACCATGCAGGAG 160680
mRNA     ------------------------------------------------------------

genome   GGCACGGTCTTGAGGTCATGCCGTCCAGAGCACACCTGAGGATAGGCCAGGACGGGCTGC 160740
mRNA     ------------------------------------------------------------

genome   ACGCTGTAGGTAAAATTCCTCCAGCAAGCTCTTCACTGGCATTGAGGAGTTCCCTGAGTG 160800
mRNA     ------------------------------------------------------------

genome   CGGTCATCTGGAAGGCAGCTGTAACAGGCACTGCAGTCTCTCCCTGGGTGGGTACCAGAG 160860
mRNA     ------------------------------------------------------------

genome   AGGAGCATAGGGGAGCATAACCGATTTAAAGAGAGGGCTTTCCTGTGGTGAGGTAAGAGA 160920
mRNA     ------------------------------------------------------------

genome   TTAGCTGGTCATTATCATAGAGCCCCCTCTGCCTTTGTGCAGATGGGCTGTGGGAATCCT 160980
mRNA     ------------------------------------------------------------
                                                rs362322
genome   GGGGTTCCGTTGGGTCCTTTGTCACCTCACTGAAGGCATGTAAGCTGAGCTGGCCAGACC 161040
mRNA     ------------------------------------------------------------

genome   GTGAGCTGATCCTGCCACTTGAACAGCATCAAGCCTGCCTCTGGATTCTTCTGTGCATGG 161100
mRNA     ------------------------------------------------------------

genome   CACTTGTCTGAGCACCTCACGCACAGAGAACTGGACTTCAGAGTTTACAGAAATAAGCTG 161160
mRNA     ------------------------------------------------------------
```

FIG. 1 YYYYY

```
genome          TATGGTTCATTTTCATGCCTGCTTGCCAATAAACATATCTGAGCTGAACCTCATTGAACG 161220
mRNA            ------------------------------------------------------------

genome          CCTGCCTTTATTCTAGCACAGCACCTGCTGTTTGTGGGCGAGGGGTGCTGTCTCTAACTC 161280
mRNA            ------------------------------------------------------------

genome          CTGCCTGCTTCTCCCAGCACTCCCTGAGTGGGGTGTGCCAGCAGCCTCAGGATGAGGACA 161340
mRNA            ------------------------------------------------------------

genome          GGAAGTGGGAGGGCAGAGCAGATTTGGGAGGGCCACTTGATGGGGAAGGAAGTCCCAGGA 161400
mRNA            ------------------------------------------------------------

genome          AGCAGTTGGAGCTGTTTTCTGGGGGAGAAGGTGCCAGCTCTGGGACAGTGTTGGGGTAGT 161460
mRNA            ------------------------------------------------------------

genome          GAGGAGGGAGCCCAGTGGAGAGAAGTCGGGCTTCCTGCTTCCTCACAGTATGTCTGTCCT 161520
mRNA            ------------------------------------------------------------

genome          GACTCAACTCGGATGATGTCACTTCCTTTTCATCTTCTCAGGTGTGGAAGCTTGGATGGT 161580
mRNA            ------------------------------------------------------------

genome          CACCCAAACCGGGAGGGGATTTTGGCACAGCATTCCCTGAGATCCCCGTGGAGTTCCTCC 161640
mRNA            ------------------------------------------------------------

genome          AGGAAAAGGAAGTCTTTAAGGAGTTCATCTACCGCATCAACACACTAGGTACTCTTGGGG 161700
mRNA            ------------------------------------------------------------

genome          CCTCTCCTTCAGGTCACCATTGTCGGACATCTACCGGGAGGAAATCCAGAGCCCCCAGTA 161760
mRNA            ------------------------------------------------------------

genome          CTGGGATCTTCTCATTTGACTCCAGAAAAGATTTAAGCATGATAATAATACAAACCTATG 161820
mRNA            ------------------------------------------------------------

genome          TGAATACATTTTGCAGTGTTGGCAAAACTCCTTTTATACTGAGAAAATAGATCCCAGTTC 161880
mRNA            ------------------------------------------------------------

genome          CTGTGTTTTGTGGCTTGAATCCCAGCTTTGTGTATTCCGGGCTTGTTTGAAGTCAGGAAA 161940
mRNA            ------------------------------------------------------------

genome          GGTTCATGTGTAGTGGACAACGTGAGACCAAATTCTGCCTTAGATTTTGCATTTAGGCTA 162000
mRNA            ------------------------------------------------------------

genome          AACAGTGGCAGCACTTGTCTCAGAATGTTTTCTTGTGTTCACCAGTCTGATCCTGTTGTG 162060
mRNA            ------------------------------------------------------------

genome          TCTCAGTGGTCCATTTTCTCATATGGGAACAAGCAGACGGGAGCAGATGGAGTCAGGTTT 162120
mRNA            ------------------------------------------------------------

genome          CTTGGCACTCGCCTTCCCCAGAGCCTAGAGGCAGCATGGGGAGAAAGCAGGCTTGGGGCT 162180
mRNA            ------------------------------------------------------------

genome          CAGACAGTCCTGGTCTGCTTCCAGCCCTCCTACCTGAGCAGCGCAGGGCAAGTCCGTCTA 162240
mRNA            ------------------------------------------------------------

genome          ACCTCTAGAGACCCTCAGTTTTGTCATATGTAAAATGGGGGTCGTGTCTATTTCATAGAA 162300
mRNA            ------------------------------------------------------------

genome          TTGTTGCAGATTTAGAAATTACATTTCTAAACAAATGTTACCCCTTATTTCTAAATAAGT 162360
mRNA            ------------------------------------------------------------

genome          GTCTAAATGAATAAGTCACCACTTTTGCCCCTATTTGATGGCAAGAGGTGTGATCTTGTG 162420
mRNA            ------------------------------------------------------------
```

FIG. 1 ZZZZZ

```
genome  GTGGGACTGTAATCAGTCAGTTCTCAGTGACTGTGCCCTGCTGTGGTGTTTCCTGGAATG 162480
mRNA    ------------------------------------------------------------

genome  TTCCTGTCTTGTCCTAGAAAGTCTGGCAGGGGCACCCTGACTCCACTGTCCAGTCCTCTC 162540
mRNA    ------------------------------------------------------------

genome  CCCAGTCCCTCGGGCTTCTGCAGATTTGAGGCTTGTTTGGATCCCAGAAGGTTGTGGCAG 162600
mRNA    ------------------------------------------------------------

genome  GAGACACCTTGCCTCTACTTTCCCCTTTATAATTCAATGTCCAAAGAGAGCCCTGAGCAG 162660
mRNA    ------------------------------------------------------------

genome  GTACCTCACGCCAGCTGCCTCACGGAGCTCCTCCTCTTCCTGGCTGTGAGGATCGGTATC 162720
mRNA    ------------------------------------------------------------

genome  AGTGGCCTCCTGCTCTCTCCCCCTTGCCTAACACGAGCACCTTTGCTTACTTGGGTGCCC 162780
mRNA    ------------------------------------------------------------

genome  TTGCTCTTGAACTGCCCATCGGACGTGCGTGACCCAAGACTGTGCCGCAGTCCTTGCCTT 162840
mRNA    ------------------------------------------------------------

genome  GTCTGTGCTCATTTTCTTTGTTCATTTTTTTCCCTGTAACGTAAATTGTTATATTTGTCT 162900
mRNA    ------------------------------------------------------------

genome  GTATCTGTGTCTGAATCAGTCCTGCACGCTCTCCTTCTCTCTGTCTCTTGTTCTTTCTTT 162960
mRNA    ------------------------------------------------------------

genome  ACCCCGTTTATCACGGGGACCCCGATGTCCATTGCTCTAGTTCTCCTGTCCTAAGCACCC 163020
mRNA    ------------------------------------------------------------

genome  CATCCCGTCTCTCTGGCCTTACCACAAGTGGCGTGGCTGCCTCAGACATCATGATGGGGA 163080
mRNA    ------------------------------------------------------------

genome  CATGAAGCACAGCTGTCAGAAACAACTGTTCGTTAGATACACTCGAATGCAGCTCATCAA 163140
mRNA    ------------------------------------------------------------

genome  TAGGGATGGAGGGTCTGTCGGATGTATTTTCACTGAATCCCCGTTCCTACCTTGATACAC 163200
mRNA    ------------------------------------------------------------

genome  TCTTTTTAATCTATTCTTCTAGACAGGTCAGAGGAACCATTACTTTGACTTTTAAATTTT 163260
mRNA    ------------------------------------------------------------

genome  TAGCAGCTTTATTGAGGTAGAATTCACATACTACAGATTTCACCCACTCTAAGCGGACAG 163320
mRNA    ------------------------------------------------------------

genome  CTTGGTGGCCATTAGTTTTATCCACAGAGTTGTGCAGCCAGCTGCACAGTCTCAGGGCTG 163380
mRNA    ------------------------------------------------------------

genome  GACTCCAGGGAAGATTTTAGCCCATTTAGTGAGTGGGGCAGAAGTGGCCCTGGCCCTGCA 163440
mRNA    ------------------------------------------------------------

genome  CGAGGTTGCCTGCATGGGCGTCCCTGCCCTGTCCCTGTGTCTGCTCCACTGGGGGTTGAC 163500
mRNA    ------------------------------------------------------------

genome  CAGGCTGCCAGGGCCGACTTGGGCCTGTGCCACCTGCCTCTCATGTGTCTCGGACAGTGC 163560
mRNA    ------------------------------------------------------------

genome  AGCCGATGTCTATACTTCGGTTTCCTCAATGATGAAATGGAGGGGATAGTGTTCCCCGCA 163620
mRNA    ------------------------------------------------------------

genome  TCATAGAACTGTGTGAGGTTTAAGGGACTCACTGCCCTTGGCGTGGAGCCTTCTCCAGGG 163680
mRNA    ------------------------------------------------------------
```

FIG. 1 AAAAAA

```
genome    GCCGTGCTGTGTCGGCGTAGCTGTCAGCTCTCCGTTACAGGCTTGAGAAGGGTTGACACT 163740
mRNA      ------------------------------------------------------------

genome    CTCTCATGTAACATTTATATTTCTAGGCTGGACCAGTCGTACTCAGTTTGAAGAAACTTG 163800
mRNA      ------------------------------------------------------------

genome    GGCCACCCTCCTTGGTGTCCTGGTGACGCAGCCCCTCGTGATGGAGCAGGAGGAGAGCCC 163860
mRNA      ------------------------------------------------------------

genome    ACCAGAAGTAAGGCCACACCCTGTGCTGGTTGGCACATGGGCAGTTATGGCCGCTTGCAG 163920
mRNA      ------------------------------------------------------------

genome    GCCTTTGGTGGGGAATAAAATAAGGCAGCAAGCTGGTGTTCTTTTTTTCTCTTACCTTAT 163980
mRNA      ------------------------------------------------------------

genome    TTTTGAAAGAGTAGCTGAATGGTGTCTTGACTGATATTCCAGAGCAGGGACAAAGCCTGC 164040
mRNA      ------------------------------------------------------------

genome    TGAGGTCTGGGGGCTGCGATTACCAATGGCTGGAATGCATTTTATTACGGTGCATTCCAT 164100
mRNA      ------------------------------------------------------------

genome    GTTAAGGATCAATACGATTGTGCCCTTTCTGGAAAATATCTTTTAGTTTATCAATATTCA 164160
mRNA      ------------------------------------------------------------

genome    GAGGAGTGTAGGTTGAATTAAAATGAAAAGGCACTTTATAAAGGCCATGAGTAGTACCTG 164220
mRNA      ------------------------------------------------------------
                                          rs362275
genome    GTTTCATTTTTCTAATGTCTTGCAGAGATTTTATCAGGCTTCTTGAAGTGTTCACGTACA 164280
mRNA      ------------------------------------------------------------

genome    TTACGCTAACACGATATTAATAATAACTGTGCTCTGGTACAGCGGAGCCAGCAGAATGGG 164340
mRNA      ------------------------------------------------------------

genome    AAGTTGTGGAATGCAGGCCCTTGATTCTGATAGAAGGTGTGGTTTGAACTCACAGAAATG 164400
mRNA      ------------------------------------------------------------

genome    ACAGTTTGGAGGGTAGACATATGTCACAAGTCATCAAGATTGTCTTTAAATTCATGCATA 164460
mRNA      ------------------------------------------------------------

genome    GAAGCTAACAGGGTGTCATAAGCAAGGCCTGTAAAATGTATGAGGGAATTCAAAGATAAT 164520
mRNA      ------------------------------------------------------------

genome    TTATTAAAAAGTAATTCATGTTTGGAGTTTTGTGCCCAAAGGAGTCCTTGATTTGAAAAA 164580
mRNA      ------------------------------------------------------------

genome    TGGGCTTTTGCCCATCAGATTGTTTCAGGGCCCGTGTGTGCGGAGGCCCTGCCTTGTGCC 164640
mRNA      ------------------------------------------------------------

genome    CCGTGAGCTCAGCCTGACAGAAATCCTTTGGTAGCACTTAAGGCTCCTCTTCCTCCCATT 164700
mRNA      ------------------------------------------------------------

genome    GAGGCAGGGAAGACTCTGGGTTCTGCAGGCAGAGGTGGTTGTGGGTGTCTTGCTGCTCTT 164760
mRNA      ------------------------------------------------------------

genome    GTTGACATGTGGGCTCTCCTTCCAGGAAGACACAGAGAGGACCCAGATCAACGTCCTGGC 164820
mRNA      ------------------------------------------------------------

genome    CGTGCAGGCCATCACCTCACTGGTGCTCAGTGCAATGACTGTGCCTGTGGCCGGCAACCC 164880
mRNA      ------------------------------------------------------------

genome    AGCTGTAAGCTGCTTGGAGCAGCAGCCCCGGAACAAGCCTCTGAAAGCTCTCGACACCAG 164940
mRNA      ------------------------------------------------------------
```

FIG. 1 BBBBBB

```
genome   GTTTGCTTGAGTTCCCACGTGTCTCTGGGACATAGCAGGTGCTGGGGACAGTGGGTTCCC 165000
mRNA     ------------------------------------------------------------

genome   CGCTGAAGCGTCCAGCAGCTTCAACCAGGCCGTTTTCCTTCATTGCTAGAATTGAAAACA 165060
mRNA     ------------------------------------------------------------

genome   CCGTCCGTGTGGCCTGTGCAGGAGATGCAGACCCAAAGGTGGCCTCCTGGTCAGTGAGAA 165120
mRNA     ------------------------------------------------------------

genome   GCTGGAAACGTGACAGGAACTGACGTGGGGTTATTGAGCATTTAGGGGAAGACGTTAGCA 165180
mRNA     ------------------------------------------------------------

genome   GAGCAGGAATGAGCAGGCAACTAGTAGAACACCCACTTAAGGGCTCACGGACAGGTGCTC 165240
mRNA     ------------------------------------------------------------

genome   ACTTAGGAAGTGAGTTTCATTTGGTATTACACCAGGTTCCTTTAGGCAAAGCGGAGGGAA 165300
mRNA     ------------------------------------------------------------

genome   AGTTCTGGTGTTTTTCACTTGTAAGATTTTGAAGGAAACAAAACACTCTTTACCTTTTTT 165360
mRNA     ------------------------------------------------------------

genome   CTAAAATGTAGGTTTGGGAGGAAGCTGAGCATTATCAGAGGGATTGTGGAGCAAGAGATT 165420
mRNA     ------------------------------------------------------------

genome   CAAGCAATGGTTTCAAAGAGAGAGAATATTGCCACCCATCATTTATATCAGGCATGGGAT 165480
mRNA     ------------------------------------------------------------

genome   CCTGTCCCTTCTCTGTCTCCGGCTACTACAGGTACCTGAGGGAAAGGGTGCGGGGGAGCG 165540
mRNA     ------------------------------------------------------------

genome   GTTGTACTTGGGCTAGAATGAGAGAAGACTGGCATGCTCACCACACCAGTGATGCGGGAA 165600
mRNA     ------------------------------------------------------------

genome   GACCTGAGTGTGGTCTGAGTTGGAGGCTGTGGTGCTAAATACGCTGCCCCTTTCATAAGC 165660
mRNA     ------------------------------------------------------------

genome   AGGAGTCTTAGTCAGGCCCAGGGAGGAAGTAAAATCTGGAAATGAATGAGAAGCATTCTC 165720
mRNA     ------------------------------------------------------------

genome   TCCTGCCAGTCAAGAAATGAGAAGCGAAAGAATTCTCACGGGCTGTAAGACCAGCAGGAT 165780
mRNA     ------------------------------------------------------------

genome   TTAAAAGTTGAATTAGTTGCTTATGTTAAGAACTCAACCAAGTTCATCTACACAAGCTGA 165840
mRNA     ------------------------------------------------------------

genome   ATCTCCAGCTTTTCCTAAGAAACCATGTGTGGCAGTGGCTGCAGGGCAGGGCACAGCTGG 165900
mRNA     ------------------------------------------------------------

genome   GCCTGAGCACCCCGCTCCCTGCACCTCTCCCCTCCCTGGGCCCTGCCTGTCACTGCCCAC 165960
mRNA     ------------------------------------------------------------

genome   TCTCCCACCAAGCCTTCCGGTTGTGTGCCTGCCCTATCACAGGCATCGGAGCTTGTCACC 166020
mRNA     ------------------------------------------------------------

genome   TGGTTTAAAAGAAGAGAGTTGTGTGGGGATTTGGGATGCACGTTTTTCACTCAAAAGTAT 166080
mRNA     ------------------------------------------------------------

genome   TTTAGCGTAGAGCTCTGTGATTCCGTAGCTATTTAGGAGTTTAAGCACCTTGAAGGCTTT 166140
mRNA     ------------------------------------------------------------

genome   AATTGCAGAAAGTTCTATGTGGACGTGCAATGTGTTATACGCAGTGTCTATGAGACTCAA 166200
mRNA     ------------------------------------------------------------
```

FIG. 1 CCCCCC

```
genome  ATGTTTATTAGGGCGTTGAAGTAAACTGAGCACTTGGAGGGCCATGGATCCAGCCTTCAA 166260
mRNA    ------------------------------------------------------------

genome  GGAGCTCATAAGTCAGGAGGACCCAGGAGCAATGACCTGTCATAGAAGGCAGAAAAGAGG 166320
mRNA    ------------------------------------------------------------

genome  GGCACAGAGGTGGGTGGGAGGCATACACAGGCAGCTCCTGGAGCTCCAAGGGGAGCAAGT 166380
mRNA    ------------------------------------------------------------

genome  GCTTCCAGGGAAGGGGGCGTGGAGGCCCCTTTGGAGGAGGCAAGTTGATCTGGGGTCTGG 166440
mRNA    ------------------------------------------------------------

genome  CAGAGGGTTAGCTGGGGACATTTAGCGGGAGGCTGGTGCCCGGGAATTGGGGGGATGCCC 166500
mRNA    ------------------------------------------------------------

genome  AGCAGAAAGACATGAGGAGGCTGGCCTGGGGCGTGGGGGGGTGTGAAAGGTTAAGTGGGG 166560
mRNA    ------------------------------------------------------------

genome  GCATTATCCTGCTCCCGCTCCTGCCGGCTGTATCTGGTCAGCCTGGGCACCGAGGTGGGG 166620
mRNA    ------------------------------------------------------------

genome  TTCTGGAAGGCACTGTTCACCAAAATGCTTATCTGGGTCCCCCAGAGAGCTTGCCTGCCT 166680
mRNA    ------------------------------------------------------------

genome  GGACTGTCGGCTCGCCTGCAACTGCTGACTCCTAAGCTTTTGCAGCTCAGCCCACAACCA 166740
mRNA    ------------------------------------------------------------

genome  GTTCCTATTCACAGAGGTGGGAGCTGAGGGGTGACAAGTGACTGCTGCAGTCTTATTTGT 166800
mRNA    ------------------------------------------------------------

genome  CATAGAGAAAAAGTGACAGAGTCCAGCTTGCCCACTGGCCCTGCCAGCTTAACTGGTTAT 166860
mRNA    ------------------------------------------------------------

genome  AAAGTGACAAATCCCCAAGACCCACAGGGCTCTGCACAACCTGGGCCCTCCTGCCAGTGG 166920
mRNA    ------------------------------------------------------------

genome  CGGCGAGGGCAGGTGGCTCACGGCTGGGTGCCTGTCTGGGCAGGAGCTGGGCTGGTATGG 166980
mRNA    ------------------------------------------------------------

genome  GGTGGGCCTGCGGCCCTGCCCCCCTGTGCAGATCAAGACTCAGGGTGCTGGTGTTCACAG 167040
mRNA    ------------------------------------------------------------

                                    rs362273
genome  GTGCCCTCATCAGCCACGAGAAGCTGCTGCTACAGATCAACCCCGAGCGGGAGCTGGGGA 167100
mRNA    ------------------------------------------------------------

genome  GCATGAGCTACAAACTCGGCCAGGTCAGTCTCGCGCCCCCGCCGCCTGGCCTCTGTCCGT 167160
mRNA    ------------------------------------------------------------

genome  TTCTGTCCTCAGACTTTGGCGCTTGACACACCCAGGAGAAAAGCTCAGTGCACTTTTTAA 167220
mRNA    ------------------------------------------------------------

genome  ATGAAAGGAAGTTTTCCTTTTTTTTAAAAAAAAATTTAATGTTCATTGTTTTTATCTGTT 167280
mRNA    ------------------------------------------------------------

genome  TTATTCCTAGGTCCCGCAAGCAGAGGAAGCATTAGTTTTGTTTTTATTTATGTTCTGTAT 167340
mRNA    ------------------------------------------------------------

genome  TCCAGAAAGTAGTTAAGAGACCTCACATGTAGCGATAGAGATGTGTGTAAGAGACAGTGA 167400
mRNA    ------------------------------------------------------------

genome  GAGGGCGTGACTTGGACTTAAGCAAGGACCGTGAGACACAAAAAGGGGGGTGAGGACAGA 167460
mRNA    ------------------------------------------------------------
```

FIG. 1 DDDDDD

```
genome    GTGGAGTCAGCTGAAATGCTCAGGAGGAAGTAGACGCCATGAAGGGCCATGGTATGGGGG 167520
mRNA      ------------------------------------------------------------

genome    GCCGCAGGCGTGGCCGTGAGTGTCCCTGGGGCCAGCTCTTGGGGGGCTCCCTGAGTGTCC 167580
mRNA      ------------------------------------------------------------

genome    CTGTCCCTGTGGCCAGTTCTGGGTGGGAGCCCCGTGTGCAGGCAGACAGCTCGGCCACTT 167640
mRNA      ------------------------------------------------------------

genome    CCTAGCAGGTCACATTGGTCTGTGCTTCTGTTTCCTCCTCAGATAAGTGAAGGGATTCAA 167700
mRNA      ------------------------------------------------------------

genome    GGGTCTGGGTGTGGTGGCTAACACCTGTAATCTATAACATTTTAGGAGGCTGAGGCAGGA 167760
mRNA      ------------------------------------------------------------

genome    GGCTTACCTGAGCTCAGGAGGTTGAGGCTGCAGTGAGCCATGATTGCACCACTGCACTCC 167820
mRNA      ------------------------------------------------------------

genome    AGCCTGGGCAACAGACCAGTACTCTGTCCCTTAAAAAAAAATGTAAACAGAAACGTAGGG 167880
mRNA      ------------------------------------------------------------

genome    CCATTTGCATATGATGGCACATGGCGTGGAGCCCTACAGGTGTATGCTGGGCGGGGCCCG 167940
mRNA      ------------------------------------------------------------

genome    GCTGTGCTGGCCGACTTGCACCTTTCCCTCCACCCCGGTGCTGTGTCTTTCGCTCACCGG 168000
mRNA      ------------------------------------------------------------

genome    GTTCCTGATTTAGTGAAAGCAGTTGTGCAGGACAGTTCTCTTTGTAGCTTTTGTTTCTGT 168060
mRNA      ------------------------------------------------------------

genome    GGAAATGGGTCAGAATATGGTGTTTAGAAACACTTATGAGCTCTGAGAGTTTCCTCTTCT 168120
mRNA      ------------------------------------------------------------

genome    GAGTTCCTGGCCTGCAGCCTTCACAGCAGAAACCCTGTGATGTCACAAGCCTGTTTCTGT 168180
mRNA      ------------------------------------------------------------

genome    TCCCTGCTCTCTGCCTGTACTGTCCTGTTTTGTGCCTGCCGGTTTCAGTGACAGGAAGCA 168240
mRNA      ------------------------------------------------------------

genome    GGGAGCTACTGGACCAGCCTGTATTTTTCTAGACATAGTTGGAAAAAGAAGTCCCACTCT 168300
mRNA      ------------------------------------------------------------

genome    TCTGTCCTTTCACCTTTGACAGATGTTTCCACCCCAAGATAAGTGAAAATGACCAATAGG 168360
mRNA      ------------------------------------------------------------

genome    ATGCACTGTATTTTTCATGAAAGTGTTTCTGAAGGGCAGGCTGAGAGTGAGAGGCCTGGG 168420
mRNA      ------------------------------------------------------------

genome    GCTCACTGGGTGCCTCTGGCCTTGTCCTGGGCCCAGGGACACTGGTCTGTGCCCGAGGTA 168480
mRNA      ------------------------------------------------------------

genome    TTCCCTATCCCCCCAACCCCGCTGCATTTGGCCACATCCTTCAATGTTTGCGTTGTGTCC 168540
mRNA      ------------------------------------------------------------

genome    AGCGTCCGCAAACCAACTGTCATGGGATCATACTGGGGCTGAAGTACGGTCCCACCCCTG 168600
mRNA      ------------------------------------------------------------

genome    CCCTGTCTGGGGCTGAAGTACAGTGCCACCCCTGCCCTGTCTGGGGCTGAAGGACAGTGC 168660
mRNA      ------------------------------------------------------------

genome    CACCCCTGCCCTGTCTGGGGCTGAAGTACAGTGCCACCCCTGCCCTGTCTGGGGCTGAAG 168720
mRNA      ------------------------------------------------------------
```

FIG. 1 EEEEEE

```
genome    GACAGTGCCACCCCTTCCCTGTCTGGGGCTGAAGGACAGTGCCACCCCTGCCCTGTCTGG 168780
mRNA      ------------------------------------------------------------

genome    GGCTGAAGGACAGTGCCACCCCTGCCCTGTCTGGGGCTGAAGGACAGTGCCACCCCTGCC 168840
mRNA      ------------------------------------------------------------

genome    CTGTCTGGGGCTGAAGGACAGTGCCACCCCTGCCCTGTCTGGGGCTGAAGGACAGTGCCA 168900
mRNA      ------------------------------------------------------------

genome    CCCCTGCCCTGTCTGGGGCTGAAGGACAGTGCCACCCCTGCCCTGTCTGGGGCTGAAGGA 168960
mRNA      ------------------------------------------------------------

genome    CAGTGCCACCCCTGCCCTGTCTGGGGCTGAAGGACAGTGCCACCCCTGCCCTGTCTGGGG 169020
mRNA      ------------------------------------------------------------

genome    CTGAAGGACAGTGCCACCCCTGCCCTGTCTGGGGCTGAAGGACAGTGCCACCCCTGCCCT 169080
mRNA      ------------------------------------------------------------

genome    GTCTGGGGCTGAAGGACAGTGCCACCCCTGCCCTGTCTGGGGCTGAAGGACAGTGCCACC 169140
mRNA      ------------------------------------------------------------

genome    CCTGCCCTGTCTGGGGCTGAAGGACAGTGCCACCCCTGCCCTGTCTGGGGCTGAAGGACA 169200
mRNA      ------------------------------------------------------------

genome    GTGCCACCCCTGCCCTGTCTGGGATGTTTAGCCCCTAGATGCCACTGGACTGAGCCGCTA 169260
mRNA      ------------------------------------------------------------

genome    CTTGCTTTTGGGAAAGAGGGGTGGGGGTTAGGGGTCTGGGCGAGGGGAGTGCAGGGGCTC 169320
mRNA      ------------------------------------------------------------

genome    CTCCTTGGCCTGAGAGCTGTTCATACAGACTCCTCGCCCACTCCCTGCAGGGTGCTGGGT 169380
mRNA      ------------------------------------------------------------

genome    CCCAGGGGGGAAATGGCCCTTGGTGCCAAGAACGTGAGTTGGGGCTAGTGCCAGTGATGA 169440
mRNA      ------------------------------------------------------------

genome    TGGAGAACAGCTTTTTATGGGCACACAGCCCACAGCACTGTGCCAAGTGCTCGAGGCTTC 169500
mRNA      ------------------------------------------------------------

genome    CCGAGAACCAGGCAGAAAGGAGGACAGTCGAGGTGTGCTGACTGCGTGGTGGCTGCGTGA 169560
mRNA      ------------------------------------------------------------

genome    TCTAGAGCGCGGGTCACAAAGGCGCGAGGGAGCTCTGGCCTTGGGTTTACCGCAATGACT 169620
mRNA      ------------------------------------------------------------

genome    GCCAGTGCGGGAGACTGGAAAAGGAATCTCACGTATTGGTTCCGTGTTTTGGGGACTCCA 169680
mRNA      ------------------------------------------------------------

genome    TTCAGATGTCACTTAGGAGTGAAAGCATCCCTTCGTAGAGCCTCTTTCTGTGTCACCCTC 169740
mRNA      ------------------------------------------------------------

genome    CTCAGCTGCTCCTGGGGTTGACTGGCCCCTGATTCATGCCTTTAGCATGTGCTGGAGCTT 169800
mRNA      ------------------------------------------------------------

genome    CCCAGCAGCTGTCCAGCCCCTGCCCCACCCTCTCTGTGGGCTCCCTTGCCCGTAACCTGG 169860
mRNA      ------------------------------------------------------------

genome    GGTGTCTGAACGACCCTTGCTAAGGGGCAGACTGTTAGACGGTAGGCATGTGCTGAGTCC 169920
mRNA      ------------------------------------------------------------

genome    CAGTGGCCACACCCACCCACCAGGAGCCTGGCACTGTGGCCGCAGCACTGAGCAGTGCCC 169980
mRNA      ------------------------------------------------------------
```

FIG. 1 FFFFFF

```
genome            CGTTTCTGTGGCAGGTGTCCATACACTCCGTGTGGCTGGGGAACAGCATCACACCCCTGA 170040
mRNA              ------------------------------------------------------------

genome            GGGAGGAGGAATGGGACGAGGAAGAGGAGGAGGAGGCCGACGCCCCTGCACCTTCGTCAC 170100
mRNA              ------------------------------------------------------------

genome            CACCCACGTCTCCAGTCAACTCCAGGTTTTCCAATGGCCTTTTTCTTTTTAACAGAAATT 170160
mRNA              ------------------------------------------------------------

genome            TGAAATTTCTTATCAGTCATTTGATTTGTTTGAGGTGCTTCTTGAAATGAGCCTCTCATC 170220
mRNA              ------------------------------------------------------------

genome            TCATGTACTTGGAAAATACCCATCTCGCATATTCCACAGGAAACACCGGGCTGGAGTTGA 170280
mRNA              ------------------------------------------------------------

genome            CATCCACTCCTGTTCGCAGTTTTTGCTTGAGTTGTACAGCCGCTGGATCCTGCCGTCCAG 170340
mRNA              ------------------------------------------------------------

genome            CTCAGCCAGGAGGACCCCGGCCATCCTGATCAGTGAGGTGGTCAGATCCGTAAGTGAGCC 170400
mRNA              ------------------------------------------------------------

genome            TTCCCATTCCCCTCACACCTGCACGTGCCACACGCACCACACACGCCACACACCCCACAC 170460
mRNA              ------------------------------------------------------------

genome            ACACACACCGCCCACACACATGCCACTTGCACACACACCCCTCATGCATGCAACACACAC 170520
mRNA              ------------------------------------------------------------

genome            ACAGGCCACACGCACCATAGACACCACACACACATGCCACATGCACACACATACACGGCA 170580
mRNA              ------------------------------------------------------------

genome            TGCACCATACACACAACACACACAGCACACATGCCACACACACACGCCACACCACATGCA 170640
mRNA              ------------------------------------------------------------

genome            CCACACACATGCCACATGCACACACACTCCACATGCATGCACCACACACACACACACACA 170700
mRNA              ------------------------------------------------------------

genome            CCACACACACCACATGCACCACACCACACAGGTTACATGCACACAACACACACATGCCAC 170760
mRNA              ------------------------------------------------------------

genome            GTGCACACACCCCACACACCACATGTATGTGCCACACACAGCACACAACCACACACATGC 170820
mRNA              ------------------------------------------------------------

genome            ACCACACACATGCCACATGTGCATGCACCAGACACATGGCACACACTACACACACGCCAC 170880
mRNA              ------------------------------------------------------------

genome            GTGCACACACCCCACACACATGTACGCACCACACACATGCCACACACACATGCACCACAC 170940
mRNA              ------------------------------------------------------------

genome            ACATGCCACATGTACACACATGTATATACACACCCCACACCACACACACACCACTTGCAC 171000
mRNA              ------------------------------------------------------------

genome            ACCACGCACACACACCACATGCGCACACACACACCACATACGCCACATGTACACACCATA 171060
mRNA              -----------------------------------GCTGCCGGGACGGGTCCAAGATGGA 25
                                                      *   **  **  ** **      *
genome            CACACACCATACATGCACCACGTGTACCACGCACCCACACAGACACAGCACACGCATACA 171120
mRNA              CG---GCCGCTCAGGTTCTGCTTTTACC-TGCGGCC-CAGAGCCCCA-TTCATTGCCCCG 79
                  *     **   ** *  *  * * ****  **  ** ** ** * **   **      *
genome            CCACACACACACGCACACATGCGTCCCGCACAGTAATGTCTCTTGGGTGTAAGAACACGA 171180
mRNA              GTGCTGAGCGGCGCCGCGAGTCGGCCCGAGGCCTCCGGGGACTGCCGTGCCGGGCGGGAG 139
                     *  *    ***    *  ** ****     *   *   **   ***   *
genome            CTTGCCAGTAGTAGCGTTCTGGATGCGTTGCCTGGATTCTAACAGCGCGATTCTCCCCTT 171240
mRNA              ACCGCCA-TGGCGAC--CCTGGAAAAGCTGATGAAGGCCT------TCGAGTC-CCTCAA 189
```

FIG. 1 GGGGGG

```
            **** * *   *   *****   * **        **       *** ** ** *
genome   GCCCTCCTGGTTTTCCACATCTCCAGCTTCTAGTGGTCTCAGACTTGTTCACCGAGCGCA 171300
mRNA     GTCCTTCCAGCAG-CAGCAGCAGCAGCAGC-AGCAGCAGCAGCAGCAGCAGC--AGCAGC 245
         * *** *  *    *  ** *  ****  * **  *   ***         *  ***
                  [rs2276881]
genome   ACCAGTTTGAGCT[G]ATGTATGTGACGCTGACAGAACTGCGAAGGGTGCACCCTTCAGAAG 171360
mRNA     AGCAGCAGCAGCAGCAACAGCCGCCACCGCCGCCGCCGCCGCCGC-CTCCTCAGCTT 304
         * ***    *** *    *   * * * * *    * **    *  ** * * ****
genome   ACGAGATCCTCGCTCAGTACCTGGTGCCTGCCACCTGCAAGGCAGCTGCCGTCCTTGGGA 171420
mRNA     CCTCAGCCGCCGCCGCAGGCACAGCCGCTGCTGCCTCAGCCGCAGCCGCCCCCGCCGCCG 364
          *     *  ***      *   *   ****  ***     ***** ***  *   *
genome   TGGTAAGTGACAGGTGGCACAGAGGTTTCTGTGCTGAAGCCACGGGGGCCCATCTGCCTT 171480
mRNA     CCCCCGCCGCCACCCGGCCCGGCTGTGGCTGAG---GAGCCGCTGCA-CCGACCAAAGAA 420
                 * **    *** *  * **   *** *    **** * *   ** * *
genome   GGGACCTGGTGTTGGCCAGAGGTGCCGGGTGCGGCTGCCTCCTTCCAAGAGTTGACCCGA 171540
mRNA     AGAACTTTCAGCTACCAAGAAAGACCGTGTG-AATCATTGTCTGACAATATGTGA---AA 476
          * ** *   *  *  * ***    *** ***          **  *** *  ***    *
genome   ACCGGACTCCACGGCCCACGTGAG---CTGCAGTGCTTCTCAGATGGAGGGGGTTCAGCG 171597
mRNA     ACATAGTGGCACAGTCTGTCAGAAATTCTCCAGAATTTCAGAAACTTCTGGGCATC-GCT 535
         **       *** * *     **    **  ***   ***  * *     ***  ** **
genome   ACGGTCAGTGCCATTCACAGGTCACTG-TGATGTGGGTTGTGGCGGCCAAGCCATGGTTT 171656
mRNA     ATGG--AACTTTTTCTGCTGTGCAGTGATGACGCAGAGTCAGATGTCAGGATGGTGGCTG 593
         * **  *      *   * *  ** ** *** *  *  *  *  * *       *** *
genome   GGGGTCCCGTATCCCTGGGCTTATGACATCATTGTAGTAGCCCATCCCCACAGAACCACG 171716
mRNA     ACGAAT--GCCTCAACAAAGTTATCAAAGCTTTGATGGATTCTAATCTTCCAAGGTTACA 651
           *     *  **       **** * * * ***  * *  * *  *   **     **
genome   GTGTGTGGTGGCGCTGAGGCATCGTAGATGGTGGAAATGCTACTGGCTTCCCCATGCTCT 171776
mRNA     GCTCG-AGCTCTATAAGGAAATTAAAAAGAATGGTGCCCCTCGGAGTTTGC----GTGCT 706
         *   *  *         *  **   * *   ***     **    * **  *    *  **
genome   GCCCTGAGGCCTGACTGCCTCACTCCCCTTCTCAGTTATGTTCCAGGCCCCCCGAGCTTC 171836
mRNA     GCCCTGTGGAG-GTTTGCTGAGCTGGCTCACCTGGTTCGGCCTCAGAAATGCAGGCCTTA 765
         ****** **   *  ***    **  *   *   ***  *   ***     * *  ***
genome   CTGGCTGGACAGCTTCTCTCCTGGGGGCCGTTTTGTCACAGTGACCCTGTGTTTCTAGTC 171896
mRNA     CCTGGTGAACCTTCTGCCGTGCCTGACTCGAACAAGCA-AGAGACCCGAAGAATC-AGTC 823
         *  * ** **    *  *      *   **      ** ** *****   *  ** ****
                  [rs3121419]
genome   CCAAATCTGGGTG[C]TATAGTCTCTTTTTAGCGTGGTGGTTGTCTTAGTCTTTTTTGGCTG 171956
mRNA     CAGGAGACCTTGGCTGCAG-CTGTTCCCAAAATTATGGCT----------TCTTTTGGCAA 873
         *   *       ***  ** ** **   *   *  *** *         * *******
genome   CTACCACAAGTTACCTTAGACTGGGTAATTTATAAACAGTGGAAATTTACTTCTCACCGT 172016
mRNA     TT-TTGCAAATGACAATGAAATTAAGGTTTTGTTAAAGGC---------CTTCATAGCGA 923
          *    *** * **  *  * *      *** * **  *          ****  * **
genome   TCTGGGGGCTGGAAGTTTTCATGGTCAAGGTGCCAGCAGATTTGGTGTGTGATGAGGGCT 172076
mRNA     ACCTGAAGTCAAGCTCCCCCACCATTCGGCGGACAGC-GGCTGGATCAGCAGTGAGCATC 982
          *  *  *           **   *   *  *  **** *  * * *  *   ****
genome   GCTCTCTGCTTCATAGATGGCATCTTCTGGCTGGGTCCTCACGGTGGAAGGAGTGAACAA 172136
mRNA     TGCCAGCACT-CAAGAAGGACACAATATTTCTATAGT-TGGCTACTAAATGTGCTCTTAG 1040
            *    ** **    * * **   * *  **      *  *     ** * *     *
genome   GCTCCCTCAGGCCTTTTAGAAGGGCCCCAATCCACAAGGGCTCTCCCATCATGACCTCAT 172196
mRNA     GCTTACTC-GTTCCTGTCGAGGATGAACACTCCACTCTG-CTGATTCTTGGCGTGCTGCT 1098
         ***  *** *  * * * ** *     ** *****   * **    * *   *  **  *
genome   CACCTCCCAAGGCCCCACCTTCTTGTACTGTGGCACTGCAAATTAGGTGTCAGTGTAGGA 172256
mRNA     CACC--CTGAGGTATTTGGTGCCCTTGCTGCAGCA--GCAGGTCA------AGGACACAA 1148
         ****  *  ***       **    * ***  ***  ***  * *      **   *  *
genome   GTTTCAGGAGGGATAGAAACATTCAGACCATCCCAGCGGTCAAGTGTTCATCCTCTTGAG 172316
mRNA     GCCT---GAAAGGCAGCTTCGGAGTGACAAGGAAAGAAATGGAAGTCTCTCCTTCTGCAG 1205
         *  *   **  *  **   *     *** *    **   *  *    **  * ***  **
genome   TTCCTCCTTATTCTGCTTCTGGTTTATCAGGATTCAGCCAGTGCAGCAT-GGTACCTGTA 172375
mRNA     AGCAGCTTGTCCAGGTTTATGAACTGAC--GTTACATCATACACAGCACCAAGACCACAA 1263
           *  * *      * ** **   *  *  * * ** *     *****     ***   *
genome   TTCTGTGGCACATCACCACATGGTATTTGC--CAAGTATCCATCACCTGCACACGTGAAA 172433
mRNA     TGTTGTGAC-CGGAGCCCTGGAGCTGTTGCAGCAGCTCTTCAGAACGCCTCCACCCGAGC 1322
```

FIG. 1 HHHHHH

```
                  *  **** * *    **     *   ****  **  * * **  **     ***  **
genome            TCATTGCCCGTGGGTCCCGACATCTGGCGAAGCATATTCAAGGATGGCAGAACTGTCAGA 172493
mRNA              T-----TCTGCAAACCCTGACCGCAGTCGGGG-GCATT-GGGCAGCTCACCGCTGCTAAG 1375
                  *      * *    ** ***  * * **  *   ***   * *   **   ***  *
genome            GCTGGCACCTCTGGTTCCTTGTCAT-GTGGCATTACCTAGTAATCCATTTTATGATAGCA 172552
mRNA              GAGGAGTCTGGTGGC-CGAAGCCGTAGTGGGAGTATTGTGGAAC------TTATAGCTGGA 1429
                  *  *   *   ***  *   * * * **** * **    * **       ****   * *
genome            ATGGAAACTCATTTCTTCAACAAACACCTGAGTGGCTGCCGTGTGCCAGCCGTCTGGGGC 172612
mRNA              GGGGG-------TTCCTCATGCAGC-CCTGTCCTTTCAAGAAAACAAAAAGGCAAAGTGC 1481
                    **       *** ***   * * ****                 *    *    * **
genome            CCTTGGTGAGAATGGCATGGTGGTGCCCATCAGGGCCTGCCTAGCCCGTGCTCTGG-ACG 172671
mRNA              TCTTAG-GAGAA------GAAGAAGCCTTGGAGGATGACTCTGAATCGAGATCGGATGTC 1534
                   *** * *****        *   *  ***    ***      **    ** * ** *
genome            GGCTCCTGTGTGTCAGGAACGACAATGCTGTCATGACGGTGAATGATTTTTTTTTTTGCC 172731
mRNA              AGCAGCTCTGCCTTAACAGCCTCAGTGAAGG-ATGA-GATCAGTGGAGAGCTG----GCT 1588
                   **  ** **  * *  * *  ** **  *  **** * * * **       *    **
genome            ATCACTCCAGCCGCTAACATTTGCGGAGCTCTTCCTCCCGCACCCCCACCTGACAAGGCC 172791
mRNA              GCTTCTTCAGGGGTTTCCACT--CCAGGGTCAGCAGGTCATGACATCATCACAGAACAGC 1646
                      ** ***  * *  ** *  *   * **  *     *     *  ** *  * **   *
genome            AAGGGTGACCTTGGCCCCACCCTAGGCGGCCAAGGTCAGAGGTTAGCTGGCTTGTCTGGG 172851
mRNA              CACGGTCACAGCA--CACACTGCAGGCGGAC----TCAGTGGAT--CTGGCCAGCTGTGA 1698
                   * *** **       * ***  ****** *     **** ** *  *****  *     *
genome            TCACACAAAATGCAGCAGAGGTTGAGGTGAGCACATGTCCGTGACCTGGAGCCTGACTCC 172911
mRNA              CTTGACAAGCTCTGCCACTGATGGGGATGAGGAGGATATCTTGAGCCACAGCTCCAG-CC 1757
                      ****  *    **  * * * * **** *     * *** *   ***   *  **
genome            CTCTCTGCGA-GTCTTGACTGCTCTTGCCTAGACTCTGTCCTCCCCGAGCCCAAACGCCA 172970
mRNA              AGGTCAGCGCCGTCCCATCTGACCCTGCCATGGACCTGAA-TGATGGGACCCAGGCC--- 1813
                     ** ***  ***      ***  * ****  *   ***   *   ****  *
genome            GTCATCTTCCCTTGTGGGTGTCCTTCAGCCTGGTGCCATGCTGG-TGACTCAGCAG----- 173025
mRNA              -TCGTCGCCCATCAGCGACAGCTCCCAGACCACCACCGAAGGGCCTGATTCAGCTGTTAC 1872
                   ** **  ** *    *   *   *** *      **     *  *** ***** *
genome            CCGTCCAGGGAGTGGAAACAATTGAGTGTGTGGGTTCCCTGTGTGGGCATCTC--TCTTC 173083
mRNA              CCCTTCAGACAGTTCTGA-AATTGTGTTAGACGGTACCGACAACCAGTATTTGGGCCTGC 1931
                  ** * ***  ***    * ***** **  *  *** **        * ** *    ** *
genome            ACGGCGAACACCCTCTGGGTGTTGCCCACACGATGTCAAAGCGGCTCTTGGAAGGGGTCC 173143
mRNA              AGATTGGACAGCCCCAGGATGAAGATGAGGAAGCCACAGGTATTCTTCCTGATGAAGCCT 1991
                  *    * *** ** * ** **   *    *         **       **     ** *  * *
genome            TTCTCCTTTGTGGGAAGTTTCAGCTGCTGGGCTAACTTGAATTGTAACTGTGGTTTTGTG 173203
mRNA              CGGAGGCCTTCAGGAACTCT----TCCATGGCC--CTTCAACAGGCACA-----TTTATT 2040
                          *   **** * *     * *  ***    *** **  *   **      *** *
genome            CTCAGGCCCAGATCCCCCTAGGCAAGTGTTGTGCCATCAGTAATCAAATGAGAAATAATC 173263
mRNA              GAAAAACATGAGTCACTGCAGGCA-GCCTTCTGACAGCAGTGTT-----GATAAATTTGT 2094
                     *   *     ** *   ***** *  ** ** ** ****  *      ** ****
genome            ATTTTGAAAAGCAGATCCTAAGGCAGGATGGTCATGGACACTCACTCCCAGCTCTTTGTG 173323
mRNA              GTTGAGAGATGAAGCTACTGAA-CCGGGTGATCAAGAAAAC---------AAGCCTTGCCG 2145
                   **  ** * * ** * ** *  * ** ** *** * * **          *   ***   *
genome            CACTCATGCTTTCTGGAAGATGGCCATCCTCTG-TGAAGGTTTTCAGCGCGTCATGCTTG 173382
mRNA              CATCAAAGGT----GACATTGGACAGTCCACTGATGATGACTCTGCACCTCTTGTCCATT 2201
                  **    * * *     *  *    * *  *** *** *** *  * *   *   *  * * *
genome            GTACCCACGTATCCAGAGCATGTCGTTTTGAGGTATTTGCCCACCGTTGTGAAATCCGTG 173442
mRNA              GTGTCCGCCTTTT------ATCTGCTTC----GTTTTTGCTAACAGGGGGAAAAAATGTG 2251
                  **  ** * * *         ** *  **       ** *****  ** *  *  ***   ***
genome            CCACCCGAGAGCAGGTCCTGATGTGGGGCTTTCAGAAGTGGGACCTGGGGCCGTACGCAG 173502
mRNA              CTGGTTCCGGACAGG----GATGTGAGGGT--CAGCGTGAAGGCCCTGGCCCT----CAG 2301
                  *      *  ****      ****** ** *  ***      * **  ** **    ***
genome            TCCTTAGGGAGGGGCCGTGTGGCGTTGTGCGTGTGAGGGGATAGCACAGGGTGAGGTGGG 173562
mRNA              CTGTGTGGGAGCAGC--TGTGGCCCTCCACCCGGAATCTTTCTTCAGCAAACTCTATAAA 2359
                     *  *****  **  ******  *    *   *   *          **           *
genome            GGCCC----AAGAAGGAAGTGACCCACAAAGAACAGCCTCCTCTTTTGGTCCTTGTTCCT 173618
mRNA              GTTCCTCTTGACACCACGGAATACCCTGAGGAACAGTATG-TCTCAGACATCTTGAAC-T 2417
                  *  **     * *     *    **   * ******  *  ***          **** * *
genome            GGGATGGCTGGGAGTGGCTTCTGTGTCGTCCGGCCATTTCCCCTG-CGGAGAGGCTCCTA 173677
mRNA              ACATCGATCATGGAGACCCACAGGTTCGAGGAGCCACTGCCATTCTCTGTGGGACCCTCA 2477
```

FIG. 1 IIIIII

```
               *     *     *  * *  ***    **** * **  *  * * * * * *  *
genome    CCACTGCCGAGAACCTCATCATTCCACAAAAACAAGAGGCCGCCTGGCCATCCAGCGCTC 173737
mRNA      TCTGCTCC----ATCCTCAGCAGGTCCCGCTTCCACGTGGGAGATTGGAT------GGGCAC 2529
           *    **   * ***** **   * *     ** * **  *  ***       * ** *
genome    CATGGGAATTCTGTGTCCCCATAGTCTTGGGCTGAAGGAGGGTGA-CATTCCTTGCTGA- 173795
mRNA      CATTAGAACCCTCACAGGAAATACATTTTCTTTGGCGGATTGCATTCCTTTGCTGCGGAA 2589
          ***  ***  **        ***   **    **  ***  *    * **   *** **
genome    -----CTTCTGCAGGGGTCTCCTCACTGTTAAAGAGCAGATTGAAA----GTGAAGAAC-G 173846
mRNA      AACACTGAAGGATGAGTCTTCTGTTACTTGCAAGTTAGCTTGTACAGCTGTGAGGAACTG 2649
              **   * * * **** **     **  *    ** *** *     **** **** *
genome    TGGGCTAAGTGTTTAGGTCGATATTTAACCCTGCTAGGTTTTGGATACTAAGTGAAATTG 173906
mRNA      TGTCATGAGTCTCTGCAGCAGCAGCTA---CAGTGAG--TTAGGACTGCAGCTGA--TCA 2702
          **   * *** * *    *   *  **   * *  **  ** ***    *  ***  *
genome    AGGCCATTTTGGTTGAAGTTGACAGAAACCACTATCAGGGATCCCCAAGACTACCCCAGG 173966
mRNA      TCGATGTGCTGACTCTGAGGAACAGTTCCTATTGGCTGGTGAGGACAGAGCTTCTGGAAA 2762
            *   *  **  *       ****   * * *  * **      **   ** *   *
genome    CTTTTCTAGAAA--GACTCTCAGCTAAGATGTGTTATGGTAAAAGCACACAAAACAAAAT 174024
mRNA      CCCTTGCAGAGATTGACTTCAGGCTGGTGAGCTTTTTGG------------AGGCAAAAG 2810
          *  **  *** *  ****    ***     *  ** ***            *  *****
genome    CAGCAAAGAAAATTAGCAAGGGCAGAGGCCCATGGGGCGATGTCCCGAGGACACCAGGCT 174084
mRNA      C-----AGAAAACTTACACAG--AGGGGCTCAT----CATTATAC--AGGGCTTT----T 2853
          *     ****** *  **  *  ** *** ***    *  * * *  *** *       *
genome    TGAGCTTCCAGAATCCTCTCCCAGCGGGGTCGTGCAGGACGCACTTAACTCCCCGCACAG 174144
mRNA      AAAACTGCAAGAACGAGTGCTCAATAATGTTGTCATCCATTTGCTTGGAGATGAAGACCC 2913
            * ** * ****      * **     ** **     *    ***          **
genome    TGAGCCGTGACAGCGCGTGTGCAGTGTCGTCGCCAGGAAAGCACACTAGAGACTCGGTGC 174204
mRNA      CAGGGTGCGACA---TGT-TGCCGCAGCATCACTAATTAGGCTTGTCCCAAAGCTGTT-T 2968
             *  * ****    ** *** *   * ** * *   * **       * *   * *
genome    CAGGGTTTTTACTGGGGGCTGGGCACATGGGCACCCTCTGCCTGCCTCGTGCCCAGACTC 174264
mRNA      TATAAATGTGACCAAGGACAAGCTGATCCAGTAGTGGCCG--TGGCAAGAGATCAAAGCA 3026
           *    * * **   ** *  *        * *    * *  ** *  * *  ** *
genome    TGGACTCCCGGAGGGAAGGCAAGTTCTCA-GCACCAACCCTGGTGCCCA-CACAAGCAGC 174322
mRNA      GTGTTTACCTGA--------AACTTCTCATGCATGAGACGCAGCCTCCATCTCATTTCTC 3078
            *  * ** **        ** ****** ***  *  *   *   *** * **     *
genome    TGAGCACAGGGAGCCCCTCCTCAGTGAGGATGGTGGGCACCGTCCCAACACCAGCCAGGG 174382
mRNA      CGTCAGCACAATAACCAGAATATATAGAGGCTATAACCTACTACCAAGCATAA--CAGAC 3136
           *    **      **    *   *   *    *   *  *  ** * **  *  ***
genome    GCCAGCCTTGCACACAGGCCTCTCAGGATGGTCTCCGGCCTGCTGTGTAGTCTCTTCTGC 174442
mRNA      GTCACTATGGAAAATAACCTTTCAAGAGTTATTGCAGCAGTTTCTCATGAACTAATC-AC 3195
          * **   * * * * *  * *   **  *  *  * *   *      *   **  **  *
genome    ACACAAGCGTGAGGGCAGCGCCCCCGCCTCGGCTGTGGGGAGGAGCCACTGGGACGTGAG 174502
mRNA      AT-CAACCACCAGAGCA----CTCACATTTGGATGCTGTGAAG---CTTTGTGTC-TTCT 3246
          *  *** *   ** ***    * *    * ** **  * ** *   *  ** * * *
genome    CTCTGGTGGCATGCAGCAGCTTTTGTCTGTGTGTGCCTAGGACAAGGCCGTGGCGGAGCC 174562
mRNA      TTCCACTGCCTTCC--CAGTTTGCATTTG---GAGTTTAGGTTGGCACTGTG---GAGTG 3298
           **   ** * * *  *** **   * **   * *  ****      * ***   ***
genome    TGTCAGCCGCCTGCTGGAGAGCACGCTCAGGAGCAGCCACCTGCCCAGCAGGGTTGGAGC 174622
mRNA      CCTCCACTGAGTGCCTCAGATGA-GTCTAGGAAGAGCTGTACCGTTGGGATGGCCACAAT 3357
            **  * *  ***   ***  * *   ****  ***          * * **    *
                rs362272
genome    CCTGCACGGCGTCCTCTATGTGCTGGAGTGCGACCTGCTGGACGACACTGCCAAGCAGCT 174682
mRNA      GATTCTGACCCTGCTCT---CGTCAGCTTGGTTCCCATTGGATCTCTCAGCCCATCAAGA 3414
            * *    * * ****    *   *  **   **   ****   * * *** * **
genome    CATCCCGGTCATCAGCGACTATCTCCTCTCCAACCTGAAAGGGATCGCCCAGTGAGTGGG 174742
mRNA      TGCTTTGATT-TTGGCCGGAAACTTGCTTGCAGCC----AGTGCTC-CCAAATCTCTGAG 3468
                * *  *  **    * **    * ** **    ** * ** ** * *   ** *
genome    AGCCTGGCTGGGG-CTGGGGCGGGGGTC---TCAGAATGAGCTGTGAAGGAAGCAGCATC 174798
mRNA      AAGTTCATGGGCCTCTGAAGAAGAAGCCAACCCAGCAGCCACCAAGCAAGAGGAGGTCTG 3528
          *   *    **   ***  *  *  * *    *** *    *   * * ** *  *  *
genome    ACCCTCTCCAAGTGCCCAGGCTCCTGGCCAGATGGCAGGCCAGGTATCAGTGGGAACCC- 174857
mRNA      GCCAGCCCTGGGGACCGGGCCCTGGTGCCCATGGTGGAGCAGCTCTTCTCTCACCTGCT 3588
           **  * *   * * ** *** *  *  *  ****  *  *** * *           *
genome    --AGGTGGGTGCCAT----GGCTGAGGTCAGTGAGACGCAAGAGCACAGGTGCGTCCTAG 174911
```

FIG. 1 JJJJJJ

```
mRNA      GAAGGTGATTAACATTTGTGCCCACGTCCTGGATGACGTG-GCTCCTGGACCCGCAATAA 3647
             *****  *  ***    * *    *  * *    ****    *   *    *   **    **

genome    AGGCTTCCTCGGGCACCTCCAGCGAGCTGGAGCTCTCGCCTCTGCTGCTGTCTCATGTGG 174971
mRNA      AGGCAGCCTTGC-CTTCTCTAACAAACC----CCCCTTCTCTAAGTCCCATCCGACGAAA 3702
          ****  *** *  *  *** * * * *      * *   *       * *  **  * *

genome    CGCTTAGCACACTCTCCCACGTGCCCATTCCTGACTCTGCTCTCGAGGCCATCGGCTCTC 175031
mRNA      GGGGAAGGAGAAAGAACCAGGAGAACAAGCAT--CTGTACCGTTGAGTCCCAAGAAAGGC 3760
           *   ** * *     *** * *  **  * *  ** * *  * *** **    *      *

genome    ATTCTCTGCTCCCAGAACCCTGTTATTACCCAGGCTAGCCTCCTCTCTGCACCTTCCCCG 175091
mRNA      AGT----GAGGCCAGTGCA--GCTTCTAGACAATCTGATAC---CTCAGGTCCTGTTAC- 3810
          * *    *    ****  *   * *  **  **  **        *** *  ***    *

genome    CCCTGGCCCAGTACCTCCCTCTTGTTTCCACTGTGATTCCGACCTCACCTTAT-CTTAAA 175150
mRNA      -----AACAAGTAAATCCTCATCACTGGGGA-GTTTCTATCATCTTCCTTCATACCTCAA 3864
               * ****  ***    *    *      **   *    * **  * * ** * * **

                             [rs362271]
genome    GCTGCTGGACGGCAGGTTCTGTACACACGTGTCCTTGACAAAGCACGGCTGGTGCCGCAA 175210
mRNA      ACTGCATGATGTCCTGAAAGCTACACACGCTAACT--ACAAGGTCACGCTGGATCTTCAG 3922
           ****  ** * *  *     ********    **  **** *     *****  *  **

genome    CCCCTCAGCGAGCAAGTCA-AGCTCTTCACAGCGATGTCTTACAAGCGCAGAGGGCTCTG 175269
mRNA      AACAGCACGGAAAAGTTTGGAGGGTTTCTCCGCTCAGCCTTGGATGTTC-------TTTC 3975
            *  **  **  *  *    **   *** * **   * ***  * *  *        * *

genome    TGACACCCTGGTCTCACCGCCACTCTTCCAAA-GTCGCAGAGGCTTTAGCAGAGATGGGC 175328
mRNA      TCAGATACTAGAGCTG--GCCACACTGCAGGACATTGGGAAGTGTGTTGAAGAGAT---C 4030
          * * *  ** *       ***** ** *   *  * *   **  * * * ******    *

genome    CCAGCCTCTCTGAGTCATAGGCTTCTGCACACGGGAGCTGTCTTTAGAGGGAGGGTGGAA 175388
mRNA      CTAGGATACCTGAA-----ATCCTGCTTTAGTCGAGAACCAA--TGATGGCAACTGTTTGT 4084
          * **  *  ****      *  ** **  *  ** ** *       * *  *  *  **

genome    TTTCATCAGCCACCCACATGGGGGAGTTGAGGGCAAGAATTAGGAGCAAAGATGGGAAGG 175448
mRNA      GTTCAACAATT---------------GTTGAAGACTCTCTTT-GGCACAAACTTGGCCTCC 4129
           **** **                  ***** * *     ** **   ****  ***

genome    GGTCTGGGAGGAATGGCCAGTGATCCCCTTTGACAAGTGGGCAGGAAACGGGGGCTAGGT 175508
mRNA      CAGTTTGATGGCTTATCTTCCAACCCCAGCAAGTCACAAGGCCGAGCACAGCGCCTTGGC 4189
              * *  **  *  *      * ***          *    *** *    ** * * * ** **

genome    CAAAGTTGAGTGGAAGACCTGGAGGGAGACGGGAAGGTCTCTGTAGGCACAGTTCAGACA 175568
mRNA      TCC--TCCAGTGTGAGGCCAGGCTTGTACCACTACTGCTTCA--TGGCCCCGTACACCCA 4245
               *  ****  ** ** **    *    *    *   *   **     *** * ** **  **

genome    GGAGGGAGGTGTGAGCCAGGGCACATGCCGGTGGCCGTCTGGCAGGATTTGGGACATGCT 175628
mRNA      C-----------TTCACCCAGGCCCTCGCTGACGCCAGCCTGA-GGAACATGGTGCAGGC- 4293
                     *   **  *** *   ** *   * * * ***   * *   ***   ** **

genome    GGAGCAGGGACAGCGGCTCATCAGGGGCCATTGCCCTCATCCAGGCCAGAGTGTCACAAG 175688
mRNA      GGAGCAGGAG-AACGACACCTCGGGATGGTTTGATGTCCTCCAG---AAAGTGTCT---A 4346
          ********    *  ** * * * ** **      ***    ** *****    * ******

genome    CCCGTGGGGAGGCCCTTCTCGCCTGTCATCCTTGCTGGGCAGTGGGTGCTGTGCTAGCAG 175748
mRNA      CCCAGTTGAAGACAAACCTCACGAGT------------GTCACAAAGAACCGTGC-----A 4390
          ***      * ** *     *** *  **              * **     *  * ****

genome    GACAGGCGGACGGCTGGCAACTGTCTCTGCATCCCTGGAGCCTGGCATAGGGCCAAGTCA 175808
mRNA      GATAAGAATGCTATTCATAATCACATTCGT-TTGTTTGAACCTCTTGTTATAAAAGCTTT 4449
          ** * *      *     *    *   *  *   * ** ***           *   *

genome    CACGGGGCACAGGCCTGCAAATCAGGCACATATGTTGGTGCAGTGACGTGATTTTGGGGG 175868
mRNA      AAAACAGTACACGACTACAA------CATGTGTGCAGTTACAGAAGCAGGTTTTAGATTT 4503
           *     * *** * ** ***       **   *  **   *  *  ***   *  * *** *

genome    GCAGCCCCAGAACAGGCCCCAGACACAGGCCAAAGCCCTGCCTGTGCTGGTGTGTTGGGC 175928
mRNA      GCTGGCGCAG--CTGGTTC-AGTTACGGGTTAAT-TACTGTCTTCTGGATTCAGATCAGG 4559
          ** * * ***   * **   *  **   ** **   **      *** **       *   *  *  *

genome    TGTTCTATGGCTCTTGCTGTGGGCATGGAGGACTCAGGGAAGGAGAGTTGAGGTGGTCCA 175988
mRNA      TGTTTATTGGCTTT---------GTATTGAAA---CAGTTTGAATACATTGAAGTGGGCCA 4608
          ****   ***** *           * ** **      ***           **** **** ***

genome    GGAGTTGCGTTTGGGATGCAGAGAGCTTGTGGCATCCAGGTAGAAATGGTGCGTGGGGCT 176048
mRNA      G---------------TTCAGGGAATCAGAGGCAATCATTCCAAA------CATCTTTTT 4647
          *               * *** **     * ****  **       **        * *      *

genome    GACCTCAGCACCATGGGCAGAGGGGCCGTGTCACGTGCCTCCGAGGTGGAGGTGGGACCA 176108
mRNA      CTTCTTGGTATTACTATCTTATGAACGCTATCAT-----TCAAAACAGATCATTGGAATT 4702
              **  *  *     *   *  *   *   * ***       **   *    *     * ***
```

FIG. 1 KKKKKK

```
genome  CGTGGTGACAGATATACGCATCACTGGGCACGTTTTTGTGGGTGTTGGGGGGCATCGTAT 176168
mRNA    CCT------AAAATCATTCAGCTCTGTG-ATGGCATCATGGCCAGTGGAAGGAA------ 4749
        * *      * *   *  ** * *** * * *   *  ***    ***  ** *

genome  TGGCTCCTCTGTTCACAGTGGCCACTCATTCAGTCCCTGGCTACCAGGTCCTCACTGTGC 176228
mRNA    -GGCTGTGACACATGCCATACCGGCTC-TGCAGCCCATAGT--CCACGACCTCTTTGTAT 4805
         ****          *  *  *  *** * *** ** * *   *** * ****  ***

genome  CATGGGGAAGGCCGGCGCTGTCGGGGGATCACAGAAGGCAGCACGTCATGATGGCATGTG 176288
mRNA    TAAGAGGAA--------------------CAAATAAAGCTG------------------- 4826
         * * ****                    ** * ** ** *

genome  CCATGAAGGAAAAGCACAGGGCACTCAGGAAGTAGAGGGGACTGGCCTGGGGTGTGGGAA 176348
mRNA    --ATGCAGGAAAAGAGCTTGAAACCCAAAAAG-AGGTGGTGGTGTCAATGTTACTGAGAC 4883
          *** ********  *  *  ** **  *** **  **   ** *   *    ** **

genome  TC-TAGGGCCTCGTTGAGGGACAGAGAGAGGAAGTGTGTGGTGGCCAGCATGGAGGTGGC 176407
mRNA    TCATCCAGTACCATCAGGTGTTGGAGATGTTCATTCT----TGTCCTGCA--GCAGTG-C 4936
        ** *   *   * *   * *   ****     * * *    ** ** ***  *  *** *

genome  CACAGGGGAGGCTGAGTTAGGCCGAGAGGGCAGGGCGTTGGGGAGGTAGACGGGCTCAGC 176467
mRNA    CACAAGGAGAATGAAGACAAGTGGAAGCGACTG---TCTCGACAGATAGCTGACATCATC 4993
        **** **       **  * *  **   * * *     * *  ** ***  *   *** *

genome  CACTCAGGGAGTGGTCAAGCAGAGGCTGAAGGGTCAGGCCAGGTTGCAGGGGCCTGGGGG 176527
mRNA    CTCCCAATGT-TAGCCAAACAGCAGATGCACATTGACTC----TCATGAAGCCCTTGGAG 5048
        * * **  *  * * *** ***  * ** *   * *  *    *      * *** ** *

genome  AGCCACTCAGGGTAGGCGCTCCCGGGAGCCCGCCTGGCCCATAGCTCTACACTCCCGCGT 176587
mRNA    TGTTAAATACATTA------TTTGAGATTT----TGGCCCCTTCCTC----CCTCCGTCC 5094
         *  *   *   **         * **       ****** *  ***    *  ***

genome  GGGGCCGGACATGCTGTGAAGCCCTCTCCACGTTGGATGGGGGTGGCTGAGCCTGGATGC 176647
mRNA    GG---TAGACATGCT-----------TTTACGGAGTATGTTCGTCACTC--CAAACACAA 5138
        **     ********           *  ***  * ***   **  **   *    *

genome  TGTCTCCCGTTTTCAGCTGCGTGAACATTCACAGCCAGCAGCACGTACTGGTCATGTGTG 176707
mRNA    TGGCGTCCGTGAGCA-CTGTTCAACTGTGGATATCGGGAATTCTGGCC--ATTTTGAGGG 5195
        ** *  ****   ** ***    *   *  * * *  * *    *  *   *  ** * *

genome  CCACTGCGTTTTACCTCATTGAGAACTATCCTCTGGACGTAGGGCCGGAATTTTCAGCAT 176767
mRNA    TTCTGATTTCCCAGTCAACTGAAGATATTGTTCTTTCTCGTATTCAGGAGCTCTCCTTCT 5255
                *   *    * ***  *   *  ***          * ***  * **    *

genome  CAATAATACAGGTGAGTGGGCCCTGGCTGTCTTCCTCTGCACACGGGGAGTGGGCTTCCC 176827
mRNA    C-----TCCGTATTTAATCTCCTGTACAGTAATTAATAGGTTAAGAGATGGGGACAGTAC 5310
        *     * *   *       **    * **  *     *   * * *  * ** *    *

genome  TTCTCTTTTCCTTGCAGGATCATACCAGTGGGCCAGTTTTGACTTGGTCGGGAGGAGGCA 176887
mRNA    TTCA----ACGCTAGAAGAACACAGTGAAGGGAAACAAATAAAGAATTTGCCAGAAGA-- 5364
        ***      *  *  * ** ** *     ***  *    * *     * *  ** **

genome  TGAACACCTGAGACTGTGCAGCGATTCTTTGACACAGAGGCCTTTCTCCCTGTGCAGATG 176947
mRNA    --AACATTTT--------CAAGGTTTCTATTACAACTGGTTGGTATTCTTTTAGAAGACA 5414
          ****  *         **  * **** * ***    *    *  **  *  * ***

genome  TGTGGGGTGATGCTGTCTGGAAGTGAGGAGTCCACCCCCTCCATCATTTACCACTGTGCC 177007
mRNA    T-TGTTACAAAACAG-CTGAAGGTG-GAAATGAGTGAGCAGCAACATA---CTTTCTATT 5468
        * **     *  * * *** * *** * * *       *  ** ***    *  * *

genome  CTCAGAGGCCTGGAGCGCCTCCTGC-TCTCTGAGCAGCTCTCCCGCCTGGATGCAGAATC 177066
mRNA    GCCAGGAACTAGGCACACTGCTAATGTGTCTGATCCACATCTTCA----AGTCTGGAAT- 5523
          ***   *  **  * *  *     * ***** *  *     *       *   ****

genome  GCTGGTCAAGCTGAGTGTGGACAGAGTGAACGTGCACAGCCCGCACCG--GGCCATGGCG 177124
mRNA    ----GTTCCGGAGAATCACAGCAGCTGCCACTAGGCTGTTCCGCAGTGATGGCTGTGGCG 5579
            **   *  ** *     ***     **  *      *****  *  ***  *****

genome  GCTCTGGGCCTGATGCTCACCTGCATGTACACAGGTGAGCATGTACACGGTGCCCATAAG 177184
mRNA    GCAGTTT-CTACACCCTGGACAGCTTGAACTTGCGGGCTCGT-TCCATGATCACCACCCA 5637
        **  *   *   *  **   * ** ** **    * *  * * * ** * *  ***

genome  GCCAGCCCAAGTCCTGTTCAAGGGAGGCAGGAGCATGCTCACTCAAGGGACCTCGACTAG 177244
mRNA    CCCGGCCCTGGTGCTGCTC--TGGTGTCAGATACTGCTGCTTGTCAACCACACCGACTA- 5694
         ** ****  ** *** **   ** * ***   *     *     *   **  ******

genome  GTGCCCTCTGATTT-CACACTTCTGGTGTTGCCCCAAGCCGGCCCCATC-ACCTTGCAAG 177302
mRNA    ----CCGCTGGTGGGCAGAAGTGCAGCAG-ACCCCGAAAAGACACAGTCTGTCCAGCACA 5749
            ** *** *   ** *  *   *     **** *   * * *  **   *  ***

genome  AAAGGCTCTGGAGCCCCCAGGGCTGGAGTACCTGGTCAGGGTTGACCGTCCCTGTGGTCA 177362
mRNA    AAGTTACTTAGTCCCCAGATGTCTGGAGAA---GAGGAGGATT--CTGACTTGGCAGCCA 5804
        **      * *  ***  * * ****** *   *   *** **  * * *   *  * **
```

FIG. 1 LLLLLL

```
genome      CTCATCCCATGTGGCTGAGCTGGGCTGGGTCCTGGGCAAGCAAGGGGCTGATATCACCTG 177422
mRNA        AACTTGGAATGTGC---AATAGAG--AAATAGTACGAAGAGGGGCTCTCATTCTCTTCTG 5859
              * *   *****    *   * *     *  *  * *     *       * **  ***

genome      CTTTCAGATCTCCAGGGACTCACTGGACCCCTGTGTACAAAGCACTGTCTACAGAGCCTA 177482
mRNA        TGATTATGTCTGTCAGAACCTCCATGACTCC-GAGCACTTAACGTGGCTCATTGTAAATC 5918
               * *  ***    * **   *  *** ** * * **  * *   *   *  *    *

genome      TTGGGTTGTATAGAGGTAACCTTCGTACTGAACACTTTTGTTACAGGAAAGGAGAAAGTC 177542
mRNA        ACATTCAAGATCTGATCAGCCTTTCCCACGAGC-------CTCCAGTACAGGACTTCATC 5971
                     **      * ****     **  *        * *** * ****     **

genome      AGTCCGGGTAGAACTTCAGACCCTAATCCTGCAGCCCCCGACAGCGAGTCAGTG-ATTGT 177601
mRNA        AGTGCCGTTCA---TCGGAACTCTGCTGCCAGCGGCCTGTTCATCCAGGCAATTCAGTCT 6028
            *** * * *     *    ** **  * *    * **    ** * ** ** *  * * *

genome      TGCTATGGAGCGGGTATCTGTTCTTTTTGATAGGTAAGAAGCGAAGCCC-CATCCCTCAG 177660
mRNA        CGTTGTGAAA-----ACCTTTCAACTCCAACCATGCTGAAGAAAACTCTTCAGTGCTTGG 6083
             * * ** *      * ** *    *   *       ****  **  *  **   **  *

genome      CCGTTAGCTTCCCTAGAACTTTGGCCTGAAGCTGTGCTTTTG-TGTGTGTCTGCTGATCC 177719
mRNA        AGGGGATCCATCTCAG----CCAGTCGGGAGCTGTGCTCACGCTGTATGTGGACAGGCTT 6139
              *  * *   *  **       * * * *********   * *** ***   * *

genome      CCTGGCGCTGTTGCTGGAGTCCTGCCAGTGATTCCCCACCACAGCCTGACCATGGGCTGC 177779
mRNA        CTGTGCACCCCTTTCCGTGTGCTGGC-----------------TCGCATGGTC---GACATC 6181
            *   ** *   *    * ** *** *                 ** **  *   * *  *

genome      CTTGGCTCAGGGTTCCACTGGCGAGCTGGTGGTCCTTGGACCCCAGCACTCAGGTGTAGC 177839
mRNA        CTTGCTT---------GTCGCCGGGTAGAAATGCTTCTGGCTGCAAATTTACAGAGCAGC 6232
            ****  *            * ** *  *     * *  * *  **    *   * * ***

genome      GTTGACCAGTTCCAAGGTTGTCCCAGTGCCTGCCCATCTCTCCTGAGGGCTCAGGGACAG 177899
mRNA        ATGGCCCAGTTGC----------CAATG---GAAGAACTCAAC--AGAATCCAGGAATAC 6277
             * * ****** *          ** **   *   * ***  *  **    **** * *

genome      TACCTGGCAGTTGGGGGTGTGGCAGGGGGCAGGAATGACCAGCCTCTGGGAGGGTGGGGC 177959
mRNA        --CTTCAGAGCAGCGGGCTCGCTCAGAGACACCAAAGGCTCTATTCCCTGCTGGACAGGT 6335
              * *   **  * ***   *    * * **  ** * *     **   *  **   **

genome      AGAAGCCTGTACAGTGAGGAGGAGCTGGCTCAGCCTGGCTGCCTATCGTGAGAGGGGAGC 178019
mRNA        TTC-GTCTCTCCACCATGCAAGA-CTCACTTAGTC------CCTCTCCTCCAGTCTCTTC 6387
                * ** * **    * * ** **  ** ** *      *** ** *          *

genome      CCACGGGGCTGTGGGAGGGGGGCCGTGGTGCCTGTGAGCAGGGTGAGGAGCAGCGGCAGG 178079
mRNA        CCAC----CCGCTGGACGGGGATGG--GCACGTGTCACTGGA------AACAGTGA-GTC 6434
            ****    * *  *** ****   *  *  * *** *   *       * *** *

genome      AGGATGAAGGTGGAACCCACACATGCATCTT-TGAGACCCGTGTGGTCAGTGGCTTCTGC 178138
mRNA        CGGACAAAG-----ACTGGTACGTTCATCTTGTCAAATCCCAGTGTTGGACCAGGTCAG- 6488
             ***  ***     **    ** * ****** * * * **  *** *        ** *

genome      CCCCCACCACCCCCCACTGCTGTGCGTGCATAGAATTGGCTTCCCTCACCTGCTCTGGAA 178198
mRNA        ---------ATTCTGCACTGCTG-GAAGGTGCAGAGCTGGTGAATCGGATTCCTGCTGAAG 6539
                    *  * ******** *   *   ***  ***     *  *      *** *

genome      GTGGGTTAGGAGCTTGGTAGGGCTTTTTCTCAAGGACAAGGGCCCCTGATTTGCTCTCAG 178258
mRNA        AT--ATGAATGCCTTCATGATGAA----CTCGGAGTTCAA---CCTAAGCCTGCT----A 6586
             *   * *    ***  *   *      ***   *   *    **      ****

genome      GCCTCAGTCCTGGCGACATGGTGGATCTGGAGCCTTGTTGCACTGCCTTGCCTGTGCTCT 178318
mRNA        GCTCCATGCTTAAGCCTAGGGATGAGTGAAATTTCTGGTG----GCCAGAAGAGTGCCCT 6642
            **  **  * *      * **  **     *    ** **    ***      **** **

genome      CCAATCAGGGTGGCCAGTGGGGAGCCATTTGGCTTTTCTCAAGAGCATACT-CAGGTGGA 178377
mRNA        TT--TTGAAGCAGCCCGTGAGGTGAC-TCTGGCCCGTGTGAGCGGCACCGTGCAGCAGCT 6699
                *    *  *** *** ** * * * ****   * * *   ***   * ***  *

                                            rs3775061
genome      CCTTGCT--CCACTGT-TTGACCAGATGAGGCATTCTGAACAGCCAAGCCTGTGCTGGTC 178434
mRNA        CCCTGCTGTCCATCATGTCTTCCAGCCCGAGCTGCCTGCAGAGCCGGCGGCCTACTGG-- 6757
            ** ****  ***   * *   ****     **   *** * ****       * ****

genome      TGTTTTCATGTTGATTTTTTTTTTTTCTTTTCTTTTTGAGATGGAGTTTTTCCCTTGTCAC 178494
mRNA        ----AGCAAGTTGAATGATCTGTTTGGGGATGCT---GCACTGTATCAGTCCCTGCCCAC 6810
                  ** ***** *  * * ***        *     *  *  *   *****   ***

genome      CCAGGCTGGAGTGCAATGGTGTGATCTCGGCTCACTGCAACCTCCGCCTCCCGGGTTCAA 178554
mRNA        TCTGGCCCGGGCCC--TGGCACAGTACC---TGGTGGTGGTCTCCAAACTGCCCAGTCAT 6865
             * ***  * *  *  ***     *  *   *    *    ****      *    ***

genome      GTGATTCTCCTGCCTCAGCCTCCCTAGTAGCTGGGATTACAGGCACACACCACCATGCCC 178614
mRNA        TTGCACCTTCCTCCTGAGA------AAGAGAAGGACATTGTGAAATTCGTGGTGGCAACC 6919
```

FIG. 1 MMMMMM

```
                 **   ** *  *** **        *  **  **   *   *  *  *         **
genome   AGCTAATTTTGTGTTTTTAGTAGAGACGGGGTTTCACCGTGTTGGCTGGGCTGGTCTCG 178674
mRNA     CTTGAGGCCCTGTCCTGGCATTTGA---------TCCATGAGCAGATCCCGCTGAGTCTG 6970
            *   ***  *  * * **           **   *  *  *     ****    *
genome   AACTCCTGAACTCAAGTGATCCACC-CTCCTTGGCCTCCCAAAGTGCTGGGATTGCAGGC 178733
mRNA     GATCTCCAGGCAGGGCTGGACTGCTGCTGCCTGGCCCTGCAGCTGCCTGGCCTCTGGAGC 7030
          *   *    *      **  *  *  ** * *****   **       ****  *     **
genome   GTGAGCCACTGCGCCCGGCCCCCATGTCGATTTTTAAATGCACCTCTGCATCGTTCTTCA 178793
mRNA     GTGGTCT-----------CCTCCACA--GAGTTTGTGACCCACGCCTGC----TCCCTCA 7073
         ***  *            ** ***    ** ***   *  ***  ****   * *  ***
genome   GTCCCCATATGCTCACTGAGCACCACTGCGACTGGCAGACGGGCACAGGGAGGCGCCACG 178853
mRNA     TCTACTGTGTGC-------------ACTTCATCCTGGAGGCCGTTGCAGTGCAGCCTGGAG 7121
            *  * ***               *** *  *  * ** * *    *** *  **     *
genome   ACCAGTCCTGGCCTTCAAGGGGCTTGTGGTCTAGTGGGCCCAATGCTAGGTGGCGAGTGC 178913
mRNA     AGCAGCTTCTTAGTCCAGAAAG---AAGGACAAATACCCCAAAAGCCAT-CAGCGAG--- 7174
         * ***       * **    *      ** * * *   ** ** ** *    *****
genome   TCCAAAGAGTGTGGTGCACGCCTTCCGCTTGACCGCTCTCCAGACGCCACAGGGAGGCAC 178973
mRNA     ---GAGGAGGAGGAAGTAGATC--CAAACACACAGAATCCTAAGTATATCACTGCAGC-- 7227
            * ***   *  *  *    *  *       ** *     * *      **  *  **
genome   CTCGCAGCTGACCACAGATTTCTCTCTGTGGAGCAGTGTCTTCAGAGCG-GCTGCCATGC 179032
mRNA     CTGTGAGATGGTGGCAGAA---------ATGGTGGAGTCTCTGCAGTCGGTGTTGGCCTTG 7279
         **   ** **    ****          *** * *** *** ***    *  * ** * *
genome   CACTGCTGGGCGAGGGTCTGCGGGCGGGTAGAGCCAGGAGCACCTGTGAGGAAGTGCACT 179092
mRNA     GGTCATAAAAGGAATAGCGGCGTGCCGGCGTTTCTCACGCCATTGCTAAGGAACATCATC 7339
                   **    * *** ** **      *      **    * *****   **
genome   GCCATTTTCGTAGCTGCTTCCCGTGTGTCT-CAGTTACACACGGCTGGCATGTGTGCACT 179151
mRNA     ATCAGCCTGGC--CCGCCTGCCCCTTGTCAACAGCTACACACG-----TGTGCCCCCACT 7392
            **   * *   * ** * **   ****  *** ********        **     ****
genome   GATGAGACGGGAACGTGATGGTTGCTTTTCAGCACTGAAAGGGATACTGCTCAGGGGGCG 179211
mRNA     GGTG---TGGAAGCTTG--GATGGTCACCCAAACCGGGAGGGGATTTGGC---ACAGCA 7444
         * **    ** * * **  * * *     **    * * * *****  **         **
genome   TGTTTCAGGATCTGGTTAGGGAAGAAGCAGCGAGAGCACAGATGGGGCCCTGTGTGGTAA 179271
mRNA     TTCCCTGAGATCCCCGTGGAGTTCCTCCAGGAAAAGGA-AGTCTTTAAGGAGTTCATCTA 7503
         *       ****    * * *     ***  * ** * **            **      *
genome   CAAGAAAAAAGTCCTGGTTGACAACAGTGCCACGAAGCGTTAGAACACATAGGGATGTTT 179331
mRNA     CCGCATCAACACACTAGGCTGGACCAGTCGTACTCAGTTTGAAGAAACTTGGGCCACCCT 7563
         *   *  **    ** *     * ****   **   **   * *   * ** * **      *
genome   GTGGAGCATTTGCATGTGGAAAGCAGCAAAAACATAATGGGAACGGGTTCTTTTGTTATG 179391
mRNA     CCTTGGTGTCCTGGTGACGCAGCCCCTCGTGATGGAGCAGGAGGAGAGCCCACCAGAAGA 7623
             *  *     **  *  *  *        *   *   ***    *   *       *
                                              rs362310
genome   ATTTTTAAAAATCTCTTTTGT-AACATCCTTCCCGC-TGCGCCGTTTCTGCA-TATTCCT 179448
mRNA     AGACACAGAGAGGACCCAGATCAACGTCCTGGCCGTGCAGGCCATCACCTCACTGGTGCT 7683
         *     * * *   *     * *** ****  ***      *** *  *   ** *  * **
genome   TTATGTAGCTTTCAAACTCCTCTTAGGAGTTCTGGTCCCTACAGGGCGTGGGAGCCCAGG 179508
mRNA     CAGTGCAATGACTGTGCCTGTGGCCGGCAACCCAG-CTGTAAGCTGCTTGGAGCAGCAGC 7742
            ** *        *    *     **     *   *  *  **    ** ***      ***
genome   CTTTACGTAGCTTTCAAACTCCTCTTAGGAGTTCTGGTCCCTACAGGGTGTGGG----AG 179564
mRNA     CCCGGAACAAGCCTCTGAAAGCTCTCGACA--CCAGGTTTGGGAGGAAGCTGAGCATTAT 7800
         *      *    **  *   ****    *   * ***        *     ** *    *
genome   CCCAGGGCCTGTGCCGAGCAGCCTGCCTCCACGAGCTAGACAGAGGAAGGGCTGGGGTTT 179624
mRNA     CAGAGGGATTGTGGAGCAAGAGATTCAAGCAATGGTTTCAAAGAGAGAGAA-TATTGCCA 7859
         *  ****  ****  *         * *    **    * *   * ****  **    *    *
genome   TGCCTTTTTAGTCTCAAAATTCGTACTCCAGTTGCTTAGGCTCTGACTTTCCCCACTTGG 179684
mRNA     CCCATCATTTATATCAGGCATGGGA-TCCTGTCCCTT---CTCTGTCTCCGGCTACTACA 7915
            * *   **  * ***    * * * *** **  ***    ***** **     * ***
genome   AAAGTCCCTCACGGCCGAGGGTCCCTCCCAGCCCTGATTTCACATCGGCATTTTCCCCAG 179744
mRNA     GGTGCCCTCATCAGCCACGAGAAGCTGCTGCTACAGATCAACCCCGAGCGGGAGCTGGGG 7975
             * **     * ***  * *    ** *      * ***     *      **      *     *
genome   TATTAGAGCCAAGGCCCTCCGCGGGCAGGTGGGGCAGCTGTGGGAGCTGGTGCCAGTCTC 179804
mRNA     AGCATGAGCTACAAACT----CGGCCAGGTGT------CCATAC-ACTCCGTGT-GGCTGG 8024
             **** *   *      *** ******       *   *    *     ***    *
genome   TGACCTGCGTCCCTCCTCCCAGGATCAGGAAAGGCTTTCCTTGTGAAGCCAGAGTGGTGG 179864
```

FIG. 1 NNNNNN

```
mRNA     GGAACAGCATCACACCCCTGAGGGAGGAGGAATGGGACGAGGAAGAGGAGGAGGAGGCCG 8084
          ** * ** ** * ** *  ***     * ** *          ** *     * **  *

genome   CCAGGATCCTGCCCCAGTTTCTAG--ACGACTTCTTCCCACCCCAGGACATCATGAACAA 179922
mRNA     ACGCCCCTGCACCTTCGTCACCACCCACGTCTCCAGTCAACTCCAGGAAAC-----ACCG 8139
          *         **   **  * *   *** ** *   * ** ****** *      **

genome   AGTCATCGGAGAGTTTCTGTCCAACCAGCAGCCATACCCCCAGTT-CATGGCCACCGTGG 179981
mRNA     GGCTGGAGTTGACATCCACTCCTGTTCGCAGTTTTTGCTTGAGTTGTACAGCCGCTGGAT 8199
          *     *  **  * *  ***     ****   *  *   ****  *  *** * *

genome   TGTATAAGGTGAGGTTGCATGTGGGATGGGGATGGAGTGGGAAAGCCTGGAGGTGGAGTT 180041
mRNA     CCTGCCGTCCAGCTCAGCCAGGAGGACCCCGGCCATCCTGATCAGTGAGGTGGTCAGATC 8259
           *             **  *  ***    *        *   **   ** ***    *

genome   GCCTCCGACTTCCCAGCAGATTCGCCAGCAGAGCCCAGCTCCTCCGCTTTAAAGCA-GCA 180100
mRNA     CCTTCTAGTGGTCT--CAGACTTGTTCACCGAGCGCAACCAGTTTGAGCTGATGTATGTG 8317
          * **       *   **** * *    * **** ** *   *  *   * * * * *

genome   ATGCCTCTGGCCCCCACCCCACCCCCGCCACCCAGGCGCAGCAGGTGCTTCCCGTCCCCC 180160
mRNA     ACGCTGACAGAACT-GCGAAGGGTGCACCCTTCAGAAGACGAGATCCTCGCTCAGTACCT 8376
         * **     *  *   *        * **   ***  *  *         * *    **

genome   CAGCCCTGACACTCAGGCACCTGCTTGCTCCTTGCAGGTGTTTCAGACTCTGCACAGCAC 180220
mRNA     GGTGCCTGCCACCTGCAAGGCAGCTGCCGTCCTTGGGATGGACAAGGCCGTG-GCGGAGC 8435
             **** ***        * ***  *  * *   * **    ** *  **  * *  *

genome   CGGGCAGTCGTCCATGGTCCGGGACTGGGTCATGCTGTCCCTCTCCAACTTCACGCAGAG 180280
mRNA     CTGTCAGCCGCC--TGCTGGAGAGCACGCTCAGGAGCAGCCACCTGCCCAGCAGGGTTGG 8493
         * * *** ** *  ** *   *  *  * *** *     ** *     *  ** *    *

genome   GGCCCCGGTCGCCATGGCC-ACGTGGAGCCTCTCCTGCTTCTTTGTCAGCGC-GTCCACC 180338
mRNA     AGCCCTGCACGGCGTCCTCTATGTGCTGGAG-TGCGACCTGCTGGACGACACTGCCAAGC 8552
          **** *  ** * *   * * ***  *    * *  * *  * * *  * * * * * *

genome   AGCCCGTG--GGTCG-CGGCGA-TGTATCCTCTCTGGGTCCCTGGTGCTGGCCCCGTTTC 180394
mRNA     AGCTCATCCCGGTCATCAGCGACTATCTCCTCTCCAA---CCTGAAA--GGGATCGCCCA 8607
         *** * *   ****  * **** * * *******      ****     **   **

genome   CCTTGTCAACACCGA-GGCTCATGTTTCATGATAAGGTTTTGAAAC-CTAACCTTTGCAA 180452
mRNA     CTGCGTGAACATTCACAGCCAGCAGCACGTACTGGTCATGTGTGCCACTGCGTTTTACCT 8667
         *   ** ****   * **         * *  *     * **   * **    *** *

genome   AAACCCCACAGATGCCAGGGTGACAGGCCCTCAGCCCCAGGGAAGTAAAATGCTGACAGG 180512
mRNA     CATTGAGAACTATCCTCTGGACGTAGGGCCGGAATTTTCAGCATCAATAAT----ACAGA 8723
          *     *   ** *   **     *** **  *       * *   * ***    ****

genome   GGTACAGAAAGGAGCACGTCCAGACATTTGCTGACCAGGGCCTCTCAGAGGGGCCGGTGT 180572
mRNA     TGTGTGGGGTGATGC-TGTCTGGAAGTGAGGAGTCCACCCCCTCCATCATTTACCACTGT 8782
          **   *   *  **  ***  **  *  *  * ***   ****    *    **  ***

genome   ATGGCAGGAGGGTCGCAGCTGAGGGGCCTTTCTGTGGAGGGCCTGGGTGAGGGGAGCGAG 180632
mRNA     GCCCTCAGAGGCCTGGAGCGCCTCCTGCTCTCTGAGCAGCTCTCCCGCCTGGATGCAGAA 8842
                ****   * ***        ** **** * **  *    *   **     **

genome   GGTGGGCGGTGGTCTCTGCAGACGTCCCGCCCACTCGCGGGCTCTGTGTGGCTGGGCTTC 180692
mRNA     ------------TCGCTG-----GTCAAGCTGA---GTGTGGACAGAGTGAACGTGCACA 8882
                     ** ***     ***  **  *   * * *  * * ***   * **

genome   TCCTGACACTGCTTCTCATTAGCTTTGGTCATTGTGCCTCGATCGCCCTCTCGGGGAAAG 180752
mRNA     GCCCG-CACCGGGCCATGGCGGCTCTGGGCCTGATGC-----TCACCTGCATGTACACAG 8936
          ** * *** *   *      *** *** * *  ***     ** **  *  *   * **

genome   GCTTAAGTAAAGATCCAGTTCCCACCCCCAGATGCTGGCTGCCAGGAGTTTCCCTTTCCA 180812
mRNA     GA--AAGGAGAAAGTCAGT--------CCGGGTA--GAACTTCAGA---CCCTAATCCTG 8981
         *   *** * * *  ****        ** * *   *     ***      *   * *

genome   CAGCCCTTCCCCAAGACAGACCACAAGAGCCTCCAAGCAGCACAGTTGTCCTGGTGCTGA 180872
mRNA     CAGCCCCCGAC--AGCGAGTCAGTGATTGTTGCTATGGAGCGGGTATCTGTTCTTTTTGA 9039
         ******    *  **  ** *    *  *   * * * ***     * *  *  *  ***

genome   CAGCACAGCCTTGCCCGGCGTGCCTGGCACGGCTCTGCCCTCACTGCATTGGAGCAGGGC 180932
mRNA     TAG---GATCAGGAAAGGCTTTCCTTGTGAAGC--------CAGAGTGGTGGCCAGGATC 9088
          **      *  *   *** * *** *    **        **  *   ***    *  *

genome   TAGTGGAGGCCAGCGGAAGCACCGGCCACCAGCGCTGCACAGGAGCCAGGCCAGGTGAGT 180992
mRNA     CTGCCCCAGTTTCTAGACG-ACTTCTTCCCACCCCAGGACATCA--TGAACAAAGTCA-- 9143
           *     *      ** * **      *** * * * ***  *      * * ** *

genome   GCTGCCGAGTGGGTGCCCTGCCTGCAGGGCATCCAGCCAGCCAAGGGTTGCAGGAATGGA 181052
mRNA     -TCGGAGAGTTTCTGTCCAACCAGCAGC-CATACCCCCAGTTCATGGCCACCGTGGTGTA 9201
            *  ****   ** **  ** **** *** *  ****   * **   * *   ** *

genome   GGTGGAGGCGCTGATGCAGCTGGAGGCATCCAGGTGGCCCTTCCGGGGCTCTG-CTCGCT 181111
```

FIG. 1 OOOOOO

```
mRNA      TAAGGTGTTTCAGACTCTGC--ACAGCA-CCGGGCAGTCGTCCATGGTCCGGGACTGGGT 9258
             ** *   * **  * **     *** ** **  * * * *  ** *   * ** * *

genome    C-TCCAGGCTCCCTGGACCCCTTTGTAGACTGTTTCAGGAGAGGAACTCCCAGGTGAGGA 181170
mRNA      CATGCTGTCCCTCTCCAACTTCACGCAGAGGGCCCCGGTCGCC--ATGGCCACGTGGAGC 9316
          * * * * * * **  * *     * ***  *   * *  *    *   *** ***  *

genome    CAGGGAGGCAGCATTCCC--CTCATTTGCCGGCCTTTTTCCTTAACTCCTGCACCAGCCT 181228
mRNA      CTCTCCTGCTTCTTTGTCAGCGCGTCCACCAGCC-------CGTGGGTCGCG-GCGATCCT 9369
          *      **  * **  *  * * *  ** ***       * *   **  *  * * ***

genome    CCCACATGTCATCAGCAGGATGGGCAAGCTGGAGCAGGTGGACGTGAACCTTTTCTGCCT 181288
mRNA      CCCACATGTCATCAGCAGGATGGGCAAGCTGGAGCAGGTGGACGTGAACCTTTTCTGCCT 9429
          ************************************************************

genome    GGTCGCCACAGACTTCTACAGACACCAGATAGAGGAGGAGCTCGACCGCAGGGCCTTCCA 181348
mRNA      GGTCGCCACAGACTTCTACAGACACCAGATAGAGGAGGAGCTCGACCGCAGGGCCTTCCA 9489
          ************************************************************

genome    GTCTGTGCTTGAGGTGGTTGCAGCCCCAGGAAGCCCATATCACCGGCTGCTGACTTGTTT 181408
mRNA      GTCTGTGCTTGAGGTGGTTGCAGCCCCAGGAAGCCCATATCACCGGCTGCTGACTTGTTT 9549
          ************************************************************

genome    ACGAAATGTCCACAAGGTCACCACCTGCTGAGCGCCATGGTGGGAGAGACTGTGAGGCGG 181468
mRNA      ACGAAATGTCCACAAGGTCACCACCTGCTGAGCGCCATGGTGGGAGAGACTGTGAGGCGG 9609
          ************************************************************

                                      rs362307
genome    CAGCTGGGGCCGGAGCCTTTGGAAGTCTGCGCCCTTGTGCCCTGCCTCCACCGAGCCAGC 181528
mRNA      CAGCTGGGGCCGGAGCCTTTGGAAGTCTGCGCCCTTGTGCCCTGCCTCCACCGAGCCAGC 9669
          ************************************************************

genome    TTGGTCCCTATGGGCTTCCGCACATGCCGCGGGCGGCCAGGCAACGTGCGTGTCTCTGCC 181588
mRNA      TTGGTCCCTATGGGCTTCCGCACATGCCGCGGGCGGCCAGGCAACGTGCGTGTCTCTGCC 9729
          ************************************************************

genome    ATGTGGCAGAAGTGCTCTTTGTGGCAGTGGCCAGGCAGGGAGTGTCTGCAGTCCTGGTGG 181648
mRNA      ATGTGGCAGAAGTGCTCTTTGTGGCAGTGGCCAGGCAGGGAGTGTCTGCAGTCCTGGTGG 9789
          ************************************************************

genome    GGCTGAGCCTGAGGCCTTCCAGAAAGCAGGAGCAGCTGTGCTGCACCCCATGTGGGTGAC 181708
mRNA      GGCTGAGCCTGAGGCCTTCCAGAAAGCAGGAGCAGCTGTGCTGCACCCCATGTGGGTGAC 9849
          ************************************************************

                                                       rs362306
genome    CAGGTCCTTTCTCCTGATAGTCACCTGCTGGTTGTTGCCAGGTTGCAGCTGCTCTTGCAT 181768
mRNA      CAGGTCCTTTCTCCTGATAGTCACCTGCTGGTTGTTGCCAGGTTGCAGCTGCTCTTGCAT 9909
          ************************************************************

genome    CTGGGCCAGAAGTCCTCCCTCCTGCAGGCTGGCTGTTGGCCCCTCTGCTGTCCTGCAGTA 181828
mRNA      CTGGGCCAGAAGTCCTCCCTCCTGCAGGCTGGCTGTTGGCCCCTCTGCTGTCCTGCAGTA 9969
          ************************************************************

genome    GAAGGTGCCGTGAGCAGGCTTTGGGAACACTGGCCTGGGTCTCCCTGGTGGGGTGTGCAT 181888
mRNA      GAAGGTGCCGTGAGCAGGCTTTGGGAACACTGGCCTGGGTCTCCCTGGTGGGGTGTGCAT 10029
          ************************************************************

genome    GCCACGCCCCGTGTCTGGATGCACAGATGCCATGGCCTGTGCTGGGCCAGTGGCTGGGGG 181948
mRNA      GCCACGCCCCGTGTCTGGATGCACAGATGCCATGGCCTGTGCTGGGCCAGTGGCTGGGGG 10089
          ************************************************************

                 rs362303
genome    TGCTAGACACCCGGCACCATTCTCCCTTCTCTCTTTTCTTCTCAGGATTTAAAATTTAAT 182008
mRNA      TGCTAGACACCCGGCACCATTCTCCCTTCTCTCTTTTCTTCTCAGGATTTAAAATTTAAT 10149
          ************************************************************

genome    TATATCAGTAAAGAGATTAATTTTAACGTAACTCTTTCTATGCCCGTGTAAAGTATGTGA 182068
mRNA      TATATCAGTAAAGAGATTAATTTTAACGTAACTCTTTCTATGCCCGTGTAAAGTATGTGA 10209
          ************************************************************

genome    ATCGCAAGGCCTGTGCTGCATGCGACAGCGTCCGGGGTGGTGGACAGGGCCCCCGGCCAC 182128
mRNA      ATCGCAAGGCCTGTGCTGCATGCGACAGCGTCCGGGGTGGTGGACAGGGCCCCCGGCCAC 10269
          ************************************************************

genome    GCTCCCTCTCCTGTAGCCACTGGCATAGCCCTCCTGAGCACCCGCTGACATTTCCGTTGT 182188
mRNA      GCTCCCTCTCCTGTAGCCACTGGCATAGCCCTCCTGAGCACCCGCTGACATTTCCGTTGT 10329
          ************************************************************

genome    ACATGTTCCTGTTTATGCATTCACAAGGTGACTGGGATGTAGAGAGGCGTTAGTGGGCAG 182248
mRNA      ACATGTTCCTGTTTATGCATTCACAAGGTGACTGGGATGTAGAGAGGCGTTAGTGGGCAG 10389
          ************************************************************
```

FIG. 1 PPPPPP

```
genome    GTGGCCACAGCAGGACTGAGGACAGGCCCCCATTATCCTAGGGGTGCGCTCACCTGCAGC 182308
mRNA      GTGGCCACAGCAGGACTGAGGACAGGCCCCCATTATCCTAGGGGTGCGCTCACCTGCAGC 10449
          ************************************************************

genome    CCCTCCTCCTCGGGCACAGACGACTGTCGTTCTCCACCCACCAGTCAGGGACAGCAGCCT 182368
mRNA      CCCTCCTCCTCGGGCACAGACGACTGTCGTTCTCCACCCACCAGTCAGGGACAGCAGCCT 10509
          ************************************************************

genome    CCCTGTCACTCAGCTGAGAAGGCCAGCCCTCCCTGGCTGTGAGCAGCCTCCACTGTGTCC 182428
mRNA      CCCTGTCACTCAGCTGAGAAGGCCAGCCCTCCCTGGCTGTGAGCAGCCTCCACTGTGTCC 10569
          ************************************************************

genome    AGAGACATGGGCCTCCCACTCCTGTTCCTTGCTAGCCCTGGGGTGGCGTCTGCCTAGGAG 182488
mRNA      AGAGACATGGGCCTCCCACTCCTGTTCCTTGCTAGCCCTGGGGTGGCGTCTGCCTAGGAG 10629
          ************************************************************

genome    CTGGCTGGCAGGTGTTGGGACCTGCTGCTCCATGGATGCATGCCCTAAGAGTGTCACTGA 182548
mRNA      CTGGCTGGCAGGTGTTGGGACCTGCTGCTCCATGGATGCATGCCCTAAGAGTGTCACTGA 10689
          ************************************************************

genome    GCTGTGTTTTGTCTGAGCCTCTCTCGGTCAACAGCAAAGCTTGGTGTCTTGGCACTGTTA 182608
mRNA      GCTGTGTTTTGTCTGAGCCTCTCTCGGTCAACAGCAAAGCTTGGTGTCTTGGCACTGTTA 10749
          ************************************************************

genome    GTGACAGAGCCCAGCATCCCTTCTGCCCCCGTTCCAGCTGACATCTTGCACGGTGACCCC 182668
mRNA      GTGACAGAGCCCAGCATCCCTTCTGCCCCCGTTCCAGCTGACATCTTGCACGGTGACCCC 10809
          ************************************************************

genome    TTTTAGTCAGGAGAGTGCAGATCTGTGCTCATCGGAGACTGCCCCACGGCCCTGTCAGAG 182728
mRNA      TTTTAGTCAGGAGAGTGCAGATCTGTGCTCATCGGAGACTGCCCCACGGCCCTGTCAGAG 10869
          ************************************************************

genome    CCGCCACTCCTATCCCCAGGCCAGGTCCCTGGACCAGCCTCCTGTTTGCAGGCCCAGAGG 182788
mRNA      CCGCCACTCCTATCCCCAGGCCAGGTCCCTGGACCAGCCTCCTGTTTGCAGGCCCAGAGG 10929
          ************************************************************

genome    AGCCAAGTCATTAAAATGGAAGTGGATTCTGGATGGCCGGGCTGCTGCTGATGTAGGAGC 182848
mRNA      AGCCAAGTCATTAAAATGGAAGTGGATTCTGGATGGCCGGGCTGCTGCTGATGTAGGAGC 10989
          ************************************************************

genome    TGGATTTGGGAGCTCTGCTTGCCGACTGGCTGTGAGACGAGGCAGGGGCTCTGCTTCCTC 182908
mRNA      TGGATTTGGGAGCTCTGCTTGCCGACTGGCTGTGAGACGAGGCAGGGGCTCTGCTTCCTC 11049
          ************************************************************

genome    AGCCCTAGAGGCGAGCCAGGCAAGGTTGGCGACTGTCATGTGGCTTGGTTTGGTCATGCC 182968
mRNA      AGCCCTAGAGGCGAGCCAGGCAAGGTTGGCGACTGTCATGTGGCTTGGTTTGGTCATGCC 11109
          ************************************************************

genome    CGTCGATGTTTTGGGTATTGAATGTGGTAAGTGGAGGAAATGTTGGAACTCTGTGCAGGT 183028
mRNA      CGTCGATGTTTTGGGTATTGAATGTGGTAAGTGGAGGAAATGTTGGAACTCTGTGCAGGT 11169
          ************************************************************

genome    GCTGCCTTGAGACCCCCAAGCTTCCACCTGTCCCTCTCCTATGTGGCAGCTGGGGAGCAG 183088
mRNA      GCTGCCTTGAGACCCCCAAGCTTCCACCTGTCCCTCTCCTATGTGGCAGCTGGGGAGCAG 11229
          ************************************************************

genome    CTGAGATGTGGACTTGTATGCTGCCCACATACGTGAGGGGGAGCTGAAAGGGAGCCCCTC 183148
mRNA      CTGAGATGTGGACTTGTATGCTGCCCACATACGTGAGGGGGAGCTGAAAGGGAGCCCCTC 11289
          ************************************************************

genome    CTCTGAGCAGCCTCTGCCAGGCCTGTATGAGGCTTTTCCCACCAGCTCCCAACAGAGGCC 183208
mRNA      CTCTGAGCAGCCTCTGCCAGGCCTGTATGAGGCTTTTCCCACCAGCTCCCAACAGAGGCC 11349
          ************************************************************

genome    TCCCCCAGCCAGGACCACCTCGTCCTCGTGGCGGGGCAGCAGGAGCGGTAGAAAGGGGTC 183268
mRNA      TCCCCCAGCCAGGACCACCTCGTCCTCGTGGCGGGGCAGCAGGAGCGGTAGAAAGGGGTC 11409
          ************************************************************

genome    CGATGTTTGAGGAGGCCCTTAAGGGAAGCTACTGAATTATAACACGTAAGAAAATCACCA 183328
mRNA      CGATGTTTGAGGAGGCCCTTAAGGGAAGCTACTGAATTATAACACGTAAGAAAATCACCA 11469
          ************************************************************

genome    TTCCGTATTGGTTGGGGGCTCCTGTTTCTCATCCTAGCTTTTTCCTGGAAAGCCCGCTAG 183388
mRNA      TTCCGTATTGGTTGGGGGCTCCTGTTTCTCATCCTAGCTTTTTCCTGGAAAGCCCGCTAG 11529
          ************************************************************

genome    AAGGTTTGGGAACGAGGGGAAAGTTCTCAGAACTGTTGGCTGCTCCCCACCCGCCTCCCG 183448
mRNA      AAGGTTTGGGAACGAGGGGAAAGTTCTCAGAACTGTTGGCTGCTCCCCACCCGCCTCCCG 11589
          ************************************************************

genome    CCTCCCCCGCAGGTTATGTCAGCAGCTCTGAGACAGCAGTATCACAGGCCAGATGTTGTT 183508
mRNA      CCTCCCCCGCAGGTTATGTCAGCAGCTCTGAGACAGCAGTATCACAGGCCAGATGTTGTT 11649
          ************************************************************
```

FIG. 1 QQQQQQ

```
genome    CCTGGCTAGATGTTTACATTTGTAAGAAATAACACTGTGAATGTAAAACAGAGCCATTCC 183568
mRNA      CCTGGCTAGATGTTTACATTTGTAAGAAATAACACTGTGAATGTAAAACAGAGCCATTCC 11709
          ************************************************************

genome    CTTGGAATGCATATCGCTGGGCTCAACATAGAGTTTGTCTTCCTCTTGTTTACGACGTGA 183628
mRNA      CTTGGAATGCATATCGCTGGGCTCAACATAGAGTTTGTCTTCCTCTTGTTTACGACGTGA 11769
          ************************************************************

genome    TCTAAACCAGTCCTTAGCAAGGGGCTCAGAACACCCCGCTCTGGCAGTAGGTGTCCCCCA 183688
mRNA      TCTAAACCAGTCCTTAGCAAGGGGCTCAGAACACCCCGCTCTGGCAGTAGGTGTCCCCCA 11829
          ************************************************************

genome    CCCCCAAAGACCTGCCTGTGTGCTCCGGAGATGAATATGAGCTCATTAGTAAAAATGACT 183748
mRNA      CCCCCAAAGACCTGCCTGTGTGCTCCGGAGATGAATATGAGCTCATTAGTAAAAATGACT 11889
          ************************************************************

genome    TCACCCACGCATATACATAAAGTATCCATGCATGTGCATATAGACACATCTATAATTTTA 183808
mRNA      TCACCCACGCATATACATAAAGTATCCATGCATGTGCATATAGACACATCTATAATTTTA 11949
          ************************************************************

genome    CACACACACCTCTCAAGACGGAGATGCATGGCCTCTAAGAGTGCCCGTGTCGGTTCTTCC 183868
mRNA      CACACACACCTCTCAAGACGGAGATGCATGGCCTCTAAGAGTGCCCGTGTCGGTTCTTCC 12009
          ************************************************************

genome    TGGAAGTTGACTTTCCTTAGACCCGCCAGGTCAAGTTAGCCGCGTGACGGACATCCAGGC 183928
mRNA      TGGAAGTTGACTTTCCTTAGACCCGCCAGGTCAAGTTAGCCGCGTGACGGACATCCAGGC 12069
          ************************************************************

genome    GTGGGACGTGGTCAGGGCAGGGCTCATTCATTGCCCACTAGGATCCCACTGGCGAAGATG 183988
mRNA      GTGGGACGTGGTCAGGGCAGGGCTCATTCATTGCCCACTAGGATCCCACTGGCGAAGATG 12129
          ************************************************************

genome    GTCTCCATATCAGCTCTCTGCAGAAGGGAGGAAGACTTTATCATGTTCCTAAAAATCTGT 184048
mRNA      GTCTCCATATCAGCTCTCTGCAGAAGGGAGGAAGACTTTATCATGTTCCTAAAAATCTGT 12189
          ************************************************************

genome    GGCAAGCACCCATCGTATTATCCAAATTTTGTTGCAAATGTGATTAATTTGGTTGTCAAG 184108
mRNA      GGCAAGCACCCATCGTATTATCCAAATTTTGTTGCAAATGTGATTAATTTGGTTGTCAAG 12249
          ************************************************************

genome    TTTTGGGGGTGGGCTGTGGGGAGATTGCTTTTGTTTTCCTGCTGGTAATATCGGGAAAGA 184168
mRNA      TTTTGGGGGTGGGCTGTGGGGAGATTGCTTTTGTTTTCCTGCTGGTAATATCGGGAAAGA 12309
          ************************************************************

genome    TTTTAATGAAACCAGGGTAGAATTGTTTGGCAATGCACTGAAGCGTGTTTCTTTCCCAAA 184228
mRNA      TTTTAATGAAACCAGGGTAGAATTGTTTGGCAATGCACTGAAGCGTGTTTCTTTCCCAAA 12369
          ************************************************************

genome    ATGTGCCTCCCTTCCGCTGCGGGCCCAGCTGAGTCTATGTAGGTGATGTTTCCAGCTGCC 184288
mRNA      ATGTGCCTCCCTTCCGCTGCGGGCCCAGCTGAGTCTATGTAGGTGATGTTTCCAGCTGCC 12429
          ************************************************************

genome    AAGTGCTCTTTGTTACTGTCCACCCTCATTTCTGCCAGCGCATGTGTCCTTTCAAGGGGA 184348
mRNA      AAGTGCTCTTTGTTACTGTCCACCCTCATTTCTGCCAGCGCATGTGTCCTTTCAAGGGGA 12489
          ************************************************************

genome    AAATGTGAAGCTGAACCCCCTCCAGACACCCAGAATGTAGCATCTGAGAAGGCCCTGTGC 184408
mRNA      AAATGTGAAGCTGAACCCCCTCCAGACACCCAGAATGTAGCATCTGAGAAGGCCCTGTGC 12549
          ************************************************************

genome    CCTAAAGGACACCCCTCGCCCCCATCTTCATGGAGGGGGTCATTTCAGAGCCCTCGGAGC 184468
mRNA      CCTAAAGGACACCCCTCGCCCCCATCTTCATGGAGGGGGTCATTTCAGAGCCCTCGGAGC 12609
          ************************************************************

genome    CAATGAACAGCTCCTCCTCTTGGAGCTGAGATGAGCCCCACGTGGAGCTCGGGACGGATA 184528
mRNA      CAATGAACAGCTCCTCCTCTTGGAGCTGAGATGAGCCCCACGTGGAGCTCGGGACGGATA 12669
          ************************************************************

genome    GTAGACAGCAATAACTCGGTGTGTGGCCGCCTGGCAGGTGGAACTTCCTCCCGTTGCGGG 184588
mRNA      GTAGACAGCAATAACTCGGTGTGTGGCCGCCTGGCAGGTGGAACTTCCTCCCGTTGCGGG 12729
          ************************************************************

genome    GTGGAGTGAGGTTAGTTCTGTGTGTCTGGTGGGTGGAGTCAGGCTTCTCTTGCTACCTGT 184648
mRNA      GTGGAGTGAGGTTAGTTCTGTGTGTCTGGTGGGTGGAGTCAGGCTTCTCTTGCTACCTGT 12789
          ************************************************************

genome    GAGCATCCTTCCCAGCAGACATCCTCATCGGGCTTTGTCCCTCCCCCGCTTCCTCCCTCT 184708
mRNA      GAGCATCCTTCCCAGCAGACATCCTCATCGGGCTTTGTCCCTCCCCCGCTTCCTCCCTCT 12849
          ************************************************************

genome    GCGGGGAGGACCCGGGACCACAGCTGCTGGCCAGGGTAGACTTGGAGCTGTCCTCCAGAG 184768
mRNA      GCGGGGAGGACCCGGGACCACAGCTGCTGGCCAGGGTAGACTTGGAGCTGTCCTCCAGAG 12909
          ************************************************************
```

FIG. 1 RRRRRR

```
genome    GGGTCACGTGTAGGAGTGAGAAGAAGGAAGATCTTGAGAGCTGCTGAGGGACCTTGGAGA 184828
mRNA      GGGTCACGTGTAGGAGTGAGAAGAAGGAAGATCTTGAGAGCTGCTGAGGGACCTTGGAGA 12969
          ************************************************************

genome    GCTCAGGATGGCTCAGACGAGGACACTCGCTTGCCGGGCCTGGGCCTCCTGGGAAGGAGG 184888
mRNA      GCTCAGGATGGCTCAGACGAGGACACTCGCTTGCCGGGCCTGGGCCTCCTGGGAAGGAGG 13029
          ************************************************************

genome    GAGCTGCTCAGAATGCCGCATGACAACTGAAGGCAACCTGGAAGGTTCAGGGGCCGCTCT 184948
mRNA      GAGCTGCTCAGAATGCCGCATGACAACTGAAGGCAACCTGGAAGGTTCAGGGGCCGCTCT 13089
          ************************************************************

genome    TCCCCCATGTGCCTGTCACGCTCTGGTGCAGTCAAAGGAACGCCTTCCCCTCAGTTGTTT 185008
mRNA      TCCCCCATGTGCCTGTCACGCTCTGGTGCAGTCAAAGGAACGCCTTCCCCTCAGTTGTTT 13149
          ************************************************************

genome    CTAAGAGCAGAGTCTCCCGCTGCAATCTGGGTGGTAACTGCCAGCCTTGGAGGATCGTGG 185068
mRNA      CTAAGAGCAGAGTCTCCCGCTGCAATCTGGGTGGTAACTGCCAGCCTTGGAGGATCGTGG 13209
          ************************************************************

genome    CCAACGTGGACCTGCCTACGGAGGGTGGGCTCTGACCCAAGTGGGGCCTCCTTGTCCAGG 185128
mRNA      CCAACGTGGACCTGCCTACGGAGGGTGGGCTCTGACCCAAGTGGGGCCTCCTTGTCCAGG 13269
          ************************************************************

genome    TCTCACTGCTTTGCACCGTGGTCAGAGGGACTGTCAGCTGAGCTTGAGCTCCCCTGGAGC 185188
mRNA      TCTCACTGCTTTGCACCGTGGTCAGAGGGACTGTCAGCTGAGCTTGAGCTCCCCTGGAGC 13329
          ************************************************************

genome    CAGCAGGGCTGTGATGGGCGAGTCCCGGAGCCCCACCCAGACCTGAATGCTTCTGAGAGC 185248
mRNA      CAGCAGGGCTGTGATGGGCGAGTCCCGGAGCCCCACCCAGACCTGAATGCTTCTGAGAGC 13389
          ************************************************************

genome    AAAGGGAAGGACTGACGAGAGATGTATATTTAATTTTTTAACTGCTGCAAACATTGTACA 185308
mRNA      AAAGGGAAGGACTGACGAGAGATGTATATTTAATTTTTTAACTGCTGCAAACATTGTACA 13449
          ************************************************************

genome    TCCAAATTAAAGGAAAAAAATGGAAACCATCAGTTGTTGCTGTGTGAGGCTTGCTTTGCT 185368
mRNA      TCCAAATTAAAGGAAAAAAATGGAAACCATCA---------------------------- 13481
          ********************************

genome    TCATGAGAACCTAGACCTTGCTGAGCTGGAGTCTTAGGAAGCAGTCTCCTAAGTGCTTCT 185428
mRNA      ------------------------------------------------------------

genome    CCAGCAGGGGCAGAAACTGTCCCACCAGCTAACATCTGGCATTATGGAGGGTCCCCCAGG 185488
mRNA      ------------------------------------------------------------

genome    CAGCTGCCAGCAGGGACAGGCCCCGTGTTTTCTGTAGCCAGGGATGAGGAAGTGGCCCCA 185548
mRNA      ------------------------------------------------------------

genome    GGGCATGGGCCTGGCTGGGTGCTTCTGCAAGGGCCTTCCCAAACCACAGTACAGGTGGTC 185608
mRNA      ------------------------------------------------------------

genome    TTCCTGCCCTGCAGATGGGAGCTGTGGGAGCTGCTGGAGCTGCTGGAGCCTTCATGGTCA 185668
mRNA      ------------------------------------------------------------

genome    AGTGACATCATAAGCTTATATGACATACACAAGCCTCAGGACTTGGCCCATGGCACTGAA 185728
mRNA      ------------------------------------------------------------

genome    GCAGGTCATCAGGCCCAGCACAGAGACTAGAGCTGTGTTCTCACAGGGCCCACCACCCTT 185788
mRNA      ------------------------------------------------------------

genome    CCACCTCCTTGGCCATTGACACCTGCGTCCCTGGCCCAGCTGCTCCCAGGTAACCCCCAA 185848
mRNA      ------------------------------------------------------------

genome    AGCAGCTGGCACATCCCACCTCTGGTGTGGCCGGGGCTGCTGTGTGTCCGCAGGGCCTGC 185908
mRNA      ------------------------------------------------------------

genome    CCCGTCTATTCTAGCTTGTTTGTCCTGTCTGAACCAGCGCCTACTCCAAGAAGCCTCTGC 185968
mRNA      ------------------------------------------------------------

genome    TCAGCCCAGCGGGGATGCTTCTAAGCTCCGGACGAGCCTCTCGGAAGCCTTGGTGATTGG 186028
mRNA      ------------------------------------------------------------
```

FIG. 1 SSSSSS

```
genome    TGGTGTAGTCATCTTGGGATGCAGATGTCTTACCAACCTGCAAGAACAAAAACCCTGTGG 186088
mRNA      ------------------------------------------------------------

genome    CTTCCTCTGGTGCAGGGTATTTAGTCAATGTTTGCTGAGGTCCCGTCTGGTTCTGGCTAA 186148
mRNA      ------------------------------------------------------------

genome    TTGGCAGGGGTCGTCCACCCATTCTTTCCCTGCTCTGCTGTCTGTGCCAGGAGAGACGGG 186208
mRNA      ------------------------------------------------------------

genome    GGCCAGTCGGCCAAGGGGCCAGCTCCTGCTGCCTGCTCCTCTTGGGCACGTGCGGGGGCC 186268
mRNA      ------------------------------------------------------------

genome    CCCTTTCTCTGAGCAGGGATAGGGATCAGTCTGCCGGAGGGATGTGGTGGACAGGCCTAA 186328
mRNA      ------------------------------------------------------------

genome    AGCATTTGGGGCGGGGCATGCCACTTGAGCTCCCTAAATCTGTCTCCTCATAGGTGACAC 186388
mRNA      ------------------------------------------------------------

genome    CGCTCCAGGGCCCCCCAGTGGCCTCTCCTTTCAGAGCTACCTAAATTCTGGTCACTTCAG 186448
mRNA      ------------------------------------------------------------

genome    AGAAATGGAGCACCCCCTTCTCCCTGGTCCAGGTGTGGACAGCCTGGCACACTGAGCACA 186508
mRNA      ------------------------------------------------------------

genome    CCTGGCATGGCTGGTAATTTCAGAAAGAAGAGGGGCCGGGGTCCAGTGGGAAGCAGCGGT 186568
mRNA      ------------------------------------------------------------

genome    GAACCCCTCGTGAGTGGGCTTTGCAGTCCCTCCCCATGCCACGGCAGAGCTGCCCTCAAC 186628
mRNA      ------------------------------------------------------------
                                           rs362296
genome    ACAGCCTTCCTCTTCCTCATCGGAGAGCACACCCTGTCCCCTTGCCGAGCTGTGCCCTGT 186688
mRNA      ------------------------------------------------------------

genome    GCCTTCGGTGGTATTTGATTTTGGCTGCTACTGGCTTTGTTGGGATCTGGAAGTCGCTTC 186748
mRNA      ------------------------------------------------------------

genome    CCCTGCGTGGTGCGTGGAGCACTGTAAGTCAGATGAGGGAAGTAGCCAGGGTGAGGTGAG 186808
mRNA      ------------------------------------------------------------

genome    TACCGGGTGGAGCCGCCACTGAAGGGACTGGGTAGGGGGGCCTTGCCTCTACATGATGTG 186868
mRNA      ------------------------------------------------------------

genome    ACACAGCCAACCGAGGACAGAGGAAGCCCCGTTCCTGGGGGTGTGGGGTGCACCCCTCAG 186928
mRNA      ------------------------------------------------------------

genome    GGAAGCCTGCAGTGGGGCCTGAGGAAAGGCATCCTCCGCGAGCCCACGAGTCTGGTCCAT 186988
mRNA      ------------------------------------------------------------

genome    GAGCACCGTGACAGTGTCTGTGGGTAGAGGTGGACCCGGCCTTGTGTCATCACCAGGACC 187048
mRNA      ------------------------------------------------------------

genome    TCTTTTGGGAAACCATGTGGACATCGCTTGCGGGTCCCCCAGGCTCTGCAGCCCCAGCAG 187108
mRNA      ------------------------------------------------------------

genome    CCTGGCTGCCTTTTGGGCAAGTGGCTTGAGCCACAGAGGACCCAGTCCTGTTGCAGCCAC 187168
mRNA      ------------------------------------------------------------

genome    ATCCTCTGGGGGGGCCCGCCAGTGTGGCCGGCTTTCTCCACCCTACACCAGGCCTCCAGG 187228
mRNA      ------------------------------------------------------------

genome    TGTCCTGGTCGGGGGTGTCTGGGCCCTGGGTGGGCCCTGTGGACCTGTGAGGTCAGGGTC 187288
mRNA      ------------------------------------------------------------
```

FIG. 1 TTTTTT

```
genome    AGGGCATCACTGGAGGCAGAGGGCTGAAGTTGTGGGTCTGGGTTCCCCTTGTGTGCACAG 187348
mRNA      ------------------------------------------------------------

genome    GCCCCTGCCCTCCATGCTTGGTCAGGCAGCTACCCCCAAAACTGCTAGGACAGGCTGGTC 187408
mRNA      ------------------------------------------------------------

genome    CTGAGGTGGATCCTGGCCCCTGTACCCTCTGGACAGCCCACCCGCCCAACCTTCTACCCT 187468
mRNA      ------------------------------------------------------------

genome    GCCCCAGCGGCGGCAGTGTTGGCCACATCCTTCCCCTCCTGGCCCCAATTGCTCTGGGGA 187528
mRNA      ------------------------------------------------------------

genome    AGTCCAGGCTCCGGAGCCTGCCCAGGGGCCCCCCGTGATTTGGGCCCAGGACTCCACGTG 187588
mRNA      ------------------------------------------------------------

genome    GTTCTCTGCCTTCACCCAAGCCCTGAACTCCTCAGCTGCCAAATCCCCACCCATCTGCAC 187648
mRNA      ------------------------------------------------------------

genome    AGGCTGTGCTCACCACTGCTGCTCCTGGAAGGTGCCCCTCAGTGGGACGCCCACCTCCTC 187708
mRNA      ------------------------------------------------------------

genome    TCTGGGCTTCTGTGTTTGGGAGCCCTGCTGCCCCCACCCTTGGTCAGTCCCCATGTCCTG 187768
mRNA      ------------------------------------------------------------

genome    CTGGCCTGTCAGGCAGGGCAGAAAATCCACCCAGAAATGCTGAGCAGGATGAGAGTCTAG 187828
mRNA      ------------------------------------------------------------

genome    TTGGGCCCAGCCTCATTATTTAGAAGGGATGGAGGCCTAGGGAGCATGCTTCTAGCCTGA 187888
mRNA      ------------------------------------------------------------

genome    GCCCAGCAGGGCCCCGCCCATGTCCCAGGTCTGCACCAGGGACAGCTCCTGCCGAGGCCT 187948
mRNA      ------------------------------------------------------------

genome    GACCTGCCCCTTCTCCCTCAGGTGCTGCTGGTTGACCAGCCTCTGGCCCTAGGAGACCCC 188008
mRNA      ------------------------------------------------------------

genome    GTAGCGACTGAGGGTCCCAGCAGGCCATGCAGCTTTGCCAAGGTACGAGCCCCTCCCCAG 188068
mRNA      ------------------------------------------------------------

genome    CAGGGGACAGATGTGGGGACCCTCCCAGGCAGGAGCAGCTGGGTGCCTGGTGCTGCCATC 188128
mRNA      ------------------------------------------------------------

genome    TGCTGCCTGCCTGGTTCTTGTCCTCACATTGGAGGTCAGTGTGAGGGCTCTGCCTCGGGA 188188
mRNA      ------------------------------------------------------------

genome    AAGGCCATGGAGCTTGCCCTGTCCAGGGCCTCCCATGTGCACTGAGCCTGGGAAGAGAGG 188248
mRNA      ------------------------------------------------------------

genome    GTTGGAGTTGAGCCTTTTACCCTGGGAATGCTGCCTGGAGGATGGTGCGGGTGTGGGGTG 188308
mRNA      ------------------------------------------------------------

genome    GCACCCTGCCAGGCAGGGCCCTGCCTCCCTGCGCCCACTGGAACTCGGGCAGGCAGGGGT 188368
mRNA      ------------------------------------------------------------

genome    GTAGGTGCCTCCTCTAGAGCCGTCCGGTGGGGGCCCCCGGCAGTGGTGGTGGTGTCCACT 188428
mRNA      ------------------------------------------------------------

genome    GGCCAGCAGCTGCCCCTTCAGCCAGGACAGTAGGCCTGACGCTGTCCCCAGCAGCTCCAA 188488
mRNA      ------------------------------------------------------------

genome    GGTGGATTTGTGGAAGGGGGTAGAGGGCACGTAGAGGCCCCATGACCTCCCCAGGGTTCT 188548
mRNA      ------------------------------------------------------------
```

FIG. 1 UUUUUU

```
genome  GGGAGGGCTGTGCCCCCTTAGCCAGCACCATGCTGGGTGATATAGTCAGATCCTGTTACC 188608
mRNA    ------------------------------------------------------------

genome  CCTGTTGTGGAGGTGAGGAAACAGGTTAGTGGGGAGGACATGACTAAGGTCCATGCTGAG 188668
mRNA    ------------------------------------------------------------

genome  TCGCTAGAGCTGCACCCAGAACCACTGCTGGGACCCCATGCCTTTCTGCTTACCCCTTGT 188728
mRNA    ------------------------------------------------------------

genome  GCCGGGAGATGCCAAGAGATGCTGGGAGCCAGCCCCACCTCTGCCCTTGGAGTCATGGCT 188788
mRNA    ------------------------------------------------------------

genome  ACGGAAAGGGCATTCGGACCGGTCCCTGACCTCACCGGGGAGGGCCGAACCCTGTTCCTG 188848
mRNA    ------------------------------------------------------------

genome  AGGAGCCAGGGCTTCCTAGAGGAGGTAGGCCTTCTAGTCACTCCTTCATCTGCAGGCACT 188908
mRNA    ------------------------------------------------------------

genome  CCACAGAGCTCTCTGTGCCAGCCCCCAGCACGGAGGGCTGACCTTAGTCGAGTGGAGATG 188968
mRNA    ------------------------------------------------------------

genome  CCCCAGTGCCAGGCAGTAGGGATGATGTCTCCTGAGGCCCAGATGGAAGGGACTGGACTA 189028
mRNA    ------------------------------------------------------------

genome  GTCTCATGGGGCTGATGGTGGGGCCAGGCCTTGACCAGGGACCCAGTGTAGGGGGTGCAG 189088
mRNA    ------------------------------------------------------------

genome  AGACCCCTCTGAGTTCCTCACACATCCCTGGGGCCCTCCCCATACACTTCCTATCCTGAC 189148
mRNA    ------------------------------------------------------------

genome  TGCGGGCAAGAGGGAGCCCCAGTTCGCCTTCCCTATGCTGGGCACCCACAGTGGGGCTGG 189208
mRNA    ------------------------------------------------------------

genome  GCACCCCCGCCATGCCCCTGCCCTGTCCTTCCCCTGAGAGCCTCGGTCCCACCTCCAAGG 189268
mRNA    ------------------------------------------------------------

genome  TGCCTCAGAGGACAGCAGGGGCAGCGGGCAGAGGCCGAGATGCCTCCTCATTCCAGGCTC 189328
mRNA    ------------------------------------------------------------

genome  AGCTGCCCTTCTTGGGGCAGCCCACACCTGAGAGTCTCCTGCAGTTGGTCAGGCCTGAGG 189388
mRNA    ------------------------------------------------------------

genome  AGGGCAGGGGGGTGCCTGCTGTCCCTCTGCTGACCACAGTGGCATTTAGCCTGGGCACCG 189448
mRNA    ------------------------------------------------------------

genome  CGCCCAGCACAGTCCATGCTGCACAGGTGCCGTGGGCTCCACAGAGCCCTGCCTGACATG 189508
mRNA    ------------------------------------------------------------

genome  CATGTGTTACGTTTCGGGTGCCGATGCCCTTGGGCGGCACTTCTCCGGGCAGAACCCCCA 189568
mRNA    ------------------------------------------------------------

genome  GGCCACCGCTCCGGTTCCGGTTCCGCTGCATCTGGGGCTCTCGGCAGGCTGTGGTCCTCC 189628
mRNA    ------------------------------------------------------------

genome  GGCCAGCCTGGGGGCATCTCAGTCCCTCAGCCCCACAGGGGCCTGCCCCGCAGCCTGGGC 189688
mRNA    ------------------------------------------------------------

genome  CTCGAGCCCCGTCTCCGCACGCTGTGCCGAATCTGGCTGCCCATCAGCTCCCTGCGTACC 189748
mRNA    ------------------------------------------------------------

genome  CAGACTGTGCCCTGCCATGCCCGTGGCTCTTCCCAGGAGTGCCCTGTGGCCTCCCCCTGG 189808
mRNA    ------------------------------------------------------------
```

FIG. 1 VVVVVV

```
genome    CTTGCTGGGCTGATTCCCTCCTGTGTCTCAAACAGAGCTCACCTTTGCCATCACTGCTGT 189868
mRNA      ------------------------------------------------------------

genome    CCTCACCGGCCGGTGCCAGAGGCCCGTGTCTGTGTACCCTGTGTCTGCACCTCTGGGCAG 189928
mRNA      ------------------------------------------------------------

genome    GGCCTGGCTCTGACCAACCCGGGCTTCCAGTGTCCACAGACCTAAGGCCCAGGGCGCCTG 189988
mRNA      ------------------------------------------------------------

genome    GGGGCTGGAGCAAGAGAAGCAAAAGGAGCCAAGGGTGGGGGTTTGGGGTTCTTGTGAGGG 190048
mRNA      ------------------------------------------------------------

genome    CCCAGCCCCAGGACCCCAGGACCAGGACACCCAGGAGCCCCAGGGCCCAGCCCCAGTTCA 190108
mRNA      ------------------------------------------------------------

genome    GAAGGCAGGGGCCTTCTGAGGGAGCTTAAGGGTCCCACAGCCCAGGACCCCCACCAGGGC 190168
mRNA      ------------------------------------------------------------

genome    CAGTGGCCAGCGTTGGGGGACTCAGCCTCCTCGTCGCTCGTCCTCTCTGTTTCTCCCACC 190228
mRNA      ------------------------------------------------------------

genome    TTTTGCCCCCTTTCTCCTTGCCTGTTCCCACCCGAGGCCCCCTCTTGGCCTGCGTGAGCC 190288
mRNA      ------------------------------------------------------------

genome    GGGGCGGCACTGAACTGGGGGCCGATCCGCCTGGGCGGCGGTGAGAGGCAGGGCCGGGAG 190348
mRNA      ------------------------------------------------------------

genome    CCGGGCCGCTGGGTTTGGGCCTGGCCCGCTCGCCGCAATATTGATGGCCCGTCAGTGCAG 190408
mRNA      ------------------------------------------------------------

genome    CCCTGATTCCTGTGCTTTCAGTTAAAAGGTTTCTGTTGTTGTAGCTTATGCAGTTGCTCT 190468
mRNA      ------------------------------------------------------------

genome    GTTGCTATGGAAACGTGACATCAAAATGACGTTTCCCGTTTAAAAGCTTTTAACTAAATT 190528
mRNA      ------------------------------------------------------------

genome    CCTGCCTGTCAGATGTAGGCCCCATTTTGAGCGTGGAGCTGCCTTCGAGCGAGCGTGAGC 190588
mRNA      ------------------------------------------------------------

genome    GGCGCCTCCCGCCCATGGTGCGTGGGGCCGGGCCGGGGCCCTCGCTGAGCGCGCTCTCTC 190648
mRNA      ------------------------------------------------------------

genome    ACCCCACAGGCGCCTCCGGCATGGCGGCGGCCGAGGGGCCCGGCTACCTCGTGTCTCCCC 190708
mRNA      ------------------------------------------------------------

genome    AGGCGGAGAAGCACCGGCGGGCCCGCAACTGGACGGACGCCGAGATGCGCGGCCTCATGC 190768
mRNA      ------------------------------------------------------------

genome    TGGTCTGGGAGGAGTTCTTCGACGAGCTCAAGCAGACCAAGCGCAACGCCAAGGTGTACG 190828
mRNA      ------------------------------------------------------------

genome    AGAAGATGGCCAGCAAGCTCTTCGAGATGACCGGCGAGCGCAGGCTGGGCGAGGAGATCA 190888
mRNA      ------------------------------------------------------------

genome    AGATCAAGATCACCAACATGACCTTCCAGTACAGGTGGGCGAGCGGGCAGTGTGGGCCCC 190948
mRNA      ------------------------------------------------------------

genome    ACCAGGACGGGCGGGCCCGGGCGTGGCGGGCCGCTCCTGACTTTCTTGGAGCTCTGAGTC 191008
mRNA      ------------------------------------------------------------

genome    GGGACGATGTGTGGGTCGTGGCCTGCCTGTCGGTCTCCTCTGGCCGGGTATGGGCAGAAC 191068
mRNA      ------------------------------------------------------------
```

FIG. 1 WWWWWW genome CCCACGGGGTGAGACGGGGCCCACGGAAACCGTGTGTGCAGCCTTCCATTGGGGAAGTGG 191128
mRNA ------------------------------------------------------------ genome GGAAACTGAGGCCCAGCAAGGGCAGGAAACCAGTCTAAGAGCTGAGGGGTAGCAGGGGTG 191188
mRNA ------------------------------------------------------------ genome GGGCTGGTGCTGGGCAGAGGCCAGGATGGCTCCCAGGACGTATGGGCGGTCTGGGCACTG 191248
mRNA ------------------------------------------------------------ genome TCCCTCGGAGGCAGCAACACTCATGGTGGTGCCCACTGACCTCACACCCTGCTCCCCCAT 191308
mRNA ------------------------------------------------------------ genome AGGGAGGCGGCGGCTGCCAGTGCCCTCCCCACCACCAAGCTCCCAAGCTCAGCAGGGGTT 191368
mRNA ------------------------------------------------------------ genome TCAGGGGCCTACTGCGTCATTGGGGAAATTGAGACTGCAAGTGAGAAGGAGGCTCAGTGC 191428
mRNA ------------------------------------------------------------ genome TCTGCGACTTGGAGCATCCACTGAGCCTCTGCCATGAGCCGGTGAGCCCCACTGGGGCTG 191488
mRNA ------------------------------------------------------------ genome GCCCTAGGGTCACGGTGGGGTATTTCCAGAAATCACCAGGTGAGGTGCAGGACCAGCCAG 191548
mRNA ------------------------------------------------------------ genome CGCATGGGTGGGGCTTACGGTGCGAAGAAGAAAGAGGTGGAGGCCTGCCCTGGCCCAGGA 191608
mRNA ------------------------------------------------------------ genome CTCCCAGCGTGGGGGCTCCCGGCCTGGCCCCACCTCTGCTCCTGCTACATGGCAGGTGGG 191668
mRNA ------------------------------------------------------------ genome CCCTTCCTGCCCTGGCAACCTGCAGGGAAGGCCGGAGGGGACCACCCAGCCAGGGAGATG 191728
mRNA ------------------------------------------------------------ genome TTGGCGTCTAGGAGGGGACAGGTGTGGTCCCACACACCCAGCATCTTAAAGTGCGTGGGT 191788
mRNA ------------------------------------------------------------ genome CCCCAGCCCATTAGGACAGGGTCCCGGGTGGGCAGGGGTCATGGTGGGGTGAAGGTCTCA 191848
mRNA ------------------------------------------------------------ genome GGCACAGGCAAGGTCACAGGTGCGGTGAGGGTCTTGCAGGGTGTGAAGGTCATAGGTGTG 191908
mRNA ------------------------------------------------------------ genome CGGTGAAGGTCACAGGTGTGGGGTGATGGTTTTGGGTGTGGGGAGGGTCTTGCACGGAGC 191968
mRNA ------------------------------------------------------------ genome GAGGGTGGCAGCAAGAGCTGGAAGCTGCAGGGGGAGAATGGCAGCAGAGAGCACCCGGCC 192028
mRNA ------------------------------------------------------------ genome CTGTGGGCGGCCTGGACAGGGCTGGGCCTGGGGCTGCCGGAGAGCCTGTCAGCTTCCAGG 192088
mRNA ------------------------------------------------------------ genome ATGGGAGTGGCCTCACTCAGCTGCTCCACCTCCGGGTCAGGCAGGTGAGCCTGGGGCAGA 192148
mRNA ------------------------------------------------------------ genome GAGGCTGAGAGCACCTGAGCCACTTGTGGGAGAGGCCACCCCCACTGCCCCCCTCAGGCG 192208
mRNA ------------------------------------------------------------ genome AGGAGCCGGCCTCCAGCACAGCAGAAGGGAACCCCCAGTCCCCAGCCCTAGTGGGAGTGG 192268
mRNA ------------------------------------------------------------ genome GGAAGAGGCCCAGCAAGGCCCCGGACAGACCGCCAGCCTGTGAGGTCTCCGCTTTCAGTT 192328
mRNA ------------------------------------------------------------

FIG. 1 XXXXXX

```
genome    GCGTTGATTTGATTTTTTCTGAGCCTTGAAGGAGGGGTCCGGGGCCTGGCCCTGCCCAAA 192388
mRNA      ------------------------------------------------------------

genome    GGCCCCTAGGCAGGCCCCAAAGCCGGGACCTAGGGTGCTGAGCATGACGGATGTTGGGTT 192448
mRNA      ------------------------------------------------------------

genome    TGAGCGGCTGGCTTGCGACGTGAGGGCTGAGGTGTGAGCCTGGGTATCTTCAGAGGTTCG 192508
mRNA      ------------------------------------------------------------

genome    GTGGACACAGGCAGCTGCCCGCGGCCCCACTGTTCCCGTGGCCTCCTAGTCCTGCTCAGG 192568
mRNA      ------------------------------------------------------------

genome    CACCTGGTGAGGAAGGGACGCAGAGGGCAGTGGGAGGTGGCCACGACTGTTCCAGCAGGC 192628
mRNA      ------------------------------------------------------------

genome    TCCCCTCTGACTCAGGAATTCACGGGCACCACCTCCCTGGCTGGCTCTGGTTGGTGTCTG 192688
mRNA      ------------------------------------------------------------

genome    GCCAGGTTATTCATTATTTATGCTGAAAGCCTCTTCAGAGTCCCAGGGGAGGGTTTCTGT 192748
mRNA      ------------------------------------------------------------

genome    CTCCATTCCTGGAGGCTGAGAGATGAGGGTGCAGCAGAGTGGGGGCCTCCACTCCAGACC 192808
mRNA      ------------------------------------------------------------

genome    CTGCAGTCTGGGCTGGCCAAGGGCTGCACCGGTGCACTGCACGTCATGGCTGATGAAGCA 192868
mRNA      ------------------------------------------------------------

genome    CTTCCACACCGCAGCCCCTCAGAGCTGCCACAGTCAGCCTTAGTTCACCGAGGGGGAAGC 192928
mRNA      ------------------------------------------------------------

genome    TGAGGCCCAGAGCATGAGAGGGACTTGCCCAGGGCCACATAGTCCTTAGCAGAGGAAGCT 192988
mRNA      ------------------------------------------------------------

genome    GTGGCTGGGTGACTCGATCTTTGTCCTTTTTCTTTATACCCGCAGTCTCCCCATAGCAGA 193048
mRNA      ------------------------------------------------------------

genome    GGCTTTTCTTTTTTTTTTCTTTTTCTTTTTTTTTTTTTTACAAGAACTCTTTATATATTA 193108
mRNA      ------------------------------------------------------------

genome    AGGCTGTTGGGCTGAAGAAGCCTGAGAGGGTGGCTGGTTCTGTGGAGCATGGTTTGTTGA 193168
mRNA      ------------------------------------------------------------

genome    AGTACAGTTTGGGGGCCTCCTACACTGAGAATAGGCCTTTTCTCGTTTCTCCAAAGAGTG 193228
mRNA      ------------------------------------------------------------

genome    GGCTGGCTCAAGTAGGGCAGAGAGAGAAGCCTGGGGCAGAGGTTAGGGATGGGCACCCAG 193288
mRNA      ------------------------------------------------------------

genome    CGCCTGCCCTCACACGCTCTGTGCTGGTGTCTTCACAGCCACGTGCCACCCTGGGCAGCA 193348
mRNA      ------------------------------------------------------------

genome    TCCCCTGCTCACCATCTGGCTGTGCCTGTTTGCTGGGGGCACCTCATTCAGAATCCAGCT 193408
mRNA      ------------------------------------------------------------

genome    TATTGTTTCCAACGGCCAATGGCCACACCCTGGCAGGTAGCAAGAGTAGGAGAGAGGAGA 193468
mRNA      ------------------------------------------------------------

genome    CACCCACTCCGAGCACAGGTTGGGTTTGGAGCCCGGCCTTGGGGCACTCTGTCACTCAAA 193528
mRNA      ------------------------------------------------------------

genome    GGCAGAGTGGGGAGTGGGCACTGGGCCTTAGGAGGTACTGGGTCCAGTGAGGCAGAGATG 193588
mRNA      ------------------------------------------------------------
```

FIG. 1 YYYYYY genome CCCCTGCCCCACCCCCACCTTGTGGCTTCTTCCCTGGCCTGGCCAGAGCTGTCTGGCCGC 193648
mRNA ------------------------------------------------------------ genome CATGGGGCCCTGTGTCTCCTGCCTTGACCTCCCAGAGGGCAGCCGAGGCCCAGGGGAGGC 193708
mRNA ------------------------------------------------------------ genome CTGGGGACTTAGCCTCTCAGGGCAGGACCTGTCTGCAGGAGTAGGTGGGTGCTGGGGGTC 193768
mRNA ------------------------------------------------------------ genome CCAGTGGTAATGAGGCATCAGGCAGTGTGGGAAGGGGCCCATCCGGCCCACCCCAGGGCC 193828
mRNA ------------------------------------------------------------ genome TCTGGGCAGGTTGCAGGTTGTAGCGCTGGATCTAGGCTCCTGCCCAGACTGTAGGTTCAA 193888
mRNA ------------------------------------------------------------ genome CCAAGAATGGCATGGGAGCCCAGCCTGCTGTTTGCTTTATTAAATCTGCCCTGTAGCTGG 193948
mRNA ------------------------------------------------------------ genome GGGAGGGGCTTACTTTGATCATCACTATGTCATTGATATAAAAATAGAGGCTCAGAGAGG 194008
mRNA ------------------------------------------------------------ genome TGAATGAACCTGCCCAAAGTCACACAGCAAAGTGTGGAGATGAGATACTGACTCAGGGCT 194068
mRNA ------------------------------------------------------------ genome GTGGACACTGAAGCCTGTGCTCTAACGCCAGTGGCTGTCGCTCCCTGAGGCATTCTCTCC 194128
mRNA ------------------------------------------------------------ genome CGAACAACACAGTTATTATATTACAAAATATTATCACTATATTTATATATCTTATAATAC 194188
mRNA ------------------------------------------------------------ genome CTTATTATTACAATAAAACCTTATTACTCTACCTTTCAAAATGAATTATTTAAAAAGCAG 194248
mRNA ------------------------------------------------------------ genome TATTTGCTCATTGCAGAGAGTCTAGAAACTATAGAAAAGCAAGGGAAAAGCAATAGGACC 194308
mRNA ------------------------------------------------------------ genome AGCCCCAAGGTCCCAGCATGCACAGATAACCTTAGTAATACTGGGACGTGTGCTTCCTTT 194368
mRNA ------------------------------------------------------------ genome TTAACATCTGAGCCCGTGTAGGTCCTGAAGCCCAGCTTCTTTCTAAGTCCATTGTCATCT 194428
mRNA ------------------------------------------------------------ genome TGACCCTGGAGCCTGGCCGATTTTGCTGGGGAGGCCCTTGCCAGCCGAGAGCGGCTCCTG 194488
mRNA ------------------------------------------------------------ genome CCTGTGCCGGCGTGGCGCGCCCCTCTGCTGAGGCTGGGCAGGACAGGGGCTGGGCCAGCT 194548
mRNA ------------------------------------------------------------ genome CTGTTTCTCACCCTTGGCTCTTGTGTCTCTCGTTTCAGGAAATTAAAATGCATGACAGAT 194608
mRNA ------------------------------------------------------------ genome AGCGAGTCCGCCCCGCCCGACTGGCCCTATTACCTAGCCATTGATGGGATTCTGGCCAAG 194668
mRNA ------------------------------------------------------------ genome GTCCCCGAGTCCTGTGATGGCAAACTGCCGGACAGCCAGCCGCCGGGGCCCTCCACGTCC 194728
mRNA ------------------------------------------------------------ genome CAGACCGAGGCGTCCCTGTCGCCGCCCGCTAAGTCCACCCCTCTGTACTTCCCGTATAAC 194788
mRNA ------------------------------------------------------------ genome CAGTGCTCCTACGAAGGCCGCTTCGAGGATGATCGCTCCGACAGCTCCTCCAGCTTACTG 194848
mRNA ------------------------------------------------------------

FIG. 1 ZZZZZZ genome TCCCTTAAGTTCAGGTAGTGTGTCTGCTTGTCCTTCCCCTGCCCTGGGGTATCTCAGCCC 194908
mRNA ------------------------------------------------------------ genome CCACCATTTAGAGAAAGGGACTGGGAGTGGCAAGGCCGGCGGCGGCGGCCACAGTGGTTG 194968
mRNA ------------------------------------------------------------ genome CAGAGGCCGTGGCTGCGGGCAGCGCCTCCAGGGACAGGCGGCCTCAGACCAGGGAGGGCT 195028
mRNA ------------------------------------------------------------ genome TTAGTGTCCACAGGCAGACCGAGTTTGTCTCCCAGCTCCATCACTTTTGAGCTGCACGGA 195088
mRNA ------------------------------------------------------------ genome AAGTTCCTTGACTTCTCTGGCCTCAGTCTCCCTCCTATAAAATGGGGGTAAATCAGTACC 195148
mRNA ------------------------------------------------------------ genome TTTCTCAGAGGGTGGCTGGGAGCATCACAGGAGAGAAGACGCAGCATGGGGCCCGGCACA 195208
mRNA ------------------------------------------------------------ genome CGGAGGGAGACCAAGCCCCAGACCCCAGAATGCGCCCCCTGGCCTCCCTTAGCCCACACA 195268
mRNA ------------------------------------------------------------ genome GACCCCACCCTCACAGGCTAGCTGCCCTCTCAGCACTGGGGAGGGTGTCGGGCTGCACCT 195328
mRNA ------------------------------------------------------------ genome CATCACGTGTTGCCGTGGGCATGACCCGTCCCCTCTGCCATCCATCCCACACCTCAGACC 195388
mRNA ------------------------------------------------------------ genome CGTCCCGTGCTGGCCACGTGACTGTGCCTGCAAGATGCTCACAGGGCAGCCGGGAGCCAG 195448
mRNA ------------------------------------------------------------ genome GCAGCATGCAGGACAGACACCTGCGGGGTGGGCCTGGGGAGCCCAGAGAAGGTGCTTTTG 195508
mRNA ------------------------------------------------------------ genome AGGAGGGGACATTTGGGGTGGGCTTTCAAGGTAAAATAGAAGTTGGCCATTTGGAGGCAA 195568
mRNA ------------------------------------------------------------ genome GAACAGGAAGATTGTGGATTTGAGTCACAGCTTCTCCCCTGCCCTGGTCTTCAAGTCTTT 195628
mRNA ------------------------------------------------------------ genome CTGACAGGAGGTGTCAGAAAAGTATCTTTAGTAGAGAAGGCGTCTCCGAGGAGGGTCCCT 195688
mRNA ------------------------------------------------------------ genome CTCATGCCGGGGGCCGCTGCTTGACTCAGGATTTCTCATTGAAGACCTGAGACAAAAACG 195748
mRNA ------------------------------------------------------------ genome CTTTTGCTGGCAGCTAGAAGGAACCAGCAGGAGGCCTGAGATTTGTGGCTGTTGTTCCCG 195808
mRNA ------------------------------------------------------------ genome TGGACTGAGCCCAGTTCTCAGACTCAGCTGCCTGGGGCCTTGCACAGGACTGGGGCGTGG 195868
mRNA ------------------------------------------------------------ genome GGGCTGCCCTCCCTGATCAGGCCCAAAGCGCGGATCTCACGCCCCTGAGGTTGGCTGTAC 195928
mRNA ------------------------------------------------------------ genome CCTCTCAGCTCAGAGCAGAGTGTGGGCCAGGGATGAGCAGGCACTGGAGCAGGGCCCTGG 195988
mRNA ------------------------------------------------------------ genome GGTCTGTGGGTTTTGGCAGCTCCCTGCCCTTCAGGGAGGTCTGCTGAGACCACGGGTGGC 196048
mRNA ------------------------------------------------------------ genome CCCTACCCCAGCAGCAGAGCTCTCAGGAGGCGCCCACAGGGCTGGACTGCCTTTACTCAC 196108
mRNA ------------------------------------------------------------

FIG. 1 AAAAAAA

| | | |
|---|---|---|
| genome | CACCTCTACCAGAGCTCTGAGGTCCTGGGGAGAGAGCCCAGGCCTCTTGTGGGCCCCACA | 196168 |
| mRNA | ------------------------------------------------------------ | |
| genome | CCCTCTAGGTGCCTGTCCTTCTGCCTCTCTACCAAGGTGTGCCGGCCCCATTTCTAGGCC | 196228 |
| mRNA | ------------------------------------------------------------ | |
| genome | GCCGGGAGATAAGGGGGCTCACATCTCAGGCCCTTCCTTCTGGGACCTCAGTTTCCCCAT | 196288 |
| mRNA | ------------------------------------------------------------ | |
| genome | CTGCCTAAGGCCGGGTGGGGCTGGTGGTCTTGGCTTCCCTACAGGGGTCCTGAGTACTCT | 196348 |
| mRNA | ------------------------------------------------------------ | |
| genome | GCACTACCCAGCACCCCCCACCCCTGCCTTCATCTCTCCCTGGGGGTGGTCTCTCCACCC | 196408 |
| mRNA | ------------------------------------------------------------ | |
| genome | CTGGCCCCCAACTGGGGCTGAGCCCCCACCTGCCCAGTTTGGTGGGTGAAGGGTGCTCCC | 196468 |
| mRNA | ------------------------------------------------------------ | |
| genome | TGGCAGGATATGCCCCTCTGCAGCCCAGAACATCCCACCCTTTCCAGACCGAAGGGGTGT | 196528 |
| mRNA | ------------------------------------------------------------ | |
| genome | GGATTGTCCTGGGACCCTGGTCATTGGGGTCATCCGCTAGTCGCAAAGGACGGCAATGCC | 196588 |
| mRNA | ------------------------------------------------------------ | |
| genome | TGTGGCCTCTCTTTCTTTCTTTTTCTTTTTTTTTTTTTTTGAGACGGAGTCTCGCTCTTG | 196648 |
| mRNA | ------------------------------------------------------------ | |
| genome | TGCAGAGAGCAGTGGCGCGATCTTGGCTCACTGCAACCTCCGCCTCGTGGGTTCAAGCGA | 196708 |
| mRNA | ------------------------------------------------------------ | |
| genome | TTCTCCTGCCTCAGCCTCCCGAGTAGCTGGGATTACAGGCACCCGCCACAACGCCTGGCT | 196768 |
| mRNA | ------------------------------------------------------------ | |
| genome | AATTTTTGTATTTTTAGTAGAGATGGGGTTTCACCATGTTGGCCAGGCTGGTCTTGAACT | 196828 |
| mRNA | ------------------------------------------------------------ | |
| genome | CCTGACCTCAGGTGATCCACCTGCCTCTGCCTCCCAAAGTGCTGGGATTACAGGCATAAG | 196888 |
| mRNA | ------------------------------------------------------------ | |
| genome | CCTCCACACCCGGCCACCCCTGTTACTTTCTGTCAAAGGCGGTGGGTTCTGGCCCCTCCT | 196948 |
| mRNA | ------------------------------------------------------------ | |
| genome | TTGCACATGGAATATGAGACCCTGAGTAAGTGACCTGACTCCCTGGGGCCTCAGTTTCCC | 197008 |
| mRNA | ------------------------------------------------------------ | |
| genome | CATTTGCCCAGTAGGATTGTCGGGAGGGTCCGGTGAGGCCCCTGGTGTGCCCAGGCTCTG | 197068 |
| mRNA | ------------------------------------------------------------ | |
| genome | TGGCCAGCACGTCCACAGCCGGCACTGTCCTTCCAGGTCGGAGGAGCGGCCGGTGAAGAA | 197128 |
| mRNA | ------------------------------------------------------------ | |
| genome | GCGCAAGGTGCAGAGCTGCCACCTGCAGAAGAAGCAGCTGCGGCTGCTGGAGGCCATGGT | 197188 |
| mRNA | ------------------------------------------------------------ | |
| genome | GGAGGAGCAGCGCCGGCTGAGCCGCGCCGTGGAGGAGACCTGCCGCGAGGTGCGCCGCGT | 197248 |
| mRNA | ------------------------------------------------------------ | |
| genome | GCTGGACCAGCAGCACATCCTGCAGGTGCAGAGCCTGCAGCTGCAGGAGCGCATGATGAG | 197308 |
| mRNA | ------------------------------------------------------------ | |
| genome | TCTGCTGGAGAGGATCATCACCAAGTCCAGCGTCTAGGCCAGCAGGCGGCGGCGGCGGCG | 197368 |
| mRNA | ------------------------------------------------------------ | |

FIG. 1 BBBBBBB

```
genome    GGGCCGGGCGGCTGGTGGTACTGCTCAGGCCACCCAGGGCAGGCCACTCAGGCCAGGCGG 197428
mRNA      ------------------------------------------------------------

genome    GCAAGGGGGCCGCCCCGCGAGCGGAGACCGCCTTCCACCTGGCCTCTGGCAGGATGTCCC 197488
mRNA      ------------------------------------------------------------

genome    TTCTGAGGGGTATTTTGAGGAACCCCCAGGCCCTGGGGACCGTGAGGCTCCAGTCTCCAG 197548
mRNA      ------------------------------------------------------------

genome    CATGAATGCCCTTCCTCGGACACAGGCCAGGGCCTCTGGGGTTCACTCCGAGTAAGAACG 197608
mRNA      ------------------------------------------------------------

genome    TCCTAGAGCCACTCTCCAGTGTCGTTACTATCAATGATACTTGACGTGGCTTTGATATTA 197668
mRNA      ------------------------------------------------------------

genome    AACGTATACTTTTTCATTCTTGCCTGGAACGCACAGTTTGCTGTTGCTGGCTTGGTGAGG 197728
mRNA      ------------------------------------------------------------

genome    ATGCCCTGATTGATGGATCCCGAAAATGAAAGCAGATGGAAACGGGTTGGGGCAGGCTGG 197788
mRNA      ------------------------------------------------------------

genome    AGCTGGGGGAGCTCTCTCCTGAAGGGAACCCTGTGTCCTCCCTCACCAGGACCTCTGCGT 197848
mRNA      ------------------------------------------------------------

genome    CTCTCCTTAAATGGCCTCTGACGCCTGATGAAAACCCCAGCGACCTTCCAGGAGGCTTTT 197908
mRNA      ------------------------------------------------------------

genome    ATTCAGCTCTGTTTGGAGCATCAGGTGTTTCCACTGCCTCCTTAGCAATGACACTAATAA 197968
mRNA      ------------------------------------------------------------
                                                             rs1006798
genome    AAGTCGTAACACCTGTTCACATGCACAGCCCTGTTGAGTGTTCTGGGTGCTGGAGATAATC 198028
mRNA      ------------------------------------------------------------

genome    ATGGTGGATGACACAAAGGCCCTGGCCTCTTGGAGCTTATGCTCCCATGCGGGGAAGACA 198088
mRNA      ------------------------------------------------------------

genome    CATGGGTCAGTAGAGAAATGGTTGCAGGTTGTGATAAGTGCTGGAAGGGAGGGGTTGGCC 198148
mRNA      ------------------------------------------------------------

genome    TGAGGACACGGAGGCAGACATACGTGGAGCTGGGAACAGTGGCCACACAGGGAACGGCCA 198208
mRNA      ------------------------------------------------------------

genome    GTGCGAAGGCCCAGAGGCAGAGGACACTGGAGCAAGCCCAGGAGCAGCTAGGAGGCTGGT 198268
mRNA      ------------------------------------------------------------

genome    GGCCAGCAGCCAGGCCACGGAAGCCCGTGCAGCCCGTGGGGAGGAGTGTTCATGCTTTTC 198328
mRNA      ------------------------------------------------------------

genome    AAGCTTAGTGGGAGTCTTTTGGCCAGTGCAGCTCTGGGTCTGACATCGGTGGGGGACAGA 198388
mRNA      ------------------------------------------------------------

genome    GGGGTGGTGGAGCGGCCACAGCTGCAAGCTCACCTCACTGCCGGCCCTTCCACCAGTTTC 198448
mRNA      ------------------------------------------------------------

genome    AAACTCTTTCTAGAAGCTCCAGCTTTCCCAAAGCTGAATTCTCTATGAGCCTCCTTGGCC 198508
mRNA      ------------------------------------------------------------

genome    GGGACTCGGGCGTCTGGTTGCCCTGGCTGCAAAGGAGGCTGGGGCCAGGTGTGTTTGAGT 198568
mRNA      ------------------------------------------------------------

genome    CACCTCCTGGAATTAGGCAAGTTGCTGCCCAAATAGAAGGTTGTTGGCAGGTGGGTCAGC 198628
mRNA      ------------------------------------------------------------
```

FIG. 1 CCCCCCC

```
genome    AGGTGAACAGCATGGTTTGACTCAGGGTTCAGAAAAATCTCCCTCTGGCTGCCAAGCGAG 198688
mRNA      ------------------------------------------------------------

genome    CAGGCCGTGGAGACAGGTGCAGAGGCAGGTGTGGCAGCAGGCATCCTGCCAGGCAGTGCT 198748
mRNA      ------------------------------------------------------------

genome    GCAGTCATCCTGCGACAAGCAGCAGCAGCTCATCCTACCCTCTAGGGGGTCTTGAGGTCA 198808
mRNA      ------------------------------------------------------------

genome    GCCAGGCAAGAGAGCAGCTTGGACTCCACTGGGTGTGGGACCAGCCTGTGGACCATGGTG 198868
mRNA      ------------------------------------------------------------

genome    GTGTGGAGGGTGCCCTCGGCCTGCCTGTGTGAAGGAGAGGCCGGCGTGTTCTGTGGAGCC 198928
mRNA      ------------------------------------------------------------

genome    CAAAGGGGAGCTGGGCAAGCAGGATTCACTTCACTCTGAGGGTCCTGGAGCTCCCACCCT 198988
mRNA      ------------------------------------------------------------

genome    CCTCAGCCATCTCCCCAGAGCCTGTGTGCCGAGGACTCGGCCCATGTTGCTGTGGGATGA 199048
mRNA      ------------------------------------------------------------

genome    GAGGCAGAGTGTCGTGAGGGTGTAAGGAGCGGCGGCAGTGGTGGGAGGAGGGAGCAGCAG 199108
mRNA      ------------------------------------------------------------

genome    CCAGCGCTACGGTGCCAGTTTCCAGCTGCCAGATGACGCCGCTGACCCTGTGGTTGAGAA 199168
mRNA      ------------------------------------------------------------

genome    GAGATGCACAGAGCCAGCTCTTGCAAGCCAGTGTGGCTGCCATAGCACCTGCCGAGAAGC 199228
mRNA      ------------------------------------------------------------

genome    AGAAGGAAGGGTGGCCCCAGGAGGACAGAGGATGCGGGCACATCTGATGCGGGCCTGAGT 199288
mRNA      ------------------------------------------------------------

genome    TTTGGGAGCTTTTGCTCTAGCCAGTTTCCAGCTCCGGGACCCACCCGCCTCGTAGGCAAG 199348
mRNA      ------------------------------------------------------------

genome    ACACCACCCAAGAAATCATTTGCTTAACAAACACACTGGGCTCCAACTGGACACCTGTGC 199408
mRNA      ------------------------------------------------------------

genome    CACCCTAGATGCTGGGAACCCAGCCATGACACAGGCACCTGCCCCCAGCTGCTGACCACT 199468
mRNA      ------------------------------------------------------------

genome    GAGGCTGGCTAGCAGCTCCCATGGGGCCAGTGTGGGGTTCCCCAGCCTCCTAACAGGGAG 199528
mRNA      ------------------------------------------------------------

genome    CCAGTCACAAGCCCTCGAGAGGGAAGGGTGCCCGCGGCCCTGGCAGGAAGGTTAGGCTGG 199588
mRNA      ------------------------------------------------------------

genome    ACGCTCCCACAAGACATAACAGATGGAGGTTCTAAATGATGTAGCAACTTCTTCACCCTG 199648
mRNA      ------------------------------------------------------------

genome    AAACTGCTGTAGAGTCAGCCATGACGCACCGGTACTTCAGTAACTGCCAGGCATCCGGGA 199708
mRNA      ------------------------------------------------------------

genome    CAGCACACCGCGAGTCGCTGCTGTGCTTGGGTTAGAAGTGGTTTGGTCTGTTTTCTTCTC 199768
mRNA      ------------------------------------------------------------

genome    GCCCTCTCTAATCAGAGTCAGTGATTCATGCCCTTCCATCACCTTAGAGAAGGGGCAGGC 199828
mRNA      ------------------------------------------------------------

genome    GCTGCCCGACCTTCTCCAGGCTGGAGCAGCATCGCCTCATGTCAGCAGAACTCAGCTGTA 199888
mRNA      ------------------------------------------------------------
```

FIG. 1 DDDDDDD

```
genome    GAATATCGTGGGGTTGGTGCCTTTCATCAGCAGCATGTCCTTAACAACTTTCTGATTTCT 199948
mRNA      ------------------------------------------------------------

genome    TCCTTAGTTGTTGGTCCATTAAGGAGAAAAAAAATGATCTCAGCCATTGCTAAAATATTT 200008
mRNA      ------------------------------------------------------------

genome    GATAAGATTCAGCAAAGCAGCATGTTAACATTGAAAACTAGAATCAGGAGCCAGGCAGAT 200068
mRNA      ------------------------------------------------------------

genome    GTGCTTGCTTTTCACCTGTAGTATTTCATGTTGTTTTGACGTTTTTAGCTAATGCATTAA 200128
mRNA      ------------------------------------------------------------

genome    GATAAATAAACAAAAGCCGGGCACGGTGGTTCACGCCTGTAATCCCAGCACTTTGGGAGG 200188
mRNA      ------------------------------------------------------------

genome    CTGAGGCGGGAGGATCCTCTGAGGTCAGGAGTTCAAGACCAGCCTGACCAACATGGAGAA 200248
mRNA      ------------------------------------------------------------

genome    ACCTCGTCATTACTAAAAATACAAAATTAGCTGGGCGTGGTGGTGCATGCCTGTAATCCC 200308
mRNA      ------------------------------------------------------------

genome    AGCTACTTGGGAGGCTGAGGCAGGAGAATCGCTTGAACCCGGGAGGCGGAGGTTGCAGTG 200368
mRNA      ------------------------------------------------------------

genome    AGCTGAGATTGCACCACTGCACTCCAGCCTGGGTGACAGTGAAACTCGGTCTCAAAAAAA 200428
mRNA      ------------------------------------------------------------

genome    AAAAAAAATTAAAAAAAGATAAATAAAATAAGCAGGATAAGAAATGAAGAAAGTAGAGTT 200488
mRNA      ------------------------------------------------------------

genome    ACCTTTGTTTTCAGATTTCATTTTTGTATACCCAGAAAGCCAAATGTACAAAAGACTGGG 200548
mRNA      ------------------------------------------------------------

genome    AGCTCTTTAAACCAGCTTAAACTTGTTGAAAATGAGGATGAAGAAATATCCCATTCAGAG 200608
mRNA      ------------------------------------------------------------

genome    TTGGAATGAATTTAACCCAGAAGGAACAGGACCTCTACTGAAGAGAACTATGCAGTCTTA 200668
mRNA      ------------------------------------------------------------

genome    CTGAAAAATCTAAATAATACCTGAGCGCTGGAGAAACTTCGCACACTCCTGAAAGCTCCA 200728
mRNA      ------------------------------------------------------------

genome    AAGTCAATGTCATCATTTTATTAATGTCATTCCAAACATAGTCTCAATAATATCACTTCT 200788
mRNA      ------------------------------------------------------------

genome    TGGTTTTGACATGGACGCGATGATGTTTAAATTCATATGAAAAAAGAACGGGGCCAAAAG 200848
mRNA      ------------------------------------------------------------

genome    TCCAAGGCCAGTCAGCGTGAGAAGACCGCTCGGCCTCCCTCGGAGTCGGGGAGTTGGAAC 200908
mRNA      ------------------------------------------------------------

genome    CGCAGACTGAGATCATGTGGCTGCTGGAGGCCAGGACGAACGTCGGGAAATGGAGACTCC 200968
mRNA      ------------------------------------------------------------

genome    TGCGTTGCTGGTGGGATGTGGTGCAGCCGCTTCCAGGAGCAATTTGGTGTCCCGTCCTAA 201028
mRNA      ------------------------------------------------------------

genome    AGCTGAAGAAACGCATTTCCTCTGGTCAGTGCCACTCCTAGACAGGCCACCCTGCGGCAG 201088
mRNA      ------------------------------------------------------------

genome    CCGTCCTCAAACTGGTCTGAGGACCCCTCAACGCTCTTAAAAATCATTAAAAGTGGGCCA 201148
mRNA      ------------------------------------------------------------
```

FIG. 1 EEEEEEE

```
genome      GGTGCGGTGGCTCACACCTGTAATCCCAGCACTTTGGGAGGCCAAGACAGGCGGATCACG 201208
mRNA        ------------------------------------------------------------

genome      AGGTCAGGACATTGAGATCATCCTGGCTAACACGGTGAAACCCCGTCTCTACTAAAAATA 201268
mRNA        ------------------------------------------------------------

genome      CAAAAAATTAGCCGGGCGTGGTGGCGGGCGCCTGTAGTCCCAGCTACTTGGGAGGCTGAG 201328
mRNA        ------------------------------------------------------------

genome      CCAGGAGAATGGCGTGAACCCAGGAGGTGGAGCTTGCAGTGAGCTGAGATCACTCCACTG 201388
mRNA        ------------------------------------------------------------

genome      CACTCCAGCCTGGGCAGCAGAGCGAGACTCTGTCTCAAAAAAAAATAATAAATAAATAAA 201448
mRNA        ------------------------------------------------------------

genome      TAAAAATAAAATAAAATAAAATTCATTAAAAGTGCCAAAGAACTTTTGCTTATGTGAGTT 201508
mRNA        ------------------------------------------------------------

genome      CTAATGACCAATATTAATACACATTAGAATATCTTATTAGAAATTAAACCTGAGACCTTT 201568
mRNA        ------------------------------------------------------------

genome      AGAAAACATGTATTCATTTCAAAATAGCAATAAACCCATGACATATTAACATAAATAACA 201628
mRNA        ------------------------------------------------------------

genome      ATTGTATGAAAAATATATTTTCCAAAACAAAAAGTTTTCGGGAGAAGTGTGGCATAGTTT 201688
mRNA        ------------------------------------------------------------

genome      TACATGGTCGTAAATCTCTGGCTTAAGAGAAGCCCACTGGCCTCTCAGCAGGCTCTGGGT 201748
mRNA        ------------------------------------------------------------

genome      CCGTCCACTTTGGGGGTGTTTTGGTTGTGAAGTATAGGAGTGAATGGAGAAGCTCATTCT 201808
mRNA        ------------------------------------------------------------

genome      TACCCAGATGTGTATTTGAAAAGAAAAGGAACATTTTAATAACCTTTGCAAATAATCGGT 201868
mRNA        ------------------------------------------------------------

genome      ATATTCTTCCGTGATCCTATTCCAACACTGGACAGGTGGTGGTTTGTTTTTTTTTTTTGG 201928
mRNA        ------------------------------------------------------------

genome      AGACGGAGTCCCGCTCTGTCACTCAGGCTGGAGTGCAGTGGCGCGATTTCAGCTCACTGC 201988
mRNA        ------------------------------------------------------------

genome      AAGCTCCGCCTCC 202001
mRNA        -------------
```

SELECTIVE REDUCTION OF ALLELIC VARIANTS

SEQUENCE LISTING

The present application is being filed along with a Sequence Listing in electronic format. The Sequence Listing is provided as a file entitled BIOL0124USC2SEQ_ST25.txt created Apr. 20, 2018, which is 343 Kb in size. The information in the electronic format of the sequence listing is incorporated herein by reference in its entirety.

FIELD OF THE INVENTION

Embodiments of the present invention provide methods, compounds, and compositions for selectively reducing expression of an allelic variant of a gene containing a single nucleotide polymorphism (SNP). Such methods, compounds, and compositions are useful to treat, prevent, or ameliorate diseases.

BACKGROUND OF THE INVENTION

Genetic diseases are caused by abnormalities in genes or chromosomes. Such abnormalities may include insertions, deletions, and expansions. Huntington's Disease (HD) is one example of a genetic disease caused by an expansion. HD is a progressive neurodegenerative disorder that is inherited in a dominant fashion and results from a mutation that expands the polymorphic trinucleotide (CAG) tract in the huntingtin gene (HTT). The average CAG tract size in the general population is 17-26 repeats (wild type allele), however, in HD patients the CAG tract has expanded to 36 repeats or more (mutant allele) (Huntington's Disease Collaborative Research Group 1993. Cell 72(6):971-83). The HTT gene encodes the HTT protein and the expanded CAG tract results in a pathological increase in the polyglutamine repeats near the N-terminal of the protein. Individuals carry two copies of the HTT gene and one mutant allele is sufficient to result in HD.

HTT protein appears to have a role during development of the nervous system and a protective role in cells. In mouse models, constitutive knockout of the HTT gene is lethal during embryonic development (Nasir et al 1995. Cell 81(5):811-23), while adult inactivation of the HTT gene leads to progressive cell death in the brain and the testes (Dragatsis et al 2000. Nat. Genet 26:300-306). Reduction of huntingtin expression from the wild type allele may, therefore, have negative consequences.

Like HD, there are disorders for which a strategy of selective reduction of a mutant allele would be beneficial. Thus, there remains an unmet need to selectively reduce expression of mutant allelic variants like that of HTT, which are causative of disease, over the wild type variant, which appears to be necessary for normal cellular processes.

BRIEF DESCRIPTION OF THE DRAWINGS

FIG. 1A-EEEEEEE provides the mRNA (SEQ ID NO:2) and genomic (SEQ ID NO:1) HTT sequence showing SNP positions.

SUMMARY OF THE INVENTION

Provided herein are methods, compounds, and compositions for selectively reducing expression of an allelic variant of a gene containing a single nucleotide polymorphism (SNP). Such methods, compounds, and compositions are useful to treat, prevent, or ameliorate diseases. SNPs may be associated with a mutant allele, the expression of which causes disease. In certain embodiments, the expressed gene product of a mutant allele results in aggregation of the mutant proteins causing disease. In certain embodiments, the expressed gene product of a mutant allele results in gain of function causing disease.

In certain embodiments, selective reduction of mRNA and protein expression of a mutant allele is achieved by targeting a SNP located on the mutant allele with an antisense compound. In certain embodiments, the antisense compound is an antisense oligonucleotide In certain embodiments, antisense compounds designed to selectively reduce an allelic variant of a gene containing a SNP are created based on potency and selectivity of the antisense compound as well as population genetics.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings: "2'-O-methoxyethyl" (also 2'-MOE and 2'-O$(CH_2)_2$—$OCH_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to an allelic variant is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to, administering by a medical professional and self-administering.

"Allele" is one member of a pair of genes or one member of a series of different forms of a DNA sequences that can exist at a single locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be 'homozygous' for that allele; if they differ, the organism or cell is said to be 'heterozygous' for that allele. "Major allele" refers to an allele containing the nucleotide present in a statistically significant proportion of individuals in the human population. "Minor allele" refers to an allele containing the nucleotide present in a relatively small proportion of individuals in the human population. "Wild type allele" refers to the genotype typically not associated with disease or dysfunction of the gene product. "Mutant allele" refers to the genotype associated with disease or dysfunction of the gene product.

"Allelic variant" refers to one of the pair of genes or DNA sequence existing at a single locus. For example, an allelic variant may refer to either the major allele or the minor allele.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two ring atoms. A bicyclic sugar is a modified sugar.

"Bicyclic nucleoside" means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-$CH(CH_3)$—O-2'.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Differentiating polymorphism" means a variation in a nucleotide sequence that permits differentiation between a wild type and a mutant allele of a nucleic acid sequence. Differentiating polymorphisms may include insertions or deletions of one or a few nucleotides in a sequence, or changes in one or a few nucleotides in a sequence. A differentiating polymorphism or polymorphic allele can be in linkage disequilibrium with one or more other polymorphisms or polymorphic alleles.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Gene product" refers to a biochemical material, such as RNA or protein, resulting from expression of a gene.

"Haplotype" means a set of alleles of closely linked loci on a chromosome that are generally inherited together. For example, a polymorphic allele at a first site in a nucleic acid sequence on the chromosome may be found to be associated with another polymorphic allele at a second site on the same chromosome, at a frequency other than would be expected for a random associate (e.g. "linkage equilibrium"). These two polymorphic alleles may be described as being in "linkage disequilibrium." A haplotype may comprise two, three, four, or more alleles. The set of alleles in a haplotype along a given segment of a chromosome are generally transmitted to progeny together unless there has been a recombination event.

"High-affinity sugar modification" is a modified sugar moiety which when it is included in a nucleoside and said nucleoside is incorporated into an antisense oligonucleotide, the stability (as measured by Tm) of said antisense oligonucleotide: RNA duplex is increased as compared to the stability of a DNA:RNA duplex.

"High-affinity sugar-modified nucleoside" is a nucleoside comprising a modified sugar moiety that when said nucleoside is incorporated into an antisense compound, the binding affinity (as measured by Tm) of said antisense compound toward a complementary RNA molecule is increased. In certain embodiments of the invention at least one of said sugar-modified high-affinity nucleosides confers a $\Delta$Tm of at least 1 to 4 degrees per nucleoside against a complementary RNA as determined in accordance with the methodology described in Freier et al., Nucleic Acids Res., 1997, 25, 4429-4443, which is incorporated by reference in its entirety. In another aspect, at least one of the high-affinity sugar modifications confers about 2 or more, 3 or more, or 4 or more degrees per modification. In the context of the present invention, examples of sugar-modified high affinity nucleosides include, but are not limited to, (i) certain 2'-modified nucleosides, including 2'-substituted and 4' to 2' bicyclic nucleosides, and (ii) certain other non-ribofuranosyl nucleosides which provide a per modification increase in binding affinity such as modified tetrahydropyran and tricycloDNA nucleosides. For other modifications that are sugar-modified high-affinity nucleosides see Freier et al., Nucleic Acids Res., 1997, 25, 4429-4443.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nuclease resistant modification" means a sugar modification or modified internucleoside linkage which, when incorporated into an oligonucleotide, makes said oligonucleotide more stable to degradation under cellular nucleases (e.g. exo- or endo-nucleases). Examples of nuclease resistant modifications include, but are not limited to, phosphorothioate internucleoside linkages, bicyclic sugar modifications, 2'-modified nucleotides, or neutral internucleoside linkages.

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Selectively reducing expression of an allelic variant" means reducing expression of one allele more than the other, differing allele among a set of alleles. For example, a mutant allele containing a single nucleotide polymorphism (SNP) may be reduced more than a wild type allele not containing the SNP.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. SNPs are thought to be mutationally more stable than other polymorphisms, lending their use in association studies in which linkage disequilibrium between markers and an unknown variant is used to map disease-causing mutations. The location of a SNP is generally flanked by highly conserved sequences. An individual may be homozygous or heterozygous for an allele at each SNP site. A heterozygous SNP allele can be a differentiating polymorphism. A SNP may be targeted with an antisense oligonucleotide, meaning that the SNP anneals to (or aligns with) position 1, 2, 3, 4, 5, 6, 7, 8, 9, 10, 11, 12, 13, 14, 15, 16, 17, 18, 19, or 20 of the antisense oligonucleotide. The remainder of the antisense oligonucleotide bases must have sufficient complementarity to the SNP site to facilitate hybridization.

"Single nucleotide polymorphism position" or "SNP position" refers to the nucleotide position of the SNP on a reference sequence.

"Single nucleotide polymorphism site" or "SNP site" refers to the nucleotides surrounding a SNP contained in a target nucleic acid to which an antisense compound is targeted.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. For example, for the purposes of this patent application, the target segment may be within the SNP site. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Embodiments of the present invention provide methods, compounds, and compositions for selectively inhibiting mRNA and protein expression of an allelic variant of a gene or DNA sequence. In certain embodiments, the allelic variant contains a single nucleotide polymorphism (SNP). In certain embodiments, the SNP is a differentiating polymorphism. In certain embodiments, a SNP is associated with a mutant allele. In certain embodiments, a SNP is in linkage disequilibrium with another polymorphism that is associated with or is causative of disease. In certain embodiments, a mutant allele is associated with disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci. 2008, 105: 4533); CCLS gene encoding the chemokine CCLS involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHMP4B gene encoding chromatin modifying protein-4B involved in progressive childhood posterior subcapsular cataracts (Am. J. Hum. Genet 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry 2006, 11: 76); TGF-beta1 gene encoding TGF-beta1 protein involved in breast cancer and prostate cancer (Cancer Epidemiol. Biomarkers Prev. 2004, 13: 759); AChR gene encoding acetylcholine receptor involved in congenital myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Gene.t 2010, 19: 671); SCA3 gene encoding ataxin-3 protein involved in Machado-Joseph disease (PLoS One 2008, 3: e3341); SCAT gene encoding ataxin-7 protein involved in spino-cerebellar ataxia-7 (PLoS One 2009, 4: e7232); and HTT gene encoding huntingtin protein involved in Huntington's disease (Neurobiol Dis. 1996, 3:183); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med Biol. 2008, 613:203)

In certain embodiments, selective reduction of mRNA and protein expression of a mutant allele is achieved by targeting a SNP located on the mutant allele with an antisense compound. In certain embodiments, the antisense compound is an antisense oligonucleotide. In certain embodiments, the antisense compound is not a ribozyme, a double stranded siRNA, or an shRNA. In certain embodiments, the antisense oligonucleotide may have one or more modified sugar(s), nucleobase(s), or internucleoside linkage(s). In certain embodiments, the antisense oligonucleotide is complementary to the SNP site. In certain embodiments, the antisense oligonucleotide is at least 65%, 70%, 75%, 80%, 85%, 86%, 87%, 88%, 89%, 90%, 91%, 92%, 93%, 94%, 95%, 96%, 97%, 98%, or 99% complementary to the SNP site. In certain embodiments, the antisense oligonucleotide is 100% complementary to the SNP site. In certain embodiments, the SNP site is 12, 13, 14, 15, 16, 17, 18, 19, 20, 21, 22, 23, 24, 25, 26, 27, 28, 29, or 30 nucleobases in length. In certain embodiments, the SNP anneals to position 1, 2, 3, 4, 5, 6, 7, 8, 9, 10, 11, 12, 13, 14, 15, 16, 17, 18, 19, or 20 of the antisense oligonucleotide.

In certain embodiments, antisense compounds designed to selectively reduce an allelic variant of a gene containing a SNP are created based on potency and selectivity of the antisense compound as well as population genetics.

In certain embodiments, selective reduction of mRNA and protein expression of an allelic variant of a gene containing a SNP occurs in a cell or tissue. In certain embodiments, the cell or tissue is in an animal. In certain embodiments, the animal is a human.

In certain embodiments, described herein are compounds comprising a modified antisense oligonucleotide consisting of 12 to 30 linked nucleosides targeted to a single nucleotide polymorphism site, wherein the modified oligonucleotide comprises a wing-gap-wing motif with a 5' wing region positioned at the 5' end of a deoxynucleoside gap, and a 3' wing region positioned at the 3' end of the deoxynucleoside gap, wherein position 5, 6, 7, 8, 9, 10, 11, 12, 13, 14, or 15 of the modified oligonucleotide, as counted from the 5' terminus of the modified oligonucleotide, or positions 1, 2, 3, 4, 5, 6, 7, 8, or 9 of the modified oligonucleotide, as counted from the 5' terminus of the gap, aligns with the single nucleotide polymorphism.

In certain embodiments, the single nucleotide polymorphism site is on a mutant allele that is associated with a disease. In certain embodiments, the single nucleotide polymorphism site contains a differentiating polymorphism.

In certain embodiments, the modified antisense oligonucleotide consists of 12 to 20 linked nucleosides. In certain embodiments, modified antisense oligonucleotide consists of 15 to 20 linked nucleosides. In certain embodiments, the modified antisense oligonucleotide consists of 15 to 19 linked nucleosides.

In certain embodiments, position 8, 9, or 10 of the modified oligonucleotide, as counted from the 5' terminus of the modified oligonucleotide, or positions 4, 5, or 6 of the modified oligonucleotide, as counted from the 5' terminus of the gap, aligns with the single nucleotide polymorphism.

In certain embodiments, the gap region is 7-11 nucleosides in length, the 5' wing region is 1-6 nucleobases in length and the 3' wing region is 1-6 nucleobases in length.

In certain embodiments, the wing-gap-wing motif is any one of the group consisting of 5-10-5, 2-9-6, 3-9-3, 3-9-4, 3-9-5, 4-7-4, 4-9-3, 4-9-4, 4-9-5, 4-10-5, 4-11-4, 4-11-5, 5-7-5, 5-8-6, 5-9-3, 5-9-5, 5-10-4, 5-10-5, 6-7-6, 6-8-5, and 6-9-2. In certain embodiments, the wing-gap-wing motif is any one of the group consisting of 2-9-6, 4-9-5, and 4-11-4.

In certain embodiments, at least one internucleoside linkage is a modified internucleoside linkage. In certain embodiments, each internucleoside linkage is a phosphorothioate internucleoside linkage.

In certain embodiments, at least one nucleoside comprises a modified nucleobase. In certain embodiments, the modified nucleobase is a 5'-methylcytosine.

In certain embodiments, at least one nucleoside of at least one of the wing regions comprises a modified sugar or sugar surrogate. In certain embodiments, each of the nucleosides of each wing region comprises a modified sugar or sugar surrogate. In certain embodiments, the sugar or sugar surrogate is a 2'-O-methoxyethyl modified sugar.

In certain embodiments, at least one of the wing regions comprises a 4' to 2' bicyclic nucleoside and at least one of the remaining wing nucleosides is a non-bicyclic 2'-modified nucleoside.

In certain embodiments, the non-bicyclic 2'-modified nucleoside is a 2'-O-methoxyethyl nucleoside.

In certain embodiments, the 4' to 2' bicyclic nucleoside is 4'-$CH(CH_3)$—O-2' bicyclic nucleoside.

In certain embodiments, the modified antisense oligonucleotide consisting of 17 linked nucleosides and wherein position 9 of the modified oligonucleotide, as counted from the 5' terminus of the modified oligonucleotide, aligns with the differentiating polymorphism. In certain embodiments, the wing-gap-wing motif is 2-9-6.

In certain embodiments, described herein are compounds comprising a modified oligonucleotide consisting of 18 linked nucleosides and 90% complementary to a differentiating polymorphism, wherein the modified oligonucleotide comprises a wing-gap-wing motif, wherein position 9 of the modified oligonucleotide, as counted from the 5' terminus of the modified oligonucleotide, aligns with the differentiating polymorphism; wherein each nucleoside of each wing segment comprises a 2'-O-methoxyethyl sugar; and wherein the wing-gap-wing motif is 4-9-5.

In certain embodiments, described herein are compounds comprising a modified oligonucleotide consisting of 19 linked nucleosides and 90% complementary to a differentiating polymorphism, wherein the modified oligonucleotide comprises a wing-gap-wing motif, wherein position 10 of the modified oligonucleotide, as counted from the 5' terminus of the modified oligonucleotide, aligns with the differentiating polymorphism; wherein each nucleoside of each wing segment comprises a 2'-O-methoxyethyl sugar; and wherein the wing-gap-wing motif is 4-11-4.

In certain embodiments, described herein are compounds comprising a modified oligonucleotide consisting of 15 to 19 linked nucleosides and fully complementary to a differentiating polymorphism, wherein the modified oligonucleotide comprises a wing-gap-wing motif, wherein position 6, 7, 8, 9, 10, 11, 12, 13, or 14 of the modified oligonucleotide, as counted from the 5' terminus of the modified oligonucleotide, aligns with the differentiating polymorphism; and at least one high-affinity sugar modification. In certain embodiments, the modified oligonucleotide is 100% complementary to the single nucleotide polymorphism site.

In certain embodiments, at least one of the wing regions comprises a high-affinity sugar modification. In certain embodiments, the high-affinity sugar modification is a bicyclic sugar. In certain embodiments, the bicyclic sugar comprises a 4'-$CH(CH_3)$—O-2' bridge.

In certain embodiments, at least one of positions 2, 3, 6, 9, 10, 11, 13, or 14 of the modified oligonucleotide, as counted from the 5' terminus of the modified oligonucleotide, comprises the at least one high-affinity sugar modification.

In certain embodiments, at least one of positions 2, 3, 13, and 14 of the modified oligonucleotide, as counted from the 5' terminus of the modified oligonucleotide, comprises the at least one high-affinity sugar modification.

In certain embodiments, each of nucleoside positions 2, 3, 13, and 14 of the modified oligonucleotide, as counted from the 5' terminus of the modified oligonucleotide, comprise the at least one high-affinity sugar modification.

In certain embodiments, the high-affinity sugar modification is a bicyclic sugar. In certain embodiments, the bicyclic sugar comprises a 4'-$CH(CH_3)$—O-2' bridge.

In certain embodiments, the wing-gap-wing motif is any of the group consisting of 3-9-3, 4-9-4, and 5-9-5.

In certain embodiments, described herein are compounds comprising a modified oligonucleotide consisting of 15, 17, or 19 linked nucleosides and fully complementary to a differentiating polymorphism, wherein the modified oligonucleotide comprises a wing-gap-wing motif, wherein position 6, 8, 10, or 14 of the modified oligonucleotide, as counted from the 5' terminus of the modified oligonucleotide, aligns with the differentiating polymorphism; and at least one high-affinity sugar modification.

In certain embodiments, at least one of positions 2, 3, 6, 9, 10, 11, 13, or 14 of the modified oligonucleotide, as counted from the 5' terminus of the modified oligonucleotide, comprises the at least one high-affinity sugar modification.

In certain embodiments, the high-affinity sugar modification is a bicyclic sugar. In certain embodiments, the bicyclic sugar comprises a 4'-$CH(CH_3)$—O-2' bridge.

In certain embodiments, the wing-gap-wing motif is any of the group consisting of 3-9-3, 4-9-4, and 5-95.

In certain embodiments, described herein are compounds comprising a modified oligonucleotide consisting of 15 linked nucleosides and 90% complementary to a differentiating polymorphism, wherein the modified oligonucleotide comprises a wing-gap-wing motif, wherein position 8 of the modified oligonucleotide, as counted from the 5' terminus of the modified oligonucleotide, aligns with the differentiating polymorphism; and at least one high-affinity sugar modification. In certain embodiments, the modified oligonucleotide is 100% complementary to the differentiating polymorphism.

In certain embodiments, each of nucleoside positions 2, 3, 13, and 14 of the modified oligonucleotide, as counted from the 5' terminus of the modified oligonucleotide, comprise the at least one high-affinity sugar modification.

In certain embodiments, the high-affinity sugar modification is a bicyclic sugar. In certain embodiments, the bicyclic sugar comprises a 4'-$CH(CH_3)$—O-2' bridge.

In certain embodiments, the wing-gap-wing motif is 3-9-3.

In certain embodiments, described herein are methods of selectively reducing expression of an allelic variant of a gene containing a single nucleotide polymorphism in a cell, tissue, or animal, comprising administering to the cell, tissue, or animal a compound comprising a modified oligonucleotide complementary to a differentiating polymorphism, wherein the modified oligonucleotide comprises a wing-gap-wing motif and wherein position 5, 6, 7, 8, 9, 10, 11, 12, 13, 14, or 15 of the modified oligonucleotide, as counted from the 5' terminus of the modified oligonucleotide, aligns with the differentiating polymorphism. In certain embodiments, the modified oligonucleotide is 90% complementary to the single differentiating polymorphism. In certain embodiments, the modified oligonucleotide is 95% complementary to the single nucleotide polymorphism site. In certain embodiments, the modified oligonucleotide is 100% complementary to the single nucleotide polymorphism site.

In certain embodiments, the single nucleotide polymorphism site is from 12 to 30 nucleobases in length. In certain embodiments, the single nucleotide polymorphism site is from 15 to 25 nucleobases in length. In certain embodiments, the single nucleotide polymorphism site is from 17 to 22 nucleobases in length. In certain embodiments, the single nucleotide polymorphism site is 17 nucleobases in length. In certain embodiments, the single nucleotide polymorphism site is 18 nucleobases in length. In certain embodiments, the single nucleotide polymorphism site is 19 nucleobases in length. In certain embodiments, the single nucleotide polymorphism site is 20 nucleobases in length.

In certain embodiments, the allelic variant is associated with disease. In certain embodiments, the disease is Huntington's Disease.

In certain embodiments, the modified oligonucleotide is a single-stranded oligonucleotide.

In certain embodiments, at least one internucleoside linkage is a modified internucleoside linkage. In certain embodiments, each internucleoside linkage is a phosphorothioate internucleoside linkage.

In certain embodiments, at least one nucleoside comprises a modified nucleobase. In certain embodiments, the at least one modified nucleobase is a 5'-methylcytosine.

In certain embodiments, at least one nucleoside comprises a modified sugar. In certain embodiments, the modified sugar is a high-affinity sugar modification. In certain embodiments, the high-affinity sugar is a bicyclic sugar. In certain embodiments, each bicyclic sugar comprises a 4'-$CH(CH_3)$—O-2' bridge.

In certain embodiments, at least one of nucleoside positions 2, 3, 13, and 14 of the modified oligonucleotide, counting from the 5' terminus of the modified oligonucleotide, comprises a nucleoside having a bicyclic sugar wherein the bicyclic sugar comprises a 4'-$CH(CH_3)$—O-2' bridge.

In certain embodiments, each of nucleoside positions 2, 3, 13, and 14 of the modified oligonucleotide, counting from the 5' terminus of the modified oligonucleotide, comprises a bicyclic sugar wherein the bicyclic sugar comprises a 4'-$CH(CH_3)$—O-2' bridge.

In certain embodiments, the at least one modified sugar comprises a 2'-O-methoxyethyl. In certain embodiments, each nucleoside positioned in a wing segment of the modified oligonucleotide comprises a 2'-O-methoxyethyl modification.

In certain embodiments, the wing-gap-wing motif is any of the group consisting of 2-9-6, 3-9-3, 3-9-4, 3-9-5, 4-7-4, 4-9-4, 4-9-5, 4-10-5, 4-11-4, 4-11-5, 5-7-5, 5-8-6, 5-9-3, 5-9-5, 5-10-4, 5-10-5, 6-7-6, 6-8-5, and 6-9-2.

In certain embodiments, the modified oligonucleotide is not a ribozyme, a double stranded siRNA, or an shRNA.

In certain embodiments, the single nucleotide polymorphism site is on a mutant allele that is associated with disease. In certain embodiments, the single nucleotide polymorphism site contains a differentiating polymorphism.

In certain embodiments, the modified antisense oligonucleotide consists of 12 to 20 linked nucleosides. In certain embodiments, the modified antisense oligonucleotide consists of 15 to 19 linked nucleosides.

In certain embodiments, the gap region is 7 to 11 nucleosides in length, the 5' wing region is 1 to 6 nucleobases in length and 3' wing region is 1 to 6 nucleobases in length.

In certain embodiments, wherein at least one nucleoside of at least one of the wing regions comprises a modified sugar or sugar surrogate.

In certain embodiments, each of the nucleosides of each wing region comprises a modified sugar or sugar surrogate. In certain embodiments, the sugar or sugar surrogate is a 2'-O-methoxyethyl modified sugar.

In certain embodiments, at least one of the wing regions comprises a 4' to 2' bicyclic nucleoside and at least one of the remaining wing nucleosides is a non-bicyclic 2'-modified nucleoside.

In certain embodiments, the non-bicyclic 2'-modified nucleoside is a 2'-O-methoxyethyl nucleoside.

In certain embodiments, 4' to 2' bicyclic nucleoside is a 4'-$CH(CH_3)$—O-2' bicyclic nucleoside.

In certain embodiments, described herein are methods of selectively reducing expression of an allelic variant of a gene containing a single nucleotide polymorphism in a cell, tissue, or animal, comprising administering to the cell, tissue, or animal a compound comprising a modified oligonucleotide complementary to a differentiating polymorphism, wherein the modified oligonucleotide comprises a wing-gap-wing motif and wherein position 5, 6, 7, 8, 9, 10, 11, 12, 13, 14, or 15 of the modified oligonucleotide, as counted from the 5' terminus of the modified oligonucleotide, aligns with the differentiating polymorphism.

In certain embodiments, described herein are methods of selectively reducing expression of an allelic variant of a gene containing a single nucleotide polymorphism in a cell, tissue, or animal, comprising administering to the cell, tissue, or animal a compound comprising a modified oligonucleotide consisting of 12 to 30 linked nucleosides and complementary to a differentiating polymorphism, wherein the modified oligonucleotide comprises a wing-gap-wing motif and wherein position 5, 6, 7, 8, 9, 10, 11, 12, 13, 14, or 15 of the modified oligonucleotide, as counted from the 5' terminus of the modified oligonucleotide aligns with the differentiating polymorphism; and wherein the allelic variant is a mutant allele.

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congenital myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

In certain embodiments, described herein are methods of treating Huntington's Disease, comprising selectively reducing expression of an allelic variant of a gene containing a single nucleotide polymorphism in a cell, tissue, or animal, comprising administering to the cell, tissue, or animal a compound comprising a modified oligonucleotide consisting of 12 to 30 linked nucleosides and complementary to differentiating polymorphism, wherein the modified oligonucleotide comprises a wing-gap-wing motif and wherein position 5, 6, 7, 8, 9, 10, 11, 12, 13, 14, or 15 of the modified oligonucleotide, as counted from the 5' terminus of the modified oligonucleotide, aligns with differentiating polymorphism; and wherein the allelic variant is associated with Huntington's Disease.

In certain embodiments, position 8, 9, or 10 of the modified oligonucleotide, as counted from the 5' terminus of the modified oligonucleotide, or positions 4, 5, or 6 of the modified oligonucleotide, as counted from the 5' terminus of the gap, aligns with the single nucleotide polymorphism.

Single Nucleotide Polymorphisms (SNPs)

Single-nucleotide polymorphisms (SNPs) are single base-pair alterations in the DNA sequence that represent a major source of genetic heterogeneity (Gene. 1999, 234:177). SNP genotyping is an important tool with which to investigate these genetic variants (Genome Res. 2000, 10:895; Trends Biotechnol. 2000, 18:77). In certain embodiments, antisense compounds designed to selectively reduce an allelic variant of a gene containing an SNP were selected based on potency, selectivity and population genetics coverage.

Potency

In certain embodiments, antisense compounds designed to selectively reduce an allelic variant of a gene containing a SNP are created based on potency of the antisense compound. Potency generally refers to how amenable the targeted sequence area is to antisense inhibition. In certain embodiments, specific SNP sites may be particularly amenable to antisense inhibition. Certain such highly amenable SNP sites may be targeted by antisense compounds for selectively reducing an allelic variant of a gene. Potency is demonstrated by the percent inhibition of mutant mRNA achieved by the antisense oligonucleotides targeting a SNP compared to the percent inhibition of mutant mRNA achieved by the benchmark oligonucleotide.

Selectivity

In certain embodiments, antisense compounds designed to selectively reduce an allelic variant of a gene containing a SNP are created based on selectivity of the antisense compound. Selectivity generally refers to antisense compounds comprising a particular sequence, motif, and chemical modification(s) that preferentially target the one or more differentiating polymorphisms (SNPs) in the RNA encoding a mutant HTT protein compared to the RNA encoding a wild type HTT protein. In certain embodiments, specific sequences, motifs, and chemical modification(s) are particularly selective in reducing an allelic variant of a gene containing a SNP. Certain such sequences, motifs, and chemical modification(s) are utilized to selectively reduce an allelic variant of a gene. Selectivity is demonstrated by the ability of the antisense oligonucleotide targeting a SNP to inhibit expression of the major allele or mutant allele preferentially compared to the minor allele or wild type allele.

Population Genetics

In certain embodiments, antisense compounds designed to selectively reduce an allelic variant of a gene containing an SNP are created based on the population genetics of a population afflicted with disease. Population genetics means the frequency at which the SNP appears in the disease chromosome of patients afflicted with a particular disease. In certain embodiments, the disease is Huntington disease. Where potency and selectivity amongst antisense compounds is equal, SNP targets that have higher population genetics coverage are favored over SNPs that have a weaker association with disease chromosomes.

Antisense Compounds

Oligomeric compounds may include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound is an antisense oligonucleotide. In certain embodiments, the antisense compound is not a ribozyme, a double stranded siRNA, or an shRNA.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, antisense compounds are 12 to 30 subunits in length. In other words, such antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a nucleic acid may be shortened or truncated. For example, a single subunit may be deleted from the 5' end (5' truncation), or alternatively from the 3' end (3' truncation). A shortened or truncated antisense compound targeted to a nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

However, selective reduction of expression of an allelic variant is optimized when the SNP contained in the target nucleic anneals to a complementary base in the antisense compound and not a mismatched base. Moreover, selectivity in general is increased when there are fewer mismatches between the SNP site and the antisense compound. However, a certain number of mismatches may be tolerated.

Antisense Compound Motifs

In certain embodiments, antisense compounds targeted to a nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In the case of an antisense oligonucleotide for selectively reducing expression of an allelic variant of a gene containing a SNP, the SNP anneals to a nucleobase within the gap segment.

In certain embodiments, the SNP anneals or is complementary to a nucleobase at position 5, 6, 7, 8, 9, 10, 11, 12, 13, or 14 of the antisense oligonucleotide, wherein position refers to the orientation of a nucleobase within the antisense oligonucleotide counting from the 5' terminus of the antisense oligonucleotide. For example, the 5' most nucleobase within the antisense oligonucleotide is in the first position of the antisense oligonucleotide. In certain embodiments, the SNP anneals or is complementary to a nucleobase at position 6, 7, 8, 9, or 10 of the antisense oligonucleotide (counting from the 5' terminus). In certain embodiments, the SNP anneals or is complementary to a nucleobase at position 9 or 10 of the antisense oligonucleotide (counting from the 5' terminus).

In certain embodiments, the SNP anneals to a nucleobase at position 1, 2, 3, 4, 5, 6, 7, 8, 9, or 10 of the gap segment, wherein position refers to the orientation of a nucleobase within the gap segment counting from the 5' terminus of the gap segment. For example, the 5' most nucleobase within the gap segment is in the first position of the gap segment. In certain embodiments, the SNP anneals to a nucleobase at position 4, 5, 6, or 7 counting from the 5' terminus of the gap segment. In certain embodiments, the SNP anneals to a nucleobase at position 4 or 5 beginning from the 5' terminus of the gap segment.

In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)$ n-O-2' bridge, where n=1 or n=2). The bicyclic moiety may be a cEt having the formula 4'-$CH(CH_3)$—O-2.'

The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In certain embodiments, Y is between 8 and 15 nucleotides. In certain embodiments, Y is comprised of deoxynucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 1-10-1, 1-18-1, 2-8-2, 2-9-6, 2-10-2, 2-13-5, 2-16-2, 3-9-3, 3-9-5, 3-10-3, 3-14-3, 4-8-4, 4-9-5, 4-10-5, 4-11-4, 4-12-3, 4-12-4, 5-8-5, 5-9-5, 5-10-4, 5-10-5, or 6-8-6.

In certain embodiments, the antisense compound has a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a nucleic acid possess a 2-9-6 gapmer motif or a 6-9-2 gapmer motif.

In certain embodiments, antisense compounds targeted to a nucleic acid possess a 3-9-3 gapmer motif.

In certain embodiments, antisense compounds targeted to a nucleic acid possess a 3-9-5 gapmer motif or 5-9-3 gapmer motif.

In certain embodiments, antisense compounds targeted to a nucleic acid possess a 4-9-5 gapmer motif or 5-9-4 gapmer motif.

In certain embodiments, antisense compounds targeted to a nucleic acid possess a 4-10-5 gapmer motif or 5-10-4 gapmer motif.

In certain embodiments, antisense compounds targeted to a nucleic acid possess a 4-11-4 gapmer motif.

In certain embodiments, antisense compounds targeted to a nucleic acid possess a 5-9-5 gapmer motif.

In certain embodiments, antisense compounds targeted to a nucleic acid possess a 5-8-6 gapmer motif or a 6-8-5 gapmer motif.

In certain embodiments, antisense compounds targeted to a nucleic acid possess a 6-7-6 gapmer motif.

In certain embodiments, antisense compounds targeted to a nucleic acid possess a 6-8-5 gapmer motif or a 5-8-6 gapmer motif.

In certain embodiments, antisense compounds targeted to a nucleic acid possess a 3-9-4 gapmer motif or a 4-9-3 gapmer motif.

In certain embodiments, antisense compounds targeted to a nucleic acid possess a 5-7-5 gapmer motif.

In certain embodiments, antisense compounds targeted to a nucleic acid possess a 4-7-4 gapmer motif.

In certain embodiments, antisense compounds targeted to a nucleic acid possess a 5-10-5 gapmer motif.

In certain embodiments, an antisense compound targeted to a nucleic acid has a gap-widened motif.

Certain Mixed Wings

In certain embodiments, the invention provides gapmer compounds wherein at least one nucleoside of one wing is differently modified compared to at least one other nucleoside of the same wing. Such antisense compounds are referred to as mixed wing antisense compounds (see WO 2008/049085). In certain embodiments, the modifications (or no modification) of one or more nucleosides of the 3' wing are different from those of one or more other nucleosides of the 3' wing. Such antisense compounds may be referred to as 3' mixed wing gapmers. In certain embodiments, the modifications (or no modification) of one or more nucleosides of the 5' wing are different from those of one or more other nucleosides of the 5' wing. Such antisense compounds may be referred to as 5' mixed wing gapmers. In certain embodiments, the modifications (or no modification) of one or more nucleosides of the 3' wing are different from those of one or more other nucleosides of the 3' wing and the modifications (or no modification) of one or more nucleosides of the 5' wing are different from those of one or more other nucleosides of the 5' wing. Such antisense compounds may be referred to as 3', 5' mixed wing gapmers. In such embodiment, the modifications and combination of modifications at the 3' wing and at the 5' wing may be the same or they may be different.

In certain embodiments, mixed wing compounds have desirable properties. Certain nucleoside modifications confer on the antisense compound a desirable property, for example increased affinity for a target or nuclease resistance, but also confer an undesirable property, for example increased toxicity. Incorporation of certain other nucleoside modifications results in antisense compounds with different profiles of properties. In certain embodiments, one may combine modifications in one or both wings to optimize desirable characteristics and/or minimize undesirable characteristics. In certain embodiments, the wings of a mixed wing antisense compound comprise one or more nucleoside comprising a first modification that increases affinity of the antisense compound for a target nucleic acid compared to an antisense compound comprising unmodified nucleosides; and one or more nucleoside comprising a second modification that results in reduced toxicity compared to an antisense compound with wings comprising nucleosides that all comprise the first modification.

In certain embodiments, an antisense compound comprises at least one wing comprising at least one MOE substituted nucleoside and at least one high affinity modification. In certain such embodiments, the at least one MOE substituted nucleoside and the at least one high affinity are in the 3' wing. In certain such embodiments, the at least one MOE substituted nucleoside and the at least one high affinity are in the 5' wing.

In certain embodiments, an antisense compound comprises 1, 2 or 3 high affinity modifications in the 5' and/or 3' wings.

Target Nucleic Acids, Target Regions and Nucleotide Sequences

In certain embodiments, an allelic variant of huntingtin is selectively reduced. Nucleotide sequences that encode huntingtin include, without limitation, the following: GENBANK Accession No. NT_006081.18, truncated from nucleotides 1566000 to 1768000 (replaced by GENBANK Accession No. NT_006051), incorporated herein as SEQ ID NO: 1, and NM_002111.6, incorporated herein as SEQ ID NO: 2.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for huntingtin can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels of a particular allelic variant. In certain embodiments, the desired effect is reduction of levels of the protein encoded by the target nucleic acid or a phenotypic change associated with a particular alleleic variant.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

Cell Lines

In certain embodiments, the GM04281, GM02171, and GM02173B cell lines are used in experiments described herein below. The GM04281 cell line has a wild-type HTT allele that contains 17 repeats and a mutant HTT allele that contains 69 repeats. The cell line was derived from a patient both of whose parents were also affected by the disease. The GM02171 cell line was chosen as a counter screen control to the GM04281. This cell line was derived from the daughter of parents, only one of whom had the disease. The daughter had not developed HD but was considered to be at risk. The GM02173B cell line was also patient-derived and was used as a haplotype test control.

Table 1 provides SNPs found in the GM04281, GM02171, and GM02173B cell lines. Also provided are the allelic variants found at each SNP position, the genotype for each of the cell lines, and the percentage of HD patients having a particular allelic variant. For example, the two allelic variants for SNP rs6446723 are T and C. The GM02171 cell line is homozygous CC, the GM02173 cell line is heterozygous TC, and the GM04281 cell line is homozygous TT. Fifty percent of HD patients have a T at SNP position rs6446723.

TABLE 1

Allelic Variations for SNPs Associated with HD

| SNP | Variation | GM02171 | GM02173 | GM04281 | TargetPOP | allele |
|---|---|---|---|---|---|---|
| rs6446723 | T/C | CC | TC | TT | 0.50 | T |
| rs3856973 | A/G | AA | AG | GG | 0.50 | G |
| rs2285086 | A/G | GG | AG | AA | 0.50 | A |
| rs363092 | A/C | AA | AC | CC | 0.49 | C |

TABLE 1-continued

Allelic Variations for SNPs Associated with HD

| SNP | Variation | GM02171 | GM02173 | GM04281 | TargetPOP | allele |
|---|---|---|---|---|---|---|
| rs916171 | C/G | GG | GC | CC | 0.49 | C |
| rs6844859 | T/C | CC | TC | TT | 0.49 | T |
| rs7691627 | A/G | AA | AG | GG | 0.49 | G |
| rs4690073 | A/G | AA | AG | GG | 0.49 | G |
| rs2024115 | A/G | GG | AG | AA | 0.48 | A |
| rs11731237 | T/C | CC | TC | TT | 0.43 | T |
| rs362296 | A/C | AC | AC | AC | 0.42 | C |
| rs10015979 | A/G | AA | AG | GG | 0.42 | G |
| rs7659144 | C/G | CG | CG | CC | 0.41 | C |
| rs363096 | T/C | CC | TC | TT | 0.40 | T |
| rs362273 | A/G | AG | AG | AA | 0.39 | A |
| rs16843804 | T/C | TC | TC | CC | 0.38 | C |
| rs362271 | A/G | AG | AG | GG | 0.38 | G |
| rs362275 | T/C | TC | TC | CC | 0.38 | C |
| rs3121419 | T/C | TC | TC | CC | 0.38 | C |
| rs362272 | A/G | — | AG | GG | 0.38 | G |
| rs3775061 | A/G | AG | AG | AA | 0.38 | A |
| rs34315806 | T/C | TC | TC | CC | 0.38 | C |
| rs363099 | T/C | TC | TC | CC | 0.38 | C |
| rs2298967 | T/C | TC | TC | TT | 0.38 | T |
| rs363088 | A/T | TA | TA | AA | 0.38 | A |
| rs363064 | T/C | TC | TC | CC | 0.35 | C |
| rs363102 | A/G | AA | AA | AA | 0.23 | G |
| rs2798235 | A/G | GG | GG | GG | 0.21 | A |
| rs363080 | T/C | CC | CC | CC | 0.21 | T |
| rs363072 | A/T | TA | AA | AA | 0.13 | A |
| rs363125 | A/C | AC | CC | CC | 0.12 | C |
| rs362303 | T/C | TC | CC | CC | 0.12 | C |
| rs362310 | T/C | TC | CC | CC | 0.12 | C |
| rs10488840 | A/G | AG | GG | GG | 0.12 | G |
| rs362325 | T/C | TC | TT | TT | 0.11 | T |
| rs35892913 | A/G | GG | GG | GG | 0.10 | A |
| rs363102 | A/G | AA | AA | AA | 0.09 | A |
| rs363096 | T/C | CC | TC | TT | 0.09 | C |
| rs11731237 | T/C | CC | TC | TT | 0.09 | C |
| rs10015979 | A/G | AA | AG | GG | 0.08 | A |
| rs363080 | T/C | CC | CC | CC | 0.07 | C |
| rs2798235 | A/G | GG | GG | GG | 0.07 | G |
| rs1936032 | C/G | CC | CC | CC | 0.06 | C |
| rs2276881 | A/G | GG | GG | GG | 0.06 | G |
| rs363070 | A/G | AA | AA | AA | 0.06 | A |
| rs35892913 | A/G | GG | GG | GG | 0.04 | G |
| rs12502045 | T/C | CC | CC | CC | 0.04 | C |
| rs6446723 | T/C | CC | TC | TT | 0.04 | C |
| rs7685686 | A/G | GG | AG | AA | 0.04 | G |
| rs3733217 | T/C | CC | CC | CC | 0.03 | C |
| rs6844859 | T/C | CC | TC | TT | 0.03 | C |
| rs362331 | T/C | CC | TC | TT | 0.03 | C |

Hybridization

In some embodiments, hybridization occurs between an antisense compound disclosed herein and a SNP site. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

In certain embodiments, the antisense compounds provided herein are specifically hybridizable with the nucleic acid of a particular allelic variant.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., selective reduction of a gene product of an allelic variant).

Non-complementary nucleobases between an antisense compound and a target nucleic acid may be tolerated provided that the antisense compound remains able to specifically hybridize to a target nucleic acid. Moreover, an antisense compound may hybridize over one or more segments of a target nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a target nucleic acid, a target region, target segment, SNP site, or specified portion thereof. Percent complementarity of an antisense compound with a target nucleic acid can be determined using routine methods. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, a SNP site, target region, target segment, or specified portion thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, SNP site, or specified portion thereof.

In certain embodiments, antisense oligonucleotides that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, SNP site, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Chemically modified nucleosides may also be employed to increase selectivity in reducing expression the gene product of an allelic variant.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioate. Methods of preparation of phosphorous-containing and non-phosphorous-containing linkages are well known.

In certain embodiments, antisense compounds comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, increased selectivity for an allelic variant, or some other beneficial biological property to the antisense compounds. In certain embodiments, nucleosides comprise a chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C(R1)(R)2 (R═H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$ and 2'-$O(CH_2)2OCH_3$ substituent groups. The substituent at the 2' position can also be selected from allyl, amino, azido, thio, O-allyl, O-C1-C10 alkyl, OCF3, O(CH2)2SCH3, O(CH2)2-O—N(Rm)(Rn), and O-CH2-C(═O)—N(Rm)(Rn), where each Rm and Rn is, independently, H or substituted or unsubstituted C1-C10 alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include but are not limited to one of the formulae: 4'-$(CH_2)$—O-2' (LNA); 4'-$(CH_2)$—S-2'; 4'-$(CH_2)_2$—O-2' (ENA); 4'-CH$(CH_3)$—O-2' and 4'-CH$(CH_2OCH_3)$—O-2' (and analogs thereof see U.S. Pat. No. 7,399,845, issued on Jul. 15, 2008); 4'-C$(CH_3)(CH_3)$—O-2' (and analogs thereof see published International Application WO/2009/006478, published Jan. 8, 2009); 4'-$CH_2$—N$(OCH_3)$-2' (and analogs thereof see published International Application WO/2008/150729, published Dec. 11, 2008); 4'-$CH_2$—O—N$(CH_3)$-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)$(CH_3)$-2' (see Chattopadhyaya, et al., *J. Org. Chem.,* 2009, 74, 118-134); and 4'-$CH_2$—C—(═$CH_2$)-2' (and analogs thereof see published International Application WO 2008/154401, published on Dec. 8, 2008). See, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); U.S. Pat. Nos. 7,053,207; 6,268,490; 6,770,748; 6,794,499; 7,034,133; and 6,525,191; Elayadi et al., *Curr. Opinion Invens. Drugs,* 2001, 2, 558-561; Braasch et al., *Chem. Biol.,* 2001, 8, 1-7; and Orum et al., *Curr. Opinion Mol. Ther.,* 2001, 3, 239-243; and U.S. Pat. No. 6,670,461; International applications WO 2004/106356; WO 94/14226; WO 2005/021570; U.S. Patent Publication Nos. US2004-0171570; US2007-0287831; US2008-0039618; U.S. Pat. No. 7,399,845; U.S. patent Ser. Nos. 12/129,154; 60/989,574; 61/026,995; 61/026,998; 61/056,564; 61/086,231; 61/097,787; 61/099,844; PCT International Applications Nos. PCT/US2008/064591; PCT/US2008/066154; PCT/US2008/068922; and Published PCT International Applications WO 2007/134181. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$ $=C(R_b)-$, $-C(R_a)=N-$, $-C(=NR_a)-$, $-C(=O)-$, $-C(=S)-$, $-O-$, $-Si(R_a)_2-$, $-S(=O)_x-$, and $-N(R_a)-$;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl ($C(=O)-H$), substituted acyl, CN, sulfonyl ($S(=O)_2$-$J_1$), or sulfoxyl ($S(=O)$-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-Cao aryl, substituted $C_5$-$C_{20}$ aryl, acyl ($C(=O)-H$), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, $-[C(R_a)(R_b)]_n-$, $-[C(R_a)(R_b)]_n-O-$, $-C(R_aR_b)-N(R)-O-$ or $-C(R_aR_b)-O-N(R)-$. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-Methyleneoxy (4'-$CH_2$—O-2') BNA, (B) β-D-Methyleneoxy (4'-$CH_2$—O-2') BNA, (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, and (F) Methyl(methyleneoxy) (4'-$CH(CH_3)$—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—$CH(CH_3)$-2') BNA, (J) propylene carbocyclic (4'-$(CH_2)_3$-2') BNA, and (K) ethylene carbocyclic (4'-$CH_2$—$CH_2$-2') (carba LNA or "cLNA") as depicted below.

(A)

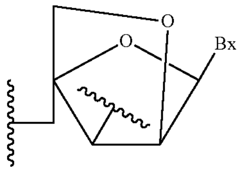

(B)

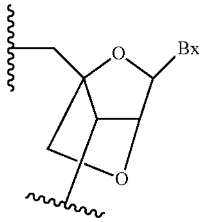

-continued (C)

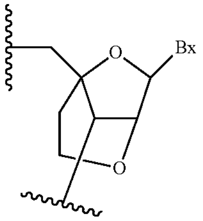

(D)

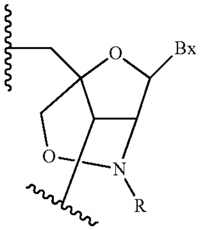

(E)

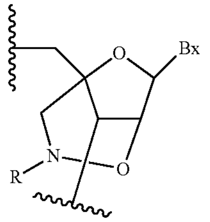

(F)

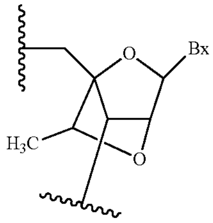

(G)

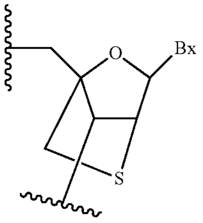

(H)

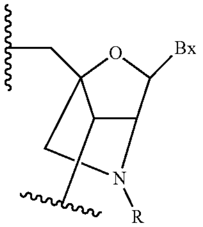

(I)

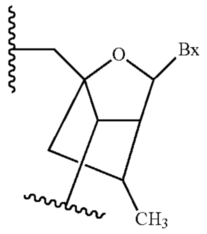

-continued (J)

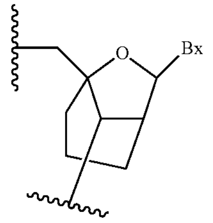

(K)

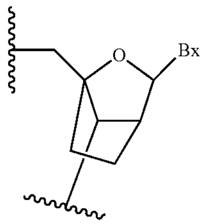

wherein Bx is the base moiety and R is independently H, a protecting group or $C_1$-$C_{12}$ alkyl.

In certain embodiments, bicyclic nucleoside having Formula I:

I

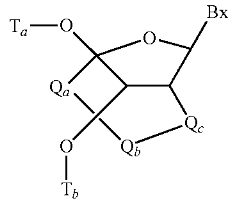

wherein:

Bx is a heterocyclic base moiety;

-$Q_a$-$Q_b$-$Q_c$- is —$CH_2$—$N(R_c)$—$CH_2$—, —C(═O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleoside having Formula II:

II

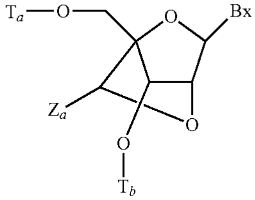

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, OC(═X)$J_c$, and $NJ_e$C(═X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

III

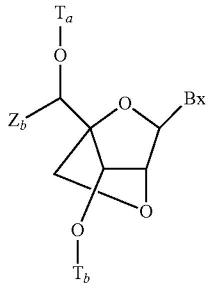

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(═O)—).

In certain embodiments, bicyclic nucleoside having Formula IV:

IV

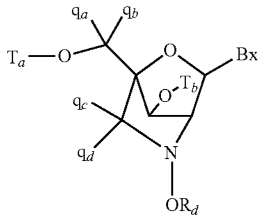

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_a$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleoside having Formula V:

V

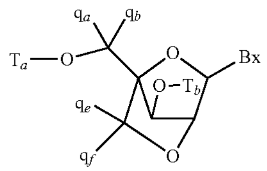

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_k$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron,* 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA and 2'-thio-BNAs, have also been prepared (Kumar et al., *Bioorg. Med. Chem. Lett.,* 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., J. Org. Chem., 1998, 63, 10035-10039). In addition, 2'-Amino- and 2'-methylamino-BNA's have been prepared and the thermal stability of their duplexes with complementary RNA and DNA strands has been previously reported.

In certain embodiments, bicyclic nucleoside having Formula VI:

VI

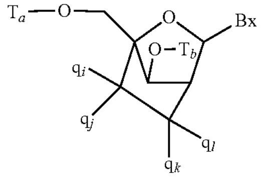

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Frier et al., *Nucleic Acids Research,* 1997, 25(22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nONH_2$, $OCH_2C(=O)N(H)CH_3$, and $O(CH_2)_nON[(CH_2)_nCH_3]_2$, where n and m are from 1 to about 10. Other 2'- substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, P., *Helv. Chico. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA) or those compounds having Formula X:

X

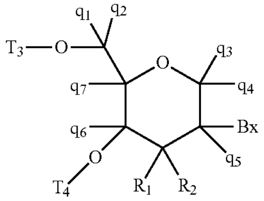

wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$ and $q_u$ are each H. In certain embodiments, at least one of $q_m$, $q_n$, $q_p$, $q_r$, $q_s$, $q_t$ and $q_u$ is other than H. In certain embodiments, at least one of $q_m$, $q_n$, $q_p$, $q_r$, $q_s$, $q_t$ and $q_u$ is methyl. In certain embodiments, THP nucleosides of Formula X are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also know in the art that can be used to modify nucleosides for incorporation into antisense compounds (see for example review article: Leumann, J. C, *Bioorganic & Medicinal Chemistry,* 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif Modified Nucleobases Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity, increased selectivity for an allelic variant, or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and 0-6 substituted purines, including 2 aminopropyladenine, 5-propynyluracil and 5-propynylcytosine.

In certain embodiments, antisense compounds comprise one or more modified nucleobases. In certain embodiments, gap-widened antisense oligonucleotides comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution, increased selectivity for an allelic variant, or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression target nucleic acids can be tested in vitro in a variety of cell types. Cell types used for such analyses are available from commercial vendors (e.g. American Type Culture Collection, Manassas, VA; Zen-Bio, Inc., Research Triangle Park, NC; Clonetics Corporation, Walkersville, MD) and are cultured according to the vendor's instructions using commercially available reagents (e.g. Invitrogen Life Technologies, Carlsbad, CA). Illustrative cell types include, but are not limited to, HepG2 cells, Hep3B cells, and primary hepatocytes. Illustrative cell lines include GM04281, GM02171, and GM02173B cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, CA). Antisense oligonucleotides are mixed with LIPOFECTIN in OPTI-MEM 1 (Invitrogen, Carlsbad, CA) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, CA). Antisense oligonucleotide is mixed with LIPOFECTAMINE in OPTI-MEM 1 reduced serum medium (Invitrogen, Carlsbad, CA) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPO- FECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, CA) according to the manufacturer's recommended protocols.

Analysis of Inhibition of Target Levels or Expression

Reduction, inhibition, or expression of a target nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, CA). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, CA). Cyclophilin A expression is quantified by real time PCR, by being run simultaneously with the target, multiplexing, or separately. Total RNA is quantified using RIBOGREEN RNA quantification reagent (Invetrogen, Inc. Eugene, OR). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to target nucleic acids. Methods for designing real-time PCR probes and primers are well known in the art, and may include the use of software such as PRIMER EXPRESS Software (Applied Biosystems, Foster City, CA).

Analysis of Protein Levels

Reduction, inhibition, or expression of target nucleic acids can be assessed by measuring target protein levels. Target protein levels can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art. Antibodies useful for the detection of mouse, rat, monkey, and human proteins are commercially available.

In Vivo Testing of Antisense Compounds

Antisense compounds, for example, antisense oligonucleotides, are tested in animals to assess their ability to selectively reduce or inhibit expression of target gene product and produce phenotypic changes, such as, amelioration of a disease symptom. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA or protein is isolated from tissue and changes in target nucleic acid or protein expression are measured.

Administration

In certain embodiments, the compounds and compositions described herein may be administered in a number of ways depending upon whether local or systemic treatment is desired and upon the area to be treated. Administration may be topical (including ophthalmic, vaginal, rectal, intranasal), oral, pulmonary (including by inhalation or insufflation of powders or aerosols, including by nebulizer; intratracheal, intranasal, epidermal and transdermal) or parenteral, for example, by intravenous drip, intravenous injection or subcutaneous, intraperitoneal, intraocular, intravitreal, or intramuscular injection.

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

In certain embodiments, methods of specifically localizing a pharmaceutical agent, such as by bolus injection, decreases median effective concentration (EC50) by a factor of 20, 25, 30, 35, 40, 45 or 50. In certain embodiments, the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

Certain Compounds and Indications

Provided herein are compounds and methods that provide potent inhibition and increased selectivity for a mutant allele. Potency is demonstrated by the percent inhibition of mutant mRNA achieved by the antisense oligonucleotides targeting a SNP compared to the percent inhibition of mutant mRNA achieved by the benchmark oligonucleotide. Selectivity is demonstrated by the ability of the antisense oligonucleotide targeting a SNP to inhibit expression of the major allele or mutant allele preferentially compared to the minor allele or wild type allele. The usage of three cell lines with different genotypes at each SNP position have facilitated the determination of design rules that provide for potent and selective SNP targeting antisense oligonucleotides.

In certain embodiments, the compounds are antisense oligonucleotides as further described herein. The antisense oligonucleotides preferentially target a SNP or differentiating polymorphism. Oligonucleotides of various lengths were tested and certain lengths were determined to be beneficial for the targeting of SNPs.

In certain embodiments, the antisense oligonucleotides have a sequence that is 12-30 nucleobases in length. In certain embodiments, the antisense oligonucleotides have a sequence that is 12-25 nucleobases in length. In certain embodiments, the antisense oligonucleotides have a sequence that is 12-21 nucleobases in length. In certain embodiments, the antisense oligonucleotides have a sequence that is 12-20 nucleobases in length. In certain embodiments, the antisense oligonucleotides have a sequence that is 13-20 nucleobases in length. In certain embodiments, the antisense oligonucleotides have a sequence that is 14-20 nucleobases in length. In certain embodiments, the antisense oligonucleotides have a sequence that is 15-20 nucleobases in length. In certain embodiments, the antisense oligonucleotides have a sequence that is 12-19 nucleobases in length. In certain embodiments, the antisense oligonucleotides have a sequence that is 13-19 nucleobases in length. In certain embodiments, the antisense oligonucleotides have a sequence that is 14-19 nucleobases in length. In certain embodiments, the antisense oligonucleotides have a sequence that is 15-19, nucleobases in length. In certain embodiments, the antisense oligonucleotides have a sequence that is 16-19 nucleobases in length. In certain embodiments, the antisense oligonucleotides have a sequence that is 17-19 nucleobases in length. In certain embodiments, the antisense oligonucleotides have a sequence that is 12, 13, 14, 15, 16, 17, 18, 19, 21, 22, 23, 24, 25, 26, 27, 28, 29, 30 nucleobases in length.

For oligonucleotides of various lengths, the position of the nucleoside complementary to the SNP position was shifted within the gap and the wings and the effect was tested. Certain positions within the antisense oligonucleotide are shown to be beneficial for targeting SNPs.

In certain embodiments, the antisense oligonucleotide is at least 12, at least 13, at least 14, at least 15, at least 16, at least 17 at least 18 or at least 19 nucleobases in length and the SNP is complementary to positions 6-15 counting from the 5' terminus of the antisense oligonucleotide and/or positions 1-9 counting from the 5' end of the gap. In certain embodiments, the antisense oligonucleotide is at least 12, at least 13, at least 14, at least 15, at least 16, at least 17 at least 18 or at least 19 nucleobases in length and the SNP is complementary to positions 8-14 counting from the 5' terminus of the antisense oligonucleotide and/or positions 1-9 counting from the 5' end of the gap. In certain embodiments, the antisense oligonucleotide is at least 12, at least 13, at least 14, at least 15, at least 16, at least 17 at least 18 or at least 19 nucleobases in length and the SNP is complementary to positions 8-14 counting from the 5' terminus of the antisense oligonucleotide and/or positions 4-7 counting from the 5' end of the gap. In certain embodiments, the antisense oligonucleotide is at least 12, at least 13, at least 14, at least 15, at least 16, at least 17 at least 18 or at least 19 nucleobases in length and the SNP is complementary to positions 8-10 counting from the 5' terminus of the antisense oligonucleotide and/or positions 4-6 counting from the 5' end of the gap.

In certain embodiments, the SNP is complementary to position 8, 9, or 10 counting from the 5' terminus of the oligonucleotide or position 4, 5, or 6, counting from the 5' end of the gap. For oligonucleotides of various lengths, the effect of the length of the gap, 5' wing, and 3' wing was tested.

Certain wing-gap-wing combinations were shown to be beneficial for a SNP targeting antisense oligonucleotide. In certain embodiments the gap is 7-11 nucleobases in length and each wing is independently 1-6 nucleobases in length. In certain embodiments the gap is 7-11 nucleobases in length and each wing is independently 2-6 nucleobases in length. In certain embodiments the gap is 8-11 nucleobases in length and each wing is independently 2-6 nucleobases in length. In certain embodiments the gap is 9-11 nucleobases in length and each wing is independently 2-6 nucleobases in length. In certain embodiments the gap is 9 nucleobases in length and each wing is independently 2-6 nucleobases in length. In certain embodiments the gap is 10 nucleobases in length and each wing is independently 2-6 or 4-5 nucleobases in length. In certain embodiments the gap is 11 nucleobases in length and each wing is independently 2-6, or 4-5 nucleobases in length. In certain embodiments, the wing-gap-wing configuration is one of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5, 5-9-3, 5-9-4, 4-9-5, 5-9-5, 4-11-4, 4-10-5 and 5-10-4.

For oligonucleotides of various lengths, the effect of certain chemistries was tested. Certain chemistry modifications were shown to be beneficial for a SNP targeting antisense oligonucleotide. In certain embodiments, each nucleoside of each wing of the modified antisense oligonucleotide has a 2'-MOE modification. In certain embodiments, each nucleoside of each wing of the modified antisense oligonucleotide has a high affinity modification. In certain embodiments, the antisense oligonucleotide is a mixed wing gapmer. In such embodiment, the modifications and combination of modifications at the 3' wing and at the 5' wing may be the same or they may be different. In certain embodiments, the antisense oligonucleotide has one or more 2'-MOE modifications in the wings and/or one or more high affinity modifications in the wings. In certain embodiments, the high affinity modification is a cEt modification. In certain embodiments, the antisense oligonucleotide has a high affinity modification at positions 2, 3, 13, and 14 of the antisense oligonucleotide (counting from the 5' terminus). In certain embodiments, the antisense oligonucleotide has one, two, three, or four high affinity modifications in at least one of the wings. In certain embodiments, the antisense oligonucleotide has one, two, three, or four high affinity modifications in each of the 5' and 3' wings independently. In certain embodiments, the antisense oligonucleotide has a high affinity modification at positions 2 and 3 in one or both of the 5' and 3' wings (counting from the 5' terminus of the 5' wing and the 3' terminus of the 3' wing). In certain embodiments, the antisense oligonucleotide has a high affinity modification at positions 2, 3 and 4 in one or both of the 5' and 3' wings (counting from the 5' terminus of the 5' wing and the 3' terminus of the 3' wing). In certain embodiments, the antisense oligonucleotide has a high affinity modification at positions 1 of the 5' and/or 3' wings (counting from the 5' terminus of the 5' wing and the 3' terminus of the 3' wing). In certain embodiments, the antisense oligonucleotide has a high affinity modification at positions 1 of the 5' and 3' wings (counting from the 5' terminus of the 5' wing and the 3' terminus of the 3' wing) and at least one other position in the wing. In certain embodiments, the antisense oligonucleotide has alternating 2'-MOE and high affinity modification in at least one of the 5' and 3' wings.

In certain embodiments, the compound comprises an antisense oligonucleotide incorporating one or more of the design rules provided above.

In certain embodiments, the compound comprises a modified antisense oligonucleotide consisting of 12 to 30 linked nucleosides, fully complementary to a single nucleotide polymorphism site, wherein the modified antisense oligonucleotide comprises a wing-gap-wing motif, wherein the single nucleotide polymorphism aligns with any one of positions 6-15 beginning from the 5' terminus of the antisense oligonucleotide or positions 1-9 beginning from the 5' end of the gap of the modified antisense oligonucleotide; and wherein each nucleoside of each wing has a modified sugar or sugar surrogate. In certain embodiments the single nucleotide polymorphism site contains a differentiating polymorphism. In certain embodiments, the single nucleotide polymorphism site is on a mutant allele. In certain embodiments, the mutant allele is associated with disease. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 12 to 20 linked nucleosides, fully complementary to a single nucleotide polymorphism site, wherein the modified antisense oligonucleotide comprises a wing-gap-wing motif, wherein the single nucleotide polymorphism aligns with any one of positions 6-15 beginning from the 5' terminus of the antisense oligonucleotide or positions 1-9 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 12 to 20 linked nucleosides, fully complementary to a single nucleotide polymorphism site, wherein the modified antisense oligonucleotide comprises a wing-gap-wing motif, wherein the single nucleotide polymorphism aligns with any one of positions 8-14 beginning from the 5' terminus of the antisense oligonucleotide or positions 1-9 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 12 to 20 linked nucleosides, fully complementary to a single nucleotide polymorphism site, wherein the modified antisense oligonucleotide comprises a wing-gap-wing motif, wherein the single nucleotide polymorphism aligns with any one of positions 8-14 beginning from the 5' terminus of the antisense oligonucleotide or positions 4-7 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 12 to 20 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 12 to 19 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 13 to 19 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 14 to 19 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein the single nucleotide polymorphism aligns with any one of positions 6-15 beginning from the 5' terminus of the antisense oligonucleotide or positions 1-9 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein the single nucleotide polymorphism aligns with any one of positions 8-10 beginning from the 5' terminus of the antisense oligonucleotide or positions 4-6 beginning from the 5' end of the gap of the modified antisense oligonucleotide; and wherein each nucleoside of each wing has a modified sugar or sugar surrogate. In certain embodiments, the wing-gap-wing motif is any one of the group consisting of 4-7-4, 5-8-6, 6-8-5, 6-7-6, 5-7-5, 6-8-5, 5-8-6, 3-9-4, 4-9-3, 2-9-6, 6,9,2,3-9-3, 3-9-5,5-9-3, 5-9-4, 4-9-5, 5-9-5, 4-11-4,4-10-5 and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein position 6, 8, 9, 10, 11, or 14 beginning from the 5' terminus of the modified antisense oligonucleotide aligns with the single nucleotide polymorphism; and wherein each nucleoside of each wing segment modified sugar or sugar surrogate. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein position 1, 4, 5, 6, 7, or 9 of the gap segment aligns with the single nucleotide polymorphism; and wherein each nucleoside of each wing segment has a modified sugar or sugar surrogate. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 15 to 19 linked nucleosides, fully complementary to a single nucleotide polymorphism site, wherein the modified antisense oligonucleotide comprises a wing-gap-wing motif, wherein position 6, 7, 8, 9, 10, 11, or 12 of the modified antisense oligonucleotide aligns with the single nucleotide polymorphism; and positions 2 and 3 of the 5' and 3' wing segments comprise a 4'-$CH(CH_3)$—O-2' bridge. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 15 to 19 linked nucleosides and fully complementary to a single nucleotide polymorphism site, wherein the modified antisense oligonucleotide comprises a wing-gap-wing motif, wherein position 3, 4, 5, 6, 7, 8 or 9 of the gap segment aligns with the single nucleotide polymorphism; and positions 2 and 3 of the 5' and 3' wing segments comprise a 4'-$CH(CH_3)$—O-2' bridge. In certain embodiments, the wing-gap-wing motif is any one of the group consisting of 2-9-6, 3-9-3, 3-9-5, 4-9-5, 4-11-4, and 5-10-4.

A compound comprising a modified antisense oligonucleotide consisting of 15 to 19 linked nucleosides and fully complementary to a single nucleotide polymorphism site, wherein the modified antisense oligonucleotide comprises a wing-gap-wing motif, wherein position 6, 7, 8, 9, 10, 11, or 12 of the modified antisense oligonucleotide aligns with the single nucleotide polymorphism; and positions 2, 3, 13, and 14 of the antisense oligonucleotide comprise a 4'-CH ($CH_3$)—O-2' bridge. In certain embodiments, the wing-gap-wing motif is any one of the group consisting of 2-9-6, 3-9-3, 3-9-5, 4-9-5, 4-11-4, and 5-10-4.

A compound comprising a modified antisense oligonucleotide consisting of 15 to 19 linked nucleosides and fully complementary to a single nucleotide polymorphism site, wherein the modified antisense oligonucleotide comprises a wing-gap-wing motif, wherein position 3, 4, 5, 6, 7, 8, or 9 of the gap segment aligns with the single nucleotide polymorphism; and positions 2, 3, 13, and 14 of the antisense oligonucleotide comprise a 4'-$CH(CH_3)$—O-2' bridge. In certain embodiments, the wing-gap-wing motif is any one of the group consisting of 2-9-6, 3-9-3, 3-9-5, 4-9-5, 4-11-4, and 5-10-4.

In certain embodiments, the compound comprise a modified antisense oligonucleotide consisting of 17 to 19 linked nucleosides, fully complementary to a single nucleotide polymorphism site, wherein the modified antisense oligonucleotide comprises a wing-gap-wing motif, wherein position 8, 9, or 10 of the modified antisense oligonucleotide aligns with the single nucleotide polymorphism; and wherein each nucleoside of each wing segment comprises a 2'-O-methoxyethyl sugar. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 17 to 19 linked nucleosides, fully complementary to a single nucleotide polymorphism site, wherein the modified antisense oligonucleotide comprises a wing-gap-wing motif, wherein position 5, 6, or 7 of the gap segment aligns with the single nucleotide polymorphism; and wherein each nucleoside of each wing segment comprises a 2'-O-methoxyethyl sugar. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 17 to 19 linked nucleosides, fully complementary to a single nucleotide polymorphism site, wherein the modified antisense oligonucleotide comprises a wing-gap-wing motif, wherein position 8, 9, or 10 of the modified antisense oligonucleotide aligns with the single nucleotide polymorphism; and positions 2 and 3 of the 5' and 3' wing segments comprise a 4'-$CH(CH_3)$—O-2' bridge. In certain embodiments, the wing-gap-wing motif is any one of the group consisting of 2-9-6, 3-9-3, 3-9-5, 4-9-5, 4-11-4, and 5-10-4.

In certain embodiments, the compound comprises a modified antisense oligonucleotide consisting of 17 to 19 linked nucleosides and fully complementary to a single nucleotide polymorphism site, wherein the modified antisense oligonucleotide comprises a wing-gap-wing motif, wherein position 5, 6, or 7 of the gap segment aligns with the single nucleotide polymorphism; and positions 2 and 3 of the 5' and 3' wing segments comprise a 4'-$CH(CH_3)$—O-2' bridge. In certain embodiments, the wing-gap-wing motif is any one of the group consisting of 2-9-6, 3-9-3, 3-9-5, 4-9-5, 4-11-4, and 5-10-4.

A compound comprising a modified antisense oligonucleotide consisting of 17 to 19 linked nucleosides and fully complementary to a single nucleotide polymorphism site, wherein the modified antisense oligonucleotide comprises a wing-gap-wing motif, wherein position 8, 9, or 10 of the modified oligonucleotide aligns with the single nucleotide polymorphism; and positions 2, 3, 13, and 14 of the antisense oligonucleotide comprise a 4'-$CH(CH_3)$—O-2' bridge. In certain embodiments, the wing-gap-wing motif is any one of the group consisting of 2-9-6, 3-9-3, 3-9-5, 4-9-5, 4-11-4, and 5-10-4.

A compound comprising a modified antisense oligonucleotide consisting of 17 to 19 linked nucleosides and fully complementary to a single nucleotide polymorphism site, wherein the modified antisense oligonucleotide comprises a wing-gap-wing motif, wherein position 5, 6, or 7 of the gap segment aligns with the single nucleotide polymorphism; and positions 2, 3, 13, and 14 of the antisense oligonucleotide comprise a 4'-$CH(CH_3)$—O-2' bridge. In certain embodiments, the wing-gap-wing motif is any one of the group consisting of 2-9-6, 3-9-3, 3-9-5, 4-9-5, 4-11-4, and 5-10-4.

In a certain embodiment, the antisense oligonucleotide is 11 to 20 linked nucleosides in length and has, independently, 2 to 5 linked nucleosides in the 5' and 3' wings and 7 to 11 linked nucleosides in the gap. The SNP is complementary to position 5, 6, 7, 8, 9, 10, 11, 12, 13, or 14 of the antisense oligonucleotide (counting from the 5' terminus of the antisense oligonucleotide) or position 1, 2, 3, 4, 5, 6, 7, 8, 9, or 10 counting from the 5' terminus of the gap segment.

In a certain embodiment, the antisense oligonucleotide is 15 to 19 linked nucleosides in length and has, independently, 2 to 5 linked nucleosides in the 5' and 3' wings and 7 to 11 linked nucleosides in the gap. The SNP is complementary to position 6, 7, 8, 9, or 10 of the antisense oligonucleotide (counting from the 5' terminus of the antisense oligonucleotide) or position 4, 5, 6, or 7 counting from the 5' terminus of the gap segment.

In a certain embodiment, the antisense oligonucleotide is 17 linked nucleosides in length and has, independently, 2 to 5 linked nucleosides in the 5' and 3' wing segments and 9 to 11 linked nucleosides in the gap segment. The SNP is complementary to position 8, 9, or 10 of the antisense oligonucleotide (counting from the 5' terminus of the antisense oligonucleotide) or position 5, 6, or 7 (counting from the 5' terminus of the gap segment).

In a certain embodiment, the antisense oligonucleotide is 18 linked nucleosides in length and has, independently, 2 to 5 linked nucleosides in the 5' and 3' wing segments and 9 to 11 linked nucleosides in the gap segment. The SNP is complementary to position 8, 9, or 10 of the antisense oligonucleotide (counting from the 5' terminus of the antisense oligonucleotide) or position 5, 6, or 7 (counting from the 5' terminus of the gap segment).

In a certain embodiment, the antisense oligonucleotide is 19 linked nucleosides in length and has, independently, 2 to 5 linked nucleosides in the 5' and 3' wing segments and 9 to 11 linked nucleosides in the gap segment. The SNP is complementary to position 8, 9, or 10 of the antisense oligonucleotide (counting from the 5' terminus of the antisense oligonucleotide) or position 5, 6, or 7 (counting from the 5' terminus of the gap segment).

In certain embodiments, the invention provides methods of treating an individual comprising administering one or more pharmaceutical compositions described herein. In certain embodiments, the individual has an allelic variant associated with a disease or disorder. The pharmaceutical compositions provided herein preferentially target a SNP. In certain embodiments, the SNP is a differentiating polymorphism.

Methods have been described for determining whether a SNP is specific to a disease associated allele and more specifically whether a SNP variant of an allele of a heterozygous patient is on the same allele as a disease-causing mutation that is at a remote region of the gene's mRNA (WO 2008/147930 and WO 2008/143774).

Diseases associated with SNPs have been described for certain genes. In certain embodiments, the gene and associated disease are any of the following: APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci.

2008, 105: 4533); CCLS gene encoding the chemokine CCLS involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHMP4B gene encoding chromatin modifying protein-4B involved in progressive childhood posterior subcapsular cataracts (Am. J. Hum. Genet 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry 2006, 11: 76); TGF-beta1 gene encoding TGF-beta1 protein involved in breast cancer and prostate cancer (Cancer Epidemiol. Biomarkers Prev. 2004, 13: 759); AChR gene encoding acetylcholine receptor involved in congenital myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Gene.t 2010, 19: 671); SCA3 gene encoding ataxin-3 protein involved in Machado-Joseph disease (PLoS One 2008, 3: e3341); SCAT gene encoding ataxin-7 protein involved in spino-cerebellar ataxia-7 (PLoS One 2009, 4: e7232); HTT gene encoding huntingtin protein involved in Huntington's disease (Neurobiol Dis. 1996, 3:183); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med Biol. 2008, 613:203)

In certain embodiments, the disease is a neurodegenerative disorder. In certain embodiments, the neurodegenerative disorder is Huntington's Disease. In certain embodiments, the targeted SNP is one or more of: rs6446723, rs3856973, rs2285086, rs363092, rs916171, rs6844859, rs7691627, rs4690073, rs2024115, rs11731237, rs362296, rs10015979, rs7659144, rs363096, rs362273, rs16843804, rs362271, rs362275, rs3121419, rs362272, rs3775061, rs34315806, rs363099, rs2298967, rs363088, rs363064, rs363102, rs2798235, rs363080, rs363072, rs363125, rs362303, rs362310, rs10488840, rs362325, rs35892913, rs363102, rs363096, rs11731237, rs10015979, rs363080, rs2798235, rs1936032, rs2276881, rs363070, rs35892913, rs12502045, rs6446723, rs7685686, rs3733217, rs6844859, rs362331, rs1143646, rs2285086, rs2298969, rs4690072, rs916171, rs3025849, rs7691627, rs4690073, rs3856973, rs363092, rs362310, rs362325, rs363144, rs362303, rs34315806, rs363099, rs363081, rs3775061, rs2024115, rs10488840, rs363125, rs362296, rs2298967, rs363088, rs363064, rs362275, rs3121419, rs3025849, rs363070, rs362273, rs362272, rs362306, rs362271, rs363072, rs16843804, rs7659144, rs363120, and rs12502045. In certain embodiments the compounds are ISIS460065, ISIS 459978, ISIS 460028, ISIS 460209, ISIS 460208, and ISIS 460206.

Therapeutically Effective Dosages

In certain embodiments, administration of a therapeutically effective amount of an antisense compound targeted to the mutant huntingtin allele is accompanied by monitoring of expression of a gene product in an individual, to determine an individual's response to administration of the antisense compound. In certain embodiments, the gene product is huntingtin mRNA or protein. An individual's response to administration of the antisense compound is used by a physician to determine the amount and duration of therapeutic intervention.

In certain embodiments, administration of an antisense compound targeted to a mutant nucleic acid results in reduction of mRNA or protein expression by at least 15, 20, 25, 30, 35, 40, 45, 50, 55, 60, 65, 70, 75, 80, 85, 90, 95 or 99%, or a range defined by any two of these values. In certain embodiments, the mutant nucleic acid is huntingtin nucleic acid, the mRNA is huntingtin mRNA, and the protein is huntingtin protein.

In certain embodiments, pharmaceutical compositions comprising an antisense compound targeted to a mutant allele are used for the preparation of a medicament for treating a patient suffering or susceptible to any of Huntington's Disease, Alzheimer's Disease, Crutzfeldt-Jakob Disease, Fatal Familial Insomnia, Huntington's Disease, Alexander Disease, Parkinson's Disease, Amyotrophic Lateral Sclerosis (ALS), Dentato-Rubral and Pallido-Luysian Atrophy, Spino-Cerebellar Ataxia 1, Pelizaeus-Merzbacher Disease, Torsion Dystonia, Cardiomyopathy, Chronic Obstructive Pulmonary Disease (COPD), liver disease and hepatocellular carcinoma, SLE, Hypercholesterolemia, breast tumors, Asthma, Type 1 Diabetes, Rheumatoid Arthritis, Graves Disease, Spinal and Bulbar Muscular Atrophy, Kennedy's Disease, progressive childhood posterior subcapsular cataracts, Cholesterol Gallstone Disease, Arthrosclerosis, cardiovascular disease, primary hypercalciuria, alpha-thallasemia, OCD, stress-related disorders (including anxiety disorders and comorbid depression), congenital visual defects, hypertension, metabolic syndrome, major depression, breast cancer, prostate cancer, congenital myasthenic syndrome, peripheral arterial syndrome, atrial fibrillation, sporadic pheochromocytoma, congenital malformations, NJD, SCAT, and autosomal dominant retinitis pigmentosa adRP.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions of the present invention. In certain embodiments, such one or more other pharmaceutical agents are designed to treat a different disease, disorder, or condition as the one or more pharmaceutical compositions of the present invention. In certain embodiments, such one or more other pharmaceutical agents are designed to treat an undesired side effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention are co-administered with another pharmaceutical agent to produce a combinational effect. In certain embodiments, one or more pharmaceutical compositions of the present invention are co-administered with another pharmaceutical agent to produce a synergistic effect.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the patents, applications, printed publications, and other published documents mentioned or referred to in this specification are herein incorporated by reference in their entirety.

Example 1: Single Nucleotide Polymorphisms (SNPs) in the Huntingtin (HTT) Gene Sequence The HTT genomic sequence, designated herein as SEQ ID NO: 1 (NT_006081.18 truncated from nucleotides 1566000 to 1768000) was aligned with the HTT mRNA, designated herein as SEQ ID NO: 2 (NM_002111.6), using the EMBL-EBI sequence database (ClustalW2, http://www.ebi.ac.uk/Tools/clustalw2/index.html), and the output is presented in FIG. 1. SNP positions (identified by Hayden et al, WO/2009/135322) associated with the HTT gene were mapped to the two sequences and have been demarcated in FIG. 1 by their reference SNP ID number from the Entrez SNP database at the National Center for Biotechnology Information (NCBI, http://www.ncbi.nlm.nih.gov/sites/entrez?db=snp), incorporated herein by reference. Table 2 furnishes further details on each SNP. The 'Reference SNP ID number' or 'RS number' is the number designated to each SNP from the Entrez SNP database at NCBI, incorporated herein by reference. 'SNP position' refers to the nucleotide position of the SNP on SEQ ID NO: 1. 'Polymorphism' indicates the nucleotide variants at that SNP position. 'Major allele' indicates the nucleotide associated with the major allele, or the nucleotide present in a statistically significant proportion of individuals in the human population. 'Minor allele' indicates the nucleotide associated with the minor allele, or the nucleotide present in a relatively small proportion of individuals in the human population.

TABLE 2

Single Nuclear Polymorphisms (SNPs) and their positions on SEQ ID NO: 1

| RS No. | SNP position | Polymorphism | Major allele | Minor allele |
|---|---|---|---|---|
| rs2857936 | 1963 | C/T | C | T |
| rs12506200 | 3707 | A/G | G | A |
| rs762855 | 14449 | A/G | G | A |
| rs3856973 | 19826 | G/A | G | A |
| rs2285086 | 28912 | G/A | A | G |
| rs7659144 | 37974 | C/G | C | G |
| rs16843804 | 44043 | C/T | C | T |
| rs2024115 | 44221 | G/A | A | G |
| rs10015979 | 49095 | A/G | A | G |
| rs7691627 | 51063 | A/G | G | A |
| rs2798235 | 54485 | G/A | G | A |
| rs4690072 | 62160 | G/T | T | G |
| rs6446723 | 66466 | C/T | T | C |
| rs363081 | 73280 | G/A | G | A |
| rs363080 | 73564 | T/C | C | T |
| rs363075 | 77327 | G/A | G | A |
| rs363064 | 81063 | T/C | C | T |
| rs3025849 | 83420 | A/G | A | G |
| rs6855981 | 87929 | A/G | G | A |
| rs363102 | 88669 | G/A | A | G |
| rs11731237 | 91466 | C/T | C | T |
| rs4690073 | 99803 | A/G | G | A |
| rs363144 | 100948 | T/G | T | G |
| rs3025838 | 101099 | C/T | C | T |
| rs34315806 | 101687 | A/G | G | A |
| rs363099 | 101709 | T/C | C | T |
| rs363096 | 119674 | T/C | T | C |
| rs2298967 | 125400 | C/T | T | C |
| rs2298969 | 125897 | A/G | G | A |
| rs6844859 | 130139 | C/T | T | C |
| rs363092 | 135682 | C/A | C | A |
| rs7685686 | 146795 | A/G | A | G |
| rs363088 | 149983 | A/T | A | T |
| rs362331 | 155488 | C/T | T | C |
| rs916171 | 156468 | G/C | C | G |
| rs362322 | 161018 | A/G | A | G |
| rs362275 | 164255 | T/C | C | T |
| rs362273 | 167080 | A/G | A | G |
| rs2276881 | 171314 | G/A | G | A |
| rs3121419 | 171910 | T/C | C | T |
| rs362272 | 174633 | G/A | G | A |
| rs362271 | 175171 | G/A | G | A |
| rs3775061 | 178407 | C/T | C | T |
| rs362310 | 179429 | A/G | G | A |
| rs362307 | 181498 | T/C | C | T |
| rs362306 | 181753 | G/A | G | A |
| rs362303 | 181960 | T/C | C | T |
| rs362296 | 186660 | C/A | C | A |
| rs1006798 | 198026 | A/G | A | G |

Example 2: Design of Antisense Oligonucleotides Targeting Huntingtin Gene SNPs and Inhibition of HTT mRNA in Coriell Fibroblast Cell Lines (GM04281, GM02171, and GM02173B)

Antisense oligonucleotides targeting nucleotides overlapping SNP positions presented in Table 1 were designed and tested for potency in three huntingtin patient-derived Coriell fibroblast cell lines, GM04281, GM02171, and GM02173B (from the Coriell Institute for Medical Research). Cultured GM04281 cells or GM02171 cells or GM02173B cells at a density of 20,000 cells per well were transfected using electroporation with 10,000 nM antisense oligonucleotide. After a treatment period of approximately 24 hours, RNA was isolated from the cells and HTT mRNA levels were measured by quantitative real time PCR using primer probe set RTS2617 (forward sequence CTCCGTCCGGTAGACATGCT, designated herein as SEQ ID NO: 3; reverse sequence GGAAATCAGAACCCTCAAAATGG, designated herein as SEQ ID NO: 4; probe sequence TGAGCACTGTTCAACTGTGGATATCGGGAX, designated herein as SEQ ID NO: 5). HTT mRNA levels were adjusted according to total RNA content, as measured by RIBOGREEN. Results are presented as percent inhibition of HTT mRNA, relative to untreated control cells.

ISIS 387916 (TCTCTATTGCACATTCCAAG, 5-10-5 MOE (SEQ ID NO: 6)) and ISIS 388816 (GCCGTAGCCTGGGACCCGCC, 5-10-5 MOE (SEQ ID NO: 7)) were included in each study as benchmark oligonucleotides against which the potency of the antisense oligonucleotides targeting nucleotides overlapping each SNP position could be compared.

The chimeric antisense oligonucleotides in Tables 3 and 4 were designed as 5-9-5 MOE gapmers. The gapmers are 19 nucleotides in length, wherein the central gap segment is comprised of nine 2'-deoxynucleotides and is flanked on both sides (in the 5' and 3' directions) by wings comprising five nucleotides each. Each nucleotide in the 5' wing segment and each nucleotide in the 3' wing segment has a 2'-MOE modification. The internucleoside linkages throughout each gapmer are phosphorothioate (P═S) linkages. All cytosine nucleobases throughout each gapmer are 5-methylcytosines.

The oligonucleotides are further described in Table 3. The percent inhibition of HTT mRNA by the antisense oligonucleotides in each cell line is shown in Table 4. ‘Target allele’ indicates whether the gapmer is targeted to the major or the minor allele at the SNP position. The number in parentheses indicates the nucleotide position in the gapmer opposite to the SNP position, starting from the 5'-terminus of the oligonucleotide. ‘Start site’ indicates the 5'-most nucleotide to which the gapmer is targeted. “Stop site” indicates the 3'-most nucleotide to which the gapmer is targeted. Each gapmer listed in Tables 3 and 4 is targeted to human HTT pre-mRNA, which is SEQ ID NO: 1.

TABLE 3

Chimeric oligonucleotides targeting SNP positions on the HTT gene

| ISIS No | SNP RS No. | Target allele | Sequence | Start Site | Stop Site | SEQ ID NO |
|---|---|---|---|---|---|---|
| 387916 | n/a | n/a | TCTCTATTGCACATTCCAAG | 145466 | 145485 | 6 |
| 388816 | n/a | n/a | GCCGTAGCCTGGGACCCGCC | 16501 | 16520 | 7 |
| 435330 | rs3856973 | Major (8) | TAACACTCGATTAACCCTG | 19815 | 19833 | 8 |
| 435348 | rs3856973 | Minor (8) | TAACACTTGATTAACCCTG | 19815 | 19833 | 9 |
| 435294 | rs3856973 | Major (10) | GTTAACACTCGATTAACCC | 19817 | 19835 | 10 |
| 435312 | rs3856973 | Minor (10) | GTTAACACTTGATTAACCC | 19817 | 19835 | 11 |
| 435864 | rs2285086 | Major (10) | GCTAGTTCATCCCAGTGAG | 28903 | 28921 | 12 |
| 435889 | rs2285086 | Minor (10) | GCTAGTTCACCCCAGTGAG | 28903 | 28921 | 13 |
| 435878 | rs7659144 | Major (10) | TGGAAATGGGTTTTTCCAC | 37965 | 37983 | 14 |
| 435903 | rs7659144 | Minor (10) | TGGAAATGGCTTTTTCCAC | 37965 | 37983 | 15 |
| 435863 | rs16843804 | Major (10) | TTTAACCGTGGCATGGGCA | 44034 | 44052 | 16 |
| 435888 | rs16843804 | Minor (10) | TTTAACCGTAGCATGGGCA | 44034 | 44052 | 17 |
| 435331 | rs2024115 | Major (8) | TTCAAGCTAGTAACGATGC | 44210 | 44228 | 18 |
| 435349 | rs2024115 | Minor (8) | TTCAAGCCAGTAACGATGC | 44210 | 44228 | 19 |
| 435295 | rs2024115 | Major (10) | ACTTCAAGCTAGTAACGAT | 44212 | 44230 | 20 |
| 435313 | rs2024115 | Minor (10) | ACTTCAAGCCAGTAACGAT | 44212 | 44230 | 21 |
| 435862 | rs10015979 | Major (10) | GCAGCTAGGTTAAAGAGTC | 49086 | 49104 | 22 |
| 435887 | rs10015979 | Minor (10) | GCAGCTAGGCTAAAGAGTC | 49086 | 49104 | 23 |
| 435880 | rs7691627 | Major (10) | AATAAGAAACACAATCAAA | 51054 | 51072 | 24 |

TABLE 3-continued

Chimeric oligonucleotides targeting SNP positions on the HTT gene

| ISIS No | SNP RS No. | Target allele | Sequence | Start Site | Stop Site | SEQ ID NO |
|---|---|---|---|---|---|---|
| 435905 | rs7691627 | Minor (10) | AATAAGAAATACAATCAAA | 51054 | 51072 | 25 |
| 435885 | rs2798235 | Major (10) | CAGAGGAGGCATACTGTAT | 54476 | 54494 | 26 |
| 435910 | rs2798235 | Minor (10) | CAGAGGAGGTATACTGTAT | 54476 | 54494 | 27 |
| 435874 | rs4690072 | Major (10) | CACAGTGCTACCCAACCTT | 62151 | 62169 | 28 |
| 435899 | rs4690072 | Minor (10) | CACAGTGCTCCCCAACCTT | 62151 | 62169 | 29 |
| 435875 | rs6446723 | Major (10) | TAATTTTCTAGACTTTATG | 66457 | 66475 | 30 |
| 435900 | rs6446723 | Minor (10) | TAATTTTCTGGACTTTATG | 66457 | 66475 | 31 |
| 435332 | rs363081 | Major (8) | GCTACAACGCAGGTCAAAT | 73269 | 73287 | 32 |
| 435350 | rs363081 | Minor (8) | GCTACAATGCAGGTCAAAT | 73269 | 73287 | 33 |
| 435296 | rs363081 | Major (10) | GAGCTACAACGCAGGTCAA | 73271 | 73289 | 34 |
| 435314 | rs363081 | Minor (10) | GAGCTACAATGCAGGTCAA | 73271 | 73289 | 35 |
| 435886 | rs363080 | Major (10) | AGAGAGAACGAGAAGGCTC | 73555 | 73573 | 36 |
| 435911 | rs363080 | Minor (10) | AGAGAGAACAAGAAGGCTC | 73555 | 73573 | 37 |
| 435914 | rs363075 | Major (6) | AGCCCCTCTGTGTAAGTTT | 77314 | 77332 | 38 |
| 435926 | rs363075 | Minor (6) | AGCCCTTCTGTGTAAGTTT | 77314 | 77332 | 39 |
| 435916 | rs363075 | Major (7) | GAGCCCCTCTGTGTAAGTT | 77315 | 77333 | 40 |
| 435928 | rs363075 | Minor (7) | GAGCCCTTCTGTGTAAGTT | 77315 | 77333 | 41 |
| 435333 | rs363075 | Major (8) | TGAGCCCCTCTGTGTAAGT | 77316 | 77334 | 42 |
| 435351 | rs363075 | Minor (8) | TGAGCCCTTCTGTGTAAGT | 77316 | 77334 | 43 |
| 435918 | rs363075 | Major (9) | ATGAGCCCCTCTGTGTAAG | 77317 | 77335 | 44 |
| 435930 | rs363075 | Minor (9) | ATGAGCCCTTCTGTGTAAG | 77317 | 77335 | 45 |
| 435297 | rs363075 | Major (10) | GATGAGCCCCTCTGTGTAA | 77318 | 77336 | 46 |
| 435315 | rs363075 | Minor (10) | GATGAGCCCTTCTGTGTAA | 77318 | 77336 | 47 |
| 435920 | rs363075 | Major (11) | TGATGAGCCCCTCTGTGTA | 77319 | 77337 | 48 |
| 435932 | rs363075 | Minor (11) | TGATGAGCCCTTCTGTGTA | 77319 | 77337 | 49 |
| 435366 | rs363075 | Major (12) | ATGATGAGCCCCTCTGTGT | 77320 | 77338 | 50 |
| 435924 | rs363075 | Minor (12) | ATGATGAGCCCTTCTGTGT | 77320 | 77338 | 51 |
| 435922 | rs363075 | Major (14) | TAATGATGAGCCCCTCTGT | 77322 | 77340 | 52 |
| 435934 | rs363075 | Minor (14) | TAATGATGAGCCCTTCTGT | 77322 | 77340 | 53 |
| 435334 | rs363064 | Major (8) | AGAATACGGGTAACATTTT | 81052 | 81070 | 54 |
| 435352 | rs363064 | Minor (8) | AGAATACAGGTAACATTTT | 81052 | 81070 | 55 |
| 435298 | rs363064 | Major (10) | GGAGAATACGGGTAACATT | 81054 | 81072 | 56 |
| 435316 | rs363064 | Minor (10) | GGAGAATACAGGTAACATT | 81054 | 81072 | 57 |
| 435335 | rs3025849 | Major (8) | TTAGTAATCAATTTTAATG | 83409 | 83427 | 58 |
| 435353 | rs3025849 | Minor (8) | TTAGTAACCAATTTTAATG | 83409 | 83427 | 59 |
| 435299 | rs3025849 | Major (10) | AGTTAGTAATCAATTTTAA | 83411 | 83429 | 60 |
| 435317 | rs3025849 | Minor (10) | AGTTAGTAACCAATTTTAA | 83411 | 83429 | 61 |

TABLE 3-continued

Chimeric oligonucleotides targeting SNP positions on the HTT gene

| ISIS No | SNP RS No. | Target allele | Sequence | Start Site | Stop Site | SEQ ID NO |
|---|---|---|---|---|---|---|
| 435877 | rs6855981 | Major (10) | GAAGGAATGCTTTTACTAG | 87920 | 87938 | 62 |
| 435902 | rs6855981 | Minor (10) | GAAGGAATGTTTTTACTAG | 87920 | 87938 | 63 |
| 435336 | rs363102 | Major (8) | CTAAAACTAACTTGAGAAT | 88658 | 88676 | 64 |
| 435354 | rs363102 | Minor (8) | CTAAAACCAACTTGAGAAT | 88658 | 88676 | 65 |
| 435300 | rs363102 | Major (10) | ATCTAAAACTAACTTGAGA | 88660 | 88678 | 66 |
| 435318 | rs363102 | Minor (10) | ATCTAAAACCAACTTGAGA | 88660 | 88678 | 67 |
| 435884 | rs11731237 | Major (10) | GGTGGGCAGGAAGGACTGA | 91457 | 91475 | 68 |
| 435909 | rs11731237 | Minor (10) | GGTGGGCAGAAAGGACTGA | 91457 | 91475 | 69 |
| 435337 | rs4690073 | Major (8) | CCTAAATCAATCTACAAGT | 99792 | 99810 | 70 |
| 435355 | rs4690073 | Minor (8) | CCTAAATTAATCTACAAGT | 99792 | 99810 | 71 |
| 435301 | rs4690073 | Major (10) | TCCCTAAATCAATCTACAA | 99794 | 99812 | 72 |
| 435319 | rs4690073 | Minor (10) | TCCCTAAATTAATCTACAA | 99794 | 99812 | 73 |
| 435883 | rs363144 | Major (10) | GAAAATGTGAGTGGATCTA | 100939 | 100957 | 74 |
| 435908 | rs363144 | Minor (10) | GAAAATGTGCGTGGATCTA | 100939 | 100957 | 75 |
| 435338 | rs3025838 | Major (8) | GTAAGGCGAGACTGACTAG | 101088 | 101106 | 76 |
| 435356 | rs3025838 | Minor (8) | GTAAGGCAAGACTGACTAG | 101088 | 101106 | 77 |
| 435302 | rs3025838 | Major (10) | AGGTAAGGCGAGACTGACT | 101090 | 101108 | 78 |
| 435320 | rs3025838 | Minor (10) | AGGTAAGGCAAGACTGACT | 101090 | 101108 | 79 |
| 435339 | rs363099 | Major (8) | CTGAGCGGAGAAACCCTCC | 101698 | 101716 | 80 |
| 435357 | rs363099 | Minor (8) | CTGAGCGAAGAAACCCTCC | 101698 | 101716 | 81 |
| 435303 | rs363099 | Major (10) | GGCTGAGCGGAGAAACCCT | 101700 | 101718 | 82 |
| 435321 | rs363099 | Minor (10) | GGCTGAGCGAAGAAACCCT | 101700 | 101718 | 83 |
| 435367 | rs363099 | Major (12) | AAGGCTGAGCGGAGAAACC | 101702 | 101720 | 84 |
| 435340 | rs363096 | Major (8) | TTCCCTAAAAACAAAAACA | 119663 | 119681 | 85 |
| 435358 | rs363096 | Minor (8) | TTCCCTAGAAACAAAAACA | 119663 | 119681 | 86 |
| 435304 | rs363096 | Major (10) | GATTCCCTAAAAACAAAAA | 119665 | 119683 | 87 |
| 435322 | rs363096 | Minor (10) | GATTCCCTAGAAACAAAAA | 119665 | 119683 | 88 |
| 435341 | rs2298967 | Major (8) | CTTTTCTATTGTCTGTCCC | 125389 | 125407 | 89 |
| 435359 | rs2298967 | Minor (8) | CTTTTCTGTTGTCTGTCCC | 125389 | 125407 | 90 |
| 435305 | rs2298967 | Major (10) | TGCTTTTCTATTGTCTGTC | 125391 | 125409 | 91 |
| 435323 | rs2298967 | Minor (10) | TGCTTTTCTGTTGTCTGTC | 125391 | 125409 | 92 |
| 435865 | rs2298969 | Major (10) | AAGGGATGCCGACTTGGGC | 125888 | 125906 | 93 |
| 435890 | rs2298969 | Minor (10) | AAGGGATGCTGACTTGGGC | 125888 | 125906 | 94 |
| 435876 | rs6844859 | Major (10) | ACCTTCCTCACTGAGGATG | 130130 | 130148 | 95 |
| 435901 | rs6844859 | Minor (10) | ACCTTCCTCGCTGAGGATG | 130130 | 130148 | 96 |
| 435872 | rs363092 | Major (10) | CAAACCACTGTGGGATGAA | 135673 | 135691 | 97 |
| 435897 | rs363092 | Minor (10) | CAAACCACTTTGGGATGAA | 135673 | 135691 | 98 |

TABLE 3-continued

| Chimeric oligonucleotides targeting SNP positions on the HTT gene | | | | | | |
|---|---|---|---|---|---|---|
| ISIS No | SNP RS No. | Target allele | Sequence | Start Site | Stop Site | SEQ ID NO |
| 435879 | rs7685686 | Major (10) | AATAAATTGTCATCACCAG | 146786 | 146804 | 99 |
| 435904 | rs7685686 | Minor (10) | AATAAATTGCCATCACCAG | 146786 | 146804 | 100 |
| 435871 | rs363088 | Major (10) | TCACAGCTATCTTCTCATC | 149974 | 149992 | 101 |
| 435896 | rs363088 | Minor (10) | TCACAGCTAACTTCTCATC | 149974 | 149992 | 102 |
| 435870 | rs362331 | Major (10) | GCACACAGTAGATGAGGGA | 155479 | 155497 | 103 |
| 435895 | rs362331 | Minor (10) | GCACACAGTGGATGAGGGA | 155479 | 155497 | 104 |
| 435881 | rs916171 | Major (10) | CAGAACAAAGAGAAGAATT | 156459 | 156477 | 105 |
| 435906 | rs916171 | Minor (10) | CAGAACAAACAGAAGAATT | 156459 | 156477 | 106 |
| 435342 | rs362322 | Major (8) | GCTTACATGCCTTCAGTGA | 161007 | 161025 | 107 |
| 435360 | rs362322 | Minor (8) | GCTTACACGCCTTCAGTGA | 161007 | 161025 | 108 |
| 435306 | rs362322 | Major (10) | CAGCTTACATGCCTTCAGT | 161009 | 161027 | 109 |
| 435324 | rs362322 | Minor (10) | CAGCTTACACGCCTTCAGT | 161009 | 161027 | 110 |
| 435868 | rs362275 | Major (10) | AAGAAGCCTGATAAAATCT | 164246 | 164264 | 111 |
| 435893 | rs362275 | Minor (10) | AAGAAGCCTAATAAAATCT | 164246 | 164264 | 112 |
| 435343 | rs2276881 | Major (8) | CATACATCAGCTCAAACTG | 171303 | 171321 | 113 |
| 435361 | rs2276881 | Minor (8) | CATACATTAGCTCAAACTG | 171303 | 171321 | 114 |
| 435307 | rs2276881 | Major (10) | CACATACATCAGCTCAAAC | 171305 | 171323 | 115 |
| 435325 | rs2276881 | Minor (10) | CACATACATTAGCTCAAAC | 171305 | 171323 | 116 |
| 435368 | rs2276881 | Major (12) | GTCACATACATCAGCTCAA | 171307 | 171325 | 117 |
| 435866 | rs3121419 | Major (10) | GAGACTATAGCACCCAGAT | 171901 | 171919 | 118 |
| 435891 | rs3121419 | Minor (10) | GAGACTATAACACCCAGAT | 171901 | 171919 | 119 |
| 435344 | rs362272 | Major (8) | TAGAGGACGCCGTGCAGGG | 174622 | 174640 | 120 |
| 435362 | rs362272 | Minor (8) | TAGAGGATGCCGTGCAGGG | 174622 | 174640 | 121 |
| 435308 | rs362272 | Major (10) | CATAGAGGACGCCGTGCAG | 174624 | 174642 | 122 |
| 435326 | rs362272 | Minor (10) | CATAGAGGATGCCGTGCAG | 174624 | 174642 | 123 |
| 435369 | rs62272 | Major (12) | CACATAGAGGACGCCGTGC | 174626 | 174644 | 124 |
| 435867 | rs3 62271 | Major (10) | ACGTGTGTACAGAACCTGC | 175162 | 175180 | 125 |
| 435892 | rs362271 | Minor (10) | ACGTGTGTATAGAACCTGC | 175162 | 175180 | 126 |
| 435873 | rs3775061 | Major (10) | TGTTCAGAATGCCTCATCT | 178398 | 178416 | 127 |
| 435898 | rs3775061 | Minor (10) | TGTTCAGAACGCCTCATCT | 178398 | 178416 | 128 |
| 435345 | rs362310 | Major (8) | AAACGGCGCAGCGGGAAGG | 179418 | 179436 | 129 |
| 435363 | rs362310 | Minor (8) | AAACGGCACAGCGGGAAGG | 179418 | 179436 | 130 |
| 435309 | rs362310 | Major (10) | AGAAACGGCGCAGCGGGAA | 179420 | 179438 | 131 |
| 435327 | rs362310 | Minor (10) | AGAAACGGCACAGCGGGAA | 179420 | 179438 | 132 |
| 435915 | rs362307 | Major (6) | AGGGCGCAGACTTCCAAAG | 181485 | 181503 | 133 |
| 435927 | rs362307 | Minor (6) | AGGGCACAGACTTCCAAAG | 181485 | 181503 | 134 |
| 435917 | rs362307 | Major (7) | AAGGGCGCAGACTTCCAAA | 181486 | 181504 | 135 |

TABLE 3-continued

| Chimeric oligonucleotides targeting SNP positions on the HTT gene | | | | | | |
|---|---|---|---|---|---|---|
| ISIS No | SNP RS No. | Target allele | Sequence | Start Site | Stop Site | SEQ ID NO |
| 435929 | rs362307 | Minor (7) | AAGGGCACAGACTTCCAAA | 181486 | 181504 | 136 |
| 435346 | rs362307 | Major (8) | CAAGGGCGCAGACTTCCAA | 181487 | 181505 | 137 |
| 435364 | rs362307 | Minor (8) | CAAGGGCACAGACTTCCAA | 181487 | 181505 | 138 |
| 435919 | rs362307 | Major (9) | ACAAGGGCGCAGACTTCCA | 181488 | 181506 | 139 |
| 435931 | rs362307 | Minor (9) | ACAAGGGCACAGACTTCCA | 181488 | 181506 | 140 |
| 435310 | rs362307 | Major (10) | CACAAGGGCGCAGACTTCC | 181489 | 181507 | 141 |
| 435328 | rs362307 | Minor (10) | CACAAGGGCACAGACTTCC | 181489 | 181507 | 142 |
| 435921 | rs362307 | Major (11) | GCACAAGGGCGCAGACTTC | 181490 | 181508 | 143 |
| 435933 | rs362307 | Minor (11) | GCACAAGGGCACAGACTTC | 181490 | 181508 | 144 |
| 435370 | rs362307 | Major (12) | GGCACAAGGGCGCAGACTT | 181491 | 181509 | 145 |
| 435925 | rs362307 | Minor (12) | GGCACAAGGGCACAGACTT | 181491 | 181509 | 146 |
| 435923 | rs362307 | Major (14) | AGGGCACAAGGGCGCAGAC | 181493 | 181511 | 147 |
| 435935 | rs362307 | Minor (14) | AGGGCACAAGGGCACAGAC | 181493 | 181511 | 148 |
| 435869 | rs362306 | Major (10) | GAGCAGCTGCAACCTGGCA | 181744 | 181762 | 149 |
| 435894 | rs362306 | Minor (10) | GAGCAGCTGTAACCTGGCA | 181744 | 181762 | 150 |
| 435347 | rs362303 | Major (8) | TGGTGCCGGGTGTCTAGCA | 181949 | 181967 | 151 |
| 435365 | rs362303 | Minor (8) | TGGTGCCAGGTGTCTAGCA | 181949 | 181967 | 152 |
| 435311 | rs362303 | Major (10) | AATGGTGCCGGGTGTCTAG | 181951 | 181969 | 153 |
| 435329 | rs362303 | Minor (10) | AATGGTGCCAGGTGTCTAG | 181951 | 181969 | 154 |
| 435882 | rs362296 | Major (10) | GGGGACAGGGTGTGCTCTC | 186651 | 186669 | 155 |
| 435907 | rs362296 | Minor (10) | GGGGACAGGTTGTGCTCTC | 186651 | 186669 | 156 |

TABLE 4

Comparison of inhibition of HTT mRNA levels by ISIS 387916 and ISIS 388816 with that by chimeric oligonucleotides targeting SNP positions on the HTT gene (SEQ ID NO: 1)

| ISIS | SNP | Target | % inhibition | | | SEQ |
|---|---|---|---|---|---|---|
| No | RS No. | allele | GM04281 | GM02171 | GM02173B | ID NO |
| 387916 | n/a | n/a | 96 | 96 | 98 | 6 |
| 388816 | n/a | n/a | 76 | 88 | 85 | 7 |
| 435330 | rs3856973 | Major (8) | 64 | 51 | 36 | 8 |
| 435348 | rs3856973 | Minor (8) | 50 | 88 | 80 | 9 |
| 435294 | rs3856973 | Major (10) | 54 | 46 | 54 | 10 |
| 435312 | rs3856973 | Minor (10) | 20 | 82 | 58 | 11 |
| 435864 | rs2285086 | Major (10) | 54 | 28 | 26 | 12 |
| 435889 | rs2285086 | Minor (10) | 17 | 43 | 41 | 13 |
| 435878 | rs7659144 | Major (10) | 43 | 32 | 39 | 14 |
| 435903 | rs7659144 | Minor (10) | 16 | 37 | 29 | 15 |
| 435863 | rs16843804 | Major (10) | 63 | 78 | 81 | 16 |
| 435888 | rs16843804 | Minor (10) | 58 | 75 | 77 | 17 |
| 435331 | rs2024115 | Major (8) | 56 | 27 | 56 | 18 |
| 435349 | rs2024115 | Minor (8) | 26 | 91 | 66 | 19 |
| 435295 | rs2024115 | Major (10) | 53 | 57 | 62 | 20 |
| 435313 | rs2024115 | Minor (10) | 25 | 87 | 53 | 21 |
| 435862 | rs10015979 | Major (10) | 8 | 51 | 40 | 22 |
| 435887 | rs10015979 | Minor (10) | 40 | 22 | 28 | 23 |
| 435880 | rs7691627 | Major (10) | 43 | 17 | 21 | 24 |

TABLE 4-continued

Comparison of inhibition of HTT mRNA levels by ISIS 387916 and ISIS 388816 with that by chimeric oligonucleotides targeting SNP positions on the HTT gene (SEQ ID NO: 1)

| ISIS No | SNP RS No. | Target allele | % inhibition GM04281 | GM02171 | GM02173B | SEQ ID NO |
|---|---|---|---|---|---|---|
| 435905 | rs7691627 | Minor (10) | 13 | 27 | 15 | 25 |
| 435885 | rs2798235 | Major (10) | 38 | 39 | 30 | 26 |
| 435910 | rs2798235 | Minor (10) | 17 | 30 | 16 | 27 |
| 435874 | rs4690072 | Major (10) | 61 | 34 | 48 | 28 |
| 435899 | rs4690072 | Minor (10) | 50 | 41 | 45 | 29 |
| 435875 | rs6446723 | Major (10) | 28 | 13 | 35 | 30 |
| 435900 | rs6446723 | Minor (10) | 24 | 56 | 37 | 31 |
| 435332 | rs363081 | Major (8) | 76 | 95 | 88 | 32 |
| 435350 | rs363081 | Minor (8) | 27 | 61 | 43 | 33 |
| 435296 | rs363081 | Major (10) | 59 | 77 | 66 | 34 |
| 435314 | rs363081 | Minor (10) | 38 | 66 | 40 | 35 |
| 435886 | rs363080 | Major (10) | 74 | 72 | 79 | 36 |
| 435911 | rs363080 | Minor (10) | 57 | 58 | 54 | 37 |
| 435914 | rs363075 | Major (6) | 95 | 92 | 95 | 38 |
| 435926 | rs363075 | Minor (6) | 88 | 81 | 79 | 39 |
| 435916 | rs363075 | Major (7) | 90 | 92 | 94 | 40 |
| 435928 | rs363075 | Minor (7) | 83 | 79 | 85 | 41 |
| 435333 | rs363075 | Major (8) | 86 | 97 | 91 | 42 |
| 435351 | rs363075 | Minor (8) | 59 | 80 | 58 | 43 |
| 435918 | rs363075 | Major (9) | 83 | 90 | 91 | 44 |
| 435930 | rs363075 | Minor (9) | 29 | 49 | 49 | 45 |
| 435297 | rs363075 | Major (10) | 74 | 84 | 83 | 46 |
| 435315 | rs363075 | Minor (10) | 47 | 63 | 45 | 47 |
| 435920 | rs363075 | Major (11) | 78 | 66 | 83 | 48 |
| 435932 | rs363075 | Minor (11) | 39 | 20 | 19 | 49 |
| 435366 | rs363075 | Major (12) | 80 | 91 | 85 | 50 |
| 435924 | rs363075 | Minor (12) | 37 | 49 | 58 | 51 |
| 435922 | rs363075 | Major (14) | 80 | 90 | 91 | 52 |
| 435934 | rs363075 | Minor (14) | 63 | 70 | 80 | 53 |
| 435334 | rs363064 | Major (8) | 50 | 59 | 44 | 54 |
| 435352 | rs363064 | Minor (8) | 12 | 37 | 48 | 55 |
| 435298 | rs363064 | Major (10) | 81 | 92 | 87 | 56 |
| 435316 | rs363064 | Minor (10) | 69 | 90 | 80 | 57 |
| 435335 | rs3025849 | Major (8) | 0 | 40 | 37 | 58 |
| 435353 | rs3025849 | Minor (8) | 0 | 29 | 18 | 59 |
| 435299 | rs3025849 | Major (10) | 0 | 34 | 67 | 60 |
| 435317 | rs3025849 | Minor (10) | 0 | 38 | 34 | 61 |
| 435877 | rs6855981 | Major (10) | 31 | 59 | 58 | 62 |
| 435902 | rs6855981 | Minor (10) | 0 | 43 | 27 | 63 |
| 435336 | rs363102 | Major (8) | 0 | 21 | 19 | 64 |
| 435354 | rs363102 | Minor (8) | 0 | 36 | 33 | 65 |
| 435300 | rs363102 | Major (10) | 0 | 34 | 24 | 66 |
| 435318 | rs363102 | Minor (10) | 0 | 30 | 20 | 67 |
| 435884 | rs11731237 | Major (10) | 7 | 46 | 51 | 68 |
| 435909 | rs11731237 | Minor (10) | 30 | 47 | 41 | 69 |
| 435337 | rs4690073 | Major (8) | 12 | 0 | 12 | 70 |
| 435355 | rs4690073 | Minor (8) | 0 | 26 | 33 | 71 |
| 435301 | rs4690073 | Major (10) | 23 | 0 | 10 | 72 |
| 435319 | rs4690073 | Minor (10) | 0 | 45 | 53 | 73 |
| 435883 | rs363144 | Major (10) | 24 | 23 | 39 | 74 |
| 435908 | rs363144 | Minor (10) | 27 | 20 | 22 | 75 |
| 435338 | rs3025838 | Major (8) | 31 | 46 | 69 | 76 |
| 435356 | rs3025838 | Minor (8) | 3 | 25 | 17 | 77 |
| 435302 | rs3025838 | Major (10) | 39 | 73 | 67 | 78 |
| 435320 | rs3025838 | Minor (10) | 21 | 49 | 32 | 79 |
| 435339 | rs363099 | Major (8) | 84 | 87 | 76 | 80 |
| 435357 | rs363099 | Minor (8) | 71 | 91 | 90 | 81 |
| 435303 | rs363099 | Major (10) | 83 | 92 | 85 | 82 |
| 435321 | rs363099 | Minor (10) | 84 | 95 | 89 | 83 |
| 435367 | rs363099 | Major (12) | 76 | 82 | 72 | 84 |
| 435340 | rs363096 | Major (8) | 0 | 47 | 52 | 85 |
| 435358 | rs363096 | Minor (8) | 0 | 25 | 35 | 86 |
| 435304 | rs363096 | Major (10) | 5 | 33 | 36 | 87 |
| 435322 | rs363096 | Minor (10) | 2 | 30 | 32 | 88 |
| 435341 | rs2298967 | Major (8) | 54 | 72 | 56 | 89 |
| 435359 | rs2298967 | Minor (8) | 25 | 59 | 63 | 90 |
| 435305 | rs2298967 | Major (10) | 66 | 80 | 78 | 91 |
| 435323 | rs2298967 | Minor (10) | 36 | 79 | 66 | 92 |
| 435865 | rs2298969 | Major (10) | 53 | 72 | 79 | 93 |
| 435890 | rs2298969 | Minor (10) | 65 | 46 | 54 | 94 |
| 435876 | rs6844859 | Major (10) | 70 | 67 | 77 | 95 |
| 435901 | rs6844859 | Minor (10) | 39 | 83 | 80 | 96 |

TABLE 4-continued

Comparison of inhibition of HTT mRNA levels by ISIS 387916 and ISIS 388816 with that by chimeric oligonucleotides targeting SNP positions on the HTT gene (SEQ ID NO: 1)

| ISIS | SNP | Target | % inhibition | | | SEQ |
|---|---|---|---|---|---|---|
| No | RS No. | allele | GM04281 | GM02171 | GM02173B | ID NO |
| 435872 | rs363092 | Major (10) | 46 | 41 | 54 | 97 |
| 435897 | rs363092 | Minor (10) | 37 | 69 | 57 | 98 |
| 435879 | rs7685686 | Major (10) | 83 | 31 | 70 | 99 |
| 435904 | rs7685686 | Minor (10) | 30 | 92 | 72 | 100 |
| 435871 | rs363088 | Major (10) | 70 | 55 | 70 | 101 |
| 435896 | rs363088 | Minor (10) | 66 | 74 | 80 | 102 |
| 435870 | rs362331 | Major (10) | 88 | 74 | 88 | 103 |
| 435895 | rs362331 | Minor (10) | 78 | 92 | 86 | 104 |
| 435881 | rs916171 | Major (10) | 0 | 57 | 51 | 105 |
| 435906 | rs916171 | Minor (10) | 14 | 26 | 17 | 106 |
| 435342 | rs362322 | Major (8) | 47 | 74 | 67 | 107 |
| 435360 | rs362322 | Minor (8) | 17 | 58 | 52 | 108 |
| 435306 | rs362322 | Major (10) | 50 | 77 | 65 | 109 |
| 435324 | rs362322 | Minor (10) | 42 | 61 | 64 | 110 |
| 435868 | rs362275 | Major (10) | 54 | 35 | 43 | 111 |
| 435893 | rs362275 | Minor (10) | 3 | 27 | 33 | 112 |
| 435343 | rs2276881 | Major (8) | 59 | 76 | 65 | 113 |
| 435361 | rs2276881 | Minor (8) | 58 | 44 | 20 | 114 |
| 435307 | rs2276881 | Major (10) | 69 | 82 | 81 | 115 |
| 435325 | rs2276881 | Minor (10) | 17 | 47 | 43 | 116 |
| 435368 | rs2276881 | Major (12) | 84 | 96 | 92 | 117 |
| 435866 | rs3121419 | Major (10) | 67 | 61 | 64 | 118 |
| 435891 | rs3121419 | Minor (10) | 53 | 76 | 73 | 119 |
| 435344 | rs362272 | Major (8) | 35 | 46 | 36 | 120 |
| 435362 | rs362272 | Minor (8) | 34 | 68 | 57 | 121 |
| 435308 | rs362272 | Major (10) | 26 | 30 | 35 | 122 |
| 435326 | rs362272 | Minor (10) | 29 | 50 | 39 | 123 |
| 435369 | rs362272 | Major (12) | 66 | 74 | 65 | 124 |
| 435867 | rs362271 | Major (10) | 73 | 74 | 75 | 125 |
| 435892 | rs362271 | Minor (10) | 52 | 74 | 79 | 126 |
| 435873 | rs3775061 | Major (10) | 40 | 32 | 47 | 127 |
| 435898 | rs3775061 | Minor (10) | 13 | 20 | 24 | 128 |
| 435345 | rs362310 | Major (8) | 38 | 55 | 52 | 129 |
| 435363 | rs362310 | Minor (8) | 45 | 67 | 60 | 130 |
| 435309 | rs362310 | Major (10) | 33 | 44 | 56 | 131 |
| 435327 | rs362310 | Minor (10) | 33 | 71 | 61 | 132 |
| 435915 | rs362307 | Major (6) | 61 | 54 | 58 | 133 |
| 435927 | rs362307 | Minor (6) | 31 | 35 | 44 | 134 |
| 435917 | rs362307 | Major (7) | 67 | 76 | 66 | 135 |
| 435929 | rs362307 | Minor (7) | 33 | 34 | 55 | 136 |
| 435346 | rs362307 | Major (8) | 67 | 89 | 66 | 137 |
| 435364 | rs362307 | Minor (8) | 46 | 72 | 66 | 138 |
| 435919 | rs362307 | Major (9) | 84 | 79 | 70 | 139 |
| 435931 | rs362307 | Minor (9) | 74 | 74 | 86 | 140 |
| 435310 | rs362307 | Major (10) | 74 | 81 | 71 | 141 |
| 435328 | rs362307 | Minor (10) | 47 | 69 | 75 | 142 |
| 435921 | rs362307 | Major (11) | 74 | 77 | 69 | 143 |
| 435933 | rs362307 | Minor (11) | 38 | 47 | 74 | 144 |
| 435370 | rs362307 | Major (12) | 64 | 74 | 38 | 145 |
| 435925 | rs362307 | Minor (12) | 60 | 66 | 80 | 146 |
| 435923 | rs362307 | Major (14) | 73 | 66 | 71 | 147 |
| 435935 | rs362307 | Minor (14) | 68 | 75 | 87 | 148 |
| 435869 | rs362306 | Major (10) | 82 | 77 | 81 | 149 |
| 435894 | rs362306 | Minor (10) | 28 | 79 | 72 | 150 |
| 435347 | rs362303 | Major (8) | 68 | 74 | 71 | 151 |
| 435365 | rs362303 | Minor (8) | 69 | 83 | 76 | 152 |
| 435311 | rs362303 | Major (10) | 46 | 56 | 72 | 153 |
| 435329 | rs362303 | Minor (10) | 49 | 62 | 39 | 154 |
| 435882 | rs362296 | Major (10) | 29 | 48 | 56 | 155 |
| 435907 | rs362296 | Minor (10) | 42 | 56 | 52 | 156 |

Example 3: Dose-Dependent Antisense Inhibition of Human Huntingtin mRNA Levels in Coriell Fibroblast Cell Lines Gapmers from the study described in Example 2 were selected and tested at various doses in GM04281, GM02171, and GM02173B cell lines. Each cell line was plated at a density of 25,000 cells per well and transfected using electroporation with 750 nM, 1,500 nM, 3,000 nM, 6,000 nM, and 12,000 nM concentrations of antisense oligonucleotide, as specified in Table 5, 6, and 7. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 5, 6, and 7.

TABLE 5

Dose-dependent antisense inhibition of human HTT in GM04281 cells

| ISIS No. | 750 nM | 1,500 nM | 3,000 nM | 6,000 nM | 12,000 nM | $IC_{50}$ (μM) |
|---|---|---|---|---|---|---|
| 387916 | 51 | 81 | 80 | 91 | 97 | 0.6 |
| 435330 | 24 | 49 | 50 | 73 | 85 | 2.5 |
| 435331 | 23 | 38 | 64 | 72 | 74 | 2.4 |
| 435868 | 3 | 17 | 7 | 29 | 63 | 6.7 |
| 435870 | 53 | 73 | 77 | 86 | 93 | 0.6 |
| 435871 | 28 | 51 | 52 | 78 | 89 | 1.7 |
| 435874 | 14 | 21 | 28 | 64 | 82 | 3.3 |
| 435879 | 42 | 57 | 57 | 81 | 91 | 1.1 |
| 435890 | 48 | 56 | 62 | 76 | 91 | 0.9 |
| 435929 | 10 | 0 | 5 | 12 | 48 | 13.8 |
| 435931 | 20 | 17 | 53 | 62 | 81 | 2.9 |
| 435933 | 0 | 7 | 24 | 43 | 49 | 10.7 |
| 435935 | 0 | 38 | 38 | 62 | 29 | 4.2 |

TABLE 6

Dose-dependent antisense inhibition of human HTT in GM02171 cells

| ISIS No. | 750 nM | 1,500 nM | 3.000 nM | 6,000 nM | 12,000 nM | $IC_{50}$ (μM) |
|---|---|---|---|---|---|---|
| 387916 | 57 | 73 | 81 | 93 | 98 | 0.4 |
| 435330 | 27 | 37 | 0 | 44 | 63 | 4.4 |
| 435331 | 35 | 34 | 19 | 41 | 63 | 3.5 |
| 435868 | 21 | 21 | 39 | 24 | 12 | >12.0 |
| 435870 | 50 | 53 | 57 | 70 | 79 | 0.9 |
| 435871 | 32 | 46 | 45 | 58 | 62 | 3.9 |
| 435874 | 1 | 0 | 4 | 11 | 6 | >12.0 |
| 435879 | 32 | 14 | 17 | 45 | 38 | >12.0 |
| 435890 | 34 | 33 | 40 | 51 | 62 | 5.4 |
| 435929 | 25 | 22 | 31 | 5 | 29 | >12.0 |
| 435931 | 15 | 28 | 27 | 60 | 79 | 3.7 |
| 435933 | 13 | 36 | 21 | 43 | 48 | 12.2 |
| 435935 | 25 | 42 | 27 | 61 | 68 | 3.2 |

TABLE 7

Dose-dependent antisense inhibition of human HTT in GM02173B cells

| ISIS No. | 750 nM | 1,500 nM | 3,000 nM | 6.000 nM | 12,000 nM | $IC_{50}$ (μM) |
|---|---|---|---|---|---|---|
| 387916 | 43 | 67 | 80 | 86 | 97 | 1.1 |
| 435330 | 22 | 21 | 0 | 52 | 62 | 5.3 |
| 435331 | 19 | 17 | 32 | 50 | 55 | 9.4 |
| 435868 | 17 | 25 | 41 | 13 | 26 | >12.0 |
| 435870 | 24 | 57 | 70 | 78 | 75 | 1.8 |
| 435871 | 8 | 30 | 42 | 50 | 48 | 5.0 |
| 435874 | 31 | 35 | 28 | 35 | 42 | >12.0 |
| 435879 | 39 | 44 | 42 | 60 | 64 | 2.5 |
| 435890 | 38 | 36 | 50 | 65 | 73 | 3.1 |
| 435929 | 19 | 17 | 19 | 42 | 35 | 7.7 |
| 435931 | 40 | 19 | 31 | 48 | 71 | 5.8 |
| 435933 | 35 | 24 | 47 | 52 | 59 | 4.4 |
| 435935 | 25 | 23 | 40 | 73 | 77 | 3.7 |

Example 4: Dose-Dependent Antisense Inhibition of Human Huntingtin mRNA Levels in Coriell Fibroblast Cell Lines Gapmers from the study described in Example 2 were selected and tested at various doses in GM04281, GM02171, and GM02173B cell lines. Each cell line was plated at a density of 25,000 cells per well and transfected using electroporation with 750 nM, 1,500 nM, 3,000 nM, 6,000 nM, and 12,000 nM concentrations of antisense oligonucleotide, as specified in Table 8, 9, and 10. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA relative to untreated control cells. $IC_{50}$ values are also provided in Tables 8, 9, and 10.

TABLE 8

Dose-dependent antisense inhibition of human HTT in GM04281 cells

| ISIS No. | 750 nM | 1,500 nM | 3,000 nM | 6,000 nM | 12,000 nM | $IC_{50}$ (μM) |
|---|---|---|---|---|---|---|
| 387916 | 61 | 78 | 90 | 94 | 97 | <0.8 |
| 435303 | 33 | 39 | 69 | 79 | 91 | 1.5 |
| 435328 | 0 | 12 | 16 | 51 | 75 | 5.3 |
| 435331 | 27 | 48 | 48 | 70 | 82 | 2.1 |
| 435339 | 46 | 37 | 61 | 73 | 89 | 2.3 |
| 435869 | 17 | 35 | 44 | 66 | 80 | 3.3 |
| 435870 | 44 | 60 | 64 | 84 | 84 | 1.1 |
| 435871 | 41 | 50 | 71 | 78 | 87 | 1.2 |
| 435874 | 24 | 36 | 35 | 65 | 73 | 3.1 |
| 435879 | 46 | 52 | 78 | 81 | 92 | 0.9 |
| 435890 | 41 | 53 | 63 | 80 | 86 | 1.3 |
| 435925 | 0 | 14 | 39 | 60 | 87 | 4.2 |
| 435926 | 20 | 28 | 67 | 81 | 89 | 2.0 |
| 435928 | 32 | 49 | 73 | 86 | 86 | 1.8 |
| 435931 | 22 | 24 | 40 | 59 | 90 | 3.8 |

TABLE 9

Dose-dependent antisense inhibition of human HTT in GM02171 cells

| ISIS No. | 750 nM | 1,500 nM | 3,000 nM | 6,000 nM | 12,000 nM | $IC_{50}$ (μM) |
|---|---|---|---|---|---|---|
| 387916 | 50 | 64 | 90 | 95 | 96 | 0.7 |
| 435303 | 14 | 32 | 68 | 79 | 85 | 2.8 |
| 435328 | 0 | 12 | 20 | 38 | 55 | 10.3 |
| 435331 | 0 | 13 | 5 | 30 | 36 | >12.0 |
| 435339 | 30 | 40 | 58 | 63 | 49 | 2.5 |
| 435869 | 13 | 25 | 31 | 47 | 87 | 4.0 |
| 435870 | 18 | 31 | 44 | 66 | 74 | 3.5 |
| 435871 | 1 | 20 | 29 | 49 | 64 | 6.5 |
| 435874 | 3 | 6 | 12 | 17 | 31 | >12.0 |
| 435879 | 0 | 2 | 12 | 35 | 44 | >12.0 |
| 435890 | 15 | 16 | 30 | 48 | 72 | 5.8 |
| 435925 | 0 | 0 | 22 | 48 | 29 | 6.3 |
| 435926 | 25 | 28 | 58 | 74 | 85 | 2.3 |
| 435928 | 18 | 53 | 61 | 86 | 83 | 2.5 |
| 435931 | 0 | 4 | 25 | 46 | 68 | 6.7 |

TABLE 10

| Dose-dependent antisense inhibition of human HTT in GM02173B cells | | | | | | |
|---|---|---|---|---|---|---|
| ISIS No. | 750 nM | 1,500 nM | 3,000 nM | 6,000 nM | 12,000 nM | $IC_{50}$ (μM) |
| 387916 | 27 | 65 | 84 | 81 | 96 | 1.9 |
| 435303 | 23 | 48 | 52 | 76 | 76 | 2.9 |
| 435328 | 8 | 14 | 19 | 34 | 50 | 15.7 |
| 435331 | 10 | 17 | 16 | 27 | 32 | >12.0 |
| 435339 | 28 | 26 | 38 | 67 | 82 | 3.8 |
| 435869 | 12 | 24 | 37 | 45 | 79 | 4.2 |
| 435870 | 20 | 26 | 58 | 53 | 78 | 2.7 |
| 435871 | 15 | 16 | 32 | 45 | 71 | 6.0 |
| 435874 | 13 | 8 | 28 | 36 | 31 | >12.0 |
| 435879 | 22 | 20 | 36 | 53 | 60 | 6.0 |
| 435890 | 21 | 28 | 34 | 54 | 71 | 4.3 |
| 435925 | 2 | 10 | 28 | 43 | 78 | 5.9 |
| 435926 | 7 | 25 | 37 | 73 | 79 | 3.5 |
| 435928 | 15 | 39 | 60 | 73 | 87 | 2.5 |
| 435931 | 13 | 13 | 32 | 61 | 62 | 6.7 |

Example 5: Antisense Inhibition of Human HTT in GM04281 Cells

Additional antisense oligonucleotides were designed based on the gapmers selected from studies described in Example 4. These oligonucleotides were designed by creating gapmers shifted slightly upstream and downstream (i.e. “microwalk”) of the original gapmers from Tables 8, 9, and 10. Antisense oligonucleotides were also created with uniform MOE, as well as with various motifs, 2-9-6 MOE, 3-9-3 MOE, 3-9-4 MOE, 3-9-5 MOE, 4-10-5 MOE, 4-11-4 MOE, 4-7-4 MOE, 4-9-4 MOE, 4-9-5 MOE, 5-10-4 MOE, 5-7-5 MOE, 5-8-6 MOE, 5-9-3 MOE, 5-9-5 MOE, 6-7-6 MOE, 6-9-2 MOE, and 6-8-5 MOE.

In addition, antisense oligonucleotides were designed targeting SNP RS Nos. rs2857936, rs12506200, rs762855, and rs1006798 (refer to Table 2). The oligonucleotides were designed targeting either the major allele or the minor allele, and with the SNP position opposite either position 8 or position 10 of the gapmer.

These gapmers were tested in vitro. Cultured GM04281 cells at a density of 25,000 cells per well were transfected using electroporation with 10,000 nM antisense oligonucleotide. After a treatment period of approximately 24 hours, RNA was isolated from the cells and HTT mRNA levels were measured by quantitative real-time PCR. HTT mRNA levels were adjusted according to total RNA content, as measured by RIBOGREEN. Results are presented in Tables 11-19 as percent inhibition of HTT mRNA, relative to untreated control cells.

The gapmers, ISIS 435869, ISIS 435870, ISIS 435874, ISIS 435879, and ISIS 435890, from which some of the newly designed gapmers were derived are marked with an asterisk (*) in the table. ISIS 387916 was included in the study as a benchmark oligonucleotide against which the potency of the antisense oligonucleotides targeting nucleotides overlapping each SNP position could be compared.

The uniform MOE oligonucleotides are 15 nucleotides in length.

The 2-9-6 gapmers are 17 nucleotides in length, wherein the central gap segment is comprised of nine 2'-deoxynucleotides and is flanked on the 5' direction by a wing comprising 2 nucleotides and on the 3' direction by a wing comprising 6 nucleotides.

The 3-9-3 gapmers are 15 nucleotides in length, wherein the central gap segment is comprised of nine 2'-deoxynucleotides and is flanked on both 5' and 3' directions by wings comprising 3 nucleotides each.

The 3-9-4 gapmers are 16 nucleotides in length, wherein the central gap segment is comprised of nine 2'-deoxynucleotides and is flanked on the 5' direction by a wing comprising 3 nucleotides and on the 3' direction by a wing comprising 4 nucleotides.

The 3-9-5 gapmers are 17 nucleotides in length, wherein the central gap segment is comprised of nine 2'-deoxynucleotides and is flanked on the 5' direction by a wing comprising 3 nucleotides and on the 3' direction by a wing comprising 5 nucleotides.

The 4-10-5 gapmers are 19 nucleotides in length, wherein the central gap segment is comprised of ten 2'-deoxynucleotides and is flanked on the 5' direction by a wing comprising 4 nucleotides and on the 3' direction by a wing comprising 5 nucleotides.

The 4-11-4 gapmers are 19 nucleotides in length, wherein the central gap segment is comprised of eleven 2'-deoxynucleotides and is flanked on both 5' and 3' directions by wings comprising 4 nucleotides each.

The 4-7-4 gapmers are 15 nucleotides in length, wherein the central gap segment is comprised of seven 2'-deoxynucleotides and is flanked on both 5' and 3' directions by wings comprising 4 nucleotides each.

The 4-9-4 gapmers are 17 nucleotides in length, wherein the central gap segment is comprised of nine 2'-deoxynucleotides and is flanked on both 5' and 3' directions by wings comprising 4 nucleotides each.

The 4-9-5 gapmers are 18 nucleotides in length, wherein the central gap segment is comprised of nine 2'-deoxynucleotides and is flanked on the 5' direction by a wing comprising 4 nucleotides and on the 3' direction by a wing comprising 5 nucleotides.

The 5-10-4 gapmers are 19 nucleotides in length, wherein the central gap segment is comprised of ten 2'-deoxynucleotides and is flanked on the 5' direction by a wing comprising 5 nucleotides and on the 3' direction by a wing comprising 4 nucleotides.

The 5-7-5 gapmers are 17 nucleotides in length, wherein the central gap segment is comprised of seven 2'-deoxynucleotides and is flanked on both 5' and 3' directions by wings comprising 5 nucleotides each.

The 5-8-6 gapmers are 19 nucleotides in length, wherein the central gap segment is comprised of eight 2'-deoxynucleotides and is flanked on the 5' direction by a wing comprising 5 nucleotides and on the 3' direction by a wing comprising 6 nucleotides.

The 5-9-3 gapmers are 17 nucleotides in length, wherein the central gap segment is comprised of nine 2'-deoxynucleotides and is flanked on the 5' direction by a wing comprising 5 nucleotides and on the 3' direction by a wing comprising 3 nucleotides.

The 5-9-5 gapmers are 19 nucleotides in length, wherein the central gap segment is comprised of nine 2'-deoxynucleotides and is flanked on both 5' and 3' directions by wings comprising 5 nucleotides each.

The 6-7-6 gapmers are 19 nucleotides in length, wherein the central gap segment is comprised of seven 2'-deoxynucleotides and is flanked on both 5' and 3' directions by wings comprising 6 nucleotides each.

The 6-9-2 gapmers are 17 nucleotides in length, wherein the central gap segment is comprised of nine 2'-deoxynucleotides and is flanked on the 5' direction by a wing comprising 6 nucleotides and on the 3' direction by a wing comprising 2 nucleotides.

The 6-8-5 gapmers are 19 nucleotides in length, wherein the central gap segment is comprised of eight 2'-deoxynucleotides and is flanked on the 5' direction by a wing comprising 6 nucleotides and on the 3' direction by a wing comprising 5 nucleotides.

For each of the motifs, each nucleotide in the 5' wing segment and each nucleotide in the 3' wing segment has a 2'-MOE modification. The internucleoside linkages throughout each gapmer are phosphorothioate (P═S) linkages. All cytosine nucleobases throughout each gapmer are 5-methylcytosines.

The oligonucleotides are organized in tables according to the SNP they target. "Start site" indicates the 5'-most nucleotide to which the gapmer is targeted. "Stop site" indicates the 3'-most nucleotide to which the gapmer is targeted. 'Target allele' indicates whether the gapmer is targeted to the major or the minor allele. The number in parentheses indicates the position on the oligonucleotide opposite to the SNP position.

TABLE 11

Comparison of inhibition of human HTT mRNA levels by ISIS 387916 and chimeric antisense oligonucleotides targeted to SNP rs2857936 (nucleobases 1952 to 1972 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAA G | 5-10-5 | 98 | 6 |
| 1952 | 1970 | Minor (8) | 459908 | GCTTTTCATTGAAAAGAA A | 5-9-5 | 26 | 157 |
| 1952 | 1970 | Major (8) | 459916 | GCTTTTCGTTGAAAAGAA A | 5-9-5 | 8 | 158 |
| 1954 | 1972 | Minor (10) | 459904 | CTGCTTTTCATTGAAAAGA | 5-9-5 | 23 | 159 |
| 1954 | 1972 | Major (10) | 459912 | CTGCTTTTCGTTGAAAAGA | 5-9-5 | 8 | 160 |

TABLE 12

Comparison of inhibition of human HTT mRNA levels by ISIS 387916 and chimeric antisense oligonucleotides targeted to SNP rs12506200 (nucleobases 3695 to 3715 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAA G | 5-10-5 | 98 | 6 |
| 3695 | 3713 | Major (8) | 459909 | ACTAGGCCGGGCATGCTG G | 5-9-5 | 48 | 161 |
| 3695 | 3713 | Minor (8) | 459917 | ACTAGGCTGGGCATGCTG G | 5-9-5 | 35 | 162 |
| 3697 | 3715 | Major (10) | 459905 | AGACTAGGCCGGGCATGC T | 5-9-5 | 33 | 163 |
| 3697 | 3715 | Minor (10) | 459913 | AGACTAGGCTGGGCATGC T | 5-9-5 | 45 | 164 |

TABLE 13

Comparison of inhibition of human HTT mRNA levels by ISIS 387916 and chimeric antisense oligonucleotides targeted to SNP rs762855 (nucleobases 14437 to 14457 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAA G | 5-10-5 | 98 | 6 |
| 14437 | 14455 | Minor (8) | 459910 | AAACAGCTGTTAGTTCCC A | 5-9-5 | 27 | 165 |

TABLE 13-continued

Comparison of inhibition of human HTT mRNA levels by ISIS 387916 and chimeric antisense oligonucleotides targeted to SNP rs762855 (nucleobases 14437 to 14457 of SEQ ID NO: 1)

| Start Site | Stop Site | Target allele | ISIS No. | Sequence | Motif | % inhibition | SEQ ID NO |
|---|---|---|---|---|---|---|---|
| 14437 | 14455 | Major (8) | 459918 | AAACAGCCGTTAGTTCCC A | 5-9-5 | 39 | 166 |
| 14439 | 14457 | Minor (10) | 459906 | AGAAACAGCTGTTAGTTC C | 5-9-5 | 24 | 167 |
| 14439 | 14457 | Major (10) | 459914 | AGAAACAGCCGTTAGTTC C | 5-9-5 | 28 | 168 |

TABLE 14

Comparison of inhibition of human HTT mRNA levels by ISIS 387916 and chimeric antisense oligonucleotides targeted to SNP rs4690072 (nucleobases 62147 to 62173 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 62147 | 62165 | Major (6) | 460145 | GTGCTACCCAACCTTTCTG | 5-9-5 | 62 | 169 |
| 62148 | 62166 | Major (7) | 460144 | AGTGCTACCCAACCTTTCT | 5-9-5 | 61 | 170 |
| 62149 | 62167 | Major (8) | 460143 | CAGTGCTACCCAACCTTTC | 5-9-5 | 65 | 171 |
| 62150 | 62168 | Major (9) | 460142 | ACAGTGCTACCCAACCTTT | 5-9-5 | 83 | 172 |
| 62151 | 62169 | Major (10) | *435874 | CACAGTGCTACCCAACCTT | 5-9-5 | 76 | 28 |
| 62151 | 62169 | Major (10) | 460022 | CACAGTGCTACCCAACCTT | 4-10-5 | 75 | 28 |
| 62151 | 62169 | Major (10) | 460033 | CACAGTGCTACCCAACCTT | 4-11-4 | 89 | 28 |
| 62151 | 62168 | Major (9) | 460063 | ACAGTGCTACCCAACCTT | 4-9-5 | 77 | 173 |
| 62151 | 62169 | Major (10) | 460073 | CACAGTGCTACCCAACCTT | 5-10-4 | 86 | 28 |
| 62151 | 62169 | Major (10) | 460093 | CACAGTGCTACCCAACCTT | 5-8-6 | 61 | 28 |
| 62151 | 62169 | Major (10) | 460169 | CACAGTGCTACCCAACCTT | 6-7-6 | 16 | 28 |
| 62151 | 62169 | Major (10) | 460188 | CACAGTGCTACCCAACCTT | 6-8-5 | 53 | 28 |
| 62152 | 62168 | Major (9) | 459978 | ACAGTGCTACCCAACCT | 2-9-6 | 87 | 174 |
| 62152 | 62167 | Major (8) | 459999 | CAGTGCTACCCAACCT | 3-9-4 | 48 | 175 |
| 62152 | 62168 | Major (9) | 460012 | ACAGTGCTACCCAACCT | 3-9-5 | 84 | 174 |
| 62152 | 62168 | Major (9) | 460052 | ACAGTGCTACCCAACCT | 4-9-4 | 51 | 174 |
| 62152 | 62168 | Major (9) | 460083 | ACAGTGCTACCCAACCT | 5-7-5 | 37 | 174 |
| 62152 | 62168 | Major (9) | 460103 | ACAGTGCTACCCAACCT | 5-9-3 | 80 | 174 |
| 62152 | 62170 | Major (11) | 460137 | TCACAGTGCTACCCAACCT | 5-9-5 | 65 | 176 |
| 62152 | 62168 | Major (9) | 460179 | ACAGTGCTACCCAACCT | 6-9-2 | 67 | 174 |
| 62153 | 62167 | Major (8) | 459989 | CAGTGCTACCCAACC | 3-9-3 | 60 | 177 |
| 62153 | 62167 | Major (8) | 460043 | CAGTGCTACCCAACC | 4-7-4 | 24 | 177 |
| 62153 | 62171 | Major (12) | 460138 | ATCACAGTGCTACCCAACC | 5-9-5 | 76 | 178 |
| 62154 | 62172 | Major (13) | 460139 | TATCACAGTGCTACCCAAC | 5-9-5 | 68 | 179 |
| 62155 | 62173 | Major (14) | 460140 | ATATCACAGTGCTACCCAA | 5-9-5 | 79 | 180 |

TABLE 15

Comparison of inhibition of human HTT mRNA levels by ISIS 387916 and chimeric antisense oligonucleotides targeted to SNP rs2298969 (nucleobases 125883 to 125911 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 125883 | 125901 | Minor (5) | 460166 | ATGCTGACTTGGGCCATTC | 5-9-5 | 83 | 181 |
| 125884 | 125902 | Minor (6) | 460165 | GATGCTGACTTGGGCCATT | 5-9-5 | 88 | 182 |
| 125885 | 125903 | Minor (7) | 460164 | GGATGCTGACTTGGGCCAT | 5-9-5 | 68 | 183 |
| 125886 | 125904 | Minor (8) | 460163 | GGGATGCTGACTTGGGCCA | 5-9-5 | 73 | 184 |
| 125887 | 125905 | Minor (9) | 460162 | AGGGATGCTGACTTGGGCC | 5-9-5 | 88 | 185 |
| 125888 | 125906 | Minor (10) | *435890 | AAGGGATGCTGACTTGGGC | 5-9-5 | 83 | 94 |
| 125888 | 125906 | Minor (10) | 460026 | AAGGGATGCTGACTTGGGC | 4-10-5 | 90 | 94 |
| 125888 | 125906 | Minor (10) | 460037 | AAGGGATGCTGACTTGGGC | 4-11-4 | 86 | 94 |
| 125888 | 125905 | Minor (9) | 460068 | AGGGATGCTGACTTGGGC | 4-9-5 | 90 | 186 |
| 125888 | 125906 | Minor (10) | 460076 | AAGGGATGCTGACTTGGGC | 5-10-4 | 90 | 94 |
| 125888 | 125906 | Minor (10) | 460096 | AAGGGATGCTGACTTGGGC | 5-8-6 | 88 | 94 |
| 125888 | 125906 | Minor (10) | 460171 | AAGGGATGCTGACTTGGGC | 6-7-6 | 87 | 94 |
| 125888 | 125906 | Minor (10) | 460190 | AAGGGATGCTGACTTGGGC | 6-8-5 | 69 | 94 |
| 125889 | 125905 | Minor (9) | 459983 | AGGGATGCTGACTTGGG | 2-9-6 | 80 | 187 |
| 125889 | 125904 | Minor (8) | 460005 | GGGATGCTGACTTGGG | 3-9-4 | 80 | 284 |
| 125889 | 125905 | Minor (9) | 460016 | AGGGATGCTGACTTGGG | 3-9-5 | 90 | 187 |
| 125889 | 125905 | Minor (9) | 460057 | AGGGATGCTGACTTGGG | 4-9-4 | 86 | 187 |
| 125889 | 125905 | Minor (9) | 460087 | AGGGATGCTGACTTGGG | 5-7-5 | 86 | 187 |
| 125889 | 125905 | Minor (9) | 460107 | AGGGATGCTGACTTGGG | 5-9-3 | 79 | 187 |
| 125889 | 125907 | Major (11) | 460157 | CAAGGGATGCTGACTTGGG | 5-9-5 | 88 | 188 |
| 125889 | 125905 | Minor (9) | 460181 | AGGGATGCTGACTTGGG | 6-9-2 | 62 | 187 |
| 125890 | 125904 | Minor (8) | 459972 | GGGATGCTGACTTGG | Uniform | 18 | 189 |
| 125890 | 125904 | Minor (8) | 459992 | GGGATGCTGACTTGG | 3-9-3 | 90 | 189 |
| 125890 | 125904 | Minor (8) | 460046 | GGGATGCTGACTTGG | 4-7-4 | 59 | 189 |
| 125890 | 125908 | Major (12) | 460158 | CCAAGGGATGCTGACTTGG | 5-9-5 | 79 | 190 |
| 125891 | 125909 | Major (13) | 460159 | GCCAAGGGATGCTGACTTG | 5-9-5 | 82 | 191 |
| 125892 | 125910 | Major (14) | 460160 | TGCCAAGGGATGCTGACTT | 5-9-5 | 87 | 192 |
| 125893 | 125911 | Major (15) | 460161 | CTGCCAAGGGATGCTGACT | 5-9-5 | 78 | 193 |

TABLE 16

Comparison of inhibition of human HTT mRNA levels by ISIS 387916 and chimeric antisense oligonucleotides targeted to SNP rs7685686 (nucleobases 146781 to 146809 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 146781 | 146799 | Major (5) | 460156 | ATTGTCATCACCAGAAAAA | 5-9-5 | 88 | 194 |

TABLE 16-continued

Comparison of inhibition of human HTT mRNA levels by ISIS 387916 and chimeric antisense oligonucleotides targeted to SNP rs7685686 (nucleobases 146781 to 146809 of SEQ ID NO: 1)

| Start Site | Stop Site | Target allele | ISIS No. | Sequence | Motif | % inhibition | SEQ ID NO |
|---|---|---|---|---|---|---|---|
| 146782 | 146800 | Major (6) | 460155 | AATTGTCATCACCAGAAAA | 5-9-5 | 89 | 195 |
| 146783 | 146801 | Major (7) | 460154 | AAATTGTCATCACCAGAAA | 5-9-5 | 89 | 196 |
| 146784 | 146802 | Major (8) | 460153 | TAAATTGTCATCACCAGAA | 5-9-5 | 93 | 197 |
| 146785 | 146803 | Major (9) | 460152 | ATAAATTGTCATCACCAGA | 5-9-5 | 95 | 198 |
| 146786 | 146804 | Major (10) | *435879 | AATAAATTGTCATCACCAG | 5-9-5 | 94 | 99 |
| 146786 | 146804 | Major (10) | 460024 | AATAAATTGTCATCACCAG | 4-10-5 | 88 | 99 |
| 146786 | 146804 | Major (10) | 460035 | AATAAATTGTCATCACCAG | 4-11-4 | 91 | 99 |
| 146786 | 146803 | Major (9) | 460065 | ATAAATTGTCATCACCAG | 4-9-5 | 96 | 199 |
| 146786 | 146804 | Major (10) | 460074 | AATAAATTGTCATCACCAG | 5-10-4 | 94 | 99 |
| 146786 | 146804 | Major (10) | 460095 | AATAAATTGTCATCACCAG | 5-8-6 | 92 | 99 |
| 146786 | 146804 | Major (10) | 460170 | AATAAATTGTCATCACCAG | 6-7-6 | 91 | 99 |
| 146786 | 146804 | Major (10) | 460189 | AATAAATTGTCATCACCAG | 6-8-5 | 94 | 99 |
| 146787 | 146803 | Major (9) | 459981 | ATAAATTGTCATCACCA | 2-9-6 | 85 | 200 |
| 146787 | 146802 | Major (8) | 460002 | TAAATTGTCATCACCA | 3-9-4 | 86 | 201 |
| 146787 | 146803 | Major (9) | 460014 | ATAAATTGTCATCACCA | 3-9-5 | 91 | 200 |
| 146787 | 146803 | Major (9) | 460055 | ATAAATTGTCATCACCA | 4-9-4 | 90 | 200 |
| 146787 | 146803 | Major (9) | 460085 | ATAAATTGTCATCACCA | 5-7-5 | 94 | 200 |
| 146787 | 146803 | Major (9) | 460104 | ATAAATTGTCATCACCA | 5-9-3 | 93 | 200 |
| 146787 | 146805 | Major (11) | 460147 | TAATAAATTGTCATCACCA | 5-9-5 | 91 | 202 |
| 146787 | 146803 | Major (9) | 460180 | ATAAATTGTCATCACCA | 6-9-2 | 91 | 200 |
| 146788 | 146802 | Major (8) | 459970 | TAAATTGTCATCACC | Uniform | 9 | 203 |
| 146788 | 146802 | Major (8) | 459990 | TAAATTGTCATCACC | 3-9-3 | 67 | 203 |
| 146788 | 146802 | Major (8) | 460045 | TAAATTGTCATCACC | 4-7-4 | 84 | 203 |
| 146788 | 146806 | Major (12) | 460148 | TTAATAAATTGTCATCACC | 5-9-5 | 88 | 204 |
| 146789 | 146807 | Major (13) | 460149 | ATTAATAAATTGTCATCAC | 5-9-5 | 32 | 205 |
| 146790 | 146808 | Major (14) | 460150 | TATTAATAAATTGTCATCA | 5-9-5 | 29 | 206 |
| 146791 | 146809 | Major (15) | 460151 | CTATTAATAAATTGTCATC | 5-9-5 | 33 | 207 |

TABLE 17

Comparison of inhibition of human HTT mRNA levels by ISIS 387916 and chimeric antisense oligonucleotides targeted to SNP rs362331 (nucleobases 155474 to 155502 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 155474 | 155492 | Major (5) | 460136 | CAGTAGATGAGGGAGCAGG | 5-9-5 | 81 | 208 |
| 155475 | 155493 | Major (6) | 460135 | ACAGTAGATGAGGGAGCAG | 5-9-5 | 84 | 209 |

TABLE 17-continued

Comparison of inhibition of human HTT mRNA levels by ISIS 387916 and chimeric antisense oligonucleotides targeted to SNP rs362331 (nucleobases 155474 to 155502 of SEQ ID NO: 1)

| Start Site | Stop Site | Target allele | ISIS No. | Sequence | Motif | % inhibition | SEQ ID NO |
|---|---|---|---|---|---|---|---|
| 155476 | 155494 | Major (7) | 460134 | CACAGTAGATGAGGGAGCA | 5-9-5 | 87 | 210 |
| 155477 | 155495 | Major (8) | 460133 | ACACAGTAGATGAGGGAGC | 5-9-5 | 85 | 211 |
| 155478 | 155496 | Major (9) | 460132 | CACACAGTAGATGAGGGAG | 5-9-5 | 86 | 212 |
| 155479 | 155497 | Major (10) | *435870 | GCACACAGTAGATGAGGGA | 5-9-5 | 91 | 103 |
| 155479 | 155497 | Major (10) | 460019 | GCACACAGTAGATGAGGGA | 4-10-5 | 92 | 103 |
| 155479 | 155497 | Major (10) | 460031 | GCACACAGTAGATGAGGGA | 4-11-4 | 95 | 103 |
| 155479 | 155496 | Major (9) | 460061 | CACACAGTAGATGAGGGA | 4-9-5 | 87 | 213 |
| 155479 | 155497 | Major (10) | 460071 | GCACACAGTAGATGAGGGA | 5-10-4 | 94 | 103 |
| 155479 | 155497 | Major (10) | 460090 | GCACACAGTAGATGAGGGA | 5-8-6 | 86 | 103 |
| 155479 | 155497 | Major (10) | 460168 | GCACACAGTAGATGAGGGA | 6-7-6 | 84 | 103 |
| 155479 | 155497 | Major (10) | 460187 | GCACACAGTAGATGAGGGA | 6-8-5 | 89 | 103 |
| 155480 | 155496 | Major (9) | 459977 | CACACAGTAGATGAGGG | 2-9-6 | 90 | 214 |
| 155480 | 155495 | Major (8) | 459996 | ACACAGTAGATGAGGG | 3-9-4 | 37 | 215 |
| 155480 | 155496 | Major (9) | 460009 | CACACAGTAGATGAGGG | 3-9-5 | 90 | 214 |
| 155480 | 155496 | Major (9) | 460051 | CACACAGTAGATGAGGG | 4-9-4 | 73 | 214 |
| 155480 | 155496 | Major (9) | 460081 | CACACAGTAGATGAGGG | 5-7-5 | 77 | 214 |
| 155480 | 155496 | Major (9) | 460101 | CACACAGTAGATGAGGG | 5-9-3 | 84 | 214 |
| 155480 | 155498 | Major (11) | 460127 | TGCACACAGTAGATGAGGG | 5-9-5 | 89 | 216 |
| 155480 | 155496 | Major (9) | 460178 | CACACAGTAGATGAGGG | 6-9-2 | 92 | 214 |
| 155481 | 155495 | Major (8) | 459967 | ACACAGTAGATGAGG | Uniform | 81 | 217 |
| 155481 | 155495 | Major (8) | 459987 | ACACAGTAGATGAGG | 3-9-3 | 18 | 217 |
| 155481 | 155495 | Major (8) | 460041 | ACACAGTAGATGAGG | 4-7-4 | 54 | 217 |
| 155481 | 155499 | Major (12) | 460128 | GTGCACACAGTAGATGAGG | 5-9-5 | 73 | 218 |
| 155482 | 155500 | Major (13) | 460129 | AGTGCACACAGTAGATGAG | 5-9-5 | 86 | 219 |
| 155483 | 155501 | Major (14) | 460130 | AAGTGCACACAGTAGATGA | 5-9-5 | 60 | 220 |
| 155484 | 155502 | Major (15) | 460131 | GAAGTGCACACAGTAGATG | 5-9-5 | 73 | 221 |

TABLE 18

Comparison of inhibition of human HTT mRNA levels by ISIS 387916 and chimeric antisense oligonucleotides targeted to SNP rs362306 (nucleobases 181739 to 181767 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 181739 | 181757 | Major (5) | 460126 | GCTGCAACCTGGCAACAAC | 5-9-5 | 87 | 222 |
| 181740 | 181758 | Major (6) | 460125 | AGCTGCAACCTGGCAACAA | 5-9-5 | 70 | 223 |
| 181741 | 181759 | Major (7) | 460123 | CAGCTGCAACCTGGCAACA | 5-9-5 | 83 | 224 |
| 181742 | 181760 | Major (8) | 460121 | GCAGCTGCAACCTGGCAAC | 5-9-5 | 47 | 225 |

TABLE 18-continued

Comparison of inhibition of human HTT mRNA levels by ISIS 387916 and chimeric antisense oligonucleotides targeted to SNP rs362306 (nucleobases 181739 to 181767 of SEQ ID NO: 1)

| Start Site | Stop Site | Target allele | ISIS No. | Sequence | Motif | % inhibition | SEQ ID NO |
|---|---|---|---|---|---|---|---|
| 181743 | 181761 | Major (9) | 460118 | AGCAGCTGCAACCTGGCAA | 5-9-5 | 75 | 226 |
| 181744 | 181762 | Major (10) | *435869 | GAGCAGCTGCAACCTGGCA | 5-9-5 | 91 | 149 |
| 181744 | 181762 | Major (10) | 460018 | GAGCAGCTGCAACCTGGCA | 4-10-5 | 86 | 149 |
| 181744 | 181762 | Major (10) | 460028 | GAGCAGCTGCAACCTGGCA | 4-11-4 | 89 | 149 |
| 181744 | 181761 | Major (9) | 460058 | AGCAGCTGCAACCTGGCA | 4-9-5 | 85 | 227 |
| 181744 | 181762 | Major (10) | 460069 | GAGCAGCTGCAACCTGGCA | 5-10-4 | 91 | 149 |
| 181744 | 181762 | Major (10) | 460089 | GAGCAGCTGCAACCTGGCA | 5-8-6 | 54 | 149 |
| 181744 | 181762 | Major (10) | 460167 | GAGCAGCTGCAACCTGGCA | 6-7-6 | 85 | 149 |
| 181744 | 181762 | Major (10) | 460186 | GAGCAGCTGCAACCTGGCA | 6-8-5 | 84 | 149 |
| 181745 | 181761 | Major (9) | 459975 | AGCAGCTGCAACCTGGC | 2-9-6 | 86 | 228 |
| 181745 | 181760 | Major (8) | 459995 | GCAGCTGCAACCTGGC | 3-9-4 | 87 | 229 |
| 181745 | 181761 | Major (9) | 460008 | AGCAGCTGCAACCTGGC | 3-9-5 | 83 | 228 |
| 181745 | 181761 | Major (9) | 460049 | AGCAGCTGCAACCTGGC | 4-9-4 | 88 | 228 |
| 181745 | 181761 | Major (9) | 460079 | AGCAGCTGCAACCTGGC | 5-7-5 | 46 | 228 |
| 181745 | 181761 | Major (9) | 460099 | AGCAGCTGCAACCTGGC | 5-9-3 | 44 | 228 |
| 181745 | 181763 | Major (11) | 460108 | AGAGCAGCTGCAACCTGGC | 5-9-5 | 50 | 230 |
| 181745 | 181761 | Major (9) | 460177 | AGCAGCTGCAACCTGGC | 6-9-2 | 67 | 228 |
| 181746 | 181760 | Major (8) | 459966 | GCAGCTGCAACCTGG | Uniform | 26 | 231 |
| 181746 | 181760 | Major (8) | 459985 | GCAGCTGCAACCTGG | 3-9-3 | 69 | 231 |
| 181746 | 181760 | Major (8) | 460039 | GCAGCTGCAACCTGG | 4-7-4 | 56 | 231 |
| 181746 | 181764 | Major (12) | 460110 | AAGAGCAGCTGCAACCTGG | 5-9-5 | 75 | 232 |
| 181747 | 181765 | Major (13) | 460113 | CAAGAGCAGCTGCAACCTG | 5-9-5 | 36 | 233 |
| 181748 | 181766 | Major (14) | 460115 | GCAAGAGCAGCTGCAACCT | 5-9-5 | 78 | 234 |
| 181749 | 181767 | Major (15) | 460117 | TGCAAGAGCAGCTGCAACC | 5-9-5 | 73 | 235 |

TABLE 19

Comparison of inhibition of human HTT mRNA levels by ISIS 387916 and chimeric antisense oligonucleotides targeted to SNP rs1006798 (nucleobases 198015 to 198035 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGCACATTCCAAG | 5-10-5 | 98 | 6 |
| 198015 | 198033 | Minor (8) | 459911 | ACCATGATATCTCCAGCAC | 5-9-5 | 33 | 236 |
| 198015 | 198033 | Minor (8) | 459919 | ACCATGACATCTCCAGCAC | 5-9-5 | 26 | 237 |
| 198017 | 198035 | Major (10) | 459907 | CCACCATGATATCTCCAGC | 5-9-5 | 32 | 238 |
| 198017 | 198035 | Minor (10) | 459915 | CCACCATGACATCTCCAGC | 5-9-5 | 51 | 239 |

Example 6: Dose-Dependent Antisense Inhibition of Human Huntingtin mRNA Levels in Coriell Fibroblast Cell Lines Gapmers from the studies described in Example 5 were selected and tested at various doses in GM04281, GM02171, and GM02173B cell lines. Each cell line was plated at a density of 25,000 cells per well and transfected using electroporation with 750 nM, 1,500 nM, 3,000 nM, 6,000 nM, and 12,000 nM concentrations of antisense oligonucleotide, as specified in Tables 20, 21, and 22. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 20, 21, and 22.

TABLE 20

Dose-dependent antisense inhibition of human HTT in GM04281 cells

| ISIS No. | 750 nM | 1,500 nM | 3,000 nM | 6,000 nM | 12,000 nM | $IC_{50}$ (μM) |
|---|---|---|---|---|---|---|
| 387916 | 56 | 81 | 89 | 96 | 98 | 0.6 |
| 435869 | 38 | 49 | 66 | 86 | 91 | 1.4 |
| 435874 | 33 | 27 | 37 | 49 | 62 | 8.4 |
| 435879 | 42 | 55 | 73 | 86 | 96 | 1.1 |
| 435890 | 39 | 51 | 74 | 83 | 89 | 1.3 |
| 459978 | 29 | 33 | 51 | 69 | 86 | 2.5 |
| 459992 | 14 | 27 | 51 | 54 | 84 | 3.2 |
| 460012 | 15 | 24 | 54 | 70 | 81 | 3.1 |
| 460016 | 3 | 36 | 48 | 71 | 77 | 3.3 |
| 460019 | 54 | 59 | 74 | 87 | 94 | 0.7 |
| 460026 | 48 | 47 | 71 | 79 | 88 | 0.8 |
| 460028 | 39 | 38 | 73 | 77 | 87 | 1.4 |
| 460031 | 44 | 62 | 72 | 87 | 92 | 0.9 |
| 460033 | 11 | 38 | 52 | 64 | 87 | 3.0 |
| 460065 | 43 | 54 | 74 | 89 | 96 | 1.1 |
| 460068 | 47 | 28 | 63 | 76 | 90 | 2.6 |
| 460069 | 38 | 50 | 65 | 77 | 91 | 1.4 |
| 460071 | 53 | 61 | 80 | 89 | 93 | 0.6 |
| 460073 | 16 | 39 | 42 | 58 | 75 | 4.0 |
| 460076 | 26 | 47 | 54 | 70 | 86 | 2.1 |
| 460085 | 48 | 60 | 79 | 89 | 94 | 0.8 |
| 460140 | 6 | 24 | 44 | 44 | 64 | 6.6 |
| 460142 | 2 | 38 | 46 | 46 | 68 | 4.8 |
| 460152 | 35 | 61 | 76 | 92 | 94 | 1.2 |
| 460157 | 51 | 36 | 53 | 74 | 89 | 2.6 |
| 460162 | 64 | 41 | 71 | 76 | 85 | 2.1 |
| 460165 | 41 | 50 | 56 | 76 | 84 | 1.5 |

TABLE 21

Dose-dependent antisense inhibition of human HTT in GM02171 cells

| ISIS No. | 750 nM | 1,500 nM | 3,000 nM | 6,000 nM | 12,000 nM | $IC_{50}$ (μM) |
|---|---|---|---|---|---|---|
| 387916 | 53 | 66 | 88 | 96 | 98 | 0.7 |
| 435869 | 4 | 20 | 36 | 63 | 86 | 3.9 |
| 435870 | 25 | 39 | 48 | 62 | 83 | 2.8 |
| 435874 | 12 | 20 | 18 | 27 | 37 | >12.0 |
| 435879 | 10 | 7 | 11 | 42 | 51 | 10.6 |
| 435890 | 10 | 23 | 29 | 29 | 55 | 9.2 |
| 459978 | 15 | 7 | 6 | 29 | 52 | 12.7 |
| 459992 | 11 | 19 | 26 | 39 | 62 | 8.7 |
| 460012 | 3 | 3 | 10 | 19 | 41 | >12.0 |
| 460016 | 0 | 14 | 12 | 22 | 48 | >12.0 |
| 460019 | 27 | 21 | 41 | 60 | 73 | 4.4 |

TABLE 21-continued

Dose-dependent antisense inhibition of human HTT in GM02171 cells

| ISIS No. | 750 nM | 1,500 nM | 3,000 nM | 6,000 nM | 12,000 nM | $IC_{50}$ (μM) |
|---|---|---|---|---|---|---|
| 460026 | 9 | 25 | 30 | 46 | 58 | 7.8 |
| 460028 | 24 | 8 | 32 | 54 | 77 | 5.3 |
| 460031 | 8 | 25 | 42 | 60 | 83 | 3.8 |
| 460033 | 11 | 25 | 30 | 40 | 75 | 4.1 |
| 460065 | 11 | 16 | 11 | 31 | 53 | 10.3 |
| 460068 | 15 | 13 | 39 | 44 | 53 | 8.8 |
| 460069 | 17 | 28 | 37 | 60 | 79 | 3.9 |
| 460071 | 16 | 36 | 58 | 70 | 88 | 2.6 |
| 460073 | 5 | 19 | 24 | 33 | 56 | 8.7 |
| 460076 | 19 | 29 | 44 | 54 | 83 | 3.3 |
| 460085 | 10 | 15 | 17 | 28 | 31 | >12.0 |
| 460140 | 8 | 22 | 22 | 28 | 47 | >12.0 |
| 460142 | 11 | 24 | 28 | 36 | 38 | >12.0 |
| 460152 | 14 | 21 | 8 | 25 | 44 | 22 |
| 460157 | 22 | 21 | 29 | 44 | 66 | 6.7 |
| 460162 | 24 | 55 | 52 | 62 | 82 | 2.8 |
| 460165 | 14 | 34 | 50 | 69 | 81 | 3.1 |

TABLE 22

Dose-dependent antisense inhibition of human HTT in GM02173B cells

| ISIS No. | 750 nM | 1,500 nM | 3,000 nM | 6,000 nM | 12,000 nM | $IC_{50}$ (μM) |
|---|---|---|---|---|---|---|
| 387916 | 37 | 63 | 86 | 88 | 98 | 1.0 |
| 435869 | 10 | 20 | 43 | 70 | 85 | 3.5 |
| 435870 | 24 | 24 | 56 | 72 | 87 | 2.3 |
| 435874 | 0 | 11 | 12 | 30 | 44 | >12.0 |
| 435879 | 4 | 17 | 43 | 64 | 74 | 4.3 |
| 435890 | 31 | 29 | 54 | 57 | 69 | 4.4 |
| 459978 | 7 | 13 | 17 | 35 | 64 | 8.4 |
| 459992 | 18 | 15 | 30 | 51 | 71 | 5.7 |
| 460012 | 0 | 10 | 24 | 37 | 72 | 7.1 |
| 460016 | 15 | 5 | 30 | 38 | 59 | 9.5 |
| 460019 | 10 | 32 | 51 | 65 | 87 | 3.1 |
| 460026 | 0 | 34 | 21 | 55 | 65 | 6.4 |
| 460028 | 0 | 14 | 31 | 51 | 77 | 5.2 |
| 460031 | 0 | 31 | 53 | 71 | 88 | 3.2 |
| 460033 | 11 | 8 | 6 | 52 | 84 | 5.0 |
| 460065 | 19 | 37 | 53 | 58 | 74 | 3.6 |
| 460068 | 17 | 11 | 31 | 59 | 69 | 5.5 |
| 460069 | 11 | 21 | 37 | 55 | 75 | 4.6 |
| 460071 | 6 | 42 | 61 | 83 | 88 | 2.6 |
| 460073 | 7 | 13 | 19 | 49 | 66 | 6.3 |
| 460076 | 27 | 31 | 49 | 43 | 81 | 2.9 |
| 460085 | 17 | 34 | 51 | 54 | 68 | 4.4 |
| 460140 | 0 | 2 | 28 | 18 | 46 | >12.0 |
| 460142 | 2 | 32 | 37 | 42 | 59 | 7.6 |
| 460152 | 17 | 32 | 35 | 51 | 66 | 5.5 |
| 460157 | 9 | 34 | 38 | 52 | 74 | 4.5 |
| 460162 | 22 | 45 | 57 | 65 | 79 | 2.5 |
| 460165 | 5 | 45 | 52 | 72 | 84 | 3.2 |

Example 7: Antisense Inhibition of Human HTT in GM04281 Cells and GM02171 Cells Additional antisense oligonucleotides were designed based on the gapmers selected from studies described in Example 2. These oligonucleotides were designed by creating gapmers shifted slightly upstream and downstream (i.e. "microwalk") of the original gapmers from Table 4.

The gapmers were tested in the GM04281 and the GM02171 cell lines. Cultured GM04281 or GM02171 cells at a density of 25,000 cells per well were transfected using electroporation with 10,000 nM antisense oligonucleotide. After a treatment period of approximately 24 hours, RNA was isolated from the cells and HTT mRNA levels were measured by quantitative real-time PCR using primer probe set RTS2617. HTT mRNA levels were adjusted according to total RNA content, as measured by RIBOGREEN. Results are presented as percent inhibition of HTT mRNA, relative to untreated control cells.

The gapmers, from which the newly designed oligonucleotides were derived, were also included in the assay. These parent gapmers, ISIS 435294, ISIS 435295, ISIS 435301, ISIS 435303, ISIS 435304, ISIS 435305, ISIS 435308, ISIS 435330, ISIS 435331, ISIS 435337, ISIS 435339, ISIS 435340, ISIS 435341, ISIS 435344, ISIS 435862, ISIS 435863, ISIS 435864, ISIS 435866, ISIS 435867, ISIS 435868, ISIS 435871, ISIS 435873, ISIS 435875, ISIS 435876, ISIS 435878, ISIS 435880, ISIS 435881, ISIS 435882, ISIS 435884, ISIS 435890, and ISIS 435897 are marked with an asterisk (*) in the table. ISIS 387916 was included in the study as a benchmark oligonucleotide against which the potency of the antisense oligonucleotides targeting nucleotides overlapping each SNP position could be compared.

The chimeric antisense oligonucleotides in Tables 23-48 were designed as 5-9-5 MOE gapmers. The 5-9-5 gapmers are 19 nucleotides in length, wherein the central gap segment is comprised of nine 2'-deoxynucleotides and is flanked on both 5' and 3' directions by wings comprising 5 nucleotides each. Each nucleotide in the 5' wing segment and each nucleotide in the 3' wing segment has a 2'-MOE modification. The internucleoside linkages throughout each gapmer are phosphorothioate (P=S) linkages. All cytosine nucleobases throughout each gapmer are 5-methylcytosines.

The gapmers are organized in Tables 23-48, according to the SNP site they target. "Start site" indicates the 5'-most nucleotide to which the gapmer is targeted. "Stop site" indicates the 3'-most nucleotide to which the gapmer is targeted. 'Target allele' indicates whether the gapmer is targeted to the major or the minor allele. The number in parentheses indicates the position on the oligonucleotide opposite to the SNP position.

TABLE 23

Comparison of inhibition of human HTT mRNA levels by ISIS 387916 and chimeric antisense oligonucleotides targeted to SNP rs3856973 (nucleobases 19815 to 19835 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 19815 | 19833 | *435330 | Major (8) | TAACACTCGATTAACCCTG | 88 | 31 | 8 |
| 19816 | 19834 | 476441 | Major (9) | TTAACACTCGATTAACCCT | 88 | 0 | 240 |
| 19817 | 19835 | *435294 | Major (10) | GTTAACACTCGATTAACCC | 72 | 30 | 10 |

TABLE 24

Comparison of inhibition of human HTT mRNA levels by ISIS 387916 and chimeric antisense oligonucleotides targeted to SNP rs2285086 (nucleobases 28901 to 28921 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 28901 | 28919 | 463570 | Major (8) | TAGTTCATCCCAGTGAGAA | 66 | 12 | 241 |
| 28902 | 28920 | 463573 | Major (9) | CTAGTTCATCCCAGTGAGA | 66 | 36 | 242 |
| 28903 | 28921 | *435864 | Major (10) | GCTAGTTCATCCCAGTGAG | 40 | 18 | 12 |

TABLE 25

Comparison of inhibition of human HTT mRNA levels by ISIS 387916 and chimeric antisense oligonucleotides targeted to SNP rs7659144 (nucleobases 37963 to 37983 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 37963 | 37981 | 476462 | Major (8) | GAAATGGGTTTTTCCACAT | 38 | 0 | 243 |

TABLE 25-continued

Comparison of inhibition of human HTT mRNA levels by ISIS 387916 and chimeric antisense oligonucleotides targeted to SNP rs7659144 (nucleobases 37963 to 37983 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 37964 | 37982 | 476439 | Major (9) | GGAAATGGGTTTTTCCACA | 80 | 45 | 244 |
| 37965 | 37983 | *435878 | Major (10) | TGGAAATGGGTTTTTCCAC | 76 | 3 | 14 |

TABLE 26

Comparison of inhibition of human HTT mRNA levels by ISIS 387916 and chimeric antisense oligonucleotides targeted to SNP rs16843804 (nucleobases 44032 to 44052 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 44032 | 44050 | 476471 | Major (8) | TAACCGTGGCATGGGCAGT | 82 | 53 | 245 |
| 44033 | 44051 | 476452 | Major (9) | TTAACCGTGGCATGGGCAG | 84 | 44 | 246 |
| 44034 | 44052 | *435863 | Major (10) | TTTAACCGTGGCATGGGCA | 89 | 89 | 16 |

TABLE 27

Comparison of inhibition of human HTT mRNA levels by ISIS 387916 and chimeric antisense oligonucleotides targeted to SNP rs2024115 (nucleobases 44210 to 44230 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 44210 | 44228 | *435331 | Major (8) | TTCAAGCTAGTAACGATGC | 84 | 20 | 18 |
| 44211 | 44229 | 476447 | Major (9) | CTTCAAGCTAGTAACGATG | 87 | 57 | 247 |
| 44212 | 44230 | *435295 | Major (10) | ACTTCAAGCTAGTAACGAT | 85 | 67 | 20 |

TABLE 28

Comparison of inhibition of human HTT mRNA levels by ISIS 387916 and chimeric antisense oligonucleotides targeted to SNP rs10015979 (nucleobases 49084 to 49104 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 49084 | 49102 | 476470 | Major (8) | AGCTAGGTTAAAGAGTCAC | 55 | 74 | 248 |
| 49085 | 49103 | 476450 | Major (9) | CAGCTAGGTTAAAGAGTCA | 44 | 5 | 249 |
| 49086 | 49104 | *435862 | Major (10) | GCAGCTAGGTTAAAGAGTC | 56 | 49 | 22 |

Comparison of inhibition of human HTT mRNA levels by ISIS 387916 and chimeric antisense oligonucleotides targeted to SNP rs7691627 (nucleobases 51052 to 51072 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 51052 | 51070 | 476467 | Major (8) | TAAGAAACACAATCAAAGA | 45 | 21 | 250 |
| 51053 | 51071 | 476445 | Major (9) | ATAAGAAACACAATCAAAG | 34 | 1 | 251 |
| 51054 | 51072 | *435880 | Major (10) | AATAAGAAACACAATCAAA | 68 | 7 | 24 |

TABLE 30

Comparison of inhibition of human HTT mRNA levels by ISIS 387916 and chimeric antisense oligonucleotides targeted to SNP rs6446723 (nucleobases 66455 to 66475 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 66455 | 66473 | 476463 | Major (8) | ATTTTCTAGACTTTATGAT | 37 | 7 | 252 |
| 66456 | 66474 | 476440 | Major (9) | AATTTTCTAGACTTTATGA | 57 | 0 | 253 |
| 66457 | 66475 | *435875 | Major (10) | TAATTTTCTAGACTTTATG | 42 | 0 | 30 |

TABLE 31

Comparison of inhibition of human HTT mRNA levels by ISIS 387916 and a chimeric antisense oligonucleotide targeted to SNP rs363064 (nucleobases 81053 to 81071 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 81053 | 81071 | 476461 | Major (9) | GAGAATACGGGTAACATTT | 87 | 62 | 254 |

TABLE 32

Comparison of inhibition of human HTT mRNA levels by ISIS 387916 and chimeric antisense oligonucleotides targeted to SNP rs11731237 (nucleobases 91455 to 91475 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 91455 | 91473 | 476468 | Major (8) | TGGGCAGGAAGGACTGAAC | 58 | 56 | 255 |
| 91456 | 91474 | 476448 | Major (9) | GTGGGCAGGAAGGACTGAA | 61 | 69 | 256 |
| 91457 | 91475 | *435884 | Major (10) | GGTGGGCAGGAAGGACTGA | 59 | 49 | 68 |

TABLE 33

Comparison of inhibition of human HTT mRNA levels by ISIS 387916 and chimeric antisense oligonucleotides targeted to SNP rs4690073 (nucleobases 99792 to 99812 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 99792 | 99810 | *435337 | Major (8) | CCTAAATCAATCTACAAGT | 69 | 7 | 70 |
| 99793 | 99811 | 476446 | Major (9) | CCCTAAATCAATCTACAAG | 61 | 0 | 257 |
| 99794 | 99812 | *435301 | Major (10) | TCCCTAAATCAATCTACAA | 63 | 1 | 72 |

TABLE 34

Comparison of inhibition of human HTT mRNA levels by ISIS 387916 and chimeric antisense oligonucleotides targeted to SNP rs34315806 (nucleobases 101676 to 101696 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 101676 | 101694 | 463569 | Major (8) | CTTTTCCGTGCTGTTCTGA | 96 | 95 | 258 |
| 101677 | 101695 | 463572 | Major (9) | ACTTTTCCGTGCTGTTCTG | 93 | 91 | 259 |
| 101678 | 101696 | 463567 | Major (10) | AACTTTTCCGTGCTGTTCT | 98 | 97 | 260 |

TABLE 35

Comparison of inhibition of human HTT mRNA levels by ISIS 387916 and chimeric antisense oligonucleotides targeted to SNP rs363099 (nucleobases 101698 to 101718 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 101698 | 101716 | *435339 | Major (8) | CTGAGCGGAGAAACCCTCC | 94 | 85 | 80 |
| 101699 | 101717 | 476458 | Major (9) | GCTGAGCGGAGAAACCCTC | 92 | 79 | 261 |
| 101700 | 101718 | *435303 | Major (10) | GGCTGAGCGGAGAAACCCT | 96 | 93 | 82 |

TABLE 36

Comparison of inhibition of human HTT mRNA levels by ISIS 387916 and chimeric antisense oligonucleotides targeted to SNP rs363096 (nucleobases 119663 to 119683 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 119663 | 119681 | *435340 | Major (8) | TTCCCTAAAAACAAAAACA | 42 | 21 | 85 |

TABLE 36-continued

Comparison of inhibition of human HTT mRNA levels by ISIS 387916 and chimeric antisense oligonucleotides targeted to SNP rs363096 (nucleobases 119663 to 119683 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 119664 | 119682 | 476451 | Major (9) | ATTCCCTAAAAACAAAAAC | 0 | 0 | 262 |
| 119665 | 119683 | *435304 | Major (10) | GATTCCCTAAAAACAAAAA | 41 | 27 | 87 |

TABLE 37

Comparison of inhibition of human HTT mRNA levels by ISIS 387916 and chimeric antisense oligonucleotides targeted to SNP rs2298967 (nucleobases 125389 to 125409 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 125389 | 125407 | *435341 | Major (8) | CTTTTCTATTGTCTGTCCC | 83 | 65 | 89 |
| 125390 | 125408 | 476459 | Major (9) | GCTTTTCTATTGTCTGTCC | 89 | 82 | 263 |
| 125391 | 125409 | *435305 | Major (10) | TGCTTTTCTATTGTCTGTC | 92 | 85 | 91 |

TABLE 38

Comparison of inhibition of human HTT mRNA levels by ISIS 387916 and a chimeric antisense oligonucleotide targeted to SNP rs2298969 (nucleobases 125888 to 125906 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 125888 | 125906 | *435890 | Minor (10) | AAGGGATGCTGACTTGGGC | 91 | 64 | 94 |

TABLE 39

Comparison of inhibition of human HTT mRNA levels by ISIS 387916 and chimeric antisense oligonucleotides targeted to SNP rs6844859 (nucleobases 130128 to 130148 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 130128 | 130146 | 476466 | Major (8) | CTTCCTCACTGAGGATGAA | 87 | 64 | 264 |
| 130129 | 130147 | 476444 | Major (9) | CCTTCCTCACTGAGGATGA | 92 | 77 | 265 |
| 130130 | 130148 | *435876 | Major (10) | ACCTTCCTCACTGAGGATG | 94 | 87 | 95 |

TABLE 40

Comparison of inhibition of human HTT mRNA levels by ISIS 387916 and chimeric antisense oligonucleotides targeted to SNP rs363092 (nucleobases 135671 to 135691 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 135671 | 135689 | 476464 | Major (8) | AACCACTTTGGGATGAATA | 51 | 71 | 266 |
| 135672 | 135690 | 476442 | Major (9) | AAACCACTTTGGGATGAAT | 58 | 59 | 267 |
| 135673 | 135691 | *435897 | Minor (10) | CAAACCACTTTGGGATGAA | 48 | 78 | 98 |

TABLE 41

Comparison of inhibition of human HTT mRNA levels by ISIS 387916 and chimeric antisense oligonucleotides targeted to SNP rs363088 (nucleobases 149972 to 149992 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGCACATTCCAAG | 100 | 99 | 6 |
| 149972 | 149990 | 476476 | Major (8) | ACAGCTATCTTCTCATCAA | 90 | 65 | 268 |
| 149973 | 149991 | 476460 | Major (9) | CACAGCTATCTTCTCATCA | 86 | 39 | 269 |
| 149974 | 149992 | *435871 | Major (10) | TCACAGCTATCTTCTCATC | 91 | 54 | 101 |

TABLE 42

Comparison of inhibition of human HTT mRNA levels by ISIS 387916 and chimeric antisense oligonucleotides targeted to SNP rs916171 (nucleobases 156457 to 156477 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGC ACATTCCAAG | 100 | 99 | 6 |
| 156457 | 156475 | 476465 | Major (8) | GAACAAAGAG AAGAATTTC | 38 | 0 | 270 |
| 156458 | 156476 | 476443 | Major (9) | AGAACAAAGA GAAGAATTT | 58 | 0 | 271 |
| 156459 | 156477 | *435881 | Major (10) | CAGAACAAAG AGAAGAATT | 59 | 16 | 105 |

TABLE 43

Comparison of inhibition of human HTT mRNA levels by ISIS 387916 and chimeric antisense oligonucleotides targeted to SNP rs362275 (nucleobases 164244 to 164264 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGC ACATTCCAAG | 100 | 99 | 6 |
| 164244 | 164262 | 476473 | Major (8) | GAAGCCTGAT AAAATCTCT | 83 | 51 | 272 |

TABLE 43-continued

Comparison of inhibition of human HTT mRNA levels by ISIS 387916 and chimeric antisense oligonucleotides targeted to SNP rs362275 (nucleobases 164244 to 164264 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 164245 | 164263 | 476454 | Major (9) | AGAAGCCTGA TAAAATCTC | 79 | 61 | 273 |
| 164246 | 164264 | *435868 | Major (10) | AAGAAGCCTG ATAAAATCT | 69 | 56 | 111 |

TABLE 44

Comparison of inhibition of human HTT mRNA levels by ISIS 387916 and chimeric antisense oligonucleotides targeted to SNP rs362273 (nucleobases 167061 to 167081 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGC ACATTCCAAG | 100 | 99 | 6 |
| 167061 | 167079 | 463568 | Major (8) | TGATCTGTAG CAGCAGCTT | 96 | 78 | 274 |
| 167062 | 167080 | 463571 | Major (9) | TTGATCTGTA GCAGCAGCT | 95 | 86 | 275 |
| 167063 | 167081 | 463566 | Major (10) | GTTGATCTGT AGCAGCAGC | 94 | 78 | 276 |

TABLE 45

Comparison of inhibition of human HTT mRNA levels by ISIS 387916 and chimeric antisense oligonucleotides targeted to SNP rs362272 (nucleobases 174622 to 174642 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGC ACATTCCAAG | 100 | 99 | 6 |
| 174622 | 174640 | *435344 | Major (8) | TAGAGGACGC CGTGCAGGG | 78 | 63 | 120 |
| 174623 | 174641 | 476456 | Major (9) | ATAGAGGACG CCGTGCAGG | 87 | 60 | 277 |
| 174624 | 174642 | *435308 | Major (10) | CATAGAGGAC GCCGTGCAG | 76 | 48 | 122 |

TABLE 46

Comparison of inhibition of human HTT mRNA levels by ISIS 387916 and chimeric antisense oligonucleotides targeted to SNP rs362271 (nucleobases 175160 to 175180 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGC ACATTCCAAG | 100 | 99 | 6 |
| 175160 | 175178 | 476472 | Major (8) | GTGTGTACAG AACCTGCCG | 85 | 52 | 278 |
| 175161 | 175179 | 476453 | Major (9) | CGTGTGTACA GAACCTGCC | 88 | 69 | 279 |
| 175162 | 175180 | *435867 | Major (10) | ACGTGTGTAC AGAACCTGC | 91 | 80 | 125 |

TABLE 47

Comparison of inhibition of human HTT mRNA levels by ISIS 387916 and chimeric antisense oligonucleotides targeted to SNP rs3775061 (nucleobases 178396 to 178416 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGC ACATTCCAAG | 100 | 99 | 6 |
| 178396 | 178414 | 476475 | Major (8) | TTCAGAATGC CTCATCTGG | 61 | 1 | 280 |
| 178397 | 178415 | 476457 | Major (9) | GTTCAGAATG CCTCATCTG | 80 | 50 | 281 |
| 178398 | 178416 | *435873 | Major (10) | TGTTCAGAAT GCCTCATCT | 80 | 43 | 127 |

TABLE 48

Comparison of inhibition of human HTT mRNA levels by ISIS 387916 and chimeric antisense oligonucleotides targeted to SNP rs362296 (nucleobases 186649 to 1786669 of SEQ ID NO: 1)

| Start Site | Stop Site | ISIS No | Target allele | Sequence | % inhibition in GM04281 | % inhibition in GM02171 | SEQ ID NO |
|---|---|---|---|---|---|---|---|
| 145466 | 145485 | 387916 | n/a | TCTCTATTGC ACATTCCAAG | 100 | 99 | 6 |
| 186649 | 186667 | 476469 | Major (8) | GGACAGGGTG TGCTCTCCG | 80 | 58 | 282 |
| 186650 | 186668 | 476449 | Major (9) | GGGACAGGGT GTGCTCTCC | 80 | 64 | 283 |
| 186651 | 186669 | *435882 | Major (10) | GGGGACAGGG TGTGCTCTC | 61 | 61 | 155 |

Example 8: Dose-Dependent Antisense Inhibition of Human Huntingtin mRNA Levels in Coriell Fibroblast Cell Lines Gapmers from the studies described in Example 7 were selected and tested at various doses in GM04281, GM02171, and GM02173B cell lines. Each cell line was plated at a density of 25,000 cells per well and transfected using electroporation with 750 nM, 1,500 nM, 3,000 nM, 6,000 nM, and 12,000 nM concentrations of antisense oligonucleotide, as specified in Tables 49, 50, and 51. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 49, 50, and 51.

TABLE 49

Dose-dependent antisense inhibition of human HTT in GM04281 cells

| ISIS No. | 750 nM | 1500 nM | 3000 nM | 6000 nM | 12000 nM | $IC_{50}$ (μM) |
|---|---|---|---|---|---|---|
| 387916 | 67 | 88 | 95 | 97 | 99 | <0.8 |
| 463566 | 25 | 65 | 79 | 88 | 95 | 1.5 |
| 463567 | 34 | 73 | 90 | 93 | 98 | 1.1 |
| 463568 | 33 | 56 | 75 | 87 | 92 | 1.3 |
| 463571 | 32 | 21 | 70 | 90 | 93 | 1.4 |
| 476441 | 11 | 27 | 50 | 70 | 87 | 3.1 |
| 476444 | 20 | 31 | 68 | 49 | 93 | 2.3 |
| 476449 | 4 | 28 | 34 | 47 | 77 | 4.9 |
| 476453 | 21 | 21 | 48 | 73 | 85 | 2.7 |
| 476455 | 5 | 19 | 34 | 56 | 80 | 4.6 |
| 476458 | 36 | 72 | 83 | 93 | 96 | 1.1 |
| 476459 | 23 | 59 | 75 | 85 | 91 | 1.5 |
| 476469 | 17 | 27 | 47 | 47 | 67 | 5.5 |
| 476473 | 0 | 6 | 32 | 50 | 68 | 6.2 |
| 476476 | 3 | 7 | 32 | 53 | 86 | 4.9 |

TABLE 50

Dose-dependent antisense inhibition of human HTT in GM02171 cells

| ISIS No. | 750 nM | 1500 nM | 3000 nM | 6000 nM | 12000 nM | $IC_{50}$ (μM) |
|---|---|---|---|---|---|---|
| 387916 | 59 | 79 | 93 | 98 | 98 | <0.8 |
| 463566 | 4 | 33 | 42 | 62 | 79 | 3.8 |
| 463567 | 38 | 41 | 69 | 85 | 94 | 1.5 |
| 463568 | 21 | 26 | 41 | 58 | 64 | 4.8 |
| 463571 | 8 | 23 | 56 | 63 | 75 | 3.7 |
| 476441 | 0 | 13 | 7 | 0 | 12 | >12.0 |
| 476444 | 11 | 0 | 0 | 67 | 59 | 8.8 |
| 476449 | 4 | 27 | 37 | 51 | 63 | 5.8 |
| 476453 | 6 | 40 | 40 | 51 | 73 | 4.9 |
| 476455 | 32 | 15 | 18 | 47 | 61 | 7.8 |
| 476458 | 42 | 54 | 71 | 86 | 84 | 1.2 |
| 476459 | 22 | 38 | 70 | 44 | 73 | 4.3 |
| 476469 | 7 | 24 | 30 | 56 | 58 | 7.8 |
| 476473 | 4 | 10 | 15 | 33 | 43 | >12.0 |
| 476476 | 5 | 16 | 18 | 23 | 41 | >12.0 |

TABLE 51

Dose-dependent antisense inhibition of human HTT in GM02171 cells

| ISIS No. | 750 nM | 1500 nM | 3000 nM | 6000 nM | 12000 nM | $IC_{50}$ (μM) |
|---|---|---|---|---|---|---|
| 387916 | 66 | 89 | 95 | 97 | 99 | <0.8 |
| 463566 | 32 | 55 | 76 | 77 | 93 | 1.3 |
| 463567 | 51 | 61 | 87 | 94 | 97 | 0.7 |
| 463568 | 26 | 23 | 72 | 87 | 94 | 1.6 |
| 463571 | 32 | 34 | 60 | 86 | 94 | 1.9 |
| 476441 | 18 | 18 | 27 | 47 | 44 | >12.0 |
| 476444 | 15 | 0 | 31 | 51 | 58 | 7.1 |
| 476449 | 27 | 33 | 56 | 80 | 81 | 2.6 |
| 476453 | 24 | 28 | 55 | 75 | 83 | 2.7 |
| 476455 | 24 | 26 | 52 | 55 | 73 | 3.7 |
| 476458 | 63 | 77 | 87 | 89 | 94 | 0.2 |
| 476459 | 37 | 55 | 56 | 62 | 86 | 1.5 |

TABLE 51-continued

Dose-dependent antisense inhibition of human HTT in GM02171 cells

| ISIS No. | 750 nM | 1500 nM | 3000 nM | 6000 nM | 12000 nM | $IC_{50}$ (μM) |
|---|---|---|---|---|---|---|
| 476469 | 22 | 41 | 40 | 63 | 76 | 2.9 |
| 476473 | 7 | 28 | 33 | 51 | 73 | 5.0 |
| 476476 | 11 | 29 | 26 | 55 | 69 | 4.6 |

Example 9: Antisense Inhibition of Human HTT in GM04281 Cells by Oligonucleotides Designed by Microwalk Additional gapmers were designed based on the gapmers selected from studies described in Example 4. These gapmers were designed by creating gapmers shifted slightly upstream and downstream (i.e. "microwalk") of the original gapmers from Tables 8, 9, and 10. Gapmers were also created with 3-9-3 or 5-9-5 motifs, and with constrained 6(S)—$CH_3$-bicyclic nucleic acid (BNA) molecules at various nucleoside positions.

These gapmers were tested in vitro. Cultured GM04281 cells at a density of 25,000 cells per well were transfected using electroporation with 5,000 nM antisense oligonucleotide. After a treatment period of approximately 24 hours, RNA was isolated from the cells and HTT mRNA levels were measured by quantitative real-time PCR. HTT mRNA levels were adjusted according to total RNA content, as measured by RIBOGREEN. Results are presented as percent inhibition of HTT mRNA, relative to untreated control cells.

The chimeric antisense oligonucleotides in Tables 52-56 were designed as 3-9-3 or 5-9-5 gapmers. The parent gapmers, ISIS 435869, ISIS 435870, ISIS 435874, ISIS 435879, and ISIS 435890, from which the newly designed gapmers were derived are marked with an asterisk (*) in the table. ISIS 387916 was included in the study as a benchmark oligonucleotide against which the potency of the antisense oligonucleotides targeting nucleotides overlapping each SNP position could be compared.

The 3-9-3 gapmers are 15 nucleotides in length, wherein the central gap segment is comprised of nine 2'-deoxynucleotides and is flanked on both 5' and 3' directions by wings comprising 3 sugar modified nucleosides each.

The 5-9-5 gapmers are 19 nucleotides in length, wherein the central gap segment is comprised of nine 2'-deoxynucleotides and is flanked on both 5' and 3' directions by wings comprising 5 sugar modified nucleosides each.

The internucleoside linkages throughout each gapmer are phosphorothioate (P═S) linkages. All cytosine nucleobases throughout each gapmer are 5-methylcytosines. Bolded and underlined nucleotides in Tables 52-56 indicate the positions of the 6(S)—$CH_3$-BNA molecules (e.g. cEt molecules) in each gapmer. Italicized nucleotides are MOE subunits.

"Start site" indicates the 5'-most nucleotide to which the gapmer is targeted. "Stop site" indicates the 3'-most nucleotide to which the gapmer is targeted. 'Target allele' indicates whether the gapmer is targeted to the major or the minor allele. The number in parentheses indicates the position on the oligonucleotide opposite to the SNP position.

TABLE 52

Comparison of inhibition of human HTT mRNA levels by ISIS 387916 and chimeric antisense oligonucleotides targeted to SNP rs4690072 (nucleobases 62147 to 62173 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | *TCTCT*ATTGC ACATT*CCAAG* | 5-10-5 | 97 | 6 |
| 62147 | 62165 | Major (6) | 460266 | *GTGCT***A**CCCA ACCT*TTCTG* | 5-9-5 | 63 | 169 |
| 62151 | 62169 | Major (10) | *435874 | *CACAG*TGCTA CCCA*ACCTT* | 5-9-5 | 50 | 28 |
| 62151 | 62169 | Major (10) | 460213 | *CACAG*TGCT**A** CCCA*ACCTT* | 5-9-5 | 22 | 28 |
| 62151 | 62169 | Major (10) | 460220 | *CACAG*TGC**T**A CCCA*ACCTT* | 5-9-5 | 24 | 28 |
| 62151 | 62169 | Major (10) | 460221 | *CACAG*TGCTA **C**CCA*ACCTT* | 5-9-5 | 28 | 28 |
| 62153 | 62167 | Major (8) | 460208 | *C***AG**TGCTACC C*A***AC***C* | 3-9-3 | 81 | 177 |
| 62155 | 62173 | Major (14) | 460267 | *ATATC*ACAGT GCT**A***CCCAA* | 5-9-5 | 37 | 180 |

TABLE 53

Comparison of inhibition of human HTT mRNA levels by ISIS 387916 and chimeric antisense oligonucleotides targeted to SNP rs2298969 (nucleobases 125884 to 125910 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | *TCTCT*ATTGC ACATT*CCAAG* | 5-10-5 | 97 | 6 |
| 125884 | 125902 | Minor (6) | 460233 | *GATGC***T**GACT TGGG*CCATT* | 5-9-5 | 76 | 182 |
| 125888 | 125906 | Minor (10) | *435890 | *AAGGG*ATGCT GACT*TGGGC* | 5-9-5 | 75 | 94 |
| 125888 | 125906 | Minor (10) | 460215 | *AAGGG*ATGC**T** GACT*TGGGC* | 5-9-5 | 26 | 94 |
| 125888 | 125906 | Minor (10) | 460224 | *AAGGG*ATG**C**T GACT*TGGGC* | 5-9-5 | 38 | 94 |
| 125888 | 125906 | Minor (10) | 460225 | *AAGGG*ATGCT **G**ACT*TGGGC* | 5-9-5 | 49 | 94 |
| 125890 | 125904 | Minor (8) | 460210 | *G***GG**ATGCTGA CT**TG***G* | 3-9-3 | 97 | 189 |
| 125892 | 125910 | Minor (14) | 460229 | *TGCCA*AGGGA TGC**T***GACTT* | 5-9-5 | 60 | 192 |

TABLE 54

Comparison of inhibition of human HTT mRNA levels by ISIS 387916 and chimeric antisense oligonucleotides targeted to SNP rs7685686 (nucleobases 146782 to 146808 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGC ACATTCCAAG | 5-10-5 | 97 | 6 |
| 146782 | 146800 | Major (6) | 460232 | AATTGTCATC ACCAGAAAA | 5-9-5 | 82 | 195 |
| 146786 | 146804 | Major (10) | *435879 | AATAAATTGT CATCACCAG | 5-9-5 | 84 | 99 |
| 146786 | 146804 | Major (10) | 460214 | AATAAATTGT CATCACCAG | 5-9-5 | 33 | 99 |
| 146786 | 146804 | Major (10) | 460222 | AATAAATTGT CATCACCAG | 5-9-5 | 87 | 99 |
| 146786 | 146804 | Major (10) | 460223 | AATAAATTGT CATCACCAG | 5-9-5 | 75 | 99 |
| 146788 | 146802 | Major (8) | 460209 | TAAATTGTCA TCACC | 3-9-3 | 96 | 203 |
| 146790 | 146808 | Major (14) | 460228 | TATTAATAAA TTGTCATCA | 5-9-5 | 0 | 206 |

TABLE 55

Comparison of inhibition of human HTT mRNA levels by ISIS 387916 and chimeric antisense oligonucleotides targeted to SNP rs362331 (nucleobases 155475 to 155501 of SEQ ID NO: 1)

| Start Site | Stop Site | Target allele | ISIS No. | Sequence | Motif | % inhibition | SEQ ID NO |
|---|---|---|---|---|---|---|---|
| 145466 | 145485 | n/a | 387916 | TCTCTATTGC ACATTCCAAG | 5-10-5 | 97 | 6 |
| 155475 | 155493 | Major (6) | 460231 | ACAGTAGATG AGGGAGCAG | 5-9-5 | 88 | 209 |
| 155479 | 155497 | Major (10) | *435870 | GCACACAGTA GATGAGGGA | 5-9-5 | 86 | 103 |
| 155479 | 155497 | Major (10) | 460212 | GCACACAGTA GATGAGGGA | 5-9-5 | 89 | 103 |
| 155479 | 155497 | Major (10) | 460218 | GCACACAGTA GATGAGGGA | 5-9-5 | 90 | 103 |
| 155479 | 155497 | Major (10) | 460219 | GCACACAGTA GATGAGGGA | 5-9-5 | 88 | 103 |
| 155481 | 155495 | Major (8) | 460207 | ACACAGTAGA TGAGG | 3-9-3 | 89 | 217 |
| 155483 | 155501 | Major (14) | 460227 | AAGTGCACAC AGTAGATGA | 5-9-5 | 45 | 220 |

TABLE 56

| Comparison of inhibition of human HTT mRNA levels by ISIS 387916 and chimeric antisense oligonucleotides targeted to SNP rs362306 (nucleobases 181740 to 181766 of SEQ ID NO: 1) | | | | | | | |
|---|---|---|---|---|---|---|---|
| Start Site | Stop Site | Target allele | ISIS No. | Sequence | Motif | % inhibition | SEQ ID NO |
| 145466 | 145485 | n/a | 387916 | *TCTCT*ATTGC ACATT*CCAAG* | 5-10-5 | 97 | 6 |
| 181740 | 181758 | Major (6) | 460230 | *AGCTG*CAACC TGGC*AACAA* | 5-9-5 | 66 | 223 |
| 181744 | 181762 | Major (10) | *435869 | *GAGCA*GCTGC AACC*TGGCA* | 5-9-5 | 69 | 149 |
| 181744 | 181762 | Major (10) | 460211 | *GAGCA*GCTGC AACC*TGGCA* | 5-9-5 | 22 | 149 |
| 181744 | 181762 | Major (10) | 460216 | *GAGCA*GCTGC AACC*TGGCA* | 5-9-5 | 18 | 149 |
| 181744 | 181762 | Major (10) | 460217 | *GAGCA*GCTGC AACC*TGGCA* | 5-9-5 | 56 | 149 |
| 181746 | 181760 | Major (8) | 460206 | *GCA*GCTGCAA CC*TGG* | 3-9-3 | 83 | 231 |
| 181748 | 181766 | Major (14) | 460226 | *GCAAG*AGCAG CTGC*AACCT* | 5-9-5 | 51 | 234 |

Example 10: Dose-Dependent Antisense Inhibition of Human Huntingtin mRNA Levels in Coriell Fibroblast Cell Lines Gapmers from studies described in Example 9 were selected and tested at various doses in GM04281, GM02171 and GM02173B cell lines. Each cell line was plated at a density of 25,000 cells per well and transfected using electroporation with 312.5 nM, 625 nM, 1,250 nM, 2,500 nM, 5,000 nM and 10,000 nM concentrations of antisense oligonucleotide, as specified in Tables 75, 58, and 59. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 57, 58, and 59.

TABLE 57

| Dose-dependent antisense inhibition of human HTTin GM04281 cells | | | | | | | |
|---|---|---|---|---|---|---|---|
| ISIS No. | 312.5 nM | 625 nM | 1,250 nM | 2,500 nM | 5,000 nM | 10,000 nM | $IC_{50}$ (μM) |
| 387916 | 26 | 49 | 68 | 86 | 94 | 97 | 0.7 |
| 435869 | 0 | 0 | 23 | 48 | 62 | 82 | 3.2 |
| 435870 | 15 | 38 | 50 | 65 | 85 | 88 | 1.3 |
| 435874 | 14 | 22 | 32 | 49 | 65 | 73 | 2.7 |
| 435879 | 0 | 17 | 40 | 61 | 83 | 94 | 1.8 |
| 435890 | 5 | 13 | 37 | 56 | 70 | 82 | 2.3 |
| 460206 | 10 | 18 | 37 | 52 | 66 | 85 | 2.3 |
| 460207 | 20 | 27 | 50 | 65 | 80 | 91 | 1.4 |
| 460208 | 21 | 34 | 51 | 63 | 70 | 79 | 1.5 |
| 460209 | 52 | 74 | 89 | 94 | 94 | 95 | 0.2 |
| 460210 | 34 | 61 | 84 | 91 | 97 | 98 | 0.5 |

TABLE 57-continued

| Dose-dependent antisense inhibition of human HTTin GM04281 cells | | | | | | | |
|---|---|---|---|---|---|---|---|
| ISIS No. | 312.5 nM | 625 nM | 1,250 nM | 2,500 nM | 5,000 nM | 10,000 nM | $IC_{50}$ (μM) |
| 460212 | 13 | 31 | 50 | 62 | 75 | 82 | 1.6 |
| 460218 | 14 | 27 | 50 | 63 | 78 | 86 | 1.8 |
| 460219 | 9 | 32 | 42 | 64 | 77 | 87 | 1.6 |
| 460222 | 19 | 21 | 42 | 57 | 73 | 78 | 1.7 |
| 460231 | 12 | 24 | 41 | 57 | 71 | 84 | 1.9 |
| 460233 | 16 | 28 | 59 | 66 | 72 | 74 | 1.8 |
| 460266 | 4 | 17 | 32 | 48 | 60 | 75 | 2.9 |

TABLE 58

| Dose-dependent antisense inhibition of human HTT in GM02171 cells | | | | | | | |
|---|---|---|---|---|---|---|---|
| ISIS No. | 312.5 nM | 625 nM | 1,250 nM | 2,500 nM | 5,000 nM | 10,000 nM | $IC_{50}$ (μM) |
| 387916 | 32 | 56 | 77 | 89 | 95 | 97 | 0.7 |
| 435869 | 0 | 6 | 22 | 40 | 69 | 84 | 2.9 |
| 435870 | 15 | 19 | 32 | 51 | 68 | 77 | 2.4 |
| 435874 | 0 | 5 | 1 | 17 | 17 | 30 | >10.0 |
| 435879 | 0 | 8 | 0 | 16 | 36 | 47 | 15.3 |
| 435890 | 14 | 16 | 19 | 19 | 39 | 57 | 9.3 |
| 460206 | 5 | 13 | 33 | 41 | 68 | 80 | 2.7 |
| 460207 | 13 | 10 | 22 | 22 | 33 | 39 | 45.6 |
| 460208 | 13 | 15 | 11 | 11 | 15 | 53 | 10.8 |
| 460209 | 8 | 27 | 46 | 70 | 80 | 86 | 1.6 |
| 460210 | 19 | 37 | 55 | 75 | 88 | 96 | 1.1 |
| 460212 | 8 | 23 | 30 | 43 | 57 | 74 | 2.2 |
| 460218 | 15 | 26 | 27 | 36 | 52 | 78 | 3.2 |
| 460219 | 16 | 17 | 32 | 44 | 69 | 76 | 2.5 |
| 460222 | 14 | 3 | 0 | 0 | 13 | 0 | >10.0 |
| 460231 | 6 | 8 | 13 | 16 | 33 | 56 | 10.4 |
| 460233 | 27 | 30 | 39 | 46 | 61 | 73 | 2.4 |
| 460266 | 0 | 15 | 20 | 15 | 18 | 34 | >10.0 |

TABLE 59

| Dose-dependent antisense inhibition of human HTT in GM02173B cells | | | | | | | |
|---|---|---|---|---|---|---|---|
| ISIS No. | 312.5 nM | 625 nM | 1,250 nM | 2,500 nM | 5,000 nM | 10,000 nM | $IC_{50}$ (μM) |
| 387916 | 22 | 47 | 76 | 88 | 96 | 98 | 0.7 |
| 435869 | 10 | 0 | 16 | 38 | 59 | 76 | 3.9 |
| 435870 | 22 | 36 | 44 | 58 | 69 | 81 | 2.0 |
| 435874 | 11 | 6 | 25 | 23 | 32 | 42 | >10.0 |
| 435879 | 0 | 9 | 21 | 30 | 52 | 68 | 4.8 |
| 435890 | 12 | 16 | 30 | 31 | 48 | 66 | 4.5 |
| 460206 | 11 | 13 | 18 | 35 | 59 | 74 | 3.5 |
| 460207 | 15 | 25 | 30 | 37 | 42 | 66 | 4.3 |
| 460208 | 5 | 14 | 27 | 32 | 52 | 51 | 9.0 |
| 460209 | 27 | 49 | 61 | 79 | 81 | 74 | 0.8 |
| 460210 | 19 | 40 | 61 | 77 | 89 | 95 | 1.0 |
| 460212 | 0 | 19 | 32 | 32 | 61 | 78 | 2.9 |
| 460218 | 4 | 17 | 26 | 38 | 64 | 82 | 3.0 |
| 460219 | 5 | 6 | 26 | 47 | 68 | 84 | 2.9 |
| 460222 | 13 | 19 | 23 | 30 | 35 | 50 | 16.1 |
| 460231 | 7 | 33 | 25 | 35 | 54 | 77 | 3.7 |
| 460233 | 11 | 20 | 37 | 52 | 68 | 69 | 2.3 |
| 460266 | 12 | 6 | 10 | 21 | 25 | 47 | >10.0 |

Example 11: Dose-Dependent Antisense Inhibition of Human HTT in GM04281 and GM02171 Cells by Oligonucleotides Designed by Microwalk Additional gapmers were designed based on the gapmers selected from studies described in Example 10. These gapmers were designed by creating gapmers shifted slightly upstream and downstream (i.e. "microwalk") of the original gapmers from Tables 57, 58, and 59. Gapmers were also created with 4-9-4 MOE or 5-9-5 MOE motifs, and with constrained 6(S)—$CH_3$-bicyclic nucleic acid (BNA) molecules at various nucleotide positions.

These gapmers were tested in the GM04281 and GM02171 cell lines. Cultured GM04281 or GM02171 cells at a density of 25,000 cells per well were transfected using electroporation with 2,500 nM or 5,000 nM antisense oligonucleotide. After a treatment period of approximately 24 hours, RNA was isolated from the cells and HTT mRNA levels were measured by quantitative real-time PCR. HTT mRNA levels were adjusted according to total RNA content, as measured by RIBOGREEN. Results are presented as percent inhibition of HTT mRNA, relative to untreated control cells.

The chimeric antisense oligonucleotides in Tables 60, 61, and 62 were designed as 3-9-3, 4-9-4, or 5-9-5 MOE gapmers. The parent gapmers, ISIS 435890, ISIS 460210, ISIS 435879, ISIS 460209, ISIS 435870, and ISIS 460207, from which the newly designed gapmers were derived are marked with an asterisk (*) in the table. ISIS 387916 was included in the study as a benchmark oligonucleotide against which the potency of the antisense oligonucleotides targeting nucleotides overlapping each SNP position could be compared.

The 3-9-3 gapmers are 15 nucleotides in length, wherein the central gap segment is comprised of nine 2'-deoxynucleotides and is flanked on both 5' and 3' directions by wings comprising 3 nucleotides each.

The 4-9-4 gapmers are 17 nucleotides in length, wherein the central gap segment is comprised of nine 2'-deoxynucleotides and is flanked on both 5' and 3' directions by wings comprising 4 nucleotides each.

The 5-9-5 gapmers are 19 nucleotides in length, wherein the central gap segment is comprised of nine 2'-deoxynucleotides and is flanked on both 5' and 3' directions by wings comprising 5 nucleotides each.

The internucleoside linkages throughout each gapmer are phosphorothioate (P═S) linkages. All cytosine nucleobases throughout each gapmer are 5-methylcytosines. Bolded and underlined nucleotides in Tables 60, 61, and 62 indicate the positions of the 6(S)—$CH_3$-BNA (e.g. cEt molecules) molecules in each gapmer. Italicized nucleotides are MOE subunits.

The gapmers are organized in Tables 60, 61, and 62, according to the SNP site they target. "Start site" indicates the 5'-most nucleotide to which the gapmer is targeted. "Stop site" indicates the 3'-most nucleotide to which the gapmer is targeted. 'Target allele' indicates whether the gapmer is targeted to the major or the minor allele. The number in parentheses indicates the position on the oligonucleotide opposite to the SNP position.

TABLE 60

Comparison of inhibition of human HTT mRNA levels by ISIS 387916 and chimeric antisense oligonucleotides targeted to SNP rs2298969 (nucleobases 125888 to 125907 of SEQ ID NO: 1)

| Start position | Stop position | ISIS No. | Sequence | Motif | Concentration (nM) | % inhibition in GM04281 | % inhibition in GM02171 | SEQ ID NO |
|---|---|---|---|---|---|---|---|---|
| 145466 | 145485 | 387916 | TCTCTATTGCACATTCCAAG | 5-10-5 | 5000 | 57 | 24 | 6 |
| 125888 | 125907 | *435890 | *AAGGG*ATGCTGACT*TGGGC* | 5-9-5 | 2500 | 22 | 0 | 94 |
| | | | | | 5000 | 41 | 23 | |
| 125890 | 125904 | *460210 | G**GG**ATGCTGACT**TG**G | 3-9-3 | 2500 | 59 | 24 | 189 |
| | | | | | 5000 | 81 | 33 | |
| 125889 | 125905 | 474870 | A**GGG**ATGCTGACT**TGG**G | 4-9-4 | 2500 | 23 | 3 | 187 |
| | | | | | 5000 | 44 | 34 | |
| 125889 | 125905 | 474890 | **A**G**GG**ATGCTGACT**TG**G**G** | 4-9-4 | 2500 | 38 | 6 | 187 |
| | | | | | 5000 | 49 | 25 | |
| 125889 | 125905 | 474910 | **A**GG**G**ATGCTGACT**T**GG**G** | 4-9-4 | 2500 | 34 | 8 | 187 |
| | | | | | 5000 | 49 | 41 | |

TABLE 60-continued

Comparison of inhibition of human HTT mRNA levels by ISIS 387916 and chimeric antisense oligonucleotides targeted to SNP rs2298969 (nucleobases 125888 to 125907 of SEQ ID NO: 1)

| Start position | Stop position | ISIS No. | Sequence | Motif | Concentration (nM) | % inhibition in GM04281 | % inhibition in GM02171 | SEQ ID NO |
|---|---|---|---|---|---|---|---|---|
| 125889 | 125905 | 474914 | AGGGATGCTGA CTTGGG | 4-9-4 | 2500<br>5000 | 44<br>44 | 14<br>21 | 187 |
| 125888 | 125907 | 474918 | AAGGGATGCT GACTTGGGC | 5-9-5 | 2500<br>5000 | 31<br>26 | 0<br>25 | 94 |
| 125888 | 125907 | 474922 | AAGGGATGCT GACTTGGGC | 5-9-5 | 2500<br>5000 | 33<br>65 | 14<br>24 | 94 |
| 125889 | 125905 | 476332 | AGGGATGCTG ACTTGGG | 4-9-4 | 2500<br>5000 | 23<br>51 | 13<br>42 | 187 |
| 125888 | 125907 | 476336 | AAGGGATGCTG ACTTGGGC | 5-9-5 | 2500<br>5000 | 5<br>43 | 0<br>9 | 94 |

TABLE 61

Comparison of inhibition of human HTT mRNA levels by ISIS 387916 and chimeric antisense oligonucleotides targeted to SNP rs7685686 (nucleobases 146786 to 146805 of SEQ ID NO: 1)

| Start position | Stop position | ISIS No. | Sequence | Motif | Concentration (nM) | % inhibition in GM04281 | % inhibition in GM02171 | SEQ ID NO |
|---|---|---|---|---|---|---|---|---|
| 145466 | 145485 | 387916 | TCTCTATTGCA CATTCCAAG | 5-10-5 | 5000 | 57 | 24 | 6 |
| 146786 | 146805 | *435879 | AATAAATTGTC ATCACCAG | 5-9-5 | 2500<br>5000 | 39<br>59 | 0<br>19 | 99 |
| 146788 | 146802 | *460209 | TAAATTGTCAT CACC | 3-9-3 | 2500<br>5000 | 3<br>13 | 0<br>5 | 203 |
| 146787 | 146803 | 474871 | ATAAATTGTCA TCACCA | 4-9-4 | 2500<br>5000 | 82<br>83 | 32<br>58 | 200 |
| 146787 | 146803 | 474891 | ATAAATTGTCA TCACCA | 4-9-4 | 2500<br>5000 | 84<br>89 | 29<br>56 | 200 |
| 146787 | 146803 | 474911 | ATAAATTGTCA TCACCA | 4-9-4 | 2500<br>5000 | 70<br>83 | 18<br>40 | 200 |
| 146787 | 146803 | 474915 | ATAAATTGTCA TCACCA | 4-9-4 | 2500<br>5000 | 38<br>74 | 9<br>14 | 200 |
| 146786 | 146805 | 474919 | AATAAATTGTC ATCACCAG | 5-9-5 | 2500<br>5000 | 80<br>84 | 7<br>37 | 99 |
| 146786 | 146805 | 474923 | AATAAATTGTC ATCACCAG | 5-9-5 | 2500<br>5000 | 74<br>83 | 32<br>51 | 99 |
| 146787 | 146803 | 476333 | ATAAATTGTCA TCACCA | 4-9-4 | 2500<br>5000 | 75<br>86 | 28<br>21 | 200 |
| 146786 | 146805 | 476337 | AATAAATTGTC ATCACCAG | 5-9-5 | 2500<br>5000 | 71<br>83 | 6<br>31 | 99 |

TABLE 62

Comparison of inhibition of human HTT mRNA levels by ISIS 387916 and chimeric antisense oligonucleotides targeted to SNP rs362331 (nucleobases 155478 to 155498 of SEQ ID NO: 1)

| Start position | Stop position | ISIS No. | Sequence | Motif | Concentration (nM) | % inhibition in GM04281 | % inhibition in GM02171 | SEQ ID NO |
|---|---|---|---|---|---|---|---|---|
| 145466 | 145485 | 387916 | TCTCTATTGCAC ATTCCAAG | 5-10-5 | 5000 | 57 | 24 | 6 |
| 155479 | 155498 | *435870 | GCACACAGTAG ATGAGGGA | 5-9-5 | 2500<br>5000 | 19<br>49 | 1<br>34 | 103 |
| 155481 | 155495 | *460207 | ACACAGTAGAT GAGG | 3-9-3 | 2500<br>5000 | 0<br>7 | 0<br>8 | 217 |
| 155480 | 155496 | 474872 | CACACAGTAGA TGAGGG | 4-9-4 | 2500<br>5000 | 35<br>63 | 9<br>37 | 214 |
| 155480 | 155496 | 474892 | CACACAGTAGA TGAGGG | 4-9-4 | 2500<br>5000 | 43<br>69 | 16<br>31 | 214 |
| 155480 | 155496 | 474912 | CACACAGTAGA TGAGGG | 4-9-4 | 2500<br>5000 | 16<br>36 | 9<br>6 | 214 |
| 155480 | 155496 | 474916 | CACACAGTAGA TGAGGG | 4-9-4 | 2500<br>5000 | 22<br>47 | 5<br>7 | 214 |
| 155479 | 155498 | 474920 | GCACACAGTAG ATGAGGGA | 5-9-5 | 2500<br>5000 | 19<br>43 | 0<br>23 | 103 |
| 155479 | 155498 | 474924 | GCACACAGTAG ATGAGGGA | 5-9-5 | 2500<br>5000 | 29<br>48 | 8<br>22 | 103 |
| 155480 | 155496 | 476334 | CACACAGTAGA TGAGGG | 4-9-4 | 2500<br>5000 | 35<br>62 | 7<br>32 | 214 |
| 155479 | 155498 | 476338 | GCACACAGTAG ATGAGGGA | 5-9-5 | 2500<br>5000 | 26<br>40 | 9<br>4 | 103 |
| 155479 | 155495 | 474873 | ACACAGTAGAT GAGGGA | 4-9-4 | 2500<br>5000 | 53<br>61 | 9<br>29 | 285 |
| 155479 | 155495 | 474893 | ACACAGTAGAT GAGGGA | 4-9-4 | 2500<br>5000 | 47<br>59 | 5<br>30 | 285 |
| 155479 | 155495 | 474913 | ACACAGTAGAT GAGGGA | 4-9-4 | 2500<br>5000 | 30<br>29 | 16<br>17 | 285 |
| 155479 | 155495 | 474917 | ACACAGTAGAT GAGGGA | 4-9-4 | 2500<br>5000 | 23<br>40 | 12<br>5 | 285 |
| 155478 | 155497 | 474921 | CACACAGTAGA TGAGGGAG | 5-9-5 | 2500<br>5000 | 28<br>43 | 0<br>23 | 212 |
| 155478 | 155497 | 474925 | CACACAGTAGA TGAGGGAG | 5-9-5 | 2500<br>5000 | 30<br>61 | 9<br>34 | 212 |
| 155479 | 155495 | 476335 | ACACAGTAGAT GAGGGA | 4-9-4 | 2500<br>5000 | 35<br>53 | 2<br>31 | 285 |
| 155478 | 155497 | 476339 | CACACAGTAGA TGAGGGAG | 5-9-5 | 2500<br>5000 | 15<br>34 | 0<br>13 | 212 |

Example 12: Dose-Dependent Antisense Inhibition of Human Huntingtin mRNA Levels in Coriell Fibroblast Cell Lines Gapmers from the studies described in Example 11 were selected and tested at various doses in GM04281, GM02171 and GM02173B cell lines. Each cell line was plated at a density of 25,000 cells per well and transfected using electroporation with 625 nM, 1,250 nM, 2,500 nM, 5,000 nM and 10,000 nM concentrations of antisense oligonucleotide, as specified in Tables 63, 64, and 65. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 63, 64, and 65.

TABLE 63

| Dose-dependent antisense inhibition of human HTT in GM04281 cells | | | | | | |
|---|---|---|---|---|---|---|
| ISIS No | 625 nM | 1250 nM | 2500 nM | 5000 nM | 10000 nM | $IC_{50}$ (μM) |
| 387916 | 70 | 83 | 94 | 96 | 98 | <0.6 |
| 460207 | 51 | 63 | 83 | 91 | 93 | 0.5 |
| 460209 | 83 | 93 | 96 | 97 | 97 | <0.6 |
| 460210 | 70 | 89 | 94 | 97 | 98 | 0.6 |
| 474871 | 94 | 97 | 96 | 96 | 95 | <0.6 |
| 474873 | 51 | 73 | 89 | 94 | 95 | 0.5 |
| 474891 | 93 | 95 | 97 | 96 | 95 | <0.6 |
| 474892 | 48 | 72 | 89 | 93 | 95 | 0.6 |
| 474911 | 85 | 92 | 96 | 95 | 94 | <0.6 |
| 474919 | 89 | 94 | 95 | 94 | 96 | <0.6 |
| 474922 | 21 | 47 | 73 | 86 | 96 | 1.5 |
| 474923 | 86 | 94 | 96 | 95 | 94 | <0.6 |
| 476333 | 92 | 94 | 95 | 95 | 96 | <0.6 |
| 476334 | 45 | 70 | 87 | 92 | 95 | 0.6 |
| 476337 | 83 | 92 | 95 | 96 | 96 | <0.6 |

TABLE 64

| Dose-dependent antisense inhibition of human HTT in GM02171 cells | | | | | | |
|---|---|---|---|---|---|---|
| ISIS No | 625 nM | 1250 nM | 2500 nM | 5000 nM | 10000 nM | $IC_{50}$ (μM) |
| 387916 | 28 | 38 | 63 | 82 | 99 | 1.6 |
| 460207 | 16 | 0 | 20 | 22 | 55 | 10.0 |
| 460209 | 27 | 50 | 61 | 87 | 94 | 9.9 |
| 460210 | 34 | 60 | 80 | 86 | 97 | 0.9 |
| 474871 | 62 | 74 | 84 | 87 | 90 | 0.1 |
| 474873 | 13 | 29 | 61 | 77 | 89 | 2.2 |
| 474891 | 57 | 72 | 80 | 83 | 88 | 0.2 |
| 474892 | 23 | 26 | 51 | 68 | 81 | 2.5 |
| 474911 | 47 | 58 | 68 | 72 | 82 | 0.7 |
| 474919 | 44 | 48 | 65 | 71 | 83 | 1.1 |
| 474922 | 15 | 27 | 49 | 74 | 79 | 2.6 |
| 474923 | 27 | 53 | 74 | 79 | 84 | 1.5 |
| 476333 | 42 | 53 | 75 | 76 | 84 | 1.0 |
| 476334 | 20 | 23 | 58 | 71 | 87 | 2.3 |
| 476337 | 23 | 34 | 60 | 62 | 75 | 2.7 |

TABLE 65

| Dose-dependent antisense inhibition of human HTT in GM02173B cells | | | | | | |
|---|---|---|---|---|---|---|
| ISIS No | 625 nM | 1250 nM | 2500 nM | 5000 nM | 10000 nM | $IC_{50}$ (μM) |
| 387916 | 38 | 75 | 89 | 95 | 99 | 0.9 |
| 460207 | 13 | 27 | 52 | 46 | 63 | 6.5 |
| 460209 | 79 | 68 | 84 | 90 | 92 | <0.6 |
| 460210 | 37 | 62 | 79 | 92 | 97 | 0.9 |
| 474871 | 74 | 83 | 87 | 92 | 89 | <0.6 |
| 474873 | 22 | 32 | 67 | 72 | 92 | 1.9 |
| 474891 | 69 | 78 | 84 | 89 | 89 | <0.6 |
| 474892 | 26 | 50 | 75 | 83 | 91 | 1.3 |
| 474911 | 50 | 66 | 76 | 86 | 86 | 0.6 |
| 474919 | 57 | 67 | 74 | 87 | 82 | <0.6 |
| 474922 | 15 | 32 | 61 | 71 | 90 | 2.2 |
| 474923 | 49 | 67 | 78 | 83 | 85 | 0.5 |
| 476333 | 58 | 71 | 78 | 87 | 89 | <0.6 |
| 476334 | 20 | 42 | 63 | 76 | 91 | 1.8 |
| 476337 | 48 | 63 | 71 | 79 | 80 | 0.6 |

Example 13: Strategy for Selection of Antisense Oligonucleotides Based on Potency and Selectivity Gapmers from each of the studies described above were selected for further analysis based on potency and selectivity.

Potency was based on the percent inhibition of HTT mRNA achieved by the antisense oligonucleotides targeting a SNP compared to the percent inhibition of HTT mRNA achieved by the benchmark oligonucleotide, ISIS 387916.

Selectivity was based on the ability of the antisense oligonucleotides targeting a SNP to inhibit expression of the major allele and not of the minor allele. The usage of the three cell lines with different genotypes at each SNP position facilitated this process.

ISIS 460065 (5'-ATAAATTGTCATCACCAG-3' (SEQ ID NO: 199)) is a 4-9-5 MOE gapmer targeted to SNP rs7685686 (major allele A, minor allele G) at position 9 of the oligonucleotide. The GM04281 cell line is homozygous AA at SNP position rs7685686. The GM02173B cell line is heterozygous AG at SNP position rs7685686. The GM02171 cell line is homozygous GG at SNP position rs7685686. Therefore, selectivity is shown if ISIS 460065 causes potent inhibition of HTT mRNA in GM04281, less potent inhibition of HTT mRNA in GM02173, and little to no significant inhibition of HTT mRNA in GM02171. $IC_{50}$ values taken from Table 20, 21, and 22, and presented below in Table 66, confirm varying degrees of inhibition in the three cell lines, wherein expression was most reduced in the homozygous AA cell line, moderately reduced in the heterozygous AG cell line, and less reduced in the homozygous GG cell line. $IC_{50}$ is the concentration of antisense oligonucleotide required for 50 percent inhibition HTT mRNA. $IC_{50}$ values are in μM.

TABLE 66

| Genotype of the Coriell cell lines for SNP rs7685686 and comparison of inhibition of HTT mRNA by ISIS 460065 in each cell line | | | |
|---|---|---|---|
| | GM04281 | GM02173B | GM02171 |
| Genotype | AA | AG | GG |
| $IC_{50}$ with ISIS 460065 | 1.1 | 3.6 | 10.3 |

ISIS 459978 (5'-ACAGTGCTACCCAACCT-3' (SEQ ID NO: 174)) is a 2-9-6 MOE gapmer targeted to SNP rs4690072 (major allele T, minor allele G) at position 9 of the oligonucleotide. The GM04281 cell line is homozygous TT at SNP position rs4690072. The GM02173B cell line is heterozygous TG at SNP position rs4690072. The GM02171 cell line is homozygous GG at SNP position rs4690072. Therefore, selectivity is shown if ISIS 459978 causes potent inhibition of HTT mRNA in GM04281, less potent inhibition of HTT mRNA in GM02173, and little to no significant inhibition of HTT mRNA in GM02171. $IC_{50}$ values taken from Table 20, 21, and 22, and presented below in Table 67, confirm varying degrees of inhibition in the three cell lines, wherein expression was most reduced in the homozygous TT cell line, moderately reduced in the heterozygous TG cell line, and less reduced in the homozygous GG cell line. $IC_{50}$ is the concentration of antisense oligonucleotide required for 50 percent inhibition HTT mRNA. $IC_{50}$ values are in μM.

TABLE 67

| Genotype of the Coriell cell lines for SNP rs4690072 and comparison of inhibition of HTT mRNA by ISIS 459978 in each cell line | | | |
|---|---|---|---|
| | GM04281 | GM02173B | GM02171 |
| Genotype | TT | TG | GG |
| $IC_{50}$ with ISIS 459978 | 2.5 | 8.4 | 12.7 |

ISIS 460028 (5'-GAGCAGCTGCAACCTGGCA-3' (SEQ ID NO: 149)) is a 4-11-4 MOE gapmer targeted to SNP rs362306 (major allele G, minor allele A) at position 10 of the oligonucleotide. The GM04281 cell line is homozygous GG at SNP position rs362306. The GM02173B and GM02171 cell lines are heterozygous GA at SNP position rs362306. Therefore, selectivity is shown if ISIS 460028 causes potent inhibition of HTT mRNA in GM04281 and less potent inhibition of HTT mRNA in GM02173 and GM02171. $IC_{50}$ values taken from Table 20, 21, and 22, and presented below in Table 68, confirm varying degrees of inhibition between the GM04281 cell line and the GM02173B and GM02171 cell lines, wherein expression was most reduced in the homozygous GG cell line and less reduced in the heterozygous AG cell line. $IC_{50}$ is the concentration of antisense oligonucleotide required for 50 percent inhibition HTT mRNA. $IC_{50}$ values are in μM.

TABLE 68

| Genotype of the Coriell cell lines for SNP rs362306 and comparison of inhibition of HTT mRNA by ISIS 460028 in each cell line | | | |
|---|---|---|---|
| | GM04281 | GM02173B | GM02171 |
| Genotype | GG | AG | AG |
| $IC_{50}$ with ISIS 460028 | 1.4 | 5.2 | 5.3 |

Example 14: Strategy for Selection of Antisense Oligonucleotides with cEt Motifs Based on Potency and Selectivity Gapmers from each of the studies described above were selected for further analysis based on potency and selectivity.

Potency was based on the percent inhibition of HTT mRNA achieved by the antisense oligonucleotides targeting a SNP compared to the percent inhibition of HTT mRNA achieved by the benchmark oligonucleotide, ISIS 387916.

Selectivity was based on the ability of the antisense oligonucleotides targeting a SNP to inhibit expression of the major allele and not of the minor allele. The usage of the three cell lines with different genotypes at each SNP position facilitated this process.

ISIS 460209 (5'-TAAATTGTCATCACC-3' (SEQ ID NO: 203)) is a 3-9-3 gapmer with cEt subunits at positions 2, 3, 13, and 14, targeted to SNP rs7685686 (major allele A, minor allele G) at position 8 of the oligonucleotide. The GM04281 cell line is homozygous AA at SNP position rs7685686. The GM02173B cell line is heterozygous AG at SNP position rs7685686. The GM02171 cell line is homozygous GG at SNP position rs7685686. Therefore, selectivity is shown if ISIS 460209 causes potent inhibition of HTT mRNA in GM04281, less potent inhibition of HTT mRNA in GM02173, and little to no significant inhibition of HTT mRNA in GM02171. $IC_{50}$ values taken from Table 57, 58, and 59, and presented below in Table 69, confirm varying degrees of inhibition in the three cell lines, wherein expression was most reduced in the homozygous AA cell line, moderately reduced in the heterozygous AG cell line, and less reduced in the homozygous GG cell line. $IC_{50}$ is the concentration of antisense oligonucleotide required for 50 percent inhibition HTT mRNA. $IC_{50}$ values are in μM.

TABLE 69

| Genotype of the Coriell cell lines for SNP rs7685686 and comparison of inhibition of HTT mRNA by ISIS 460209 in each cell line | | | |
|---|---|---|---|
| | GM04281 | GM02173B | GM02171 |
| Genotype | AA | AG | GG |
| $IC_{50}$ with ISIS 460209 | 0.2 | 0.8 | 1.6 |

ISIS 460208 (5'-CAGTGCTACCCAACC-3' (SEQ ID NO: 177)) is a 3-9-3 gapmer with cEt subunits at positions 2, 3, 13, and 14, targeted to SNP rs4690072 (major allele T, minor allele G) at position 8 of the oligonucleotide. The GM04281 cell line is homozygous TT at SNP position rs4690072. The GM02173B cell line is heterozygous TG at SNP position rs4690072. The GM02171 cell line is homozygous GG at SNP position rs4690072. Therefore, selectivity is shown if ISIS 460208 causes potent inhibition of HTT mRNA in GM04281, less potent inhibition of HTT mRNA in GM02173, and little to no significant inhibition of HTT mRNA in GM02171. $IC_{50}$ values taken from Table 57, 58, and 59, and presented below in Table 70, confirm varying degrees of inhibition in the three cell lines, wherein expression was most reduced in the homozygous TT cell line, moderately reduced in the heterozygous TG cell line, and less reduced in the homozygous GG cell line. $IC_{50}$ is the concentration of antisense oligonucleotide required for 50 percent inhibition HTT mRNA. $IC_{50}$ values are in μM.

TABLE 70

| Genotype of the Coriell cell lines for SNP rs4690072 and comparison of inhibition of HTT mRNA by ISIS 460208 in each cell line | | | |
|---|---|---|---|
| | GM04281 | GM02173B | GM02171 |
| Genotype | TT | TG | GG |
| $IC_{50}$ with ISIS 460208 | 1.5 | 9.0 | 10.8 |

ISIS 460206 (5'-GCAGCTGCAACCTGG-3' (SEQ ID NO: 231)) is a 3-9-3 gapmer with cEt subunits at positions 2, 3, 13, and 14, targeted to SNP rs362306 (major allele G, minor allele A) at position 8 of the oligonucleotide. The GM04281 cell line is homozygous GG at SNP position rs362306. The GM02173B and GM02171 cell lines are heterozygous GA at SNP position rs362306. Therefore, selectivity is shown if ISIS 460206 causes potent inhibition of HTT mRNA in GM04281 and less potent inhibition of HTT mRNA in GM02173 and GM02171. $IC_{50}$ values taken from Table 57, 58, and 59, and presented below in Table 71, confirm varying degrees of inhibition between the GM04281 cell line and the GM02173B and GM02171 cell lines, wherein expression was most reduced in the homozygous GG cell line and less reduced in the heterozygous AG cell line. $IC_{50}$ is the concentration of antisense oligonucleotide required for 50 percent inhibition HTT mRNA. $IC_{50}$ values are in μM.

TABLE 71

| Genotype of the Coriell cell lines for SNP rs362306 and comparison of inhibition of HTT mRNA by ISIS 460206 in each cell line | | | |
|---|---|---|---|
| | GM04281 | GM02173B | GM02171 |
| Genotype | GG | AG | AG |
| $IC_{50}$ with ISIS 460206 | 2.3 | 2.7 | 2.7 |

Example 15: Comparison of SNPs in Various Cell Lines and Mouse Models Associated with Huntington's Disease The genotype at various SNP positions associated with Huntington's disease was compared amongst the three Coriell cell lines, used in the above Examples, as well as with the GM04022 fibroblast, the BACHD mouse model and the YAC18 mouse model.

The donor patient of the GM04022 fibroblast cell line was heterozygous at SNP position rs363125 (NCBI Entrez SNP database), harboring an A allele (adenine) and a C allele (cytosine) at nucleotide 5310 of SEQ ID NO: 2 (van Bilsen, P. H. J. et al., Human Gene Therapy. 19: 710-718, 2008). YAC18 mice were developed with a YAC transgene containing human huntingtin gene (Hodgson, et al. Hum. Mol. Genet. 5: 1875-85, 1996). BACHD mice were developed expressing a full-length mutant huntingtin gene with 97 glutamine repeats under the control of a bacterial artificial chromosome (Gray, M. et al., J. Neurosc. 28: 6182-95, 2008). The comparative genotype at the indicated SNP positions in all four cell lines and mouse models is presented in Table 72.

TABLE 72

| Genotypes of the Coriell cell lines and Huntington mouse models | | | | | | |
|---|---|---|---|---|---|---|
| SNP | GM02171 | GM02173 | GM04281 | GM04022 | BACHD | YAC18 |
| rs3856973 | AA | AG | GG | AG | GG | AA |
| rs2285086 | GG | AG | AA | AG | AA | GG |
| rs7659144 | CG | CG | CC | CG | CC | GG |
| rs16843804 | TC | TC | CC | CC | CC | TT |
| rs2024115 | GG | AG | AA | AG | AA | GG |
| rs3733217 | CC | CC | CC | CC | CC | CC |
| rs10015979 | AA | AG | GG | AA | AA | AA |
| rs7691627 | AA | AG | GG | AG | GG | AA |
| rs2798235 | GG | GG | GG | AG | GG | GG |
| rs4690072 | GG | TG | TT | TG | TT | GG |
| rs6446723 | CC | TC | TT | TC | TT | CC |
| rs363081 | GG | GG | GG | GG | GG | GG |
| rs363080 | CC | CC | CC | TC | CC | CC |
| rs363075 | GG | GG | GG | GG | GG | GG |
| rs363064 | TC | TC | CC | CC | CC | TT |
| rs3025849 | AA | AA | AA | AA | AA | AA |
| rs363102 | AA | AA | AA | AG | AA | AA |
| rs11731237 | CC | TC | TT | CC | CC | CC |
| rs4690073 | AA | AG | GG | AG | GG | AA |
| rs363144 | TT | TT | TT | TT | TT | TT |
| rs3025838 | CC | CC | CC | CC | CC | CC |
| rs34315806 | TC | TC | CC | CC | CC | TT |
| rs363099 | TC | TC | CC | CC | CC | TT |
| rs363096 | CC | TC | TT | CC | TT | CC |
| rs2298967 | TC | TC | TT | TT | TT | CC |
| rs2298969 | GG | AG | AA | AG | AA | GG |
| rs6844859 | CC | TC | TT | TC | TT | CC |
| rs363092 | AA | AC | CC | AC | AA | AA |
| rs7685686 | GG | AG | AA | AG | AA | GG |
| rs363088 | TA | TA | AA | AA | AA | TT |
| rs362331 | CC | TC | TT | TC | TT | CC |
| rs916171 | GG | GC | CC | GC | CC | GG |
| rs362322 | AA | AA | AA | AA | AA | AA |
| rs362275 | TC | TC | CC | CC | CC | TT |
| rs362273 | AG | AG | AA | AA | AA | GG |
| rs2276881 | GG | GG | GG | GG | GG | GG |
| rs3121419 | TC | TC | CC | CC | CC | TT |
| rs362272 | — | AG | GG | GG | GG | AA |
| rs362271 | AG | AG | GG | GG | GG | AA |
| rs3775061 | AG | AG | AA | AA | AA | GG |
| rs362310 | TC | CC | CC | TC | CC | CC |
| rs362307 | CC | TC | CC | CC | CC | CC |
| rs362306 | AG | AG | GG | GG | GG | AA |
| rs362303 | TC | CC | CC | TC | CC | CC |
| rs362296 | AC | AC | AC | CC | CC | AA |

Example 16: Allele-Specific Inhibition Measured in BacHD Cortical Neurons

Antisense oligonucleotides, ISIS 460209 (5'-TAAATTGTCATCACC-3' (SEQ ID NO: 203)), targeting SNP rs7685686 of human HTT, and ISIS 387916 (TCTCTATTGCACATTCCAAG (SEQ ID NO: 6)), and with no human or murine SNP target site, were tested for their effect on Htt protein levels in vitro. ISIS 387916 is cross-reactive with murine Htt mRNA (GENBANK Accession No. NM_010414.1, designated herein as SEQ ID NO: 286) at target start site 5763 with one mismatch. ISIS 460209 is cross-reactive with murine Htt mRNA at target start site 6866 with three mismatches.

Primary BacHD cortical neurons, which express human Htt and murine Htt, were isolated in the following way: Embryos were dissected from E15.5-E17.5 pregnant females. Cortices were dissected into ice-cold divalent-free Hank's Balanced Salt Solution (Invitrogen, 14025-134). The cortices were chopped into pieces and digested with 0.05% Trypsin-EDTA (Invitrogen, 25300-120) at 37° C. for 8 minutes. The digestion was halted by addition of complete neurobasal media (Invitrogen, 10888-022). Cells were resuspended in media and treated with DNAse I (Invitrogen, 18047-019). After titration through a 100 ul pipette tip, cells are resuspended in neurobasal media with B27 supplement (Invitrogen, 17504-044), and counted. $1.7\times10^5$ cells/well were plated in 24-well plates precoated with poly-D-lysine (BD Biosciences, 354210). Neurons were fed with 200 µl neurobasal media with B27 on the second day in vitro.

ISIS 460209 or ISIS 387916 was added to the supplementary media fed to neurons on division 2 at 0.7 µM, 1.4 µM or 1.5 µM final concentrations. Cells were harvested after 8 days with into 1 mL of media using a cell scraper. Cells were centrifuged at 2,500 rpm for 5 min at 4° C. and the pellets were resuspended in a buffer of 50 mM Tris, pH=8.0, 150 mM NaCl, 1% Igepal, 40 mM β-glycerophosphate, 10 mM NaF, 1× Roche complete protease inhibitor, 1 mM Sodium Orthovanadate and 800 µM PMSF. The lysates were centrifuged after 15 min incubation and protein concentration was measured with the DC assay (BioRad).

Protein lysates were run on low-bis gels to separate huntingtin alleles (resolving gel—2001:Acrylamide:BIS (10% acrylamide, 0.5% BIS, 375 mMTris pH 8.8; stacking gel—4% Acrylamide-BIS (29:1), 156 mM Tris pH6.8; Running buffer—25 mM Tris, 190 mM Glycine, 0.1% SDS+10 µM beta-mercaptoethanol added fresh). After electrophoresis, proteins in the gel were transferred to a nitrocellulose membrane (Hybond-C Extra; GE Healthcare Bio-Sciences) at 90V for 40' to allow samples to penetrate the stacking gel and then at 190V for 2.5 h to resolve proteins.

Primary antibodies specific for human Htt and murine calnexin protein were used at 1:10,000 dilutions. HRP-conjugated anti-mouse secondary antibody (1:10,000, Jackson ImmunoResearch Laboratories) was used for visualizing proteins using SuperSignal West Pico Chemiluminescent Substrate (Thermo Scientific). Protein bands were quantified using ImageJ software and normalized to calnexin levels. Protein bands were quantified using ImageJ software. Table 73 provides an estimate of the percentage inhibition relative to the negative control sample. The comparative percent inhibitions of the human Htt protein and the murine Htt protein are presented.

TABLE 73

Effect of antisense inhibition on mutant human and wild-type murine Htt protein (percent inhibition normalized to PBS control)

| | Dose (µM) | Human | Murine |
|---|---|---|---|
| ISIS 387916 | 0.7 | 54 | 38 |
| | 1.4 | 75 | 58 |
| | 1.5 | 92 | 88 |
| ISIS 460209 | 0.2 | 71 | 35 |
| | 0.4 | 82 | 41 |
| | 1.5 | 94 | 56 |

Example 17: Dose-Dependent Antisense Inhibition of Human Huntingtin mRNA Levels in Coriell Fibroblast Cell Lines Gapmers from the studies described in Examples, 3, 4, 10, and 12 were selected and tested at various doses in GM04281, GM02171 and GM02173B cell lines. Each cell line was plated at a density of 25,000 cells per well and transfected using electroporation with 0.4747 nM, 1.5011 nM, 4.7463 nM, 15.0079 nM 45.455 nM, 150.0527 nM, 474.4673 nM, 1,500.27 nM, 4,743.833 nM, and 15,000 nM concentrations of antisense oligonucleotide, as specified in Tables 72, 73, and 74. After a treatment period of approximately 16 hours, RNA was isolated from the cells and HTT mRNA levels were measured by quantitative real-time PCR. Human HTT primer probe set RTS2617 was used to measure mRNA levels. HTT mRNA levels were adjusted according to total RNA content, as measured by RIBOGREEN. Results are presented as percent inhibition of HTT mRNA, relative to untreated control cells. $IC_{50}$ values are also provided in Tables 72, 73, and 74.

TABLE 74

Dose-dependent antisense inhibition of human HTT in GM04281 cells

| ISIS No | 0.4747 nM | 1.5011 nM | 4.7463 nM | 15.0079 nM | 47.455 nM | 150.0527 nM | 474.4673 nM | 1500.27 nM | 4743.833 nM | 15000.0 nM | $IC_{50}$ (µM) |
|---|---|---|---|---|---|---|---|---|---|---|---|
| 387916 | 15 | 12 | 4 | 5 | 7 | 26 | 70 | 89 | 98 | 99 | 0.33 |
| 435879 | 0 | 8 | 19 | 13 | 24 | 23 | 45 | 53 | 84 | 93 | 0.25 |
| 435890 | 16 | 1 | 8 | 12 | 25 | 23 | 32 | 52 | 61 | 91 | 0.82 |
| 460209 | 2 | 9 | 21 | 17 | 36 | 46 | 80 | 89 | 94 | 93 | 0.09 |
| 460210 | 4 | 7 | 5 | 19 | 20 | 35 | 69 | 85 | 98 | 98 | 0.21 |
| 476333 | 7 | 10 | 8 | 11 | 42 | 65 | 86 | 93 | 93 | 95 | 0.05 |

TABLE 75

Dose-dependent antisense inhibition of human HTT in GM02171 cells

| ISIS No | 0.4747 nM | 1.5011 nM | 4.7463 nM | 15.0079 nM | 47.455 nM | 150.0527 nM | 474.4673 nM | 1500.27 nM | 4743.833 nM | 15000.0 nM | $IC_{50}$ (μM) |
|---|---|---|---|---|---|---|---|---|---|---|---|
| 387916 | 22 | 8 | 0 | 9 | 0 | 32 | 60 | 90 | 96 | 97 | 0.27 |
| 435879 | 0 | 1 | 6 | 2 | 0 | 0 | 8 | 9 | 46 | 57 | 7.62 |
| 435890 | 0 | 0 | 0 | 6 | 0 | 0 | 0 | 31 | 27 | 71 | 4.37 |
| 460209 | 11 | 5 | 15 | 0 | 0 | 7 | 30 | 69 | 82 | 88 | 0.96 |
| 460210 | 0 | 0 | 0 | 2 | 17 | 18 | 38 | 70 | 93 | 95 | 0.56 |
| 476333 | 0 | 0 | 0 | 0 | 13 | 18 | 44 | 69 | 72 | 91 | 0.75 |

TABLE 76

Dose-dependent antisense inhibition of human HTT in GM02173B cells

| ISIS No | 0.4747 nM | 1.5011 nM | 4.7463 nM | 15.0079 nM | 47.455 nM | 150.0527 nM | 474.4673 nM | 1500.27 nM | 4743.833 nM | 15000.0 nM | $IC_{50}$ (μM) |
|---|---|---|---|---|---|---|---|---|---|---|---|
| 387916 | 3 | 17 | 7 | 25 | 27 | 33 | 65 | 88 | 98 | 99 | 0.19 |
| 435879 | 0 | 6 | 0 | 8 | 3 | 10 | 16 | 24 | 50 | 68 | 3.72 |
| 435890 | 0 | 13 | 0 | 1 | 2 | 12 | 16 | 23 | 49 | 82 | 4.60 |
| 460209 | 0 | 7 | 29 | 2 | 9 | 32 | 52 | 71 | 82 | 86 | 0.27 |
| 460210 | 0 | 13 | 0 | 5 | 16 | 18 | 49 | 74 | 93 | 97 | 0.27 |
| 476333 | 11 | 13 | 20 | 7 | 23 | 36 | 63 | 75 | 83 | 90 | 0.13 |

Example 18: Validation of the Specificity of ISIS Oligonucleotides Targeting SNPs of Human Huntingtin by the Molecular Beacon Assay Some of the gapmers from the study described in Example 17 were tested in GM04022 fibroblasts (from the Coriell Institute for Medical Research).

To verify allele-specific suppression of HTT mRNA in GM04022 fibroblasts by ISIS 435879, ISIS 460209, and ISIS 476333, the Molecular Beacon assay, as described in the van Bilsen at el publication (van Bilsen, P. H. J. et al., Human Gene Therapy. 19: 710-718, 2008), was conducted using 'molecular beacon' synthetic oligonucleotides linked with a fluorophore and quencher. GM04022 fibroblasts were transfected by electroporation with ISIS 435879, ISIS 460209, or ISIS 476333 at 0.06 μM, 0.19 μM, 0.56 μM, 1.67 μM, 5 μM and 15 μM concentrations of antisense oligonucleotide, as specified in Tables 75-77. ISIS 387916 was included in the assay as a benchmark oligonucleotide. The qRT-PCR assay for molecular beacon for the A allele was conducted with the annealing temperature at 56.5° C. The qRT-PCR assay for molecular beacon for the C allele was conducted with the annealing temperature at 62.0° C. Primer probe set RTS2617 was used to measure the total HTT mRNA reduction. The results of the assay are presented in Tables 77-79 as percent inhibition over the PBS control. The results demonstrate that the SNP-specific ISIS oligonucleotides specifically target the C allele of rs7685686 compared to the A allele (Table 80).

TABLE 77

Dose-dependent antisense inhibition of the A allele of rs7685686 in GM04022 fibroblasts

| ISIS No | 0.06 μM | 0.19 μM | 0.56 μM | 1.67 μM | 5.00 μM | 15.00 μM | $IC_{50}$ (μM) |
|---|---|---|---|---|---|---|---|
| 387916 | 33 | 40 | 53 | 90 | 99 | 98 | 0.56 |
| 435879 | 0 | 0 | 50 | 29 | 38 | 47 | 10.8 |
| 460209 | 14 | 4 | 54 | 73 | 81 | 95 | 0.53 |
| 476333 | 2 | 44 | 41 | 77 | 91 | 86 | 0.64 |

TABLE 78

Dose-dependent antisense inhibition of the C allele of rs7685686 in GM04022 fibroblasts

| ISIS No | 0.06 μM | 0.19 μM | 0.56 μM | 1.67 μM | 5.00 μM | 15.00 μM | $IC_{50}$ (μM) |
|---|---|---|---|---|---|---|---|
| 387916 | 41 | 42 | 46 | 86 | 95 | 92 | 0.54 |
| 435879 | 0 | 0 | 75 | 60 | 68 | 81 | 2.9 |
| 460209 | 35 | 48 | 76 | 84 | 88 | 92 | 0.19 |
| 476333 | 22 | 60 | 75 | 84 | 90 | 93 | 0.15 |

TABLE 79

Dose-dependent antisense inhibition of total HTT mRNA in GM04022 fibroblasts

| ISIS No | 0.06 μM | 0.19 μM | 0.56 μM | 1.67 μM | 5.00 μM | 15.00 μM |
|---|---|---|---|---|---|---|
| 387916 | 32 | 59 | 49 | 89 | 98 | 99 |
| 435879 | 0 | 0 | 42 | 25 | 41 | 62 |
| 460209 | 26 | 27 | 54 | 75 | 84 | 96 |
| 476333 | 25 | 51 | 58 | 82 | 92 | 90 |

TABLE 80

| $IC_{50}$ ratio (A/C) in GM04022 fibroblasts | |
|---|---|
| ISIS No | Ratio |
| 387916 | 1.0 |
| 435879 | 4.2 |
| 460209 | 2.8 |
| 476333 | 4.3 |

Example 19: Allele-Specific Inhibition Measured in Cortical Neurons from BACHD and YAC18 Mice In order to identify potential SNPs for screening of human allele-specific ISIS oligonucleotides, the HTT mRNA of YAC18 and BACHD mice were sequenced by the Goldengate 96SNP assay. It was determined that the BAC and YAC mice carried different alleles at several key SNP positions (Table 72) and could therefore be used as a screening tool for allele-specific knockdown. Each of the SNP positions chosen for targeting in the mouse strains were also compared to human HD chromosomes. For each target, approximately 50% of the human HD population is heterozygous for the target expressed in the BACHD mice, but not the YAC18 mice.

In order to verify the allele-specificity of the ISIS oligonucleotides (described in Examples 2, 9, 17 and 18), the antisense oligonucleotides, ISIS 460207, targeting SNP rs362331; ISIS 460209, targeting SNP rs7685686; ISIS 435879, targeting SNP rs7685686; ISIS 476333, targeting SNP rs7685686; ISIS 460210, targeting SNP rs2298969; ISIS 435874, targeting SNP rs4690072; ISIS 460208, targeting SNP rs4690072; ISIS 435331, targeting SNP rs2024115; and ISIS 435871, targeting SNP rs363088, were tested for their effect on HTT protein levels in BACHD and YAC18 cortical neurons. ISIS 387916, which has no human or murine SNP target site, was used as the benchmark. ISIS 387916 is cross-reactive with murine HTT mRNA (GENBANK Accession No. NM_010414.1, designated herein as SEQ ID NO: 286) at target start site 5763 with one mismatch. It was expected that treatment with the allele-specific antisense oligonucleotides would cause significant inhibition of HTT mRNA in the BACHD neurons and not in the YAC18 neurons. It was also expected that treatment with ISIS 387916 would cause inhibition of HTT mRNA in both sets of neurons.

YAC18 cultures were prepared from E16.5 pregnant female YAC18 (line 60, +/+) mice who had been bred with YAC18 (line 60, +/+) males. All progeny are thus homozygous YAC18 (line 60), facilitating pooled cortical cultures. BACHD E16.5 embryos were isolated from pregnant BACHD (+/−) mice who had been bred with pregnant BACHD (+/−) male mice, necessitating single pup cultures and genotyping. Single cortices were isolated, using caution to prevent cross-contamination of samples. Each dissociated cortex was used to seed 5 wells of a 6-well plate. After genotyping, only BACHD (+/−) cultures were used for ASO treatment. The antisense oligonucleotides were added to the supplementary media fed to the neurons on division 2. Cells were harvested after 8 days with into 1 mL of media using a cell scraper. Cells were centrifuged at 2,500 rpm for 5 min at 4° C. and the pellets were resuspended in a buffer of 50 mM Tris, pH=8.0, 150 mM NaCl, 1% Igepal, 40 mM β-glycerophosphate, 10 mM NaF, 1× Roche complete protease inhibitor, 1 mM Sodium Orthovanadate and 800 μM PMSF. The lysates were centrifuged after 15 min incubation and protein concentration was measured with the DC assay (BioRad).

Protein lysates were run on low-bis gels to separate huntingtin alleles (resolving gel—2001:Acrylamide:BIS (10% acrylamide, 0.5% BIS, 375 mMTris pH 8.8; stacking gel—4% Acrylamide-BIS (29:1), 156 mM Tris pH6.8; Running buffer—25 mM Tris, 190 mM Glycine, 0.1% SDS+10 μM beta-mercaptoethanol added fresh). After electrophoresis, proteins in the gel were transferred to a nitrocellulose membrane (Hybond-C Extra; GE Healthcare Bio-Sciences) at 90V for 40' to allow samples to penetrate the stacking gel and then at 190V for 2.5 h to resolve proteins.

Primary antibodies specific for human HTT and murine calnexin protein were used at 1:10,000 dilutions. HRP-conjugated anti-mouse secondary antibody (1:10,000, Jackson ImmunoResearch Laboratories) was used for visualizing proteins using SuperSignal West Pico Chemiluminescent Substrate (Thermo Scientific). Protein bands were quantified using ImageJ software and normalized to calnexin levels. Tables 81-91 provide the percentage inhibition relative to the untreated control sample. The percentage inhibition of human HTT protein levels in BACHD and YAC18 neurons are presented.

TABLE 81

HTT SNPs in BACHD and YAC18 mice and correlation with human HTT SNPs

| SNP | Allele present in YAC18 Mice | Allele present in BACHD Mice | Allele present in human patients with high CAG repeats | % of human patients heterozgous at the SNP position |
|---|---|---|---|---|
| rs2024115 | G | A | A | 48 |
| rs2298969 | G | A | A | 52 |
| rs362331 | C | T | T | 49 |
| rs363088 | G | T | T | 38 |
| rs4690072 | T | A | A | 49 |
| rs7685686 | G | A | A | 49 |

TABLE 82

Effect of antisense inhibition by ISIS 387916 in BACHD and YAC18 neurons

| | 500 nM | 1500 nM |
|---|---|---|
| YAC18 | 69 | 81 |
| BACHD | 84 | 90 |

TABLE 83

Effect of antisense inhibition by ISIS 435331, targeting rs2024115 in BACHD and YAC18 neurons

| | 500 nM | 1500 nM |
|---|---|---|
| YAC18 | 0 | 0 |
| BACHD | 39 | 43 |

TABLE 84

| Effect of antisense inhibition by ISIS 460210, targeting rs2298969 in BACHD and YAC18 neurons | | |
|---|---|---|
| | 500 nM | 1500 nM |
| YAC18 | 31 | 51 |
| BACHD | 79 | 89 |

TABLE 85

| Effect of antisense inhibition by ISIS 460207, targeting rs362331 in BACHD and YAC18 neurons | | |
|---|---|---|
| | 500 nM | 1500 nM |
| YAC18 | 0 | 0 |
| BACHD | 29 | 44 |

TABLE 86

| Effect of antisense inhibition by ISIS 435871, targeting rs363088 in BACHD and YAC18 neurons | | |
|---|---|---|
| | 500 nM | 1500 nM |
| YAC18 | 0 | 0 |
| BACHD | 51 | 68 |

TABLE 87

| Effect of antisense inhibition by ISIS 435874, targeting rs4690072 in BACHD and YAC18 neurons | | |
|---|---|---|
| | 500 nM | 1500 nM |
| YAC18 | 9 | 5 |
| BACHD | 30 | 44 |

TABLE 88

| Effect of antisense inhibition by ISIS 460208, targeting rs4690072 in BACHD and YAC18 neurons | | |
|---|---|---|
| | 500 nM | 1500 nM |
| YAC18 | 1 | 8 |
| BACHD | 54 | 68 |

TABLE 89

| Effect of antisense inhibition by ISIS 460209, targeting rs7685686 in BACHD and YAC18 neurons | | |
|---|---|---|
| | 500 nM | 1500 nM |
| YAC18 | 12 | 32 |
| BACHD | 72 | 83 |

TABLE 90

| Effect of antisense inhibition by ISIS 435879, targeting rs7685686 in BACHD and YAC18 neurons | | |
|---|---|---|
| | 500 nM | 1500 nM |
| YAC18 | 0 | 7 |
| BACHD | 36 | 58 |

TABLE 91

| Effect of antisense inhibition by ISIS 476333, targeting rs7685686 in BACHD and YAC18 neurons | | |
|---|---|---|
| | 500 nM | 1500 nM |
| YAC18 | 46 | 61 |
| BACHD | 89 | 91 |

What is claimed is:

1. A compound comprising a modified oligonucleotide consisting of 20 linked nucleosides and comprising a nucleobase sequence having at least 95% sequence identity to the nucleobase sequence of SEQ ID NO: 274, wherein the modified oligonucleotide comprises at least one nucleoside comprising a modified sugar and at least one modified internucleoside linkage, wherein each T in SEQ ID NO: 274 is independently a T or a U, and wherein the modified oligonucleotide is a gapmer.

2. The compound of claim 1, wherein the modified oligonucleotide comprises a nucleobase sequence having 100% sequence identity to the nucleobase sequence of SEQ ID NO: 274, wherein each T in SEQ ID NO: 274 is independently a T or a U.

3. The compound of claim 1, wherein the modified sugar is a 2'MOE sugar.

4. The compound of claim 1, wherein the modified sugar is a 2'-OMe sugar.

5. The compound of claim 1, wherein the at least one modified internucleoside linkage is a phosphorothioate internucleoside linkage.

6. The compound of claim 1, wherein at least one nucleoside comprises a modified nucleobase.

7. The compound of claim 6, wherein the modified nucleobase is a 5-methylcytosine.

8. The compound of claim 1, wherein the gapmer has a 5-10-5 wing-gap-wing motif.

9. A pharmaceutical composition comprising the compound of claim 1 and a pharmaceutically acceptable diluent or carrier.

10. A compound comprising a modified oligonucleotide consisting of 20 linked nucleosides, wherein the modified oligonucleotide is complementary to a differentiating polymorphism site, wherein the modified oligonucleotide comprises at least a 16 contiguous nucleobase portion of the nucleobase sequence of any of SEQ ID NOs: 274-276, wherein position 8, 9, or 10 of the modified oligonucleotide, as counted from the 5' terminus of the modified oligonucleotide, aligns with the differentiating polymorphism site, wherein the modified oligonucleotide comprises at least one nucleoside comprising a modified sugar and at least one modified internucleoside linkage, and wherein each T in SEQ ID NO: 274, 275, or 276 is independently a T or a U, and wherein the modified oligonucleotide is a gapmer.

11. The compound of claim 10, wherein the modified oligonucleotide comprises a 17 contiguous nucleobase portion of the nucleobase sequence of any of SEQ ID NOs: 274-276, wherein each Tin SEQ ID NO: 274, 275, and 276 is independently a T or a U.

12. The compound of claim 10, wherein the modified sugar is a 2'MOE sugar.

13. The compound of claim 10, wherein the modified sugar is a 2'-OMe sugar.

14. The compound of claim 10, wherein the at least one modified internucleoside linkage is a phosphorothioate internucleoside linkage.

15. The compound of claim 10, wherein at least one nucleoside comprises a modified nucleobase.

16. The compound of claim 15, wherein the modified nucleobase is a 5-methylcytosine.

17. The compound of claim 10, wherein the gapmer has a 5-10-5 wing-gap-wing motif.

18. A pharmaceutical composition comprising the compound of claim 10 and a pharmaceutically acceptable diluent or carrier.

19. A compound comprising a modified oligonucleotide consisting of 20 linked nucleosides and having a nucleobase sequence comprising a portion that is complementary to at least 16 contiguous nucleobases of nucleobases 167062-167080 or nucleobases 167063-167081 of SEQ ID NO: 1, wherein the modified oligonucleotide comprises at least one nucleoside comprising a modified sugar and at least one modified internucleoside linkage, and wherein the modified oligonucleotide is a gapmer.

20. The compound of claim 19, wherein the modified oligonucleotide has a nucleobase sequence comprising a portion that is complementary to at least 17 contiguous nucleobases of nucleobases 167062 to 167080 of SEQ ID NO: 1.

21. The compound of claim 19, wherein the modified oligonucleotide has a nucleobase sequence comprising a portion that is complementary to at least 18 contiguous nucleobases of nucleobases 167062 to 167080 of SEQ ID NO: 1.

22. The compound of claim 19, wherein the modified oligonucleotide has a nucleobase sequence comprising a portion that is complementary to at least 19 contiguous nucleobases of nucleobases 167062 to 167080 of SEQ ID NO: 1.

23. The compound of claim 19, wherein the modified oligonucleotide has a nucleobase sequence comprising a portion that is complementary to at least 17 contiguous nucleobases of nucleobases 167063 to 167081 of SEQ ID NO: 1.

24. The compound of claim 19, wherein the modified oligonucleotide has a nucleobase sequence comprising a portion that is complementary to at least 18 contiguous nucleobases of nucleobases 167063 to 167081 of SEQ ID NO: 1.

25. The compound of claim 19, wherein the modified oligonucleotide has a nucleobase sequence comprising a portion that is complementary to at least 19 contiguous nucleobases of nucleobases 167063 to 167081 of SEQ ID NO: 1.

26. The compound of claim 19, wherein the modified sugar is a 2'MOE sugar.

27. The compound of claim 19, wherein the modified sugar is a 2'-OMe sugar.

28. The compound of claim 19, wherein the at least one modified internucleoside linkage is a phosphorothioate internucleoside linkage.

29. The compound of claim 19, wherein at least one nucleoside comprises a modified nucleobase.

30. The compound of claim 29, wherein the modified nucleobase is a 5-methylcytosine.

31. The compound of claim 19, wherein the gapmer has a 5-10-5 wing-gap-wing motif.

32. A pharmaceutical composition comprising the compound of claim 19 and a pharmaceutically acceptable diluent or carrier.

33. A compound comprising a modified oligonucleotide consisting of 20 linked nucleosides and comprising the nucleobase sequence of SEQ ID NO: 275, wherein the modified oligonucleotide comprises at least one nucleoside comprising a modified sugar and at least one modified internucleoside linkage, wherein each T in SEQ ID NO: 275 is independently a T or a U, and wherein the modified oligonucleotide is a gapmer.

34. The compound of claim 33, wherein the modified sugar is a 2'MOE sugar.

35. The compound of claim 33, wherein the modified sugar is a 2'-OMe sugar.

36. The compound of claim 33, wherein the at least one modified internucleoside linkage is a phosphorothioate internucleoside linkage.

37. The compound of claim 33, wherein at least one nucleoside comprises a modified nucleobase.

38. The compound of claim 37, wherein the modified nucleobase is a 5-methylcytosine.

39. The compound of claim 33, wherein the gapmer has a 5-10-5 wing-gap-wing motif.

40. A pharmaceutical composition comprising the compound of claim 33 and a pharmaceutically acceptable diluent or carrier.

41. A compound comprising a modified oligonucleotide consisting of 20 linked nucleosides and comprising the nucleobase sequence of SEQ ID NO: 276, wherein the modified oligonucleotide comprises at least one nucleoside comprising a modified sugar and at least one modified internucleoside linkage, wherein each T in SEQ ID NO: 276 is independently a T or a U, and wherein the modified oligonucleotide is a gapmer.

42. The compound of claim 41, wherein the modified sugar is a 2'MOE sugar.

43. The compound of claim 41, wherein the modified sugar is a 2'-OMe sugar.

44. The compound of claim 41, wherein the at least one modified internucleoside linkage is a phosphorothioate internucleoside linkage.

45. The compound of claim 41, wherein at least one nucleoside comprises a modified nucleobase.

46. The compound of claim 45, wherein the modified nucleobase is a 5-methylcytosine.

47. The compound of claim 41, wherein the gapmer has a 5-10-5 wing-gap-wing motif.

48. A pharmaceutical composition comprising the compound of claim 41 and a pharmaceutically acceptable diluent or carrier.

49. The compound of claim 10, wherein the modified oligonucleotide comprises an 18 contiguous nucleobase portion of the nucleobase sequence of any of SEQ ID NOs: 274-276, wherein each Tin SEQ ID NO: 274, 275, and 276 is independently a T or a U.

50. The compound of claim 10, wherein the modified oligonucleotide comprises a 19 contiguous nucleobase portion of the nucleobase sequence of any of SEQ ID NOs: 274-276, wherein each Tin SEQ ID NO: 274, 275, and 276 is independently a T or a U.

* * * * *

UNITED STATES PATENT AND TRADEMARK OFFICE

CERTIFICATE OF CORRECTION

PATENT NO. : 12,110,491 B2
APPLICATION NO. : 17/577832
DATED : October 8, 2024
INVENTOR(S) : C. Frank Bennett et al.

It is certified that error appears in the above-identified patent and that said Letters Patent is hereby corrected as shown below:

In the Claims

In Claim 11, Column 406, Line 48 should read:
--274-276, wherein each T in SEQ ID NO: 274, 275, and 276--

In Claim 49, Column 408, Line 49 should read:
--274-276, wherein each T in SEQ ID NO: 274, 275, and 276--

In Claim 50, Column 408, Line 54 should read:
--274-276, wherein each T in SEQ ID NO: 274, 275, and 276--

Signed and Sealed this
Thirty-first Day of December, 2024

Derrick Brent
*Acting Director of the United States Patent and Trademark Office*

SEQUENCE LISTING

```
<160> NUMBER OF SEQ ID NOS: 288

<210> SEQ ID NO 1
<211> LENGTH: 202001
<212> TYPE: DNA
<213> ORGANISM: Homo sapiens

<400> SEQUENCE: 1

gcccagcagg tgtcagcctc attttacccc gcccctattc aagatgaagt tgttctggtt      60

ccaacgcctc tgacatatta gctgcatcat tttacatttc tttttttttt ttccttttaa     120

atggggtctt gctctgtcac ccaggctgga gtgctgtggt atgatctcgg ctcactgcaa     180

tctccacctc cgaggttcca gcgattctct tgcctcagcc tcccgagtag ctgggactac     240

aggcacccac catcatactg ggctaatttt tgtgttttta gtagagatgg ggtttcccca     300

tgttgcccag gctgatctca aactcctggg cttaagcaat acagccgcgt tggcctccca     360

aagtgttggg attacaagca tgagctaccc cacccagctc attttacatt tccacttgtt     420

aaactgaaaa ctggcccgag aaagcttctg tactgccatc cttgcgtcct tgcagatgaa     480

tcgtaaccta gcatagtagg taggcagact gaaaacctaa cttagcagta ggcttctgta     540

acaacagctg tgtctcagcc agttcctgca gccagacttc aaccactcac aggccgcaaa     600
```

```
ctgttcaaac tgtgttcgga gaaggcgaat tcatctggct gttaacgtgc ctcacttctg    660
ctttctgtgg ccactttccc ttttctgtcc ataaatttgc tttgaccaca cagcatccct    720
agagtctccc tgaatctgct gtgattctgg gacctgcacc atttgtgaat tgttttttt    780
ttccttgatc agctaaactc tgttcaattc aatttgttgg aagtttttaa cataccaatg    840
gtgcaccaag gttccaattt ctccacttcc tcataaataa gtcattttaa atggcttttc    900
agtattccaa tatttggaag tattaatgtt tctaccaatt ttctattttt ggacattgag    960
gttgtttcat ttttttttc tttttttgag acagagtctc gctccgtcac ccaggctgga   1020
gtgcagtggc ctgatcccgg cccactgcaa cctccacctc cctcctcagc ctcctgagta   1080
gctgggatta caggtgcatg caccaccaca cccagctaat ttttgtattt ttagtagaga   1140
tggggtttca ccatgttggt caggctggtc tcaaactcct gacctcaggt ggtccacctg   1200
ccttggcctc ccaaaatgct gggattacag gcctgagcca ctgcgcctgg cctcatcttc   1260
ttgatattaa tgttgcttta acatctttgt ccctgtgttt tttgtttttt tttttgagac   1320
ggagtctcat tcattctgtc acccaggctg gagttcagtg gcgtgatctc agctcactgc   1380
aacctctgtc tcctgggttc cagtgattct cctgcgtcgg tctcctgagt agctgtgttc   1440
ctgggtcttt cgatggttat ttaatacttc cctacagtaa tgccctgtgc gtacatgcta   1500
agtgtgatga aatggttggc acagttaaat cttttgaaag acattgccaa gtcactcttc   1560
agaaaagtga taggaggtca tagcaatttt aagaagtcct catttctaca tttccttact   1620
aatctcggtt ggtgtctctt caatctttcc tcacactttt cttgggtttt tcctgaatca   1680
tgagtctact acatttacac attttaaagc atctttagaa acaggatctc attttgttgc   1740
ccaggctaga gtttggtggc atgattatag ctcctcatac tcctgggctc aagtgatcct   1800
tccacctctg aaaccccaaa atttgagaaa ggtctcattt aatttagaaa gtttattttg   1860
ccaaggttga gggtgcacac ctgtgatgat atacgagtta aaaagaaatt atttaggcag   1920
atactgaggg taagaaagtc ctcggtaagg ttttcttttc aatgaaaagc agcccccaag   1980
cattttcttt tctaacaaag agcagcctgt aaaatcgagc tgcagacata cacaagcaag   2040
ctggaagctt gcacaggtga atgctggcag ctgtgccaat aagaaaaggc tacctggggc   2100
caggcagatc caacatggcg gctccatctt ccctttcctt gtcaaccatg tgcacagtaa   2160
ggagcaggca acatagtgtc ccccgagtag agaccaattt gcataataaa aggtgagggt   2220
agggtgggca gcttctttgc atgctatgta aacattatgc ctggtccaac caatctttgg   2280
gccctgtgta aattagacac cacctcctca agcctgtcta taaaaccctg tccattctgc   2340
cgcaggctgg aagacccact ggggcacccc tctctctcta taggagacag ctattcattt   2400
ttctctttct ttcacctatt aaagctccac tcttaacccc actccgtgtg tatctatgtt   2460
cttgatttcc ttggcatgag gcaatgaacc ttgggtatta ccccagaacc ttgggtatta   2520
tgccacttca gtgacacagc ctcaggaaat cctgatgaca tgttcccaag atggtcgggg   2580
cacagcttgg ttttatacat tttagggaga catgagacgt caattcatat atgtaagaag   2640
tacattggtt ccgtccagaa aggcggggac aacttgaggc agggagagag cttctaggtc   2700
acaggtagac aaatggttgc attcttttga atctccgata agcctttcca aaggaggcaa   2760
tcagaatatg cgtctattga ctgggcgcag tggctcatgc ctgtaatgcc agcactttgg   2820
gaggcggagg tgggtggatc acctgaggtc aggagtttga gagcagcccg gccaacatgg   2880
tgaaaccctg tctctactaa aaatacaaaa aattagctgg gcgtggtggc gggcgcctgt   2940
aatcccagct actcgggagg ctgaggcagg agaatagctt gaacccagaa ggaagaggtt   3000
```

```
gcagtgagct gagatggtgc cattgcactc cagcctgggc aacaagagtg aaactccatc   3060
tcagaaaaaa aaaaaaaagg cctgggcaaa gtggctcacg cctgtaatcc cagcactttg   3120
ggaagccgag gcgggcaggt cacaaagtca ggagattgag accatcctgg ctaacatgat   3180
gaaaccccat ctctactaaa aatacaaaa aactagctgg gtgtggtggc gagcacctgt   3240
agtcccagct actcggcagg ctgaggcagg agaatggcgt gaaccgggga ggcggagctt   3300
gcagtgagcc gagatcacac cactgcactc cagcccggac gacagggcaa gactctatct   3360
caaattaaaa aaaaaaaaaa aaaaaaaaaa aaagagagag agaatatgca tctatctcag   3420
tgagcagaag gatgactttg aatggaatgg gagcagttcc tagcttgaac ttcccctta   3480
gcttcagtga tttgggggct caaggtatgt tcctttcaca tacctcagcc tcccaagtag   3540
ctgggaccac aagtgcatgc caccacacgt ggctaatgtt ttattttttt tgtaggaata   3600
gggtctcact atgtgtccag gctggtctaa aacccctgag ctcaaatggt cctcccgcct   3660
cagcctcccg aaatgctggg attacaggca tgagccagca tgcccggcct agtctacatt   3720
tttataaatt gctaattcaa agttccctct ccaaaacctc atggttttcc ctgttctcat   3780
cccctgcacc ctcccttccc ctggagtact cacctggcct tggaggtctg gtgtgagccc   3840
ggacttcgat tctaggcaca gcatgtgatg agcgccccca ggtcaaacac ctcccctctg   3900
cggcctgtgc ttcaccgcct tgacagtgag aaaggtctcc cttcggctca ttctcgaagt   3960
ctcaaacttc acttctcctg tgcgctgatt ctgaattcag cccccgtcca aggtcctggc   4020
ccctttctct tctgcttggc gtgttgttca tcaccactgt gcactgctga gggtaagtgc   4080
ggttctctgg acctctgctt tatcattaga acagactctt gcggtttccc acgacattcc   4140
tttcacttct cacttggaag atgagccgtg aggaaatcct gtgttgtgtg gtatgtgggc   4200
tgtgcttctg cttgacttga gggccaagca gcattgcaag ccatggtttt aaataagaaa   4260
gaacatttct aaccttcatc ttctagtaag gaaacaagtg ggctttagag ttcttgctca   4320
ggaaagacct atgtcccagt ccaaccggac cttttactaa agagatcttc ctgatcctcc   4380
tccccaggcc aggggagggg tcctccctgg ggttggagcc tttagtaggg ggtcggagac   4440
acgacgtagc cttcatgaca ttcatagtct agttacacga tccctgtaag ggtcagttga   4500
agtaagtgct acaaaggaag ggaggtgctc agtggagagg gctctctttt atgtattata   4560
tttctttcat ggggagggat atggatcagg gatcagcaga ggtgtttcag tcccgaggga   4620
aagaaagtca gcgtggcttg ggagttggga gcagcaagac agtggctcaa gatatcttaa   4680
gactagtgga gtacaccttg catgttaaaa gccttgctca gggctgcctg gttcttgtag   4740
gacgacagag atggcctagc tctgcatact gcacccccag gggctcagaa cagtgcaaat   4800
gtcagtctat ctgtcagtgg cagagccagc cttggagcag gggtgcaagg aggtctctgc   4860
actggccagg catgcagaac attctgttca gtagcactgg acagaaggcc ccatctagat   4920
gagacagagc tggtggggca ggacaaagac tcctggcagc tcaaacggcc tggcagatgc   4980
ttggagagag gggcttctt gagacagcac catttctggg aagagagtca cctgggaggg   5040
atgaggccac gctccggctt ggaggtgaag agaggggctg ctgcaagaaa gaattagaga   5100
catgccagcc tttgctgtgt tgcccaggct ggtcatgaac tcttggcctc aagcaatctt   5160
cccacctcag cctccccaag cgctgggatt atagacatga gcccccatgc tggccaataa   5220
aagatgattt tatggagggg atggtggtga aggttgtggg tggtatgaaa tagtaagaaa   5280
tatatattgg tctgcaccca gttcctgcca cagagctcct aaaatcctga gaacttcctg   5340
```

```
ggtgagcatc ttttgttcta atgaggtgac tcttggtggc tcctggatag gagtgaatca   5400
ccagaaagat caagccagag ttagaagcag aaagtgctgg ctataacaca ggaaagctgt   5460
aacacaaata ataaagtttt tttttttttt tttgagatgg agcctcactc tgttgcccag   5520
gctggagtgc aatggtgcaa tctcagctca ctacaagctc tgcctcccag gttcaagtga   5580
ttctcctgcc tcagcctcct gagcagttgg gactacaggt gtgtgccacc acatctggct   5640
aatttttgta tttttagcag agacggggtt tcaccatatt aaccaggctg gcctcaaact   5700
ccttaccttg tgatccgcct gcctcagcct cccaaagtgc tgggattaca ggcatgagcc   5760
accgtgcctg gccaaaagac attgttctta aaagaatcaa ctaactaacc aaataaataa   5820
aaatctaacc taattaagaa actaaaaata cacaaaaatt aatttcaagg ggagaaaaat   5880
catgtaaaga gagaaagata atgaatactt tgcagaaatt tatgaacata aacataaaac   5940
ttggatgaaa tgcatttcta ggaaaacata atttatcaaa actaaccaca agtaaaatag   6000
aagcctaaat aggatatttt caagagaaga agtaaagttg tcaaagtgct acccttcaaa   6060
aaaacaccag gctcaaacaa tctgacatgg gaatgttagc acaccttaga gagcaaataa   6120
aactttgaat gggcttgaaa tattccagac tctagaaaaa caaaacttcc caattctttt   6180
tataaagcaa gtataaattg ataccaaaat cttataaaga ccttatacaa aacttcatac   6240
caatctcttt tatgaataca aaacccttaa taaagtatta ccagacagaa cccaacaata   6300
cataaaaatg tcacatcata acatagtggg gtttatttca ataatgcatg gatggttcaa   6360
tacaaggaaa ttcagtaaca caatataata gatcatgtga atatacccaa agaaaaaata   6420
gattattttc atagatgctg taaaggcatt tgaccaaatt caacacctac tttttaggtg   6480
gtcaataaaa taaattagtt actccttctt tagcatgata aaatatattt atcagcccag   6540
aaggcatcat tttacccgat aagggcacac gctggaggga ataatgttaa aattaggaat   6600
aagaggatag ctagtttctt tcttcttttt ttttttgag acggagtctt gctctgttgc   6660
caggctggag tgcagtggtg caatgttggc tcactgcacg ccccccgcct cccaggttca   6720
agcgattctc ctgcctcagc ctcccgagta gctgggacta caggcgcgca ccaccatgcc   6780
cggctaattt ttttttgtat tttagtagag atggggtttc accatgttgg tcaggctggt   6840
cttgaactcc caacctcacg tactgggatt accggtgtga gccaccacgc cagcccaact   6900
actttcaaca ttatccttaa tactgatgct tattgactta ctatggggtt acctctagat   6960
aaatccataa taagttgaaa atataagtaa aaaatgccct taatacacct aacctaccaa   7020
acatcatagc tgagcccagc ctgccttagc tatgctcaga cactgacgtc agcctacaat   7080
tggcaaaatc acacagcagc acagtctact gcagagcatc tgctgtttgc ccttgtgact   7140
gcgtggctgc ctgggagctt cccagcttca caagacagta ttacgtagca catcactagc   7200
ctggggaaag atcaaagttg aaaatttgaa gtgtggtttc cattgaatgt gtactgcttt   7260
tgcaccatca tcaagtcaaa aaattttagt tgaaccagcc taagtttggg accatcttta   7320
ttttcaggag gaacttccat gtacattgat gacggacgat agaatccgtt tctatcatcc   7380
taatgaacat aatgaataaa tccagacaaa cataaacatt aacagagtaa gcagctttcg   7440
gggctggaag ccagaagagg gtgggagcgc agagagagag gccaaacacc agggctgctt   7500
ctgctttgcg ggtatttgct gatctggaca aggtatctgg aaggctgagc taagcctcct   7560
tttttttga ggtggcgtct cactctgttg ccaggctgga gtgcaatggt gcgatctcag   7620
ctcactgcaa cctccacctc cctggttcaa gcgattctcc tgcctcagcc tcccgagtag   7680
ctgggattac aggctcccgc cactacaccc agctgatttt tgtaatttta gtagagacgg   7740
```

```
ggtttcacca tgttggccag gatggtctcg atctcttgac gtcatgatct gtccacctcg   7800
gcctcccaaa gtgctgggat tataggcgtg acccaccgtg ccccgtctga gctaagcctc   7860
ttgagcatag ggactaaaa atgaaatcta gcgcatgcca agtttagggt cccaggcaat   7920
tcctttccac tttggggtcc actttggggt ccacccccacc caagaagaag gatgacttgg   7980
aagtaaacca gctctgaaat atggatggtc ctctgggacc ataccaatcc cttcatatca   8040
accacatcca gttcctcaaa actggaactt ggattaagat ggcctaggac ttctagtgtc   8100
ccaggagcct ggcattgcaa acaaaaatcc tctccggaag aagataatac cttaagcttc   8160
aaatgactct ctaataaatt tcaaatacaa tgtccagcac acaaacacaa attaccagga   8220
acgtgatatg aggcctgatg gatgggaatt agcagaaact tcaggcatga gaaacatacc   8280
ctcagaggcc tagaatctat ctagtgtcta gataatggag atatgaaata cagacactta   8340
aacaactatg tttcccatgt tcaaagagga aatttgcaaa acttgaaagt gttggcagga   8400
aatcagaaac tataaaatgt gacaacagca tactttagag tcagtataaa ttacggtccc   8460
gaaaactgca gaattccaga acttaatggt aaagcaaggg tttaacagca gaatagaaat   8520
agccagagag aactaggaag taagtcagat gacactaccc agaataaggc actgagaggc   8580
caaggaatgg aaaatgcaga agaaaggata tggtgagagg atctaatata catttatttg   8640
gagtaccagg gagagagaga aggagaagaa cagaagccgt gtttcaagga cggtgactga   8700
gaggcttcga aactgatgaa agccatcagt tcacaaattc aaagcccagt gaattccaag   8760
gagaaaaaaa gaaatccata ctgtgaaagc aagtccagac aatgacaaac accatcaaca   8820
atacacagga caggcataag atgcatttaa tggggacact cagaggcaga gggttatcag   8880
aaggaggcac ttctctccca agttctcatc atcccagggc cagggacagc tggtcacacc   8940
ttagggagtt cactaggaga gggatctggc ttcttgtcat tctgggtatt tgtagggaaa   9000
ttggaaggga accgagagca cctagccaat cgcatagcaa tgggagattt caggctgtgg   9060
ggaatgtctt tgctggtgaa aagaacatcc tgaccttaga aatctttcac cgagggggat   9120
ctgcgttcca gaacttctgg agctggtata ggtaaggctt tgagctttcc tactgagcca   9180
gcctgttgct aggttaccaa aggggacctc gagggccatc tggccaacaa gcagacttgt   9240
ctctccttac acccccagac gtatcactgc aaaactacag aaaaccaaag acagagaaaa   9300
tcttaaaagc agccagattt aaaaaatggc atattagttt caaagcagca gccatgaaat   9360
tgacagctga tgtctcaaca gcaagaatga aaagtggaag acaggccagg tgtggtggct   9420
caggcctgta atcccagcac tttgggaggc cgaggcgggt ggatcacgag gtcaggagac   9480
caagaccatc ctggctaaca tggtgaaacc ccgtctctac taaaaataca aaaaaattag   9540
tcgggcatgg tggtgggtgc ctgtagtccc agctactcgg gaggctgagg caggagaatg   9600
gcgtgaaccc gggaggcgga gcttgcagtg agccgagatt gtgccactgc actccagcct   9660
gggtgacaga gcaagactct gtctcaaaaa aaaaaaaaaa aaaaaaaaaa aaagggtgac   9720
gaagcttcaa tctcctgaaa ggaagcaact gccgcctttg attcgatacc caccaaaatc   9780
cgtgaagaag gaaggcaaaa taaaaacact tcctgattga actggaaaga tttccgcaat   9840
agaagaccca ctgtccaagg aattctaaag gatgctttcc aggcagaaga aaatgacccc   9900
agaggaagat cagagattca ggaaagaaat ggagagtgat aaaaatggaa aattcggggg   9960
ccaatttaaa caaaagctga ctgctctaca actgttgtgt ctctatcttt tgtaacatat  10020
atgtgtgtgt agcttttttt tttttttttg tcaagatgga ttctcactct gtcgcccagg  10080
```

```
ctacagtgaa atggcacggt ctcggctcac tgcaacctct gcccccttggg ctcaaatgat  10140
tctcttgcct cagcctcctg agtagctgag attacaggtg cctggcacaa tgcctggcta  10200
atttttgtat ttttactaga gatgggattt ctccatgttg gccaggctgg tcttgaacac  10260
ctgacctcag gtgatccacc tgcctgggcc tcccaaagtg ctaggattac aggcgcgagc  10320
cactgcatct ggcctatgtg tgtgtttata tggaattaaa acacatggca ataataccct  10380
ccaaattggg agaaaccaaa aatagcattt aaatgttgta agctccctgc ataatcaaga  10440
agagaataga tttacgttag attttgatac ctggaggatg aatgttgtaa tttctagggt  10500
gaccatgaaa agaggagaca acggtgtatg tttttttttt tttgagatgg agtctcactt  10560
tgtcacccag gctggagtgt tgtggtgtga tcttggctca ctgcaacctc ctcctcttgg  10620
gttcaggcca tcctcccacc taggcctcca gagtaggtgg gatcacaggc acctgccacc  10680
acacctggct aatttttttt ttttttaaa tatttagtag agatggggtt tcaccatgtt  10740
ggccaggctg gtcttgaact cctgacctca ggcgatctgc ctacctctgc ctctcaaagt  10800
gctgggatta caggtgtgag ccatcgcgcc cggccaacag tgatcacttt caaactaaca  10860
gaggttcaaa aataaaatca gacttaacca aaaaccaggt aacagagctg gtaggatata  10920
cagaaagact gacctcacgt atatcaacga ttacagttaa tattaatgaa ggaaatgctc  10980
tagtttaaaa acgagggttg tcaaagaccc cacataagaa gctccttacc agcggtgcac  11040
ctagaaccta aggaaacagg acagatgaag gaggacgcgc ccccgccgct gtcctgcgcc  11100
tcagccatcc tatgagacgg gaaaggtttc tgtctgcagc tgggcccgtg ctctttacca  11160
gctcctggct ttcttctctg gaaggttcct gcctgttttg ccctcacacc tgctcctctc  11220
tcagccctct caggggtggg gctggaggcc accaaagagc ctcctctgct ctccagttgc  11280
tcgactgctc ctcatttccc cctggggtct gcgtcagggt ttccttcttt tccagcccca  11340
ccccgcgtgc atcccacctg gtctcgggtc ggggctgctc ccgcttactg ccccctgccc  11400
aggctggtgt gcaccccctc tggctgcttt caaggcctct tctctcttct cggcaggaca  11460
ggcacaggca ggtggccagg tgtcatgctt agctccccgc ccagtgagat tctttcattt  11520
aacaatcttc ccctgaatag ttcatgttca ttgctgaaaa tttgaaaaat atggaaaagc  11580
acaaagatta agatataaac cgccctcaat tcccctgccc agagagagtc actgctatga  11640
cttggtgact aggaacctta tttctctctc gctctttttt ttttttttga gacagagtct  11700
tgctctgtca cccaggctgg agtgcagtgg ctcgatctca gctcactgca acctccgcct  11760
cctgggttca agcgattctc ctgcctcagc ctcttgagta gctgggatta caggcacctg  11820
ccaccatgcc cggctaattt ttgtattttt agttgagaga gggtttcatc ttgttggtca  11880
ggcggacttg aactcctgac ctcaggtgat cagcccacct cggcctccca aagtgctggg  11940
attacaggtg tgagccactg cgccttcatc tctcttctgt gtatgtgtac gctgtttttt  12000
ctttagaatg ggggacgtta tcaggctcta catggtgtgt agtcggctag catgttgtaa  12060
gcctttccct gtgtcacaag tgctcatctg gaacaggatt ctaatgactg cctgtggcta  12120
tgttgggatt cctttaactc agctccttct gcccagcatc tatctttttt ccatcttttg  12180
tcctaagtgt tgctataata aatcattgat cacacatgcc tgactgtttg cataggataa  12240
attacgggaa atgtttttgc tgttcaggga ctgtgcccat ttttaggcct cagagacacc  12300
atgccagact gcccagtatt gatctttact ctttttagat gatgccaaac ttttctgtga  12360
actttaaaaa cctgtgtctt gacagtccat ttctgtaagt ctttcacatt agatttcctg  12420
tcaggatgat agtcaattct aggcagatga tgttttctca gccatggctg aagcagttgt  12480
```

```
gatttgttgt ggccatgtaa agtcccgatg atccattgcc tccctggatg ggttggaata  12540
atttggtttg ggagcatata acagaatgac ctggagtcac agcagctcag acggaagtgt  12600
atttctccct tacagatgaa agaattccag gccaggctgg aatgacaact gcacacagtc  12660
atctgggccc cctccttcca gctcccatca ccccaggatg tggcttttat gcagatgatc  12720
caaaatggct gctcaagtcc cagccaacac atcccattcc agggagcagg aaaaaggtgt  12780
gtctttccct tcattttatg tgattccttt ctagaagtac tactcattac ttctgcttgc  12840
atctccctgg ctagcactta cttagttata tggccatagc tagctgaagg aaggacaggg  12900
actgtcatac actagctaag aggcaaactg cttagataaa aaggtctcta aagaaggtca  12960
gagcggctgc tagggtgcaa ctctattact tattgttatg ggacgaactg tgtccctcat  13020
tcaggttgat gtcctaagcc ccagaacctc agaatgggat tgtatttgga gacaggttct  13080
ttaaggaggt aaggaggcta aaatgagatc attagggtgg gccataatcc gactgatgtc  13140
ttacaagaag agattaggac acggacatgc tcagagggac ggccacgtga ggacaccaag  13200
aaaggcagct gtctgcaagt caaggacagg gctcagggga aaccaacctt gccaacacct  13260
tcatctcgga cttctagcct ctaggaccat gagaagatac atttctgttg tttaagctgc  13320
ccggtctgtg gtactttgtt atggcagccc aagtaaacaa atacagtcat ctgctgctgg  13380
aacaaatcac cccagcactg tggcttggca gcacacatgt ctagtcatag agttatatgt  13440
agttacgtgt agagccatat gtatcgtcac acgttctgtg ggtcaggaat ttggacccag  13500
cttaaccagc tccacttctc gccagggttc agtcaaatac cagctgcctc ccacctgaga  13560
gctcagccgg ggaagggtcc ctttccaatc tcacgtggtg ttggcaggat ccagttcctc  13620
atggcctgct ggactgagaa cctcagttct cactgcctgt tggccagagg ccgcctttat  13680
gtcctcgcca tgtgggcctc tccaacatgg cagctgactt catcagagca tccatgccaa  13740
gaaggcaaca gagagggcca gggagactga agtcataccc ttttgcgacc tagtcatggg  13800
gtgacattcc atcacctttg cccattggtt agaagcaggc caccaggtac agcccaagct  13860
cacggggagg ggtcatacaa gggtgtcaat accaggaggt gaggggtgct ggggccatct  13920
tatgagtctg cccactgagg taactaacaa ccttgaggcc tgacacagtg gacaaaggcc  13980
cttattaaca gcagagaact gggaacttta tttatttatt tatttttgag acagagtctc  14040
actcttgtca cccaggctgg agtgcaatgg catgatcttg gctcactgca acctccacct  14100
cccaggttca agcaattctg cctcagcctc cggaatagct gggactacag gcatgcacca  14160
ctacacccgg ctaatttttg tatttttagt agagacaggg tttcgccatg ttggccaggc  14220
tggtctcgaa ctcctgacct ctggtgatct gcctgccttg gcctcccaaa gtgctgggat  14280
tacaggcgtg agccaccgca cctcgctgga acttaatttt tttagagaca gtgtcgctct  14340
atcacccaag ctggagtgca gtggtgcaat cctagctcac ttgcagcctc aaattcctgg  14400
gttcaggtga tcctcccaca tcagcctccc aagaactggg aactaacagc tgtttctctg  14460
ctgtccttct caagaaaagg gaggctactg ctaccccact ggggacaatg ctgggtttcc  14520
ctttaggaca ggctctgaga caaggcggag gtgctgtttg tggccacaga gcaggggact  14580
ctgggttgca ggtgtggcct ggctaaagta ggctttactg ggctcctctc tgcctgcatc  14640
accccccggc tgggcggttg tctctgaggc caaccttact ccctgctggg caggctggac  14700
agctgccctc tccgtttgcc cctctaccac ccaaaaggca ggaggctctg gagaccagga  14760
ccctgcccgc cacggcctgt gtcccaggcg tgagggggtg ccccacagac ctctgctgag  14820
```

-continued

```
ctgctgctga atgacgcccc ttgggggtcc tgccggaagg tcagagcagg ggtgcactcc  14880
cataaagaaa cgcccccagg tcgggactca ttcctgtggg cggcatcttg tggccatagc  14940
tgcttctcgc tgcactaatc acagtgcctc tgtgggcagc aggcgctgac cacccaggcc  15000
tgccccagac cctctcctcc cttccggggc gctgcgctgg gaccgatggg gggcgccagg  15060
cctgtggaca ccgccctgca ggggcctctc cagctcactg gggtggggt gggggtcaca  15120
cttggggtcc tcaggtcgtg ccgaccacgc gcattctctg cgctctgcgc aggagctcgc  15180
ccaccctctc cccgtgcaga gagccccgca gctggctccc cgcagggctg tccgggtgag  15240
tatggctctg gccacgggcc agtgtggcgg gagggcaaac cccaaggcca cctcggctca  15300
gagtccacgg ccggctgtcg ccccgctcca ggcgtcggcg ggggatcctt tccgcatggg  15360
cctgcgcccg cgctcggcgc cccctccacg gccccgcccc gtccatggcc ccgtccttca  15420
tgggcgagcc cctccatggc cctgcccctc cgcgccccac ccctccctcg ccccacctct  15480
caccttcctg ccccgccccc agcctcccca cccctcaccg gccagtcccc tcccctatcc  15540
cgctccgccc ctcagccgcc ccgcccctca gccggcctgc ctaatgtccc cgtccccagc  15600
atcgccccgc cccgcccccg tctcgccccg cccctcaggc ggcctccctg ctgtgccccg  15660
ccccggcctc gccacgcccc tacctcacca cgccccccgc atcgccacgc cccccgcatc  15720
gccacgcctc ccttaccatg cagtcccgcc ccgtcccttc ctcgtcccgc ctcgccgcga  15780
cacttcacac acagcttcgc ctcaccccat tacagtctca ccacgccccg tcccctctcc  15840
gttgagcccc gcgccttcgc ccgggtgggg cgctgcgctg tcagcggcct tgctgtgtga  15900
ggcagaacct gcgggggcag gggcgggctg gttccctggc cagccattgg cagagtccgc  15960
aggctagggc tgtcaatcat gctggccggc gtggccccgc ctccgccggc gcggccccgc  16020
ctccgccggc gcagcgtctg ggacgcaagg cgccgtgggg gctgccggga cgggtccaag  16080
atggacggcc gctcaggttc tgcttttacc tgcggcccag agccccattc attgccccgg  16140
tgctgagcgg cgccgcgagt cggcccgagg cctccgggga ctgccgtgcc gggcgggaga  16200
ccgccatggc gaccctggaa aagctgatga aggccttcga gtccctcaag tccttccagc  16260
agcagcagca gcagcagcag cagcagcagc agcagcagca gcagcagcag cagcaacagc  16320
cgccaccgcc gccgccgccg ccgccgcctc ctcagcttcc tcagccgccg ccgcaggcac  16380
agccgctgct gcctcagccg cagccgcccc cgccgccgcc cccgccgcca cccggcccgg  16440
ctgtggctga ggagccgctg caccgaccgt gagtttgggc ccgctgcagc tccctgtccc  16500
ggcgggtccc aggctacggc ggggatggcg gtaaccctgc agcctgcggg ccggcgacac  16560
gaacccccgg ccccgcagag acagagtgac ccagcaaccc agagcccatg agggacaccc  16620
gccccctcct ggggcgaggc cttcccccac ttcagccccg ctccctcact tgggtcttcc  16680
cttgtcctct cgcgagggga ggcagagcct tgttggggcc tgtcctgaat tcaccgaggg  16740
gagtcacggc ctcagccctc tcgcccttcg caggatgcga agagttgggg cgagaacttg  16800
tttcttttta tttgcgagaa accagggcgg gggttctttt aactgcgttg tgaagagaac  16860
ttggaggagc cgagatttgc tcagtgccac ttccctcttc tagtctgaga gggaagaggg  16920
ctgggggcgc gggacacttc gagaggaggc ggggtttgga gctggagaga tgtgggggca  16980
gtggatgaca taatgctttt aggacgcctc ggcgggagtg gcggggcagg ggggggcgg  17040
ggagtgaggg cgcgtccaat gggagatttc ttttcctagt ggcacttaaa acagcctgag  17100
atttgaggct cttcctacat tgtcaggaca tttcatttag ttcatgatca cggtggtagt  17160
aacacgattt taagcaccac ctaagagatc tgctcatcta agcctaagtt ggtctgcagg  17220
```

cgtttgaatg agttgtggtt gccaagtaaa gtggtgaact tacgtggtga ttaatgaaat 17280
tatcttaaat attaggaaga gttgattgaa gtttttttgcc tatgtgtgtt gggaataaaa 17340
ccaacacgtt gctgatgggg aggttaattg ccgagggatg aatgaggtgt acattttacc 17400
agtattccag tcaggcttgc cagaatacgg ggggtccgca gactccgtgg gcatctcaga 17460
tgtgccagtg aaagggtttc tgtttgcttc attgctgaca gcttgttact ttttggaagc 17520
taggggtttc tgttgcttgt tcttggggag aatttttgaa acaggaaaag agagaccatt 17580
aaaacatcta gcggaacccc aggactttcc ctggaagtct gtgtgtcgag tgtacagtag 17640
gagttaggaa gtactctggt gcagttcagg cctttctctt acctctcagt attctatttc 17700
cgatctggat gtgtcccaga tggcatttgg taagaatatc tctgttaaga ctgattaatt 17760
tttagtaata tttcttgttc tttgtttctg ttatgatcct tgtctcgtct tcaaagttta 17820
attagaaaat gattcggaga gcagtgttag cttatttgtt ggaataaaat ttaggaataa 17880
attattctaa aggatggaaa aactttttgg atatttggag aaattttaaa acaatttggc 17940
ttatctcttc agtaagtaat ttctcatcca gaaatttact gtagtgcttt tctaggaggt 18000
aggtgtcata aaagttcaca cattgcatgt atcttgtgta aacactaaac agggctcctg 18060
atgggaagga agacctttct gctgggctgc ttcagacact tgatcattct aaaaatatgc 18120
cttctctttc ttatgctgat ttgacagaac ctgcatttgc ttatcttcaa aatatgggta 18180
tcaagaaatt tcctttgctg ccttgacaaa ggagatagat tttgtttcat tactttaagg 18240
taatatatga ttaccttatt taaaaaattt aatcaggact ggcaaggtgg cttacacctt 18300
taatccgagc actttgggag gcctaggtgg acgaatcacc tgaggtcagg agtttgagac 18360
cagcctggct aacatggtga aaccctgtct ctactaaaaa tacaaaaatt agctggtcat 18420
ggtggcacgt gcctgtaatc caagctacct gggaggctga ggcaggaaaa tcgcttgaac 18480
ccgggaggca gagtctgcag tgagttgaga tcacgccact gcactccagc ctgggtgaca 18540
gagcgagact ctatctcaaa aaaaattttt tttaatgtat tatttttgca taagtaatac 18600
attgacatga tacaaattct gtaattacaa aagggcaata attaaaatat cttccttcca 18660
cccctttcct ctgagtacct aactttgtcc ccaagaacaa gcactatttc agttcctcat 18720
gtatcctgcc agatataacc tgttcatatt gtaagataga tttaaaatgc tctaaaaaca 18780
aaagtagttt agaataatat atatctatat attttttgag atgtagtctc acattgtcac 18840
ccaggctgga gtgcagtgat acaatctcgg ctcactgcag tctctgcctc ccaggttcaa 18900
atgcttctcc tgcctcagcc ttctgagtag ctgggattac aggcgcccac caccatgtcc 18960
agctaatttt tgtattttta gtagagatgg ggtttcacca tgttggccag gctggtcttg 19020
aactcctgac cttgtgatct gtccacctcg gcctcccaaa gtgctgggat tacaggtgtg 19080
agccaccatg cctggctaga ataataactt ttaaaggttc ttagcatgct ctgaaatcaa 19140
ctgcattagg tttatttata gttttatagt tattttaaat aaaatgcata tttgtcatat 19200
ttctctgtat tttgctgttg agaaaggagg tattcactaa ttttgagtaa caaacactgc 19260
tcacaaagtt tggattttgg cagttctgtt cacgtgcttc agccaaaaaa tcctcttctc 19320
aaagtaagat tgatgaaagc aatttagaaa gtatctgttc tgtttttatg gctcttgctc 19380
tttggtgtgg aactgtggtg tcacgccatg catgggcctc agtttatgag tgtttgtgct 19440
ctgctcagca tacaggatgc aggagttcct tatggggctg gctgcaggct cagcaaatct 19500
agcatgcttg ggagggtcct cacagtaatt aggaggcaat taatacttgc ttctggcagt 19560

-continued

```
ttcttattct ccttcagatt cctatctggt gtttccctga ctttattcat tcatcagtaa  19620
atatttacta aacatgtact atgtgcctgg cactgttata ggtgcagggc tcagcagtga  19680
gcagacaaag ctctgccctc gtgaagcttt cattctaatg aaggacatag acagtaagca  19740
agatagataa gtaaaatata cagtacgtta atacgtggag gaacttcaaa gcagggaagg  19800
ggatagggaa atgtcagggt taatcgagtg ttaacttatt tttattttta aaaaaattgt  19860
taagggcttt ccagcaaaac ccagaaagcc tgctagacaa attccaaaag agctgtagca  19920
ctaagtgttg acatttttat tttattttgt tttgttttgt ttttttgag acagttcttg  19980
ctctatcagc caggctggag tgcactagtg tgatcttggc tcactgcaac ctctgcctct  20040
tgggttcaag tgattctcat gcctcagcct cctgtttagc tgggattata gacatgcact  20100
gccatgcctg ggtaattttt tttttttccc ccgagacgga gtcttgctct gtcgcccagg  20160
ctggagtgca gtggcgcgat ctcagctcac tgcaagctcc gcttcccgag ttcacgccat  20220
tctcctgcct cagtctccca agtagctggg actacaggcg cctgccacca cgtccagcta  20280
atttttttgt atttttaata gagacggggt ttcaccgtgt tagccaggat gatcttgatc  20340
tcctgacctc gtcatccgcc gaccttgtga tccgcccacc tcggcctccc aaagtgctgg  20400
gattacaggc atgagccact gtgcccggcc acgcctgggt aatttttgta tttttagtag  20460
agatggggtt ttgccatgat gagcaggctg gtctcgaact cccggcctca tgtgatctgc  20520
ctgccttggc ctcccaaagt gctaggatta caggcatgag ccaccatacc tggccagtgt  20580
tgatatttta aatacggtgt tcagggaagg tccactgaga agacagcttt tttttttttt  20640
ttttttgggg ttggggggca aggtcttgct ctttaaccca ggctggaatg cagtatcact  20700
atcgtagctc acttcagcct tgaactcctg ggctcaagtg atcctcccac ctcaacctca  20760
caatgtgttg ggactatagg tgtgagccat cacacctggc cagatgatgg cttttgagta  20820
aagacctcaa gcgagttaag agtctagtgt aagggtgtat gaagtagtgg tattccagat  20880
ggggggaaca ggtccaaaat cttcctgttt caggaatagc aaggatgtca ttttagttgg  20940
gtgaattgag tgagggggac atttgtagta agaagtaagg tccaagaggt caagggagtg  21000
ccatatcaga ccaatactac ttgccttgta gatggaataa agatattggc atttatgtga  21060
gtgagatggg atgtcactgg aggattagag cagaggagta gcatgatctg aatttcaatc  21120
ttaagtgaac tctggctgac aacagagtga aggggaacac cggcaaaagc agaaaccagt  21180
taggaagcca ctgcagtgct cagataagca tggtgggttc tgtcagggta ccggctgtcg  21240
gctgtgggca gtgtgaggaa tgactgactg gattttgaat gcggaaccaa ctgcacttgt  21300
tgaactctgc taagtataac aatttagcag tagcttgcgt tatcaggttt gtattcagct  21360
gcaagtaaca gaaaatcctg ctgcaatagc ttaaactggt aacaagcaag agcttatcag  21420
aagacaaaaa taagtctggg gaaattcaac aataagttaa ggaacccagg ctctttcttt  21480
tttttttttt tgaaacggag tttcgctctt gtcacccggg ctggagtgca atgatgtgat  21540
ctcagctcac taaaacctct acctcctggg ttcaagtgat tcttctgcct cagcctccca  21600
agtaactggg attacaggcg tataccacca tgcccagcta atttttgtgt ttttagtaga  21660
gatggggttt caccatgttg gccaggctgg tctcgaactt ctgacctcag gtgatccact  21720
cgcctcagcc tgccaaagtg ctgggattac aggtttgggc cactgcaccc ggtcagaacc  21780
caggctcttt cttatactta ccttgcaaac ccttgttctc atttttttccc tttgtatttt  21840
tattgttgaa ttgtaatagt tctttatata ttctggatac tggattctta tcagatagat  21900
gatttgtaaa aactctccct tcctttggat tgtcttttta ctttcttgat agtgtctttt  21960
```

-continued

```
gaagtgtaaa agtttttaat tttgatgaag tcgagtttat ctattttgtc tttggttgct  22020
gtgcttcaag tgtcatatct aagaaatcat tgtctaatcc aaagtcaaaa aggtttactc  22080
ctatgttttc ttctaagaat tttagagttt tacatttaag tctgatccat tttgagttaa  22140
tttttatata tggttcaggt agaagtccaa ctttattctt ttccatgtgg ttattcagtt  22200
gtcccagcac tgtttgttga agagactatt ctttccccat ggaattatct tagtaccctt  22260
gttgaaaatt aatcgtcctt aattgtataa atttatttct agactgtcag ttctacctgt  22320
tggtctttat gtcgatcctg tgccagtacc atacagtctt gattactgaa gtttgtgtca  22380
cagtttaaat tcatgaaatg tgagttctcc aactttgttc cttttcaaga ttgatttggc  22440
catgctgggt cccttgcatt tccgtacgaa ttgtaggatc agcttgtcag tttcaacaaa  22500
gaagccaagt aggattctga gagggattgt gttgaatctg tagatcaact tggggagtat  22560
tcgcatctta acaatattgt cttccaccta tgaacatggg caaactttgt gtaaatggtc  22620
agattgtaag tatttcgggc tgtgtgggca cagtgtctct gtcacagcta cgcggctctg  22680
ccattgtagc atgaaagtag ccataagcaa tatgtatgag tgtctgtgtt ccaatagaat  22740
tttattaatg acaaggaagt ttgaatttca tataattttc acctgtcatg agatagtatt  22800
tgattatttt ggtcaaccat ttaaaaatgt aaaaacattt cttagcttgt gaactagcca  22860
aaaatatgca ggttatagtt ttcccactcc taggttaaaa tatgatagga ccacatttgg  22920
aaagcatttc tttttttttt tttttttttt tttttgagac ggagtttcac tcttgttgcc  22980
caggctggag tgcagtggcg cgatctcggc tcactgcaac ctctgcctcc caggttcaag  23040
acattctcct gcacggcctc cctagtagct gggattacag gcatgcgcca ccacacccag  23100
ctaattttgt atttttagta gagacggggt ttctccatgt tggtcaggct ggtcttgaac  23160
tcctgacctc aggtgatcca cccgcctcag cctcccaaag tgctgggatt acagggtgtg  23220
agccaccaca ccctgctgga aagcatttct tttttggctg tttttgtttt ttttttaaac  23280
tagttttgaa aattataaaa gttacacata tacattataa aaatatcttc aagcagcaca  23340
gatgaaaaac aaagcccttc ttgcaagtct gtcatctttg tctaacttcc taagaacaaa  23400
agtgtttctt gtgtcttctt cccagatttt aatatgcata tacaagcatt taaatgtgtc  23460
attttttgtt tgcttgactg agatcacatt acatatgtat ttttttactt aacaatgtgt  23520
catagatatt gttccatagc agtacctgta attcttatta attgctatgt aatattttag  23580
aatttctttt taaaagagga cttttggaga tgtaaaggca aaggtctcac atttttgtgg  23640
ctgtagaatg tgctggtgac atattctctc taccttgaga agtccccatc cccatcacct  23700
ccatttcctg taaataagtc aaccacttga taaactacct ttgaatggat ccacactcaa  23760
aacatttagt cttattcaga caacaaggag gaaaaataaa ataccttata aagcactgtt  23820
taatattgta ttaaattgga tcaatttggg ggctagaatg tatgttagag acatgatatg  23880
tccataggtc cttgctatca cagtgaggtc tcagggacag tcgtttggta tcatttggga  23940
tctcataagc agactctctc tgcttgacct gacaaatcag agtctgtgtt ttaacaggtt  24000
cagtgagtga cttacatgca cattggagtt tgggaagctc cactgtaggt gcttagacct  24060
tacctttgtt gttgctaata acaatgcaag catttgggag gaagacctgt gttgctcata  24120
tgtgtccagg tgtagctgag gtggccttgc ttatctgctg tagggccgtt gagcatttct  24180
gtagctgtga tgagtgagct gaggtgagcc tgcggagagc tcccagccat tggtagtggg  24240
actcgcttag atgaactgga aggacccttt catctgagca gccactatgg agaaaaacaa  24300
```

-continued

```
ccgaatgagg ggagagacaa tgtgcaattt tatttagggc acaaaggaga gctgtggtta  24360
gaaggtgaca tttgagtgga aagggggcaa gccatgtgta tagcgggaga agagaggtcc  24420
aggcagagtt aacagaaggc agaaatgctt tccatgtttg agaaccagta aggaggccag  24480
tggctgaagt aaggtgaagg gcagaaataa ggatgaggct gcgagagatg agaggttaga  24540
gacgagcgtc ttgtgcacca agataagctt gtgtggtcaa aacaagtagt ttaatttatg  24600
tttttaaaag atcattttgg ctgggcacaa tggttcatgc ctgtaatacc agtagtttga  24660
gacggtgtgg tgggaggatt gcctgaggcc agacgaccag catagccaac atagcagcac  24720
ctataaggtc tctacaaaaa actttaaaaa attagctggg catagtggtg tgtgcctgta  24780
gtcccagcta ctcaggaggc tgaggaggct ggaggattgc ttgagtccag gagtttgagg  24840
ctgcagtgag ctatgattat gccactacac tacaacctgg gcaagagagt gagaccctgt  24900
ctctaaatat acacacacac acacacacac acacacacac acacacacac acacacacac  24960
acacacatat atatgtatat atatgcattt agatgaaaag atcactttga caataccaca  25020
tgctggtgag gatttagaaa aactaggtca cttattgctg gtgggaatat aatatagtac  25080
ggccactctg gaaaacagtt tggcagtttg tcataaaact gaacataccg ttagtataca  25140
gcccagcagc aactacaatc ctgggcatta atcctagaga aatgaaacct taatgttcac  25200
ataaaaacct atactcaagt atgcatagca gctttaccca taatatctaa gaactggaat  25260
cagctcagat gtccttcaac aggtgaatgg ttaaactact cagtaataaa aaggaatgag  25320
ctactgatag catgcaacag tttaggtgaa gttatgctaa tgaaaaaagc caatcccaaa  25380
aggttataca tactgtatga ttctatgttt ttttgcaatg gcacagtttt agggatggag  25440
aatagattag tggttgcctg gggttagaga tggggtagta gagtaggtta gtggtggcag  25500
aggagagaaa agagagggag gtgaatgtgg ttataaaagg acaacacagg ggaatacttg  25560
taatggaaat gctttgtctt tttttttttt tttttttttt tggcgacaga gtcttgctct  25620
gttgcccagg ctggagtgca gtggcatgat cttttctcac tgcaacctct gcctcctggg  25680
ttcaagtgat acttgtgtct cagtctccca tgttcagagt gaaacaaacc agaggtaatg  25740
ttcatccaaa taatccaaca cacatgacat taaaacatca agatcaggtc ggacgtggtg  25800
gctcatgcct gtaatcccag cacttttggg aggccaaggt gggcagatca cttgaggtca  25860
ggagttcgag accagccggg ccaacatgat gaaaccccat cttgactaaa aatacaaaaa  25920
ttagccgggc atggtggtgt gcacctgtag tcccagctac ttgggaggct gaggcaagag  25980
aactgcttga acccgagggg cagaggttgc agtgagctga gagtgcgcca ttgcacttca  26040
gcctgtgtga cagagtaaga ctccatctcc aaaaaaaaaa aaccaagatc aattaaaata  26100
cagcattact gggccgggtg tggtggctca cacctgtaat cccagcactt tgggaggccg  26160
agatgggcag atcacgaggt caggagatcc agaccatccc ggctaacacg gtgaaacccc  26220
gtctctacta aaaaatacaa aaaattagcc gggtatagtg gtgggtgcct gtagtcccag  26280
ctacttggga ggctgaagca ggagaatggt gtgaacccgg gaggcagagc tggcagtgag  26340
ctgagatcgc gccactgcac tccagcctgg gcgacagagc aagactccgt ctcgggggaa  26400
aaaaaaaaat aaataaatag aatgctgtag tgtccttgag tttacatgcc cctccttacg  26460
cttgtgtgcc cgtgcagatt gcttgattac acaattagag gaggctggcg gaggattgtt  26520
ttaatttttt tttttttgag acagtctggc tctgttcccc aggctagagt gcaatggcgc  26580
aatcttggtg cactgcaacc tctgcctcct gggttcaagc agttcttctg ccgcagcctc  26640
ccgagtagct gggattatag gcgcccgcca ccacgcccaa ctattttttg tatttttagt  26700
```

agagcagcgt ttcaccatgc tggccaggct ggtctcgaac tcctgacctc agatgatctg 26760
ctgccccagc ctcccaaagt gctgggatta caggcgtgag ccacacctgg ccgtttgttt 26820
taattttgaa ggtgaagtga aagtgactac atttaccaaa agtgattgaa aagccaggac 26880
tgttcttacc ctgtttttcc agttcttgct cagagcaagg tggtttcttt ttcacttaat 26940
caccatactt acttttcatg tagaacaagt cagtttgagt tatcagttca tcatcttaac 27000
taaattccat gggggaagga attagtttta gtttcttaaa cttccaggtt tgcttattgg 27060
acaaaatgag atagcaaggc agtgttttta agttagattt tttatttctt tggtaataca 27120
attttctcag aaacttagta gtcttttagt ttagttgttt ttagttggtc ctatgttttg 27180
gatcacccct ctctacttta ttttgatagt gccaactgtg aagacatctg aagccatagg 27240
tttggatggg aaggaggcat ctttagcctg atcatcttcg ccaggctgtt tatctccttt 27300
tgcttggctg agaagtctta ataggaggct tattcccagc tatttgggga catagaagca 27360
gttagccatt gcttatattt tactgaggtc tgtgtggtat gttgattgta gtcagttaac 27420
gattttgaga actgaaggca gcctggtata tatagagtag gtattagact gtgtttcttc 27480
taattgaatt tcccatctct tgtaatctat gccatcatct tctgtactgc tgagaaagaa 27540
agaaagtttc taatcaaact ataccactgg ttgtaagatg cagtttggct ttagtgatgt 27600
taacacatga ttcaaacgtg aaattgattg agtattggtg aaatacagag gagatttaaa 27660
gccagaagac ctgggtttaa atgctggctg tatgacttca tatctgtgtg atcttgggca 27720
tgtcatggtt ggcacttcaa tttcttctct ctataatggg ggaagtgagg ccagtcatgg 27780
tggctcatac ctataatccc agtgctttgg gaggccaaga tgggaagatc gcttgaggcc 27840
aggagtttga gcaattgggc aacatcgtga ggccccgtct ctacaaaata ttttgaaaaa 27900
attagccagg cccagtggtg cgtgcctgtg gtccgcgcca ctcaggaggc tgagacggga 27960
ggatcctttc agcctaggag tttaaggcta aagtgagcca tgattgtgct atcgtactcc 28020
agcctgggca gcagagcaag atcctgactc taaaaaaaag taaaataaag taaaatgggg 28080
gaaatgaact gctttagtaa catcatctgt tttttctgtg agcagcgtag cttgacagcc 28140
attggtgaac tcgtgccctg tgcttccctg tccagatccc cattctgccc gcaacatgga 28200
gtataacggt ttattcatag tagtcgagaa acactcactg aatgaatgaa tgaggtgtag 28260
aactaagtgg agtgggtaat tcaacacata ttaatttcct tctttttttt atttttagaa 28320
agaaagaact ttcagctacc aagaaagacc gtgtgaatca ttgtctgaca atatgtgaaa 28380
acatagtggc acagtctgtc aggtaattgc actttgaact gtctagagaa aataagaact 28440
ttgtatattt tcagtcttaa tgggctagaa tattctttgt gtcccagcta ttttaaatgg 28500
attcagaaat ccatttaaga tgaagaagga ccctttttccc atatttctgg ctatatacaa 28560
ggatatccag acactgaaat gaataatgtt cccttttttgt aatcttttat gcaaaaatta 28620
aaaccattat ggtaattgaa caacatgttt atgtttagtt aacaccctta gcaactatag 28680
ttattttaaa accatctatg gtttgatatt tttgcatttg ttgcaatagt aggaacagca 28740
caagacagtt cagtttgtct ctcttatttg ctttttcttg gcagtttgct gtcctattgt 28800
acctctgctc ctagcagtgg ctggagccca ctcctctgtg cttcgggatt agtggggatc 28860
gtggggcatt gactgtaggt cagctttcct tgcttgatct ttctcactgg gatgaactag 28920
cagcaccttc ttttgtagct gctttgcttt tgactatctt tctgaccgtt gttcctagta 28980
gctgtagatg gtaaatatat ttaggcctgt ttccaatggc tcagtaggag acatattcac 29040

-continued ctatgatatc tgaattctgt tacccacatg ggcatgcgtg aaatagttgc cttgccttac 29100
tttcccttgg aataaataat tcatgttatt ctcctggtag aagctagaaa aagcctttat 29160
agtcagtcag aaaaaaattt ttagacaaat aatcttgatt ttagtactga caaaaacgtg 29220
tggtgattct ttttttaatt ttttttgag acggagtttc actcttgttg cccaggctgg 29280
agtgcaatgg cgtgatctcg gctcactgca acctctgcct cctgggttca agtgattctc 29340
ctgcctcagc ctcccaagta gctggagtta caggcatgtg ctactgtgcc cagctaattt 29400
tgtattttta gtagagatgt tggtcaggct gatctcgaac tcccaacctt aggtgatctg 29460
cccgcctcag cctcccaaag tgctgggatt acaggcgtga gccagggcgc ccggtgattc 29520
atttgttttt tcaaaaaatt tcctcttggc cattgctttt cacttttgtt tttttttttt 29580
ttttgagacg gagtcacgat ctgtcaccca ggctggagtg cagtggcatg atcttggctt 29640
actgcaagct ctgcctccca ggttcacgcc attctcctgc ttcagcctgg cgagtagctg 29700
ggactacagg tgctcgccac cacacccggc taattttttg tatttttagt agagatgggg 29760
tttcaccgtg gtcttgatct cctgacctca tgacccgctc aactcagcct cccaaagtgc 29820
tgggattaca ggcgtgagcc accgcgcccg gccctctctt gtctttttat tgtggtaaaa 29880
tgcacataaa attgactgtc ttaaccattt ttaggggtac agttcagtat atatattcgt 29940
aatgttgtac agccatcact gccatctact tcataagttt ttcttctgtc aaaactgaac 30000
atctgtcttc attaaactcc ctatcatcca ttctttcctg tagtcccttt ctactttctg 30060
tctgtatgag tgtaactgct ctggagacct catgtaagtg gattcctaca ggatttgtgt 30120
tttttttttg gtgatctgct tatttttaat gcctctgtgc atttgtatta tatactttca 30180
aagtgatttc acaaaaccgt ttcattttag gttaactcat ttctgttgtt tgtgaaatac 30240
tgtgtatgat tctgttctgt ttctgtctaa tttgtggaaa tgttgtggga agaaaatgaa 30300
ataacaaatg agcatatgtc ctgaaaataa aaatataaaa attctaagtt agcatgctat 30360
tgtagaatac aacgctatga taaaagtagg aaaaaaaaag gtttgaattc tatctctgct 30420
acctgtgtaa gctgggtgac tttagataag ctgtaacgtg tttgagcctt actggctcat 30480
ttttgaaatg taatccctag ttacacagtt cttgtgggat cagatggtac atgtgaaaca 30540
ctgtgaaaaa gcaactgcat agatatgttc attagccacc tgagcgggaa gcgtatccca 30600
ttgcgatgcc catcatccaa agctatatgt tatctttact tttttttttt tgagacagag 30660
tcttgctctg ttgcccaggc tagagtgcag tggtgcaatc tcagctcact gcaagctcca 30720
cctcccgggt tcacgctatt ctcctgcccc agcctcccaa gtagctggga ctacaggcac 30780
ccgccaccat gcctggctaa atttttgtat ttttagtaga gatggggttt caccgtgtta 30840
gccaggatgg tcttgatctc ctgacctcgt gatccgcccg cctcggcctc ccaaagtgct 30900
gggattacag gcgtgagcca ctgcccctgg ccatctttac ttttttttgtg aaatgacttt 30960 aaatacttgg caaacatttg gtcattgttc atctgatctc caccatccag gtctcagaga 31020
acataatttc tctctgaaag cttattgacc caggaaataa gatctctttc aatctgagtg 31080
cgtcaggctt tattcttgtc attttgtctt ttgataattt tcaaatggaa ttcatggaat 31140
gttggcttat attcatatat tagtaaagta tgttgagaca tcttaagatt gatttgtggt 31200
tctatatgcc atattaaatc aaaataatag ctgttaatgg ttttcacatt agtctgtctc 31260
ttgtttttat ggagtaatgc tgagagttca ttatgcttgt tctacagaag agcatgttaa 31320
aaggagtttt tggagtcaga gaggttattc ttggtttcat aggatacact ctatactttt 31380
tagggatttc agagtatata gctgaaggtg atattttatg taaatatgtt ttatggaaac 31440
ttattgctca tcgctgtttc ctgttaactc tcctaaaata taattaaact tttggaactt 31500
ttttatagct tttgtgctag actaattttt gtctctaatg aggttatata aatggcagct 31560
tctgacgttt tcaatgtagg aagtcattta aaacttcatg tatattgtga aaatgtagtc 31620
tgctttaagc tctctaaagt ggtctaagtt actggttcct aagtatggat gagcatcaaa 31680
atcatctgga aaatttgtta aaaatacagt aatgaaggca cctcactgtc ctttttccca 31740
aacatacttc tgcattctgt ttgagtaggt agggactaca catttttcac aagtatcctc 31800
ttgggaatac ccaggaatgc ttacttgagc aacctcttac taatatgtac cttgataagg 31860
tggctaggta aacataaata tacaaaaatc catagatctc ccatatatta gcataaatca 31920
gctagaaaat ataacgttta aagatctagt tcacagtagc accaatatat cgaactctaa 31980
ggaatcgata aatatgcaaa aactttataa aaacttctgt taatgtttct gaaagatata 32040
ggtgaccact ttctagatag gaagatttta tattactaag ttgaattttc tctaaattaa 32100
cacagaaatt taaaataatc ttgatcaaaa ttctagtaga ggtatttttg aacttgttca 32160
ctgcaagaat aaatacataa ttgcaaagaa tatctcaaaa tcatcaccag gcctggtgtg 32220
gtggcccatg cctgtaatcc cagcactttg ggaggctgag gcaggcagat cacctgaggt 32280
caagagtttg agaccagctg gaccagtgcg gtgaaacact gcctctacta aaaatacaaa 32340
aattagctgg gtgtggtggt gcatgcctgt agtcccagct acttgggagg ctgaggcagg 32400
agaattgctt gaacccagga ggtacaggtt gcggtgagcc tagatcgcac cactgcattc 32460
cagcctgggc gacaagagca aaattctgtc tcaagaaaaa agagaaaaaa gaaaaagaaa 32520
tcaacactaa tatggtgaga cttaatgtat gtgacattaa aatagtgatt ggatgttaaa 32580
acaggtatag aacagaaaga agagtgtatg tgtgtatctg tatgaattta tgatgggtgt 32640
aacatatatg tattagggaa atgagggaaa tgatacattt ctctgacttt gggagaacat 32700
tatatctcta cctcatattg caaacaaaca taaagttcag attaattacc taaatgtgaa 32760
aaaatgaaat aatttcttta aaaaatgtaa tcttagtttg aggaaggtta acattataaa 32820
ggaaaaaact gttttgagtg gaatatagtt caatatgtca aaatccacct tcaacaaaat 32880
tgaaagtaaa ttgaacttgg ggaaagtatt gacagcatat agatcaaagg ttactagcct 32940
gtgtaaagag cagttataaa tatcgttaag aaaaacactg tcgacctgtc ggcaccttgt 33000
tctccgactc ccagcctcca gaactgtgac gagtaagtgc ttattgttta aaccacccag 33060
tctgtatgtg gtattttgtt atagaaactc aagctgatta ggacactagt aatcagtaga 33120
ctgaaactga aacaaaaata agaacctttt ttacctgtca aattggcaaa cattaagaat 33180
attcagattt ttgtcagagg tgatacaacc ttctaagaag gcaatttggg aaaatataaa 33240
gctttagatt attatatgtc tgacctagca gttttacctc tagggtgctt acccctagga 33300
aagtgtgtaa tgatattggt gcagtgccct tcatcccatt agaaaattaa aaataacctt 33360
aatggcctac cactaaaagg ggattgaaaa tttaagatat atttatttat gtgtttattg 33420
agatggagtc ttgcactgtc cgcctgggcc agagtgcaat ggtgcgatct cggctcactg 33480
caacctctgc ttcccgggtt catgtgattc tcctgcctca gcctcctgag tagctgggat 33540
tacaggctca caccaccgca cccggctaat tttttgtatt tttagtagag atggggtttc 33600
actgtgttgg ccagactggt ctcgaactcc tgacctcatg atccgcgccc ctcggcctcc 33660
cagtgttggg attacaggtg tgagccactg cgcctggcca gatacattta tacaagagaa 33720
tgttagttaa cattcataga tatttatatt ttgtttactt tttattaaaa aaattttttt 33780
tagagacagg atcttactct gtcacccagg caggatgcag ttgcacaatc atagcccact 33840
gcagcctgaa ctcctgggct taagtgatcc ttctgcctca gccttttgag tacctggggg 33900
actttaggca gtgctactat acctggctaa tttttaaatg ttttatagat gagatcttgc 33960
tgtattgccc aggctggtct agaattcctg ggcccaagtg atcctcccac cttggcctcc 34020
caaagcgctg agattacagg catgagccac cacttctgac caatagatat ttatatttgt 34080
gactggaaaa tatattaaca atgtgttaaa aaattcagtt aaaaaataat gaaagatttt 34140
tgcttctggc taagatagaa taacaaggac agcatttatc ttcttgcctt gaaatagttg 34200
aaaacggaag aaatatatgt aacagtggtt ttcaagttat tgggcatcag gcaaagaaga 34260
atagttatcc caggaaaatg aatgtggaga gccctacaat ttccttacat tactgcctgg 34320
tcatggcaag aggaaaaact gagaggagac tgaggctgag ccagtggttt gctgggttga 34380
ggaggcagag ctgggagtgc agagatgcaa ggtggtgaga gcccatatgg aagaatacca 34440
gggaagagag ctgcagaggg agctccggag acctgcaccc tgccctctca gtaccctgtc 34500
atgtgtgtag ctgagtactg acgagcactt gcttgtgcgg aaatgaccca gggctggagg 34560
tagagccacc tgaaaggatt agaaggaaca gttgctgaaa gtcacacagg gccaggaaga 34620
atttctaatc acaccagttg gagtggaaaa cctcagctct catagagcag gtagggtact 34680
cagaagggtt tgcccaccta gccccagact aagtttcgtt actctgaccc tacctaatat 34740
taaaaagaga ttaattaaat tgttcgcaac aaaaataata tatttcagtg tttgtaacac 34800
gtagaagtga attgtatgac aatagcataa aggctggaag agcagaaatt gacatgtatt 34860
tgcgctgggc agaataatgc tcccctcttt ccccaaaaga tatcaagtcc taatccctgg 34920
agcctgtaaa tattacttta tatggaaaat tgttttatga tgtgattaaa ttcaggatct 34980
tgagatgagg gggctatctt ggatgatctg ggtaggcact aaatgcaatc acatatatat 35040
aaaaaggagg cagagggaga ttttacacac agagagaagg ccctgtgaag atggaacaga 35100
aagatttgaa ggtgctggcc ttgaaaattg gagtgatgaa gctataagcc aaggaatgca 35160
gcagccacca aagctggaag aggcacggag cagttctcat ttagagccta ctccagaggg 35220
aatgtggtgc tgccaattcc tttttttttt ttttttttaa gatatcattt accccttttaa 35280 gttggttttt tttttttttt ttttttttta gtatttattg atcattcttg ggtgtttctt 35340
ggagaggggg atttggcagg gtcataggac aatagtggag ggaaggtcag cagataaaca 35400
tgtaaacaaa ggtctctggt tttcctaggc agagggccct gccacgttct gcagtgtttg 35460
tgtccctggg tacttgagat tagggagtgg tgatgactct taacgagtat gctgccttca 35520
agcatctgtt taacaaagca catcttgcac cgcccttaat ccatttaacc cttagtggac 35580
acagcacatg tttcagagag cacggggttg ggggtaaggt tatagattaa cagcatccca 35640
aggcagaaga atttttctta gtacagaaca aaatggagtg tcctatgtct acttctttct 35700
acgcagacac agtaacaatc tgatctctct ttcttttccc acatttcctc cttttctatt 35760
cgacaaaact gccaccgtca tcatggactg ttctcaatga gctattgggt acacctccca 35820
gatggggtgg cggccgggca gaggggctcc tcacttccca gatggggcgg ccgggcagag 35880
gcgcccccca acctcccaga cggggcggcg gctgggcggg ggctgccccc cacctcccgg 35940
acggggcggg tggccgggcg ggggctgccc accacctccc ggacggggcg gctggccggg 36000
cgggggctgc cccccacctc ccggacgggg cgggtggccg ggcgggggct gccccccacc 36060
tcccggacgg ggcggctggc cgggcggggg ctgcccccca cctcccggac ggagcggctg 36120
ccgggcggag ggctcctca cttcccggac ggggcggctg ctgggcggag ggctcctca 36180

```
cttctcagac ggggcggctg gtcagagacg ctcctcacct cccagacggg gtggcagtgg  36240
ggcagagaca ttcttaagtt cccagacgga gtcacggccg ggcagaggtg ctcttcacat  36300
ctcagacggg gcggcggggc agaggtgctc cccacttccc agacgatggg cggccgggca  36360
gagatgctcc tcacttccta gatgggatga cagccgggaa gaggcgctcc tcacttccca  36420
gactgggcag ccaggcagag gggctcctca catcccagac gatgggcggc caggcagaaa  36480
cgctcctcac ttcctagacg gggtggcggc tgggcagagg ccgcaatctt ggcactttgg  36540
gaggccaagg caggcggctg ggaggtgaag gttgtagtga cccgagatca cgccactgca  36600
ctccagcctg ggcaacactg agcactgagt gagcgagact ccgtctgcaa tcccggcacc  36660
tcgggaggcc gaggctggca gatcacttgc agtcaggagc tggagaccag cccggccaac  36720
acggcgaaac cccgtctcca ccaaaaaaca cgaaaaccag tcagacatgg cggtgcgtgc  36780
ctgcaatccc aggcacttgg caggctgagg caggagaatc aggtagggag gttgcagtga  36840
gtagagatgg tggcagtaca gtccagcctt ggctcggcat cagagggaga ctgtgcgagg  36900
gcgagggcga gggcgaggga attccttaat ttcagtttag tgatactaat tttggactct  36960
ggcctctaaa actgtgaaag aaaaaatttt ttgtttgttt gtttctttta agccacatag  37020
tttgtggtaa tttgttacag cagctgcagg aaactaattt atgctgcatg tgaaatggtg  37080
taataaggta gattgtgatg aagatacata gtataaacaa ttaagcaaca actaaaagca  37140
caacaaggaa ttatagctaa tgaaccaaaa aaggagatta gaataataaa aatggtgaat  37200
cccaaagaag ccagaaatag gggaagaggc aaataaagga aagaaagagc ttgatggtag  37260
atttcaacct aactatgtca aaaaggacat tacatgtaaa aggcagcgat ttttcagatt  37320
gaatggaaaa gtaagactcg gtatatgctg ctgcctgcaa gaaacacatt ctaaatataa  37380
aggcaaaaat aacctacagg taacagaacg gaaagaagtt cactgtgctt acaagaatta  37440
gatgcaagct agactggttc tgttaatatc agacaaagtg gatttcaaag caaaggctct  37500
tgcccaggat gagatggtca tttcataatg atgaagggga ttcgttcatc agcctggcat  37560
agcaagctga aatgtttatg caccggacta cagagctaaa atacatgaag caaagcctga  37620
cagaactaca agtagaaaca gacaaatcca cagtgataga gatttcagta gccgctctca  37680
atgatttgta gaacacgtag ccataaatatc tggatctaga acacttgacc aacactgtcc  37740
cctgtgcaac ctcattggca tttacaggac actccaccca gcaccagcag aagagacact  37800
ctctcaagtg ctcacagaat gtttgccaag atagagcaga tgctgggcca taaaacaagt  37860
ctctaaatta aaagcattca aattattcag agtatgtttt ctgacctcag tatcattaag  37920
ttggaatata ttataggaag ataacctgga aaagcctcag atatgtggaa aaacccattt  37980
ccacatggcc catgggtcag aagtgaagtc aaaagggaaa tttgaaagtc ttttggattg  38040
actgatataa aaacaataga tttctaaact tgtggggtgc tgttacagca tagtaaatgg  38100
aaatttctag cattaaatgc ctgttttagg aaagaaagat ttcaaatcaa tgacctcagc  38160
ttctaccttt ggaaacttga aaatgacaag caaatggaat ccagagttac cagaagggcc  38220
aggtacggtg gcttatgcct gcagttctgc cactttggga ggccgaggca ggtggattgt  38280
ttgagactgg cagttgaaga ccagcctggg cagcctaggg agaccccata tctacaaaaa  38340
acaaaaaaat tagccaggtg tggtggcatg tgcctgtagt cccagctaac caggagtcta  38400
aggtgggagg attgcttgag tctgggaggt tgaggctgca gtgaactgtg attgtgccac  38460
tgtgttccat cctgggcaac agaatgagac cctgtctcaa aaacaaaaac agttactaga  38520
```

agaatggaca tcataaagat aggagcagaa gtcagtaaaa tagaaaacaa aaatacatag 38580
gaaatcaata aaaccaaaag ctggttcatc aagaacatca ataaattggt aaagctgata 38640
ggaaaaacag tgaagtcaca aattagcaat atcaggaatg agggagatga cagtagtata 38700
gattatatag atattaaaag gactgtatga ggcaggtgtg gtggttcacg cctgtaatcc 38760
cagcaccttg ggaggccgag gtggacagat cacctgaggt caggagtttg ggaccagcct 38820
ggccaacatg gtgaaactct gtctctacta aaaatacaaa aattagttgg tcgtggtgct 38880
gtgtgcctgt aatcccagct acttgggagg ctgaggcagg agaattgctt gaacctggga 38940
ggcggaggtt gcagtgagct gagattgtgc cgttgcactc cagcctgggt gacagagcaa 39000
gactccatct caaaacaaat aaataaataa aaaggactat atggtaatat tatgaacaac 39060
tttatgccaa taaatttgac aacttataga tgaaatggat gagttccttg aaagacacag 39120
aaactattaa agctctctca agaagatata gataagctga ttagccctat atctatttta 39180
ttgaatttaa atgtaaaaat caatatttag ttactggaaa acttttaagt gtggttggaa 39240
atggtatacg aactttttca actgaatttt atgaagtcta atcacaggta aaggttttct 39300
gatgaaaatt tagtgtctga attgagatat actgtaaaaa atgttatata tcttaattat 39360
ttcttcacat taattacatg ttgaaataat actttgggtg tattgggtta aattaaatat 39420
tatgaaaatc ttgcctgttt tctttttact tttgatgcgt cagctaggaa atataaaagt 39480
gtagctcaca ttctgtttct gttgacagta ctgctttgga gcacagtgtt tgaatgatct 39540
atcatttcaa agacctttcc tcagttcgtt attcatggct gtctgtattc cacatagata 39600
aggtctgaaa tactgctaag tggcatgttt tgttttatgc ttttataagt ttgttgatca 39660
ttactgatgt ggacttttgg tgcctcttag gctcattgct atcttccaac cattgtttgc 39720
aatttttacc tagagataaa gagaaagaga catttggttt cagagtagtt agattgggat 39780
catgaaagag caacctcatt ttgatgcttc aaaaatagca catccccctgt attactggga 39840
tttgctattc ttgggattac ttcaagaaca tccttgtgtt actggtttgg atgcttctga 39900
atgctgtgaa gtcagtttca tgtacatggc tcatcagttt agctctctct tggctttgtt 39960
tagacagttg gagcatgatg gcctaaacag cttctttcaa ttaaacattt taaaatagtt 40020
tacaaatagt aaacaaactc cagtttttgt gactctttgt ctcgcacaac aaaaacacaa 40080
tctgaccatg atcatctggc atcttagggt gaaatatggt tatactttgg cccataccga 40140
aagcaagatt aaaaaggggc aggagagata gactgctgaa ctgattttca aggttccaag 40200
aatattgtag gttaagagta aaagtaaact tttggtagaa agcagtgggt tgtctaggat 40260
tgaagtatct gaagttttta aacgaaaatt taaaaagaaa aatgagaatt gccttacaag 40320
tacaatctct tctttttaa aaaataaact ttattttgaa atagttttag atttatagaa 40380
aaaaattaga tagggtagga agttttcata taccctacat ccagttaccc cagttattat 40440
catcctaatt tagtgtgaga cattttcatg tttaatgaat caatattgat atgctattaa 40500
cttaagtcca gactttattc agattttctt aatttctatg taatgtcctt tttctgttcc 40560
agaattccat gcaggacacc ggatacctca ttacatttca ttgtcatgtc accttaggct 40620
cctcttgaca gtttctcttc tttttttgct tagaaattct ccagaatttc agaaacttct 40680
gggcatcgct atggaacttt ttctgctgtg cagtgatgac gcagagtcag atgtcaggat 40740
ggtggctgac gaatgcctca acaaagttat caaagtaaga accgtgtgga tgatgttctc 40800
ctcagagcta tcattgttgt aggctgagag aagaagcgat cattgagtgt tcttctgttt 40860
tgagtccctg aggatgtctg cacttttttc ctttctgatg tatggtttgg aggtgctctg 40920
ttgtatggtt tggaggtgct ctgttgtatg gtttggaggt gctctattgt atggtttgga 40980
ggtgctctgt tgtatggttt ggaggtgctc ttgtatggtt tggaggtgct cttgtatggt 41040
ttggaggtgc tctgttgtat ggtttggagg tggtcttgta tggtttgcag gtgctctatt 41100
gcatggtttg caggtgctct attgtatggt ttggaagtgc tcttgtatgg tttggaggtg 41160
ctcttgtatg gtttggagat gctctattgt atggtttgca ggtgctctat tgtatggttt 41220
ggaagtgctc ttgtatggtt tggaggtgct cttgtatggt ttggaggtgc tctgttgtat 41280
ggtttggagg tgctctgttg tatggtttgg aggtgctctt gtatggtttg gaggtgctct 41340
attgtatggt ttggagatgc tctggtatct gcctgcattg cttgccacac ctgcccggtc 41400
agaaggcgct atgttgacaa ttgtgcctgc acggtgccta ggtcaatgaa gggaaccgat 41460
ggtagccact ggatgctcct gggaaaatgt cactacaggc accagagaag ccagagctat 41520
gcccaaattt ctatgagtct cagttttctt aaccataaaa tgggatcaat gtttttgtgg 41580
catgtgtatg agtgtgtgtc tgtgtatgtg tgaggattaa attgtgtatg tgtgaggact 41640
aattgccact actggatcct caaagtggta agaagtgttc ttattaataa tgacatcctt 41700
acactcttac ccagcaagat tgatgggtgt ggcactgctt ctctttttcc atcacatggt 41760
ttccatggta tccttttgcc cagggaatct ttgctttgtg gctagcactt tgttgtttgg 41820
ctaatcacgc tttctgtggt caggacgctg gcttctctgg agccatggga ttctagctcc 41880
ctgtcttgtc cctagagtgg tcactgtctt ctctctccgc ttgcaattcc tgctttgctc 41940
gcatctcact tatgcagtga cgtatatcag tttcaccttg ttctccgtgc ctgctgatca 42000
ttggcaccac ttgcatggtg ccatttaggg cctgcttcca gttaagcttg cttctccaca 42060
ggcctaaata tccttgcttg cttcttttat tctcactggc aggaccaggg cggtctgtct 42120
ttgcatgaga cagggtctcg ctcagtcacc caggctggag tgcagtggct gatcacggct 42180
cattgcagcc ttgagctacc gggctcaagc tatcctcctg gcttggcccc ttgagtagct 42240
gggactacag gcgtgcacca ccatgcccag ctaattttta aaattatttg tagagatggg 42300
atctcgccag gttgcccagg ctggtcttga acgcctgggc tcaagtgatc ctccctcctt 42360
ggtttcccaa agtgctggga tcacaggtgt gagccactgt gcctggccct tgatgtttca 42420
gttcttgata tttgatcctc agagtcagaa aatctaaaaa gagggctatc ccaggttgcc 42480
ttggttcatg gcaaatggga cgttaagagg gcagagagaa tatgaacaga aactgttcta 42540
atattggtca tttaatgtgt aagtattgtt ctttttaaa cctccttcat ttttttcca 42600
ggaattgctg gacacagtgg cttggtgtgt gtctgaggac tgtaggccat ggccctaggt 42660
tgtggtttta ggtctcaggt gctcttcctg gctgtctcct tgcttctttc ccatgtcctc 42720
ttctttgttt ccagccattt ctcccttatg cttaagtttg gtgcagcagg gtttggctgc 42780
tctcagattc ctgcttcctc agatgctgta gttgtcaggc ccagcgggct ggcagcggga 42840
tcaggatctg gctaggtttg ctctcactgt ggcagagtag ggggaggcgt gggagagcac 42900
gtgtgacccc aggccagctg tagggagcat aggcatggtc acgtagcctt caggtcctag 42960
actttgtctt ctcatgagta tggctgtgtg tgtatggtga aaactaggtt ctacttagcc 43020
caagaaaatg ggcacatttt gcatgtggtt tctgtagaga aatgcactgg gtatctgaca 43080
tagcctggca gcatgcctcc ctcaggtagg ttagtctcag gcggtgaagc acgtgtgtcc 43140
agcaagaact tcatatgtgg cataaagtct ccgttctgtg aggtgctggc aaatcaccac 43200
caccgtcaag aggctgaagt gatttttgtc tagggaggca ggaaaggctt cctggagtca 43260
gcagccagta ggtgaaagag tagattggag accttcttaa tcatcaccgc ctcttgtctc 43320
aaggggtgcc aggaagctgt ggaggctgaa cccatcttat gctgccagag agtgggacac 43380
catgagggtc aggtcaaggg gttgtacctt gtttggtaga gaattagggg ctcttgaaga 43440
ctttggatgt ggtcagggga gtgtatcatt taggaagagt gacccggtga ggacgtgggg 43500
tagaggagga caggtgggag ggagtccagg tgggagtgag tagacccagc aggagtgcag 43560
ggcctcgagc caggatggtg gcagggctgt gaggagaggc agccacctgt gtgtctgcgg 43620
aagcaggggc aagagggaag aggccagcag cgtgctgcca tcacccagcg actggcgtag 43680
attgtgagag accattccct gctcttagga ggggctgagt tttagttttc tcttgttata 43740
caataagctt ggtatttgtt tacaaaacat ttgtaaagct aaatcaaggt ttgataaggc 43800
ttctagtttt atttaagaag taatgttgaa ataaatgttt gtccaattcg ctttgctcat 43860
ttaaggactt tcagtacaaa ctgcaacaac aggattagga tttaaacgtt tctgagatgt 43920
ttttactcct cagaatttcc cagaatgtga tctggttttg attttcaagc ttgctgaccc 43980
aataggttaa cccacaagtt ttacgaagac catctcagtc cacttacatc aactgcccat 44040
gccacggtta aagagatcat cgactgatgt ttggcacagc ttcctccctc ttgggtgggc 44100
aagcatttgg aagagaaggc tcctatgggt gagagtgggg caccaaagtc ttccctgtcc 44160
catcccctag cttgagaagc ccttctctaa tgtggacttt gtgccgttag catcgttact 44220
agcttgaagt tgaccatctg gacgtacttt ctggtttagc ctcacaagtg agcaaggagg 44280
gttgagagat gtgctgtgag gaatgtgggg ccccagctgg cagcaggctc tgggtcaggg 44340
gggcagggac cacgggcata cctgacagtg aggaggggcc acacctgcag aaaaggatgc 44400
aggactccgc cttgggaagt gttctaggcc agagcgaggg tctgtggttt ataagtacac 44460
ccacagtgct cgggaccctg cagatgtcca gggtgccgtc tgagcccgta tcatccaaca 44520
gaatgttctg ctagtgaaga ttaaagattt actccagggg ctttaggatt tattatatat 44580
atataaatcc tatatatata attttttttt tttttttttt tgagatggag tttcgctctt 44640
gttgcccagg ctggagtgca atggcgtgat cttggctcac tgcaacctcc gcctcccggg 44700
ttcaaactat tctcctgcct cagcctctcg agtagctggg attacaggcg cccaccacca 44760
cacccggcta atttttgtat tttttagtag agacggagtt tctccatgtt ggtcaggctg 44820
gtcttgaact cctgacctca ggtgatctgc ccgccttggc ctcccaaagt gctgggatta 44880
caggcatgag ccaccccacc tggccaggat ttattgtatt tgaaccatct accattttaa 44940
ttttgatgtt atgtagtatt tgatgataat gaaagttaaa ttgtttttct ttccattttt 45000
ctgtttaagt gaatgacctg tatctagttt attcagtaac ttcctgcata tatttgtttc 45060
tttcattctt aatgaatata ttcttaattt agttgctatt atgttttgct ttgccccaaa 45120
attgaaatct tagtttcctt ttagctcgtt ttagaactag tgatgggatg tgtcttccat 45180
aaatctcttg tgatttgttg taggctttga tggattctaa tcttccaagg ttacagctcg 45240
agctctataa ggaaattaaa aaggtgggcc ttgcttttct tttttaaaaa tgttttaaat 45300
tttaaatttt tataggtaca cgtattttgt aggtacatgt aaatgtatat atttatgggg 45360
tacatgagat attttgatac aggtatacaa tacataataa tcacaccatg gaaagttgga 45420
tatccatgcc ctcaagcatt tatcctttgt gttacaaaca atccagttac atgctttact 45480
tattttattt tatttttgag acagagtctt gctttcaccc atgctagagt acagtggcat 45540
gaccttggct cactgcaacc tccgcctccc gggttcaacc gaactttggg ctggtctcaa 45600
actcctgacc tcaggtgatc cgcccgcctc ggcctcccaa agtgttggga ttacaggcgt 45660
gagccactgt gccgggcctg attgtacatt ttaaaataac taaaacagtc agggcacagt 45720
ggctcatgcc tgtaatccca gcattttggg aggctgaggc aggtgatcac ctgagatcag 45780
gagttcgaga ccagcctggc caacatggag aaaccctgtc tctactaaaa atacaaaaat 45840
tagccaagtg tggtggcggg cgcctgtaat cctggctact cgggaggctg aggtagggga 45900
atcgcttgaa cctgggggtg gaggttgcag tgagccgaga tcacgccact gcattccagc 45960
ctgagcgaca gagtgagact ttgtctcaaa aaataaaaat gaaataaaat tgggccgggt 46020
gtggtggctc acaccttagt cccagcactt tgggaacctg aggcaggtgg atgcttgaga 46080
ccaggagttt gagaccagca tgggcaacat ggcaaaacgc tgtctgtaca gaaattagct 46140
gggtgtggtg gtgcacaact atagtctcag ctacttggga gattgaggtg ggaggattaa 46200
ttgagcctgg aaggttgaat ctataggtag ctgagattgt gccactgccc ttcagcctgg 46260
gcgaccaagt gagaccctgt ctcaaaagaa aaacaaaaaa acaaaaaaca aaccactatt 46320
atcgactata tattattgtc tatgatccct ctgctgtgct gtcgaatacc aggtcttggg 46380
cccttatttc catcactgag caaacttcac tctgttaagc agcaggtgtg ggatttcatc 46440
gttattcagt aattcacaat gttagaagga aatgctgttt ggtagacgat tgctttactt 46500
ttcttcaaaa ggttactctt tattagatga gatgagaatt aaaaatggta acttacttta 46560
tatctttata attgaagccc actagacctt aaagtagtta ccagatgttt tatgcattta 46620
aatggccttt tctctaaaat tagaaagtaa caaggaaaga aaatgcttcg tttctatgca 46680
accctcttgg tgactagtat gtgactctta atgcaaccct cattgcaccc cctcagaatg 46740
gtgcccctcg gagtttgcgt gctgccctgt ggaggtttgc tgagctggct cacctggttc 46800
ggcctcagaa atgcaggtaa gttgtacact ctggatgttg gtttttgtcg ggggccagct 46860
gctactgatc ctttatgtct cagctcagat gtcatttcaa aagtctgctc tgccctctcc 46920
aaattgcagt cgaccttgcc ctgtttatgt ttccctcata gcactaatcc atgtcagaaa 46980
ttgtcacgta cagtctatct gtgtgcttgt ttattttcta tcccaccctt ccgcaagaga 47040
cttatgggat gtgtgcccca ggacagcagg ggtcttactg tcttatgctc tgttgcagcc 47100
cagcagcgat aacagtgtct gcacatagta cttgcttaaa agatacttgc caaattgttg 47160
aaggttgagg taccaatttc attattgctg actataggag ttatagcaaa atatccattt 47220
gtctgttaca tgagttaaaa atatggttgt tgcactgtga atagtttggt ttagtcaaaa 47280
cagttgtatc ttaacggatt gagaaacaaa agcaggacca cttttcatca gctccctcct 47340
tctccttaac cagcaataca tgctgatgct gatatcccat agaccctcag ctccatcctg 47400
agtcactggg aatgtggtct aaaccctcac tattaatatg aactgagttt caataagaat 47460
cttatatggg tcgggcatag tggctcatac ctttgatccc agcacttcag gaggccaagg 47520
caggtggatt gcttgaccca gactaggcaa catggtgaaa cgccgcctct acaaaaaata 47580
caaaacttag ccaggcatgg tggtgcgtgc ctgtggtcac agccactcga gaggctgagg 47640
tgggaggatc acttgagcct gggaggtgga ggtcgtgttg agccaagatc gcaccactgc 47700
actccagcct gggcaacaga gtgagacctg tctcaaaaaa accaaaatcc agaaaagaac 47760
ttatatggct gcagaggtat aatcactaag gaaatttcct tttgtataat ctttttttctt 47820
ttactatcat ttaaaaaaat gtgttatatt tctgaagcaa cacatccagg ttctgcacat 47880
agcagccaaa gtgaccttaa agaatataac tgggtcttgt cattccctta tttaaactct 47940
tgtacccatt tcccagtgcc gtttagatag agattccaga ctcgtcaatg gctctgtcac 48000
ctcagacacc ctgcattgac tcattagtct gattagagtc aggtttttct tcctcctgat 48060
ggtttttttt tcccccttag ttctcagcgg aacagtcact tccttaggga ggtttcccca 48120
gccaccctct gaggccgtgc ttgttgccag actctgccac tagagggcag ggctgcacca 48180
ctcctggcac ctcgcacccg gcctgccctg tcactctgtg tgttgggtga attcctgtga 48240
tctgtgactc actgctctgt gtcctacaca ttcggctttt cttctctccc cacaacccca 48300
ttttataatt ctccttttc aggaaagctt tattcccatt taaaaatttt tgtttttaaa 48360
atggtatttt cttacactta ttttctaatt aaaaatgagt gttttaagaa gtattatgat 48420
ttactgcaaa taatttttaa acccagcctt ttagatcctc tgtgatcata agagaaatga 48480
aggatgtctc ccaacacttg agcttcatcc acatttcatc ctcctgttct ttcagctgag 48540
ttttccccat cccattaggg actgttggaa tataaaactg gcttttccct aacagggaat 48600
gaattgcttc tgtttctcct gaaggagagc tggaagaatg acttgcgttc ttttgcatac 48660
acaggcctta cctggtgaac cttctgccgt gcctgactcg aacaagcaag agacccgaag 48720
aatcagtcca ggagaccttg gctgcagctg ttcccaaaat tatggcttct tttggcaatt 48780
ttgcaaatga caatgaaatt aaggtatgat tgttgcctca ggtcacaaac atgcgagtga 48840
tgctgtgagt gagtctgtgg agggtgaggg cttctgaaca gggagtcctg tgggagtgct 48900
tcttggggta tgttgtatgt cgtaatttag actaccatca tttgtgttat ttttgaggca 48960
cctaaggact tctttccact tctcatttct tactgtgggg tgaagagttg aattgggaga 49020
tggtttctag atgcaaattg aaaaggcatt tttccagagc agatttgttt tcggcgtact 49080
agagtgactc tttaacctag ctgcgggaag atgactgtgc caagactgca ggtaggagaa 49140
agctcactga cgaggccttg tgggtctgaa cgtcctgcag ctatcagagc ctgttggctt 49200
cctgttgtgc attccaacaa atcatcttca aacccacttt agtgttttgt ttataatgtc 49260
cagaaatagt gaccctgtca catgctctac agattacagg attcttagcc tcttcctttt 49320
tggtaggtca gtcctgggtt tgagcccaag tgaccctcct gggaggtgat gatacacact 49380
gggtagagtg gaatcagatg gacttggatt agaattctgt cctctttact agttattttc 49440
ctctaggcaa actgcccaac agctctaagc tatttccttc gtattctgaa aaataagcct 49500
taatgggacc catatagggc aactctgaga gtaaaataaa ggaatatgtg ttagagtgta 49560
gcatagtcac ccacgggaag ggcttagatg ttagctgcta ctgctcttat tagctgaatg 49620
atttggaata aactgttagc ctctctcatg ttttttctct tgagcttcga agttttcttg 49680
ttaatactaa ggagatattc aaactagtca tggggttttg gaatgacgaa gggagatgat 49740
gaatctaaag aatttagtgt aatatttctt catgctcagt aaatggtagt ttctgctgct 49800
gttattttta ttaccatctc tttggaatgg gagtaggtgc tcctttgtgg tcagaggctg 49860
tgagagctcc acagcgccag tttgcccatc tgtacactgg ggtctgttga aggcagtccc 49920
ctctgtgata tctctggctg tcagagctca gatgatagat ggtatttttg tactcttagt 49980
tctcatcatt ttcatgattt cgatcaccat ttgagtatga tgatgctaac actttgttga 50040
acgtagaatc cgttaattac ttccttcctg aacctttggc attaaaaaaa atctattctg 50100
ctacctctct gctcatttat ggttattcaa atttattatc aagagcctgg tacagtggct 50160
tgtgcctata attgtagcta cttgggaggc tgaggtagga ggattgcttg aggccaggag 50220
tttgagacca gcctgggcaa gatagtgaga ccctatctct aaaaaaactg aaaaaaaatt 50280
agctggacat gatggcatgt gcctgtggtc ctagctactc aggaggctga gacaggaggc 50340
tcggttgagc ccaggagttg gagttcgagg ctacactgag ctgtgattgt gccaccacac 50400
tccagcatgg gtggtaaaac aagatgccat ttcttaaaaa aaaaaaatat atatatatat 50460
attatcaatg aaattcagta gtaccaacag gattataaac aaagatagta gttcccttcc 50520 tacttttct cttaatcctt gtgtctcaca ggcaaacata actcttagta tttcttccaa 50580
tatttacttt catgtttctt tctttctttc tttttttttc tttgagatgg agttttgctc 50640
ttgttgccaa ggctggagtg caatgacgca atcttggctc accacaacct ctgtctcccg 50700
ggttcaagcg attctcctgc ctcagcctcc tagtagctgg gattacaggc atgcatcacc 50760
acgctcggct aattttgtac ttttagtaga gatggggttt ctccgggttg gtcaggctgg 50820
tctcgaactc ctgacctcag gtgatcctcc cacctcagcc tcccaaagtg ctgggattac 50880
aggcgtgagc cactgcgccc agcaacttcc acatttctaa ataacatgct tctactgcta 50940 ttttttttt caattttaga cattttttta ctttcactat agttctatca gaattcagtg 51000
tgtacgttat tatgcctaag taaatagtca tggttgctta cgtattatat ttctttgatt 51060
gtgtttctta tttgatgaga aagctgtgtt ttttgctctg ggttgaaact ggagagagga 51120
cctggggagg aggaggagga cagatgaagt tggtgactgt accttcatgg ccatagctgg 51180
gttctcagca cccggggatc tgctgatcac ctactcatag gccaggcccc tatcgaagtt 51240
ctaggtgacc cagtgctggg gacggggggg ccacctgcaa ggtctaatca tggaggtggg 51300
ggctacagtg ttggcttgtg ctggggccag catccttagg aaggcatctt ggaggtggag 51360
gagacagccg cccacttctt gattggggcc ttcagcagca ccagcttctt gggcaggctg 51420
gtgctggctt tcatcaccat gtcgtgttca atcttcttcc agatcctgac ttctaggttc 51480
agctttcctc agaccctggt tcctttcaga ggccattgct gctgccttgc tctttgctgg 51540
cttgtgcctt gattatatgt ctttgtacaa ctttttgttt tcctggagtt aatcttcaca 51600
tctgttttct tggagttaat cgttacctct atatcgcttg cttattattc tttggccttt 51660
ttgtcttctc acaccttcca acttctttgt aatatgtgtt tagtacaatt tttcatgaca 51720
ggtagtttac tgaatcagtt tttccccagt gtggtcatcc aacttgagtt atccagctct 51780
ctgccccagt ctgggcaggt tgatcttcag gtctgtagta cacttgtatc ctaggacttc 51840
tctttgccat tagcctggaa tttcctttgc agttctcccg ttggatgccc agttcctaga 51900
tgccatatgt ttttctatcg tctagtagct tcctgagaga agatgaatgg gagggaaatt 51960
gtatgaggtt ttgcattcat aaaaatgcca tttttttttcc tgtacacttg gctgggtatg 52020
gtgttctggg gtagaaatca ttttccctca gaaatgcaaa gtctttgccc tgttgtctta 52080
aaatctccaa cgtgacccga ttccttaacc tatgaatgta cttttctttg gaagctttcc 52140
atttttgggg aggtgaagtg ctaggtactt agtaggcctt ttaatttgga aacttacatc 52200
ccttcagttc tgggaaaatt ttcttaacat ttctctgaga agttcttgcc ttttattttc 52260
tgtgttctct cctgaaattg gttagttgga tgttggtcct cctagattga ctcacatctt 52320
acctttttct tttcttttc tggtactttt tagatatcca tctcaaactc ttctattcat 52380
tgttatgttt ttaacttctt tcttttcttt gtctcttgat ggggtcttgc cctgttgccc 52440
aggttgtggt gcagtggtgc gatcatagct cactgcagcc tcaaattcct gggctcaagc 52500
agctgttctg cctcaccctc ccaagtagtt gggactacag gtatgcacca ccacgtccag 52560
ctattttctt tactttttt tttttttttt tgagatggag tcctactctg tcgcccaggc 52620
tagagtgcgg tggtgggatt ttggctcact taagcctctg cctcccaggt tcaagcagtt 52680
ctcctgcctc agcctctcaa gtagctggga ttacaggtgt gcaccaccat gcccggctaa 52740
tttttgtatt tttagtagag ccagagtttc accatgttgg ccaggctggt ctcgaacgcc 52800
tgacctcagg tgatccgcct gccttggcct ccgaaagtgc cgggattaca ggcgtgagcc 52860
catcattaga tctttaaata ccagtatcta taagtctttt cctcttgagt cagctagtat 52920
ccctggaagg aaattactca ttttcctgct tggaggctat aagcttggct atgtttatcc 52980
tgcaaccggg gactggaagg gaggggactg acagtgttgc tggtcagggt gccctcttac 53040
tttttgtttt ctgtgtgcat ctcacgtctg tcctcagcct atgtaaacac ctcttgagat 53100
tatccctctc aatctttgcc ggaggtgggg gaggggctgc ttcctgggct gccttggatt 53160
ggagggaaga cctcaggtga gtgggtggga atttgcccaa ggagccatga gaccagccac 53220
tatttcaccc tctccatccc tccactttca gatgtatgtg gcgcctccaa agcccgagct 53280
cttcttggcg tctgtggctt caataagctt gctttttgct ggtatccctc ctaccctccc 53340
ctgtccccag caaagcttgc atttgaactt cttcctacgg gctaacaaat cagtcagtta 53400
tgtagctctt gttacttttt agcttccgaa gttttgttga cacccgtagt ctgctaatgt 53460
ccctgttctg ttctttctgt tcgtgtaaat atatgcttta tacaacttct ttacatgatt 53520
tttgtggggt ttctgggtag cagagcttca caagttcaat ccagcgtgtt ggattagaaa 53580
tctcccaccc tctggtttat tcttattctc aaaattacct gccaaacact gatactccct 53640
tgtttttcct tttcctgaca ggaaatgtac ataccataca ggacagaaat cattagtgta 53700
tcccttggtg aataaccaca aagtgaactt aacccttgta accgccaccc aggtcaagac 53760
agaatattac caagcactca gaagcctctc ccctattccc ccgtcactgc tcctgccttc 53820
ctccccaagg tcatgactgc tggcttctaa ttccagagtc tgtttttaaa ttctgtgtac 53880
atagaccatg gattaagtgt tctttttgtc tggtttattt tggtcgacat taagttcatg 53940
agagtcttct atattatcgt gtgtattagt attcctgtag ttttaggagc ttcatagcat 54000
tccattgtag ggatatacca cagtttattc attgtattat cactgggttg tttctagttc 54060
ttggctattg cgagcagtgc tactgtgacc actcttaggt gtgtcttttg gagtacatgt 54120
gcaggtttcc atcttgcaca gctagaggtg gagttgttgg gtgatagggt gtgtgcatct 54180
cagctgcagt agaaactgcc aaatagcttt ccttgagtgc ttgtaccagc tcaccctttt 54240
gccactgtgt atggggattc caggagctct ggtcctcgct agcacttgga attgctgatg 54300
cttttactct tagccttcct gatgggtgtt ttctggaatc acattatgat tttaatttcc 54360
attccttaaa gtacccttgg ctctgaagtt taatgattca tgcatctctt ccccttttgaa 54420
gtactcttac aggtatgttg tgcatgtgtt gaaaagtggc actatctatt ctaaaataca 54480
gtatgcctcc tctgtgtttg aacagttgta gcgtggcctt ggggcctcct gttagctggc 54540
ttggagaagg gattcttggg attgtagaga ttagacctga ggaggcccct tggagctctc 54600
tgactaaatt ttattcttta ttattccaaa ctatttaagc tcaccgtgtg ctgactcatc 54660
ataataatga gtagctctca ttgtgcttgt ctatttggac tcatacaatg attttttttt 54720
tttctttgag acagagtctt gctctgttgc ctaggctgga gtgcagtggc acaatctcgg 54780
ctcactgcag cctccacctc ccaggttcaa gtgattcttg tgcctcagct tctcaagtag 54840
ctgagactgc aggtgcgtac caccatgcct ggctaatgtt tgtattttta gtagagacgg 54900
ggtttcacca tgttggccag gttggtctca aactcctgac ctcaagtgat ctgccttctt 54960
cagcctccca aagtgctggg attacaggtg tgagccactg agcttggcca aagtagtttt 55020
ttaagatgtt agtatctttt cttgcagcta aaaaagtttg tcagagatga ttctactttg 55080
ttctccaggt gttttctcag ggagaaattg gaggcagtaa gccactgggg gagtcctgtg 55140
gctggggggt ggggtagtcc tgtggctcct tgtcagggag tcctgtggct ggcaaggaga 55200
gaagtcctgt ggctgggttg ggagggagtc ctgtggctgg ggtctcatcc tgtgcctaac 55260
agtgtccaga ggtgccgaga ccagctcagt cggggagacc ctaacccagc agcgctagag 55320
gaattaaaga cacacacaca gaaatataga ggtgtgaagt gggaaatcag gggtctcaca 55380
gcctttagag ctgagagccc tgaacagaga tttacccaca tatttattaa tagcaaacca 55440
gtcattagca ttgtttctat agatgttaaa ttaactaaaa gtatccctta tgggaaacga 55500
ggggatgggc cgaattaaaa gaagaggttg ggctagttaa ccgcagcagg agcatgtcct 55560
taaggcacag atcgctcatg ctattgtttg tggcttaaga atgcctttaa gcggttttcc 55620
accctgggtg ggccaggtgt tccttgccct cattcctgtc aacccacaac cttccagtgt 55680
gggcattagg gccattatga acatgttaca gtgcttcaga gattttgttt atggccagtt 55740
ttggggccag tttatggcca gattttgggg ggcctgctcc caatacagag gtctcgtgta 55800
aattccctgg gaggcgataa gcctctgaga aacagactat gctaaccacg ccatgaaaga 55860
gaaacttatt tataaatcag atgccagtta ctagtttact gcttatttgc ccaggcgtag 55920
ctctgacaga gtccccgact catagtgctt gctcagtgca tgctgaacaa tgattggaat 55980
caagtcatgg ctcagagcat agttttgaat aatgggaaat ggatgttctt aagtaacata 56040
gtcaccaaga taatgcgact agctgggtca ccccttttca attttaggat atttttatca 56100
agatttaaat ggccatcatt agagttatag cactttctcc tttggattgt cctagaggcc 56160
catgagaaag tattccctaa tttcttagga gaacagtttg tgggtagtat gcggtcatgt 56220
ccagttaaat tgcagatatt tccgatcgaa gatgttccag tcctgagaac ttcgtgacat 56280
tagcaggact tctacaagcc atctcttagg gtggggcatt tactgcagtt ggctagtact 56340
cttttctcct taactttgtc atttgttgat ttttttttaa ctgtccccaa atactgtggg 56400
cagagtgtat ctagaattga ggcctccacc attgcggaga ggacatggat gctgagcagt 56460
cccctgagtg aaggttataa agaagcaaat agactacaca tgtctgtaaa ctgctcttga 56520
gtgtcccaaa tttggggtac ttcagttcag ctgtaggaaa agcctcaaac tgtttatact 56580
ttgcaagaat tggaaacttc taattcacgt taagttttat gtaatacatg ataagcttca 56640
taggagcttc atcttttatc tacttggact tttgcttccg taggttttgt taaaggcctt 56700
catagcgaac ctgaagtcaa gctcccccac cattcggcgg acagcggctg gatcagcagt 56760
gagcatctgc cagcactcaa gaaggacaca atatttctat agttggctac taaatgtgct 56820
cttaggtaag gtggaggcat atgagtggaa gagtctccag catgtactca agatagacct 56880
ttgaaataaa taaaaccaga tgatccctca gcttctagac caggctattt ggcactggtt 56940
gattgaatgt gaactgcact ggggctgctg tgagcccgca tgggtctctg tgaccctgca 57000
gatgcagccg tgcccaggga ctgggcagtg ggtgtgggct ggtgtgagcc ctgtctgcca 57060
cccagggcct ggccctctgt ctgtgtcggc catgactatg gtgagtcttg taggcttgag 57120
actgtgcctc gggttcctgc gggttctctg taggtcagtt gacagtttct cctgttgttt 57180
gggtaactgt ggaaacgaac actggcaagt gctgaagcga gcatgtggac gtgcgatatg 57240
aaataacgac ctggctttca aaggcagtga ggctctctgg aaaggacctt gctgagctag 57300
ggatgtgggt gtgtagccat tcccagtggg cctcatggcg tactcgttca tgatcatgtt 57360
tgtgccatct tgatctctca ggatctcttc tttttaaca gattaagccg ggaatctcca 57420
aacagtgagt cagatgttaa gatgtcttgc ttccaccccc acaggcttac tcgttcctgt 57480

-continued

```
cgaggatgaa cactccactc tgctgattct tggcgtgctg ctcaccctga ggtatttggt  57540
gcccttgctg cagcagcagg tcaaggacac aagcctgaaa ggcagcttcg gagtgacaag  57600
gaaagaaatg gaagtctctc cttctgcaga gcagcttgtc caggtaggag cacagggttt  57660
actctaggcc ctgcatgtga atgactgaca ttcaaagaac cgattaattt ggaagagaag  57720
cggcagaacc gagagttaga ggtgtggact ctggagctgc gctgctcgtt tccaacccta  57780
ggtgctgacc tctagctgtc ttccctctgt atgtccctgt caccgtgagt caaatgcggg  57840
tgatgcctcc tcaggtgccg tgttacctaa gcctctcaga gaccactgct accctgtttc  57900
taaaaccaga ggtcacgata tgtgttcatc cacccagtaa atactgattg agcacccact  57960
gtgtgctagg ctctgggata ggggctgggt atacaatggt gagtatttca gctgcagctt  58020
ctgccccgtg gaggctgtgg cctagcacac tggtctaggc acggtggtat atgctcactc  58080
aaggagatag ggacgtggtc gtttggggtg tcggaacaaa atgtcggaac ttctctttcc  58140
aatgcagaga aaccttgcag taattctaat gtactgtgat tggcagttga cttcagttct  58200
ttgtagcacg cttactcagg ttatttcact aactatgtaa ccatgcagcc tcattttaag  58260
caattggatt ttttgaactt tacttaaaat gttatgtcag ggtttttatt gtgcttaatg  58320
tgtgccattt agctaagttt tgtaggatac gaaattgtaa gtggcttaaa atgattctta  58380
atagaatcat gaattgaaga taatgctaat aatttaagca ctgagttagg tagtgtttgt  58440
aaaatgctta gaatgcttcc tggcacatgt taaggccatg taagtgctgc gtgttgataa  58500
acagctgagc aaaagtggac tcttaagaaa gtattggggc tgagagttct gttccaacca  58560
gctgcccttt ggttattttt cagaataaaa gcagagtctc atgggatatg acatttatat  58620
ttccttcaca aaaaacactg ctgagtgttt tgttgagtaa aaagggtgta gccatggtaa  58680
taatacattt aaaatatagt ttatttcatc tttaccttgc cttgtttttt ttttaagcta  58740
gctttttatt gagaattcca cacatacaaa agtatcaact catgaccagt tatatttcat  58800
ttataatcct acttctccct ttttttatta tttgaaagca aaccccaatt atcctcttat  58860
ttcatctata agtatttcag tatctctata gatgaggact cttctttatt tttaaaactt  58920
tatttttaaa atgatggtca gatgcagtgt tcatgcctgt aatcccagaa ctttgggagg  58980
ccaagctggg cggatcactt gaacctggga gtttgagacc agcccgggaa acatggcgaa  59040
accccatgtc ttaaagaaaa aaatcagcca agtgtggtga tgcatgcctg tagtcccagc  59100
tacttgggag gctgagatgg gagggtcaca tgagcctgga agatcaaggc tgcagtgatc  59160
catgattgta ccactgcact ccatcctggg tgatggagca agattctgtc tcaaaaaaac  59220
aaaactgcaa aacaacgtca caaaacagtg ccattgttag acctgaaaat attaaacatt  59280
tcctacatca aatacccacc aactcattat caatttttct ctctactctt ttggaatcag  59340
catctaaata aaattggtcg ataaggattg taaatctctt tgatgaactg gttcccctcc  59400
atcccagttt ttttccctta gagttcattt attgagaaac cagattgttt gtcttctaag  59460
ttttcctgtg gtctgatata ctgcttccat ctccactgtg taaattaaca ccttttttctc  59520
ttctctgtat ttcctgtaaa tcaataattg gaggaaaagc cttgtcagat ttagtgtata  59580
ttttatatct gagtccagta tttcttatat aatattttaa gataagtgta ctcttttaaa  59640
aagtattgaa actatatgct caattttttt taactgatgc ttttaagaag gctgcttgat  59700
cataaaagtt tagagatcat tggtctgatg ggaaaagcaa ataattacta aaccgtttag  59760
caaggttgag gtgcacatgg tggggcctgg agaagttcag tcatgagccg tcacttatgg  59820
gcacgtggaa tctgacccgg cacagagttg ggagaagaca ggagctttat agacagaaaa  59880
```

```
tgtggtcttt gctaagtccc aggagtgaaa gggtgagaca gtgctcacag cacacgagtg  59940
tgggtgcgta gacagagcaa gggtgggtcc tgaaaaggcc tgcaggcttt ctcatagatt  60000
agcaagagtg ctggttacgg aggtttctaa catttgtgaa cagatcgaaa ctgtgttaaa  60060
ttgggattgc agtaatcctg gaaggacagg gatagagggt gaaggggaaa aaagggtatg  60120
gatgtgagac ttaattgctg attttcttaa gacctttctc caaagtaaat aaatgatgtg  60180
gcacattttt gaactggcaa attctaaact ctagatatga ttatctctat aacatatctt  60240
actccatctt cttttgacta aaaactgttc ttaattaaat taccatgaga cgttcaattc  60300
agcaaatgta gtttggctaa ccatatttaa ttagaattta atataatcct aggcctggcc  60360
aaactattaa gcaagtgtgg gcaaaatatt gataatttta gatatgcagg aacttagttt  60420
gctttccatg tgtgcttttc gaaaaaggaa taaattgaaa aatagaggaa gccctgaaat  60480
ccaagaagca aactctctca cctaggcatg cagtaaaagc aattctagga tgattgctgt  60540
ttggcgcgta gttcgtatta gaaaccattc ttcttgaata aatagtatgt ttaagaagct  60600
gggcagaggg aaggcatatg catatattat caacaaggag ggagaaaaag gcaattagta  60660
accatccata ggagggtcag caagatttat aaaggaaatt tgtgatccaa gtatgaagca  60720
aaataaggtg cagaataaat tttaagcaag taatagatta gagtaagaga acccatttga  60780
ccattaacct tgggacattc tctttcaaat gacatggagt agtactgaaa tctttctttc  60840
tttctgagtc taggttattg tgactggact cagaaagaaa tatttcatta ttgcagtgaa  60900
taacatttgt gaacattatt gttcataaat tatgcagtga ataacattta tgaacacgtg  60960
atgtgtaaga tacatactgt ttatttttag ttaagttttt tggctcaact tctaggcaga  61020
gaacattaaa tgtaaatagt gttacctagg agcatgtaaa tggaaatctc catagtatga  61080
aagcagtgct gttgctaaca gaatttagga gggggcagat gaggtgaagg aaatgtgggt  61140
gctgatttcc ttattacatt gagaggagcc aggagattct ttgttcaaaa tggatggctt  61200
aagaagtcaa agtataagct gattacgtag agcaggtacc caaaaatgtt ttgtgtaagg  61260
ggccagatag taaatatttt cagtcttgca ggccatccca agtctgtggc agctactcaa  61320
cactaccttt gtagcatgaa agcagccaca ggcagcccat aaatgtggct ctgttccggt  61380
gaaactttag gtacaaaagc aggtgcaggc cagacctgac ctgtgcactg tggtttgctg  61440
acctgggatt caggggtata gaagttacca tcagaagagc taaaagtgag actttttact  61500
ttatactctt ctacactgtc tgattttgaa aaaaagaaac atgtatttta taatattaaa  61560
gatagggttg gcaaatagca aataaaaata cagaatacca gtgaaatttg aacttcagat  61620
acattatgag taattttatg gtgtaagtat attccaaatc atgtgggaca tacttacact  61680
acaaaattat ttgttgtttg tttacagttt aaatttgagt gccttgtatt ttatctggca  61740
actgtaatta aagggaaaaa gaataaattc attatgttca tataatgtga tatagcaggg  61800
gtccccaacc cccaggctgc agagtggtac tggtccatgg gtccccaacc cccaggctgc  61860
agagcggtat tggtccatgg cctgttagga accaggctgc ccagcaggaa gtgagcagca  61920
ggtgagctgg cattcccacc tgagcaccgc ctcctgtcag atcagtggca gcattagatt  61980
cccataggag tgcaaaccct attgtgaact gcacatgtga ggggtctagg ttgtgcgctc  62040
cttatgagaa tctaatgcct gatgatctga ggtggaacag tctcgtcttg aaaccatccc  62100
ctggccctgt ggaaaaattg tctcccatga aaccagtctc tggtgccaga aaggttgggt  62160
agcactgtga tatagtatta aaagtgctaa taaatatggc atactgcctt taaaatgtct  62220
```

-continued

```
ggtagctctt tctcagtggc actcataata gtgtttttg atttttaaat gtgtgtcaag  62280
ctgactctcc cctccgtgta tgctgggctt tattttccct ttcctagtca ccagttttgg  62340
gaaatagaga tcttcattct catgctgctc ctctagtgca agtgctccat ttatttttaa  62400
ggaattaata taacaaaaaa tcatgggaat ttagaaaaca acatggaagc taatgatcac  62460
attggtggaa gtgataggga aatatttagg gggagaagtt aaggtataaa ctttgtcaat  62520
gaagtcctat taaaaacaac aaaaaagtga agcttaggat gcattttata aactctgacc  62580
agaacacctg tgtttctctg tttctaggtt tatgaactga cgttacatca tacacagcac  62640
caagaccaca atgttgtgac cggagccctg gagctgttgc agcagctctt cagaacgcct  62700
ccacccgagc ttctgcaaac cctgaccgca gtcgggggca ttgggcagct caccgctgct  62760
aaggaggagt ctggtggccg aagccgtagt gggagtattg tggaacttat aggcaagtta  62820
ttagcaaggt ctactcttac aattaacttt gcagtaatac tagttacact ctattgatta  62880
tgggcctgcc ctgtgctaag cagtctgcat tccatcttcc ttgccaaaac ttataataca  62940
aatttcatct ttattttata aataggggag ttgggctggg tgtggtggct cacgcctgta  63000
atttcagcac tttggaagga tcgcttcagc ccaggagttt gagacaacct ggccaagtga  63060
gaccctgtct ctacaaaaaa aaaaaaaaaa aaaaaaattag ctgggcatgg tggcacatgc  63120
ctgtagtccc agctgctttg gaggctgagg tggtaggatt gcttaagccc aagaggttga  63180
ggctgcagtg aatcttgatg gcagctgcac tgagcctggt gacagagcaa gatgctgtct  63240
caaaataaat ttaaaaataa aataagagaa ttaaagttta gcaggttggg tggcaaaatg  63300
aggccacaca tttaaagccc ctcctcctga ttcttttctc tgccttggct gcctcctgtg  63360
gcattttagg tgctgagaaa tgaaaacagt agggaaaata gttccaggat cctcatgtta  63420
atttgccaga aatggcatct tcaagtcgtc agagggatct gagagttcct tcctggcctg  63480
acttgagaaa atccgtctgt ccccagctct gcgtctgcct ccactgccca gtcacctcct  63540
ctccatgctc ttggggctgg gccctacccc accatgcagt gctgccctgg agcagtgagc  63600
ttggtgggtc ctgtctggca tgagagctgc ctttgggagc tggatcccag cctctaccac  63660
tgggtctggt gcctagcagg ctatggataa acttctgctg actccggcct ctcctaagcc  63720
actgcaacgt ggtcggtgta gtgcacagtg tgtgtgcagc gtggccttac tcacagcctc  63780
cacattagag agaatctgac tgaagtctta ctgctgcctc gtgtgaacat aaatgtttgc  63840
cagaaccatg agcaggaaat gttaatctgc cttgtttcct gtcctttaca cggaagaatt  63900
tttttctgta tggaatgcgt gccttacaaa taatgagtgg aaataccat cgctaatgaa  63960
aagttatact tgactgttag tcagctaaat aatctgagat ttctaatact tttaatttgg  64020
cttttacaat gcaatttatc ttagcttttt tgatttctta ggtcatatct ttagaactat  64080
atatttgaat gttaatgtaa ttttcatatt gaaattaaaa tgttgaactg cgatgttaag  64140
tgtttcctgt ggaaaaacgt tcacattttc tctagtttta aagttgaatc aagctgtttg  64200
aagattttca catttcttct agattttatc agcttgttac tttatctgtc actttctgtg  64260
atttgcagct ggaggggggtt cctcatgcag ccctgtcctt tcaagaaaac aaaaaggtga  64320
ttatttcaga aatcagagtc ttgtgttgaa tcttactgat tttcttgtat ttctgtaatg  64380
taatgtatct tgtatttctt gtaatactgt attggactct gtgtatatct cttctcagat  64440
gagtgattat atgtgtgaat gttgctggaa tctgataacc aggcctgaat agttttgtag  64500
ggtggctttt aaaaattact ttcatatcag aattgctttg tcataaattt tgaacgcatc  64560
ataaatttct aatgttcggg gtcagcagac tttttttgta aagggacaga gtgtaaacat  64620
```

cttagcttta tgggccatat ggtctctttt gcaacattca gctctgccct gtgacaggaa 64680
tgcagttgta aagacatgag ctactggcca gctatgttcc agtagaactt tacttacaga 64740
aacagacagg ctgtagtttg ccaatacctg ccttagggaa tgtgttgtta tattttgtga 64800
gttaccttct cagtaaattt tatttagtat tagtcaggaa tattattaag tagcttcttt 64860
tccagcctgg tcaacatagt gagacccggt ctctaccaaa acaaaacaaa acaaaaaaac 64920
agccacgcat gtggcatgtg cctgtagcct cagctgctgc tcagggggct gaggcaagag 64980
gattgtttga gcccaggagt ttgaggtcac agtgagctgt agtcatgcca ctgcactcca 65040
gcctaggcaa cagaatgaga ccttgtgtct taaaaaaaaa aagtttcctt tgttgggtta 65100
ttttaatttg gacctggtta tcatttttca gccatattta actttgtaca tatcagaatg 65160
ttctgataaa acttaacttt tattaaagtg tttgtgatat aatctgctag ttttggtaca 65220
cattatcttt tgcaatgcca gttattttct tttccagtgt gggtttgcat aggaaaagaa 65280
ttgctgtcac tttctatttt gaaatcttaa aagactgatc ctttttgtg tcatgatttg 65340
agtatttaat tgagagccta atgcctaata ttatttgcag tattaaatgg gatcttaaca 65400
ggaatagcat tctagccttc attgaattaa gtaaacattt cttaagagaa cttggaatct 65460
ataatatttg cgtcatcata gtatgagata cttaatcaag tttgagattt tagtgaaaca 65520
ttgtttagaa gccaaaagga ttctaggaaa aattaatgtc tatattcttg aattaggaga 65580
gattttggga cgtgtgacta agttacgctg acacttgttt gtttcttagt cgctttttcc 65640
agtggcggtg agaacgaaga tgactgattc acattgctca gatgagttta tcctcttctg 65700
gctgggacat gggatatatc ctgtctcttt taagcctttt tggtattttt cccccattga 65760
gagctgtgtc ttcaaactct tctgttatag ctggaaaatc ctttttaagt gaaatctgcc 65820
caaattataa gacagatgaa ggtagagttg tgttggatat aggattaggg tgaaagtagt 65880
gggggtgtcc tggagcctct cttctggtgg cagcctagct cttgtgcctt tgaggaaatt 65940
accctgggga cggctctgtg gaacatattt gcaaaccact gatttggaag atagagatgg 66000
cttttgttaa gatctgaatt caccttttg gcattttatt tgatttctca aggtaaagaa 66060
cttattttgt aataaagttt cctattattt agtagatagg ccaagttgct gtgttaattc 66120
catgtagatt ttgggtttcc tttgctcatt ttttcactct taatctcaca tcattgtaag 66180
tttatggaag ttatcatact tctgactttt tctttgaaga gcagaaatta gaaattccca 66240
ataattattt tgatagtgtc atttaatgac actcacatgt gatgtagcca caaagattta 66300
atgagttcag ttttaaatca tattaagact gttggtttca tttgttctca ttaatgtaat 66360
tctgaagatg aacaataaaa tgtattttta gaactttcaa atgaaatatt atttcatcct 66420
tccagatcat ataatgctta agttctgatt gttaatcata aagtctagaa aattaaaaga 66480
taataaaatg aaagtgactt ttaggtatta gagttttatt ataaattctg gtgtgtcatt 66540
ggagctatga catgaatatt tcaaaggcca atagcattgg atctttacag ttataactta 66600
ccatttttaa gtttaagtag taatatagat tatttaataa tcaaaatcaa taaatattaa 66660
ttattaaaat gttttgtggt atagtttgag aatcattgct tttaactttt tccatatagg 66720
tttattgact ttaatagcat tctaaacata acatctctac attctttgtg tttaatactg 66780
tggaggtata aaaatactta tatatgatga taaactatat tagagtaaat taaatattct 66840
tatgagtttc attttagagt gcatttactt aattttgaag tccttatttt tagcaaacta 66900
aaaggaatgt tggtacatta tttactaggc aaagtgctct taggagaaga agaagccttg 66960

-continued

```
gaggatgact ctgaatcgag atcggatgtc agcagctctg ccttaacagg tagttctcac  67020
tagttagccg ctggtgtgga ccttcactgt ctgccttcca ccccttgccc ttcctgctcg  67080
tccccctgca cctggtggac agcacgactg gggcagcag tggagccagg ttgcttaaat  67140
ggggcatatt cgggcttctt ttataatact tactctgaag cttgtgtgtc tgtggtgttt  67200
gcatcatata tttgttgttt tccatggttt aggctgtttt aaaattaggt ttatggcttg  67260
agcatagggc tttgtgagta ggggatggca ggtcgaaaca tctcatgagt tggatgggtt  67320
atgctggggg ttgggaaatg ggatgaaaaa ttatgggatg aaaaattgcc tatggatagt  67380
ttaacttgaa agaatctgcc tttgtttaca gatagttatc tttttcttt tttgagatag  67440
agtctcacac tgtcacccag tgcagatacc cagtgtcact ggagtgcagt ggtgtgctct  67500
tggtgcactg cagcctccgc cttctgggtt ccagcgattc tcctgcctca gcctcccaag  67560
tagctgggac tacaggtgcc cgccaccacg cttggctaat ttttgtattt ttttgtggag  67620
acgggttttt gccatgttgg tcaggctggt cttgaactcc tgacctcaag tgatctgcct  67680
gcctcagcct cccacagtgc cgggattaca ggagtgagcc actgtgcccg gccagttaca  67740
gatacttatc taatgaaatt ctctgtgtac tttataaaag atgaggatta actgaaggta  67800
ctaataactg gattatatga gggtggtttt ggttgtataa tcctatctaa aagaatattt  67860
tagctataac tgaaagtaag acttaaatat ttagagagga aaatctgaat aattctagta  67920
gtaattattt atttacaaaa taaaaataga tttttttttg attacacaaa ttaaacaaca  67980
ataaaacatc acagcaatcc ggatactata aagctcacat gcttaccgac ccaactgccc  68040
caggagtgac cactgccaac agcttcatgt cgaccttttt gccataattt ttatatagcc  68100
tttttgttt ttaaatggta atttagaaag tcaactagga aaatgtgtta caggtttatc  68160
ttccaggaga ataggactgg agtcgagatc ttgaatgtgg cttggaagaa ggcaagccca  68220
ccccagagag atgagttgac agttgtttct gaccactgct tgcttagagg gcctgcgtgt  68280
ctgtgaccgc ctagctttgc gcccctgact aggctgcccc ttaattacaa atgtctttat  68340
atattgctcc agctaaggct tggagtagtc ggttaagaac ttgaacttcg gtttttgcag  68400
tgaaacagca tttgagaata tcaccttctg ataagcctta ttttataagg tgggtactgt  68460
agtgggaggc agtgtgagag atgcttgaag gatgcactgc tgtcctgcat ttcagcatct  68520
tcaggatgct gtgcagctga aacatttgat aacggtggaa ctgttcgtta ttttgcaagc  68580
ctgtgattcc ctattgaatg ttttctctcg ccatttgaca aatgagtgtt tctctgtctt  68640
cagcctcagt gaaggatgag atcagtggag agctggctgc ttcttcaggg gtttccactc  68700
cagggtcagc aggtcatgac atcatcacag aacagccacg gtcacagcac acactgcagg  68760
cggactcagt ggatctggcc agctgtgact tgacaagctc tgccactgat ggggatgagg  68820
aggatatctt gagccacagc tccagccagg tcagcgccgt cccatctgac cctgccatgg  68880
acctgaatga tgggacccag gcctcgtcgc ccatcagcga cagctcccag accaccaccg  68940
aagggcctga ttcagctgtt accccttcag acagttctga aattgtaagt gggcagaggg  69000
gcctgacatc ttttttttta ttttttattt gagacagagt ctcactccat agtgcagtgg  69060
aggccgggca caggggctca tgcctgtaat cccagcactt tgggagactg aggcaggcgg  69120
atcacttgag gtcaggagtt cgagaccagc ctggccaaca tggtgaaacc ctgtctctac  69180
taaaaataca aaaattagtt gggcgtggtg gcacatgtct gtagtcccag ctgttaggga  69240
ggctgaggca ggagaattgc ttgagcctgg gaggcagagg ttgcaatgag ccgagatcgt  69300
gacactgcac tccagcccgg gcaacagagc aagactccat ttcaaaaaaa ataaaaaaat  69360
```

```
aaagtgcagt ggctcgttct cagcccactg caacttctgc ctcccaggct cgagcgattc  69420
tcccgcctca gcctcctgag taggtgggat tacaggtggg caccaccaca ctcagctaat  69480
gtttgtattt tcagtagaga cagggtttca ccatgttggc caggctggtc tcaaactcct  69540
gaccttagat gatccaccca ccttggcctc ctaaagtatt gggattatag ttgtgagcca  69600
ccatgcccgg ccctgccacc tgccatcttt tgagttcttc cctggagacc tagacctgaa  69660
ccctcctgct tgttctcttg ttatctaata cccctattga cagcgcagct tagatcatta  69720
atggagagct tgacctcatc tgataccttc actgaaggaa acaacttagt gtcttttgtg  69780
ttgaacactg aggtaaaaaa ttggaatagt tgattatatg aactctgcta aaattgagtg  69840
cattttacat tttttaaggc cttgttgggc cctggttaaa taattatttt taaaaatcct  69900
taaggagcct attataaaca gatctgtggt cttaatgaaa tgtgattaat actgtgcatt  69960
attttaagaa cttttgactt ttcaaaaaac ttttacaaca tttcccattt gatagcggca  70020
taggtttaag cacttctcat ctctaagtta gtggacaaaa aaccctcatg gatagtctaa  70080
taatgtttgc tacaagtcca tgttgagttt tatactccat tttattttca gttttaaaaa  70140
ctgtggttaa atatgtgtaa cataaaattt atgttcttaa ccattttttg cgtatacagt  70200
tcgctggtat taaatacatt taaataatgt catggaatca ttgctaccac ccatctctgt  70260
aacctttga tcatgtaaca ctgaagctct gttcccattg aactctattc ctcctttccc  70320
gccaagtccc tggcaaccac gattcttctt tctgtcttct gaatttgact actttgggtt  70380
ctcatatact ttaggagtca cacagtattt gttttactta gcataatgtc cccaaagctc  70440
atgcatgttg tagcctatgt tagaacttcc taatgtttca ggccaaatac tattccattg  70500
tatggatagg ccacattttg cttttccatt cctctgtcca tggacacttg tattgcttca  70560
tgttttagcc attgtgaatc atgctgttat gaacgtgggt gtacagatag ctcctggaga  70620
ctctgctttc catttttttg gctaaatacc cagaaatgga gttgctttta cattccaatt  70680
ttaatttaaa acattcatat cattgagtgt tttacttaat agtatagtag ttaacaaact  70740
taataaaata gtattttggt aataatttgc tggtagtcca ttgttcagtt tttttaggta  70800
aattacacag gacatttcaa gtggacatga aacatcttgt gatgtggaat catgccccaa  70860
gctgatggct aaacatatga aataccatac cctaaattta gtagatttag tctttgcaat  70920
ttaggagata acctgttata ttgttaggtt tttgtcgaaa agctttgtcc tcatatttcc  70980
aacttgctgt aaaatttgtt tgtgaagaca aatattttg tatgggtttt ttctttttca  71040
tattaaaaag aaatgtccac attggaattt ttttggagtt tttagagcta atagagcttt  71100
tcataatgta gtgggaatga gtgatcagta agctcttagc agtttccatg cgtgcatttc  71160
tgtgccttga aataaatgac agatgagtac atttgtgttc tgtgtgtaaa atgtgctctt  71220
tcctcattgc acttccatgt tggagggctt gtctcttggt gatcacactt caaaattctc  71280
acagcccccc ttgaaccgtt taggtgttag acggtaccga caaccagtat ttgggcctgc  71340
agattggaca gccccaggat gaagatgagg aagccacagg tattcttcct gatgaagcct  71400
cggaggcctt caggaactct tccatgggta tgtggactac aggtgatgcg ctacaaagtg  71460
gtttgtattc agacctggac atcttaatta tatctttgct tccaagaaga agtcctttga  71520
tactgttttc tgagttctga atagctgatg aaaatgacca attgaggaat aatcatactt  71580
tttcttgatc taaatcttat acttttgagt tatcttagca taaatgtata attgtatttt  71640
aagtggaaat ttgtcactta atcttgattt ctctgttttt aaagcccttc aacaggcaca  71700
```

```
tttattgaaa aacatgagtc actgcaggca gccttctgac agcagtgttg ataaatttgt  71760
gttgagagat gaagctactg aaccgggtga tcaagaaaac aaggtgaggg acataggctt  71820
gagacgactt ggtgtttctg agcttgtgtg aggatttaaa atcgccctgg ctactgtcta  71880
ctttattgct ttcccatccc tgggccttta aatttcccct ttaaatacca gctcttccca  71940
ggcctgttgt tttctgcctt tccaggtact acccacagcc ttgagaattg cctgagttct  72000
gcctcctttg agagtgtgcc ccagacaaat ctattctgta ctgaatgttt ccttgtctga  72060
tttcttggat cattcatttg atggttgcgt atggcctgca acgtttcttg ttttggttct  72120
actgaactgt tctaaaagtc tctcttcata ttatcttttt acatgtaaat gtaactgtct  72180
tcacttttaa ttcctcaagg acaaggaata gcgtttcaca gttcgtccca tcaatcagaa  72240
ttatagcctt tggcatctcc ctatctacca ggcccacttc ctcttagatt tgggcttccc  72300
caggctgttg cctttcccca agtagcttct gcttgtcctg tagaagacct ttcatgcttt  72360
gcttctgcag cagccgttcc tgaatgccta gtgtcaactg ccttcttacc acgcccaccc  72420
tccctgcatg ctgcatttat cccctgccac agccctgtga ccctgtgtcc tgctgcctct  72480
gacttgtctg tttctgcttg gccatggtct ctgtgaggtc aggtgtgcat atgggcacaa  72540
accagggcat ctctttatcc ccagcacctg gcttaagtgc tgctctggaa ctatctgttg  72600
aatgaactaa tgcatgaatg tattgttgag tatgagacaa acaagtgtca ttgtctcctt  72660
tctagccttg ccgcatcaaa ggtgacattg gacagtccac tgatgatgac tctgcacctc  72720
ttgtccattg tgtccgcctt ttatctgctt cgtttttgct aacaggggga aaaaatggtg  72780
agtacaaaag gggatgtgca cagttgaagg aaataactag gtttcagagg tcagcttggt  72840
ggcctgtttt tgccttgcgt gcagcagagg aagtagaatc tgaggatgag tttggttttc  72900
actagccgag gggagggagg aaatgatggg agcaggtagg ttattgggtc tggttttgtt  72960
catttgaaaa caatctgttg tttgaggctg aaggtggctt gggtgatttc ttggcagtgc  73020
tggttccgga cagggatgtg agggtcagcg tgaaggccct ggccctcagc tgtgtgggag  73080
cagctgtggc cctccacccg gaatctttct tcagcaaact ctataaagtt cctcttgaca  73140
ccacggaata ccctggtatg ttaaaagttc acatcttatt ttctcagatt taatcattat  73200
tgtaaaaact atttcagtat tgactatttt agttttagag cagtaagtgt tttgagttca  73260
tttgggatat ttgacctgcg ttgtagctct tcagaaaaca catgaatagt gaagttcttt  73320
gtttcatggg ttccctttag atgaaaccca tagaggagaa aagtagaaac ctcagcacgt  73380
aagagccaac atatatacac atcggattta aacctaaagc acaaattgtg cctggtcgca  73440
gtggcgctga gtcgcactca gccaggccag gcattcacac tcagggtgag tgggaaccag  73500
gactggctga ggcagcagtg gacccaagtc tccatcgcgc ccatgcttac tatggagcct  73560
tctcgttctc tctttttctt tgggtgagag ggtacacttg tgtttttgaa tttatatgag  73620
gtaagtgtgt aatagggttt tttctaatct tttttaagtg gaatctggaa ttttaatcag  73680
atttattatc tgacaaccta gaattataat ccagaaagtc tgtggtattg aggacatatt  73740
ggcaatatga tgaatctcta attcttaaat cctgaaactt ttttttttt aatcacttag  73800
ggttattata gtgaagtcat ttctgaattt ggatcttctc ttcacacctc tttttctctt  73860
tcctgagaat taagcttttg tttcgagtta gaaagttgat agtagggaat tgttccatgg  73920
ctgagcaatt tatctccaca gaggaacagt atgtctcaga catcttgaac tacatcgatc  73980
atggagaccc acaggttcga ggagccactg ccattctctg tgggaccctc atctgctcca  74040
tcctcagcag gtcccgcttc cacgtgggag attggatggg caccattaga accctcacag  74100
```

gtaacggcca gtttttcagc tgtgtttttt ctagttatgc ttactaaggt ttaagtttag 74160
atgatgatgt ttgttgcttg ttcttctggt taggaaatac attttctttg gcggattgca 74220
ttcctttgct gcggaaaaca ctgaaggatg agtcttctgt tacttgcaag ttagcttgta 74280
cagctgtgag ggtgagcata atcttctgtg gaaccatttc ttcacttagt ggacatttta 74340
tcattgctac aattaaaatt ggagcttaat aggaaatatt tccatgcact ctaaagctgt 74400
aaccagtaat acccaccatg tatccatctc tcagctttag aaagaaaacg ttgccagtaa 74460
agttaatgct tcataaactt cagtttaagt tctaattctc agaatatttg tttgaaatag 74520
acctcttcct aaaggatata tttagaaata acctatcatt aagtgtaaag tctgttgaat 74580
atgctgggca cggtgactca cacctgtaat ctgaccactt tgggaggcca aggtggaagg 74640
attgcttgag cccaggagtt caagactatg ggcaacatag ttgaccctgt ccctacagaa 74700
aattaaaaaa aaaaaaaaaa aaagtagctg ggtatggtgg tgcatacctg tagtctcagc 74760
tactcgggaa gctgaggtgg aggggggatt gcttgagccc cagagatcaa ggctgcagta 74820
aggcgtggtt acaccactgc cctctagcct gggcaacaga gtgagactgt ctcaaaaata 74880
atagtaataa taatcagttg aattaaaaaa aaaaaaaaaa aaaccactgt gctaggccca 74940
tagtatggta agagttaaag tgagccttag ggattattta ctcaacctct gtttctgtat 75000
aaagtggaat aggctcaatt ctttaagtga tagcatgttg aacctttcca taccaactgg 75060
ctcataagtc acaactggcc agtcaacaag agtaaaaatt aactggtaaa aatcaaagca 75120
aaaaacctac aattgtcaaa tttgtgggat aactccccct tttaaaatgt catgcctgac 75180
agtaatttct ctctagtttc caggttttca gtcagttgtg tctttttga gcagaaggaa 75240
gcatgctaag agctcaatct tgtggctagc tgggggtctt tgtgtcagcc atgcatgtga 75300
tggtgcccct gggtgcttgg ggctgcaggg gaggggtaca gcagtagggg cctgttctgt 75360
tctctcgtgc tgtggagtac atagtgacat agtggggtgg tccttggtgt aggtcccttg 75420
ttcctacccc tgggtctgag atttatttag aagtggtgtt ggggctgtgc ggcaggcccc 75480
tctgtaactg atcaatgttt gtgaagttgc tgtttgagag ttgaaaccat gacataagca 75540
gaaatggaag gaagaaagaa ccagttatgt gaaagggaca catttacttt taagcttgta 75600
tttactgaga taaagtattc ttaatcaatg ttcttgagag gtgtgggaaa aatgcaacat 75660
cctggttgca gttaaaccca gaacattgtg tgttgaagag tgacggttct caaaccgtca 75720
agacgcgggt actgagtggg actaacctgc tgtcctcttg ccttggacct tgtgttccag 75780
aactgtgtca tgagtctctg cagcagcagc tacagtgagt taggactgca gctgatcatc 75840
gatgtgctga ctctgaggaa cagttcctat tggctggtga ggacagagct tctggaaacc 75900
cttgcagaga ttgacttcag gtaagtgagt cacatccatt agatttcatg aactaagctc 75960
aattgaaagt tctgggatca cttgatgcaa ggaatgatgt tatcaagtac cctgtccatc 76020
agaaatccga gtggtttagg tagatgacag tgattttctc ctcccagtgg ctttttgctg 76080
aactttgccc tatgcttgga attttatttt attttattat ttatttagag acaagatctt 76140
gctctgtcgc ccaggcttga atgcagtagc acaatcatag ctcactgaag ctttgaactc 76200
taggactcaa gtggtcctcc tgcctcagcc tcccgattag ctaggagaat aggtgtgtgc 76260
cgtcacactg gctaatattt tttgtagaaa tggggtcttg ctatgttgcc caggctggtc 76320
tcaaactcct gggcttgatt gatcctccat cttggcctcc caaagtgctg ggattacagg 76380
catgagccac tgtgcctggc ctagaatttt aaaatataag tagaagagta gatttttttt 76440

```
tttggtagtc ctcgtcattt aagtattctg gatagtggga ataaaagagc ttagaatttt  76500
tcatctttgt cttaaacttt taaaaaaatg tagcttatat taattctgct tgtttaaaaa  76560
gaatatactc ttcattatac tgaacctagg taagacagct ggtttatatt ttgttgcaat  76620
taaaaaacgt gagctgtggt tgcagtgagc caagattgtg gccattgcac ttcagcctgg  76680
caacagagtg agacttggcc tcaaaaaaaa aaaaataaca tgagctgtgt tggcactttc  76740
attttctaag agtagttttg gctggagaag ttttctttca gtactttctt ttagaaggga  76800
aattttcctt tataatttag ggtttgtttt tttttttcc aagccacctt ttatagagcc  76860
cttgtgggtt atttcattta atccttagaa tgtttataaa tctgggcttg ttctcggctc  76920
cacccacaga tagggacgct gagcgtgcat gagtgggcag caagatagca ggttatggag  76980
ggcccagctc accccttctg tggcttgagc caattttata gggcacttac agagtctttt  77040
gaaatagtat ttattttgaa gaaaaagaaa aacagtttac tgagtactgt cttattgagt  77100
ctggaattgt gagaggaatg ccacctctat ttatttaaag ccattggcct tttttgttgt  77160
tttgagtaag tgctgcccaa ggtccttcca gggcacctgg atgagcctgc tctggagcaa  77220
gctggcggta agtgtttact gagtaactaa atgatttcat tgttaaatgt gctcttttgt  77280
taggctggtg agctttttgg aggcaaaagc agaaaactta cacagagggg ctcatcatta  77340
tacaggggta agcggtttat ttttgtgaga tgctgtttta ccttcaagaa ggtgaaagtg  77400
aggctttcct tgtggaattt ctctaaatgc attcgtcatg ttttagatgt ttatttcaca  77460
gtttatatca tgaaagttat aatcttgtca tatggattta agtctagtaa tgttgagttc  77520
tttctcacta gctttccaaa atatcttacc taaaatttag tcaaatacaa gattatgttt  77580
atttttatta tccttctctc taaagctttt aaaactgcaa gaacgagtgc tcaataatgt  77640
tgtcatccat ttgcttggag atgaagaccc cagggtgcga catgttgccg cagcatcact  77700
aattaggtat ttaccaatat tttatctctt ttcctttttt ggttgaagta ctaaaagata  77760
cgagaatgga aagagaggga agaattcaaa ggatgtagag cagtattcct gaatctgagc  77820
tcatttcagc cattctattc ttaaactata atgaaaaaaa aatccaaaaa agtctaaaat  77880
tataattaaa aaaacaacaa aatactaact gtccattgta aaaagtaatg cactttcatt  77940
gtaaaaattt tggactatag agaatagtac taagaagaaa aaaaaaatca ccttcaattc  78000
tgctgccacc tggaggtaat cactgttaat attttgctat atactctatg agtttcttgt  78060
tcaaaatcag gtcaaaatta catgcaattt tgtaatctga caatttccac ttaatatttt  78120
attagcattt tcctgttatg aaacagtaat tttagttatg ggtcgttgtt ttgctatgcg  78180
gttgggataa aattttatat actttttttg gcaattactt attatacata aatgtttgtg  78240
tatagttttc tttttctgag aattcctgga agttgagtta ccaggcccgg ctttgaattt  78300
ttttttttat ttttttttg agacagagtc ctgctctatt gtccaggtgc tatctcggct  78360
cactgcaacc tctgtctccc tggttcaagc gattctcctg cctcagcctc ccgagtagct  78420
gggattacag gggcacacca ccacgcccaa ttaatttttg tatttttagt agagacaggg  78480
tttcacgata ttggccaggc tggtctcgaa cttctgaccc cgtgatccac ctgcattggc  78540
ctcccaaagt gctgggatta caggcgtgag ccatggcgcc tggccaggct ttaaatttaa  78600
aacaaatctt ctaatagctt tatggaggtt ataatttaca tttcttgaaa tgtactcact  78660
ttgagtgtat agtaaactcc aattttatca catttctgtc accccaaatg tatccttgtg  78720
cccatttgct gtaacctccg gttcctgccc caactcctag gcagccactc atctattttc  78780
tgtcccttaa gatttgtgtt ttcgccaggc gctcatgcct gtaatcccag cactttggga  78840
```

ggccgaggtt ggtggatcac ttgaggtcag gagttcgaga ccagcctggc caacatggtg 78900
aaaccttgtc tctactaaaa atacaaaaat tagtcggatg tggtggcaca cgcctgtaat 78960
cccagctact cgggaggctg aggcaggaga atcacttgaa cctgggaggc ggaggttgca 79020
gtgagcagag atcgcgccac tgccttccaa cctgggcaac agagagagac tgtctcaaaa 79080
caaacaaaga tttgtatttt ctggacattt tatagtactg gggtcatagt atagatggac 79140
ttttgcattt ggcttctttt acttaattgt gagattggtt cttgttgtag catgtatcag 79200
tagtttgttc atttttattg gcgaaagtat tctattatat gaataatacc atattttatc 79260
tatccatcag atggatatta tagagttcat gttttggcta atttatgaat tatggtactg 79320
tgaacatttg cctgcaagat tttgtgtaga catgtcttca tttctcttga gtagatcacc 79380
tagaagtgga tttttaaata attttggtac ttactgtgaa actgctcttc aaaaacatac 79440
cattgttcct tccttccttc cttccttcct tccttccttc tttccttcct cccttcctcc 79500
ctcccttccc tacttccctc tccctttccc tttcccttcc ccttttccct tccccttccc 79560
gcctgcctgc ctgcctgcct tccttccttc cttccttcgt ttctttctac atatacacat 79620
ttttttaaat ttcaatggtt tttggggtac aagtggtttt tggttacatg gctgaatttt 79680
ggttacatgg tgaagtctga gattttagta cacctgtcac ccgagtagtg taccttgtac 79740
ccaatatgta gtttttttgtc cctcaccttc cagccttccg ccttgtgagt ctccaatgtc 79800
cattatacca cactgtatgc ccttgcgtac ccacagctca gctcccactt ctgagaacat 79860
atagcagaaa catgccaaag tatactccca ctaccagaat gtgattgtgc ctgattcttc 79920
tcaccagtac aaatatttca aaaaaagtta aatatgtatc agtttttttgg gcagaagttg 79980
atacttctct ttatttattt atttttttttg agatagggtc tcattctatg atgcccaggc 80040
tggagtgtgg tggtgcgatc tcggctcact gcagtctctg cctcccaggt tcaagtgatt 80100
cccacgtcag cctcccagga agctggaatt acaggcgagg gccaccactg ccagctaatt 80160
tttgtatttt ttggtagaga tggggtttca ccatgttggc cagactggtc tcaagctcct 80220
gacctcaagt gatccacctg ccttggcctt ccaaagtgct gggattacag gcgtgagcta 80280
ccacacccgg ctgatatttc tttttaaaat aacttacctt cttttgaaag taatacatgt 80340
ttaatgaaca gaatttaagg aaaatataaa aaaacgaaat aatctttgta atcaaactac 80400
tgaaaagaaa accaaagtta cattttggtg catattcttt ttcattttca tcattgtaat 80460
ttgcatttct ttgattactt gtgagacact cctttcattt acttaatagg tttatatgac 80520
ttgcctattc agagatttttg cagctttacc attttctgca aatgatagca acttcttttt 80580
gtttgtttgt ttgtggagac agagtctcgc tctgtcactc aggcaggaat gcagtggtgg 80640
aatcttggct cattgcaact attgcctcct gggttcaagc gattttcctg cctcagcctc 80700
ccaagtagct gggattacag gagtgtgcca ccatgcccgg ctaatttttg tatctttagt 80760
agagatgggg ttttgccatg ttggccgggc tgatcttgaa ctcctggcct caagcggtcc 80820
ccctgtctcg gcctcccaaa gtgctgggat tacaggcgtg agccaccgta cccagccagt 80880
agttacttct tatattctag aaaaaattct actcatgatc aagtctccat gaggaaagag 80940
actttaattg aagatcatgg ggcttgcaga ccaatatgat aaaatagttc attgtttcta 81000
aaagtattac tgagtgttga tggcagatat gaaccctttt gtttttgtag gaaaatgtta 81060
cccgtattct ccatttgaat tcagtttaga tttgttagga atcgcagctt aagctttgcc 81120
atctgggagt gtttgggaca gttttgcaga caaaattgca aaagtgccta aggaatgcag 81180
ctggcattca gacctgctct gtgctcagta ctctgtggac agacactgtt cagcacttgt 81240
tgatcagaag gtttagaaag agaactttca aagttggttt ttaattaaag catttaatag 81300
tgtaaataga aagggattaa attttatgac agacaaaaga aagtacagca cccagctggg 81360
cgtgggggct cacgcctgta atccagcact atggggggct gaggtgggtg gatcacgagg 81420
tcaggagttc aagagttcaa gaacagcctg gccaaggtga tgaaaccctg tctctactaa 81480
aactacaaaa attagccggg cgcggtggca ggcgcctgta atcccagcta ctcaggaggc 81540
tgaggcagga gaatcacttg aacctggacg gcagaggttg cagtgagcca agattgcacc 81600
attgtactcc ggcctgggcc acagagtgac attctgtctc aaaaaaaaaa aaaaaagaaa 81660
aaaagaaagt acagcaccca gttatgtccg agtgggtgca tgagagtgac cctgagattg 81720
gagacaacgc tgtcacgtgc ttgaagaacg ccacctgaga aagggggcga gaagtggtgt 81780
ccgctggtaa ccagaggtgt tggcttagcc atctgcaggg aggagggtgg tctatcacag 81840
gtgagtttca tctactttct taagcaaatt aaccttactt ttgtgttagg cttgtcccaa 81900
agctgtttta taaatgtgac caaggacaag ctgatccagt agtggccgtg gcaagagatc 81960
aaagcagtgt ttacctgaaa cttctcatgc atgagacgca gcctccatct catttctccg 82020
tcagcacaat aaccaggtat gctgacccag tggcatcttc acattgtcgg gaaaatgccc 82080
tttcctgatg cctttcttta ggctttaatt gaaaacattt tattttctag aaaaaagctt 82140
cagctcagga tgtttgagtg taggtcagtc ctttgatagg atattatcat tttgaggatt 82200
gaccacacca cctctgtatt taagctctgc cacaatcact cagctgtgac actgtaaatc 82260
tcttaatagt ttattacatt ccatgtgctg acagttgtat ttttgtttgt gacacttacg 82320
tattatctgt taaaacattt tcactttagt tgtgttacct ttaaagagga ttgtattcta 82380
tcatgcctgt tgattttttg gtgagcgggc tattaaagtc agtgttattt agggttatcc 82440
actagttcag tgatttgcga gattatcatt cacatttatt gtggagcttt tgaatatcgt 82500
gtcaaatggc cacatatatc ccattcttat ctgcttctta ggtgagtggg acacagtgct 82560
ttaatgaagc tataatcttc agaattctag cttgcagaga agattgcaga agtgataaga 82620
cttgtgcttt ttaattttgt cttttaaatg ttattttaaa aattggcttt atatgatact 82680
cttttttttct gctgagtaac agtgttttac aaaacttgga ctaaatgact tctaagctta 82740
aatgatcact tgatgctttt tttctgaatt aggaactcag cttatcaaat atcaaagtca 82800
taattcctga ataaataacg tctttttttca tgtaaagact gctttaaaaa acacatggaa 82860
ggctgggtgc ggtggctcac gcctgtaatc ctaacacttt gggaggccca ggtgggcagg 82920
tcgcttgagc tcaggggttc aagaccaccc agggcaacat ggcaaaaccc acctctactc 82980
aaatacaaaa aattagccag gcgtggtggc gggcccctgt aatcccagct actcgggagg 83040
ctgagggatg agaatcactt gagccccgga ggcagaggtt gcagtgagcc aagattgtgc 83100
cattgcactc ccagcttggg ctacagagtg agactctgtc tcaaaaaaag acacacacac 83160
aaacaaaaaa aacatggaga catttttttg gccaccttaa tatttcccct cagataattt 83220
cctttgttta aactcagaac tggcattttc tctcttggag aagattcagg acaaatactc 83280
ctttaagata agtagaagca gtgaaagagg atttgattat caggaatttg ataagcttag 83340
aataaattgt tgcttcttaa tgtcatttca gaagatgaat atttattaat agatgccaac 83400
tgagatatca ttaaaattga ttactaacta ctacttggaa aagtctccca gttccaaact 83460
tcagcaggcc tcttgacaat tcagctgtgg tcaattgggt cttgcgtgat agatacaatg 83520
accaattgtg cagcagagtg tgctgcttag ctgcctattc tgttagcatt catgtgttaa 83580
cttaaaatca taatctcctt agttttgttg agtgtctccg tggacaagac actgtgaggg 83640
atacaaaatc agattggctt tattcaaacc actggggtat tataattcat ttataattta 83700
ttttattttt tgcctttttt ccatgtgttc taaaggaatt agagtttgta tataactata 83760
atgggggata gaaattgaca tgtgccatga agggaatgca aaaaagtgcc gtgggagatg 83820
agaagtggag aaaggaattt cttttttctt ggaagcagga ataacttcat gaagcatgta 83880
tttcaactta aacagatagt aggcaacgct gtaaggggag tatggctgca gcaaaagtgt 83940
tcggggcaga ctgggaggaa gggagggaat aaattcagcc attgttatgg aataatgatc 84000
aaaatttatt ttcagcccgt ttcacttaaa agttgagact gcttaacttt ttttaatctt 84060
taatcttaaa cttttaaatg ccatttgatc tttaaaaata tatgttttaa tagtgtattt 84120
taagtctcta tatttttgtt attagaatat atagaggcta taacctacta ccaagcataa 84180
cagacgtcac tatggaaaat aacctttcaa gagttattgc agcagtttct catgaactaa 84240
tcacatcaac caccagagca ctcacagtaa gtctctttct tgatcggtct tactgacatt 84300
gtaatagttt ttggtagctt gtatggccag ttagttgtat ggtcatctta cggtgaggtg 84360
cttgtcttac agctcttact tatccatgag gcttgctaag aaattgtgct tctgtgaaaa 84420
gaatctcagc ttactccagg aatgtaaatg actatgtttt ttctgattat taaagtaata 84480
cacgcccaaa ataaaaaaat tcagccaatt taggaagaca caacaattaa aataagccag 84540
gcatggtggc tcatgcctgt aatcccagca ctttgggagg ccaaggttgg gggctcactt 84600
gaggtcagga gtcggatacc agcctggcca acgtggtgaa accccatctc tactaaaaat 84660
acaaaaatta gctgggcgtg gtggcgggcg cctgtaatcc cagctactca ggaggctgag 84720
gcaggagaat cgcttgaacc tgggaggtag aggttgcagt gagctgaggt caagccactg 84780
cactccagcc tgtgcaatag agcgagactc tgtctcaaaa aaaaaaaaaa aaaaagaaaa 84840
gaaaaaagta aactactgtc acctgcattg gtaatgtatc agaagtttaa aatgtctaga 84900
ttataattaa ctcagtgacc tggtaatata tactaaggga aaaatattta taatttacat 84960
ttttacattt ttattttttt aattttatta tttttttttt gagacagagt tttgctcttg 85020
ttgcccaggc tggagtgcaa tggcatgatc tcagctcacc acaacctcca cctcccgggt 85080
tcaagcaatt ctcctgcctc agcctcctga gtagctggga ttacaggcat gcaccaccat 85140
gcccggctaa ttttgtattt ttagtagaga cagggtttct ccatgttggt caggctggtc 85200
tcaaactccc aacctcaggt gatccgccct cctcgacccc ccaaagtgct gggattacag 85260
gtgtgagcca ccatgcctgg ccttacattt ttataataag aatttatgtt gctgacatta 85320
gaaaagaacc ataatatcca agaatccaag aataattaaa ttatgtacat atgctagtat 85380
atagtgtgat gctttggaga atttttaaca atatggagat gtataatctg gattgtaata 85440
ttgagtgaaa aaaggcagaa tacaaacctg gtgggggtat agtcggattt cagttaagaa 85500
aaataatatt tacatatata catttctcac actggcagat aatcaccaag ataaattttg 85560
ggattgtgga tgattttttt cttctttata tttttcagat attctcaaat tttctaaaat 85620
gagcaagtat aacttttgtt atcagaaaaa aataatatac aaaagtaatg ttaatttgct 85680
ggtgaccagg ttaaaccttt ttatttttat tttttgagat ggaatctcac tctgttgccc 85740
aggctagagc acagtggcat gatcttggct cactgcagcc tccgcttcct gggttcaaat 85800
gattctctgg ccccagcctc ctgagtggct ggaattacag gcgtgtggca ccacacctgg 85860
ctaatttttg tatttttagt agaggtaggg tttcaccagg ttggtcaggc tggtctcgaa 85920
ctcctgacct cgtgatccac ccacctcggc ctcccaaagt gctgggatta caggcgtgag 85980
ctactgcgcc cagccagacc tttttatttt atttgacaaa agaaatactt ccatgttata 86040
gaagactaaa tattgtttgg gctgtctgca gtatggtctt cccttgattt gttcaaaata 86100
tcgtaaactt tgcttattta tttttattgt ggccgactgt gtcgggcact gttgtaggct 86160
tgggatggaa aaacaggatt cctgccctta gggtttctgc aggctggtca gggagacgat 86220
gtggtaagct ggagctcagc tcctaaggat gtgcaggggc agttgagagg cggaagggtg 86280
ggagatcatt ccagggtgtg ggcagcacag gaacctctct tcattgggat ataattgcca 86340
ttctgataac acgtgtttga ggtgtctaaa gtaggaagtt gtaccatggt gggacagata 86400
tcctgtggtt atcatacaca gatctcagtt ttcttctcat tgtttgtact ttttataaag 86460
ggtaacagga gatataattc aataaacctt tgtggtgttt gggtgtgatt ttattgtttc 86520
tttcttctca gtttggatgc tgtgaagctt tgtgtcttct ttccactgcc ttcccagttt 86580
gcatttggag tttaggttgg cactgtgggt atgtattttc ctcagtatat attaatagtt 86640
gtctacaaca gtatgacata aacatagtta ttaggatgcc ctttttcttt ctttttaagt 86700
cttttatcaa tttggctttt tggaaaaata tctgatggaa tacttgtttc tgctatatta 86760
gctgtgtgag actagtgaca ggagctgtgg gaaatgaatg ccaaatgttc ttaggcattg 86820
atgggaattt cagggtgtgg tcttcaagtt catttaaggg aattttcata tgctggcaaa 86880
aggcttttct cattagcttg actctttcca aaattatttg ctgtgaatta gaagtttagg 86940
aaccttttt cacttaattg tgacctagca tacgaaatgg tgatgattta ggaactactg 87000
ttcttgtatt aacagctttt atttaaaaat gattttcctc cagtagatgg ccctactagc 87060
atctgggaaa taatttcaag tcttctccag cattcaggaa taggctttca ttttgtgtat 87120
caattactga gaatgatttt ggtgactcac atcacatttg agaagtaaac ctgcagattt 87180
cttgtgtgtg tcagcaaatg accaactgat atttgcttga agtggattac attatctgct 87240
ctagaatgat tgctttccca ccttcctcac atacagactg agcagctacg gtttctaatc 87300
ataggtctgg cactagactt cacttctggg caactttggc attggagtaa aatgtattaa 87360
tttaaagaaa gttaaaaatc cgttcaagta aacatacagt tctaatactt tttacaattt 87420
aaaatataga tttaaatgat aaaataaaaa agaaaatatg ggtagacacc ataatcctcg 87480
tttctgcatc tgttcacaag gggttgatat ttatgagttc tattctccat atccattcta 87540
tgttctctta atgctcagtc agcacctcag gtggttggag ttcaatgctt ggtagtttga 87600
cttacactgt cttttctagg ggattgagcc ctgggtagtc ctgcttattt gaggttgcaa 87660
tttgtctttc aataactttt actacaagat atggcgtgtt aaaggatacc attggggaac 87720
caacataata atatcaggaa aactaaccac gtcagacctg ccccattgtg tatcaagtac 87780
actatttttc catagtaata aagagttcac cccagccaat tctcttttat tttgtgcctg 87840
tttactcaat ggcattaaca tgcccaaatg tctgggtagc tgtctcatct ccagttcagc 87900
agaaccattg tcatatgccc tagtaaaagc attccttcat tggacactta ggccccaata 87960
ctttcattca gatctactac ctgatttcat ttctcaaatg atttttatgg agctctgatt 88020
tataggaaag atgttagttg attaaaaata aaacaatttc tgagctggta taaaatgtat 88080
tgtgacatgc cttcctcttg gaattgcaag agaaaggaag actgttgttt gcttaaaaat 88140
tgtctataat ttgactttgc aaatgtctgc ttccagagtg cctccactga gtgcctcaga 88200
tgagtctagg aagagctgta ccgttgggat ggccacaatg attctgaccc tgctctcgtc 88260
agcttggttc ccattggatc tctcagccca tcaagatgct ttgattttgg ccggaaactt 88320

```
gcttgcaggt actggtactg agttgaaaca gggactccag gacttggatt ttgatttcct  88380
tagggggaat gggggtggtg agcatatgag gggaaaatac tataaggtca ttgccagtga  88440
tggcttgtcc ctttagtcaa atttcagatg ttacctatat gcataaacac atgcagttgg  88500
cagctgttct gtgctgagta ttttaaagta gcctcttccc aatatagccc ctcagttaac  88560
tacaagtaaa ctcattttga atttcatttt aatgggcacc atatgccagt actccctcgg  88620
gcactgggat gttaagaaag tataatgtat ggacttcatt ctcaagttag ttttagatta  88680
gagggggata cacgtaaaca aaagtgcagt ggtcacacag agtggcccta atcactctcc  88740
ttgggcagat ttatgggctg gtaggaaaga gcacaacacg gagagggtgt agcaccttgg  88800
cgatgataat ggaggatgtg gccagcaagg aagacggagt ccattgaaat tgattttggg  88860
agaagttgcc aatctccatg aaagaattgg ggcctgtgct atttgcttca gggggctata  88920
ggagagtttc gtgaaaggga ctaaaagatg agtattttaa taagatcatt catccaactt  88980
gaacatgggc tggaggagaa ggtagggaga ctcaggagat taatgttgat gctaaggcaa  89040
gataatggct ttgggactgt agggaagaca ctgattgtaa gagaatgaag gaggcagaat  89100
tgccaggcct ggttcaccaa ctgaacttcg gttgtgaaga caaagaaacc tgggatgact  89160
tcacatcctg ggcaggtgtg tggtggtgac agtcatggaa attgggaaca cagatttgtg  89220
cgggaaacat cagtttcagt ttgagtttgg cttatcagtt gaatatcagg cacagatgtc  89280
tggccaactc tcaacatagg gtcttaaatg acttcagttc cccaagcaat ttgtccttcc  89340
catgctattg gggtggagag gtaatgtctg tgcccatatc acagccagtg ctcccaaatc  89400
tctgagaagt tcatgggcct ctgaagaaga agccaaccca gcagccacca agcaagagga  89460
ggtctggcca gccctggggg accgggccct ggtgcccatg gtggagcagc tcttctctca  89520
cctgctgaag gtgattaaca tttgtgccca cgtcctggat gacgtggctc ctggacccgc  89580
aataaaggta atgtcccact tgggtgctgg attcatacag ccttaatgac tatgggtttc  89640
cagactacct ttgtttagta atctgtccct tctttattct ctttttgctt taaatgaaca  89700
aaattgctca gattgtgaca ctaaatttaa catcaaaatg tgaccatgtg gatgggtgca  89760
gtggctcgtg cctgttattc cagcactttg ggagactgag gcaagtggat cacttgaggc  89820
caagagttcg agaccagcct gggcaacatc acgaaacccc ctctctacta aaaatacaaa  89880
aaattagatg ggttgggccg ggcgtggtgg ctcaagcctg taatcccagc actttgggag  89940
gccgaggtgg gcggatcacg aggtcaagag atcaagacca tcctggctaa cacagtgaaa  90000
ccccgtctct actaaaaata caaaaaaatt atctgagcat ggtggcgggc gcctgtagtc  90060
ccagctgctc gggaggctga ggcaggagaa tggcgtgaat ccgggaggcg gagcttgcag  90120
tgagccgaga tcgtgccact gcactccagc ctgggtgaca gagcgagact ccgtctcaaa  90180
aaaaaaatta gatgggcatg gtggtgcgtg cctgtaatcc cagctacttg ggaggctgag  90240
gcaagagagt tgcttgaacc tgggaggcgg agtttgcagt aagccttgat tgtgccgctg  90300
cactccagcc tgggtgacag agtcagactc tttccaaaag aagaaaaaaa tgtgaccatg  90360
tgttttatag ctcttttagt atcatcagtc actgttatcc ctaagaggga aatacctagc  90420
tttagtttta ggtttccagc attagccaag aaagctcaga attgatgttc ctggccaagt  90480
acctcattgc tgtctcctta aatcttggtt aatggctact gtcctggcta gcatagttat  90540
ggagcatttc catggttgta gaatgttctg ccaatctcag ggacagtttt gcttttctgt  90600
gaagcaataa aatcaacttc aaaacaaatg ttaactattt gtacaatgga tttaagatag  90660
```

-continued

```
accagttcac atactttttt tttttttttt ttttgagatg gagtttcatt cttgttgcct  90720
gggctggagt gcaatggtgt gatctcagct cactgcaact tctgcctcct gggttcaaac  90780
gattcttctg cctcagcctc tcgaggcaga ttacagctgg gattacaggc atgcaccacc  90840
acacccagct aatttttttg tagttttagt agagacgggg tttcaccatg ttggtcaggt  90900
tggtctcaaa ctcctgacct gaagtgatct atccgcttcg gcctcccaaa gtgttgggat  90960
tacgggcatg agccaccacg cccagcctaa gatagaccag ttcacttact gtttatatct  91020
gattactctc tctttgcctt gtcttctacc tttaaaaatc tccctactaa cttcccattc  91080
tcctttagct gccatcagtc ttctcccttc tctgcaaaca tctctggaga gtcccagcct  91140
cagcccacag agcttcccac tgctctgagg tggaccttgt ttgcaaggct tctttggctc  91200
tcttggcctg gaccctgtct actacttcag ccatccttcc ttaacccctg ctggtggttt  91260
ctgttgccac actccatagc agcgtttccc gcccagatca tgtctttaca tctctgggca  91320
ctgctctggt cctgcctgcc tttccctctt tgtatcctgc aggctgctac cccatcttg  91380
agtgtcctct tcagttggct ttcagagggc ctcctgggtg ttcccttacc cacttgccac  91440
tccccagtca ctgggttcag tccttcctgc ccaccagcac atgctttcta ggctctgtcc  91500
taggccgtct tctctctttg tagtctctgg gccagtgctg ttctagagag tggcagaatt  91560
ttctataacc atggcagtgc tccatagcta tgccaggcaa gacagtagcc actaaacaca  91620
tatagctgtt gagcccttga aatgcagcta gtgtgactga agaactgaac cccgattcgg  91680
tttaattttc attaaattta aatttaaata accttatgtg ggtagtggct ccagtattgg  91740
gcagggcagc ctgagagtcg gggctgttct cctgtcttca gtgtctagat gagggacctc  91800
agaggacctg tctctggagc tgcagttcaa tgtagccagc tgccccgtga cacttacata  91860
tagctgattt gtggatatgt cagacacggt gtgatgagct cagctttctg tcctcctccc  91920
cacatctgcc cctgccccat ttaccccact ttgtgtctta tcaagctaga aacaggtcac  91980
cacaagtctt catttccact caccaagtct tttgtttccc ctactaaata ttttgcgaga  92040
agaaagtgtg tacctttgta ttcacataca tgtacatgca catatacatg cacatatgca  92100
ggggtcccca acctctgtta aaaaccggac tgcaggccgt gcgtggtggc tcacgcctgt  92160
aattccagaa ctttgggagg ccgagaccag tgcatcacaa ggtcaggaga tcgagaccat  92220
tccggctcac acggtgaaac cccgtctcta ctaaaaatac aaaaaaaaat tagccgggtg  92280
tggtggcggg cgcccatagt cccagctacc tgggaggctg atgcaggaga acggcgtgaa  92340
cctgggaggc ggagcttgca gtgagccgag attgtgccat tgcactccag cctgggcgac  92400
agagcgagac tctgtctcaa aaacaaaaca aaacaaaaaa aaaaaaaacc aggctgcaca  92460
ggaagaagtg agcaagcatt accatctgag ctctatctcc tctcaggcca gtggtggcat  92520
tagattctca taggagcgtg tatgagttcg ttctcacact tctgtaaaga catacctgag  92580
acatataaag aaaagaggtt taattggctc acagttctgc aggctgtaca ggcttctgtt  92640
tctgggaagg cctcaggaaa cttgcagtca tggcagaagg tgaaggggaa gtaggcacat  92700
cttcacatgg cccacaggaa aaagagagaa ggagagagag agagagacag agagagagag  92760
agaaaaagaa agattgagag ggagagagga gggagaaagg agagtgcctg taggggggagt  92820
tgctacacaa aggagcacca gggggatggt gctcaaccat tagaaactac ccccatgatc  92880
caatcacctc ccaccaggcc ccacctccga cactggagat tacaattcag catgagattt  92940
gggtggggac acagagccaa accatatcag agcatgaacc ctattgtgaa ctgcacattt  93000
gagggatcta ggttgcatgc tccttatgag aatctaatgc ctgatgatga tttgaggtgg  93060
```

aacagtttca tcccgaaacc atccccccgcc aaccctggtt tgtggaaaaa ttgtcttcca 93120
cagaaccggt ccctggtgcc aaaaagtttg gggacctctg cacatatgca tgcacctgta 93180
catggacaca taatacatgt acatatgcat actttatatt ctctgccact tctggtccag 93240
actgatatac tatctcattt ggattactgc actagccttt tgttttggaa acagcatttt 93300
ttaaaaaatt taatttaatt tttttgagat agggtgtcat tctgttgccc agcttggagt 93360
gcagtgtcat gatcatagct cactgcggcc tcgatctccc aggctcaagt gatccttctg 93420
cctcagcctt ctcagtagtt gggactacag gcatacccac catgcccagc taattttttg 93480
attttttttt ttttttgaga cagagtctca gcctgtcgcc caggctggag tgggttggcg 93540
cgatctcagc tcactgcaac ttctgcctcc caggttcaag tgattctcct gcctcagcct 93600
cccgagtagt tgggattaca ggcgcctgcc accacaccca gctaactttt tgtattttta 93660
gtagagacgg ggtttcacca tgttggccag gctggtctcg aacttgtgac ctcgtgatta 93720
gcccgcctcg gcctcccaaa gtgctgggat tacaggcgtg agctaccgct cccagccagg 93780
aaacagcatt cttgagataa ttcatataat tcacccattt aaagtatata attcattctc 93840
tttagtatgc ccacagagtt gtacagccat caccagaatc agttttagaa cccataaagg 93900
aactctgtac tctttaccca aaacctccat gcctccagct gcaggcagcc actaacctgc 93960
cttctgtctc tgtgactcta cgtcttctgg acattactgt ggatgggctc atacagtcag 94020
tgagcttgtg actggtgcct tctaccaagc agggttttca gtgtagcagc ctctctgttt 94080
ttcttttttt tttaaattgt gacggaactt ctgcctcccg ggttcaagcg attctcctgc 94140
ctcagcctcc cgagtggctg ggactacagg cccatgtcac catgcctggc taattttttt 94200
tttttttttt tttagtagag atgggtttca acatgttagc cagggtggtc tcgatctcct 94260
gacttcatga tccgcctgcc tcggcctccc aaagtgctgg gattacaggc gtgagccacc 94320
atgcccggct aacctttcat ttactgtctg catttcttcc ctgatgcctt ccagtccatg 94380
cacccgattg tagccattca tcctattatg gtttaaggtg actgtcttag tcagcatggg 94440
ttgccataac aaaataccat agcctgggtg gcttcaacaa cagaatttac ttctcacact 94500
tctggaggtt gggaagtcca agatccagga ctttcgcctt gccctcatgt ggtgaggggg 94560
tgaggaagct ctgtggggcc tcttatatat ggatgctaat ctcattcatg aggggtctgc 94620
cctcatgacc cagtcacctc ccaaaggccc cacctcctaa taccatcacc ctggtaatta 94680
agtttcagtg tataaatttg gggactata gacattgaaa ccataacaag cacttttcta 94740
agatcaggga gtgagtaagt agcagagcta ggacctcaat tccacatgtc agtcatcttg 94800
ccttcactct gctccatgat ggctgcctcc tagagcattg ggagtctcga tgttctatat 94860
gctctcatgt gttgtgtatt ggagatagtt gaggctttat gaatacatct ggatttgttg 94920
acttctagct ttgctggtaa ccagctgtga ccttgaataa gttacttcat ctctgagcct 94980
gtttcctctt ttagaaacag gagtttaaaa tgctgctttg ggttgggcac ggtggctcat 95040
gcctgtaatt ccagcacttt gggaggctga gatgggagga tcactggagc ttggagttcg 95100
agaccagcct gggcatcata gtgtgagatc ctgtctcctc aagaaattaa aaaattagct 95160
gggtgatgtg gcgtgtgcct gtggtcccat ctactctgga ggctgaggtg ggaggattgc 95220
ttgagcccag gaggttgagg ctacaatgaa atatgattgc accccatcct gggtgacgag 95280
tgagaccctg tctcaaaaaa gaaaaaaaaa atgctgcttt gtaccccttt catgtcatgg 95340
cgtcatggcc aacatagaat gccctggttg tttgctgttg gagggcatgg gcctgggggc 95400

```
tccctgaggg ctccttccat cttcaactca ttctctgtgc acctgttagg aagttgtggg  95460
ccagtcccta ccatgtatca ttgtgtgggt aaaagtaaat aaaatgtgta cagtgtctga  95520
actgtacata tcagggtcca agaacaaaat gagtgacatg ggttagctct ttttaataaa  95580
tggtaaaacc aaatattcta attttcagtt ttgttatact tccatcacat gtttttgttt  95640
ttttgttttt tgtttttgtt tttctatttt aggcagcctt gccttctcta acaaaccccc  95700
cttctctaag tcccatccga cgaaagggga aggagaaaga accaggagaa caagcatctg  95760
taccgttgag tcccaagaaa ggcagtgagg ccagtgcagg taggaaacag cgtggggaag  95820
ggagggacat gagtgcagca tctgtcatgt agaaacatag gatttaagta acttggtgtt  95880
ttagagaaat aaatataata cacatcagta aagtgagaga aagtttctcc aggtgcggtt  95940
caagatatta gaaactaatg actgatgtac acagaccacc ttttggtctg aagcatttct  96000
aagtgccact ggctgacatg cagcccctac agcctccagg cttccagccc tagcatggag  96060
catcactctc ctatgcttcc ctggttgcag gtgatggctg gagaggcctc ctgattttca  96120
gtaagggaag tggtgtagat gcttaggaat agatgtagtg agtgaaaaaa ctgattctga  96180
tatgtcaaaa attctgattg gaaatggaat atttacattt ggaagagcta aaggcgagag  96240
aaagtgggga taaagtcatc tgagttggag gagcttaaac cattcacaag tttggaggac  96300
ctttttttac ccatgaaaag gtcagaacag aaggggctag gatttaggtg tgactgcagt  96360
ttattgaatt cccatccata ctgctctcgg tgggcagtgg caggggcagg agaggagcct  96420
ggcaaagcat gaagtgactg ctgctgcctc tgctatctgg gacgcctggc cacctgtctg  96480
tacagtctcc ctccagaccc attctcacgc tgtctcttgg cacccagggg ccagtgatgg  96540
ttctcccatt tgttttgtgt atatagcatt tatatcaagg ctatttattt atttatttat  96600
tttatttatt tattttttg agacagagtc tcactctgtc acccaggctg gagtgcagtg  96660
gtgcaatctc ggctcagtgc aagctctgcc tcctgggttc aagcaattct cctgcctcag  96720
cctcctgagt agctgggact acaggtgtgc accaccacac ctggctaatt ttttgtattt  96780
tttattagtg gagacggggt ttcaccttgt tggccaggat ggtcttgatc tcctgacctc  96840
gtgatccgtc cacctcagcc tctcaaagtg ctgggattac aggcatgagt cactgtaccc  96900
ggcctattta tttattttta attgacaaaa ttgtatatat ctgtaatata caacatgatg  96960
tttgaaatat gtgtacattg gccaggcgtg gtggctcaca cctgtaatcc cagcactttg  97020
ggaggctgag gtgggcggat cacgaggtcg ggagttcaag accaaactgg ccagcatggt  97080
gaaatcctgt ctctactaaa aataccacaa aaaaaaaaaa aaaaaaaaaa agccgggcat  97140
ggtggctcgc gccagtcgtc ccagctactt gggaggctga ggcaggagaa ttgcttgaat  97200
ctggcaggtg gaggttgcag tgagctgagt tcatgccact gcactctagc ctgggcgata  97260
gagcgagact ccgtctcaaa aaaaaaaaaa aaagaagaaa tacatatgca ttgtggaatg  97320
gctaattaac ctgtgcatca cctcacgtat cattgttttg tggtgagaac acttaaaatc  97380
tactctttca gtgattttct tgcatatggt acattgctat taactgcagt caccatgcta  97440
tacagtagat ctcttgaact cattcctcct gtctataaat gaaattttgt atccttgacc  97500
aacacattca aggttttttt tgagatggag tcttcttcac ccaggctgga gtaccatggc  97560
acgatctcat ctcactgcaa cctccgcctc ccaggttcaa gcaattctcc tgcctcagcc  97620
tcctgagtag ctgggattac aggcacatgc tactgcacct ggctaatttt tgtattttta  97680
gtagaagtgg agtttcacca tgttggccag gctggtctcg aactcctgac ctcaagtgat  97740
ccgcctgcct tggcctgcca aagtgctggg attacaggtg tgagccactg cacccggcct  97800
```

caagcgtttt aaaagatgct cttttctaag gattgactgt agtacaggag gaagattgac 97860
ctgttgaaaa gcctcagcct ttacaagtgt aaaattatca gtatattact atcatctttc 97920
tgatgaatta aataaactaa ggactccaag tcaaaagtct tcaaactgaa gtagaatagt 97980
tgtatatagt gcttggcact ttaatattta gtatcggttt aatgataatg tttgtgcctt 98040
tgccgtcttt aaaacatttt tacatcatcc ctgtttgatt acttggtgtg ctcatgaagt 98100
tgttggccac taaggaatct taggctcaga gaggttctgg aattggccag tggtccttga 98160
atcagctgct cctatgattc tctaactgat ttctcacaaa gcaaacaagc aatcataaca 98220
aaacaactgt gcacactgct cttcttattt tgttatttaa aaagtactta ggctctactt 98280
atgtttgtta gtcaatttct cattacttct agttaatcaa aaggtcagag gaaatacttg 98340
aatattttca tactagaata ctttaaaaaa tcatgatttc cagtaatctc tttaaaactt 98400
ggcaagttat tttgatctaa aagtttatct tttgtgtgca tatttttaaa gcttctagac 98460
aatctgatac ctcaggtcct gttacaacaa gtaaatcctc atcactgggg agtttctatc 98520
atcttccttc atacctcaaa ctgcatgatg tcctgaaagc tacacacgct aactacaagg 98580
tatgggcctc tgcatctttt aaaaatatat atgcacacat acttacgtct aatggatagt 98640
tgatgttttt cttatgattt gtaggatgta taagcccttt gagatatgag ttacatttag 98700
tttttcaag tttgtttgtc tttcagcttt gtttatgata gcttctatca tacaggtgtt 98760
ttggatttc atattgtttg tactcacagc taagattgat tacagtgaca gagctaggat 98820
gtgcagccag gttatagggg gaagtggccc tggtggagtc tggagggatc cgtgtacagg 98880
cttccttccc tcccgtgagg ctcacacaaa aatacagcaa catgctggtc ctgcaggtac 98940
cctctgccta acatgagcca caattccaga ctcacagaag aaaagcaggt gttcggcata 99000
aaccatgtgt ttcaaatagt ctgggcatgg tgagccactt gttatcagct agggaaagtt 99060
tatgtcagcg taagaaactg ttcaccagat acccccaaga gccagccttt ctgtctaggg 99120
atgttttagt tttttagttc attttttttt ttaactttaa aattttctgt tcatctgcaa 99180
tttgttagat atgaagtatg tgtctaattt aatttttgtt tttggttgtc cccaataatg 99240
tttacagaag aatttttctg cactaattgg cttgagttac ttacattctc atagttctct 99300
agtttcagta gtttcattta ttattttgtt atatcaatct atctgtctgc tcatctatta 99360
gaagcatcct tgtttttttt ttttcttttt tagacagagt cttgctctgt ccccaggttg 99420
gagtgcagtg gtgcaaccat gcctccctgc agtctcaggg ctcaagtgat cctcccacct 99480
cagctcctga gtacctggga ctaccggcat gtgccaccac acccagctaa tttttacatt 99540
ttttgtagag acagggtctc cctaagttgc ctgggctggt ctcaagctcc tggcttaagt 99600
aatcctccct ccttggcctc ccaaagtgct gggattacag gtgtgagcaa ctgcacccgg 99660
ctacaagtat acttcttaat tattgtagct taatggtatt tatgagggga tcagttcccc 99720
tgttgttctt tagaattttc tggatattct tctttattga ttttgggatg tgaacaatag 99780
aatcaacttc tacttgtaga ttgatttagg gagaacttat acctcagatg ttaagtcacc 99840
ctgtccagaa tgtgggatgc tttcctattt gttcagaact ttttaaatta cctcagaagc 99900
acatgaaatt taaaggattt taaaaaaaac ttaaagatta tttcacatag ctcttgcaca 99960
tttcttgata aatgaatcct caggtattcc tctgtttttg ttactaatag ttacttctta 100020
tgggtttttt ttcccctgaa aatcatttat caaacgtatg tggcttattt tctgaaggat 100080
gtttgataat tttggaagat atgaaagtct tcatatttta caaggtttga ggtctcttta 100140
agctgcatgg ttctcatgtc agctcccaaa gcagaagacg gcatgttgaa aaatgccgta 100200
gagaagatac ttcttttcca cctgttttca actcatatca tcttgaattt cagggcacct 100260
ttccatgctc ctagtgcttg ctatctgttt attattttcc ttcctgaata ccctgaactc 100320
cagcatgttc tgctgtaatt ctggcctccc tggcatcttg gactcctgtt tcctttgctc 100380
tgtcatcccc gcggtcagct cctgctgcgc agcttctcag ctgaagtgcg tttggagtgc 100440
ctggcgtgtc ttgctggatc tttgagtatt gcctctggtt tccttggttc cttctgctga 100500
gttgctcagc gtctccactc cccatttctt gtgtggccct tcctgcactc ctctgattcc 100560
ttttgtcttc cctggtttct tgctttggtt tcgagtctcc acagaacttt tgcagctctt 100620
ctgaagacct ggaagctttt tcatcttaat tctcatctca tgacctcttt tcccttcttt 100680
gagagctaga acttcccatg gtgaacttct ctttccagaa ttccatgcct tcttttccct 100740
cccacttacc tgttgtccag gagaggtcag attgctgtgc atattggagg agaacccttt 100800
cttccctggg ctcttcatct cacatgacat caccacatca cctcgttcct tggaccctca 100860
gtggtgtcac tgctggattt ttctttcctt tggctggcct tagggcacac ccaggttgac 100920
tagcgtagtc atggtattta gatccactca cattttcagt ttctgtgtct gtctcttgcc 100980
tgcttctgac ttcgcccaga gaaagcttct ctttcacaag ggttcttaga tttatgttca 101040
ctgagcacct tcttttctga ggcagtgttt taccaatatt tattttccta gtcagtctcg 101100
ccttaccttt cttgttatgc atgtctttgg tcctgaccca ttctctgagt ctgtaaaata 101160
gaattgctgt ataatttaat tacatgaaat cctttagaat cttaacacat cttacacctg 101220
atttaatatt ttattgtatc caaattgaac caaccctatg tgaatttgac agtgatttct 101280
cccagggatc ctagtgtata aggaatagga cttagtattt tctatttttt gatataccac 101340
ataccagata ctgattatga tggacattta acccttttttt ctcattatga aagaaagtta 101400
ggaattattt cttccagtag cgccagtgta acctgaaagc ctttgaaaga gtagtttttg 101460
tatagctatc tgaaaggaat ttctttccaa aatatttttc cagtgctgac aacaaacacg 101520
cagacacacc ctgcaaggtg agtgtacggc gccgcacagt ggaggcatct gctgcagccg 101580
tcgatgtttg tgtctttggt tgtacattat gagatcgtga cagggccagt aaccgtgtgt 101640
tctctccttc accttcccaa ggtcacgctg gatcttcaga acagcacgga aaagtttgga 101700
gggtttctcc gctcagcctt ggatgttctt tctcagatac tagagctggc cacactgcag 101760
gacattggga aggtttgtgt cttgtttttt ctccttgggt tgtggctggc acacttgatg 101820
tgcgtcttct gggctgagtt catctaggat ggagcctggt tctccagggt gcctccggga 101880
gactcctccc tgccccacgt gcttgcgtca caggacccaa gtctgactct gccttagcca 101940
tgaagtttag ggggaagttt ctatttgtat tctatttttg tctgttatca tgtattagct 102000
tagacccagt ttagtttgga aaatcagtgg gtttcaaaat gtgtttgtag agtcctttat 102060
ttcttaactt gaccttttca agtggaaagg ggcaaaacag acgggtaagg gggcggggcg 102120
ggaggtgtga cttgctcttt tgtgcctgag gaagtaacag agctggggtt gacagtcata 102180
ttctctgaca cagatagtct ctgacttatc tcacagaaag tcagcggcag agcctgagtt 102240
aaaagtctcg tagattttct ttttcttttt tttggtggct aatttcagtt ttatttatat 102300
ttgtttattt atttattata ctttaagttc tgggttacat gtgcagaatg tgcagttttg 102360
ttacataggt atacacgtgc catgatggtt tgctgcaccc atcaacccat cacctacatt 102420
aggtatttct cctaatgtta tccctccccc agtcccctca ctccccatgg gccccggtgt 102480
gtgatgttct cctccctgtg cccatgtgtt ctcattgttc aatttccact tgtgagtgag 102540

-continued aacatgcggt gtttggtttt ctgatcttgt gatagtttgc tgagaatgat ggtttccagc 102600
atcatccatg tgcctgcaaa ggacatgaac tcatcctttt ttatggctgt atagtattcc 102660
atggtgtata tgtgccacat tttcttaatc cagtctatca ttgatggaca ttcgggttgg 102720
ttccaagtct ttgctattgt gactagtgcc acaataaaca tacatgtgca tgtgtcttta 102780
tcgtagaatg atttataatc ctttgggtat atgcccagta atgggattgc tgggtcaaat 102840
ggtatttcta gttctagacc tttgaggaat cgccagactg tcttccacaa tagttgaact 102900
aatttacact cccaccaaca gtgtaaaagt gttcctattt ttccacaacc tctccagcat 102960
ctgttgtttc gtgacttttt aacgatcgcc atcctaactg gcgtgagatg gtatctcatt 103020
gtgattttga tctgcatttc tctaatgacc agtggtgatg agcatttttt cgtatgtctg 103080
ttggctgcat aaatgtcttc ttttgcgaag tgtctgttca tatcctttgt ccattttttg 103140
atggggttgt ttgctttttt ttcgtaaatt tgtttaagtt ctttgtagat tctggatgtt 103200
aatcttttgt cagatgggta gattgcaaaa attttatccc attctgtagg ttgcctgttc 103260
actctgatga tagtttcttt tgctatgcag aagctcttta gtttaattag atcccgtttg 103320
tcaattttgg cttttgttgc cattgctttt ggtgttttag acatgaagtc tttgcctatg 103380
cctatgtcct gaatgttatg gcccaggttt tcttctagga tttttatggt cctaggtctt 103440
atgtttaagt ctttgatcca tcttgagttg atttttgtgt aaggtataag gaaggggtcc 103500
agtttcagtt ttctgcatgt ggctagccag ttttcccaac accatttatt aaatagggaa 103560
tcttttcccc attgcttatg tgtgtcaggt ttgtcaaaga tcagatgatt gtagatgtgt 103620
ggtggtattt ctgaggcctc tgttctgttc cattggtcta tatatctgtt ttggtaccag 103680
taccatgcag ttttggttac tgtagtgttg tagtatagtt tgaagtcagg tagtgtgatg 103740
cctccagctt tgttcttcta gcccaggatt gtcttggcta tgcaggctct tttttggttc 103800
catatgaagt ttaaaatagt tttttccaat tctgtgaaga aagtcagtga tagcttgatg 103860
gggggatagc attgaatcta taaattactt tgggcagcaa ggccattttc acgatattga 103920
ttcgtcctat ccatgaacat ggaatgtttt tctatttgtt tgtgtcctct cttatttcct 103980
tgagcagtgg tttgtagttc tccttgaaga ggtccttcac atcccttgta agttgtcttc 104040
ctaggtgttt cattccctta gtagcatttg tgaatgggag ttcactcatg atttggctct 104100
ctgtttgtct gttattggtg tataggaatg cttgtgattt ttgcacattg attttgtatc 104160
ctgagacttt gctgaagttg ctaatcagct taaggagatt ttgagctgaa ccaatagggt 104220
tttctaaata tacaatcatg tcatctgcaa acagggacag ttttacttcc tctcttccta 104280
tttgaatacc ctttattgct ttctcttgcc tgattgcgct ggccagaact tccaatacta 104340
tgttgaatag gagtggtgag agagggcatc cttgtcttgt gccggttttc gaagggaatg 104400
cttccagttt ttgcccattc agtatgatat tagctgtggg tttgtcataa atagctctta 104460
ctatgttgag atacgttcca tcgataccta gtttattgag agtttttagc atgaaaggct 104520
gttgaatttt gtcaaaggcc ttttctgcat ctgttgagat aatcatatgg tttttgttgt 104580
tggttctgtt tatgtgatgg attacgttta ttgatttgcg tatgttgaac cagccttgca 104640
ttccagggat gaagctgact tgattgtggt ggataagctt tttgatgtgc tgctggattc 104700
agtttgccag tattttattg aggattttca catcgatgtt catcagggat attggcctaa 104760
aattctcttt ttttgttgtg tctctgccag gctttggtat caggatgatg ctggcctcat 104820
aaaatgagtt agggaggatt ctctcttttt ctattgattg gaatagtttc agaaggaatg 104880
gtaccatctc ctctttgtac ctctggtaga attcggctgt gaatccatcc tggacttttt 104940
ttggttagta ggctattaac tattgcctca agtttagaac ctgttatcag tctattcaga 105000
gattcagctt ttttctggtt tagtcttggg agggtgtatg tgtccaggaa tttatccatt 105060
tcttctagat tttctagttt atttgggtag agatgtttat agtattctct gatggtagtt 105120
tgtatttctg tgggatcggt ggtgatatcc cctttatcgt ttttattgag tctatttgat 105180
tcttctctct tttcttcttt attagtcttg ctagcggtct acctatttta ttgatctttt 105240
caaaaaacca gcacctggat tcattgattt tttttggagg gttttttttc gtgtctctat 105300
ctccttcagt tctgctctga tcttagttat tttttgtctt ctgctagctt ttgaatttgt 105360
ttgctcttgc ttttctagtt cttttaattg tgatgttagg gtgttaattt tagatctttt 105420
ctgctttctc ttgtgggcat ttagtgctat aaatttccct ctacacactg ctttaaatgt 105480
gtcccagaga ttctggtatg ttgtgtcttc gttctcattg gtttccaaga aaatttttat 105540
ttctgccttc atttcgttat ttacccagta gtcattcaag agcaggttgt tcagtttcca 105600
tgtagttgtg tggttttgag tgagattctc aatcctgagt tctaatttga ttgcactgtg 105660
gtctgacaga cagtttgttg tgatttctgt tcttttacat ttgctgagga gtgttttact 105720
tccaactatg tggtcagttt tagaataagt gcaatgtggt gctgagaaga atgtatgttc 105780
tgttgatttg gggtgcagag ttctgtagat gtctattagg tccgcttggt ccagtgctga 105840
gttcaagtcc tggatatcct tgttaatttt ctggctcatt gatctgccta atattgacag 105900
tggggtgtta aagtctccca ctattaccgg gtgggagtct ctttgtaggt ctctaagaac 105960
ttgcttcatg aatctgggtg ctcctgtatt gggggcgtgt atatttagga tagttagctc 106020
ttcttgttga attgatccct ttaccattat gtaatggcct tctttgtctc ctttgaactt 106080
tgttgattta aagtctgttt tatcagagac taggattgca atccctgctt tttttttgct 106140
ttccatttgc ttgttagatc ttcctccatc cctttatttt gagccaatga gtgtctttgc 106200
atgtgagatg ggtctcctga atacagcaca ccaatgggtc ttgactcttt atccaatttg 106260
ccagtctgtg tcttttaatt ggggcattta gcccatttac atttaaggtt aatattgcta 106320
tgtgtgaatt tgatcctgtc attatgatcc tagttggtta ttttgcccgt taactgatgc 106380
agtttcttca tagcgtcagt agtctttaca atttggcatg tttttgcagt ggctggtact 106440
ggttgttcct ttccatgttt agtgcttcct tcaggagctc ttgtaaggca ggcctggtgg 106500
tgacaaaatc tctgcatttg cttgtctgta aaggatttta tttctcgttc acttatgaag 106560
cttagtttgg ctggatatga aattctgggt tgaaaatact ttttttaaag aatgttgaat 106620
attggctccc actcttttct ggcttgtagg atttctgcag agagatctgc tgttagtctg 106680
atgggcttcc ctttgtgggt aacccgacct ttctctctgg ctgccctttc cttcatttca 106740
atcttggtgg atctgatgat tatgtgtctt ggggttgctc ttctcgagga gtatctttgt 106800
ggtgttctct gtatttcctg aatttgaatg ttggtctgcc ttgctaggtt ggggaagttc 106860
tcctggataa tatcctgaag agtgttttct aacttggttc tattctcccc atcactttca 106920
ggtacaccaa tcaaacgtag atttggtctt ttcacatagt cccatatttc ttggaggctt 106980
ggttcatttc ttttcactct tttttctcta atcttgtctt ctcgctttat ttcattaatt 107040
tgatcttcaa tcactgatat cctttcttct gcttgattga atcggctgtc gaagcttgtg 107100
tatacttcac aaaattctcg ttctgtggtt tttagctcca tcaggtcatt taagctcttc 107160
tctacactgg ttattctagc cattagtcta acattttttt caaggttttt agcttccttg 107220
tgatgggtta gaacatgctc ctttagctcg gagaagtttg ttattaccga ccttctgaag 107280
cctacttctg tcaattcatc aaactcattc tccatccagt tttgttccct tgctggtgag 107340
gagttgtgat cctttggagg agaagaggtg ttctggtttt tggaattttc agcctttctg 107400
ctatggtttc tccccatcat tgtggtttta tctacctttg gtctttgatg ttggtgacct 107460
acggatgggg ttttggtgtg ggtgtccttt ttgttgatgt tgatgctatt cctttctgtt 107520
tgttagtttt ccttctaaca gacaggcccc tcagctgcag gtctgttgga gtttgctgga 107580
ggtccactcc aggccctgtt tgcctgggca tcaccagcag aggctgcaga acagcaaata 107640
ttgctgcctg atccttcctc tggaaacatc gtcccagagc acgaaggtgt ctgcctgtat 107700
gaggtgtttg ttggccccta ctgggaggtg tctcccagtc aggctacatg gggtcaggg 107760
acccacttga ggcagtctgt tcattatcgg agcttgaatg ccgtaccggg agaaccactg 107820
ctctcttcag agctgtcagg cacgtatgtt taaatctgga gaagctgtct gctgcctttt 107880
gttcagatgt gcccttcccc cagaggtgga atctagagag gcagtaggcc ttgctgagct 107940
gcagtgggct ctgcccagtt cgagcttccc tgctgctttg tttacactgt gagcatagaa 108000
ccacctactc tagcctcagc agtggtggac acccctcccc cagccaagct cctgcatccc 108060
aggtcgattt cagagtgctg cgctagcagt gagcaaggcc ccatgggcgt gggacccgct 108120
gagccaggca caggagagaa tctcctggtc tgctggttgt gaagactgtg ggaaaagtgc 108180
agtatttggg caggagtgta ctgctccttc aggtacagtc actcatggct tcctttggct 108240
tggaaaggga agtcccccga ccccttgtgc ttcccaggtg aggcaacacc ccgccctgct 108300
tcggcttgcc ctccgtgggc tgcacccact gtccagcaag tcccagtgag atgaactagg 108360
tacctcagtt ggaaatgcag aaatcacctg tcttctgtgt cgatctcact gggagctgta 108420
gactggagct gttcctattc ggccattttg gaagcatccc ttgtttttttg aggtggagtc 108480
ttgctctgtc gcccaggctg acgtgcatcg gcacaatctc ggcccactgc aacctttgcc 108540
tcctggtttc aagcgattct cctacctcag cctccggagt agctgggatt acaggcacct 108600
gccaccatgc ctggctaatt ttttgtattt ttagtggaga tggggtttca ccacattggc 108660
caggctagtc tcgaactcct gaccttgtga tccacccacc tcagcctcct agagtgctgg 108720
gatcacaggt gtcagccacc acgcccagcc atattttcag atctccctct ctttgcccta 108780
aaccactgtg cttaataagt agtttttagt ggccagcagt ctccatgtat aacacatttt 108840
agcaaaatgg aaaatactat atgttttaaa tttgaacgtg agattatact gaaataaaaa 108900
tcatctaact gggattcttt aaatagtaag attttctttt ttgtatgtgg gttttttttt 108960
aaccttatta ttatgactgt catatataga aatggctgtt tttcagttac agtcagtgaa 109020
tgtatcaaat gctgccttat ccaaataata aaagtaaatt attaataagt cacaatttaa 109080
tgaagattga tgttagttga tctttatatt cttgaaatca gccatatggt tgtgtgtgta 109140
tgtatatatt tttaaaggta cataaagata ataagctcat ctctgaaaat ttttacattt 109200
ggcataagaa taactggata attaagcatc ttattctctg gcctgtgtct ttacagttaa 109260
aggtagattt actcacctct cctttttttgt ttttctaagt tcatcttttt tgctgtttca 109320
agacagaggc ccattttagc tttctcgcat atccttttgt ttgtactttg gaagcctcac 109380
ctgcttaatt gttgagtttt tatccgtggt cttttagagg gggatatgta gggtagaagc 109440
tttcacaggt tcttgtttgc acttggcccc tgactgtttt gaggaatctc cctcactgac 109500
tcacagcatg gcaaggtttc agatctcttt ctgccacaca gcagttctga ggcagctgga 109560
aagatatcca gatgcttaga ttgtcaggcc aggcttgaga tatacaaact attgagcctt 109620
atctgtgacc ttgcttaggt gaaggcatca gagcccctgc accaacatgc ataggcctct 109680
gcatgtgtgc ggggctgggt gttgaggtct gagcacaagt gtagctggag aggtgagctt 109740
gatgtggcga cgggtatgag caggttttct tcagacttct gtgagtttac ctagttccag 109800
gatttaaagg cacagagact ttagaattaa aatagaatca ttttcttttt ctaaatagca 109860
acactaggaa taaaaaataa taattccaca ttcttgacag gtaatgtttt ttcttgtctt 109920
ctaatcctta tttattccat actcattttt atacataatt gaaatgtatt atgcattgga 109980
tttttctttt gcattatatt atagacgatt tttcatgtaa ctccttactg ttccatttta 110040
tatgttttgt ctggtttaag actttatctg caaaccggga aactgtctct acaaaaagaa 110100
aaacaaaaat agttggccgc agtggcatgc gtctgtggtc ccagctactc ggggctgagg 110160
tgggaggatt gcttgagcct tgggaggttg aggctgcaaa gagccatgat catgccattg 110220
cactccagca tgggtgacag actttatact gtctgttttg ggtgatttga taatgatatg 110280
ccctgatgta gtttttttat atcttgtgtt tcttgtgcct gggtttattg aggttgggtc 110340
tgtggcttca tagtattttt aaagtttgga aaattttagg ccattctttc tttctttctt 110400
tctttttttt tttttgaga cagtgtctcg ctctgtcgcc tgcgttggag tgcagtgaca 110460
ctatcttggc tcactgcaag ctctgcctcc tgggttcacg ccattctcct gcctcagcct 110520
cctgagtagc tgggactaca ggcgcctgcc accacgcctg gctaattttt tgtattttta 110580
gtagagacga ggtttcactg tgttagccag gatggtctca atctcctgac ctcgtgatct 110640
gcccgcctgg gcctcccaaa gtgctgggat tacaggcgtg agccactgca cccagctagg 110700
ccattatttc ttcaaagatt ttttttctgc cctgcctccc tcctttttc cctctcttaa 110760 aggggctgtg atttcctgaa tgattgctta gtgttgtccc atagcttact gatgctcttt 110820
tcagtgtttg attgttttat gtgttttctg ttttgtatag tttctattat tgtgttttca 110880
agttctctga tcttttcttc tacagtgtct actctgttgt taatctgtta atctgttgtt 110940
aatcctgtcc agcgtatttt tttttttgtt tttgaaacag tctcactctg ttgcccaggc 111000
tggagtttag tggtgcgata tcagctcact gcaacctcca cctcccaggc tcaagcaatt 111060
cttctgcctc agcctcccga gtagctggga ctataggcac gtgccaccac acctggctaa 111120
tttgtgtatt tttattagag atggggtttc accatgttgg ccaaactggc cttgaactcc 111180
tgacctcagg tgattcatcc gcctcggtct cccaaagtgt tgggattata ggcatgagcc 111240
accgtgtctg gcccctgttc agtgtatatc actaattttg tttttatctc tagaagtttg 111300
atttaggtct tttaaaaatg tctccctgtg tttctgttta gctttgtgaa cacaattgta 111360
ataactgttt taatatcctt ctctgctagt tctaagatct tctaataact tcccagttct 111420
tggtgtttct cattggttga ttgatactcc tcgttttggg ttgtattttc ctgcctcttt 111480
gtatggctgc caattttttta ttggatgccc aaccttgtga attttacttt gttggatgct 111540
atatattttt gtgttcccat agatcttctt gagctttgtt ctgaggttag ttgagttaca 111600
tatagatggt ttactctttt gggtcttgct ttataatttg tcagatgggt tggagcagtg 111660
cttagtttag gactaatttt ttttttggac taattattcc tctttaggaa taattaggta 111720
ccatgcttag gaggcaagac catcctgagt actctaccta atgaaccaga aagtttgggt 111780
tttccagtcc gcctgctgag aacagtgact ttctagccct gtgtgagcgc tgagctctgc 111840
tccttctaat cctttccaat gcttctttcc ctggcctcag ggagttttct cacacacata 111900
tctctgctga gtactcgaga gggaccttcc ccagatctcc agagctctct ctgtcttgtt 111960
ttctcttctc tggtgctctg tcttatgaac tgtggctgtc ttggtctcct tagattctca 112020
gcacctcttc aattcagagg gttgcctgtc cctcctcctt gtgccacagc ctaggaactc 112080
tctcaaagca gcgagttggg gcagccatag ggctgactta gtctctcgtc tcccagggat 112140
cactgtcctt cattgctcat gtccagtgtc ttgaggactc tgggttttgt ctgttttgtt 112200
ttttggtttg ctttggttgt ctcaggcagg agggtaaacc cagtccctca ccctcattgt 112260
gctcagtagt ggaagtctca ctctattaca ttagatatta gtatttgtag cagagccctg 112320
gttccctggt acttggggag ctcttgaaag gccagaaaca gcatgctttc tcaccttttc 112380
cagggcttca gtttctggtg cacatcaagc attccataca catttgttaa agtcctttgt 112440
tagacaagta gtgattcaca ggttctattt gtaatttttt cagttaacat gtattgggta 112500
tctgctggga gctagtaaaa acaaaaagtg gtgtgtgaca aattcaattc tgacaagaac 112560
aaccttaaac acttagaata tactttgagc atatcagaat tttaaaaatg tgtggccctt 112620
gagtatttga aaccaacaag aatctattgc ttattagtag aggatatttt gttaaacaag 112680
tggagagaga ggcatttttca gtctaattgg tgttggcttt tagcagctga tggaaaccag 112740
ttcgtgatta gccaggcagt ggtgaaacag gctgtgcatt ctgaatgcct aggtatctag 112800
gcattcagaa tggtggcgct ctttgagtta gcatcttctt ctttcttgat tctttttttt 112860
tttttttga gatggacttt cgctcttgtt gcccaggtaa caactccagt gcaatggcgc 112920
catctcggct cactgtaacc tctgcctccc tggttcaagc gattctcctg cctcagcctc 112980
tcaagtagct gggattacag gtgtgcgcca ccacgcctgg ctaattttgt atttttggta 113040
gagatggggt ttcactatat tggtcaggct ggtcttgaac tcctgacctc aagtgatgca 113100
cctgcctcga tctcccaaaa tgctgggatt acaggcgtga gccaccactc ccagcccctt 113160
cttgattctt gaaaaggaca ttgggtgctg tacatctcgt tatagatgtt gataaaaatg 113220
cttgtgagaa gagtaacatt aaggtagtta tttggtcatt tttgcagatt attttaagac 113280
aattctagga ctgatttgtg gtaaatcaca cattgctgta tcatagttgt gttcactgaa 113340
catattcagg ggctctacag atgcagggct cttagctgct ttgcacactt ctgaattcct 113400
gccctgcgaa caggactgga tacctaatag acaacaggta cttgataaca gtttattgaa 113460
ttaatgagtg aatgaacaga tacataaatg catgaaagaa tggttgtaat gtatataact 113520
tggatttcaa gactttttac tgactgttca aaataagaaa ttgaaaactt tcctctgatt 113580
ttcctctact atttacacaa tttaaatgga agttatcttg taccttcaat ttctgtctag 113640
gattcgtaca ataacgggtc atctctgagt cgcttaatgt ctcacttgtc tttctacagt 113700
gtgttgaaga gatcctagga tacctgaaat cctgctttag tcgagaacca atgatggcaa 113760
ctgtttgtgt tcaacaagta agagcttcat tcttttcctc ttctgttaag acgttcgggt 113820
atgacagcaa aacgctgcta ctccttaaga ggcaggcgct gttggcataa tcagctggga 113880
ggattgtggg gtccagcgca gcactttttg gctcagtcca tgattgagcc aagaggccat 113940
ccttcccttc actccccagg aggacgaggt ctgtcactgt ggagggcaga ggacaccaga 114000
agctcctctg caacctcgct agttaacttc cagtccctcg gagtttctgt ttagaatgct 114060
caatctcatt tagaattgca aggaaaccca aaacgcctat ttaaggtaca aacagcactt 114120
catacaatat ctcatgaggt attaatagtg attcacagga agaatttcac gctgtgagtc 114180
tttgctaaca tatccagtta tttacagatg gatttgatat ttgtgtggga gattcttaaa 114240
agtgttgttc acgccacatt gttgatgcct cattttttc actgtagttg ttgaagactc 114300
tctttggcac aaacttggcc tcccagtttg atggcttatc ttccaacccc agcaagtcac 114360
aaggccgagc acagcgcctt ggctcctcca gtgtgaggcc aggcttgtac cactactgct 114420
tcatggcccc gtacacccac ttcacccagg ccctcgctga cgccagcctg aggaacatgg 114480
tgcaggcgga gcaggagaac gacacctcgg ggtaacagtt gtggcaagaa tgctgtcgtt 114540
ggtggaagca cgaaagagca agcaggaaat actttgtaaa agaataaaaa cgaaaaatgt 114600
tagcgaacat cttctaatag tctgctgtat tcagagaact ctaggagata tatatggttg 114660
atgcaaagat gatttaaggc atagcccggc cttccaagaa gtgtgtggcc agtgagtgag 114720
atgggcttgg gacttacaca tctcagaggt gggggtagag gaggaggaac actgagtggg 114780
ctgagaagca gccagctctc attgccaaag tgtgtcagca aaccagaatg cagttcataa 114840
tgtccccacc cattcaaagc acaggacctg tagagtggtg tggcatgtgt tggtggcact 114900
tttcaggcct gtaacaagga tgaaagaaca gcttcatagc agcacagtag tgctggtgtt 114960
cagaggtgtg tgaaggccat agaagcatct tggatatatt accttgtgtt ttgtcagctt 115020
tatgactaga agtctctttt cacttaaatt tgtttttttt tttttgagga cggagtcttg 115080
ctctgtcgcc caggctggag tgcagtggtg caatctcagc tcactgcaag ctctgcatcc 115140
tgggttcatg ccattctcct gcctcagcct cccgagtagc tgggactaca ggcgcctgcc 115200
atcacgcctg gctaactttt ttttgtattt ttagtagaga cggggtttca ccatgttagc 115260
caggatggtc tcgatctcct gacctcgtga tctgcccgtc ccggcctccc aaagtgctgg 115320
gattacaggc gtgagccacc gcgcccggcc tcttttcact taaatttatg tttgtgtttt 115380
taatgcctag tatacaggac ttcttaaatt gccttaagta tgaacaggta tttgagttgc 115440
taatctgtat agtagcaata atagaatccc ttgtttttcc ttttataaat ttagcgatta 115500
aatagctaca attaaaacac tagagtcagg agtcaaggaa aatacccatg ttccaggctg 115560
tatgttagtg atgtacttac tatatattgg agtttcagga gtaagtctgt ttcaatgctt 115620
tctgtaacca tttggggtat taataagcat gtgagtgtgt gcatgtttgg gttaatttca 115680
tatatgtttc ttagaaggga tatcattgat gtaaatattt taaaggcttg tcctccaaaa 115740
aaatcatgta atttcttcta aattactgat cttttaaatg accttcacct ttctctcaaa 115800
tctcacttaa gactgggctg agtagtcagt ttcctgtagc agaaaaaagc tcagacttga 115860
gtagccttct gcgagtgagg agacttgatg gctgtcaggc agctgtaaac tctaaataga 115920
gtgtcattat ctgaagaggg cgatgctgcc acactgagtg gcctttcaag ttgtttctca 115980
atctgacacg ttctgatcgt gtgaatgtga aattggtttg agcaggagta tatctgagtg 116040
cagaggagat tatttaaaga tattctcatt ctctgcttcc cttttattcc catttggcag 116100
atggtttgat gtcctccaga aagtgtctac ccagttgaag acaaacctca cgagtgtcac 116160
aaagaaccgt gcagataagg taaatggtgc cgtttgtggc atgtgaactc aggcgtgtca 116220
gtgctagaga ggaaactgga gctgagactt tccaggtatt ttgcttgaag cttttagttg 116280
aaggcttact tatggattct ttctttcttt ttttcttttt tatagaatgc tattcataat 116340
cacattcgtt tgtttgaacc tcttgttata aaagctttaa aacagtacac gactacaaca 116400
tgtgtgcagt tacagaagca ggttttagat ttgctggcgc agctggttca gttacgggtt 116460
aattactgtc ttctggattc agatcaggtt tgtcactttt atctttcatc catcatacct 116520
gttcctaatt tagtacaaat taccctaaaa gacactgaaa tctactttaa agaaatgtgg 116580
tctgcatgtt tccctcatca gttgctgctg cttatctttt tcatgcacct agctggtgca 116640
gaaggcctgg ggcatagcca gcctcagcaa gtcagcatcc ttgccccagc tccctggact 116700
caaggctaac ctggggttgg ctgttaggga tttccaaagg tttgtcccat ccacttgcct 116760
cccctccaaa ataagtttga atttaaattg tgagatacaa ttaagattta ttgtttgggg 116820
aacatttttg caaaatctag agttagttta aacagattat caattattac cataattgat 116880
catctgcagt ttcaagctat ctaacaggtt cacttacctc tttaaaaagg aatggaattt 116940
agcaggacag taactgagac ccgtgctcct ggagtccatg tgggagctgt gtggctctgc 117000
acaagcattt gcacgcttcc cctcttgact gcattacctt cctcctatag ttgctgtggg 117060
caccagattc tggctagtcc tgtcccttca tgatgcacat tttcctcaag attcgtccca 117120
gttaaatcac tgcagatgaa actgcctttt catcgtcaaa atttaactgt catttttgag 117180
ccgtgatctt gggctacttt cttatgtggg gtaggaatat ttgtgagtta gaaatattac 117240
acttctctat ttccttctag acgtaaatct gttaatcctg tcagcactgt tactcacctg 117300
aaagggtctg tttccctagg agaactgagg gcactcggtc aacactgatt ttccacagtg 117360
ggtattgggg tggtatctgc ttgttttttt tgttgttgtt gtttgttttt ttttgttttt 117420
tttttgagat ggagtctcgc tctgtcaccc aggctggagt gcaggggtgc gatctcggct 117480
cactgccagc tccgcctcag aggttcacgc cattctcctg cctcagcctc ccgagtagct 117540
gggactacag gcacccacca ctacgccagg ctaatttttt gtatttttag tagagacgag 117600
gtttcactgt gttagccagg atggtctcca tctcctgacc tcgtgatctg cccgcctcgg 117660
cctcccaaag tgctgggatg acaggcgtga gccaccgcgc ccggcctggg gtctgctttt 117720
aatgaaggag gcatcaaggg gtgggctttg cgttggcctg atgctttcat ctttctttca 117780
caaaacctgt ccgaagaaaa tccgtctaaa tgggccattg ctctcctcag gaaatagtca 117840
ttgggaactt cttttccttt cctttgacac taggaggctg actggggaga agccctggtc 117900
tatggctgtg ggcagcaggg gctgagagga gcaggctctc agggggcac gggtacccca 117960
agggaagcca gagccctgat ttgttccatt ctagtaagaa caaagactgc tctggtttca 118020
tgtttgttct gattgccttt catcaaccgg tcccctttct cccagttctt aagattcagt 118080
acagtgacag ttttatgaac aagaatagaa cactagaaca gacaaaccat tgaactctat 118140
gctgataaag atttattgag ctcctgctgt atgtttgcat tctgcccaga ggctctgaga 118200
aaaccaggcc atatgctcca tgctttatcc atggaagctc cccgtcaggt tgggaaagct 118260
gacagctgca gggaatacag tgtgacacaa aactggctcc catgcagccc ttacgtgtcg 118320
cctctcagat ggttggggga cgaaggtcga ctcctttggg tatcttatta ctaaaccagt 118380
ttcagggaat ctgtgccacc ctatctgcca ttaacgtgaa cagatgagtc cccaaggtgt 118440
aattttgggt attgtctgat gtctcttgga atttattatt tgtttttcca atgagatttc 118500
acctcagggt atagtaaagt tgttgagggg attcctggat gtgttctgca attatctagg 118560
ctgatttcag aatagagtta tgcttatagt caaatttatc agctgtcaag aattttattt 118620
aaaatttatg cagataagca ggaggaaaag aagcctggtt tttacatttt aatcctatta 118680
ttgatgtgaa attttatttt ccttcctgta ggtgtttatt ggctttgtat tgaaacagtt 118740
tgaatacatt gaagtgggcc agttcaggta atagcatttt attattttag attttttttct 118800
tcttcttgtg tacttacatg taatttaggt tattaagtga atgtttaaac tactgttagg 118860
catttttgct gttttcttta aatggaaatc tgactaacat actgtgcatt tttgcttctc 118920
ttaaaaatta atgtatatct caagacttgt ttggaagtag ttatgtatct gaaaattcca 118980
tatgttgtca gtattcattg cacatttcaa agcatttaat tgtgttgaca gatggtggaa 119040
tgaaatcttg tggtggagca ctagttttta aatcttctta gagaaagcag ttttatataa 119100
tgttgtcttt agtaattatt atgcatttgt attctctgca gctttttctt gctagatgtt 119160
gaggttttaa tacttcttgc tagtccatta caggtttata attattaaaa gttaaaattc 119220
ttttagtacc taaaatgctt aataaacatt gtaattagga aaatttagtg cagaaggaaa 119280
gtgttcccag attccctggg gtctggaaac atagtgttta ttctaattac atgacacctc 119340
cactgtgttt tggggcaagt tactgtttct cttttgagtt tcaatttctt caagagcaaa 119400
gaggcagagg agagctagga agatcgtagc tgctgtgccc ctgtgccgtc gggtgccttc 119460
tacctgctgc ctccgaacct ttacacatgt ccctgctctg cgcgagggca cagatgggat 119520
gcactgtggc aggggtgggg ttagagtaga tcacggacac ctgttagctt gatgtgtgct 119580
tgctgtcaag gttgaatcat gaattatttt atgttgctta tattgatatg tatcttaatt 119640
ttaaaagaaa ggtctaaatg gatgtttttg tttttaggga atcagaggca atcattccaa 119700
acatcttttt cttcttggta ttactatctt atgaacgcta tcattcaaaa cagatcattg 119760
gaattcctaa aatcattcag ctctgtgatg gcatcatggc cagtggaagg aaggctgtga 119820
cacatggtaa cgggacacac ctttcactgt cgtcttcggt gtcgtgatgt gcttggcagt 119880
gttcgttttc atatacccac tttgaacgtt gtcagtggca gccatgtgct tctcaggctc 119940
tgcatgtgtg tctgtgtatg tgaaggtact ggttagagac gtttcaaaag agaagagagc 120000
atattcttta ctctcagcaa tttgtaatct tctcagggaa aaaaattcaa gaaacagtaa 120060
gataacctaa ggtacagata gattctgaat ataaagttcc tgttcattca catgaaacgc 120120
taaaagttct tcacttgatc ttagccaaaa ggccaagaag cgatgcaaca ctaaaaattc 120180
ttaaatcgaa cttgccgtga attaaatttt gatctctcat ccagtggtat tggagatata 120240
gtttgacttg ggttcagggc tttctgtttt gcctgatgat tttgctggag cttaaataag 120300
gaacccagga gatggccagc tgtgcaagcc cccagcctgt ggaaggagct agtgtggttt 120360
tatgaatgag ttgcaaatct ttctttgagc tttttgaact gatcttccag cattgcccta 120420
ttgacccctc cctgactcct ttgctggaat ctgtaggctt ttgaactttg acagggacac 120480
atcctaagac ccttgcaaac tcccagatgt gagaatggca ctactactta gagtcttttc 120540
gactcagcgt gtgtgcagaa gagcatcaac cgggctgtgt tgcgaggcag ggccttggct 120600
gacctctcag tgtttacata gctaagccag ttagtgtttg ccacggcctc acaagggctt 120660
cagattcaca cagccaaagt atagattatt aaaggcatag gtgtttggtt tcctggactt 120720
ggagggtctt tggacagaaa atcagtaggc aaccacaccc agtactttgt gctgggaagc 120780
ttggtcatct gtgagagggt cagagagtat acccatgcgt gcatgccacc gaagggtcag 120840
tgagtattcc tgtgtgtgca tgtctcaggg ccggagagag tatgtgtcac tgagaggtca 120900
gagtgtttgt gtgtgtgtca aagagggttg cattgtgccc ttcactgagg ggtcagaggg 120960
tgcctcgcgt gtgtgtgtgt gtacgtgtgt gtgtgtcact gaggggtcag agtgtgcctg 121020
tgtgtgtgct tgtgtgtgcg tacatgtcac tgaggggtca gagtgtgcct ctgtgtgtgt 121080
gctcatgtgt gtgcatacgt gtcactgagg ggtcagagtg tgcctctgtg tgtgctcatt 121140
tgtgagcgta tgtgtcactg agggggtcag agtgtgcctc tgtgtgtgtg ctcatgtgtg 121200
agcgtatgtg tcactgaggg ggtcagagtg tgcctctgtg tgtgtgctca tgtgtgagcg 121260
tatgtgtcac tgaggggtca gtgttcctat gtgctcatga cattgagggt cagagtgtgc 121320
ctgtgtgcca atgaaaggca tttcttatat ttttttatat gtggtcatag tagaccagtt 121380
aatttatttt gactcctgtg ttagaccaaa ataagacttg gggaaaagtc ccttatctat 121440
ctaatgacag agtgagttta cttaaaaaag cataataatc cagtggcttt gactaaatgt 121500
attatgtgga agtctttatt gtcttttcag atgaatcaag tagattattc ttgagaccag 121560
gaatgttgct gttttggtta tttggaaagt tttatcattt tcaaattgac ttttgaattt 121620
gagtcacctt ttttcagaag tggtgttaaa ttataggagc cctaggtttt ttttcttttt 121680
ttagaagtca tcacaaaatg atcagtgttc agaggaagag ctttgacctt ccacatggta 121740
taatgattga taaccttaat tcatctctta ccataaacca agtatgtgta agggttttct 121800
ttatttcttg aaagcatttt gtagatgttg agagcagttt tccaaatgta atttccatga 121860
aatgcctgat aagggtaccc ttttgtcccc acagccatac cggctctgca gcccatagtc 121920
cacgacctct ttgtattaag aggaacaaat aaagctgatg caggaaaaga gcttgaaacc 121980
caaaaagagg tggtggtgtc aatgttactg agactcatcc agtaccatca ggtaagagga 122040
atgtatgttg gaactgtcgt ggatacttta ttgacccgtg cagatggaag gaagtgccat 122100
gtggtaacgc tcactgttaa ctgtgttact ttgaaccagg tttgggcttt ctggggcctg 122160
ggtagatgcc ggtgcagggg gatggggagg gaggcggggg gtggggggt gtggtggagt 122220 tggggaggtg cagtggcagg aggtgttgtt ggtgtgtatc cttttttttt ttttgagatg 122280
gagtctctct ccgtcgccca ggctggagtg tggtggcacg atcttggctc attgcaagct 122340
ccacctcccg ggtttaagca attctcctgc ctccacctcc cgagtagctg ggattacagg 122400
catgcaccac catgcccagc aaattttttt ttttgtattt ttagtagaga tggggtttca 122460
ccatgatggc caagctgttt cgaactcctg acctcaagtg atcctcctgc cttggcctcc 122520
caaagtgcta ggattacagg cgtgagccac catgcccagc ctggtgttta tctttaaagt 122580
gggcacagcc acaggagttc acctgactcc tggtctgaga gtcacgagat cgttcaagat 122640
agtgaggccc tcttttccaa aacgaggacc aaaaatcaat tgacagtgtt ggtcaagatg 122700
gtagaaacct taaaatgata gaaatctcaa ctctgaaata aaaactttat ttgtatattt 122760
atttaccact attttgacat agggctaagg tctttttctt tgagctgatt tctggttttg 122820
ttttcttaaa gtggcataag aattcaaaga cattttgagg aaggctgagt gcagaaatct 122880
ctctttttaa atgacttctc ctttctttta acttgcactg ttgtctagcc ctcacttatt 122940
ttgtcaattc tttttagctg tttgtctttg aatcttcata aagccatagc ttttctcata 123000
agaagcagca ctttctttgt tcattcatat tttaatgaac ccctgtagta tttaattaaa 123060
tacttaatgc ctaattaaat cacataattg caatgcaaaa gtacatgtat cataaagagg 123120
tctgaaaatg agcaactggc aagcaggtgg tggcaggcag agctgcttgg gtgggtgggt 123180
gtcatggaga ggagttcatc agccacatgt tcagtgagct ctggatatgt ctgtttagaa 123240
atgatcacta ataaacttgt gctcaaccat gtatacctct gggaagcagg tgctcttcag 123300
tagattgcct ctgcagagaa cacagaattg aagtgaatgt ccacaaaggc aatgagccac 123360
ctgcagaata gtttagtcaa ggctgtgttt gaagtttgcc aaagattaat atacatttga 123420
ttttcatgtt gtgccttttc tctgattgtg aaatattaca aattctatac aaataacaat 123480
gatggcaaat cctcctgagc aaagtgtgca ccttgtatgt gccctagagg aacttgtgtt 123540
tcgttctgat tcccctacat ttctcatgtc atagagtggg ggttgcatta gtgtccccct 123600
gtcctcgctg ggatcacatc tgtttggatc ctagagtctt ccagctgaac tgggacaagt 123660
ataacagacg gacacgtagg ggtggaaagg cgtctcttgg cagcagactt tctaattgtg 123720
cacgctctta taggtgttgg agatgttcat tcttgtcctg cagcagtgcc acaaggagaa 123780
tgaagacaag tggaagcgac tgtctcgaca gatagctgac atcatcctcc caatgttagc 123840
caaacagcag gtttgtcccc gcagccttgg cttgttgttg catagtgatg gtagcttaag 123900
gtccttgtga aaggtgggtg gctggaatca gctcttcctt cagtcctaat ctgtgccttg 123960
atagcagttc tccgtgctag tcatgggaca gctgacttca tttcttctca caatgccatc 124020
tcaggttggt attgcccacc tactttacag gggggatccc acagctccga gaggttatgg 124080
aggtgatcag gcagcacaca gctttagagt gctggggtga gggcgggcca aggctaactc 124140
taaagcccga acccttacct cctacactgc ctcctgcatt ctggtcaacc cagtgtttta 124200
tttggtggtt agatttttgt ttttgttacc ttactgcttg taatttagca gttttccttt 124260
cctttccctt cctttccttt ccgacagggt ctcactctgt cacccaggct agagtgcagt 124320
cgtgtaatct cactgcaaca acctctgcct cccaggttca accaattctc ccacctcagc 124380
ctcctgagta gcaaggacca caggtgtgca ccactacgcc tggctagttt tttgtatttt 124440
tagtagagat gaggtctcgc tgtgttgccc aggctggttt taaactcctg ggcgcaagtg 124500
atccaccaac cttggcctgc caaagtgctg gcattacagg tgtgagccac ctcgcctggc 124560
ctattcatca ctaatcagaa tttctatgat caaatgacat gaatcattgt ttccacaact 124620
gcagtggaag gaaatggcct ggcagtgcca gtttcagaag cagcctgccc ccagtcaggc 124680
acaggccact gtgcccccag tgtagcagca cctctgtagc tcacagagaa gggtggtggg 124740
gacctccttg aggcagctct gccagaaaat ctcatgagct gcctggcaca gcttgaggtt 124800
gccttttaag tggactcagc aaatacatgt ttgttcatct tgattataca caataaacaa 124860
ctactctgta tagtacgagt agtccgtggt ttttggcatt tgatttaaac ttagaggcat 124920
gtgatattga tgttactgcc ttcatgactg cacccccatt ctgatttcat aatggaatgt 124980
tatcttgaga ccagttagac aacaggacag ggatcttggc ttctggtgag attgacagca 125040
gttttagtgt ggtcagggtc tccctgccta cagatggttt tagaatggtg ccctggaagc 125100
tttatcccat tcttttctgt gcgtaatctg agtagagtgg agatcgaagg cctgaataca 125160
tagtaaatac ctgacttaat atctgccgca atggaaattg tgtgatacaa catttatgaa 125220
acgcttagtg cagcacctgc caggtagctc accacaggtg catgttgcat tcagaagtag 125280
tgctagatac tatcctgtta ctggcagtgc atacatcagt gatcaaagca gattaaagaa 125340
agaccccctg ccttcttgga gtgaagattt tgttgggatg cgggtaaggg gacagacaat 125400
agaaaagcaa gtgagtgaag tctataccat ggcggctgat caggaacacc gtacagaaga 125460
atccaggagg gaagagagtt aggtggtgtc tgcggtggga gtggcattgt tcagctggtg 125520
atgagaagaa gctttggtga tctggtgaca tttgagtgaa tttgcagaaa ggaaagatac 125580
aagcctagga gatacctggg gaaggaacat tccaggcaga gcaaatagca gtgcaaaggc 125640
cctggcgggg ggcggacatg ctgttagggt acaagcaatg agggtggagg agtggggcag 125700
ccatggggag ggaagggagt gaggcctggt ggggtgaggc cagtgtggag gagccttgag 125760
agggtttgcg ctgatgtggt gtaggtttta gcaggatcat tcttattcct gagttgagaa 125820
tagccttgag gggaggtga gggcagagca gggccaccca tgtgagaccc ggcactggag 125880
tggaatggcc caagtcagca tcccttggca gcatgaaagc aaaaccagca aggtttgctg 125940
gtggcttaga tgtggcatgt gagagagagc agggctttgg gggtgatttc agggtgagga 126000
cagggtggct gtggacaagg tagggcagac attgggggca gcaggaggtc agagcctgtc 126060
tggatgtagc agttgagacc ccataggtgc ctaatgaggt gaggccagca tcaggtgtat 126120
gagcctggag ttgtcgagag actgtggggc agggggtcag catctgagat gtccactcac 126180
agtggaccca gactggctgg agaggaggag gagcttgaat accgagcctg ctgagtccca 126240

-continued gctccaaggt caggtaggtg aggggagcca gtgctggggc agggggagta ggcaggtgtg 126300
gggttcctaa agccaagatt ttttttaagg cattttgtgc aggagggcga catctgctgt 126360
cagcaccttg ggaacttggc ccaggtttgg cagcaccgag ggcactgatg agtgcttttg 126420
gaggagcaaa gggagccaaa ccctaatggg aatgtgttcc tgaaaggaca ggagagagac 126480
ttgggaaaag gttttacttg aagagggaac ggagaaatag ggcagtagcc agaggaggag 126540
aggagtcggc aatgggttaa gttggcagaa atgaaggcct gtttacgcac tgagggcaga 126600
agcaacaggg aggatcagtt catgacacag gagacacaaa tcgccgttgt ggtgttcaca 126660
gacatgggtt aggattggct gcatggatga cagagcactg tgggttctcc cagagttgct 126720
ggggaggagg cagagttggt gagcacaggc gagggtccag gatgcaggaa tcctggagct 126780
caagtcagtt gttcccttgt tgtaagatgt ggccagtgtt gtgagcttca catctgtgcc 126840
ttgaaaaaca ccacatctgt ttgcagagtt gtttactatg tatacacact cagtagaaac 126900
aaaaattgga aacagtcagt gcccaccatc aataagtaat ggttgaacac actgtggtat 126960
aagcttagac tattttagct tgggctattt tgcatgatta aaaatgttct ggccaggtgt 127020
ggtggctcat gcctgtaatc ccagcacttt gggaggccaa ggcaggcaga ttgcttgagc 127080
tcaggagttt gagaccagcc tgggcaacat ggtgaaaccc tgtctctact agaaatacaa 127140
aaagtagctg ggtgtggtgg tgtgcgcctg tagtcctggc taactcagga ggctgaggtg 127200
ggaggatcac ttgagcccat tcgtgcgcca ctgcactcct ggggcacaga gtgagactct 127260
gttagaaaga gagagagaga aagaagagag agggagggag gaaggaagga aggaaataaa 127320
tggaagaaat ggaagggagg aaggggaggg aggaaggaag aaaggaagtt cagccagttg 127380
ccttgggagt tctccattgc actgggttaa gtgagaagag cagagacgtt tatgattttt 127440
caaaacaact aaaacaaaac ctctgtgggt gagggggcaa ggatatggct ataggaacat 127500
ggggcagatt aagaaaggga tatacacaca ccacttagca tttgttacaa ctgttgtggg 127560
agggatggag tgcagaaaaa gaaaaaaaaa agtgcacacc atcccatgta tgtgtataca 127620
aagggacgct tggaagactg gtccccaaaa tgttggtaat gattgtgtca gggtgctgca 127680
gtgctagttg atttttttc acacttttgt atatttgagt cttttacaga aagcatttat 127740
tatttatgta ataaaaatct aaatgacaag atttctgtta tgggaaaaat gtagctatac 127800
agtgttgttg taaaaatgtt tgcttggttc accactgaac ttaaaatgct tttaaatgag 127860
ggaaggtgac gatgagatga ttatgatgat ttgcccttga gttacatagc tggtgtacag 127920
gaagctgtcg tttcttttgg cttacgtaga aatgtttgtg gtgtctaatt ccacagatgc 127980
acattgactc tcatgaagcc cttggagtgt taaatacatt atttgagatt ttggcccctt 128040
cctccctccg tccggtagac atgcttttac ggagtatgtt cgtcactcca aacacaatgg 128100
tgagtctctc gcctggctca gcagatgaat ctggacggct tgttcaggct ctgattactg 128160
ggaccacccc cagaatgtct gagtcagtca gtttgggtag ggcttcttga gagtttgctt 128220
ttttttttt ttttttttt ggtgtggggg tggtgcggaa cagagtctca ctctgtcgcc 128280
caggctggag tacagtgtca tgatctcggc tcactgcaag ctctgccttc cagcttcaca 128340
ccattctcct gcctcagcct cccgagttgc tgggactaca agcgcccacc accacgcccg 128400
gctaattttt ttgtattttt agtagagatg gggtttcacc gtgttagcca ggatggtctt 128460
gatctcctga cctcgtgacc cgcccatctc agcctcccaa agtgctggga ttacaggcgt 128520
gagccaccgc acccggcctt tttattttt ttggagatgg agccttgctc tgtcacccag 128580
gctggagtac agtggcgcta cctcgactca ctgcaacctc cgcctcccgg gttcaagcaa 128640
ttttcctgcc tcagcctccc gagtagctgg gactacaggt gcgtgccact gtgcccggct 128700
aatttttgt atttttagta gagacggggt ttcactgtgt tagccaggat ggtcgcgatc 128760
tcctgacctt gtgatccgcc cgcctcggcc tcccaaagtg ttgggattac aggtggctct 128820
cgcaccaagc caagagtttg catttttagc aaattcccag gtgaaactaa tgcctgcttt 128880
tctgggagca cactttggga ctcagtgata gagaggttta ttggtaggat agtaaaatag 128940
gagttatttt ctttcacaaa attggcaatt gggggaaatt taatcttcct tttttcttca 129000
gctgtgactt atgtattatg tttattttag gcgtccgtga gcactgttca actgtggata 129060
tcgggaattc tggccatttt gagggttctg atttcccagt caactgaaga tattgttctt 129120
tctcgtattc aggagctctc cttctctccg tatttaatct cctgtacagt aattaatagg 129180
ttaagagatg gggacagtac ttcaacgcta gaagaacaca gtgaagggaa acaaataaag 129240
aatttgccag aagaaacatt ttcaaggtat gctttctatc tgagcctata actaacccat 129300
gccttttggg aagtcacgtg atgtttcaca gtcagtaagt ctggaataat acctggtctt 129360
gcttcacttc tgagttgggt aaagaagtct gtatcagtgt aattttctaa tccgtcctgc 129420
attatctatg gctcttggtt catacctgtc ttgaagttct gtcatgttct gtctcttgtc 129480
ctcagtagag atgctacagc agtggctcgc ctcaggcagg gcagggcagt ggggtggctg 129540
tcctggggc aggcagtagg ggcacgctga cgtcagggaa gttgaaaccc aagagaagcc 129600
agtaaaagtg agtctcagat tgtcaccatg tgctggcagt tttacacgct gtcagtaata 129660
aaagtcttct ccctgcaggg cagcctgcct ccaataaata cgtgtagtat caaatcctgt 129720
cttccctcat aaattgtttg gaagctcccc aaggacagtg atgaggcact cgtaagtgct 129780
tgctgcctag atgggtccct ctccaccttt gctagattct gagcattcac tgagttagag 129840
ctgcttctgc aaatgtgctg cttctgctaa gtggctgtga cttcatgcag ccttcacttg 129900
gtttgtcatc agtggagatg ccctgtgttg tcgaaggaga taagcccagt aagcctgctg 129960
ggcacctttt ggtttgcagg ttcagcaggc agcccatggc tttccctgtg tcgcattgaa 130020
gcagctggct aaaattgatg atacattaaa ttcctgtgac agatgatcag cttgtatttg 130080
tgtaatggtg tacagttcac aaagcttaaa aaaatgctac ctgccatttc atcctcagtg 130140
aggaaggtga tacacagaga gaccaagtga ctgtgtccac ggcgacggcg ctctgcattt 130200
cactttagcg gttaatgtac tctacctata tttttacttt atatttacca tatatctttt 130260
catgtatact tggcgtaagt gctttatagt agtcacctaa ttcactgtca tcttttttgt 130320
ttcttggaag gtttctatta caactggttg gtattctttt agaagacatt gttacaaaac 130380
agctgaaggt ggaaatgagt gagcagcaac atactttcta ttgccaggaa ctaggcacac 130440
tgctaatgtg tctgatccac atcttcaagt ctggtaggtg aatcacatta gtcttcctgg 130500
agtgtctcgt tccccattct gcactataca ctctcagagt gtaggagctg tgctgcccgg 130560
tagaaactct gccttgccca gtgtgccagt tgaaaatatt tgttgctgta agagtacacc 130620
tgataccatg tgacccagca gttccactct tgggtatata cccaaaagaa tggaaagcag 130680
ggtggtgaaa agatatttgc atgccagcat tcatagcagc attattcacg atagctaaaa 130740
tgtggaacca actgaagtgt ccctcgatgg atgaatggat aagcaaaatc tggtgtatat 130800
ttacagtgga atattattca gccttaaaaa aaggacattc tgacacatgc tacaacatgg 130860
gtgaccctta aggacattat gctaaatgaa ataagccagt cacaaaagga caaatactat 130920
gtgattccac ttacatgagg gacctggagt agttaattca tagatataga aagtagaatg 130980
gtggttgcca ggggctgcag gggaggggag ttattttttac aagatgaaga gagttattct 131040
agaaatgaat ggtggtgatg gttgtataac attatgaatg tacttaatgc tactgaactg 131100
tacagttaaa aatagttaag aggaccaggt gtcatggctc atgcctgaaa tccaagcact 131160
ttgagaggcc aaggcaggag gattgcttga gccaaggagt ttgagaccag cctcagcaac 131220
atggtaggac cccatctgta caaacaaact agccggggat agtggtgtgc atgtggtccc 131280
agctactcag gagactgagg ctggaggatc gcttgagccc aggaggttaa gtctctagtg 131340
agatgtgttc atgccactgc actccagcct cggctataga gtaagaccct gcctcaaaaa 131400
aacaaaacaa aacaagacaa gagccaaaaa tggttaagat gggccaatca cagtggctta 131460
tgcctgtaat cccaacactt tgggaggtca aggtaaaagg atcacttgaa gccaggagct 131520
tgggaccagc ctgagcaaca tatcgagacc cctatctcta caaagaaaat caaaaactag 131580
ctagatatgg tgggcacatg cctgtagtcc cagctacttg ggaggctgag gtgggaggat 131640
ctcttgagct caggagttcg aggctgcagg gagctattat tgcactccag cctgggctac 131700
agaatgatac cctgcctctt attaaaaaaa aatccaaaaa aaaaaaaaag taaacctgag 131760
agcttcctcc tcctgtgtta aatttggagg ccaagatgtt tttgttactt ttacaaatga 131820
tcaaggacgg tgaaggttgg gcatggtagc tcacacctga aatcccagca ctttgggagg 131880
ctgaggcggg gtgatcgctt gagcttgaga ccagcctgga caacatagca agagacccca 131940
tctccacaaa aataaaaaaa taaaaaaaaa tagccaggag tagtggcatg agcctgagcc 132000
caggaggtca agctgtagtg agccatgatc atgccactgc actccagcct gggcgagatc 132060
gagaccatgt ctctagagaa agaaaatgac aaggacagtg aacccaagaa agtcataaga 132120
tgccagctgt gcagcaagca tggaaagcag ccagtccaaa ttaggacagt gtgttttcca 132180
agaagaacga tcgtttgtaa tgagaatgct ttgctttaaa taaatgacta aatagctaga 132240
agcctagttc taggggatag gcacgtcttt cttctctcaa gaaaatagaa aggcaattct 132300
aatttctagt aacagcaaac agcattaagt catggtccaa atatgaggca aaccaaaatg 132360
tggcttgatt gttcagcagt tgatctgttg gaagcccttg atattaaaaa ggttctcctt 132420
taagcggctt aggagtcacg atcaaagacc tatagaaaga gatgccatcc ttctaggatc 132480
cttggctctc ttgggaacta gattcagata gtcataatgt aaatactgct tgagctttct 132540
ttctttcttt ctttctttct tttttttttt gagacagagt ttcactcttg ttgcccatcc 132600
tggagtgcaa tggtgccatc tcggctcacc gcaacctctg cctcccaggt tcaagcaatt 132660
ctcctgcctc agcctcccga gtagctggga ttacgggcat gcaccaccac gcctggctaa 132720 tttttgtat ttttagtaga gacagggttt ctccatgttg aggctggtct cgaactcctg 132780
acctcaggtg atccacccgc ctcggcctcc caaagtgctg ggattacagg tgtgagccac 132840
cgcacccggc ccgagctttc atttttgaaa tcaatgtatg actgaaacac tgaagactta 132900
ctgacttaat tatggtttca gaacagaatg aaaatgtctt cggttctgat gaatataaaa 132960
ggaaaactaa ccaagttaat ttggcaagta gatggtagag atagaggtgg ggagtggaag 133020
gggaactaaa atcttcacct agcattgttg ggattatatg gttacatcat ctgaagttga 133080
cagaccaaaa tatagaggct tcagaggtct ccaaatagaa ctaaacatgt aattcagatt 133140
gttaggaggt agtataaatg agctaaatct catctttatt acggtagagt taatgggtga 133200
tgtctaaagt tgtctgaagt ctataaatca tgacaaatta tgatgtggtg attgtattca 133260
acagtctttc agttgcaggg ataaaacccc agtttaaact agagtaagag aaagaatgtg 133320

-continued ttggtttaag ctcctggaaa gtgcaggcaa gggtagttgg taggactgca tctagtgttg 133380
taattctgtg gtctgcattg tatatttatg catctcagct ctgctttctt cttttcattt 133440
atataatttt taaattttat tttaaagata gggtctcact ttgtcgccta ggctgaagtg 133500
cagtggcatg aagtgcagtg cgaggctcac tctagcctcg aactcctggg ctctagagtt 133560
cttcctgcct cagccttcta agtagctgag acaataggca tgtaccaaca tgcctggata 133620
ggttttaaaa ttttttgta gaaatggaag tcttgctgtg ttgcccaggc gggtctttaa 133680
ctcttagctt caggcgatcc tcctgcctct gcctcccaaa atgctgaggt tataggtgtc 133740
acccaccacg cccagtctca tctctgcttc ctgtgttagt tttgttctct ggtgggctgt 133800
tttcacatga ccgaagatga cctctagcag gctgtgttct cagcccctca agtaggccta 133860
tgtgattggc cttgcatgag taatatgggt gaccataaac ccctgaatgc tctggtccac 133920
atgggccaaa tgggagactg gacagcattc cattgatgag gaggtggggc tggtctccgg 133980
gagtaaggga gaggagcaca tgcagtaact gatggtctgc tgcaagggat agcagcacag 134040
cagttagaat tttggaggta actaccagaa ctgaaaacag aaatgataac aagtagttgc 134100
cttaaaaagg gatgggagca gggtgctttt gtgatcaaag ctcctttctc ttactggatt 134160
tttgtacaca ttttgcatac atatcttaga gtaaaagata gcattttcag ccttggtcca 134220
tttgaggata ctcttggcgt ggcccgcctc catgctagca ggctctggtt gtgccaagtt 134280
cagttgagca tcctggctct tgcctgcacg gaacttccag tcagtgcgtc agtatcacaa 134340
gtcttgatat ttcctatgaa gaagaacagt agtgcagtga cagacgaaat gggtgggcag 134400
gcagaggcag gatttctgag ggagagaagt agctagcttt ttgcagagaa gagttccggc 134460
acccaagaga gcagctgaga gtacaggcag gcaggcagga tgccggtagg gcccggccgc 134520
acggcgccac agaatcctgg agaaaggggc ctcttcatgg cctctgcatt cagctgctgt 134580
caccctccgc acaggccatg gccaaaattt aattttcata gtggactcta gtttttgagc 134640
cttacttgct attattgaaa taattttctt gtttcttttt aaagatcttc ggattatgct 134700
tcactgacca ctgtaataag tttaaagttg agaaaatatg gcttgttaat gaatgatagg 134760
tcaattttag tatgttggtc attttaatat tttgccacca gttggtttgg atttgatgcc 134820
aggaggagac agcctcattt ctaaggacta gtcttgcctt tgtgggataa gggtggtgtg 134880
ttctgtgtcc ttctacatgt ccgagcgatc tctgtgcagc tcaaatgtgg tcactgtctt 134940
attgcgctga tttcctctcc ttccatctca caattgaggc aaaatattgt tactgttgaa 135000
gtgttgtcca ataggacttc cagcagagac aggatgtctg cactgtctaa tttagttgcc 135060
tttagccaca tgtggtgttc tgtacctgaa atgtggctgg tctgattgga tagcttaatt 135120
tataatttta tttaatttta attaacttaa atttaaacag ctctgtgtgg atagtggctc 135180
ctgtatgaga cagtgcaggt ctgttgagaa gcagctttac tggtgggagt ggagggcttg 135240
gagagggcac gtgggtttcc tgctggtatc ttttgacctt atttaatctg cccaacattt 135300
gcaagtaagt tgtgtgtgtg tgtatatata aatgtgtgtt tctgtcttct tgtttccttt 135360
gactgcattt atttgaaaga cactaggtgg cagaattact gtatttgatt ggtttcaaga 135420
taagagttga aataattcat ctcgtgtttt tatataagta aggtgtgttt agcatgtaaa 135480
attggtaata tgtattcacg tactgcttaa acaaaggcta tgaattccac ccataaaccg 135540
aaaatgaaga cctttaaatt tgtccatttc aggcgtgggt acttcttaaa taatacctgg 135600
ttcaggaact agtcagaatg gcacccttga ctttttgttt cctgctttc ctcttgttgg 135660 gagaggaggg tattcatccc aaagtggttt gcctatttca cattccatct aggataagca 135720
gaatagccaa gaaagatagc tgtcctcctg tttacaacat ttggggtaac cagcatccct 135780
ctcttttggt ccaagataga ctggtttaga aacagatgat ggcaccagag gcccaggagg 135840
tggaaacatc agctttgttt gttgtccatg tggctgaatt agagctgtct ggccttgtag 135900
cctcaacacg gccttccagc tttgctcacc gtgattttca aggacacatc ttgtgctctt 135960
ccctgcctgc catccagact atacccagtc agggtggcag gagctgctgc cccttcctcc 136020
ctgagtcctg gtcgtgggtg gtggagatgt gccatgacgc tcacggaggc atgctcaccc 136080
cttcctctgt ggcagagggg atggctgcac gacagctctt ccctgtcctt tccaaagcgt 136140
ctgtggttcc actttttggg gcaaagcagg aatactggaa gagagagaaa gtggtccttt 136200
ctatagtaat aaagttgaca ttgattcaag ttcatgcttg gggaaaggac agggctacta 136260
acaattataa tgctgggagc aatggaattt tctcatgggt atgtggtagg tttaatttta 136320
attatcccag ttaattctta gaactgctct gtgaagtatt tcccgctttg tgcttaagtt 136380
ctaaaagatc ctgtgccaaa accaagaatg aaaacccaag cattctttct tgcccatcga 136440
tctttctctc atcaggccac ttcttgggtt gatagtggtg agtgtagccg ctgccacttt 136500
cagaataccc accatgggcc ccagtcactg tgtggcgtgg agaagagatg gttctctctg 136560
tgtcatagct gaacaagccc agcccagaga ggtttctgcc ctaggagctc tcgatggtgg 136620
aattgggatg cgatcccaca tcctgcctgt tttgaaaaca gcattcttta tttccaattc 136680
ctgcttccat tgttcctttt aatatttctt tgtttagctc acaaaaacac ggcttgcgga 136740
gctgctgcgt gcagctgtag ctgtttctct gggtgcagcc tgcatccgcc ttcctgcccg 136800
cctcctttcc tgcactgcca tcgtggtctc cgggcacttg gtccctttct cttcccctga 136860
gtccctttgg ctcccctgtg ccacccttgt gatccacagg ctctgccttc tttctgtctc 136920
agactgctgc tcatcactac tcgggaccct aggaagggag gttccaccga gaagcatctt 136980
ctcatctcag ccacgttctc agtgccactg ttgtctttgt taggtaatgg tagctactgt 137040
aacaaataaa ccaacatttc catggcttca caccagagaa ggttgtttct tggttttatg 137100
acaatgtatt gagggtgttc ttggttcacg gatggttttc ctccatgtgg gaattcgggg 137160
acccaggctc ctttccttct tttggttctg ttctccaggc cttcacatcc tctgtgtctg 137220
gttggggaca aggagaggga aggtaaagaa ggctttgtgg ccttggataa gtgacaggca 137280
tgcctttgct ggtgttctct cgtggtgaca ggtcacagcc ccaccctgta aaaggggact 137340
gagagacgtc gtcctgctgc ttcccagcag cagcactgtg gtctctgatg tgttttctgt 137400
gaggataaaa acaggtgatt ccaggatgag gaaagtcagg gaaacccttg gaaggagggg 137460
accaggcggg tgtcaccatg ggattagtgg tggcttcaga atgagctgca gcgagtgcca 137520
tgccttctaa agcttttgct attctgatat gcccacacca tgcccagcag gtgtctgcct 137580
tgctctccgc agagagagtg atgaatcctt ctcatgagcc tctgtccagt tgttcctccc 137640
tccacctgga agggaccctg ggttcctcat aacatcccag cggaacaggg gaccttctat 137700
cctgtcccca agttcatcct catcctcctg ccggcttcct ggcccctctt atgtctgctt 137760
cctgacgcca catccttctg gattctctgg aattgaattt tgcctttgat gcttatttaa 137820
aaatatccat tgcaggccag gtgtggtggc tcacacctgt aatcctgtgc actttgggaa 137880
gccaaggtgg gcagattgct tgagcccagg agtttgagat tagcctgagc aacatgttga 137940
aatcctgttt ctatagaaaa tacaaaaatt agctgggcat ggtggcgcac acctatactc 138000
ccagctactc aggaacctga gacaggagga tcaattgagc cccggaggcc aaagctacag 138060

-continued tgggctgtga tcgtgccact gtactccagt ctggtcaaac agagtgagac cctgtctgaa 138120
aaaaaaaaaa aaatccattg catacttcac cgtagcgaaa catgtatgtc ttacctttcc 138180
tttcctgcct gtagctgctc ttttacactt aacagccaca ctaagccagc cttaaatgaa 138240
aaacaaacca gcacttcctg tgccctcctg cttccttcat gaggggtccc tccctctgtg 138300
tacactccat tctcattgcc catggtggtt tgtttccctc ttgtttctca agccatggca 138360
gcctgcctct tgccctcttt actaaaaagg cctttgcaga ggctgcctgt gttctttctt 138420
tctaggtctc tctcatccta ggccctccag cttgattctg tggagctgcc ctcttgtcac 138480
tcagtagctt gtggggtctt ctctgtctag ccacttaatt gattgtgttc ctcgagttgc 138540
tgtccatggt ctctcgttac tgttttctct gtgtttctgc ctctctcctt ggccttggta 138600
ggtccatccc ctttgtgacc ttggctgttg ctctcatgga caactttctc ttgctggtcc 138660
ttgtagtcct ggcatccagc ttctcgacac gggacttgtc ctgccagtac ctcagacttg 138720
cacttaaaat tgaactagca ccactgtcac tctccagggc ctcttcttgt taattagatc 138780
attagggatg ttcagaatcc cagcatcata gtatgttcct cctcccgcta ccccaggaac 138840
cctaacctta cctcctcctc tctatctact aggaggtggc cctcagagtc cgtctcatct 138900
tccacctgaa cttccctaat aggctccagc agctgccacc ccgggggctg agtacttcct 138960
ccatgccttg tgcagtgctg agccctttac ctgggttctc ctgtttgctc cttattacag 139020
ccctgcgaac agatactgct cttaattcca tcttacacct aaggaagctg aggccccagg 139080
taaggtgcat ccaaggtcac ccaggtagta gacagtagag ccacgatctg aaccaggcag 139140
tctgattcag agcctgtgtt gacactcagc cacctagaac acagcttgga ttgtgggttt 139200
ctattacctg ttcaaaaccc ctacatcccg ggtctgtccc tgcacgtgct ctgtggcctg 139260
gctgcatctt ccttgaaggc agtgcatgcc tcttcactca gggggcccat gcaggaacag 139320
agggccccac agaaggatga ggccagtgca gaatgggctg gaggggacaa tgctgaccag 139380
gaagcaagtg tagagaaatc ccaggaaacc tggaggagcc agagacaagg cattagaact 139440
cctcgtcgtg acctggtctg cattctctga gtgtgctgct tctgttagct cgcttccttg 139500
gtctcaggtt atagtttaag gcattgtgga gccctaaaaa gcctgtactc tgtttttacc 139560
tgttttagga ccctttcact ttggggatgt gttgattttt tttttttttt tttttttttt 139620
tttgagatag agtctcgctc cattgcccag gctagagtgc agtggcacga tcttggccac 139680
tgctgcccct gcctcctggg ttcaagcaat tcttgtgctc ccgcctccca aatacctggg 139740
attacaggca cccgccacca cactcggcca atttttgtat ttttagtgga gacagggttt 139800
taccatgttg gtcaggctgg tctcgaactc ctgacctcaa gtgatctgcc caccttggcc 139860
tcccaaagtg ctgtgattat aggcgtgagc caccacaccc ggcctgaaat ttaaatcaga 139920
aataaaattt tgatcccaac agtgatgcca ggcagcccag atctggggga gagggtggcc 139980
ttggccagct gggcctttct ctgtttccca agtcttgctg cctctccctg ctgggctttg 140040
cagcctgtgc atgtctctgt gcctttgacc ttgtttatcc aaaggagagg atagaatgaa 140100
gtcatgattc ctggagccct gagaaggatg ctgtggagaa atttgccggt agaatctagc 140160
tgagtgtgtt gctgaggtgc cagcattgtg tgtggggagg ctgaccgctt ggcctgccta 140220
ggcccaggat gctccatggc cgggcacaga ggccacttgg ctgtcaggtg tcaggagcct 140280
gcagagggca cacagagcct ggaccgcagg ggggtcctgc tttctcacct ggcctccttc 140340
agcatttctg tccctcagtc cttagcaagc ccaggagctg ttgagtttgg caggtgccga 140400
gtgctgttcc tgcctgtgta gctgtggctc agtcctgtgg gggccccgct gtggcccgag 140460
tgcagtgatt cgaggcgctg agtgttccct gactccttct ccaggagctg tgttcagact 140520
ttcgcagctc ttggcttgga gctcctggag ggcttggcat tgccgaccaa tgtggaggtc 140580
gacagtgaga gaggaggaat gctagctttc ttgaccagtc cattaaataa gtgggatatt 140640
ggccaggcac ggcggctcac gccttaatcc cagcactttg ggaggctgag gcgggtggat 140700
cacgagctca ggagttcaag accagcctgg ccaacatggt gaaacccccct ctatactaaa 140760
aatacaaata ttagctgggc gtggtggcag gcgcctgtaa tcctagctac ttgggaggct 140820
gaggcaggag aacagcttga aaccggaagg tggagtttgc agtgagccaa gattgcgcca 140880
ctgcactcca acctgggcaa caagagcaaa actctatctc aaaaaaaaaa aaaaaagtag 140940
gatatctgtt tctgcttaga aaaatcagaa ttttctaaat gccaggtgtt ctgaatacgt 141000
aagtatggga gacgactcag cctgtttcat ttttatgtaa aatcttcgcg tagccatgtg 141060
gcactggacc gagatgaaag caaagacatt tctccttaac tttgtttcta ggaatgttcc 141120
ggagaatcac agcagctgcc actaggctgt tccgcagtga tggctgtggc ggcagtttct 141180
acaccctgga cagcttgaac ttgcgggctc gttccatgat caccacccac ccggccctgg 141240
tgctgctctg gtgtcagata ctgctgcttg tcaaccacac cgactaccgc tggtgggcag 141300
aagtgcagca gaccccgaag taggttcata atgccccaca gcccagggcg ccagcccagc 141360
accctgtcct gagactccca gtaacctgag ctttggccac cgttaaagca ttttcatttt 141420
ccattttttg tgagggcttg tgaaatttct gctgcatatt aatattcctt tcatggacag 141480
catattattg ggacaaacat gcggtccagc taaaggcatt caaaatagca gttgctttct 141540
aaatgcgatt ttctttggca ggttctttga caccattgca tcttgtggga tatgcttgtc 141600
atgctctgtg gctcctacta agttctagtc cttaaattgg ttccatagcc agacatgttg 141660
caatgtctta acctcattat aaagtaaatg tggttctggt tatccttaga taatgaagta 141720
acagtgtagc aaatttcaaa acctcttgga aatgttattt taccattcaa aaaggcttac 141780
taaggttctc gttatgggtg gccctctttt tgcaaaaggt tttcaggctt aagctccatt 141840
tctaggtgct ccaacactcc attatttgta tatgtatgga aataaaagct gtgaccaccc 141900
ccaaccctgg cccccgccca gctgaatcct cagcacagta tttctggaag gctcaagatc 141960
ccacgctggg gaaaagaagt tctggagaca aaagagggca ggtgctgccg tgcctctctg 142020
ctcagtatgg atactggacc ttgtgctgcc agggctccca gtagggccag ttcatggcac 142080
tcagctggaa agtccactgt tgggaggcat tcttaaccat ccactctgtg ccgtatgtag 142140
tggggtctgg tcattctgtt ggaggagaca gaccagtgac gacatttgaa atgcttggtg 142200
gatgtcttag gcctgttacg atgactgagc actgtggggg caggagacag aaagtcagtg 142260
tctcctagtt ctgtgctgct ttaacgtgca tagaaatcag ctgcggattc agcagatcac 142320
tccttttctg acagatgggc ctgcttactc tgatgttata tcagaaagct ctgaatctgg 142380
gaattgtgtc ccctgaattg gagtaacaga aatgcttaga tgatgagtgt ttaaaagaaa 142440
taaaccaaag gtaaatttag tttggaattc agcaagcgtc ttcattcagc cctctgaggg 142500
caaactacag ctttttgtaa atgtaggtaa attctgtgac tgtttcgtga ccccctctga 142560
tccagttttc ctttataacc ttctgtattg ttccttctat tatcctgaaa taacattaat 142620
agattaggct gggcgtggtg gctcatgcct ataatcccag caccttggga agccaaggcg 142680
ggcagatcac ctgaggccag gacttcgaga ccagcctggc caacatgatg aaatgctgtc 142740
tctactgaaa ataacaaaaa ttagccgagc atggtgacag gtgcctgtag tccctgctac 142800
tcagaaggct gaggcgggag aatcgcttga acctaggagg aaaaggttgc agtgagctga 142860
gatcgcgcca ctgcactcta gcctgggtga cagagtgaga ctccatctca aaaaaaaaaa 142920
aaaaaaaaaa aaattaatgg atcaatggat ttttaaccta ataattaaat ttcaaaaaat 142980
atcgttcttt aatggtaatg taaaggtaaa attaagataa tatgtaacaa gcatgtgagt 143040
gtctaaggtg tccccgtggt ggaaggaaaa aataaatccc cataagtgtc caagatgccc 143100
atagagagca gagctgttct ggtttaaacc cctgctctta gcactgtgtt tttccagctg 143160
tgggtggtgg gggatgagta tctttttatt tccatgagat gagaaaaatg aattactaga 143220
agtgtgaaat acaaaacaca gctgctcttt ttttagccat agactcagca gccataaaat 143280
tgctgtatcc agttgcagaa attcctgctg cttactcttg accctctctc ggtttgtgtg 143340
catctcctct caggctggct cccagatggg agctggctcc aggcgacact gggtgctctg 143400
ctccaggagg tccttatgtg ggtcctgccc tagcctagcc cctctcttat ggactctgtc 143460
actgtgggtt tatgattcac tctcaatctg tcttacctct tggtgaactg ttagagtcct 143520
gcctatactt tggcgcttgt gggtgtgttg tggtacacat gatgtgttgg tcacttccca 143580
gctcatcttg ttctgagtca ccctagattt gggacattca ttcgccacca gtaccgggcg 143640
gtgtatggcc tgagatttgg gggggcttgt gctgctacaa attggggctg aatttgagtt 143700
gacagtggac cttctttatg tctactgctc atatttgaat tgcaaatact gcctcttctc 143760
tttcagaggc tcattaccct atagctgtat tattgcaaag tgcacaatta cagcttgagt 143820
gtaagtcaca ctgcgctggc aggacggccc actgagaaag ggcacgtttc ctgttcgtta 143880
gttttcacat tgacacataa tttacaatac agtaaaatgt acttttctat caactgtagt 143940
cagtaacagc ccccctcccc caaccacatc aagatataga ggagtgctgt cacttcaaac 144000
agttccctct tcctctgcca catcctgccc ctccccaggt ctaaccacca atccgtgctc 144060
tgtccctctg ttcagcccat tgcagaaggc catagaaata gaatctatag gctaggtgtg 144120
gtggctcatg cctgtaatcc cagtattttg agaggctgaa gtgggaggat gacttgaggc 144180
tgggagttca agactagcct gggctgccta gcaagacccc atctccagaa aaaaaaaatt 144240
taaaaattac aatcacgtcc ctgtagttca gctgcttggg aggctgaggc aggaggatca 144300
cttgagctca ggagttagag gttacagtga gctatgatcg tgccactgtg ctccagccta 144360
ggtgacacag caagacgttg tctctgggga aaaaagaaag aaacggaacc acgcggtgtg 144420
cagccttctg agtctggccc ctttcggtga gcagtgtcta aagttctgtc gcgtgttgcc 144480
cacgcgtcgg tggctcgctc cttgcaactg ctgagcattg tatggctagg ctgtagtttg 144540
ttttcacttc accagttggg aaacagagaa aaggcacttt ttaaaaagtt taaatctgta 144600
gaattttggt ttttaccagt tctcttctaa atcctgaggg attacaggaa aagttgttgt 144660
atttcagaat attcttagct tgatgtgacc tctgtccccg ttaaggccct ttgccgcaat 144720
gggaaggacg tcgctcggtc agaccctgaa ggtcagaggg gcagtttggg agtgtgtcaa 144780
cattttaact gtatggacta gagccaagag tctcaaggtt tataattccc acgtattcaa 144840
aaagaaaaaa acaataaagt gagaagtcag tgtagagtga aataacctgt gttagtgggg 144900
aagaagtgtt tttaaacagg atttccataa cgtataacat caacatgttt agagtggtga 144960
tgtttcattg ggaaacgaac agtaaaacat gaaagcaggg aggttttcat tctggcagtt 145020
ggcaactttc acggcagatg gagaatttca aaagcaattg ctcaattatc aaacatagcc 145080
agtgtgagtt ctgaaataaa ggtgctgatt gaatgtgcag ctttatggtg gattttgcta 145140
ttcaggcaag cattttaatt ttctgcctgt taaattctgt tttctttagt ttttcatatg 145200
tggtttattg tagcttagga atagataact gagagtatat attacacata caacattctg 145260
atatggcaat atttaaaaca acttgtctgt tttagaacta gaattaaaca taatcatctt 145320
cagtattttg caaataagct cactgccatc cagaaacatt gtcaatgcat ctgttgctcc 145380
ttctagaaga cacagtctgt ccagcacaaa gttacttagt ccccagatgt ctggagaaga 145440
ggaggattct gacttggcag ccaaacttgg aatgtgcaat agagaaatag tacgaagagg 145500
ggctctcatt ctcttctgtg attatgtcgt aagtttgaaa tgcctgtaaa cggggttgag 145560
ggaggtgggg accaggagaa catcctgtgt agatgacact tgcatggacc ctctggaacc 145620
cagaccgccc ggtgtcctgc caagctccat cgaaactaaa tctagaatga atgtttactt 145680
ctgctgtgac atataattgg agaccaggcc tggccttcca gtcactggat tctaagttgg 145740
actgtgagag tttttgcagc tgactcattt atcaaatgcc cggctattgg ctcacgccta 145800
catgatgctg ggtatgtttg ttaatttgag ggaagcaatg gaataataat aactaatgat 145860
ttaaaaaaca aagtaagtgc attgactgta gtggggttct gattttaaat ttttttaaaa 145920
attaatacca ggagcagtgg cttatgccta aattccagca actcgagagg ctgaggtagg 145980
aagatcactt gagcccagga gtttgagaca agcctgggct atggtgtgag acacccatct 146040
ctaaaaaaat aaaaaataaa aaattatcca agtgtggtgg ctcgtgcctg taatcacagc 146100
tctttgagaa gctgagggcg gaggatggct tgagcctggg agttcgagac cagcctggca 146160
acacagagaa accctgcctc taccaaaaaa agaaagagag gaagaaagaa aaattagcct 146220
ggcgtggtgg tgcatgcctg tggtcccagc cacctgagag actgagaagg gaggattgct 146280
tgagcccaga agtttgaggc tgcagtgagc tgtgactgtg tcactgcact ccggcctggg 146340
tgacaaggcg agacccctgc tctaaaataa tttttttaag ttaatttgta gaaaaggtgt 146400
tagatgttct ttgtcacatt ttatgatgga ttcctgttta aatgccgttc tctttaaaga 146460
aaaaaaaata acttgtggga gtttttaacc ataaaactag catcacatat ttaccatgga 146520
gaatttacaa aaaaacaaat aaacggagga aaataaaacc tcctgtaatc atactactca 146580
gagataactt gctgttagat tttggtctag atttaatact ttttctatat ttatattaaa 146640
aatatttaaa acatatgcat ttctttgtca caaacatggt atcttataga tactactgtc 146700
acatagcaaa acagtgttaa atattctgaa tcagaaaagg aagccgactc tccaactgaa 146760
agaggtgtta tcctagagac tttttctggt gatgacaatt tattaatagt cactttttgc 146820
tttactttct ctattgaagt agtttttcta ttttgttcta cttttaagga taatataatt 146880
tataatgctg tttttcacag aaatataaga aaaaagatac taattttata agttaataaa 146940
gtttgatcat cccaaatcca aaaatctgaa atccaaaatg ctccaaattc tgaagctttt 147000
tgagtgctga cattatgttc aaaggaaatg ttcattggaa ggtttcagat tttcggattt 147060
agggagctca acaaataagt ataatgcaca tatttcaaaa cctgaaaaaa atcctaaatt 147120
cagaatactt ctgatcccaa acatttcaga taagggttat tcaacctgta ctgtcagatg 147180
atcccaaatg aaaaatatta atcgttaacc aaatatcaag gaattgatca cattttacag 147240
tttctgccta ggattatgaa tcaagatgaa aaggctctgc atgtttaaaa atatatattt 147300
ttattttctt ataaatctta aatatctaca cttaagattt atttgatatg tgggatccat 147360
tcatattttg gattcaacag ttctgtcaaa actgtggcag tgatagggga ttcttttttt 147420
cccactgaac tatcacaaaa ttggaaaaag agtaattgga gaaccccact ggcttagccg 147480
gcccgaagcc cgggagaggg caggcagtgc tgtggatggg gtcatcccag cgcaacgctg 147540
cccctgctac ctgcggatct cgctgaggcc tgcctttgtc ctttgaccct tggccatttg 147600
ttagtgtctc tgagagctgg actgctgtac cctacttccc caggggggcct aacttcacac 147660
agcctctgcc gcagtgcgtg gttggaggtg acggccttgg taaatcgagt ttcctacctc 147720
ctcaattatt tgtgctcata cactgtatat ttttagtgag gtttatattt gggatgtgtt 147780
ttctccttct taccctttct ggcctttcta tggcattaat acctggtctc ttcttgtgta 147840
cttgaaaatg aatctctcat catatttttc cttagtgtca gaacctccat gactccgagc 147900
acttaacgtg gctcattgta aatcacattc aagatctgat cagcctttcc cacgagcctc 147960
cagtacagga cttcatcagt gccgttcatc ggaactctgc tgccagcggc ctgttcatcc 148020
aggcaattca gtctcgttgt gaaaaccttt caactgtacg tcttcatcct gccgactatt 148080
gccagttgca gttttccctg ccttaaaaat ggagtattga aatttttaac tttaatttct 148140
gatttgcaaa atagtcatct tttgttcttt tccttcttgc tgttagccaa ccatgctgaa 148200
gaaaactctt cagtgcttgg aggggatcca tctcagccag tcgggagctg tgctcacgct 148260
gtatgtggac aggcttctgt gcaccccttt ccgtgtgctg gctcgcatgg tcgacatcct 148320
tgcttgtcgc cgggtagaaa tgcttctggc tgcaaattta caggtattgg gaagagaaac 148380
cctgatattg atttatattg aaaatttagc aggccaagca aaacaggtgg ctggcttttt 148440
cctccgtaag tatggtcttg acatggtcac cgatagaaac atggaaacat ctgcaaactt 148500
gccgttactc gtgtgtccga tctgactgtt tcttgtattt ttttctagtc tgcccttact 148560
aggatgaact gtacacatca gttcatcctt tttaaatgag catgaggtta ttttgggttg 148620
ttaggtgtta caaacacact aatgtgtttt tgtctattag agcagcatgg cccagttgcc 148680
aatggaagaa ctcaacagaa tccaggaata ccttcagagc agcgggctcg ctcagaggta 148740
atgctggaaa cacaggtcgt ccttgtgtta ggacaaccca ggatataaag gatatagatt 148800
tgtacgggaa taaattcaca ggacaagaaa tcgatgtgcc ttataggtgg gtttactgca 148860
gaagtgccat aatagaacct tcctactttt aaaacaacca gatctcactt tctaaagagt 148920
aaaggatgac cggcaggatc acgtctgtga cgtgagtgga ggcagtttgc actcctggtg 148980
gctgtttgag aggtagcatt tagaatgcct gtattcactg tcctgtgatg agtgggaaaa 149040
taggttatca ggtttatctt agcaaaatca aagcatgtca tctaattgct aaacaagagt 149100
tggcaaatct gagagacatt actcaatcct tggcatgcag gacttacatc tgcatcctgt 149160
tgccatttta tgtcttcaaa gcatttaatc atttagttgt gtttgcaaag tctttgagaa 149220
gcctttgtca gaaatcccta catctcctat gtgagtgtat ttccatgact gcagaataag 149280
ttaaactttt accttttcc ttcccttgcg gggcggggtg gggggcaggg attgtgtgtg 149340
tgagagggag agagagacag cagagaagga gaatataatt atcatgctgt gtactttgag 149400
ctgaaactgc aaaaaaggaa aaacacacaa aaattattat gcttttcagt ctttagagta 149460
ccttgtctat tatgcttttc agtctttaga gtaccttgtt gatggtgttt ttaaatggga 149520
ttgggcacaa ttaggtggac agtttgggat gatttttcag tctgtagggc caagctcttt 149580
tgtaatttgc attatgaagt tgtcactctc atagcagatg gcgggagata aactattatt 149640
actttttgac cctagactta gtcttcagtc cagatgaggg agattaaaag attataaata 149700
tcttgtgcca gatgaggtga ttttattttg aaatgaccat gaattcctat cagttgtctt 149760
actgggatat ttgatagtgg aatttgtgca tttgagtctt agatgatctg ttttacattt 149820
attaagaaag cctttattag cttttatact gtgtattgcc tgttgcagtg tttgagtata 149880
aatgaaattt ctggaaaata ttaatggagt acaaactgtg atacttaaaa gtaaactagg 149940
gcctgcattt gtatcatgac ctgtttgagt attgatgaga agatagctgt gaagaaaaag 150000
gtttaaacaa gtgtattttc ctttaagaag ccactaatag tgcatctcct tagagtgtat 150060
atttctagaa tcctagtgtg cagagtttag actaagacta aaaaaaaaaa aaaacaaatt 150120
atactgtaat ttcattttta tttgtatttt agacaccaaa ggctctattc cctgctggac 150180
aggtttcgtc tctccaccat gcaagactca cttagtccct ctcctccagt ctcttcccac 150240
ccgctggacg gggatgggca cgtgtcactg gaaacagtga gtccggacaa agtaagtgtc 150300
cagcgtgtct gcatgggagg cacagggcgc tgagtgcctc tgtcacctgt ggcagataca 150360
gagagtgcag aggaggtgcc gtggacccaa ggagttctgg cgctcggctc ggctcagtga 150420
agctgtggtt agagacgtgg ggggccatca aggtctgagg gagccaagca gtgctgatgt 150480
gggacccttt tggtaggagt gtggggtgag tagttagtgg gtgaatcaag gaatagtcgg 150540
ccgtggcctg caggcccctg actgcacagg ccttcaagca catgtcaatg ccgttagcct 150600
ccctccatct cctcatacct tctggccacc tgtgagttgc actgccactg ccagccattc 150660
tggtatgttg tcagcacctc cactgctcat acctcatggt tagggaccac ctggagcctt 150720
ggtagagcct tggtagagcc ttggtactct actttcctgg acaaagttca gcttatgaat 150780
atgaatttag atttcaaaaa ccagcagccc aagtataaga aagcgaaggt tcagtcctgc 150840
cttcttaggc tctattcgct aagcacctgc cctgccctgg ttgctgggga gagatgagta 150900
aagcagacaa cccaggagag gatggcaaag gggccgctaa cccttagtgg tttagctata 150960
tttggaaggc ctattggaag ttcaccaggt gaagggggag gctgtgaggg tgcccaggca 151020
ggtaacagaa gtccaaaggg gaaaacctgt ggtgtggtga gccgtatagc cacagcctgc 151080
cggccggcag ccctctcagc ctagtgcggt gttcccaagc actggcctag gcctgtagct 151140
ccagggatgt gaagtcccct tgaacgccgc ccatcatgtt ccccttatcc atttttttct 151200
tcccaggact ggtacgttca tcttgtcaaa tcccagtgtt ggaccaggtc agattctgca 151260
ctgctggaag gtgcagagct ggtgaatcgg attcctgctg aagatatgaa tgccttcatg 151320
atgaactcgg tacgggggga gcagtggagg caaggaatcc tcagcttttc ttgtgacttc 151380
caagtgggat ttgtctcatc atcatgtgac ccacttgttg acaacacatg ttggggactc 151440
cagtctgggc agggacggga tgtcggagag actccactct gaatggggcc gggaagtggg 151500
gaggactcca tttcagatgg ggtcgggaca tgggggttat gctgatcgag acagaaaagc 151560
acattgtttc agccacatta gaatccacgg aggtgttgtt ttgaaatcca gctggcccca 151620
aggctgggtg tatggtttgg gatgagaact atctggcctc cactggagga acaaacacag 151680
gatgttatca tctaagctcc atggccaaga cagaatggaa gtcaaggttg cgtatttgcc 151740
gtagacttca acacagtgtc gtaatgcgtg acgtcaataa cttgtttcta gtgtcttgga 151800
agttgatctt tagtcgtaaa agagaccctt ggatgcagcg agatttcctc tactcacacc 151860
tctgttagat gtagtgaggt tcttcacccc ccaaccccag atgtcagagg gcaccctgcg 151920
cagagctagg aggccatgca aagccttggt gtccctgtcc ctcacccgtg ggcaggtcct 151980
gtgagcagtg ggggggccac ctcttgggta tggtgcagcc atggcccaag cagggcttct 152040
tctcagacct actaggacgg gagaaacctc ctggtgcttt agccctgcgt tgatatgcag 152100
caaatgggag ggaagtgggc acctgggagg acaaatgcct gtagaggccg ggagtgacgg 152160
caggtgttca tgaaaagaga ccttgtgggg agggcaacac aacagtgtgt tctgatgtac 152220
tgaagagctc aactgaaaac aacaggagaa ttagcccaaa atccatttac taaaattgtt 152280

-continued tatcttttt ttttttttg agacaaagtc tcgctgttgt cccccaggct ggagtgcaat 152340
ggcgctatct tggctcactg caacctccgc ctcctgggtt catacgattc tcctgcctca 152400
gcctcccaaa tagctggtat taacaggcat gcaccaccac gcccggctaa tttttgtatt 152460
tttagtagag acgggatttc accatgttgg ccaggctggt ctcaaactcc tgacctcagg 152520
tgatccgccc acctcggcct cccaaagtgc tgggattata ggcctgagcc accacgcccg 152580
gcctaaaatt gtttatctta agattcatgc agtgaaagct aacttactga gtgataaatt 152640
tgcttagtga tctgtttatt aggttttcca aatttgctaa ttgggctttg aacagctgta 152700
aaagttctga ctgtaaaaga aagcttcaac ttttggcatt catgatgctt ttctgagtat 152760
taaactaaga tagatgtttt acctgaagga tcggccacca atctttaaat ggctaaacaa 152820
aagggttgct aaaacataat ccaaattgac ataagaaata ccatttttcc aaccaaaatt 152880
ttggcattca tatggctact tttacgtatt tcagctgcat ttgaacatct ttttcaaact 152940
ttagggtggt tggtgtatca ctgaggtctt ggatgacact ttagctttga ttttgttttt 153000
atgaattaaa attgtcatac caaaattttt atttcaagca aatccaagag cataaaaaat 153060
taaaatatta cttaaaatac taagagagaa cagatatata ttttactaag catatgttga 153120
atgaaattgt tcaaatattt ataacaggca tagagtagaa ttttcttaaa aatatttttg 153180
atggtatacc aatttgtatt ttctcagaaa catttgcctt attctttttt ctgttgtgtt 153240
tttcttacct gattgaaagc tcataatctg ttgttattgt ttgttaacct ttaatgctct 153300
gatttcagga gttcaaccta agcctgctag ctccatgctt aagcctaggg atgagtgaaa 153360
tttctggtgg ccagaagagt gcccttttttg aagcagcccg tgaggtgact ctggcccgtg 153420
tgagcggcac cgtgcagcag ctccctgctg tccatcatgt cttccagccc gagctgcctg 153480
cagagccggc ggcctactgg agcaagttga atgatctgtt tggtaattaa aattaaaatt 153540
tatcttattt ttaaaaagca ttccagggcc agtatagtac tttgcaccaa gtaaatgtac 153600
aataaaggca gtggatctaa tacattgaaa gcgtttacag aggtagctaa agagcagcac 153660
gggtgtcctc ggctcagaat ttcttcctgt gtgtttgcca ctttgccatt cattgacatg 153720
gtcatggaca tagggctcta agcccttgag gaaggctggg ccagacctca ggggagatgc 153780
agccccaaac cacgtgcagt cctgtggacg gatgtgtaga tgtgccactg aggaacaatg 153840
tcttgagctt tcatcagatt ctcagagaat tgcttgactg cctttcgaag ttgatgcatc 153900
tgtgctcacg tttgcaccca cccacgaggt ccttctgttt caggggatgc tgcactgtat 153960
cagtccctgc ccactctggc ccgggccctg gcacagtacc tggtggtggt ctccaaactg 154020
cccagtcatt tgcaccttcc tcctgagaaa gagaaggaca ttgtgaaatt cgtggtggca 154080
acccttgagg taagaggcag ctcgggagct cagtgttgct gtggggaggg ggcatggggc 154140
tgacactgaa gagggtaaag cagttttatt tgaaaagcaa gatctctgac cagtccagtc 154200
acttttccat ctcagcctgg cagtaagtct tgtcaccgtc aagttattgt agccatcctt 154260
caccctcacc tcgccactcc tcatggtggc ctgtgaggtc agccaggtcc ccttctcatc 154320
tgcacctacc atgttaggtg gatcctaatt ttagagacat gaaaaataat catctggaag 154380
tactttatgt cttaagttgg cctggacatg tcagccaagg aatacttact tggtttgtgt 154440
tagtgcttgt aattcgcccc cagaatgtgt acacgttctg gatgcattaa agtctggcct 154500
gtatccttaa agggccatcg ctgtgctgcc tgccctcagc aaggacacac tttgcagacc 154560
cacagaggct ccgcctccac ctcacaccaa agaaagggag gagtccaaag ggcatcagtg 154620
ccattactca caaaatgata aatacaccct tattctgaac cacgtggagt catatggttt 154680
gtgatccctg tccttcaggt ttcagcttag tggggaagtg ggaaagtcag cgtgtgatca 154740
cagcacaggg tgattgctgc tgattatatt atgtgcctgc tgtatgcagg atgaaatact 154800
ttatatgcgt catcttattt gactctcaca accccctgtg agataggctc tgttactccc 154860
atttgacagg tgaggaaagc aaggcttaga gaatttcagt gacttgccca ggtcctctga 154920
gctaggaagt agccattctg gcatttgaac ccaaggcctg ctatccctag aacccacgct 154980
ctcaaattca acctatgaca gaggcaagcc ctggtgctgt gggagcccca aggaagagcc 155040
tctggcctgg tggccacgta gcccaggaga gatttctaca ggagcccaca gcgctgaagg 155100
agagagaggc agcagagtaa gggggctttg tggcagagag gggactggca ctttggggaa 155160
taggtgggtc aggactgaat gtaatggagc catgtcagag ctgtccttct ggaagggcaa 155220
gggcacctgg acgcgctgcc cctcagtgct ttggacggtt ccacaactgt gattcacacg 155280
gcttccccaa acgaaggtac acgagtgggc attctgtgac tcggtacttc cctttaggcc 155340
ctgtcctggc atttgatcca tgagcagatc ccgctgagtc tggatctcca ggcagggctg 155400
gactgctgct gcctggccct gcagctgcct ggcctctgga gcgtggtctc ctccacagag 155460
tttgtgaccc acgcctgctc cctcatctac tgtgtgcact tcatcctgga ggccggtgag 155520
tccccgtcca tgaacggtgg gttcctatca tagttcctgt ctgcttcacc atgtttttat 155580
tttgtgctgc ctgtttgcca ggtactaagc taggaattgg ggatggagag gtagataaaa 155640
tatgcatcag gaagggctgg gccccatctc ttactctcca atatattgga gtctacactg 155700
gaatttaact ggaatttgct tttttagtca ttttatttag attttgaagt ttcagctttc 155760
atcaaaaata cctctaaact ttatgtctct gtgatctttg gtcttagctg ttttatgtat 155820
ttagtcttat atgatcataa gattaataac attacattca gaagattatt tgttttctgt 155880
cagagttaaa atgtttgttt ttatactgca ttgtaatatt aacgtactgt aaaataaaag 155940
tggcttgttc ttttcaagga acagtatcct caacaagggt cattagccac aatttttaaa 156000
aaattggacg tcatagttta catgttagag ggcgttttga agctttgtat ttttaaatta 156060
aatgttatag agtgatgttt tcatgtttca taattgtttt catctgtgca tttgtagcca 156120
acttgaaaac aaagatccag ggattactac ttaaaagcca gacttcttgg aggttatagt 156180
gatgattttg atagtatctt gagccgtctc ataataacct cagggtgaga gatggccaac 156240
aggagacagt cgagggactt agaaatctga atgaaatctg aagttcaaat cttcagacat 156300
ataccactaa ccaagagatt ggtacctcag tctagtattg tctgtttgtc taaaattggt 156360
tctaaggaat ctaggctagt ctgtctatcc ctttcaactt ttgtgaggct gcacaaatgt 156420
aaaatgttga ataaaaagca ctgatggaag tgtgtagaaa ttcttctctt tgttctgttg 156480
taattttagt tgcagtgcag cctggagagc agcttcttag tccagaaaga aggacaaata 156540
ccccaaaagc catcagcgag gaggaggagg aagtagatcc aaacacacag agtaagtctc 156600
aggacccatt tttttcttac atgttgttcc tccaggactt aaaaatcatt cacagagacg 156660
tgcaccgcgg tgagtgtgga ctcctggaag cgcaccgtag ctccgctgtg tcctgctgct 156720
cctccctagc tgtcagggag gctgtagtcc attgctttgc cagctctttt gtttccgagt 156780
gaacacctta tccgtacaca tgcggctgtc tctgacccta cagaccagct gggatgccac 156840
tgggggagcg ctcccttccc cccgcacttc ccacactctg cagttattct gagatccttg 156900
agggcaggga acaggtttgt cttctttgtg ttctcagaaa ttaatgctcg gcctctggtc 156960
agcaagcaac aacctttgt tgagtgataa tgaataaata aatgtttccc acatgagtat 157020
tcagtaacct cagtgtcagg ttcagccatc tgttttggtg gatatttaaa agaaaattcc 157080
gcttttccta cagaaaaaaa aaaaaatcca aatcccagtg atttaagcca gttatagact 157140
tagacatata ctacggcttt tcatgcactt tcctcccaat tctagagtag gtattttact 157200
aggaaaatgg tggcagtgcc tgttgggagg aagattcttt ggccaagtgt cttttgttct 157260
tgccagggcc cctaggctgc tggggtgctt cagcttcttt agcccagtgt ctggtgggga 157320
atggcccctg ttgcctgtcc cacagaggtg ggggtgcctc acctggagcc tgtccacaca 157380
ttttacacag cacgcttacc tggagcatca ggcatctttt ccatgctctg tggctcagga 157440
aacacgcctt ttcaatcatg agtgcaccag tgcttttggg ctttttctcc ccgcttttgt 157500
gcaatcctgg ttgtggatgg agttttcctg tctttagtct tctgcatagt acttttctct 157560
tctggttccc ggttcaaggt tttgtaatta gagaatgacc cagaagcaat ggcattttaa 157620
tgcacagcca aggacttctc tgaatttgta tctcaaacct ctgtgggtcc ttcaggcttc 157680
agtttgtgat ttcatgattt cttgttgcta cctaaggaat atgaaaacac ccacctccct 157740
actctgcatc ttccagccga gtggcacctc aggctgtgga tcctgtgctt ctgtggtgag 157800
gataagaata gtgccaaccg tgtggattga aatcaatcag ttaatccctc catgtaaagc 157860
acctggaacg gatgacagtc ttgttatgaa tactcaacaa atgctatcat gatttttagt 157920
tagatttcca ttgctttaaa acagttgaga catcttggcg gtttgagtta gagcaacggg 157980
ccctgaagtg ggttctgttt gggtgaagat gattatgctt attccccatg gccctcttta 158040
ggcaagagtg ggaagctttc tttgtttttt taatcacctc gataggacgt tacttcttaa 158100
aggtcatcca ataaatatta ataggccggg cgcggtggct cacgcctgta atcccagcac 158160
tttgggaggc cgaggcgggc ggatcacgag gtcaggagat cgagaccatc ccagctaaaa 158220
cggtgaaacc ccgtctctac taaaaataca aaaaattagc cgggcgtagt ggcgggcgcc 158280
tgtagtccca gctacttggg aggctgaggc aggagaatgg cgtgaacccg ggaggcggag 158340
cttgcagtga gccgagatcc cgccactgca ctccagcctg ggcgacagag caagactccg 158400
tctcaaaaaa aaaaaaaaat attaataaag ccaactcgtt agcgtggggc ttaattgctt 158460
aagtccaatg agaagtcctt ctctatccta ggaagttgcc caaactgtag aatctcgtgg 158520
cctgtgggta atagccacgt aatacacact cactgcctca acaaatcata ttttagtagg 158580
tatgatattc tagactcaag acaccattct gtggatcttc ccaagggtgt gaagtgtcca 158640
cagcgtctgc cttgggagtt tccatgccca ccagaaccat gccccaagcc cctcaagcac 158700
tctgacctag gaaagccagt gaagcaagga tgacaacatg gccctttgat actagctgag 158760
ggacagacac aggtcctggg agaccagaga aagacgaggg gcagaggagg tgtcctaaag 158820
gaagtctgag gctgaggagc cacaggatgg cttccagctg tcacaggctg ctgctggcct 158880
tatcacagag agtgggccag agggctggga accaaggcca gagctcaggt tcaggaccat 158940
tccagcaatc ccagcagaaa atggggagaa ttgtatggta taggcggata tgaaggtaga 159000
atctgcaggc cttcagtggc caactcagag tctaagtgga ttccacagtt acagcttgag 159060
cagctggttg taggtcatgc tttctacact gggcatatag gatgtgtttt ttaaaaagtc 159120
ctctcttaac cgttgcttgt ttagatccta agtatatcac tgcagcctgt gagatggtgg 159180
cagaaatggt ggagtctctg cagtcggtgt tggccttggg tcataaaagg aatagcggcg 159240
tgccggcgtt tctcacgcca ttgctaagga acatcatcat cagcctggcc cgcctgcccc 159300
ttgtcaacag ctacacacgt gtgcccccac tggtgagtct gctcgttcct tgcagaagac 159360
caagtacggt gaaaggcacc ggtaggccct gggctgggca cacgtgagag ggcgggacag 159420
aatccccgca gcccagaggc tgcctgctgt ggttctggtg cccactgtgg ttctggtgcc 159480
aggctgcttt cctcaggcac cacgtgtgga ggtcgctagt agaaatactg ggttttctaa 159540
aatgaactga ggccctacat ccctaagaga ttagtgttag acctgattct agagcaacta 159600
gaccactttg cttaatagca gaccagaaac cacacccccct cgagtgagtg agattttcct 159660
ttggagataa ttcatgtttt tctacacagt tttgcagttg tcttcagaat tggtttaaag 159720
taggtgttat tgccaggcgc agtagctcat gcctgtaatc ccagcacttt gggaagccaa 159780
ggtgggcgga tcacttgagg tcaggatttc gagaccagcc tggccaacat ggtgaaaccc 159840
catctctact aaaaatataa aaattagcca ggtgtggtgg tgtacgcctg taatcccagc 159900
tactcaggag actgagacag gagaatcgct tgaacccagg aggcgaaggt tgcagtaagc 159960
cgagatcgcg ccactgcact ctagcctggg caacagagca agactccgtc tcaaaaaaaa 160020
aaaaggtagg tgttattgat cagaaccctt gtttcagata acatgaggag cttagcttga 160080
ggagagtgag ggttgatgga gggggactga cttctgccca gtgaaatggc atcatctccc 160140
accagcccgc tgaaataaga tgatggggcc tgttccttag ggcctgcagc atcctcaggc 160200
aggaaagaaa ggccgacctg gcagggtgtg agccagcagg tgtaggtcag ggagaatgga 160260
gccaggtccc agggaagagg cttgtggctg cctgagaagg gtgcgtgcct gcctgtgtgt 160320
gtgtgtgcac gtgtgtgtat gtatgctgga gagtctaggg aggcttgctc caaggacgca 160380
gtattgtttg atcctgagag ataaggattc tgccgcaggg aatgaaggta ttccagatgg 160440
cgggcttatt ccgaagaaga ggccagtgcc tggcggtgct ggaagcagtt gcagaacagg 160500
gagttgtagg ctttcctggg aagagagcag caggggtgct ggagaagcag gccacacttg 160560
ctgcatgggg ttgctctcgg ccccactctt ggtgcacagc gagtcactgt gggttcatta 160620
gcatctggtt atgagacagt aactgctcct ttggaggggc tcgtggagac catgcaggag 160680
ggcacggtct tgaggtcatg ccgtccagag cacacctgag gataggccag gacgggctgc 160740
acgctgtagg taaaattcct ccagcaagct cttcactggc attgaggagt tccctgagtg 160800
cggtcatctg gaaggcagct gtaacaggca ctgcagtctc tccctgggtg ggtaccagag 160860
aggagcatag gggagcataa ccgatttaaa gagagggctt tcctgtggtg aggtaagaga 160920
ttagctggtc attatcatag agccccctct gcctttgtgc agatgggctg tgggaatcct 160980
ggggttccgt tgggtccttt gtcacctcac tgaaggcatg taagctgagc tggccagacc 161040
gtgagctgat cctgccactt gaacagcatc aagcctgcct ctggattctt ctgtgcatgg 161100
cacttgtctg agcacctcac gcacagagaa ctggacttca gagtttacag aaataagctg 161160
tatggttcat tttcatgcct gcttgccaat aaacatatct gagctgaacc tcattgaacg 161220
cctgccttta ttctagcaca gcacctgctg tttgtgggcg aggggtgctg tctctaactc 161280
ctgcctgctt ctcccagcac tccctgagtg gggtgtgcca gcagcctcag gatgaggaca 161340
ggaagtggga gggcagagca gatttgggag ggccacttga tggggaagga agtcccagga 161400
agcagttgga gctgttttct gggggagaag gtgccagctc tgggacagtg ttggggtagt 161460
gaggagggag cccagtggag agaagtcggg cttcctgctt cctcacagta tgtctgtcct 161520
gactcaactc ggatgatgtc acttcctttt catcttctca ggtgtggaag cttggatggt 161580
cacccaaacc gggaggggat tttggcacag cattccctga gatccccgtg gagttcctcc 161640
aggaaaagga agtctttaag gagttcatct accgcatcaa cacactaggt actcttgggg 161700
cctctccttc aggtcaccat tgtcggacat ctaccgggag gaaatccaga gcccccagta 161760

-continued ctgggatctt ctcatttgac tccagaaaag atttaagcat gataataata caaacctatg 161820
tgaatacatt ttgcagtgtt ggcaaaactc cttttatact gagaaaatag atcccagttc 161880
ctgtgttttg tggcttgaat cccagctttg tgtattccgg gcttgtttga agtcaggaaa 161940
ggttcatgtg tagtggacaa cgtgagacca aattctgcct tagattttgc atttaggcta 162000
aacagtggca gcacttgtct cagaatgttt tcttgtgttc accagtctga tcctgttgtg 162060
tctcagtggt ccattttctc atatgggaac aagcagacgg gagcagatgg agtcaggttt 162120
cttggcactc gccttcccca gagcctagag gcagcatggg gagaaagcag gcttggggct 162180
cagacagtcc tggtctgctt ccagccctcc tacctgagca gcgcagggca agtccgtcta 162240
acctctagag accctcagtt ttgtcatatg taaaatgggg gtcgtgtcta tttcatagaa 162300
ttgttgcaga tttagaaatt acatttctaa acaaatgtta ccccttattt ctaaataagt 162360
gtctaaatga ataagtcacc acttttgccc ctatttgatg gcaagaggtg tgatcttgtg 162420
gtgggactgt aatcagtcag ttctcagtga ctgtgccctg ctgtggtgtt tcctggaatg 162480
ttcctgtctt gtcctagaaa gtctggcagg ggcaccctga ctccactgtc cagtcctctc 162540
cccagtccct cgggcttctg cagatttgag gcttgtttgg atcccagaag gttgtggcag 162600
gagacacctt gcctctactt tcccctttat aattcaatgt ccaaagagag ccctgagcag 162660
gtacctcacg ccagctgcct cacggagctc ctcctcttcc tggctgtgag gatcggtatc 162720
agtggcctcc tgctctctcc cccttgccta acacgagcac ctttgcttac ttgggtgccc 162780
ttgctcttga actgcccatc ggacgtgcgt gacccaagac tgtgccgcag tccttgcctt 162840
gtctgtgctc attttctttg ttcatttttt tccctgtaac gtaaattgtt atatttgtct 162900
gtatctgtgt ctgaatcagt cctgcacgct ctccttctct ctgtctcttg ttctttcttt 162960
accccgttta tcacggggac cccgatgtcc attgctctag ttctcctgtc ctaagcaccc 163020
catcccgtct ctctggcctt accacaagtg gcgtggctgc ctcagacatc atgatgggga 163080
catgaagcac agctgtcaga aacaactgtt cgttagatac actcgaatgc agctcatcaa 163140
tagggatgga gggtctgtcg gatgtatttt cactgaatcc ccgttcctac cttgatacac 163200
tctttttaat ctattcttct agacaggtca gaggaaccat tactttgact tttaaatttt 163260
tagcagcttt attgaggtag aattcacata ctacagattt cacccactct aagcggacag 163320
cttggtggcc attagtttta tccacagagt tgtgcagcca gctgcacagt ctcagggctg 163380
gactccaggg aagattttag cccatttagt gagtggggca gaagtggccc tggccctgca 163440
cgaggttgcc tgcatgggcg tccctgccct gtccctgtgt ctgctccact gggggttgac 163500
caggctgcca gggccgactt gggcctgtgc cacctgcctc tcatgtgtct cggacagtgc 163560
agccgatgtc tatacttcgg tttcctcaat gatgaaatgg aggggatagt gttccccgca 163620
tcatagaact gtgtgaggtt taagggactc actgcccttg gcgtggagcc ttctccaggg 163680
gccgtgctgt gtcggcgtag ctgtcagctc tccgttacag gcttgagaag ggttgacact 163740
ctctcatgta acatttatat ttctaggctg gaccagtcgt actcagtttg aagaaacttg 163800
ggccaccctc cttggtgtcc tggtgacgca gcccctcgtg atggagcagg aggagagccc 163860
accagaagta aggccacacc ctgtgctggt tggcacatgg gcagttatgg ccgcttgcag 163920
gcctttggtg gggaataaaa taaggcagca agctggtgtt cttttttttct cttaccttat 163980
ttttgaaaga gtagctgaat ggtgtcttga ctgatattcc agagcaggga caaagcctgc 164040
tgaggtctgg gggctgcgat taccaatggc tggaatgcat tttattacgg tgcattccat 164100
gttaaggatc aatacgattg tgccctttct ggaaaatatc ttttagttta tcaatattca 164160
gaggagtgta ggttgaatta aaatgaaaag gcactttata aaggccatga gtagtacctg 164220
gtttcatttt tctaatgtct tgcagagatt ttatcaggct tcttgaagtg ttcacgtaca 164280
ttacgctaac acgatattaa taataactgt gctctggtac agcggagcca gcagaatggg 164340
aagttgtgga atgcaggccc ttgattctga tagaaggtgt ggtttgaact cacagaaatg 164400
acagtttgga gggtagacat atgtcacaag tcatcaagat tgtctttaaa ttcatgcata 164460
gaagctaaca gggtgtcata agcaaggcct gtaaaatgta tgagggaatt caaagataat 164520
ttattaaaaa gtaattcatg tttggagttt tgtgcccaaa ggagtccttg atttgaaaaa 164580
tgggcttttg cccatcagat tgtttcaggg cccgtgtgtg cggaggccct gccttgtgcc 164640
ccgtgagctc agcctgacag aaatcctttg gtagcactta aggctcctct tcctcccatt 164700
gaggcaggga agactctggg ttctgcaggc agaggtggtt gtgggtgtct tgctgctctt 164760
gttgacatgt gggctctcct tccaggaaga cacagagagg acccagatca acgtcctggc 164820
cgtgcaggcc atcacctcac tggtgctcag tgcaatgact gtgcctgtgg ccggcaaccc 164880
agctgtaagc tgcttggagc agcagccccg gaacaagcct ctgaaagctc tcgacaccag 164940
gtttgcttga gttcccacgt gtctctggga catagcaggt gctggggaca gtgggttccc 165000
cgctgaagcg tccagcagct tcaaccaggc cgttttcctt cattgctaga attgaaaaca 165060
ccgtccgtgt ggcctgtgca ggagatgcag acccaaaggt ggcctcctgg tcagtgagaa 165120
gctggaaacg tgacaggaac tgacgtgggg ttattgagca tttaggggaa gacgttagca 165180
gagcaggaat gagcaggcaa ctagtagaac acccacttaa gggctcacgg acaggtgctc 165240
acttaggaag tgagtttcat ttggtattac accaggttcc tttaggcaaa gcggagggaa 165300
agttctggtg tttttcactt gtaagatttt gaaggaaaca aaacactctt taccttttt 165360
ctaaaatgta ggtttgggag gaagctgagc attatcagag ggattgtgga gcaagagatt 165420
caagcaatgg tttcaaagag agagaatatt gccacccatc atttatatca ggcatgggat 165480
cctgtccctt ctctgtctcc ggctactaca ggtacctgag ggaaagggtg cgggggagcg 165540
gttgtacttg ggctagaatg agagaagact ggcatgctca ccacaccagt gatgcgggaa 165600
gacctgagtg tggtctgagt tggaggctgt ggtgctaaat acgctgcccc tttcataagc 165660
aggagtctta gtcaggccca gggaggaagt aaaatctgga aatgaatgag aagcattctc 165720
tcctgccagt caagaaatga gaagcgaaag aattctcacg ggctgtaaga ccagcaggat 165780
ttaaaagttg aattagttgc ttatgttaag aactcaacca agttcatcta cacaagctga 165840
atctccagct tttcctaaga aaccatgtgt ggcagtggct gcagggcagg gcacagctgg 165900
gcctgagcac cccgctccct gcacctctcc cctccctggg ccctgcctgt cactgcccac 165960
tctcccacca agccttccgg ttgtgtgcct gccctatcac aggcatcgga gcttgtcacc 166020
tggtttaaaa gaagagagtt gtgtggggat ttgggatgca cgtttttcac tcaaaagtat 166080
tttagcgtag agctctgtga ttccgtagct atttaggagt ttaagcacct tgaaggcttt 166140
aattgcagaa agttctatgt ggacgtgcaa tgtgttatac gcagtgtcta tgagactcaa 166200
atgtttatta gggcgttgaa gtaaactgag cacttggagg gccatggatc cagccttcaa 166260
ggagctcata agtcaggagg acccaggagc aatgacctgt catagaaggc agaaaagagg 166320
ggcacagagg tgggtgggag gcatacacag gcagctcctg gagctccaag gggagcaagt 166380
gcttccaggg aagggggcgt ggaggcccct ttggaggagg caagttgatc tggggtctgg 166440
cagagggtta gctggggaca tttagcggga ggctggtgcc cgggaattgg ggggatgccc 166500

-continued agcagaaaga catgaggagg ctggcctggg gcgtgggggg gtgtgaaagg ttaagtgggg 166560
gcattatcct gctcccgctc ctgccggctg tatctggtca gcctgggcac cgaggtgggg 166620
ttctggaagg cactgttcac caaaatgctt atctgggtcc cccagagagc ttgcctgcct 166680
ggactgtcgg ctcgcctgca actgctgact cctaagcttt tgcagctcag cccacaacca 166740
gttcctattc acagaggtgg gagctgaggg gtgacaagtg actgctgcag tcttatttgt 166800
catagagaaa aagtgacaga gtccagcttg cccactggcc ctgccagctt aactggttat 166860
aaagtgacaa atccccaaga cccacagggc tctgcacaac ctgggccctc ctgccagtgg 166920
cggcgagggc aggtggctca cggctgggtg cctgtctggg caggagctgg gctggtatgg 166980
ggtgggcctg cggccctgcc cccctgtgca gatcaagact cagggtgctg gtgttcacag 167040
gtgccctcat cagccacgag aagctgctgc tacagatcaa ccccgagcgg gagctgggga 167100
gcatgagcta caaactcggc caggtcagtc tcgcgccccc gccgcctggc ctctgtccgt 167160
ttctgtcctc agactttggc gcttgacaca cccaggagaa aagctcagtg cactttttaa 167220
atgaaaggaa gttttccttt tttttaaaaa aaaatttaat gttcattgtt tttatctgtt 167280
ttattcctag gtcccgcaag cagaggaagc attagttttg tttttattta tgttctgtat 167340
tccagaaagt agttaagaga cctcacatgt agcgatagag atgtgtgtaa gagacagtga 167400
gagggcgtga cttggactta agcaaggacc gtgagacaca aaaagggggg tgaggacaga 167460
gtggagtcag ctgaaatgct caggaggaag tagacgccat gaagggccat ggtatggggg 167520
gccgcaggcg tggccgtgag tgtccctggg gccagctctt ggggggctcc ctgagtgtcc 167580
ctgtccctgt ggccagttct gggtgggagc cccgtgtgca ggcagacagc tcggccactt 167640
cctagcaggt cacattggtc tgtgcttctg tttcctcctc agataagtga agggattcaa 167700
gggtctgggt gtggtggcta acacctgtaa tctataacat tttaggaggc tgaggcagga 167760
ggcttacctg agctcaggag gttgaggctg cagtgagcca tgattgcacc actgcactcc 167820
agcctgggca acagaccagt actctgtccc ttaaaaaaaa atgtaaacag aaacgtaggg 167880
ccatttgcat atgatggcac atggcgtgga gccctacagg tgtatgctgg gcggggcccg 167940
gctgtgctgg ccgacttgca cctttccctc caccccggtg ctgtgtcttt cgctcaccgg 168000
gttcctgatt tagtgaaagc agttgtgcag gacagttctc tttgtagctt ttgtttctgt 168060
ggaaatgggt cagaatatgg tgtttagaaa cacttatgag ctctgagagt ttcctcttct 168120
gagttcctgg cctgcagcct tcacagcaga aaccctgtga tgtcacaagc ctgtttctgt 168180
tccctgctct ctgcctgtac tgtcctgttt tgtgcctgcc ggtttcagtg acaggaagca 168240
gggagctact ggaccagcct gtatttttct agacatagtt ggaaaaagaa gtcccactct 168300
tctgtccttt cacctttgac agatgtttcc accccaagat aagtgaaaat gaccaatagg 168360
atgcactgta tttttcatga aagtgtttct gaagggcagg ctgagagtga gaggcctggg 168420
gctcactggg tgcctctggc cttgtcctgg gcccagggac actggtctgt gcccgaggta 168480
ttccctatcc ccccaacccc gctgcatttg gccacatcct tcaatgtttg cgttgtgtcc 168540
agcgtccgca aaccaactgt catgggatca tactggggct gaagtacggt cccacccctg 168600
ccctgtctgg ggctgaagta cagtgccacc cctgccctgt ctggggctga aggacagtgc 168660
cacccctgcc ctgtctgggg ctgaagtaca gtgccacccc tgccctgtct ggggctgaag 168720
gacagtgcca ccccttccct gtctggggct gaaggacagt gccacccctg ccctgtctgg 168780
ggctgaagga cagtgccacc cctgccctgt ctggggctga aggacagtgc cacccctgcc 168840
ctgtctgggg ctgaaggaca gtgccacccc tgccctgtct ggggctgaag gacagtgcca 168900

-continued

```
cccctgccct gtctggggct gaaggacagt gccacccctg ccctgtctgg ggctgaagga 168960
cagtgccacc cctgccctgt ctggggctga aggacagtgc cacccctgcc ctgtctgggg 169020
ctgaaggaca gtgccacccc tgccctgtct ggggctgaag gacagtgcca cccctgccct 169080
gtctggggct gaaggacagt gccacccctg ccctgtctgg ggctgaagga cagtgccacc 169140
cctgccctgt ctggggctga aggacagtgc cacccctgcc ctgtctgggg ctgaaggaca 169200
gtgccacccc tgccctgtct gggatgttta gcccctagat gccactggac tgagccgcta 169260
cttgcttttg ggaaagaggg gtgggggtta ggggtctggg cgaggggagt gcaggggctc 169320
ctccttggcc tgagagctgt tcatacagac tcctcgccca ctccctgcag ggtgctgggt 169380
cccagggggg aaatggccct tggtgccaag aacgtgagtt ggggctagtg ccagtgatga 169440
tggagaacag ctttttatgg gcacacagcc cacagcactg tgccaagtgc tcgaggcttc 169500
ccgagaacca ggcagaaagg aggacagtcg aggtgtgctg actgcgtggt ggctgcgtga 169560
tctagagcgc gggtcacaaa ggcgcgaggg agctctggcc ttgggtttac cgcaatgact 169620
gccagtgcgg gagactggaa aaggaatctc acgtattggt tccgtgtttt ggggactcca 169680
ttcagatgtc acttaggagt gaaagcatcc cttcgtagag cctctttctg tgtcaccctc 169740
ctcagctgct cctggggttg actggcccct gattcatgcc tttagcatgt gctggagctt 169800
cccagcagct gtccagcccc tgccccaccc tctctgtggg ctcccttgcc cgtaacctgg 169860
ggtgtctgaa cgacccttgc taaggggcag actgttagac ggtaggcatg tgctgagtcc 169920
cagtggccac acccacccac caggagcctg gcactgtggc cgcagcactg agcagtgccc 169980
cgtttctgtg gcaggtgtcc atacactccg tgtggctggg gaacagcatc acacccctga 170040
gggaggagga atgggacgag gaagaggagg aggaggccga cgcccctgca ccttcgtcac 170100
cacccacgtc tccagtcaac tccaggtttt ccaatggcct ttttcttttt aacagaaatt 170160
tgaaatttct tatcagtcat ttgatttgtt tgaggtgctt cttgaaatga gcctctcatc 170220
tcatgtactt ggaaaatacc catctcgcat attccacagg aaacaccggg ctggagttga 170280
catccactcc tgttcgcagt ttttgcttga gttgtacagc cgctggatcc tgccgtccag 170340
ctcagccagg aggaccccgg ccatcctgat cagtgaggtg gtcagatccg taagtgagcc 170400
ttcccattcc cctcacacct gcacgtgcca cacgcaccac acacgccaca caccccacac 170460
acacacaccg cccacacaca tgccacttgc acacacaccc ctcatgcatg caacacacac 170520
acaggccaca cgcaccatag acaccacaca cacatgccac atgcacacac atacacggca 170580
tgcaccatac acacaacaca cacagcacac atgccacaca cacacgccac accacatgca 170640
ccacacacat gccacatgca cacacactcc acatgcatgc accacacaca cacacacaca 170700
ccacacacac cacatgcacc acaccacaca ggttacatgc acacaacaca cacatgccac 170760
gtgcacacac cccacacacc acatgtatgt gccacacaca gcacacaacc acacacatgc 170820
accacacaca tgccacatgt gcatgcacca gacacatggc acacactaca cacacgccac 170880
gtgcacacac cccacacaca tgtacgcacc acacacatgc cacacacaca tgcaccacac 170940
acatgccaca tgtacacaca tgtatataca caccccacac cacacacaca ccacttgcac 171000
accacgcaca cacaccacat gcgcacacac acaccacata cgccacatgt acacaccata 171060
cacacaccat acatgcacca cgtgtaccac gcacccacac agacacagca cacgcataca 171120
ccacacacac acgcacacat gcgtcccgca cagtaatgtc tcttgggtgt aagaacacga 171180
cttgccagta gtagcgttct ggatgcgttg cctggattct aacagcgcga ttctcccctt 171240
```

gccctcctgg ttttccacat ctccagcttc tagtggtctc agacttgttc accgagcgca 171300
accagtttga gctgatgtat gtgacgctga cagaactgcg aagggtgcac ccttcagaag 171360
acgagatcct cgctcagtac ctggtgcctg ccacctgcaa ggcagctgcc gtccttggga 171420
tggtaagtga caggtggcac agaggtttct gtgctgaagc cacgggggcc catctgcctt 171480
gggacctggt gttggccaga ggtgccgggt gcggctgcct ccttccaaga gttgacccga 171540
accggactcc acggcccacg tgagctgcag tgcttctcag atggaggggg ttcagcgacg 171600
gtcagtgcca ttcacaggtc actgtgatgt gggttgtggc ggccaagcca tggtttgggg 171660
tcccgtatcc ctgggcttat gacatcattg tagtagccca tccccacaga accacggtgt 171720
gtggtggcgc tgaggcatcg tagatggtgg aaatgctact ggcttcccca tgctctgccc 171780
tgaggcctga ctgcctcact cccettctca gttatgttcc aggccccccg agcttcctgg 171840
ctggacagct tctctcctgg gggccgtttt gtcacagtga ccctgtgttt ctagtcccaa 171900
atctgggtgc tatagtctct ttttagcgtg gtggttgtct tagtcttttt tggctgctac 171960
cacaagttac cttagactgg gtaatttata aacagtggaa atttacttct caccgttctg 172020
ggggctggaa gttttcatgg tcaaggtgcc agcagatttg gtgtgtgatg agggctgctc 172080
tctgcttcat agatggcatc ttctggctgg gtcctcacgg tggaaggagt gaacaagctc 172140
cctcaggcct tttagaaggg ccccaatcca caagggctct cccatcatga cctcatcacc 172200
tcccaaggcc ccaccttctt gtactgtggc actgcaaatt aggtgtcagt gtaggagttt 172260
caggagggat agaaacattc agaccatccc agcggtcaag tgttcatcct cttgagttcc 172320
tccttattct gcttctggtt tatcaggatt cagccagtgc agcatggtac ctgtattctg 172380
tggcacatca ccacatggta tttgccaagt atccatcacc tgcacacgtg aaatcattgc 172440
ccgtgggtcc cgacatctgg cgaagcatat tcaaggatgg cagaactgtc agagctggca 172500
cctctggttc cttgtcatgt ggcattacct agtaatccat tttatgatag caatggaaac 172560
tcatttcttc aacaaacacc tgagtggctg ccgtgtgcca gccgtctggg gcccttggtg 172620
agaatggcat ggtggtgccc atcagggcct gcctagcccg tgctctggac gggctcctgt 172680
gtgtcaggaa cgacaatgct gtcatgacgg tgaatgattt tttttttgc catcactcca 172740
gccgctaaca tttgcggagc tcttcctccc gcacccccac ctgacaaggc caagggtgac 172800
cttggcccca ccctaggcgg ccaaggtcag aggttagctg gcttgtctgg gtcacacaaa 172860
atgcagcaga ggttgaggtg agcacatgtc cgtgacctgg agcctgactc cctctctgcg 172920
agtcttgact gctcttgcct agactctgtc ctccccgagc ccaaacgcca gtcatcttcc 172980
cttgtgggtg tccttcagcc tggtgccatg ctggtgactc agcagccgtc cagggagtgg 173040
aaacaattga gtgtgtgggt tccctgtgtg ggcatctctc ttcacggcga acaccctctg 173100
ggtgttgccc acacgatgtc aaagcggctc ttggaagggg tccttctcct ttgtgggaag 173160
tttcagctgc tgggctaact tgaattgtaa ctgtggtttt gtgctcaggc ccagatcccc 173220
ctaggcaagt gttgtgccat cagtaatcaa atgagaaata atcattttga aaagcagatc 173280
ctaaggcagg atggtcatgg acactcactc ccagctcttt gtgcactcat gctttctgga 173340
agatggccat cctctgtgaa ggttttcagc gcgtcatgct tggtacccac gtatccagag 173400
catgtcgttt tgaggtattt gcccaccgtt gtgaaatccg tgccacccga gagcaggtcc 173460
tgatgtgggg ctttcagaag tgggacctgg ggccgtacgc agtccttagg gaggggccgt 173520
gtggcgttgt gcgtgtgagg ggatagcaca gggtgaggtg ggggcccaag aaggaagtga 173580
cccacaaaga acagcctcct cttttggtcc ttgttcctgg gatggctggg agtggcttct 173640

-continued gtgtcgtccg gccatttccc ctgcggagag gctcctacca ctgccgagaa cctcatcatt 173700
ccacaaaaac aagaggccgc ctggccatcc agcgctccat gggaattctg tgtccccata 173760
gtcttgggct gaaggagggt gacattcctt gctgacttct gcaggggtct cctcactgtt 173820
aaagagcaga ttgaaagtga agaacgtggg ctaagtgttt aggtcgatat ttaaccctgc 173880
taggttttgg atactaagtg aaattgaggc cattttggtt gaagttgaca gaaaccacta 173940
tcagggatcc ccaagactac cccaggcttt tctagaaaga ctctcagcta agatgtgtta 174000
tggtaaaagc acacaaaaca aaatcagcaa agaaaattag caagggcaga ggcccatggg 174060
gcgatgtccc gaggacacca ggcttgagct tccagaatcc tctcccagcg gggtcgtgca 174120
ggacgcactt aactccccgc acagtgagcc gtgacagcgc gtgtgcagtg tcgtcgccag 174180
gaaagcacac tagagactcg gtgccagggt ttttactggg ggctgggcac atgggcaccc 174240
tctgcctgcc tcgtgcccag actctggact cccggaggga aggcaagttc tcagcaccaa 174300
ccctggtgcc cacacaagca gctgagcaca gggagcccct cctcagtgag gatggtgggc 174360
accgtcccaa caccagccag gggccagcct tgcacacagg cctctcagga tggtctccgg 174420
cctgctgtgt agtctcttct gcacacaagc gtgagggcag cgcccccgcc tcggctgtgg 174480
ggaggagcca ctgggacgtg agctctggtg gcatgcagca gcttttgtct gtgtgtgcct 174540
aggacaaggc cgtggcggag cctgtcagcc gcctgctgga gagcacgctc aggagcagcc 174600
acctgcccag cagggttgga gccctgcacg gcgtcctcta tgtgctggag tgcgacctgc 174660
tggacgacac tgccaagcag ctcatcccgg tcatcagcga ctatctcctc tccaacctga 174720
aagggatcgc ccagtgagtg ggagcctggc tggggctggg gcgggggtct cagaatgagc 174780
tgtgaaggaa gcagcatcac cctctccaag tgcccaggct cctggccaga tggcaggcca 174840
ggtatcagtg ggaacccagg tgggtgccat ggctgaggtc agtgagacgc aagagcacag 174900
gtgcgtccta gaggcttcct cgggcacctc cagcgagctg gagctctcgc ctctgctgct 174960
gtctcatgtg gcgcttagca cactctccca cgtgcccatt cctgactctg ctctcgaggc 175020
catcggctct cattctctgc tcccagaacc ctgttattac ccaggctagc ctcctctctg 175080
caccttcccc gccctggccc agtacctccc tcttgtttcc actgtgattc cgacctcacc 175140
ttatcttaaa gctgctggac ggcaggttct gtacacacgt gtccttgaca aagcacggct 175200
ggtgccgcaa cccctcagcg agcaagtcaa gctcttcaca gcgatgtctt acaagcgcag 175260
agggctctgt gacaccctgg tctcaccgcc actcttccaa agtcgcagag gctttagcag 175320
agatgggccc agcctctctg agtcataggc ttctgcacac gggagctgtc tttagaggga 175380
gggtggaatt tcatcagcca cccacatggg ggagttgagg gcaagaatta ggagcaaaga 175440
tgggaagggg tctgggagga atggccagtg atcccctttg acaagtgggc aggaaacggg 175500
ggctaggtca aagttgagtg gaagacctgg agggagacgg gaaggtctct gtaggcacag 175560
ttcagacagg agggaggtgt gagccagggc acatgccggt ggccgtctgg caggatttgg 175620
gacatgctgg agcagggaca gcggctcatc aggggccatt gccctcatcc aggccagagt 175680
gtcacaagcc cgtggggagg cccttctcgc ctgtcatcct tgctgggcag tgggtgctgt 175740
gctagcagga caggcggacg gctggcaact gtctctgcat ccctggagcc tggcataggg 175800
ccaagtcaca cggggcacag gcctgcaaat caggcacata tgttggtgca gtgacgtgat 175860
tttggggggc agccccagaa caggccccag acacaggcca aagccctgcc tgtgctggtg 175920
tgttgggctg ttctatggct cttgctgtgg gcatggagga ctcagggaag gagagttgag 175980
gtggtccagg agttgcgttt gggatgcaga gagcttgtgg catccaggta gaaatggtgc 176040
gtggggctga cctcagcacc atgggcagag gggccgtgtc acgtgcctcc gaggtggagg 176100
tgggaccacg tggtgacaga tatacgcatc actgggcacg tttttgtggg tgttgggggg 176160
catcgtattg gctcctctgt tcacagtggc cactcattca gtccctggct accaggtcct 176220
cactgtgcca tggggaaggc cggcgctgtc gggggatcac agaaggcagc acgtcatgat 176280
ggcatgtgcc atgaaggaaa agcacagggc actcaggaag tagaggggac tggcctgggg 176340
tgtgggaatc tagggcctcg ttgagggaca gagagaggaa gtgtgtggtg gccagcatgg 176400
aggtggccac aggggaggct gagttaggcc gagagggcag ggcgttgggg aggtagacgg 176460
gctcagccac tcagggagtg gtcaagcaga ggctgaaggg tcaggccagg ttgcaggggc 176520
ctgggggagc cactcagggt aggcgctccc gggagcccgc ctggcccata gctctacact 176580
cccgcgtggg gccggacatg ctgtgaagcc ctctccacgt tggatggggg tggctgagcc 176640
tggatgctgt ctcccgtttt cagctgcgtg aacattcaca gccagcagca cgtactggtc 176700
atgtgtgcca ctgcgtttta cctcattgag aactatcctc tggacgtagg gccggaattt 176760
tcagcatcaa taatacaggt gagtgggccc tggctgtctt cctctgcaca cggggagtgg 176820
gcttcccttc tcttttcctt gcaggatcat accagtgggc cagttttgac ttggtcggga 176880
ggaggcatga acacctgaga ctgtgcagcg attctttgac acagaggcct ttctccctgt 176940
gcagatgtgt ggggtgatgc tgtctggaag tgaggagtcc accccctcca tcatttacca 177000
ctgtgccctc agaggcctgg agcgcctcct gctctctgag cagctctccc gcctggatgc 177060
agaatcgctg gtcaagctga gtgtggacag agtgaacgtg cacagcccgc accgggccat 177120
ggcggctctg ggcctgatgc tcacctgcat gtacacaggt gagcatgtac acggtgccca 177180
taaggccagc ccaagtcctg ttcaagggag gcaggagcat gctcactcaa gggacctcga 177240
ctaggtgccc tctgatttca cacttctggt gttgccccaa gccggcccca tcaccttgca 177300
agaaaggctc tggagccccc agggctggag tacctggtca gggttgaccg tccctgtggt 177360
cactcatccc atgtggctga gctgggctgg gtcctgggca agcaaggggc tgatatcacc 177420
tgctttcaga tctccaggga ctcactggac ccctgtgtac aaagcactgt ctacagagcc 177480
tattgggttg tatagaggta accttcgtac tgaacacttt tgttacagga aaggagaaag 177540
tcagtccggg tagaacttca gaccctaatc ctgcagcccc cgacagcgag tcagtgattg 177600
ttgctatgga gcgggtatct gttctttttg ataggtaaga agcgaagccc catccctcag 177660
ccgttagctt ccctagaact ttggcctgaa gctgtgcttt tgtgtgtgtc tgctgatccc 177720
ctggcgctgt tgctggagtc ctgccagtga ttccccacca cagcctgacc atgggctgcc 177780
ttggctcagg gttccactgg cgagctggtg gtccttggac cccagcactc aggtgtagcg 177840
ttgaccagtt ccaaggttgt cccagtgcct gcccatctct cctgagggct cagggacagt 177900
acctggcagt tgggggtgtg gcagggggca ggaatgacca gcctctggga gggtggggca 177960
gaagcctgta cagtgaggag gagctggctc agcctggctg cctatcgtga gaggggagcc 178020
cacggggctg tgggaggggg gccgtggtgc ctgtgagcag ggtgaggagc agcggcagga 178080
ggatgaaggt ggaacccaca catgcatctt tgagacccgt gtggtcagtg gcttctgccc 178140
cccaccaccc cccactgctg tgcgtgcata gaattggctt ccctcacctg ctctggaagt 178200
gggttaggag cttggtaggg ctttttctca aggacaaggg cccctgattt gctctcaggc 178260
ctcagtcctg gcgacatggt ggatctggag ccttgttgca ctgccttgcc tgtgctctcc 178320
aatcagggtg gccagtgggg agccatttgg cttttctcaa gagcatactc aggtggacct 178380
tgctccactg tttgaccaga tgaggcattc tgaacagcca agcctgtgct ggtctgtttt 178440
catgttgatt tttttttttc ttttcttttt gagatggagt ttttcccttg tcacccaggc 178500
tggagtgcaa tggtgtgatc tcggctcact gcaacctccg cctcccgggt tcaagtgatt 178560
ctcctgcctc agcctcccta gtagctggga ttacaggcac acaccaccat gcccagctaa 178620
tttttgtgtt tttagtagag acggggtttc accgtgttgg ctgggctggt ctcgaactcc 178680
tgaactcaag tgatccaccc tccttggcct cccaaagtgc tgggattgca ggcgtgagcc 178740
actgcgcccg gcccccatgt cgatttttaa atgcacctct gcatcgttct tcagtcccca 178800
tatgctcact gagcaccact gcgactggca gacgggcaca gggaggcgcc acgaccagtc 178860
ctggccttca aggggcttgt ggtctagtgg gcccaatgct aggtggcgag tgctccaaag 178920
agtgtggtgc acgccttccg cttgaccgct ctccagacgc cacagggagg cacctcgcag 178980
ctgaccacag atttctctct gtggagcagt gtcttcagag cggctgccat gccactgctg 179040
ggcgagggtc tgcgggcggg tagagccagg agcacctgtg aggaagtgca ctgccatttt 179100
cgtagctgct tcccgtgtgt ctcagttaca cacggctggc atgtgtgcac tgatgagacg 179160
ggaacgtgat ggttgctttt cagcactgaa agggatactg ctcagggggc gtgtttcagg 179220
atctggttag ggaagaagca gcgagagcac agatggggcc ctgtgtggta acaagaaaaa 179280
agtcctggtt gacaacagtg ccacgaagcg ttagaacaca tagggatgtt tgtggagcat 179340
ttgcatgtgg aaagcagcaa aaacataatg ggaacgggtt cttttgttat gatttttaaa 179400
aatctctttt gtaacatcct tcccgctgcg ccgtttctgc atattccttt atgtagcttt 179460
caaactcctc ttaggagttc tggtccctac agggcgtggg agcccaggct ttacgtagct 179520
ttcaaactcc tcttaggagt tctggtccct acagggtgtg ggagcccagg gcctgtgccg 179580
agcagcctgc ctccacgagc tagacagagg aagggctggg gttttgcctt tttagtctca 179640
aaattcgtac tccagttgct taggctctga ctttccccac ttggaaagtc cctcacggcc 179700
gagggtccct cccagccctg atttcacatc ggcattttcc ccagtattag agccaaggcc 179760
ctccgcgggc aggtggggca gctgtgggag ctggtgccag tctctgacct gcgtccctcc 179820
tcccaggatc aggaaaggct ttccttgtga agccagagtg gtggccagga tcctgcccca 179880
gtttctagac gacttcttcc caccccagga catcatgaac aaagtcatcg gagagtttct 179940
gtccaaccag cagccatacc cccagttcat ggccaccgtg gtgtataagg tgaggttgca 180000
tgtgggatgg ggatggagtg ggaaagcctg gaggtggagt tgcctccgac ttcccagcag 180060
attcgccagc agagcccagc tcctccgctt taaagcagca atgcctctgg cccccacccc 180120
acccccgcca cccaggcgca gcaggtgctt cccgtccccc cagccctgac actcaggcac 180180
ctgcttgctc cttgcaggtg tttcagactc tgcacagcac cgggcagtcg tccatggtcc 180240
gggactgggt catgctgtcc ctctccaact tcacgcagag ggccccggtc gccatggcca 180300
cgtggagcct ctcctgcttc tttgtcagcg cgtccaccag cccgtgggtc gcggcgatgt 180360
atcctctctg ggtccctggt gctggccccg tttcccttgt caacaccgag gctcatgttt 180420
catgataagg ttttgaaacc taacctttgc aaaaacccca cagatgccag ggtgacaggc 180480
cctcagcccc agggaagtaa aatgctgaca ggggtacaga aaggagcacg tccagacatt 180540
tgctgaccag ggcctctcag aggggccggt gtatggcagg agggtcgcag ctgaggggcc 180600
tttctgtgga gggcctgggt gaggggagcg agggtgggcg gtggtctctg cagacgtccc 180660
gcccactcgc gggctctgtg tggctgggct tctcctgaca ctgcttctca ttagctttgg 180720

-continued tcattgtgcc tcgatcgccc tctcggggaa aggcttaagt aaagatccag ttcccacccc 180780
cagatgctgg ctgccaggag tttccctttc cacagccctt ccccaagaca gaccacaaga 180840
gcctccaagc agcacagttg tcctggtgct gacagcacag ccttgcccgg cgtgcctggc 180900
acggctctgc cctcactgca ttggagcagg gctagtggag gccagcggaa gcaccggcca 180960
ccagcgctgc acaggagcca ggccaggtga gtgctgccga gtgggtgccc tgcctgcagg 181020
gcatccagcc agccaagggt tgcaggaatg gaggtggagg cgctgatgca gctggaggca 181080
tccaggtggc ccttccgggg ctctgctcgc tctccaggct ccctggaccc ctttgtagac 181140
tgtttcagga gaggaactcc caggtgagga cagggaggca gcattcccct catttgccgg 181200
cctttttcct taactcctgc accagcctcc cacatgtcat cagcaggatg ggcaagctgg 181260
agcaggtgga cgtgaacctt ttctgcctgg tcgccacaga cttctacaga caccagatag 181320
aggaggagct cgaccgcagg gccttccagt ctgtgcttga ggtggttgca gccccaggaa 181380
gcccatatca ccggctgctg acttgtttac gaaatgtcca caaggtcacc acctgctgag 181440
cgccatggtg ggagagactg tgaggcggca gctggggccg gagcctttgg aagtctgcgc 181500
ccttgtgccc tgcctccacc gagccagctt ggtccctatg ggcttccgca catgccgcgg 181560
gcggccaggc aacgtgcgtg tctctgccat gtggcagaag tgctctttgt ggcagtggcc 181620
aggcagggag tgtctgcagt cctggtgggg ctgagcctga ggccttccag aaagcaggag 181680
cagctgtgct gcaccccatg tgggtgacca ggtcctttct cctgatagtc acctgctggt 181740
tgttgccagg ttgcagctgc tcttgcatct gggccagaag tcctccctcc tgcaggctgg 181800
ctgttggccc ctctgctgtc ctgcagtaga aggtgccgtg agcaggcttt gggaacactg 181860
gcctgggtct ccctggtggg gtgtgcatgc cacgccccgt gtctggatgc acagatgcca 181920
tggcctgtgc tgggccagtg gctgggggtg ctagacaccc ggcaccattc tcccttctct 181980
cttttcttct caggatttaa aatttaatta tatcagtaaa gagattaatt ttaacgtaac 182040
tctttctatg cccgtgtaaa gtatgtgaat cgcaaggcct gtgctgcatg cgacagcgtc 182100
cggggtggtg gacagggccc ccggccacgc tccctctcct gtagccactg gcatagccct 182160
cctgagcacc cgctgacatt tccgttgtac atgttcctgt ttatgcattc acaaggtgac 182220
tgggatgtag agaggcgtta gtgggcaggt ggccacagca ggactgagga caggccccca 182280
ttatcctagg ggtgcgctca cctgcagccc ctcctcctcg ggcacagacg actgtcgttc 182340
tccacccacc agtcagggac agcagcctcc ctgtcactca gctgagaagg ccagccctcc 182400
ctggctgtga gcagcctcca ctgtgtccag agacatgggc ctcccactcc tgttccttgc 182460
tagccctggg gtggcgtctg cctaggagct ggctggcagg tgttgggacc tgctgctcca 182520
tggatgcatg ccctaagagt gtcactgagc tgtgttttgt ctgagcctct ctcggtcaac 182580
agcaaagctt ggtgtcttgg cactgttagt gacagagccc agcatccctt ctgcccccgt 182640
tccagctgac atcttgcacg gtgacccctt ttagtcagga gagtgcagat ctgtgctcat 182700
cggagactgc cccacggccc tgtcagagcc gccactccta tccccaggcc aggtccctgg 182760
accagcctcc tgtttgcagg cccagaggag ccaagtcatt aaaatggaag tggattctgg 182820
atggccgggc tgctgctgat gtaggagctg gatttgggag ctctgcttgc cgactggctg 182880
tgagacgagg caggggctct gcttcctcag ccctagaggc gagccaggca aggttggcga 182940
ctgtcatgtg gcttggtttg gtcatgcccg tcgatgtttt gggtattgaa tgtggtaagt 183000
ggaggaaatg ttggaactct gtgcaggtgc tgccttgaga cccccaagct tccacctgtc 183060
cctctcctat gtggcagctg gggagcagct gagatgtgga cttgtatgct gcccacatac 183120
gtgaggggga gctgaaaggg agcccctcct ctgagcagcc tctgccaggc ctgtatgagg 183180
cttttcccac cagctcccaa cagaggcctc cccagccag gaccacctcg tcctcgtggc 183240
ggggcagcag gagcggtaga aaggggtccg atgtttgagg aggcccttaa gggaagctac 183300
tgaattataa cacgtaagaa aatcaccatt ccgtattggt tgggggctcc tgtttctcat 183360
cctagctttt tcctggaaag cccgctagaa ggtttgggaa cgaggggaaa gttctcagaa 183420
ctgttggctg ctccccaccc gcctcccgcc tcccccgcag gttatgtcag cagctctgag 183480
acagcagtat cacaggccag atgttgttcc tggctagatg tttacatttg taagaaataa 183540
cactgtgaat gtaaaacaga gccattccct tggaatgcat atcgctgggc tcaacataga 183600
gtttgtcttc ctcttgttta cgacgtgatc taaaccagtc cttagcaagg ggctcagaac 183660
accccgctct ggcagtaggt gtcccccacc cccaaagacc tgcctgtgtg ctccggagat 183720
gaatatgagc tcattagtaa aaatgacttc acccacgcat atacataaag tatccatgca 183780
tgtgcatata gacacatcta taattttaca cacacacctc tcaagacgga gatgcatggc 183840
ctctaagagt gcccgtgtcg gttcttcctg gaagttgact ttccttagac ccgccaggtc 183900
aagttagccg cgtgacggac atccaggcgt gggacgtggt cagggcaggg ctcattcatt 183960
gcccactagg atcccactgg cgaagatggt ctccatatca gctctctgca gaagggagga 184020
agactttatc atgttcctaa aaatctgtgg caagcaccca tcgtattatc caaattttgt 184080
tgcaaatgtg attaatttgg ttgtcaagtt ttgggggtgg gctgtgggga gattgctttt 184140
gttttcctgc tggtaatatc gggaaagatt ttaatgaaac cagggtagaa ttgtttggca 184200
atgcactgaa gcgtgtttct ttcccaaaat gtgcctccct tccgctgcgg gcccagctga 184260
gtctatgtag gtgatgtttc cagctgccaa gtgctctttg ttactgtcca ccctcatttc 184320
tgccagcgca tgtgtccttt caaggggaaa atgtgaagct gaacccccctc cagacaccca 184380
gaatgtagca tctgagaagg ccctgtgccc taaaggacac ccctcgcccc catcttcatg 184440
gagggggtca tttcagagcc ctcggagcca atgaacagct cctcctcttg gagctgagat 184500
gagccccacg tggagctcgg gacggatagt agacagcaat aactcggtgt gtggccgcct 184560
ggcaggtgga acttcctccc gttgcggggt ggagtgaggt tagttctgtg tgtctggtgg 184620
gtggagtcag gcttctcttg ctacctgtga gcatccttcc cagcagacat cctcatcggg 184680
ctttgtccct cccccgcttc ctccctctgc ggggaggacc cgggaccaca gctgctggcc 184740
agggtagact tggagctgtc ctccagaggg gtcacgtgta ggagtgagaa gaaggaagat 184800
cttgagagct gctgagggac cttggagagc tcaggatggc tcagacgagg acactcgctt 184860
gccgggcctg ggcctcctgg gaaggaggga gctgctcaga atgccgcatg acaactgaag 184920
gcaacctgga aggttcaggg gccgctcttc ccccatgtgc ctgtcacgct ctggtgcagt 184980
caaaggaacg ccttcccctc agttgtttct aagagcagag tctcccgctg caatctgggt 185040
ggtaactgcc agccttggag gatcgtggcc aacgtggacc tgcctacgga gggtgggctc 185100
tgacccaagt ggggcctcct tgtccaggtc tcactgcttt gcaccgtggt cagagggact 185160
gtcagctgag cttgagctcc cctggagcca gcagggctgt gatgggcgag tcccggagcc 185220
ccacccagac ctgaatgctt ctgagagcaa agggaaggac tgacgagaga tgtatattta 185280
attttttaac tgctgcaaac attgtacatc caaattaaag gaaaaaaatg gaaaccatca 185340
gttgttgctg tgtgaggctt gctttgcttc atgagaacct agaccttgct gagctggagt 185400
cttaggaagc agtctcctaa gtgcttctcc agcaggggca gaaactgtcc caccagctaa 185460
catctggcat tatggagggt cccccaggca gctgccagca gggacaggcc ccgtgttttc 185520
tgtagccagg gatgaggaag tggccccagg gcatgggcct ggctgggtgc ttctgcaagg 185580
gccttcccaa accacagtac aggtggtctt cctgccctgc agatgggagc tgtgggagct 185640
gctggagctg ctggagcctt catggtcaag tgacatcata agcttatatg acatacacaa 185700
gcctcaggac ttggcccatg gcactgaagc aggtcatcag gcccagcaca gagactagag 185760
ctgtgttctc acagggccca ccacccttcc acctccttgg ccattgacac ctgcgtccct 185820
ggcccagctg ctcccaggta acccccaaag cagctggcac atcccacctc tggtgtggcc 185880
ggggctgctg tgtgtccgca gggcctgccc cgtctattct agcttgtttg tcctgtctga 185940
accagcgcct actccaagaa gcctctgctc agcccagcgg ggatgcttct aagctccgga 186000
cgagcctctc ggaagccttg gtgattggtg gtgtagtcat cttgggatgc agatgtctta 186060
ccaacctgca agaacaaaaa ccctgtggct tcctctggtg cagggtattt agtcaatgtt 186120
tgctgaggtc ccgtctggtt ctggctaatt ggcaggggtc gtccacccat tctttccctg 186180
ctctgctgtc tgtgccagga gagacggggg ccagtcggcc aaggggccag ctcctgctgc 186240
ctgctcctct tgggcacgtg cgggggcccc ctttctctga gcagggatag ggatcagtct 186300
gccggaggga tgtggtggac aggcctaaag catttggggc ggggcatgcc acttgagctc 186360
cctaaatctg tctcctcata ggtgacaccg ctccagggcc ccccagtggc ctctcctttc 186420
agagctacct aaattctggt cacttcagag aaatggagca ccccctctc cctggtccag 186480 gtgtggacag cctggcacac tgagcacacc tggcatggct ggtaatttca gaaagaagag 186540
gggccggggt ccagtgggaa gcagcggtga acccctcgtg agtgggcttt gcagtccctc 186600
cccatgccac ggcagagctg ccctcaacac agccttcctc ttcctcatcg gagagcacac 186660
cctgtcccct tgccgagctg tgccctgtgc cttcggtggt atttgatttt ggctgctact 186720
ggctttgttg ggatctggaa gtcgcttccc ctgcgtggtg cgtggagcac tgtaagtcag 186780
atgagggaag tagccagggt gaggtgagta ccgggtggag ccgccactga agggactggg 186840
taggggggcc ttgcctctac atgatgtgac acagccaacc gaggacagag gaagccccgt 186900
tcctgggggt gtggggtgca cccctcaggg aagcctgcag tggggcctga ggaaaggcat 186960
cctccgcgag cccacgagtc tggtccatga gcaccgtgac agtgtctgtg ggtagaggtg 187020
gacccggcct tgtgtcatca ccaggacctc ttttgggaaa ccatgtggac atcgcttgcg 187080
ggtcccccag gctctgcagc cccagcagcc tggctgcctt ttgggcaagt ggcttgagcc 187140
acagaggacc cagtcctgtt gcagccacat cctctggggg ggcccgccag tgtggccggc 187200
tttctccacc ctacaccagg cctccaggtg tcctggtcgg gggtgtctgg gccctgggtg 187260
ggccctgtgg acctgtgagg tcagggtcag ggcatcactg gaggcagagg gctgaagttg 187320
tgggtctggg ttccccttgt gtgcacaggc ccctgccctc catgcttggt caggcagcta 187380
cccccaaaac tgctaggaca ggctggtcct gaggtggatc ctggcccctg taccctctgg 187440
acagcccacc cgcccaacct tctaccctgc cccagcggcg gcagtgttgg ccacatcctt 187500
cccctcctgg ccccaattgc tctggggaag tccaggctcc ggagcctgcc caggggcccc 187560
ccgtgatttg ggcccaggac tccacgtggt tctctgcctt cacccaagcc ctgaactcct 187620
cagctgccaa atccccaccc atctgcacag gctgtgctca ccactgctgc tcctggaagg 187680
tgcccctcag tgggacgccc acctcctctc tgggcttctg tgtttgggag ccctgctgcc 187740
cccacccttg gtcagtcccc atgtcctgct ggcctgtcag gcagggcaga aaatccaccc 187800
agaaatgctg agcaggatga gagtctagtt gggcccagcc tcattattta gaagggatgg 187860
aggcctaggg agcatgcttc tagcctgagc ccagcagggc cccgcccatg tcccaggtct 187920
gcaccaggga cagctcctgc cgaggcctga cctgcccctt ctccctcagg tgctgctggt 187980
tgaccagcct ctggccctag gagaccccgt agcgactgag ggtcccagca ggccatgcag 188040
ctttgccaag gtacgagccc ctccccagca ggggacagat gtggggaccc tcccaggcag 188100
gagcagctgg gtgcctggtg ctgccatctg ctgcctgcct ggttcttgtc ctcacattgg 188160
aggtcagtgt gagggctctg cctcgggaaa ggccatggag cttgccctgt ccagggcctc 188220
ccatgtgcac tgagcctggg aagagagggt tggagttgag ccttttaccc tgggaatgct 188280
gcctggagga tggtgcgggt gtggggtggc accctgccag gcagggccct gcctccctgc 188340
gcccactgga actcgggcag gcaggggtgt aggtgcctcc tctagagccg tccggtgggg 188400
gcccccggca gtggtggtgg tgtccactgg ccagcagctg ccccttcagc caggacagta 188460
ggcctgacgc tgtccccagc agctccaagg tggatttgtg gaagggggta gagggcacgt 188520
agaggcccca tgacctcccc agggttctgg gagggctgtg ccccccttagc cagcaccatg 188580
ctgggtgata tagtcagatc ctgttacccc tgttgtggag gtgaggaaac aggttagtgg 188640
ggaggacatg actaaggtcc atgctgagtc gctagagctg cacccagaac cactgctggg 188700
accccatgcc tttctgctta ccccttgtgc cgggagatgc caagagatgc tgggagccag 188760
ccccacctct gcccttggag tcatggctac ggaaagggca ttcggaccgg tccctgacct 188820
caccggggag ggccgaaccc tgttcctgag gagccagggc ttcctagagg aggtaggcct 188880
tctagtcact ccttcatctg caggcactcc acagagctct ctgtgccagc ccccagcacg 188940
gagggctgac cttagtcgag tggagatgcc ccagtgccag gcagtaggga tgatgtctcc 189000
tgaggcccag atggaaggga ctggactagt ctcatggggc tgatggtggg gccaggcctt 189060
gaccagggac ccagtgtagg gggtgcagag acccctctga gttcctcaca catccctggg 189120
gccctcccca tacacttcct atcctgactg cgggcaagag ggagccccag ttcgccttcc 189180
ctatgctggg cacccacagt ggggctgggc acccccgcca tgcccctgcc ctgtccttcc 189240
cctgagagcc tcggtcccac ctccaaggtg cctcagagga cagcaggggc agcgggcaga 189300
ggccgagatg cctcctcatt ccaggctcag ctgcccttct tggggcagcc cacacctgag 189360
agtctcctgc agttggtcag gcctgaggag ggcagggggg tgcctgctgt ccctctgctg 189420
accacagtgg catttagcct gggcaccgcg cccagcacag tccatgctgc acaggtgccg 189480
tgggctccac agagccctgc ctgacatgca tgtgttacgt ttcgggtgcc gatgcccttg 189540
ggcggcactt ctccgggcag aacccccagg ccaccgctcc ggttccggtt ccgctgcatc 189600
tggggctctc ggcaggctgt ggtcctccgg ccagcctggg ggcatctcag tccctcagcc 189660
ccacaggggc ctgccccgca gcctgggcct cgagccccgt ctccgcacgc tgtgccgaat 189720
ctggctgccc atcagctccc tgcgtaccca gactgtgccc tgccatgccc gtggctcttc 189780
ccaggagtgc cctgtggcct ccccctggct tgctgggctg attccctcct gtgtctcaaa 189840
cagagctcac ctttgccatc actgctgtcc tcaccggccg gtgccagagg cccgtgtctg 189900
tgtaccctgt gtctgcacct ctgggcaggg cctggctctg accaacccgg gcttccagtg 189960
tccacagacc taaggcccag ggcgcctggg ggctggagca agagaagcaa aaggagccaa 190020
gggtgggggt ttggggttct tgtgagggcc cagccccagg accccaggac caggacaccc 190080
aggagcccca gggcccagcc ccagttcaga aggcaggggc cttctgaggg agcttaaggg 190140
tcccacagcc caggaccccc accagggcca gtggccagcg ttgggggact cagcctcctc 190200

-continued

```
gtcgctcgtc ctctctgttt ctcccacctt ttgccccctt tctccttgcc tgttcccacc 190260
cgaggccccc tcttggcctg cgtgagccgg ggcggcactg aactgggggc cgatccgcct 190320
gggcggcggt gagaggcagg gccgggagcc gggccgctgg gtttgggcct ggcccgctcg 190380
ccgcaatatt gatggcccgt cagtgcagcc ctgattcctg tgctttcagt taaaaggttt 190440
ctgttgttgt agcttatgca gttgctctgt tgctatggaa acgtgacatc aaaatgacgt 190500
ttcccgttta aaagctttta actaaattcc tgcctgtcag atgtaggccc cattttgagc 190560
gtggagctgc cttcgagcga gcgtgagcgg cgcctcccgc ccatggtgcg tggggccggg 190620
ccggggccct cgctgagcgc gctctctcac cccacaggcg cctccggcat ggcggcggcc 190680
gaggggcccg gctacctcgt gtctccccag gcggagaagc accggcgggc ccgcaactgg 190740
acggacgccg agatgcgcgg cctcatgctg gtctgggagg agttcttcga cgagctcaag 190800
cagaccaagc gcaacgccaa ggtgtacgag aagatggcca gcaagctctt cgagatgacc 190860
ggcgagcgca ggctgggcga ggagatcaag atcaagatca ccaacatgac cttccagtac 190920
aggtgggcga gcgggcagtg tgggccccac caggacgggc gggcccgggc gtggcgggcc 190980
gctcctgact ttcttggagc tctgagtcgg gacgatgtgt gggtcgtggc ctgcctgtcg 191040
gtctcctctg gccgggtatg ggcagaaccc cacggggtga gacggggccc acggaaaccg 191100
tgtgtgcagc cttccattgg ggaagtgggg aaactgaggc ccagcaaggg caggaaacca 191160
gtctaagagc tgaggggtag caggggtggg gctggtgctg ggcagaggcc aggatggctc 191220
ccaggacgta tgggcggtct gggcactgtc cctcggaggc agcaacactc atggtggtgc 191280
ccactgacct cacaccctgc tcccccatag ggaggcggcg gctgccagtg ccctccccac 191340
caccaagctc ccaagctcag caggggtttc aggggcctac tgcgtcattg gggaaattga 191400
gactgcaagt gagaaggagg ctcagtgctc tgcgacttgg agcatccact gagcctctgc 191460
catgagccgg tgagccccac tggggctggc cctagggtca cggtggggta tttccagaaa 191520
tcaccaggtg aggtgcagga ccagccagcg catgggtggg gcttacggtg cgaagaagaa 191580
agaggtggag gcctgccctg gcccaggact cccagcgtgg gggctcccgg cctggcccca 191640
cctctgctcc tgctacatgg caggtgggcc cttcctgccc tggcaacctg cagggaaggc 191700
cggaggggac cacccagcca gggagatgtt ggcgtctagg aggggacagg tgtggtccca 191760
cacacccagc atcttaaagt gcgtgggtcc ccagcccatt aggacagggt cccgggtggg 191820
caggggtcat ggtggggtga aggtctcagg cacaggcaag gtcacaggtg cggtgagggt 191880
cttgcagggt gtgaaggtca taggtgtgcg gtgaaggtca caggtgtggg gtgatggttt 191940
tgggtgtggg gagggtcttg cacggagcga gggtggcagc aagagctgga agctgcaggg 192000
ggagaatggc agcagagagc acccggccct gtgggcggcc tggacagggc tgggcctggg 192060
gctgccggag agcctgtcag cttccaggat gggagtggcc tcactcagct gctccacctc 192120
cgggtcaggc aggtgagcct ggggcagaga ggctgagagc acctgagcca cttgtgggag 192180
aggccacccc cactgccccc ctcaggcgag gagccggcct ccagcacagc agaagggaac 192240
ccccagtccc cagccctagt gggagtgggg aagaggccca gcaaggcccc ggacagaccg 192300
ccagcctgtg aggtctccgc tttcagttgc gttgatttga ttttttctga gccttgaagg 192360
aggggtccgg ggcctggccc tgcccaaagg cccctaggca ggccccaaag ccgggaccta 192420
gggtgctgag catgacggat gttgggtttg agcggctggc ttgcgacgtg agggctgagg 192480
tgtgagcctg ggtatcttca gaggttcggt ggacacaggc agctgcccgc ggccccactg 192540
ttcccgtggc ctcctagtcc tgctcaggca cctggtgagg aagggacgca gagggcagtg 192600
```

ggaggtggcc acgactgttc cagcaggctc ccctctgact caggaattca cgggcaccac 192660
ctccctggct ggctctggtt ggtgtctggc caggttattc attatttatg ctgaaagcct 192720
cttcagagtc ccaggggagg gtttctgtct ccattcctgg aggctgagag atgagggtgc 192780
agcagagtgg gggcctccac tccagaccct gcagtctggg ctggccaagg gctgcaccgg 192840
tgcactgcac gtcatggctg atgaagcact tccacaccgc agcccctcag agctgccaca 192900
gtcagcctta gttcaccgag ggggaagctg aggcccagag catgagaggg acttgcccag 192960
ggccacatag tccttagcag aggaagctgt ggctgggtga ctcgatcttt gtccttttc 193020
tttataccg cagtctcccc atagcagagg cttttctttt ttttttcttt ttcttttttt 193080
tttttttaca agaactcttt atatattaag gctgttgggc tgaagaagcc tgagagggtg 193140
gctggttctg tggagcatgg tttgttgaag tacagtttgg gggcctccta cactgagaat 193200
aggccttttc tcgtttctcc aaagagtggg ctggctcaag tagggcagag agagaagcct 193260
ggggcagagg ttagggatgg gcacccagcg cctgccctca cacgctctgt gctggtgtct 193320
tcacagccac gtgccaccct gggcagcatc ccctgctcac catctggctg tgcctgtttg 193380
ctgggggcac ctcattcaga atccagctta ttgtttccaa cggccaatgg ccacaccctg 193440
gcaggtagca agagtaggag agaggagaca cccactccga gcacaggttg ggtttggagc 193500
ccggccttgg ggcactctgt cactcaaagg cagagtgggg agtgggcact gggccttagg 193560
aggtactggg tccagtgagg cagagatgcc cctgccccac ccccaccttg tggcttcttc 193620
cctggcctgg ccagagctgt ctggccgcca tggggccctg tgtctcctgc cttgacctcc 193680
cagagggcag ccgaggccca ggggaggcct ggggacttag cctctcaggg caggacctgt 193740
ctgcaggagt aggtgggtgc tgggggtccc agtggtaatg aggcatcagg cagtgtggga 193800
aggggcccat ccggcccacc ccagggcctc tgggcaggtt gcaggttgta gcgctggatc 193860
taggctcctg cccagactgt aggttcaacc aagaatggca tgggagccca gcctgctgtt 193920
tgctttatta aatctgccct gtagctgggg gaggggctta ctttgatcat cactatgtca 193980
ttgatataaa aatagaggct cagagaggtg aatgaacctg cccaaagtca cacagcaaag 194040
tgtggagatg agatactgac tcagggctgt ggacactgaa gcctgtgctc taacgccagt 194100
ggctgtcgct ccctgaggca ttctctcccg aacaacacag ttattatatt acaaaatatt 194160
atcactatat ttatatatct tataatacct tattattaca ataaaacctt attactctac 194220
ctttcaaaat gaattattta aaaagcagta tttgctcatt gcagagagtc tagaaactat 194280
agaaaagcaa gggaaaagca ataggaccag ccccaaggtc ccagcatgca cagataacct 194340
tagtaatact gggacgtgtg cttccttttt aacatctgag cccgtgtagg tcctgaagcc 194400
cagcttcttt ctaagtccat tgtcatcttg accctggagc ctggccgatt ttgctgggga 194460
ggcccttgcc agccgagagc ggctcctgcc tgtgccggcg tggcgcgccc ctctgctgag 194520
gctgggcagg acaggggctg ggccagctct gtttctcacc cttggctctt gtgtctctcg 194580
tttcaggaaa ttaaaatgca tgacagatag cgagtccgcc ccgcccgact ggccctatta 194640
cctagccatt gatgggattc tggccaaggt ccccgagtcc tgtgatggca aactgccgga 194700
cagccagccg ccggggccct ccacgtccca gaccgaggcg tccctgtcgc cgcccgctaa 194760
gtccacccct ctgtacttcc cgtataacca gtgctcctac gaaggccgct tcgaggatga 194820
tcgctccgac agctcctcca gcttactgtc ccttaagttc aggtagtgtg tctgcttgtc 194880
cttcccctgc cctggggtat ctcagccccc accatttaga gaaagggact gggagtggca 194940

-continued

```
aggccggcgg cggcggccac agtggttgca gaggccgtgg ctgcgggcag cgcctccagg 195000
gacaggcggc ctcagaccag ggagggcttt agtgtccaca ggcagaccga gtttgtctcc 195060
cagctccatc acttttgagc tgcacggaaa gttccttgac ttctctggcc tcagtctccc 195120
tcctataaaa tgggggtaaa tcagtacctt tctcagaggg tggctgggag catcacagga 195180
gagaagacgc agcatggggc ccggcacacg gagggagacc aagccccaga ccccagaatg 195240
cgccccctgg cctcccttag cccacacaga ccccaccctc acaggctagc tgccctctca 195300
gcactgggga gggtgtcggg ctgcacctca tcacgtgttg ccgtgggcat gacccgtccc 195360
ctctgccatc catcccacac ctcagacccg tcccgtgctg gccacgtgac tgtgcctgca 195420
agatgctcac agggcagccg ggagccaggc agcatgcagg acagacacct gcggggtggg 195480
cctggggagc ccagagaagg tgcttttgag gaggggacat ttggggtggg ctttcaaggt 195540
aaaatagaag ttggccattt ggaggcaaga acaggaagat tgtggatttg agtcacagct 195600
tctcccctgc cctggtcttc aagtctttct gacaggaggt gtcagaaaag tatctttagt 195660
agagaaggcg tctccgagga gggtccctct catgccgggg gccgctgctt gactcaggat 195720
ttctcattga agacctgaga caaaaacgct tttgctggca gctagaagga accagcagga 195780
ggcctgagat ttgtggctgt tgttcccgtg gactgagccc agttctcaga ctcagctgcc 195840
tggggccttg cacaggactg gggcgtgggg gctgccctcc ctgatcaggc ccaaagcgcg 195900
gatctcacgc ccctgaggtt ggctgtaccc tctcagctca gagcagagtg tgggccaggg 195960
atgagcaggc actggagcag ggccctgggg tctgtgggtt ttggcagctc cctgcccttc 196020
agggaggtct gctgagacca cgggtggccc ctaccccagc agcagagctc tcaggaggcg 196080
cccacagggc tggactgcct ttactcacca cctctaccag agctctgagg tcctggggag 196140
agagcccagg cctcttgtgg gccccacacc ctctaggtgc ctgtccttct gcctctctac 196200
caaggtgtgc cggccccatt tctaggccgc cgggagataa gggggctcac atctcaggcc 196260
cttccttctg ggacctcagt ttccccatct gcctaaggcc gggtggggct ggtggtcttg 196320
gcttccctac aggggtcctg agtactctgc actacccagc accccccacc cctgccttca 196380
tctctccctg gggtggtct ctccacccct ggcccccaac tggggctgag cccccacctg 196440
cccagtttgg tgggtgaagg gtgctccctg gcaggatatg cccctctgca gcccagaaca 196500
tcccaccctt tccagaccga aggggtgtgg attgtcctgg gaccctggtc attggggtca 196560
tccgctagtc gcaaaggacg gcaatgcctg tggcctctct ttctttcttt ttcttttttt 196620
tttttttga gacggagtct cgctcttgtg cagagagcag tggcgcgatc ttggctcact 196680
gcaacctccg cctcgtgggt tcaagcgatt ctcctgcctc agcctcccga gtagctggga 196740
ttacaggcac ccgccacaac gcctggctaa tttttgtatt tttagtagag atggggtttc 196800
accatgttgg ccaggctggt cttgaactcc tgacctcagg tgatccacct gcctctgcct 196860
cccaaagtgc tgggattaca ggcataagcc tccacacccg gccacccctg ttactttctg 196920
tcaaaggcgg tgggttctgg cccctccttt gcacatggaa tatgagaccc tgagtaagtg 196980
acctgactcc ctggggcctc agtttcccca tttgcccagt aggattgtcg ggagggtccg 197040
gtgaggcccc tggtgtgccc aggctctgtg gccagcacgt ccacagccgg cactgtcctt 197100
ccaggtcgga ggagcggccg gtgaagaagc gcaaggtgca gagctgccac ctgcagaaga 197160
agcagctgcg gctgctggag gccatggtgg aggagcagcg ccggctgagc cgcgccgtgg 197220
aggagacctg ccgcgaggtg cgccgcgtgc tggaccagca gcacatcctg caggtgcaga 197280
gcctgcagct gcaggagcgc atgatgagtc tgctggagag gatcatcacc aagtccagcg 197340
```

tctaggccag caggcggcgg cggcggcggg gccgggcggc tggtggtact gctcaggcca 197400
cccagggcag gccactcagg ccaggcgggc aagggggccg ccccgcgagc ggagaccgcc 197460
ttccacctgg cctctggcag gatgtccctt ctgaggggta ttttgaggaa cccccaggcc 197520
ctggggaccg tgaggctcca gtctccagca tgaatgccct tcctcggaca caggccaggg 197580
cctctggggt tcactccgag taagaacgtc ctagagccac tctccagtgt cgttactatc 197640
aatgatactt gacgtggctt tgatattaaa cgtatacttt ttcattcttg cctggaacgc 197700
acagtttgct gttgctggct tggtgaggat gccctgattg atggatcccg aaaatgaaag 197760
cagatggaaa cgggttgggg caggctggag ctgggggagc tctctcctga agggaaccct 197820
gtgtcctccc tcaccaggac ctctgcgtct ctccttaaat ggcctctgac gcctgatgaa 197880
aaccccagcg accttccagg aggcttttat tcagctctgt ttggagcatc aggtgtttcc 197940
actgcctcct tagcaatgac actaataaaa gtcgtaacac ctgttcacat gcacagccct 198000
gttgagtgtt ctgggtgctg gagatatcat ggtggatgac acaaaggccc tggcctcttg 198060
gagcttatgc tcccatgcgg ggaagacaca tgggtcagta gagaaatggt tgcaggttgt 198120
gataagtgct ggaagggagg ggttggcctg aggacacgga ggcagacata cgtggagctg 198180
ggaacagtgg ccacacaggg aacggccagt gcgaaggccc agaggcagag gacactggag 198240
caagcccagg agcagctagg aggctggtgg ccagcagcca ggccacggaa gcccgtgcag 198300
cccgtgggga ggagtgttca tgcttttcaa gcttagtggg agtcttttgg ccagtgcagc 198360
tctgggtctg acatcggtgg gggacagagg ggtggtggag cggccacagc tgcaagctca 198420
cctcactgcc ggcccttcca ccagtttcaa actctttcta gaagctccag ctttcccaaa 198480
gctgaattct ctatgagcct ccttggccgg gactcgggcg tctggttgcc ctggctgcaa 198540
aggaggctgg ggccaggtgt gtttgagtca cctcctggaa ttaggcaagt tgctgcccaa 198600
atagaaggtt gttggcaggt gggtcagcag gtgaacagca tggtttgact cagggttcag 198660
aaaaatctcc ctctggctgc caagcgagca ggccgtggag acaggtgcag aggcaggtgt 198720
ggcagcaggc atcctgccag gcagtgctgc agtcatcctg cgacaagcag cagcagctca 198780
tcctaccctc tagggggtct tgaggtcagc caggcaagag agcagcttgg actccactgg 198840
gtgtgggacc agcctgtgga ccatggtggt gtggagggtg ccctcggcct gcctgtgtga 198900
aggagaggcc ggcgtgttct gtggagccca aaggggagct gggcaagcag gattcacttc 198960
actctgaggg tcctggagct cccaccctcc tcagccatct ccccagagcc tgtgtgccga 199020
ggactcggcc catgttgctg tgggatgaga ggcagagtgt cgtgagggtg taaggagcgg 199080
cggcagtggt gggaggaggg agcagcagcc agcgctacgg tgccagtttc cagctgccag 199140
atgacgccgc tgaccctgtg gttgagaaga gatgcacaga gccagctctt gcaagccagt 199200
gtggctgcca tagcacctgc cgagaagcag aaggaagggt ggccccagga ggacagagga 199260
tgcgggcaca tctgatgcgg gcctgagttt tgggagcttt tgctctagcc agtttccagc 199320
tccgggaccc acccgcctcg taggcaagac accacccaag aaatcatttg cttaacaaac 199380
acactgggct ccaactggac acctgtgcca ccctagatgc tgggaaccca gccatgacac 199440
aggcacctgc ccccagctgc tgaccactga ggctggctag cagctcccat ggggccagtg 199500
tggggttccc cagcctccta acagggagcc agtcacaagc cctcgagagg gaagggtgcc 199560
cgcggccctg gcaggaaggt taggctggac gctcccacaa gacataacag atggaggttc 199620
taaatgatgt agcaacttct tcaccctgaa actgctgtag agtcagccat gacgcaccgg 199680
tacttcagta actgccaggc atccgggaca gcacaccgcg agtcgctgct gtgcttgggt 199740
tagaagtggt ttggtctgtt ttcttctcgc cctctctaat cagagtcagt gattcatgcc 199800
cttccatcac cttagagaag gggcaggcgc tgcccgacct tctccaggct ggagcagcat 199860
cgcctcatgt cagcagaact cagctgtaga atatcgtggg gttggtgcct ttcatcagca 199920
gcatgtcctt aacaactttc tgatttcttc cttagttgtt ggtccattaa ggagaaaaaa 199980
aatgatctca gccattgcta aaatatttga taagattcag caaagcagca tgttaacatt 200040
gaaaactaga atcaggagcc aggcagatgt gcttgctttt cacctgtagt atttcatgtt 200100
gttttgacgt ttttagctaa tgcattaaga taaataaaca aaagccgggc acggtggttc 200160
acgcctgtaa tcccagcact ttgggaggct gaggcgggag gatcctctga ggtcaggagt 200220
tcaagaccag cctgaccaac atggagaaac ctcgtcatta ctaaaaatac aaaattagct 200280
gggcgtggtg gtgcatgcct gtaatcccag ctacttggga ggctgaggca ggagaatcgc 200340
ttgaacccgg gaggcggagg ttgcagtgag ctgagattgc accactgcac tccagcctgg 200400
gtgacagtga aactcggtct caaaaaaaaa aaaaaaattaa aaaaagataa ataaaataag 200460
caggataaga aatgaagaaa gtagagttac ctttgttttc agatttcatt tttgtatacc 200520
cagaaagcca aatgtacaaa agactgggag ctctttaaac cagcttaaac ttgttgaaaa 200580
tgaggatgaa gaaatatccc attcagagtt ggaatgaatt taacccagaa ggaacaggac 200640
ctctactgaa gagaactatg cagtcttact gaaaaatcta aataatacct gagcgctgga 200700
gaaacttcgc acactcctga aagctccaaa gtcaatgtca tcattttatt aatgtcattc 200760
caaacatagt ctcaataata tcacttcttg gttttgacat ggacgcgatg atgtttaaat 200820
tcatatgaaa aaagaacggg gccaaaagtc caaggccagt cagcgtgaga agaccgctcg 200880
gcctccctcg gagtcgggga gttggaaccg cagactgaga tcatgtggct gctggaggcc 200940
aggacgaacg tcgggaaatg gagactcctg cgttgctggt gggatgtggt gcagccgctt 201000
ccaggagcaa tttggtgtcc cgtcctaaag ctgaagaaac gcatttcctc tggtcagtgc 201060
cactcctaga caggccaccc tgcggcagcc gtcctcaaac tggtctgagg acccctcaac 201120
gctcttaaaa atcattaaaa gtgggccagg tgcggtggct cacacctgta atcccagcac 201180
tttgggaggc caagacaggc ggatcacgag gtcaggacat tgagatcatc ctggctaaca 201240
cggtgaaacc ccgtctctac taaaaataca aaaaattagc cgggcgtggt ggcgggcgcc 201300
tgtagtccca gctacttggg aggctgagcc aggagaatgg cgtgaaccca ggaggtggag 201360
cttgcagtga gctgagatca ctccactgca ctccagcctg ggcagcagag cgagactctg 201420
tctcaaaaaa aaataataaa taaataaata aaaataaaat aaaataaaat tcattaaaag 201480
tgccaaagaa cttttgctta tgtgagttct aatgaccaat attaatacac attagaatat 201540
cttattagaa attaaacctg agacctttag aaaacatgta ttcatttcaa aatagcaata 201600
aacccatgac atattaacat aaataacaat tgtatgaaaa atatattttc caaaacaaaa 201660
agttttcggg agaagtgtgg catagtttta catggtcgta aatctctggc ttaagagaag 201720
cccactggcc tctcagcagg ctctgggtcc gtccactttg gggg tgtttt ggttgtgaag 201780
tataggagtg aatggagaag ctcattctta cccagatgtg tatttgaaaa gaaaaggaac 201840
attttaataa cctttgcaaa taatcggtat attcttccgt gatcctattc caacactgga 201900
caggtggtgg tttgtttttt ttttttggag acggagtccc gctctgtcac tcaggctgga 201960
gtgcagtggc gcgatttcag ctcactgcaa gctccgcctc c 202001

<210> SEQ ID NO 2
<211> LENGTH: 13481
<212> TYPE: DNA
<213> ORGANISM: Homo sapiens

<400> SEQUENCE: 2
gctgccggga cgggtccaag atggacggcc gctcaggttc tgcttttacc tgcggcccag 60
agccccattc attgccccgg tgctgagcgg cgccgcgagt cggcccgagg cctccgggga 120
ctgccgtgcc gggcgggaga ccgccatggc gaccctggaa aagctgatga aggccttcga 180
gtccctcaag tccttccagc agcagcagca gcagcagcag cagcagcagc agcagcagca 240
gcagcagcag cagcagcagc aacagccgcc accgccgccg ccgccgccgc cgcctcctca 300
gcttcctcag ccgccgccgc aggcacagcc gctgctgcct cagccgcagc cgcccccgcc 360
gccgcccccg ccgccacccg gcccggctgt ggctgaggag ccgctgcacc gaccaaagaa 420
agaactttca gctaccaaga aagaccgtgt gaatcattgt ctgacaatat gtgaaaacat 480
agtggcacag tctgtcagaa attctccaga atttcagaaa cttctgggca tcgctatgga 540
actttttctg ctgtgcagtg atgacgcaga gtcagatgtc aggatggtgg ctgacgaatg 600
cctcaacaaa gttatcaaag ctttgatgga ttctaatctt ccaaggttac agctcgagct 660
ctataaggaa attaaaaaga atggtgcccc tcggagtttg cgtgctgccc tgtggaggtt 720
tgctgagctg gctcacctgg ttcggcctca gaaatgcagg ccttacctgg tgaaccttct 780
gccgtgcctg actcgaacaa gcaagagacc cgaagaatca gtccaggaga ccttggctgc 840
agctgttccc aaaattatgg cttcttttgg caattttgca aatgacaatg aaattaaggt 900
tttgttaaag gccttcatag cgaacctgaa gtcaagctcc cccaccattc ggcggacagc 960
ggctggatca gcagtgagca tctgccagca ctcaagaagg acacaatatt tctatagttg 1020
gctactaaat gtgctcttag gcttactcgt tcctgtcgag gatgaacact ccactctgct 1080
gattcttggc gtgctgctca ccctgaggta tttggtgccc ttgctgcagc agcaggtcaa 1140
ggacacaagc ctgaaaggca gcttcggagt gacaaggaaa gaaatggaag tctctccttc 1200
tgcagagcag cttgtccagg tttatgaact gacgttacat catacacagc accaagacca 1260
caatgttgtg accggagccc tggagctgtt gcagcagctc ttcagaacgc ctccacccga 1320
gcttctgcaa accctgaccg cagtcggggg cattgggcag ctcaccgctg ctaaggagga 1380
gtctggtggc cgaagccgta gtgggagtat tgtggaactt atagctggag ggggttcctc 1440
atgcagccct gtcctttcaa gaaaacaaaa aggcaaagtg ctcttaggag aagaagaagc 1500
cttggaggat gactctgaat cgagatcgga tgtcagcagc tctgccttaa cagcctcagt 1560
gaaggatgag atcagtggag agctggctgc ttcttcaggg gtttccactc cagggtcagc 1620
aggtcatgac atcatcacag aacagccacg gtcacagcac acactgcagg cggactcagt 1680
ggatctggcc agctgtgact tgacaagctc tgccactgat ggggatgagg aggatatctt 1740
gagccacagc tccagccagg tcagcgccgt cccatctgac cctgccatgg acctgaatga 1800
tgggacccag gcctcgtcgc ccatcagcga cagctcccag accaccaccg aagggcctga 1860
ttcagctgtt accccttcag acagttctga aattgtgtta gacggtaccg acaaccagta 1920
tttgggcctg cagattggac agccccagga tgaagatgag gaagccacag gtattcttcc 1980
tgatgaagcc tcggaggcct tcaggaactc ttccatggcc cttcaacagg cacatttatt 2040
gaaaaacatg agtcactgca ggcagccttc tgacagcagt gttgataaat ttgtgttgag 2100
agatgaagct actgaaccgg gtgatcaaga aaacaagcct tgccgcatca aaggtgacat 2160

```
tggacagtcc actgatgatg actctgcacc tcttgtccat tgtgtccgcc ttttatctgc   2220
ttcgtttttg ctaacagggg gaaaaaatgt gctggttccg gacagggatg tgagggtcag   2280
cgtgaaggcc ctggccctca gctgtgtggg agcagctgtg gccctccacc cggaatcttt   2340
cttcagcaaa ctctataaag ttcctcttga caccacggaa taccctgagg aacagtatgt   2400
ctcagacatc ttgaactaca tcgatcatgg agacccacag gttcgaggag ccactgccat   2460
tctctgtggg accctcatct gctccatcct cagcaggtcc cgcttccacg tgggagattg   2520
gatgggcacc attagaaccc tcacaggaaa tacattttct ttggcggatt gcattccttt   2580
gctgcggaaa acactgaagg atgagtcttc tgttacttgc aagttagctt gtacagctgt   2640
gaggaactgt gtcatgagtc tctgcagcag cagctacagt gagttaggac tgcagctgat   2700
catcgatgtg ctgactctga ggaacagttc ctattggctg gtgaggacag agcttctgga   2760
aacccttgca gagattgact tcaggctggt gagctttttg gaggcaaaag cagaaaactt   2820
acacagaggg gctcatcatt atacagggct tttaaaactg caagaacgag tgctcaataa   2880
tgttgtcatc catttgcttg gagatgaaga ccccagggtg cgacatgttg ccgcagcatc   2940
actaattagg cttgtcccaa agctgtttta taaatgtgac caaggacaag ctgatccagt   3000
agtggccgtg gcaagagatc aaagcagtgt ttacctgaaa cttctcatgc atgagacgca   3060
gcctccatct catttctccg tcagcacaat aaccagaata tatagaggct ataacctact   3120
accaagcata acagacgtca ctatggaaaa taacctttca agagttattg cagcagtttc   3180
tcatgaacta atcacatcaa ccaccagagc actcacattt ggatgctgtg aagctttgtg   3240
tcttctttcc actgccttcc cagtttgcat ttggagttta ggttggcact gtggagtgcc   3300
tccactgagt gcctcagatg agtctaggaa gagctgtacc gttgggatgg ccacaatgat   3360
tctgaccctg ctctcgtcag cttggttccc attggatctc tcagcccatc aagatgcttt   3420
gattttggcc ggaaacttgc ttgcagccag tgctcccaaa tctctgagaa gttcatgggc   3480
ctctgaagaa gaagccaacc cagcagccac caagcaagag gaggtctggc cagccctggg   3540
ggaccgggcc ctggtgccca tggtggagca gctcttctct cacctgctga aggtgattaa   3600
catttgtgcc cacgtcctgg atgacgtggc tcctggaccc gcaataaagg cagccttgcc   3660
ttctctaaca aaccccccctt ctctaagtcc catccgacga aaggggaagg agaaagaacc   3720
aggagaacaa gcatctgtac cgttgagtcc caagaaaggc agtgaggcca gtgcagcttc   3780
tagacaatct gatacctcag gtcctgttac aacaagtaaa tcctcatcac tggggagttt   3840
ctatcatctt ccttcatacc tcaaactgca tgatgtcctg aaagctacac acgctaacta   3900
caaggtcacg ctggatcttc agaacagcac ggaaaagttt ggagggtttc tccgctcagc   3960
cttggatgtt ctttctcaga tactagagct ggccacactg caggacattg ggaagtgtgt   4020
tgaagagatc ctaggatacc tgaaatcctg ctttagtcga gaaccaatga tggcaactgt   4080
ttgtgttcaa caattgttga agactctctt tggcacaaac ttggcctccc agtttgatgg   4140
cttatcttcc aaccccagca agtcacaagg ccgagcacag cgccttggct cctccagtgt   4200
gaggccaggc ttgtaccact actgcttcat ggccccgtac acccacttca cccaggccct   4260
cgctgacgcc agcctgagga acatggtgca ggcggagcag gagaacgaca cctcgggatg   4320
gtttgatgtc ctccagaaag tgtctaccca gttgaagaca aacctcacga gtgtcacaaa   4380
gaaccgtgca gataagaatg ctattcataa tcacattcgt ttgtttgaac ctcttgttat   4440
aaaagcttta aaacagtaca cgactacaac atgtgtgcag ttacagaagc aggttttaga   4500
tttgctggcg cagctggttc agttacgggt taattactgt cttctggatt cagatcaggt   4560
```

gtttattggc tttgtattga aacagtttga atacattgaa gtgggccagt tcagggaatc 4620
agaggcaatc attccaaaca tctttttctt cttggtatta ctatcttatg aacgctatca 4680
ttcaaaacag atcattggaa ttcctaaaat cattcagctc tgtgatggca tcatggccag 4740
tggaaggaag gctgtgacac atgccatacc ggctctgcag cccatagtcc acgacctctt 4800
tgtattaaga ggaacaaata aagctgatgc aggaaaagag cttgaaaccc aaaaagaggt 4860
ggtggtgtca atgttactga gactcatcca gtaccatcag gtgttggaga tgttcattct 4920
tgtcctgcag cagtgccaca aggagaatga agacaagtgg aagcgactgt ctcgacagat 4980
agctgacatc atcctcccaa tgttagccaa acagcagatg cacattgact ctcatgaagc 5040
ccttggagtg ttaaatacat tatttgagat tttggcccct tcctccctcc gtccggtaga 5100
catgctttta cggagtatgt tcgtcactcc aaacacaatg gcgtccgtga gcactgttca 5160
actgtggata tcgggaattc tggccatttt gagggttctg atttcccagt caactgaaga 5220
tattgttctt tctcgtattc aggagctctc cttctctccg tatttaatct cctgtacagt 5280
aattaatagg ttaagagatg gggacagtac ttcaacgcta gaagaacaca gtgaagggaa 5340
acaaataaag aatttgccag aagaaacatt ttcaaggttt ctattacaac tggttggtat 5400
tcttttagaa gacattgtta caaaacagct gaaggtggaa atgagtgagc agcaacatac 5460
tttctattgc caggaactag gcacactgct aatgtgtctg atccacatct tcaagtctgg 5520
aatgttccgg agaatcacag cagctgccac taggctgttc cgcagtgatg gctgtggcgg 5580
cagtttctac accctggaca gcttgaactt gcgggctcgt tccatgatca ccacccaccc 5640
ggccctggtg ctgctctggt gtcagatact gctgcttgtc aaccacaccg actaccgctg 5700
gtgggcagaa gtgcagcaga ccccgaaaag acacagtctg tccagcacaa agttacttag 5760
tccccagatg tctggagaag aggaggattc tgacttggca gccaaacttg gaatgtgcaa 5820
tagagaaata gtacgaagag ggctctcat tctcttctgt gattatgtct gtcagaacct 5880
ccatgactcc gagcacttaa cgtggctcat tgtaaatcac attcaagatc tgatcagcct 5940
ttcccacgag cctccagtac aggacttcat cagtgccgtt catcggaact ctgctgccag 6000
cggcctgttc atccaggcaa ttcagtctcg ttgtgaaaac ctttcaactc caaccatgct 6060
gaagaaaact cttcagtgct tggaggggat ccatctcagc cagtcgggag ctgtgctcac 6120
gctgtatgtg gacaggcttc tgtgcacccc tttccgtgtg ctggctcgca tggtcgacat 6180
ccttgcttgt cgccgggtag aaatgcttct ggctgcaaat ttacagagca gcatggccca 6240
gttgccaatg gaagaactca acagaatcca ggaatacctt cagagcagcg ggctcgctca 6300
gagacaccaa aggctctatt ccctgctgga caggtttcgt ctctccacca tgcaagactc 6360
acttagtccc tctcctccag tctcttccca cccgctggac ggggatgggc acgtgtcact 6420
ggaaacagtg agtccggaca aagactggta cgttcatctt gtcaaatccc agtgttggac 6480
caggtcagat tctgcactgc tggaaggtgc agagctggtg aatcggattc ctgctgaaga 6540
tatgaatgcc ttcatgatga actcggagtt caacctaagc ctgctagctc catgcttaag 6600
cctagggatg agtgaaattt ctggtggcca gaagagtgcc ctttttgaag cagcccgtga 6660
ggtgactctg gcccgtgtga gcggcaccgt gcagcagctc cctgctgtcc atcatgtctt 6720
ccagcccgag ctgcctgcag agccggcggc ctactggagc aagttgaatg atctgtttgg 6780
ggatgctgca ctgtatcagt ccctgcccac tctggcccgg gccctggcac agtacctggt 6840
ggtggtctcc aaactgccca gtcatttgca ccttcctcct gagaaagaga aggacattgt 6900
gaaattcgtg gtggcaaccc ttgaggccct gtcctggcat ttgatccatg agcagatccc 6960
gctgagtctg gatctccagg cagggctgga ctgctgctgc ctggccctgc agctgcctgg 7020
cctctggagc gtggtctcct ccacagagtt tgtgacccac gcctgctccc tcatctactg 7080
tgtgcacttc atcctggagg ccgttgcagt gcagcctgga gagcagcttc ttagtccaga 7140
aagaaggaca aataccccaa aagccatcag cgaggaggag gaggaagtag atccaaacac 7200
acagaatcct aagtatatca ctgcagcctg tgagatggtg gcagaaatgg tggagtctct 7260
gcagtcggtg ttggccttgg gtcataaaag gaatagcggc gtgccggcgt ttctcacgcc 7320
attgctaagg aacatcatca tcagcctggc ccgcctgccc cttgtcaaca gctacacacg 7380
tgtgccccca ctggtgtgga agcttggatg gtcacccaaa ccgggagggg attttggcac 7440
agcattccct gagatccccg tggagttcct ccaggaaaag gaagtcttta aggagttcat 7500
ctaccgcatc aacacactag gctggaccag tcgtactcag tttgaagaaa cttgggccac 7560
cctccttggt gtcctggtga cgcagcccct cgtgatggag caggaggaga gcccaccaga 7620
agaagacaca gagaggaccc agatcaacgt cctggccgtg caggccatca cctcactggt 7680
gctcagtgca atgactgtgc ctgtggccgg caacccagct gtaagctgct tggagcagca 7740
gccccggaac aagcctctga aagctctcga caccaggttt gggaggaagc tgagcattat 7800
cagagggatt gtggagcaag agattcaagc aatggtttca aagagagaga atattgccac 7860
ccatcattta tatcaggcat gggatcctgt cccttctctg tctccggcta ctacaggtgc 7920
cctcatcagc cacgagaagc tgctgctaca gatcaacccc gagcgggagc tggggagcat 7980
gagctacaaa ctcggccagg tgtccataca ctccgtgtgg ctggggaaca gcatcacacc 8040
cctgagggag gaggaatggg acgaggaaga ggaggaggag gccgacgccc ctgcaccttc 8100
gtcaccaccc acgtctccag tcaactccag gaaacaccgg gctggagttg acatccactc 8160
ctgttcgcag tttttgcttg agttgtacag ccgctggatc ctgccgtcca gctcagccag 8220
gaggaccccg gccatcctga tcagtgaggt ggtcagatcc cttctagtgg tctcagactt 8280
gttcaccgag cgcaaccagt ttgagctgat gtatgtgacg ctgacagaac tgcgaagggt 8340
gcacccttca gaagacgaga tcctcgctca gtacctggtg cctgccacct gcaaggcagc 8400
tgccgtcctt gggatggaca aggccgtggc ggagcctgtc agccgcctgc tggagagcac 8460
gctcaggagc agccacctgc ccagcagggt tggagccctg cacggcgtcc tctatgtgct 8520
ggagtgcgac ctgctggacg acactgccaa gcagctcatc ccggtcatca gcgactatct 8580
cctctccaac ctgaaaggga tcgcccactg cgtgaacatt cacagccagc agcacgtact 8640
ggtcatgtgt gccactgcgt tttacctcat tgagaactat cctctggacg tagggccgga 8700
attttcagca tcaataatac agatgtgtgg ggtgatgctg tctggaagtg aggagtccac 8760
cccctccatc atttaccact gtgccctcag aggcctggag cgcctcctgc tctctgagca 8820
gctctcccgc ctggatgcag aatcgctggt caagctgagt gtggacagag tgaacgtgca 8880
cagcccgcac cgggccatgg cggctctggg cctgatgctc acctgcatgt acacaggaaa 8940
ggagaaagtc agtccgggta gaacttcaga ccctaatcct gcagcccccg acagcgagtc 9000
agtgattgtt gctatggagc gggtatctgt tctttttgat aggatcagga aaggctttcc 9060
ttgtgaagcc agagtggtgg ccaggatcct gccccagttt ctagacgact tcttcccacc 9120
ccaggacatc atgaacaaag tcatcggaga gtttctgtcc aaccagcagc catacccccca 9180
gttcatggcc accgtggtgt ataaggtgtt tcagactctg cacagcaccg ggcagtcgtc 9240
catggtccgg gactgggtca tgctgtccct ctccaacttc acgcagaggg ccccggtcgc 9300

-continued

```
catggccacg tggagcctct cctgcttctt tgtcagcgcg tccaccagcc cgtgggtcgc   9360
ggcgatcctc ccacatgtca tcagcaggat gggcaagctg gagcaggtgg acgtgaacct   9420
tttctgcctg gtcgccacag acttctacag acaccagata gaggaggagc tcgaccgcag   9480
ggccttccag tctgtgcttg aggtggttgc agccccagga agcccatatc accggctgct   9540
gacttgttta cgaaatgtcc acaaggtcac cacctgctga gcgccatggt gggagagact   9600
gtgaggcggc agctggggcc ggagcctttg gaagtctgcg cccttgtgcc ctgcctccac   9660
cgagccagct tggtccctat gggcttccgc acatgccgcg ggcggccagg caacgtgcgt   9720
gtctctgcca tgtggcagaa gtgctctttg tggcagtggc caggcaggga gtgtctgcag   9780
tcctggtggg gctgagcctg aggccttcca gaaagcagga gcagctgtgc tgcaccccat   9840
gtgggtgacc aggtcctttc tcctgatagt cacctgctgg ttgttgccag gttgcagctg   9900
ctcttgcatc tgggccagaa gtcctccctc ctgcaggctg gctgttggcc cctctgctgt   9960
cctgcagtag aaggtgccgt gagcaggctt tgggaacact ggcctgggtc tccctggtgg  10020
ggtgtgcatg ccacgccccg tgtctggatg cacagatgcc atggcctgtg ctgggccagt  10080
ggctgggggt gctagacacc cggcaccatt ctcccttctc tcttttcttc tcaggattta  10140
aaatttaatt atatcagtaa agagattaat tttaacgtaa ctctttctat gcccgtgtaa  10200
agtatgtgaa tcgcaaggcc tgtgctgcat gcgacagcgt ccggggtggt ggacagggcc  10260
cccggccacg ctccctctcc tgtagccact ggcatagccc tcctgagcac ccgctgacat  10320
ttccgttgta catgttcctg tttatgcatt cacaaggtga ctgggatgta gagaggcgtt  10380
agtgggcagg tggccacagc aggactgagg acaggccccc attatcctag ggtgcgctc   10440
acctgcagcc cctcctcctc gggcacagac gactgtcgtt ctccacccac cagtcaggga  10500
cagcagcctc cctgtcactc agctgagaag gccagccctc cctggctgtg agcagcctcc  10560
actgtgtcca gagacatggg cctcccactc ctgttccttg ctagccctgg ggtggcgtct  10620
gcctaggagc tggctggcag gtgttgggac ctgctgctcc atggatgcat gccctaagag  10680
tgtcactgag ctgtgttttg tctgagcctc tctcggtcaa cagcaaagct tggtgtcttg  10740
gcactgttag tgacagagcc cagcatccct tctgccccg ttccagctga catcttgcac   10800
ggtgacccct tttagtcagg agagtgcaga tctgtgctca tcggagactg ccccacggcc  10860
ctgtcagagc cgccactcct atccccaggc caggtccctg gaccagcctc ctgtttgcag  10920
gcccagagga gccaagtcat taaaatggaa gtggattctg gatggccggg ctgctgctga  10980
tgtaggagct ggatttggga gctctgcttg ccgactggct gtgagacgag gcaggggctc  11040
tgcttcctca gccctagagg cgagccaggc aaggttggcg actgtcatgt ggcttggttt  11100
ggtcatgccc gtcgatgttt tgggtattga atgtggtaag tggaggaaat gttggaactc  11160
tgtgcaggtg ctgccttgag acccccaagc ttccacctgt ccctctccta tgtggcagct  11220
ggggagcagc tgagatgtgg acttgtatgc tgcccacata cgtgaggggg agctgaaagg  11280
gagcccctcc tctgagcagc ctctgccagg cctgtatgag gcttttccca ccagctccca  11340
acagaggcct cccccagcca ggaccacctc gtcctcgtgg cggggcagca ggagcggtag  11400
aaaggggtcc gatgtttgag gaggccctta agggaagcta ctgaattata acacgtaaga  11460
aaatcaccat tccgtattgg ttgggggctc ctgtttctca tcctagcttt ttcctggaaa  11520
gcccgctaga aggtttggga acgaggggaa agttctcaga actgttggct gctccccacc  11580
cgcctcccgc ctcccccgca ggttatgtca gcagctctga gacagcagta tcacaggcca  11640
```

gatgttgttc ctggctagat gtttacattt gtaagaaata acactgtgaa tgtaaaacag 11700
agccattccc ttggaatgca tatcgctggg ctcaacatag agtttgtctt cctcttgttt 11760
acgacgtgat ctaaaccagt ccttagcaag gggctcagaa caccccgctc tggcagtagg 11820
tgtcccccac ccccaaagac ctgcctgtgt gctccggaga tgaatatgag ctcattagta 11880
aaaatgactt cacccacgca tatacataaa gtatccatgc atgtgcatat agacacatct 11940
ataattttac acacacacct ctcaagacgg agatgcatgg cctctaagag tgcccgtgtc 12000
ggttcttcct ggaagttgac tttccttaga cccgccaggt caagttagcc gcgtgacgga 12060
catccaggcg tgggacgtgg tcagggcagg gctcattcat tgcccactag gatcccactg 12120
gcgaagatgg tctccatatc agctctctgc agaagggagg aagactttat catgttccta 12180
aaaatctgtg gcaagcaccc atcgtattat ccaaattttg ttgcaaatgt gattaatttg 12240
gttgtcaagt tttgggggtg ggctgtgggg agattgcttt tgttttcctg ctggtaatat 12300
cgggaaagat tttaatgaaa ccagggtaga attgtttggc aatgcactga agcgtgtttc 12360
tttcccaaaa tgtgcctccc ttccgctgcg ggcccagctg agtctatgta ggtgatgttt 12420
ccagctgcca agtgctcttt gttactgtcc accctcattt ctgccagcgc atgtgtcctt 12480
tcaaggggaa aatgtgaagc tgaacccccct ccagacaccc agaatgtagc atctgagaag 12540
gccctgtgcc ctaaaggaca cccctcgccc ccatcttcat ggagggggtc atttcagagc 12600
cctcggagcc aatgaacagc tcctcctctt ggagctgaga tgagccccac gtggagctcg 12660
ggacggatag tagacagcaa taactcggtg tgtggccgcc tggcaggtgg aacttcctcc 12720
cgttgcgggg tggagtgagg ttagttctgt gtgtctggtg ggtggagtca ggcttctctt 12780
gctacctgtg agcatccttc ccagcagaca tcctcatcgg gctttgtccc tcccccgctt 12840
cctccctctg cggggaggac ccgggaccac agctgctggc cagggtagac ttggagctgt 12900
cctccagagg ggtcacgtgt aggagtgaga agaaggaaga tcttgagagc tgctgaggga 12960
ccttggagag ctcaggatgg ctcagacgag gacactcgct tgccgggcct gggcctcctg 13020
ggaaggaggg agctgctcag aatgccgcat gacaactgaa ggcaacctgg aaggttcagg 13080
ggccgctctt cccccatgtg cctgtcacgc tctggtgcag tcaaaggaac gccttcccct 13140
cagttgtttc taagagcaga gtctcccgct gcaatctggg tggtaactgc cagccttgga 13200
ggatcgtggc caacgtggac ctgcctacgg agggtgggct ctgacccaag tggggcctcc 13260
ttgtccaggt ctcactgctt tgcaccgtgg tcagagggac tgtcagctga gcttgagctc 13320
ccctggagcc agcagggctg tgatgggcga gtcccggagc ccccacccaga cctgaatgct 13380 tctgagagca aagggaagga ctgacgagag atgtatattt aattttttaa ctgctgcaaa 13440
cattgtacat ccaaattaaa ggaaaaaaat ggaaaccatc a 13481

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ctccgtccgg tagacatgct 20

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ggaaatcaga accctcaaaa tgg 23

<210> SEQ ID NO 5
<211> LENGTH: 29
<212> TYPE: DNA
<213> ORGANISM: Artificial Sequence
<220> FEATURE:
<223> OTHER INFORMATION: Probe

<400> SEQUENCE: 5
tgagcactgt tcaactgtgg atatcggga 29

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
tctctattgc acattccaag 20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
gccgtagcct gggacccgcc 20

<210> SEQ ID NO 8
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 8
taacactcga ttaaccctg 19

<210> SEQ ID NO 9
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 9
taacacttga ttaaccctg 19

<210> SEQ ID NO 10
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 10
gttaacactc gattaaccc 19

<210> SEQ ID NO 11
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 11
gttaacactt gattaaccc 19

<210> SEQ ID NO 12
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 12
gctagttcat cccagtgag 19

<210> SEQ ID NO 13
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 13
gctagttcac cccagtgag 19

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 14
tggaaatggg tttttccac 19

<210> SEQ ID NO 15
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 15
tggaaatggc tttttccac 19

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 16
tttaaccgtg gcatgggca 19

<210> SEQ ID NO 17
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 17
tttaaccgta gcatgggca 19

<210> SEQ ID NO 18
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 18
ttcaagctag taacgatgc 19

<210> SEQ ID NO 19
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 19
ttcaagccag taacgatgc 19

<210> SEQ ID NO 20
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 20
acttcaagct agtaacgat 19

<210> SEQ ID NO 21
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 21
acttcaagcc agtaacgat 19

<210> SEQ ID NO 22
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 22
gcagctaggt taaagagtc 19

<210> SEQ ID NO 23
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 23
gcagctaggc taaagagtc 19

<210> SEQ ID NO 24

<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 24
aataagaaac acaatcaaa 19

<210> SEQ ID NO 25
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 25
aataagaaat acaatcaaa 19

<210> SEQ ID NO 26
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 26
cagaggaggc atactgtat 19

<210> SEQ ID NO 27
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 27
cagaggaggt atactgtat 19

<210> SEQ ID NO 28
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 28
cacagtgcta cccaacctt 19

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 29
cacagtgctc cccaacctt 19

<210> SEQ ID NO 30
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 30
taattttcta gactttatg 19

<210> SEQ ID NO 31
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 31
taattttctg gactttatg 19

<210> SEQ ID NO 32
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 32
gctacaacgc aggtcaaat 19

<210> SEQ ID NO 33
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 33
gctacaatgc aggtcaaat 19

<210> SEQ ID NO 34
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 34
gagctacaac gcaggtcaa 19

<210> SEQ ID NO 35
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 35
gagctacaat gcaggtcaa 19

<210> SEQ ID NO 36
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 36
agagagaacg agaaggctc 19

<210> SEQ ID NO 37
<211> LENGTH: 19
<212> TYPE: DNA

<213> ORGANISM: Artificial Sequence
<220> FEATURE:
<223> OTHER INFORMATION: Synthetic Oligonucleotide

<400> SEQUENCE: 37
agagagaaca agaaggctc 19

<210> SEQ ID NO 38
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 38
agcccctctg tgtaagttt 19

<210> SEQ ID NO 39
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 39
agcccttctg tgtaagttt 19

<210> SEQ ID NO 40
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 40
gagcccctct gtgtaagtt 19

<210> SEQ ID NO 41
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 41
gagcccttct gtgtaagtt 19

<210> SEQ ID NO 42
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 42
tgagcccctc tgtgtaagt 19

<210> SEQ ID NO 43
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 43
tgagcccttc tgtgtaagt 19

<210> SEQ ID NO 44
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 44
atgagcccct ctgtgtaag 19

<210> SEQ ID NO 45
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 45
atgagccctt ctgtgtaag 19

<210> SEQ ID NO 46
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 46
gatgagcccc tctgtgtaa 19

<210> SEQ ID NO 47
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 47
gatgagccct tctgtgtaa 19

<210> SEQ ID NO 48
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 48
tgatgagccc ctctgtgta 19

<210> SEQ ID NO 49
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 49
tgatgagccc ttctgtgta 19

<210> SEQ ID NO 50
<211> LENGTH: 19
<212> TYPE: DNA
<213> ORGANISM: Artificial Sequence
<220> FEATURE:

<223> OTHER INFORMATION: Synthetic Oligonucleotide

<400> SEQUENCE: 50
atgatgagcc cctctgtgt 19

<210> SEQ ID NO 51
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 51
atgatgagcc cttctgtgt 19

<210> SEQ ID NO 52
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 52
taatgatgag cccctctgt 19

<210> SEQ ID NO 53
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 53
taatgatgag cccttctgt 19

<210> SEQ ID NO 54
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 54
agaatacggg taacatttt 19

<210> SEQ ID NO 55
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 55
agaatacagg taacatttt 19

<210> SEQ ID NO 56
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 56
ggagaatacg ggtaacatt 19

<210> SEQ ID NO 57
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 57
ggagaataca ggtaacatt 19

<210> SEQ ID NO 58
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 58
ttagtaatca attttaatg 19

<210> SEQ ID NO 59
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 59
ttagtaacca attttaatg 19

<210> SEQ ID NO 60
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 60
agttagtaat caattttaa 19

<210> SEQ ID NO 61
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 61
agttagtaac caattttaa 19

<210> SEQ ID NO 62
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 62
gaaggaatgc ttttactag 19

<210> SEQ ID NO 63
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 63
gaaggaatgt ttttactag 19

<210> SEQ ID NO 64
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 64
ctaaaactaa cttgagaat 19

<210> SEQ ID NO 65
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 65
ctaaaaccaa cttgagaat 19

<210> SEQ ID NO 66
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 66
atctaaaact aacttgaga 19

<210> SEQ ID NO 67
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 67
atctaaaacc aacttgaga 19

<210> SEQ ID NO 68
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 68
ggtgggcagg aaggactga 19

<210> SEQ ID NO 69
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 69
ggtgggcaga aaggactga 19

<210> SEQ ID NO 70
<211> LENGTH: 19

<212> TYPE: DNA
<213> ORGANISM: Artificial Sequence
<220> FEATURE:
<223> OTHER INFORMATION: Synthetic Oligonucleotide

<400> SEQUENCE: 70
cctaaatcaa tctacaagt 19

<210> SEQ ID NO 71
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 71
cctaaattaa tctacaagt 19

<210> SEQ ID NO 72
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 72
tccctaaatc aatctacaa 19

<210> SEQ ID NO 73
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 73
tccctaaatt aatctacaa 19

<210> SEQ ID NO 74
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 74
gaaaatgtga gtggatcta 19

<210> SEQ ID NO 75
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 75
gaaaatgtgc gtggatcta 19

<210> SEQ ID NO 76
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 76
gtaaggcgag actgactag 19

<210> SEQ ID NO 77
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 77
gtaaggcaag actgactag 19

<210> SEQ ID NO 78
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 78
aggtaaggcg agactgact 19

<210> SEQ ID NO 79
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 79
aggtaaggca agactgact 19

<210> SEQ ID NO 80
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 80
ctgagcggag aaaccctcc 19

<210> SEQ ID NO 81
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 81
ctgagcgaag aaaccctcc 19

<210> SEQ ID NO 82
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 82
ggctgagcgg agaaaccct 19

<210> SEQ ID NO 83
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 83
ggctgagcga agaaaccct 19

<210> SEQ ID NO 84
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 84
aaggctgagc ggagaaacc 19

<210> SEQ ID NO 85
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 85
ttccctaaaa acaaaaaca 19

<210> SEQ ID NO 86
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 86
ttccctagaa acaaaaaca 19

<210> SEQ ID NO 87
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 87
gattccctaa aaacaaaaa 19

<210> SEQ ID NO 88
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 88
gattccctag aaacaaaaa 19

<210> SEQ ID NO 89
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 89
cttttctatt gtctgtccc 19

<210> SEQ ID NO 90
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 90
cttttctgtt gtctgtccc 19

<210> SEQ ID NO 91
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 91
tgcttttcta ttgtctgtc 19

<210> SEQ ID NO 92
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 92
tgcttttctg ttgtctgtc 19

<210> SEQ ID NO 93
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 93
aagggatgcc gacttgggc 19

<210> SEQ ID NO 94
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 94
aagggatgct gacttgggc 19

<210> SEQ ID NO 95
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 95
accttcctca ctgaggatg 19

<210> SEQ ID NO 96
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 96
accttcctcg ctgaggatg 19

<210> SEQ ID NO 97
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 97
caaaccactg tgggatgaa 19

<210> SEQ ID NO 98
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 98
caaaccactt tgggatgaa 19

<210> SEQ ID NO 99
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 99
aataaattgt catcaccag 19

<210> SEQ ID NO 100
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 100
aataaattgc catcaccag 19

<210> SEQ ID NO 101
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 101
tcacagctat cttctcatc 19

<210> SEQ ID NO 102
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 102
tcacagctaa cttctcatc 19

<210> SEQ ID NO 103

<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 103
gcacacagta gatgaggga 19

<210> SEQ ID NO 104
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 104
gcacacagtg gatgaggga 19

<210> SEQ ID NO 105
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 105
cagaacaaag agaagaatt 19

<210> SEQ ID NO 106
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 106
cagaacaaac agaagaatt 19

<210> SEQ ID NO 107
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 107
gcttacatgc cttcagtga 19

<210> SEQ ID NO 108
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 108
gcttacacgc cttcagtga 19

<210> SEQ ID NO 109
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 109
cagcttacat gccttcagt 19

<210> SEQ ID NO 110
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 110
cagcttacac gccttcagt 19

<210> SEQ ID NO 111
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 111
aagaagcctg ataaaatct 19

<210> SEQ ID NO 112
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 112
aagaagccta ataaaatct 19

<210> SEQ ID NO 113
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 113
catacatcag ctcaaactg 19

<210> SEQ ID NO 114
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 114
catacattag ctcaaactg 19

<210> SEQ ID NO 115
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 115
cacatacatc agctcaaac 19

<210> SEQ ID NO 116
<211> LENGTH: 19
<212> TYPE: DNA

<213> ORGANISM: Artificial Sequence
<220> FEATURE:
<223> OTHER INFORMATION: Synthetic Oligonucleotide

<400> SEQUENCE: 116
cacatacatt agctcaaac 19

<210> SEQ ID NO 117
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 117
gtcacataca tcagctcaa 19

<210> SEQ ID NO 118
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 118
gagactatag cacccagat 19

<210> SEQ ID NO 119
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 119
gagactataa cacccagat 19

<210> SEQ ID NO 120
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 120
tagaggacgc cgtgcaggg 19

<210> SEQ ID NO 121
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 121
tagaggatgc cgtgcaggg 19

<210> SEQ ID NO 122
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 122
catagaggac gccgtgcag 19

<210> SEQ ID NO 123
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 123
catagaggat gccgtgcag 19

<210> SEQ ID NO 124
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 124
cacatagagg acgccgtgc 19

<210> SEQ ID NO 125
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 125
acgtgtgtac agaacctgc 19

<210> SEQ ID NO 126
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 126
acgtgtgtat agaacctgc 19

<210> SEQ ID NO 127
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 127
tgttcagaat gcctcatct 19

<210> SEQ ID NO 128
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 128
tgttcagaac gcctcatct 19

<210> SEQ ID NO 129
<211> LENGTH: 19
<212> TYPE: DNA
<213> ORGANISM: Artificial Sequence
<220> FEATURE:

<223> OTHER INFORMATION: Synthetic Oligonucleotide

<400> SEQUENCE: 129
aaacggcgca gcgggaagg 19

<210> SEQ ID NO 130
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 130
aaacggcaca gcgggaagg 19

<210> SEQ ID NO 131
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 131
agaaacggcg cagcgggaa 19

<210> SEQ ID NO 132
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 132
agaaacggca cagcgggaa 19

<210> SEQ ID NO 133
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 133
agggcgcaga cttccaaag 19

<210> SEQ ID NO 134
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 134
agggcacaga cttccaaag 19

<210> SEQ ID NO 135
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 135
aagggcgcag acttccaaa 19

<210> SEQ ID NO 136
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 136
aagggcacag acttccaaa 19

<210> SEQ ID NO 137
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 137
caagggcgca gacttccaa 19

<210> SEQ ID NO 138
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 138
caagggcaca gacttccaa 19

<210> SEQ ID NO 139
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 139
acaagggcgc agacttcca 19

<210> SEQ ID NO 140
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 140
acaagggcac agacttcca 19

<210> SEQ ID NO 141
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 141
cacaagggcg cagacttcc 19

<210> SEQ ID NO 142
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 142
cacaagggca cagacttcc 19

<210> SEQ ID NO 143
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 143
gcacaagggc gcagacttc 19

<210> SEQ ID NO 144
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 144
gcacaagggc acagacttc 19

<210> SEQ ID NO 145
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 145
ggcacaaggg cgcagactt 19

<210> SEQ ID NO 146
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 146
ggcacaaggg cacagactt 19

<210> SEQ ID NO 147
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 147
agggcacaag ggcgcagac 19

<210> SEQ ID NO 148
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 148
agggcacaag ggcacagac 19

<210> SEQ ID NO 149
<211> LENGTH: 19

<212> TYPE: DNA
<213> ORGANISM: Artificial Sequence
<220> FEATURE:
<223> OTHER INFORMATION: Synthetic Oligonucleotide

<400> SEQUENCE: 149
gagcagctgc aacctggca 19

<210> SEQ ID NO 150
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 150
gagcagctgt aacctggca 19

<210> SEQ ID NO 151
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 151
tggtgccggg tgtctagca 19

<210> SEQ ID NO 152
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 152
tggtgccagg tgtctagca 19

<210> SEQ ID NO 153
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 153
aatggtgccg ggtgtctag 19

<210> SEQ ID NO 154
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 154
aatggtgcca ggtgtctag 19

<210> SEQ ID NO 155
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 155

-continued

| | |
|---|---|
| ggggacaggg tgtgctctc | 19 |

<210> SEQ ID NO 156
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 156

| | |
|---|---|
| ggggacaggt tgtgctctc | 19 |

<210> SEQ ID NO 157
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 157

| | |
|---|---|
| gcttttcatt gaaaagaaa | 19 |

<210> SEQ ID NO 158
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 158

| | |
|---|---|
| gcttttcgtt gaaaagaaa | 19 |

<210> SEQ ID NO 159
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 159

| | |
|---|---|
| ctgcttttca ttgaaaaga | 19 |

<210> SEQ ID NO 160
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 160

| | |
|---|---|
| ctgcttttcg ttgaaaaga | 19 |

<210> SEQ ID NO 161
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 161

| | |
|---|---|
| actaggccgg gcatgctgg | 19 |

<210> SEQ ID NO 162
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 162
actaggctgg gcatgctgg 19

<210> SEQ ID NO 163
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 163
agactaggcc gggcatgct 19

<210> SEQ ID NO 164
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 164
agactaggct gggcatgct 19

<210> SEQ ID NO 165
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 165
aaacagctgt tagttccca 19

<210> SEQ ID NO 166
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 166
aaacagccgt tagttccca 19

<210> SEQ ID NO 167
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 167
agaaacagct gttagttcc 19

<210> SEQ ID NO 168
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 168
agaaacagcc gttagttcc 19

<210> SEQ ID NO 169
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 169
gtgctaccca acctttctg 19

<210> SEQ ID NO 170
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 170
agtgctaccc aacctttct 19

<210> SEQ ID NO 171
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 171
cagtgctacc caacctttc 19

<210> SEQ ID NO 172
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 172
acagtgctac ccaaccttt 19

<210> SEQ ID NO 173
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 173
acagtgctac ccaacctt 18

<210> SEQ ID NO 174
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 174
acagtgctac ccaacct 17

<210> SEQ ID NO 175
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 175
cagtgctacc caacct 16

<210> SEQ ID NO 176
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 176
tcacagtgct acccaacct 19

<210> SEQ ID NO 177
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 177
cagtgctacc caacc 15

<210> SEQ ID NO 178
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 178
atcacagtgc tacccaacc 19

<210> SEQ ID NO 179
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 179
tatcacagtg ctacccaac 19

<210> SEQ ID NO 180
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 180
atatcacagt gctacccaa 19

<210> SEQ ID NO 181
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 181
atgctgactt gggccattc 19

<210> SEQ ID NO 182

<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 182
gatgctgact tgggccatt 19

<210> SEQ ID NO 183
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 183
ggatgctgac ttgggccat 19

<210> SEQ ID NO 184
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 184
gggatgctga cttgggcca 19

<210> SEQ ID NO 185
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 185
agggatgctg acttgggcc 19

<210> SEQ ID NO 186
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 186
agggatgctg acttgggc 18

<210> SEQ ID NO 187
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 187
agggatgctg acttggg 17

<210> SEQ ID NO 188
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 188

-continued caagggatgc tgacttggg 19

<210> SEQ ID NO 189
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 189
gggatgctga cttgg 15

<210> SEQ ID NO 190
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 190
ccaagggatg ctgacttgg 19

<210> SEQ ID NO 191
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 191
gccaagggat gctgacttg 19

<210> SEQ ID NO 192
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 192
tgccaaggga tgctgactt 19

<210> SEQ ID NO 193
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 193
ctgccaaggg atgctgact 19

<210> SEQ ID NO 194
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 194
attgtcatca ccagaaaaa 19

<210> SEQ ID NO 195
<211> LENGTH: 19
<212> TYPE: DNA

<213> ORGANISM: Artificial Sequence
<220> FEATURE:
<223> OTHER INFORMATION: Synthetic Oligonucleotide

<400> SEQUENCE: 195
aattgtcatc accagaaaa 19

<210> SEQ ID NO 196
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 196
aaattgtcat caccagaaa 19

<210> SEQ ID NO 197
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 197
taaattgtca tcaccagaa 19

<210> SEQ ID NO 198
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 198
ataaattgtc atcaccaga 19

<210> SEQ ID NO 199
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 199
ataaattgtc atcaccag 18

<210> SEQ ID NO 200
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 200
ataaattgtc atcacca 17

<210> SEQ ID NO 201
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 201
taaattgtca tcacca 16

<210> SEQ ID NO 202
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 202
taataaattg tcatcacca 19

<210> SEQ ID NO 203
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 203
taaattgtca tcacc 15

<210> SEQ ID NO 204
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 204
ttaataaatt gtcatcacc 19

<210> SEQ ID NO 205
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 205
attaataaat tgtcatcac 19

<210> SEQ ID NO 206
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 206
tattaataaa ttgtcatca 19

<210> SEQ ID NO 207
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 207
ctattaataa attgtcatc 19

<210> SEQ ID NO 208
<211> LENGTH: 19
<212> TYPE: DNA
<213> ORGANISM: Artificial Sequence
<220> FEATURE:

<223> OTHER INFORMATION: Synthetic Oligonucleotide

<400> SEQUENCE: 208
cagtagatga gggagcagg 19

<210> SEQ ID NO 209
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 209
acagtagatg agggagcag 19

<210> SEQ ID NO 210
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 210
cacagtagat gagggagca 19

<210> SEQ ID NO 211
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 211
acacagtaga tgagggagc 19

<210> SEQ ID NO 212
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 212
cacacagtag atgagggag 19

<210> SEQ ID NO 213
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 213
cacacagtag atgaggga 18

<210> SEQ ID NO 214
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 214
cacacagtag atgaggg 17

<210> SEQ ID NO 215
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 215
acacagtaga tgaggg 16

<210> SEQ ID NO 216
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 216
tgcacacagt agatgaggg 19

<210> SEQ ID NO 217
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 217
acacagtaga tgagg 15

<210> SEQ ID NO 218
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 218
gtgcacacag tagatgagg 19

<210> SEQ ID NO 219
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 219
agtgcacaca gtagatgag 19

<210> SEQ ID NO 220
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 220
aagtgcacac agtagatga 19

<210> SEQ ID NO 221
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 221
gaagtgcaca cagtagatg 19

<210> SEQ ID NO 222
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 222
gctgcaacct ggcaacaac 19

<210> SEQ ID NO 223
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 223
agctgcaacc tggcaacaa 19

<210> SEQ ID NO 224
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 224
cagctgcaac ctggcaaca 19

<210> SEQ ID NO 225
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 225
gcagctgcaa cctggcaac 19

<210> SEQ ID NO 226
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 226
agcagctgca acctggcaa 19

<210> SEQ ID NO 227
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 227
agcagctgca acctggca 18

<210> SEQ ID NO 228
<211> LENGTH: 17

<212> TYPE: DNA
<213> ORGANISM: Artificial Sequence
<220> FEATURE:
<223> OTHER INFORMATION: Synthetic Oligonucleotide

<400> SEQUENCE: 228
agcagctgca acctggc 17

<210> SEQ ID NO 229
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 229
gcagctgcaa cctggc 16

<210> SEQ ID NO 230
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 230
agagcagctg caacctggc 19

<210> SEQ ID NO 231
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 231
gcagctgcaa cctgg 15

<210> SEQ ID NO 232
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 232
aagagcagct gcaacctgg 19

<210> SEQ ID NO 233
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 233
caagagcagc tgcaacctg 19

<210> SEQ ID NO 234
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 234
gcaagagcag ctgcaacct 19

<210> SEQ ID NO 235
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 235
tgcaagagca gctgcaacc 19

<210> SEQ ID NO 236
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 236
accatgatat ctccagcac 19

<210> SEQ ID NO 237
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 237
accatgacat ctccagcac 19

<210> SEQ ID NO 238
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 238
ccaccatgat atctccagc 19

<210> SEQ ID NO 239
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 239
ccaccatgac atctccagc 19

<210> SEQ ID NO 240
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 240
ttaacactcg attaaccct 19

<210> SEQ ID NO 241
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 241
tagttcatcc cagtgagaa 19

<210> SEQ ID NO 242
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 242
ctagttcatc ccagtgaga 19

<210> SEQ ID NO 243
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 243
gaaatgggtt tttccacat 19

<210> SEQ ID NO 244
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 244
ggaaatgggt ttttccaca 19

<210> SEQ ID NO 245
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 245
taaccgtggc atgggcagt 19

<210> SEQ ID NO 246
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 246
ttaaccgtgg catgggcag 19

<210> SEQ ID NO 247
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 247
cttcaagcta gtaacgatg 19

<210> SEQ ID NO 248
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 248
agctaggtta aagagtcac 19

<210> SEQ ID NO 249
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 249
cagctaggtt aaagagtca 19

<210> SEQ ID NO 250
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 250
taagaaacac aatcaaaga 19

<210> SEQ ID NO 251
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 251
ataagaaaca caatcaaag 19

<210> SEQ ID NO 252
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 252
attttctaga ctttatgat 19

<210> SEQ ID NO 253
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 253
aattttctag actttatga 19

<210> SEQ ID NO 254
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 254
gagaatacgg gtaacattt 19

<210> SEQ ID NO 255
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 255
tgggcaggaa ggactgaac 19

<210> SEQ ID NO 256
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 256
gtgggcagga aggactgaa 19

<210> SEQ ID NO 257
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 257
ccctaaatca atctacaag 19

<210> SEQ ID NO 258
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 258
cttttccgtg ctgttctga 19

<210> SEQ ID NO 259
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 259
acttttccgt gctgttctg 19

<210> SEQ ID NO 260
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 260
aacttttccg tgctgttct 19

<210> SEQ ID NO 261

<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 261
gctgagcgga gaaaccctc 19

<210> SEQ ID NO 262
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 262
attccctaaa aacaaaaac 19

<210> SEQ ID NO 263
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 263
gcttttctat tgtctgtcc 19

<210> SEQ ID NO 264
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 264
cttcctcact gaggatgaa 19

<210> SEQ ID NO 265
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 265
ccttcctcac tgaggatga 19

<210> SEQ ID NO 266
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 266
aaccactttg ggatgaata 19

<210> SEQ ID NO 267
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 267
aaaccacttt gggatgaat 19

<210> SEQ ID NO 268
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 268
acagctatct tctcatcaa 19

<210> SEQ ID NO 269
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 269
cacagctatc ttctcatca 19

<210> SEQ ID NO 270
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 270
gaacaaagag aagaatttc 19

<210> SEQ ID NO 271
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 271
agaacaaaga gaagaattt 19

<210> SEQ ID NO 272
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 272
gaagcctgat aaaatctct 19

<210> SEQ ID NO 273
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 273
agaagcctga taaaatctc 19

<210> SEQ ID NO 274
<211> LENGTH: 19
<212> TYPE: DNA

<213> ORGANISM: Artificial Sequence
<220> FEATURE:
<223> OTHER INFORMATION: Synthetic Oligonucleotide

<400> SEQUENCE: 274
tgatctgtag cagcagctt 19

<210> SEQ ID NO 275
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 275
ttgatctgta gcagcagct 19

<210> SEQ ID NO 276
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 276
gttgatctgt agcagcagc 19

<210> SEQ ID NO 277
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 277
atagaggacg ccgtgcagg 19

<210> SEQ ID NO 278
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 278
gtgtgtacag aacctgccg 19

<210> SEQ ID NO 279
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 279
cgtgtgtaca gaacctgcc 19

<210> SEQ ID NO 280
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 280
ttcagaatgc ctcatctgg 19

<210> SEQ ID NO 281
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 281
gttcagaatg cctcatctg 19

<210> SEQ ID NO 282
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 282
ggacagggtg tgctctccg 19

<210> SEQ ID NO 283
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 283
gggacagggt gtgctctcc 19

<210> SEQ ID NO 284
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 284
gggatgctga cttggg 16

<210> SEQ ID NO 285
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 285
acacagtaga tgaggga 17

<210> SEQ ID NO 286
<211> LENGTH: 10081
<212> TYPE: DNA
<213> ORGANISM: Mus musculus

<400> SEQUENCE: 286
gcactcgccg cgagggttgc cgggacgggc ccaagatggc tgagcgcctt ggttccgctt 60
ctgcctgccg cgcagagccc cattcattgc cttgctgcta agtggcgccg cgtagtgcca 120
gtaggctcca agtcttcagg gtctgtccca tcgggcagga agccgtcatg gcaaccctgg 180
aaaagctgat gaaggctttc gagtcgctca agtcgtttca gcagcaacag cagcagcagc 240
caccgccgca ggcgccgccg ccaccgccgc cgccgcctcc gcctcaaccc cctcagccgc 300

-continued

```
cgcctcaggg gcagccgccg ccgccaccac cgccgctgcc aggtccggca gaggaaccgc    360
tgcaccgacc aaagaaggaa ctctcagcca ccaagaaaga ccgtgtgaat cattgtctaa    420
caatatgtga aaacattgtg gcacagtctc tcagaaattc tccagaattt cagaaactct    480
tgggcatcgc tatggaactg tttctgctgt gcagtgacga tgcggagtca gatgtcagaa    540
tggtggctga tgagtgcctc aacaaagtca tcaaagcttt gatggattct aatcttccaa    600
ggctacagtt agaactctat aaggaaatta aaaagaatgg tgctcctcga agtttgcgtg    660
ctgccctgtg gaggtttgct gagctggctc acctggttcg acctcagaag tgcaggcctt    720
acctggtgaa tcttcttcca tgcctgaccc gaacaagcaa aagaccggag gaatcagttc    780
aggagacctt ggctgcagct gttcctaaaa ttatggcttc ttttggcaat ttcgcaaatg    840
acaatgaaat taaggttctg ttgaaagctt tcatagcaaa tctgaagtca agctctccca    900
ccgtgcggcg gacagcagcc ggctcagccg tgagcatctg ccaacattct aggaggacac    960
agtacttcta caactggctc cttaatgtcc tcctaggtct gctggttccc atggaagaag   1020
agcactccac tctcctgatc ctcggtgtgt tgctcacatt gaggtgtcta gtgcccttgc   1080
tccagcagca ggtcaaggac acaagtctaa aaggcagctt tggggtgaca cggaaagaaa   1140
tggaagtctc tccttctaca gagcagcttg tccaggttta tgaactgact ttgcatcata   1200
ctcagcacca agaccacaat gtggtgacag gggcactgga gctcctgcag cagctcttcc   1260
gtacccctcc acctgaactc ctgcaagcac tgaccacacc aggagggctt gggcagctca   1320
ctctggttca agaagaggcc cggggccgag gccgcagcgg gagcatcgtg gagcttttag   1380
ctggaggggg ttcctcgtgc agccctgtcc tctcaagaaa gcagaaaggc aaagtgctct   1440
taggagagga agaagccttg gaagatgact cggagtccag gtcagatgtc agcagctcag   1500
cctttgcagc ctctgtgaag agtgagattg gtggagagct cgctgcttct tcaggtgttt   1560
ccactcctgg ttctgttggt cacgacatca tcactgagca gcctagatcc cagcacacac   1620
ttcaagcaga ctctgtggat ttgtccggct gtgacctgac cagtgctgct actgatgggg   1680
atgaggagga catcttgagc cacagctcca gccagttcag tgctgtccca tccgaccctg   1740
ccatggacct gaatgatggg acccaggcct cctcacccat cagtgacagt tctcagacca   1800
ccactgaagg acctgattca gctgtgactc cttcggacag ttctgaaatt gtgttagatg   1860
gtgccgatag ccagtattta ggcatgcaga taggacagcc acaggaggac gatgaggagg   1920
gagctgcagg tgttctttct ggtgaagtct cagatgtttt cagaaactct tctctggccc   1980
ttcaacaggc acacttgttg gaaagaatgg gccatagcag gcagccttcc gacagcagta   2040
tagataagta tgtaacaaga gatgaggttg ctgaagccag tgatccagaa agcaagcctt   2100
gccgaatcaa aggtgacata ggacagccta atgatgatga ttctgctcct ctggtacatt   2160
gtgtccgtct tttatctgct tcctttttgt taactggtga aaagaaagca ctggttccag   2220
acagagacgt gagagtcagt gtgaaggccc tggccctcag ctgcattggt gcggctgtgg   2280
cccttcatcc agagtcgttc ttcagcagac tgtacaaagt acctcttaat accacggaaa   2340
gtactgagga acagtatgtt tctgacatct tgaactacat cgatcatgga gacccacagg   2400
tccgaggagc tactgccatt ctctgtggga cccttgtcta ctccatcctc agtaggtccc   2460
gtctccgtgt tggtgactgg ctgggcaaca tcagaaccct gacaggaaat acattttctc   2520
tggtggactg cattccttta ctgcagaaaa cgttgaagga tgaatcttct gttacttgca   2580
agttggcttg tacagctgtg aggcactgtg tcctgagtct ttgcagcagc agctacagtg   2640
acttgggatt acaactgctt attgatatgc tgcctctgaa gaacagctcc tactggctgg   2700
```

```
tgaggaccga actgctggac actctggcag agattgactt caggctcgtg agtttttttgg   2760
aggcaaaagc agaaagttta caccgagggg ctcatcatta tacagggttt ctaaaactac   2820
aagaacgagt actcaataat gtggtcattt atttgcttgg agatgaagac cccagggttc   2880
gacatgttgc tgcaacatca ttaacaaggc ttgtcccaaa gctgttttac aagtgtgacc   2940
aaggacaagc tgatccagtt gtggctgtag cgagggatca gagcagtgtc tacctgaagc   3000
tcctcatgca tgagacccag ccaccatcac acttttctgt cagcaccatc accagaatct   3060
atagaggcta tagcttactg ccaagtataa cagatgtcac catggaaaac aatctctcaa   3120
gagttgttgc cgcagtttct catgaactca ttacgtcaac aacacgggca ctcacatttg   3180
gatgctgtga agccttgtgt cttctctcag cagcctttcc agtttgcact tggagtttag   3240
gatggcactg tggagtgccc ccactgagtg cctctgatga gtccaggaag agctgcactg   3300
ttgggatggc ctccatgatt ctcaccttgc tttcatcagc ttggttccca ctggatctct   3360
cagcccatca ggatgccttg attttggctg gaaacttgct agcagcgagt gcccccaagt   3420
ctctgagaag ttcatggacc tctgaagaag aagccaactc agcagccacc agacaggagg   3480
aaatctggcc tgctctgggg gatcggactc tagtgccctt ggtggagcag cttttctccc   3540
acctgctgaa ggtgatcaat atctgtgctc atgtcttgga cgatgtgact cctggaccag   3600
caatcaaggc agccttgcct tctctaacaa acccccccttc tctaagtcct attcgacgga   3660
aagggaagga gaaagaacct ggagaacaag cttctactcc aatgagtccc aagaaagttg   3720
gtgaggccag tgcagcctct cgacaatcag acacctcagg acctgtcaca gcaagtaaat   3780
catcctcact ggggagtttc taccatctcc cctcctacct caaactgcat gatgtcctga   3840
aagccactca cgccaactat aaggtcacct tagatcttca gaacagcact gaaaagtttg   3900
gggggttcct gcgctctgcc ttggacgtcc tttctcagat tctagagctg gcgacactgc   3960
aggacattgg aaagtgtgtt gaagaggtcc ttggatacct gaaatcctgc tttagtcgag   4020
aaccaatgat ggcaactgtc tgtgtgcagc agctattgaa gactctcttt gggacaaact   4080
tagcctcaca gtttgatggc ttatcttcca accccagcaa gtctcagtgc cgagctcagc   4140
gccttggctc ttcaagtgtg aggcccggct tatatcacta ctgcttcatg gcaccataca   4200
cgcacttcac acaggccttg gctgacgcaa gcctgaggaa catggtgcag gcggagcagg   4260
agcgtgatgc ctcggggtgg tttgatgtac tccagaaagt gtctgcccaa ttgaagacga   4320
acctaacaag cgtcacaaag aaccgtgcag ataagaatgc tattcataat cacattaggt   4380
tatttgagcc tcttgttata aaagcattga agcagtacac cacgacaaca tctgtacaat   4440
tgcagaagca ggttttggat ttgctggcac agctggttca gctacgggtc aattactgtc   4500
tactggattc agaccaggtg ttcatcgggt ttgtgctgaa gcagtttgag tacattgaag   4560
tgggccagtt cagggaatca gaggcaatta ttccaaatat atttttcttc ctggtattac   4620
tgtcttatga gcgctaccat tcaaaacaga tcattggaat tcctaaaatc atccagctgt   4680
gtgatggcat catggccagt ggaaggaagg ccgttacaca tgctatacct gctctgcagc   4740
ccattgtcca tgacctcttt gtgttacgag gaacaaataa agctgatgca gggaaagagc   4800
ttgagacaca gaaggaggtg gtggtctcca tgctgttacg actcatccag taccatcagg   4860
tgctggagat gttcatcctt gtcctgcagc agtgccacaa ggagaatgag gacaagtgga   4920
aacggctctc tcggcaggtc gcagacatca tcctgcccat gttggccaag cagcagatgc   4980
atattgactc tcatgaagcc cttggagtgt taaatacctt gtttgagatt ttggctcctt   5040
```

-continued

```
cctccctacg tcctgtggac atgcttttgc ggagtatgtt catcactcca agcacaatgg   5100
catctgtaag cactgtgcag ctgtggatat ctggaatcct cgccattctg agggttctca   5160
tttcccagtc aaccgaggac attgttcttt gtcgtattca ggagctctcc ttctctccac   5220
acttgctctc ctgtccagtg attaacaggt taaggggtgg aggcggtaat gtaacactag   5280
gagaatgcag cgaagggaaa caaaagagtt tgccagaaga tacattctca aggtttcttt   5340
tacagctggt tggtattctt ctagaagaca tcgttacaaa acagctcaaa gtggacatga   5400
gtgaacagca gcatacgttc tactgccaag agctaggcac actgctcatg tgtctgatcc   5460
acatattcaa atctggaatg ttccggagaa tcacagcagc tgccactaga ctcttcacca   5520
gtgatggctg tgaaggcagc ttctatactc tagagagcct gaatgcacgg gtccgatcca   5580
tggtgcccac gcacccagcc ctggtactgc tctggtgtca gatcctactt ctcatcaacc   5640
acactgacca ccggtggtgg gcagaggtgc agcagacacc caagagacac agtctgtcct   5700
gcacgaagtc acttaacccc cagaagtctg gcgaagagga ggattctggc tcggcagctc   5760
agctgggaat gtgcaataga gaaatagtgc gaagaggggc ccttattctc ttctgtgatt   5820
atgtctgtca gaatctccat gactcagaac acttaacatg gctcattgtg aatcacattc   5880
aagatctgat cagcttgtct catgagcctc cagtacaaga ctttattagt gccattcatc   5940
gtaattctgc agctagtggt ctttttatcc aggcaattca gtctcgctgt gaaaatcttt   6000
caacgccaac cactctgaag aaaacacttc agtgcttgga aggcatccat ctcagccagt   6060
ctggtgctgt gctcacacta tatgtggaca ggctcctggg cacccccttc cgtgcgctgg   6120
ctcgcatggt cgacaccctg gcctgtcgcc gggtagaaat gcttttggct gcaaatttac   6180
agagcagcat ggcccagttg ccagaggagg aactaaacag aatccaagaa cacctccaga   6240
acagtgggct tgcacaaaga caccaaaggc tctattcact gctggacaga ttccgactct   6300
ctactgtgca ggactcactt agcccettgc ccccagtcac ttcccaccca ctggatgggg   6360
atgggcacac atctctggaa acagtgagtc cagacaaaga ctggtacctc cagcttgtca   6420
gatcccagtg ttggaccaga tcagattctg cactgctgga aggtgcagag ctggtcaacc   6480
gtatccctgc tgaagatatg aatgacttca tgatgagctc ggagttcaac ctaagccttt   6540
tggctccctg tttaagcctt ggcatgagcg agattgctaa tggccaaaag agtcccctct   6600
ttgaagcagc ccgtggggtg attctgaacc gggtgaccag tgttgttcag cagcttcctg   6660
ctgtccatca agtcttccag cccttcctgc ctatagagcc cacggcctac tggaacaagt   6720
tgaatgatct gcttggtgat accacatcat accagtctct gaccatactt gcccgtgccc   6780
tggcacagta cctggtggtg ctctccaaag tgcctgctca tttgcacctt cctcctgaga   6840
aggaggggga cacggtgaag tttgtggtaa tgacagttga ggccctgtca tggcatttga   6900
tccatgagca gatcccactg agtctggacc tccaagccgg gctagactgc tgctgcctgg   6960
cactacaggt gcctggcctc tggggggtgc tgtcctcccc agagtacgtg actcatgcct   7020
gctccctcat ccattgtgtg cgattcatcc tggaagccat tgcagtacaa cctggagacc   7080
agcttctcgg tcctgaaagc aggtcacata ctccaagagc tgtcagaaag gaggaagtag   7140
actcagatat acaaaacctc agtcatgtca cttcggcctg cgagatggtg gcagacatgg   7200
tggaatccct gcagtcagtg ctggccttgg gccacaagag gaacagcacc ctgccttcat   7260
ttctcacagc tgtgctgaag aacattgtta tcagtctggc ccgactcccc ctagttaaca   7320
gctatactcg tgtgcctcct ctggtatgga aactcgggtg gtcacccaag cctggagggg   7380
attttggcac agtgtttcct gagatccctg tagagttcct ccaggagaag gagatcctca   7440
```

```
aggagttcat ctaccgcatc aacaccctag ggtggaccaa tcgtacccag ttcgaagaaa   7500
cttgggccac cctccttggt gtcctggtga ctcagcccct ggtgatggaa caggaagaga   7560
gcccaccaga ggaagacaca gaaagaaccc agatccatgt cctggctgtg caggccatca   7620
cctctctagt gctcagtgca atgaccgtgc ctgtggctgg caatccagct gtaagctgct   7680
tggagcaaca gccccggaac aagccactga aggctctcga taccagattt ggaagaaagc   7740
tgagcatgat cagagggatt gtagaacaag aaatccaaga gatggtttcc cagagagaga   7800
atactgccac tcaccattct caccaggcgt gggatcctgt cccttctctg ttaccagcta   7860
ctacaggtgc tcttatcagc catgacaagc tgctgctgca gatcaaccca gagcgggagc   7920
caggcaacat gagctacaag ctgggccagg tgtccataca ctccgtgtgg ctgggaaata   7980
acatcacacc cctgagagag gaggaatggg atgaggaaga agaggaagaa agtgatgtcc   8040
ctgcaccaac gtcaccacct gtgtctccag tcaattccag aaaacaccgt gccggggttg   8100
atattcactc ctgttcgcag tttctgcttg aattgtacag ccgatggatc ctgccatcca   8160
gtgcagccag aaggaccccc gtcatcctga tcagtgaagt ggttcgatct cttcttgtag   8220
tgtcagactt attcaccgaa cgtacccagt ttgaaatgat gtatctgacg ctgacagaac   8280
tacggagagt gcacccttca gaagatgaga tcctcattca gtacctggtg cctgccacct   8340
gtaaggcagc tgctgtcctt ggaatggaca aaactgtggc agagccagtc agccgcctac   8400
tggagagcac actgaggagc agccacctgc ccagccagat cggagccctg cacggcatcc   8460
tctatgtgtt ggagtgtgac ctcttggatg acactgcaaa gcagctcatt ccagttgtta   8520
gtgactatct gctgtccaac ctcaaaggaa tagcccactg cgtgaacatt cacagccagc   8580
agcatgtgct ggtaatgtgt gccactgctt tctacctgat ggaaaactac cctctggatg   8640
tgggaccaga attttcagca tctgtgatac agatgtgtgg agtaatgctg tctggaagtg   8700
aggagtccac cccctccatc atttaccact gtgccctccg gggtctggag cggctcctgc   8760
tgtctgagca gctatctcgg ctagacacag agtccttggt caagctaagt gtggacagag   8820
tgaatgtaca aagcccacac agggccatgg cagccctagg cctgatgctc acctgcatgt   8880
acacaggaaa ggaaaaagcc agtccaggca gagcttctga ccccagccct gctacacctg   8940
acagcgagtc tgtgattgta gctatggagc gagtgtctgt tctctttgat aggatccgca   9000
agggatttcc ctgtgaagcc agggttgtgg caaggatcct gcctcagttc ctagatgact   9060
tctttccacc tcaagatgtc atgaacaaag tcattggaga gttcctgtcc aatcagcagc   9120
catacccaca gttcatggcc actgtagttt acaaggtttt tcagactctg cacagtgctg   9180
ggcagtcatc catggtccgg gactgggtca tgctgtccct gtccaacttc acacaaagaa   9240
ctccagttgc catggccatg tggagcctct cctgcttcct tgttagcgca tctaccagcc   9300
catgggtttc tgcgatcctt ccacatgtca tcagcaggat gggcaaactg gaacaggtgg   9360
atgtgaacct tttctgcctg gttgccacag acttctacag acaccagata gaggaggaat   9420
tcgaccgcag ggctttccag tctgtgtttg aggtggtggc tgcaccagga agtccatacc   9480
acaggctgct tgcttgtttg caaaatgttc acaaggtcac cacctgctga gtagtgcctg   9540
tgggacaaaa ggctgaaaga aggcagctgc tggggcctga gcctccagga gcctgctcca   9600
agcttctgct ggggctgcct tggccgtgca ggcttccact tgtgtcaagt ggacagccag   9660
gcaatggcag gagtgctttg caatgagggc tatgcaggga acatgcacta tgttggggtt   9720
gagcctgagt cctgggtcct ggcctcgctg cagctggtga cagtgctagg ttgaccaggt   9780
```

-continued

```
gtttgtcttt ttcctagtgt tcccctggcc atagtcgcca ggttgcagct gccctggtat   9840

gtggatcaga agtcctagct cttgccagat ggttctgagc ccgcctgctc cactgggctg   9900

gagagctccc tcccacattt acccagtagg catacctgcc acaccagtgt ctggacacaa   9960

aatgaatggt gtgtggggct gggaactggg gctgccaggt gtccagcacc attttccttt  10020

ctgtgttttc ttctcaggag ttaaaattta attatatcag taaagagatt aattttaatg  10080

t                                                                  10081


<210> SEQ ID NO 287
<211> LENGTH: 20
<212> TYPE: DNA
<213> ORGANISM: Artificial Sequence
<220> FEATURE:
<223> OTHER INFORMATION: Primer

<400> SEQUENCE: 287

attacagtct caccacgccc                                                 20


<210> SEQ ID NO 288
<211> LENGTH: 20
<212> TYPE: DNA
<213> ORGANISM: Artificial Sequence
<220> FEATURE:
<223> OTHER INFORMATION: Primer

<400> SEQUENCE: 288

gacaagggaa gacccaagtg                                                 20
```